US006300064B1

(12) United States Patent
Knappik et al.

(10) Patent No.: US 6,300,064 B1
(45) Date of Patent: Oct. 9, 2001

(54) PROTEIN/(POLY)PEPTIDE LIBRARIES

(75) Inventors: Achim Knappik, Gräfelfing; Peter Pack, München; Liming Ge, München; Simon Moroney, München, all of (DE); Andreas Plückthun, Zürich (CH)

(73) Assignee: Morphosys AG, Munich (DE)

( * ) Notice: Subject to any disclaimer, the term of this patent is extended or adjusted under 35 U.S.C. 154(b) by 0 days.

(21) Appl. No.: 09/025,769

(22) Filed: Feb. 18, 1998

Related U.S. Application Data

(63) Continuation of application No. PCT/EP96/03647, filed on Aug. 19, 1996.

(30) Foreign Application Priority Data

Aug. 18, 1995 (EP) .................................................. 95113021

(51) Int. Cl.[7] ........................... G01N 33/53; A61K 39/29

(52) U.S. Cl. ............................ 435/6; 435/7.1; 435/320.1; 435/440; 435/455; 435/471; 435/328; 435/69.1; 435/69.3; 435/DIG. 2; 435/DIG. 3; 435/DIG. 15; 435/DIG. 17; 435/DIG. 51; 536/23.1; 536/24.1; 514/44

(58) Field of Search .............................. 435/6, 71.1, 69.7, 435/69.1, 7.1, 320.1, 440, 455, 471, 328, 69.3, DIG. 2, DIG. 3, DIG. 15, DIG. 17, DIG. 51; 536/23.1, 24.1; 514/44

(56) References Cited

U.S. PATENT DOCUMENTS

| | | | |
|---|---|---|---|
| 5,395,750 | 3/1995 | Dillon et al. | 435/5 |
| 5,693,493 * | 12/1997 | Robinson et al. | 435/69.1 |
| 5,693,761 * | 12/1997 | Queen et al. | 536/23.1 |
| 6,096,551 * | 8/2000 | Barbas et al. | 436/6 |

FOREIGN PATENT DOCUMENTS

| | | |
|---|---|---|
| A 0368684 A1 | 5/1990 | (EP) . |
| WO 95/11998 A1 | 5/1995 | (WO) . |

OTHER PUBLICATIONS

Branden et al. "Introduction to Protein Structure." pp. 179–199, 1991.*

Knappik et al., Combinatorial Biology with Human Antibodies, Abstract and slides from a presentation given at a conference on *Applied Molecular Evolution* in San Diego, CA in Dec., 1995.

Barbas, C. F. III, et al., "Semisynthetic combinatorial antibody libraries: A chemical solution to the diversity problem," *Proc. Natl. Acad. Sci. USA,* 89, 4457–4461 (1992).

Collet, T.A., et al., "A binary plasmid system for shuffling combinatorial antibody libraries," *Proc. Natl. Acad. Sci. USA,* 89(21), 10026–10030 (1992).

Foote, J. and Winter, G., "Antibody framework residues affecting the conformation of the hypervariable loops," *J. Mol. Biol.,* 224, 487–499 (1992).

(List continued on next page.)

*Primary Examiner*—Marianne P. Allen
*Assistant Examiner*—Mary K Zeman
(74) *Attorney, Agent, or Firm*—Heller Ehrman White & McAuliffe

(57) ABSTRACT

The present invention relates to synthetic DNA sequences which encode one or more collections of homologous proteins/(poly)peptides, and methods for generating and applying libraries of these DNA sequences. In particular, the invention relates to the preparation of a library of human-derived antibody genes by the use of synthetic consensus sequences which cover the structural repertoire of antibodies encoded in the human genome. Furthermore, the invention relates to the use of a single consensus antibody gene as a universal framework for highly diverse antibody libraries.

25 Claims, 220 Drawing Sheets

OTHER PUBLICATIONS

Figure 1:
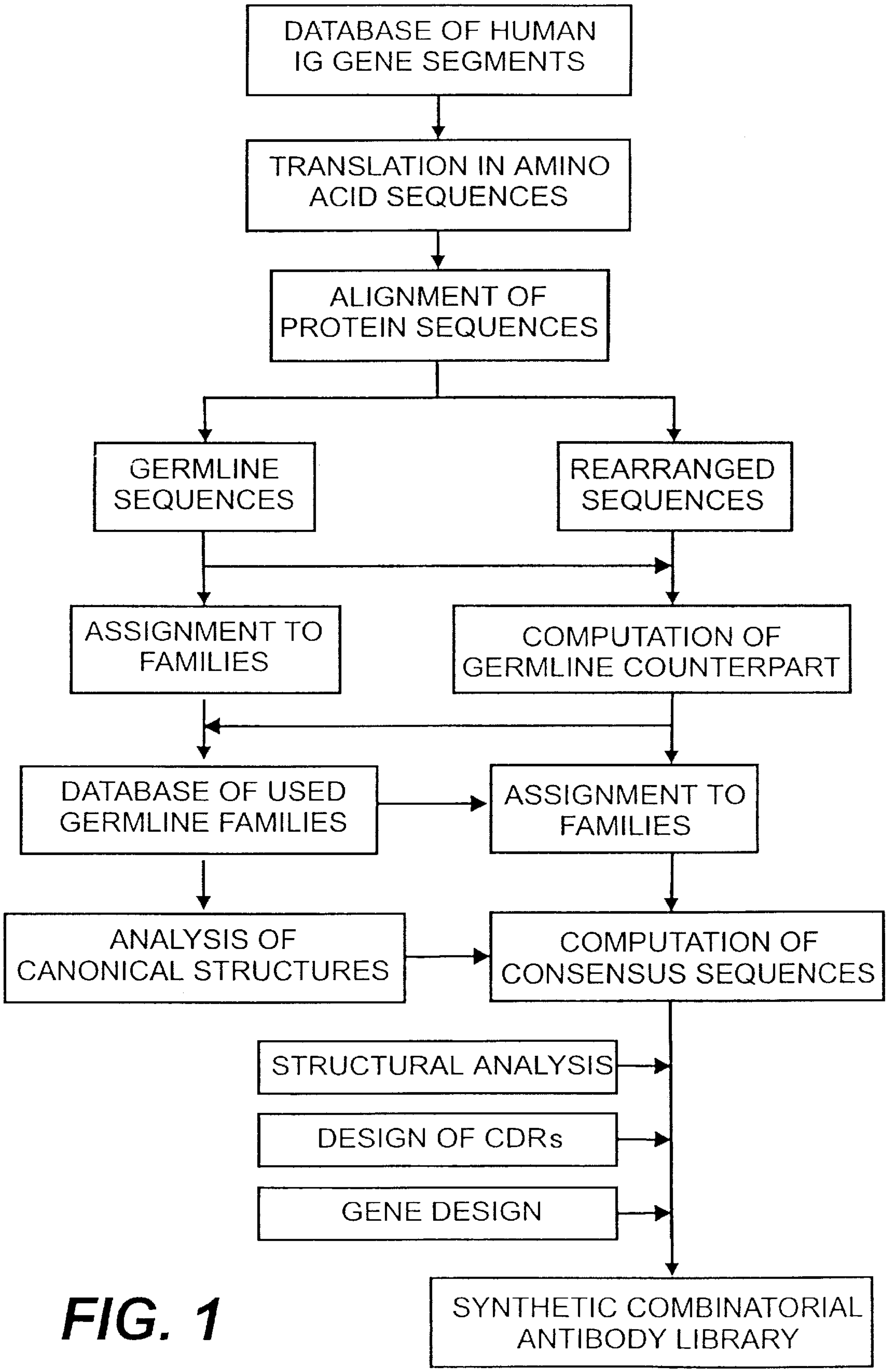

Gram, Hermann, et al., "In vitro and affinity maturation of antibodies from a naive combinatorial immunoglobulin library," *Proc. Natl. Acad. Sci. USA,* 89(8), 3576–3580 (1992).

Knappik, A. and Plückthun, A., "Engineered turns of a recombinant antibody improve its in vivo folding," *Protein Engineering,* 8(1), 81–89 (1995).

Waterhouse, P. et al., "Combinatorial infection and in vivo recombination: a strategy for making large phage antibody repertorires," *Nucl. Acids Res.,* 21(9), 2265–2266 (1993).

Williams, S.C. and Winter , G., "Cloning and sequencing of human immunoglobulin $V_\lambda$ gene segments," *Eur. J. Immunol.,* 23, 1456–1461 (1993).

* cited by examiner

| | framework 1 | | | | | | | | | | | | | | | | | | | | | | | CDRI | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C |
| Vk1 | D | I | Q | M | T | Q | S | P | S | S | L | S | A | S | V | G | D | R | V | T | I | T | C | R | A | S | Q | - | - | - |
| Vk2 | D | I | V | M | T | Q | S | P | L | S | L | P | V | T | P | G | E | P | A | S | I | S | C | R | S | S | Q | S | L | L |
| Vk3 | D | I | V | L | T | Q | S | P | A | T | L | S | L | S | P | G | E | R | A | T | L | S | C | R | A | S | Q | S | - | - |
| Vk4 | D | I | V | M | T | Q | S | P | D | S | L | A | V | S | L | G | E | R | A | T | I | N | C | R | S | S | Q | S | V | L |

| | CDRI | | | | | | | | | | framework 2 | | | | | | | | | | | | | | | CDR II | | | | |
|---|---|---|---|---|---|---|---|---|---|---|---|---|---|---|---|---|---|---|---|---|---|---|---|---|---|---|---|---|---|---|
| | D | E | F | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 |
| Vk5 | - | - | - | G | I | S | S | Y | L | A | W | Y | Q | Q | K | P | G | K | A | P | K | L | L | I | Y | A | A | S | S | L |
| Vk6 | H | S | - | N | G | Y | N | Y | L | D | W | Y | L | Q | K | P | G | Q | S | P | Q | L | L | I | Y | L | G | S | N | R |
| Vk7 | - | - | - | V | S | S | S | Y | L | A | W | Y | Q | Q | K | P | G | Q | A | P | R | L | L | I | Y | G | A | S | S | R |
| Vk8 | Y | S | S | N | N | K | N | Y | L | A | W | Y | Q | Q | K | P | G | Q | P | P | K | L | L | I | Y | W | A | S | T | R |

FIG. 2A

| | CDRII | | framework 3 | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
| Vk1 | Q | S | G | V | P | S | R | F | S | G | S | G | S | G | T | D | F | T | L | T | I | S | S | L | Q | P | E | D | F | A |
| Vk2 | A | S | G | V | P | D | R | F | S | G | S | G | S | G | T | D | F | T | L | K | I | S | R | V | E | A | E | D | V | G |
| Vk3 | A | T | G | V | P | A | R | F | S | G | S | G | S | G | T | D | F | T | L | T | I | S | S | L | E | P | E | D | F | A |
| Vk4 | E | S | G | V | P | D | R | F | S | G | S | G | S | G | T | D | F | T | L | T | I | S | S | L | Q | A | E | D | V | A |

| | framework 3 | | | | | CDRIII | | | | | | | framework 4 | | | | | | | | | | | | |
|---|---|---|---|---|---|---|---|---|---|---|---|---|---|---|---|---|---|---|---|---|---|---|---|---|---|
| | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 |
| Vk1 | T | Y | Y | C | Q | Q | H | Y | T | T | P | P | T | F | G | Q | G | T | K | V | E | I | K | R | T |
| Vk2 | V | Y | Y | C | Q | Q | H | Y | T | T | P | P | T | F | G | Q | G | T | K | V | E | I | K | R | T |
| Vk3 | V | Y | Y | C | Q | Q | H | Y | T | T | P | P | T | F | G | Q | G | T | K | V | E | I | K | R | T |
| Vk4 | V | Y | Y | C | Q | Q | H | Y | T | T | P | P | T | F | G | Q | G | T | K | V | E | I | K | R | T |

FIG. 2B

| | framework 1 | | | | | | | | | | | | | | | | | | | | | | | CDRI | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | D | E | 28 |
| vλ1 | Q | S | V | L | T | Q | P | P | S | - | V | S | G | A | P | G | Q | R | V | T | I | S | C | S | G | S | S | S | N | I |
| vλ2 | Q | S | A | L | T | Q | P | A | S | - | V | S | G | S | P | G | Q | S | I | T | I | S | C | T | G | T | S | S | D | V |
| vλ3 | S | Y | E | L | T | Q | P | P | S | - | V | S | V | A | P | G | Q | T | A | R | I | S | C | S | G | D | A | - | - | L |

| | CDRI | | | | | | | framework 2 | | | | | | | | | | | | | | | CDR II | | | | | | | |
|---|---|---|---|---|---|---|---|---|---|---|---|---|---|---|---|---|---|---|---|---|---|---|---|---|---|---|---|---|---|---|
| | 29 | 30 | 31 | A | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 |
| vλ1 | G | S | N | - | Y | V | S | W | Y | Q | Q | L | P | G | T | A | P | K | L | L | I | Y | D | N | N | Q | R | P | S | G |
| vλ2 | G | G | Y | N | Y | V | S | W | Y | Q | Q | H | P | G | K | A | P | K | L | M | I | Y | D | V | S | N | R | P | S | G |
| vλ3 | G | D | K | - | Y | A | S | W | Y | Q | Q | K | P | G | Q | A | P | V | L | V | I | Y | D | D | S | D | R | P | S | G |

FIG. 2C

| | framework 3 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
| vλ1 | V | P | D | R | F | S | G | S | K | S | G | T | S | A | S | L | A | I | T | G | L | Q | S | E | D | E | A | D | Y | Y |
| vλ2 | V | S | N | R | F | S | G | S | K | S | G | N | T | A | S | L | T | I | S | G | L | Q | A | E | D | E | A | D | Y | Y |
| vλ3 | I | P | E | R | F | S | G | S | N | S | G | N | T | A | T | L | T | I | S | G | T | Q | A | E | D | E | A | D | Y | Y |

| | | CDRIII | | | | | | | | | framework 4 | | | | | | | | | | |
|---|---|---|---|---|---|---|---|---|---|---|---|---|---|---|---|---|---|---|---|---|---|
| | 88 | 89 | 90 | 91 | 92 | 93 | 94 | 95 | 96 | 97 | 98 | 99 | 100 | 101 | 102 | 103 | 104 | 105 | 106 | A | 107 |
| vλ1 | C | Q | Q | H | Y | T | T | P | P | V | F | G | G | G | T | K | L | T | V | L | G |
| vλ2 | C | Q | Q | H | Y | T | T | P | P | V | F | G | G | G | T | K | L | T | V | L | G |
| vλ3 | C | Q | Q | H | Y | T | T | P | P | V | F | G | G | G | T | K | L | T | V | L | G |

FIG. 2D

| | framework 1 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| VH1A | Q | V | Q | L | V | Q | S | G | A | E | V | K | K | P | G | S | S | V | K | V | S | C | K | A | S | G | G | T | F | S |
| VH1B | Q | V | Q | L | V | Q | S | G | A | E | V | K | K | P | G | A | S | V | K | V | S | C | K | A | S | G | Y | T | F | T |
| VH2 | Q | V | Q | L | K | E | S | G | P | A | L | V | K | P | T | Q | T | L | T | L | T | C | T | F | S | G | F | S | L | S |
| VH3 | E | V | Q | L | V | E | S | G | G | G | L | V | Q | P | G | G | S | L | R | L | S | C | A | A | S | G | F | T | F | S |
| VH4 | Q | V | Q | L | Q | E | S | G | P | G | L | V | K | P | S | E | T | L | S | L | T | C | T | V | S | G | G | S | I | S |
| VH5 | E | V | Q | L | V | Q | S | G | A | E | V | K | K | P | G | E | S | L | K | I | S | C | K | G | S | G | Y | S | F | T |
| VH6 | Q | V | Q | L | Q | Q | S | G | P | G | L | V | K | P | S | Q | T | L | S | L | T | C | A | I | S | G | D | S | V | S |

| | CDRI | | | | | | | framework 2 | | | | | | | | | | | | | | CDR II | | | | | | | | | | |
|---|---|---|---|---|---|---|---|---|---|---|---|---|---|---|---|---|---|---|---|---|---|---|---|---|---|---|---|---|---|---|---|---|
| | 31 | A | B | 32 | 33 | 34 | 35 | 36 | 37 | 38 | 39 | 40 | 41 | 42 | 43 | 44 | 45 | 46 | 47 | 48 | 49 | 50 | 51 | 52 | A | B | C | 53 | 54 | 55 | 56 | 57 |
| VH1A | S | - | - | Y | A | I | S | W | V | R | Q | A | P | G | Q | G | L | E | W | M | G | G | I | I | P | - | - | I | F | G | T | A |
| VH1B | S | - | - | Y | Y | M | H | W | V | R | Q | A | P | G | Q | G | L | E | W | M | G | W | I | N | P | - | - | N | S | G | G | T |
| VH2 | T | S | G | V | G | V | G | W | I | R | Q | P | P | G | K | A | L | E | W | L | A | L | I | D | - | - | - | W | D | D | D | K |
| VH3 | S | - | - | Y | A | M | S | W | V | R | Q | A | P | G | K | G | L | E | W | V | S | A | I | S | G | - | - | S | G | G | S | T |
| VH4 | S | - | - | Y | Y | W | S | W | I | R | Q | P | P | G | K | G | L | E | W | I | G | Y | I | Y | - | - | - | Y | S | G | S | T |
| VH5 | S | - | - | Y | W | I | G | W | V | R | Q | M | P | G | K | G | L | E | W | M | G | I | I | Y | P | - | - | G | D | S | D | T |

FIG. 2E

VH6 S N S A A W N W I R Q S P G R G L E W L G R T Y Y R - S K W Y N

| | CDRII | | | | | | | | | | framework 3 | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C | 83 | 84 | 85 |
| VH1A | N | Y | A | Q | K | F | Q | G | R | V | T | I | T | A | D | E | S | T | S | T | A | Y | M | E | L | S | S | L | R | S | E |
| VH1B | N | Y | A | Q | K | F | Q | G | R | V | T | M | T | R | D | T | S | I | S | T | A | Y | M | E | L | S | S | L | R | S | E |
| VH2 | Y | Y | S | T | S | L | K | T | R | L | T | I | S | K | D | T | S | K | N | Q | V | V | L | T | M | T | N | M | D | P | V |
| VH3 | Y | Y | A | D | S | V | K | G | R | F | T | I | S | R | D | N | S | K | N | T | L | Y | L | Q | M | N | S | L | R | A | E |
| VH4 | N | Y | N | P | S | L | K | S | R | V | T | I | S | V | D | T | S | K | N | Q | F | S | L | K | L | S | S | V | T | A | A |
| VH5 | R | Y | S | P | S | F | Q | G | Q | V | T | I | S | A | D | K | S | I | S | T | A | Y | L | Q | W | S | S | L | K | A | S |
| VH6 | D | Y | A | V | S | V | K | S | R | I | T | I | N | P | D | T | S | K | N | Q | F | S | L | Q | L | N | S | V | T | P | E |

| | framework 3 | | | | | | | | | | CDRIII | | | | | | | | | | | | | | framework 4 | | | | | | | |
|---|---|---|---|---|---|---|---|---|---|---|---|---|---|---|---|---|---|---|---|---|---|---|---|---|---|---|---|---|---|---|---|
| | 86 | 87 | 88 | 89 | 90 | 91 | 92 | 93 | 94 | 95 | 96 | 97 | 98 | 99 | 100 | A | B | C | 101 | 102 | 103 | 104 | 105 | 106 | 107 | 108 | 109 | 110 | 111 | 112 | 113 |
| VH1A | D | T | A | V | Y | Y | C | A | R | W | G | G | D | G | F | Y | A | M | D | Y | W | G | Q | G | T | L | V | T | V | S | S |
| VH1B | D | T | A | V | Y | Y | C | A | R | W | G | G | D | G | F | Y | A | M | D | Y | W | G | Q | G | T | L | V | T | V | S | S |
| VH2 | D | T | A | T | Y | Y | C | A | R | W | G | G | D | G | F | Y | A | M | D | Y | W | G | Q | G | T | L | V | T | V | S | S |
| VH3 | D | T | A | V | Y | Y | C | A | R | W | G | G | D | G | F | Y | A | M | D | Y | W | G | Q | G | T | L | V | T | V | S | S |
| VH4 | D | T | A | V | Y | Y | C | A | R | W | G | G | D | G | F | Y | A | M | D | Y | W | G | Q | G | T | L | V | T | V | S | S |

FIG. 2F

| | |
|---|---|
| VH5 | D T A M Y Y C A R W G G D G F Y A M D Y W G Q G T L V T V S S |
| VH6 | D T A V Y Y C A R W G G D G F Y A M D Y W G Q G T L V T V S S |

FIG. 2G

```
.D  I  Q  M   T  Q  S   P  S  S   L  S  A  S   V  G  D
 EcoRV                BanII
~~~~~~~              ~~~~~~~~~
GATATCCAGA TGACCCAGAG CCCGTCTAGC CTGAGCGCGA GCGTGGGTGA
CTATAGGTCT ACTGGGTCTC GGGCAGATCG GACTCGCGCT CGCACCCACT

  R  V  T   I  T  C  R   A  S  Q   G  I  S   S  Y  L
                   PstI
                 ~~~~~~~~
TCGTGTGACC ATTACCTGCA GAGCGAGCCA GGGCATTAGC AGCTATCTGG
AGCACACTGG TAATGGACGT CTCGCTCGGT CCCGTAATCG TCGATAGACC

A  W  Y  Q   Q  K  P   G  K  A  P   K  L  L   I  Y  A
    KpnI            SexAI                    AseI
   ~~~~~~~          ~~~~~~~~~~             ~~~~~~~~
CGTGGTACCA GCAGAAACCA GGTAAAGCAC CGAAACTATT AATTTATGCA
GCACCATGGT CGTCTTTGGT CCATTTCGTG GCTTTGATAA TTAAATACGT

 A  S  S  L   Q  S  G   V  P  S   R  F  S  G   S  G  S
                     SanDI                       BamHI
                    ~~~~~~~~~~                   ~~~~~
GCCAGCAGCT TGCAAAGCGG GGTCCCGTCC CGTTTTAGCG GCTCTGGATC
CGGTCGTCGA ACGTTTCGCC CCAGGGCAGG GCAAAATCGC CGAGACCTAG
```

FIG. 3A

```
  G   T   D   F   T   L   T   I   S   S   L   Q   P   E   D   F
                                                  Eco57I
                                                  ~~~~~~~~
BamHI                                                 BbsI
~                                                    ~~~~~~~
CGGCACTGAT TTTACCCTGA CCATTAGCAG CCTGCAACCT GAAGACTTTG
GCCGTGACTA AAATGGGACT GGTAATCGTC GGACGTTGGA CTTCTGAAAC

A   T   Y   Y   C   Q   Q   H   Y   T   T   P   P   T   F   G   Q
                                                          MscI
                                                         ~~~~~~
CGACCTATTA TTGCCAGCAG CATTATACCA CCCCGCCGAC CTTTGGCCAG
GCTGGATAAT AACGGTCGTC GTAATATGGT GGGGCGGCTG GAAACCGGTC

 G   T   K   V   E   I   K   R   T
                             BsiWI
                            ~~~~~
GGTACGAAAG TTGAAATTAA ACGTACG
CCATGCTTTC AACTTTAATT TGCATGC
```

FIG. 3B

```
 D  I  V  M   T  Q  S   P  L  S   L  P  V  T   P  G  E
 EcoRV             BanII
~~~~~~          ~~~~~~~
GATATCGTGA TGACCCAGAG CCCACTGAGC CTGCCAGTGA CTCCGGGCGA
CTATAGCACT ACTGGGTCTC GGGTGACTCG GACGGTCACT GAGGCCCGCT

  P  A  S   I  S  C  R   S  S  Q   S  L  L   H  S  N
                 PstI
               ~~~~~~~
GCCTGCGAGC ATTAGCTGCA GAAGCAGCCA AAGCCTGCTG CATAGCAACG
CGGACGCTCG TAATCGACGT CTTCGTCGGT TTCGGACGAC GTATCGTTGC

G  Y  N  Y   L  D  W   Y  L  Q  K   P  G  Q   S  P  Q
                  KpnI           SexAI
                ~~~~~~~        ~~~~~~~
GCTATAACTA TCTGGATTGG TACCTTCAAA AACCAGGTCA AAGCCCGCAG
CGATATTGAT AGACCTAACC ATGGAAGTTT TTGGTCCAGT TTCGGGCGTC
```

FIG. 3C

```
 L  L  I  Y   L  G  S   N  R  A   S  G  V  P   D  R  F
  AseI                               SanDI
 ~~~~~~~                            ~~~~~~~~~
CTATTAATTT ATCTGGGCAG CAACCGTGCC AGTGGGGTCC CGGATCGTTT
GATAATTAAA TAGACCCGTC GTTGGCACGG TCACCCCAGG GCCTAGCAAA

  S  G  S   G  S  G  T   D  F  T   L  K  I   S  R  V
            BamHI
           ~~~~~~~
TAGCGGCTCT GGATCCGGCA CCGATTTTAC CCTGAAAATT AGCCGTGTGG
ATCGCCGAGA CCTAGGCCGT GGCTAAAATG GGACTTTTAA TCGGCACACC

E  A  E  D   V  G  V   Y  Y  C  Q   Q  H  Y   T  T  P
  Eco57I
  ~~~~~~~
     BbsI
    ~~~~~~~~
AAGCTGAAGA CGTGGGCGTG TATTATTGCC AGCAGCATTA TACCACCCCG
TTCGACTTCT GCACCCGCAC ATAATAACGG TCGTCGTAAT ATGGTGGGGC
```

FIG. 3D

```
P  T  F  G    Q  G  T    K  V  E    I  K  R  T
         MscI                              BsiWI
        ~~~~~~~~                          ~~~~~~
CCGACCTTTG GCCAGGGTAC GAAAGTTGAA ATTAAACGTA CG
GGCTGGAAAC CGGTCCCATG CTTTCAACTT TAATTTGCAT GC
```

FIG. 3E

```
 D  I  V  L   T  Q  S   P  A  T   L  S  L  S   P  G  E
 EcoRV                BanII
~~~~~~               ~~~~~~~
GATATCGTGC TGACCCAGAG CCCGGCGACC CTGAGCCTGT CTCCGGGCGA
CTATAGCACG ACTGGGTCTC GGGCCGCTGG GACTCGGACA GAGGCCCGCT

  R  A  T   L  S  C  R   A  S  Q   S  V  S   S  S  Y
                 PstI
                ~~~~~~~
ACGTGCGACC CTGAGCTGCA GAGCGAGCCA GAGCGTGAGC AGCAGCTATC
TGCACGCTGG GACTCGACGT CTCGCTCGGT CTCGCACTCG TCGTCGATAG

L  A  W  Y   Q  Q  K   P  G  Q  A   P  R  L   L  I  Y
       KpnI            SexAI                  AseI
      ~~~~~~~         ~~~~~~~~               ~~~~~~
```

FIG. 3F

```
TGGCGTGGTA CCAGCAGAAA CCAGGTCAAG CACCGCGTCT ATTAATTTAT
ACCGCACCAT GGTCGTCTTT GGTCCAGTTC GTGGCGCAGA TAATTAAATA

 G  A  S  S   R  A  T   G  V  P   A  R  F  S   G  S  G
                         SanDI                     BamHI
                        ~~~~~~~~                      ~~
GGCGCGAGCA GCCGTGCAAC TGGGGTCCCG GCGCGTTTTA GCGGCTCTGG
CCGCGCTCGT CGGCACGTTG ACCCCAGGGC CGCGCAAAAT CGCCGAGACC

  S  G  T   D  F  T  L   T  I  S   S  L  E   P  E  D
                                             Eco57I
                                             ~~~~~~~
BamHI                                          BbsI
~~~~                                          ~~~~~~~
ATCCGGCACG GATTTTACCC TGACCATTAG CAGCCTGGAA CCTGAAGACT
TAGGCCGTGC CTAAAATGGG ACTGGTAATC GTCGGACCTT GGACTTCTGA
```

FIG. 3G

```
F  A  V  Y   Y  C  Q   Q  H  Y  T   T  P  P   T  F  G
                                                 MscI
                                                 ~~~~
TTGCGGTGTA TTATTGCCAG CAGCATTATA CCACCCCGCC GACCTTTGGC
AACGCCACAT AATAACGGTC GTCGTAATAT GGTGGGGCGG CTGGAAACCG

 Q  G  T  K   V  E  I   K  R  T
MscI                     BsiWI
~~                      ~~~~~~
CAGGGTACGA AAGTTGAAAT TAAACGTACG
GTCCCATGCT TTCAACTTTA ATTTGCATGC
```

*FIG. 3H*

```
 D  I  V  M   T  Q  S   P  D  S   L  A  V  S   L  G  E
 EcoRV                BanII
~~~~~~              ~~~~~~~~
GATATCGTGA TGACCCAGAG CCCGGATAGC CTGGCGGTGA GCCTGGGCGA
CTATAGCACT ACTGGGTCTC GGGCCTATCG GACCGCCACT CGGACCCGCT

  R  A  T   I  N  C  R   S  S  Q   S  V  L   Y  S  S
                  PstI
                ~~~~~~~~
ACGTGCGACC ATTAACTGCA GAAGCAGCCA GAGCGTGCTG TATAGCAGCA
TGCACGCTGG TAATTGACGT CTTCGTCGGT CTCGCACGAC ATATCGTCGT

N  N  K  N   Y  L  A   W  Y  Q  Q   K  P  G   Q  P  P
                         KpnI            SexAI
                       ~~~~~~~        ~~~~~~~~~
ACAACAAAAA CTATCTGGCG TGGTACCAGC AGAAACCAGG TCAGCCGCCG
TGTTGTTTTT GATAGACCGC ACCATGGTCG TCTTTGGTCC AGTCGGCGGC
```

*FIG. 3I*

```
 K  L  L  I   Y  W  A   S  T  R   E  S  G  V   P  D  R
     AseI                                   SanDI
    ~~~~~~~~                               ~~~~~~~~~
AAACTATTAA TTTATTGGGC ATCCACCCGT GAAAGCGGGG TCCCGGATCG
TTTGATAATT AAATAACCCG TAGGTGGGCA CTTTCGCCCC AGGGCCTAGC

  F  S  G   S  G  S  G   T  D  F   T  L  T   I  S  S
               BamHI
              ~~~~~~~
TTTTAGCGGC TCTGGATCCG GCACTGATTT TACCCTGACC ATTTCGTCCC
AAAATCGCCG AGACCTAGGC CGTGACTAAA ATGGGACTGG TAAAGCAGGG

L  Q  A  E   D  V  A   V  Y  Y  C   Q  Q  H   Y  T  T
      Eco57I
      ~~~~~~~~
         BbsI
        ~~~~~~~~
```

FIG. 3J

```
TGCAAGCTGA AGACGTGGCG GTGTATTATT GCCAGCAGCA TTATACCACC
ACGTTCGACT TCTGCACCGC CACATAATAA CGGTCGTCGT AATATGGTGG

 P   P   T   F    G   Q   G    T   K   V    E   I   K   R    T
               MscI                                      BsiWI
              ~~~~~~                                    ~~~~~~
CCGCCGACCT TTGGCCAGGG TACGAAAGTT GAAATTAAAC GTACG
GGCGGCTGGA AACCGGTCCC ATGCTTTCAA CTTTAATTTG CATGC
```

FIG. 3K

```
  Q   S   V   L    T   Q   P    P   S   V    S   G   A   P    G   Q   R
                                                          SexAI
                                                         ~~~~~~~~~
CAGAGCGTGC TGACCCAGCC GCCTTCAGTG AGTGGCGCAC CAGGTCAGCG
GTCTCGCACG ACTGGGTCGG CGGAAGTCAC TCACCGCGTG GTCCAGTCGC
                           Eco57I
                           ~~~~~~~

   V   T   I    S   C   S   G    S   S   S    N   I   G    S   N   Y
              BssSI
             ~~~~~~~~
TGTGACCATC TCGTGTAGCG GCAGCAGCAG CAACATTGGC AGCAACTATG
ACACTGGTAG AGCACATCGC CGTCGTCGTC GTTGTAACCG TCGTTGATAC

V   S   W   Y    Q   Q   L    P   G   T   A    P   K   L    L   I   Y
        KpnI                 XmaI      BbeI
       ~~~~~~~~             ~~~~~~~   ~~~~~~~~
TGAGCTGGTA CCAGCAGTTG CCCGGGACGG CGCCGAAACT GCTGATTTAT
ACTCGACCAT GGTCGTCAAC GGGCCCTGCC GCGGCTTTGA CGACTAAATA
```

FIG. 4A

```
 D   N   N   Q    R   P   S    G   V   P    D   R   F   S    G   S   K
                      Bsu36I                                 BamHI
                      ~~~~~~~~~                             ~~~~~~~
GATAACAACC AGCGTCCCTC AGGCGTGCCG GATCGTTTTA GCGGATCCAA
CTATTGTTGG TCGCAGGGAG TCCGCACGGC CTAGCAAAAT CGCCTAGGTT

  S   G   T    S   A   S   L    A   I   T    G   L   Q    S   E   D
                                                              BbsI
                                                            ~~~~~~~
AAGCGGCACC AGCGCGAGCC TTGCGATTAC GGGCCTGCAA AGCGAAGACG
TTCGCCGTGG TCGCGCTCGG AACGCTAATG CCCGGACGTT TCGCTTCTGC

E   A   D   Y    Y   C   Q    Q   H   Y   T    T   P   P    V   F   G
AAGCGGATTA TTATTGCCAG CAGCATTATA CCACCCCGCC TGTGTTTGGC
TTCGCCTAAT AATAACGGTC GTCGTAATAT GGTGGGGCGG ACACAAACCG
```

FIG. 4B

```
 G  G  T  K  L  T  V  L  G
             HpaI       MscI
            ~~~~~~~     ~~~
GGCGGCACGA AGTTAACCGT TCTTGGC
CCGCCGTGCT TCAATTGGCA AGAACCG
```

FIG. 4C

```
  Q  S  A  L   T  Q  P   A  S  V   S  G  S  P   G  Q  S
                                            SexAI
                                           ~~~~~~~~~
CAGAGCGCAC TGACCCAGCC AGCTTCAGTG AGCGGCTCAC CAGGTCAGAG
GTCTCGCGTG ACTGGGTCGG TCGAAGTCAC TCGCCGAGTG GTCCAGTCTC
                         Eco57I
                         ~~~~~~~

   I  T  I   S  C  T  G   T  S  S   D  V  G   G  Y  N
            BssSI
           ~~~~~~~~
CATTACCATC TCGTGTACGG GTACTAGCAG CGATGTGGGC GGCTATAACT
GTAATGGTAG AGCACATGCC CATGATCGTC GCTACACCCG CCGATATTGA

Y  V  S  W   Y  Q  Q   H  P  G  K   A  P  K   L  M  I
            KpnI             XmaI      BbeI
           ~~~~~~~~         ~~~~~~~   ~~~~~~~
ATGTGAGCTG GTACCAGCAG CATCCCGGGA AGGCGCCGAA ACTGATGATT
TACACTCGAC CATGGTCGTC GTAGGGCCCT TCCGCGGCTT TGACTACTAA
```

*FIG. 4D*

```
 Y  D  V  S   N  R  P   S  G  V   S  N  R  F   S  G  S
                   Bsu36I                          BamHI
                   ~~~~~~~~~                       ~~~~~
TATGATGTGA GCAACCGTCC CTCAGGCGTG AGCAACCGTT TTAGCGGATC
ATACTACACT CGTTGGCAGG GAGTCCGCAC TCGTTGGCAA AATCGCCTAG

  K  S  G   N  T  A  S   L  T  I   S  G  L   Q  A  E
BamHI                                               BbsI
~                                                   ~~~~
CAAAAGCGGC AACACCGCGA GCCTGACCAT TAGCGGCCTG CAAGCGGAAG
GTTTTCGCCG TTGTGGCGCT CGGACTGGTA ATCGCCGGAC GTTCGCCTTC

D  E  A  D   Y  Y  C   Q  Q  H  Y   T  T  P   P  V  F
BbsI
~~
ACGAAGCGGA TTATTATTGC CAGCAGCATT ATACCACCCC GCCTGTGTTT
TGCTTCGCCT AATAATAACG GTCGTCGTAA TATGGTGGGG CGGACACAAA
```

FIG. 4E

```
  G   G   G   T    K   L   T    V   L   G
                     HpaI            MscI
                   ~~~~~~~          ~~~~
GGCGGCGGCA CGAAGTTAAC CGTTCTTGGC
CCGCCGCCGT GCTTCAATTG GCAAGAACCG
```

FIG. 4F

```
 S  Y  E  L   T  Q  P   P  S  V   S  V  A  P   G  Q  T
                                              SexAI
                                             ~~~~~~~~~
AGCTATGAAC TGACCCAGCC GCCTTCAGTG AGCGTTGCAC CAGGTCAGAC
TCGATACTTG ACTGGGTCGG CGGAAGTCAC TCGCAACGTG GTCCAGTCTG
                         Eco57I
                         ~~~~~~~

  A  R  I   S  C  S  G   D  A  L   G  D  K   Y  A  S
           BssSI
          ~~~~~~~~
CGCGCGTATC TCGTGTAGCG GCGATGCGCT GGGCGATAAA TACGCGAGCT
GCGCGCATAG AGCACATCGC CGCTACGCGA CCCGCTATTT ATGCGCTCGA

W  Y  Q  Q   K  P  G   Q  A  P  V   L  V  I   Y  D  D
 KpnI            XmaI     BbeI
~~~~~~          ~~~~~~~  ~~~~~~~
```

FIG. 4G

```
GGTACCAGCA GAAACCCGGG CAGGCGCCAG TTCTGGTGAT TTATGATGAT
CCATGGTCGT CTTTGGGCCC GTCCGCGGTC AAGACCACTA AATACTACTA

 S  D  R  P   S  G  I   P  E  R   F  S  G  S   N  S  G
           Bsu36I                          BamHI
           ~~~~~~~~                       ~~~~~~~~
TCTGACCGTC CCTCAGGCAT CCCGGAACGC TTTAGCGGAT CCAACAGCGG
AGACTGGCAG GGAGTCCGTA GGGCCTTGCG AAATCGCCTA GGTTGTCGCC

  N  T  A   T  L  T  I   S  G  T   Q  A  E   D  E  A
                                          BbsI
                                        ~~~~~~~~
```

FIG. 4H

```
CAACACCGCG ACCCTGACCA TTAGCGGCAC TCAGGCGGAA GACGAAGCGG
GTTGTGGCGC TGGGACTGGT AATCGCCGTG AGTCCGCCTT CTGCTTCGCC

D  Y  Y  C   Q  Q  H   Y  T  T  P   P  V  F   G  G  G
ATTATTATTG CCAGCAGCAT TATACCACCC CGCCTGTGTT TGGCGGCGGC
TAATAATAAC GGTCGTCGTA ATATGGTGGG GCGGACACAA ACCGCCGCCG

 T  K  L  T   V  L  G
     HpaI        MscI
    ~~~~~~~~     ~~~~
ACGAAGTTAA CCGTTCTTGG C
TGCTTCAATT GGCAAGAACC G
```

FIG. 4I

```
 Q   V   Q   L    V   Q   S    G   A   E    V   K   K   P    G   S   S
       MfeI
      ~~~~~~~~
CAGGTGCAAT TGGTTCAGTC TGGCGCGGAA GTGAAAAAAC CGGGCAGCAG
GTCCACGTTA ACCAAGTCAG ACCGCGCCTT CACTTTTTTG GCCCGTCGTC

  V   K   V    S   C   K   A    S   G   G    T   F   S    S   Y   A
                                  BspEI
                                 ~~~~~~~
CGTGAAAGTG AGCTGCAAAG CCTCCGGAGG CACTTTTAGC AGCTATGCGA
GCACTTTCAC TCGACGTTTC GGAGGCCTCC GTGAAAATCG TCGATACGCT

I   S   W   V    R   Q   A    P   G   Q   G    L   E   W    M   G   G
                       BstXI                   XhoI
                 ~~~~~~~~~~~~~~~              ~~~~~~~
TTAGCTGGGT GCGCCAAGCC CCTGGGCAGG GTCTCGAGTG GATGGCGGC
AATCGACCCA CGCGGTTCGG GGACCCGTCC CAGAGCTCAC CTACCCGCCG
```

FIG. 5A

```
 I  I  P  I   F  G  T   A  N  Y   A  Q  K  F   Q  G  R
ATTATTCCGA TTTTTGGCAC GGCGAACTAC GCGCAGAAGT TTCAGGGCCG
TAATAAGGCT AAAAACCGTG CCGCTTGATG CGCGTCTTCA AAGTCCCGGC

  V  T  I   T  A  D  E   S  T  S   T  A  Y   M  E  L
BstEII
~~~~~~~~
GGTGACCATT ACCGCGGATG AAAGCACCAG CACCGCGTAT ATGGAACTGA
CCACTGGTAA TGGCGCCTAC TTTCGTGGTC GTGGCGCATA TACCTTGACT

S  S  L  R   S  E  D   T  A  V  Y   Y  C  A   R  W  G
                        EagI            BssHII
                       ~~~~~~~          ~~~~~~~~
GCAGCCTGCG TAGCGAAGAT ACGGCCGTGT ATTATTGCGC GCGTTGGGGC
CGTCGGACGC ATCGCTTCTA TGCCGGCACA TAATAACGCG CGCAACCCCG
```

FIG. 5B

```
 G   D   G   F    Y   A   M    D   Y   W    G   Q   G   T    L   V   T
                                                  StyI
                                                 ~~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

  V   S   S
     BlpI
    ~~~~~~~
GGTTAGCTCA G
CCAATCGAGT C
```

FIG. 5C

```
 Q  V  Q  L   V  Q  S   G  A  E   V  K  K  P   G  A  S
    MfeI
   ~~~~~~~~
CAGGTGCAAT TGGTTCAGAG CGGCGCGGAA GTGAAAAAAC CGGGCGCGAG
GTCCACGTTA ACCAAGTCTC GCCGCGCCTT CACTTTTTTG GCCCGCGCTC

  V  K  V   S  C  K  A   S  G  Y   T  F  T   S  Y  Y
                          BspEI
                         ~~~~~~~
CGTGAAAGTG AGCTGCAAAG CCTCCGGATA TACCTTTACC AGCTATTATA
GCACTTTCAC TCGACGTTTC GGAGGCCTAT ATGGAAATGG TCGATAATAT

M  H  W  V   R  Q  A   P  G  Q  G   L  E  W   M  G  W
                 BstXI                XhoI
             ~~~~~~~~~~~~~~~        ~~~~~~~
TGCACTGGGT CCGCCAAGCC CCTGGGCAGG GTCTCGAGTG GATGGCTGG
ACGTGACCCA GGCGGTTCGG GGACCCGTCC CAGAGCTCAC CTACCCGACC
```

FIG. 5D

```
 I  N  P  N   S  G  G   T  N  Y   A  Q  K  F   Q  G  R
ATTAACCCGA ATAGCGGCGG CACGAACTAC GCGCAGAAGT TTCAGGGCCG
TAATTGGGCT TATCGCCGCC GTGCTTGATG CGCGTCTTCA AAGTCCCGGC

  V  T  M   T  R  D  T   S  I  S   T  A  Y   M  E  L
BstEII
~~~~~~~~
GGTGACCATG ACCCGTGATA CCAGCATTAG CACCGCGTAT ATGGAACTGA
CCACTGGTAC TGGGCACTAT GGTCGTAATC GTGGCGCATA TACCTTGACT

S  S  L  R   S  E  D   T  A  V  Y   Y  C  A   R  W  G
                        EagI             BssHII
                       ~~~~~~~           ~~~~~~~~
GCAGCCTGCG TAGCGAAGAT ACGGCCGTGT ATTATTGCGC GCGTTGGGGC
CGTCGGACGC ATCGCTTCTA TGCCGGCACA TAATAACGCG CGCAACCCCG
```

FIG. 5E

```
 G  D  G  F   Y  A  M   D  Y  W   G  Q  G  T   L  V  T
                                      StyI
                                     ~~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

  V  S  S
     BlpI
    ~~~~~~~
GGTTAGCTCA G
CCAATCGAGT C
```

FIG. 5F

```
 Q  V  Q  L   K  E  S   G  P  A   L  V  K  P   T  Q  T
      MfeI
     ~~~~~~~
CAGGTGCAAT TGAAAGAAAG CGGCCCGGCC CTGGTGAAAC CGACCCAAAC
GTCCACGTTA ACTTTCTTTC GCCGGGCCGG GACCACTTTG GCTGGGTTTG

  L  T  L   T  C  T  F   S  G  F   S  L  S   T  S  G
                         BspEI
                        ~~~~~~
CCTGACCCTG ACCTGTACCT TTTCCGGATT TAGCCTGTCC ACGTCTGGCG
GGACTGGGAC TGGACATGGA AAAGGCCTAA ATCGGACAGG TGCAGACCGC

V  G  V  G   W  I  R   Q  P  P  G   K  A  L   E  W  L
                         BstXI              XhoI
                     ~~~~~~~~~~~~~~      ~~~~~~~
TTGGCGTGGG CTGGATTCGC CAGCCGCCTG GGAAAGCCCT CGAGTGGCTG
AACCGCACCC GACCTAAGCG GTCGGCGGAC CCTTTCGGGA GCTCACCGAC
```

FIG. 5G

```
 A   L   I   D   W   D   D   D   K   Y   Y   S   T   S   L   K   T
                                                              MluI
                                                                ~~
GCTCTGATTG ATTGGGATGA TGATAAGTAT TATAGCACCA GCCTGAAAAC
CGAGACTAAC TAACCCTACT ACTATTCATA ATATCGTGGT CGGACTTTTG

  R   L   T   I   S   K   D   T   S   K   N   Q   V   V   L   T
MluI                            NspV
~~~~                          ~~~~~~~
GCGTCTGACC ATTAGCAAAG ATACTTCGAA AAATCAGGTG GTGCTGACTA
CGCAGACTGG TAATCGTTTC TATGAAGCTT TTTAGTCCAC CACGACTGAT

M   T   N   M   D   P   V   D   T   A   T   Y   Y   C   A   R   W
                                                 BssHII
                                                 ~~~~~~~~
TGACCAACAT GGACCCGGTG GATACGGCCA CCTATTATTG CGCGCGTTGG
ACTGGTTGTA CCTGGGCCAC CTATGCCGGT GGATAATAAC GCGCGCAACC
```

FIG. 5H

```
  G  G  D  G   F  Y  A   M  D  Y   W  G  Q  G   T  L  V
                                           StyI
                                         ~~~~~~~~
GGCGGCGATG GCTTTTATGC GATGGATTAT TGGGGCCAAG GCACCCTGGT
CCGCCGCTAC CGAAAATACG CTACCTAATA ACCCCGGTTC CGTGGGACCA

  T  V  S   S
         BlpI
        ~~~~~~~
GACGGTTAGC TCAG
CTGCCAATCG AGTC
```

FIG. 5I

```
 E  V  Q  L   V  E  S   G  G  G   L  V  Q  P   G  G  S
      MfeI
     ~~~~~~~~
GAAGTGCAAT TGGTGGAAAG CGGCGGCGGC CTGGTGCAAC CGGGCGGCAG
CTTCACGTTA ACCACCTTTC GCCGCCGCCG GACCACGTTG GCCCGCCGTC

  L  R  L   S  C  A  A   S  G  F   T  F  S   S  Y  A
                           BspEI
                          ~~~~~~~
CCTGCGTCTG AGCTGCGCGG CCTCCGGATT TACCTTTAGC AGCTATGCGA
GGACGCAGAC TCGACGCGCC GGAGGCCTAA ATGGAAATCG TCGATACGCT

M  S  W  V   R  Q  A   P  G  K  G   L  E  W   V  S  A
                  BstXI            XhoI
             ~~~~~~~~~~~~~~~      ~~~~~~~
TGAGCTGGGT GCGCCAAGCC CCTGGGAAGG GTCTCGAGTG GGTGAGCGCG
ACTCGACCCA CGCGGTTCGG GGACCCTTCC CAGAGCTCAC CCACTCGCGC
```

FIG. 5J

```
 I  S  G  S   G  G  S   T  Y  Y   A  D  S  V   K  G  R
ATTAGCGGTA GCGGCGGCAG CACCTATTAT GCGGATAGCG TGAAAGGCCG
TAATCGCCAT CGCCGCCGTC GTGGATAATA CGCCTATCGC ACTTTCCGGC

  F  T  I   S  R  D  N   S  K  N   T  L  Y   L  Q  M
             PmlI        NspV
            ~~~~~~~     ~~~~~~~
TTTTACCATT TCACGTGATA ATTCGAAAAA CACCCTGTAT CTGCAAATGA
AAAATGGTAA AGTGCACTAT TAAGCTTTTT GTGGGACATA GACGTTTACT

N  S  L  R   A  E  D   T  A  V  Y   Y  C  A   R  W  G
                         EagI             BssHII
                        ~~~~~~~          ~~~~~~~~
ACAGCCTGCG TGCGGAAGAT ACGGCCGTGT ATTATTGCGC GCGTTGGGGC
TGTCGGACGC ACGCCTTCTA TGCCGGCACA TAATAACGCG CGCAACCCCG
```

FIG. 5K

```
 G  D  G  F   Y  A  M   D  Y  W   G  Q  G  T   L  V  T
                                      StyI
                                     ~~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

 V  S  S
     BlpI
    ~~~~~~~
GGTTAGCTCA G
CCAATCGAGT C
```

FIG. 5L

```
 Q   V   Q   L    Q   E   S    G   P   G    L   V   K   P    S   E   T
       MfeI
      ~~~~~~~~
CAGGTGCAAT TGCAAGAAAG TGGTCCGGGC CTGGTGAAAC CGAGCGAAAC
GTCCACGTTA ACGTTCTTTC ACCAGGCCCG GACCACTTTG GCTCGCTTTG

  L   S   L    T   C   T   V    S   G   G    S   I   S    S   Y   Y
                               BspEI
                              ~~~~~~~
CCTGAGCCTG ACCTGCACCG TTTCCGGAGG CAGCATTAGC AGCTATTATT
GGACTCGGAC TGGACGTGGC AAAGGCCTCC GTCGTAATCG TCGATAATAA

W   S   W   I    R   Q   P    P   G   K   G    L   E   W    I   G   Y
                    BstXI                     XhoI

                 ~~~~~~~~~~~~~~          ~~~~~~
```

FIG. 5M

```
GGAGCTGGAT TCGCCAGCCG CCTGGGAAGG GTCTCGAGTG GATTGGCTAT
CCTCGACCTA AGCGGTCGGC GGACCCTTCC CAGAGCTCAC CTAACCGATA

 I  Y  Y  S   G  S  T   N  Y  N   P  S  L  K   S  R  V
                                                BstEII
                                                   ~~~
ATTTATTATA GCGGCAGCAC CAACTATAAT CCGAGCCTGA AAAGCCGGGT
TAAATAATAT CGCCGTCGTG GTTGATATTA GGCTCGGACT TTTCGGCCCA

  T  I  S   V  D  T  S   K  N  Q   F  S  L   K  L  S
BstEII              NspV
~~~~               ~~~~~~~~
GACCATTAGC GTTGATACTT CGAAAAACCA GTTTAGCCTG AAACTGAGCA
CTGGTAATCG CAACTATGAA GCTTTTTGGT CAAATCGGAC TTTGACTCGT

S  V  T  A   A  D  T   A  V  Y  Y   C  A  R   W  G  G
                    EagI              BssHII
                   ~~~~~~~~          ~~~~~~~
```

FIG. 5N

```
GCGTGACGGC GGCGGATACG GCCGTGTATT ATTGCGCGCG TTGGGGCGGC
CGCACTGCCG CCGCCTATGC CGGCACATAA TAACGCGCGC AACCCCGCCG

 D  G  F  Y   A  M  D   Y  W  G   Q  G  T  L   V  T  V
                                   StyI
                                 ~~~~~~~~
GATGGCTTTT ATGCGATGGA TTATTGGGGC CAAGGCACCC TGGTGACGGT
CTACCGAAAA TACGCTACCT AATAACCCCG GTTCCGTGGG ACCACTGCCA

  S  S
   BlpI
  ~~~~~~
TAGCTCAG
ATCGAGTC
```

FIG. 5O

```
 E  V  Q  L   V  Q  S   G  A  E   V  K  K  P   G  E  S
      MfeI
     ~~~~~~~~
GAAGTGCAAT TGGTTCAGAG CGGCGCGGAA GTGAAAAAAC CGGGCGAAAG
CTTCACGTTA ACCAAGTCTC GCCGCGCCTT CACTTTTTTG GCCCGCTTTC

  L  K  I   S  C  K  G   S  G  Y   S  F  T   S  Y  W
                          BspEI
                         ~~~~~~~
CCTGAAAATT AGCTGCAAAG GTTCCGGATA TTCCTTTACG AGCTATTGGA
GGACTTTTAA TCGACGTTTC CAAGGCCTAT AAGGAAATGC TCGATAACCT

I  G  W  V   R  Q  M   P  G  K  G   L  E  W   M  G  I
                 BstXI              XhoI
              ~~~~~~~~~~~~~~       ~~~~~~~
TTGGCTGGGT GCGCCAGATG CCTGGGAAGG GTCTCGAGTG GATGGGCATT
AACCGACCCA CGCGGTCTAC GGACCCTTCC CAGAGCTCAC CTACCCGTAA
```

FIG. 5P

```
 I  Y  P  G   D  S  D   T  R  Y   S  P  S  F   Q  G  Q
ATTTATCCGG GCGATAGCGA TACCCGTTAT TCTCCGAGCT TTCAGGGCCA
TAAATAGGCC CGCTATCGCT ATGGGCAATA AGAGGCTCGA AAGTCCCGGT

  V  T  I   S  A  D  K   S  I  S   T  A  Y   L  Q  W
BstEII
~~~~~~~
GGTGACCATT AGCGCGGATA AAAGCATTAG CACCGCGTAT CTTCAATGGA
CCACTGGTAA TCGCGCCTAT TTTCGTAATC GTGGCGCATA GAAGTTACCT

S  S  L  K   A  S  D   T  A  M  Y   Y  C  A   R  W  G
                                       BssHII
                                       ~~~~~~~
GCAGCCTGAA AGCGAGCGAT ACGGCCATGT ATTATTGCGC GCGTTGGGGC
CGTCGGACTT TCGCTCGCTA TGCCGGTACA TAATAACGCG CGCAACCCCG
```

FIG.5Q

```
 G  D  G  F   Y  A  M   D  Y  W   G  Q  G  T   L  V  T
                                      StyI
                                     ~~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

  V  S  S
     BlpI
    ~~~~~~~
GGTTAGCTCA G
CCAATCGAGT C
```

FIG.5R

```
 Q   V   Q   L    Q   Q   S    G   P   G    L   V   K   P    S   Q   T
      MfeI
     ~~~~~~~~
CAGGTGCAAT TGCAACAGTC TGGTCCGGGC CTGGTGAAAC CGAGCCAAAC
GTCCACGTTA ACGTTGTCAG ACCAGGCCCG GACCACTTTG GCTCGGTTTG

  L   S   L    T   C   A   I    S   G   D    S   V   S    S   N   S
                                BspEI
                               ~~~~~~~
CCTGAGCCTG ACCTGTGCGA TTTCCGGAGA TAGCGTGAGC AGCAACAGCG
GGACTCGGAC TGGACACGCT AAAGGCCTCT ATCGCACTCG TCGTTGTCGC

A   A   W   N    W   I   R    Q   S   P   G    R   G   L    E   W   L
                                BstXI              XhoI
                          ~~~~~~~~~~~~~~~~     ~~~~~~~~
CGGCGTGGAA CTGGATTCGC CAGTCTCCTG GGCGTGGCCT CGAGTGGCTG
GCCGCACCTT GACCTAAGCG GTCAGAGGAC CCGCACCGGA GCTCACCGAC
```

*FIG. 5S*

```
 G  R  T  Y   Y  R  S   K  W  Y   N  D  Y  A   V  S  V
GGCCGTACCT ATTATCGTAG CAAATGGTAT AACGATTATG CGGTGAGCGT
CCGGCATGGA TAATAGCATC GTTTACCATA TTGCTAATAC GCCACTCGCA

  K  S  R   I  T  I  N   P  D  T   S  K  N   Q  F  S
             BsaBI                 NspV
          ~~~~~~~~~~~~           ~~~~~~~
GAAAAGCCGG ATTACCATCA ACCCGGATAC TTCGAAAAAC CAGTTTAGCC
CTTTTCGGCC TAATGGTAGT TGGGCCTATG AAGCTTTTTG GTCAAATCGG

L  Q  L  N   S  V  T   P  E  D  T   A  V  Y   Y  C  A
                                   EagI          BssHII
                                 ~~~~~~~          ~~~~~
TGCAACTGAA CAGCGTGACC CCGGAAGATA CGGCCGTGTA TTATTGCGCG
ACGTTGACTT GTCGCACTGG GGCCTTCTAT GCCGGCACAT AATAACGCGC
```

FIG. 5T

```
 R  W  G  G   D  G  F   Y  A  M   D  Y  W  G   Q  G  T
BssHII                                        StyI
~                                            ~~~~~~~
CGTTGGGGCG GCGATGGCTT TTATGCGATG GATTATTGGG GCCAAGGCAC
GCAACCCCGC CGCTACCGAA AATACGCTAC CTAATAACCC CGGTTCCGTG

  L  V  T   V  S  S
              BlpI
             ~~~~~~~
CCTGGTGACG GTTAGCTCAG
GGACCACTGC CAATCGAGTC
```

FIG. 5U

O1K1 5'- GAATGCATACGCTGATATCCAGATGACCCAGAG-CCCGTCTAGCCTGAGC -3'

O1K2 5'- CGCTCTGCAGGTAATGGTCACACGATCACCCAC-GCTCGCGCTCAGGCTAGACGGGC -3'

O1K3 5'- GACCATTACCTGCAGAGCGAGCCAGGGCATTAG-CAGCTATCTGGCGTGGTACCAGCAG -3'

O1K4 5'- CTTTGCAAGCTGCTGGCTGCATAAATTAATAGT-TTCGGTGCTTTACCTGGTTTCTGCTGGTACCACGCCAG -3'

O1K5 5'- CAGCCAGCAGCTTGCAAAGCGGGGTCCCGTCCC-GTTTTAGCGGCTCTGGATCCGGCACTGATTTTAC -3'

O1K6 5'- GATAATAGGTCGCAAAGTCTTCAGGTTGCAGGC-TGCTAATGGTCAGGGTAAAATCAGTGCCGGATCC -3'

O2K1 5'- CGATATCGTGATGACCCAGAGCCCACTGAGCCT-GCCAGTGACTCCGGGCGAGCC -3'

O2K2 5'- GCCGTTGCTATGCAGCAGGCTTTGGCTGCTTCT-GCAGCTAATGCTCGCAGGCTCGCCCGGAGTCAC -3'

O2K3 5'- CTGCTGCATAGCAACGGCTATAACTATCTGGAT-TGGTACCTTCAAAAACCAGGTCAAAGCCC -3'

O2K4 5'- CGATCCGGGACCCCACTGGCACGGTTGCTGCCC-AGATAAATTAATAGCTGCGGGCTTTGACCTGGTTTTTG -3'

O2K5 5'- AGTGGGGTCCCGGATCGTTTTAGCGGCTCTGGA-TCCGGCACCGATTTTACCCTGAAAATTAGCCGTGTG -3'

O2K6 5'- CCATGCAATAATACACGCCCACGTCTTCAGCTT-CCACACGGCTAATTTTCAGGG -3'

O3K1 5'- GAATGCATACGCTGATATCGTGCTGACCCAGAG CCCGG -3'

O3K2 5'- CGCTCTGCAGCTCAGGGTCGCACGTTCGCCCGG-AGACAGGCTCAGGGTCGCCGGGCTCTGGGTCAGC -3'

O3K3 5'- CCCTGAGCTGCAGAGCGAGCCAGAGCGTGAGCA-GCAGCTATCTGGCGTGGTACCAG -3'

FIG. 6A

O3K4 5'- GCACGGCTGCTCGCGCCATAAATTAATAGACGC-GGTGCTTGACCTGGTTTCTGCTGGTACCACGCCAGATAG -3'

O3K5 5'- GCGCGAGCAGCCGTGCAACTGGGGTCCCGGCGC-GTTTTAGCGGCTCTGGATCCGGCACGGATTTTAC -3'

O3K6 5'- GATAATACACCGCAAAGTCTTCAGGTTCCAGGC-TGCTAATGGTCAGGGTAAAATCCGTGCCGGATC -3'

O4K1 5'- GAATGCATACGCTGATATCGTGATGACCCAGAG-CCCGGATAGCCTGGCG -3'

O4K2 5'- GCTTCTGCAGTTAATGGTCGCACGTTCGCCCAG-GCTCACCGCCAGGCTATCCGGGC -3'

O4K3 5'- CGACCATTAACTGCAGAAGCAGCCAGAGCGTGC-TGTATAGCAGCAACAACAAAAACTATCTGGCGTGGTACCAG

3'

O4K4 5'- GATGCCCAATAAATTAATAGTTTCGGCGGCTGA-CCTGGTTTCTGCTGGTACCACGCCAGATAG -3'

O4K5 5'- AAACTATTAATTTATTGGGCATCCACCCGTGAA-AGCGGGGTCCCGGATCGTTTTAGCGGCTCTGGATCCGGCAC-

3'

O4K6 5'- GATAATACACCGCCACGTCTTCAGCTTGCAGGG-ACGAAATGGTCAGGGTAAAATCAGTGCCGGATCCAGAGCC-

3'

O1L1 5'- GAATGCATACGCTCAGAGCGTGCTGACCCAGCC-GCCTTCAGTGAGTGG -3'

O1L2 5'- CAATGTTGCTGCTGCTGCCGCTACACGAGATGG-TCACACGCTGACCTGGTGCGCCACTCACTGAAGGCGGC -3'

O1L3 5'- GGCAGCAGCAGCAACATTGGCAGCAACTATGTG-AGCTGGTACCAGCAGTTGCCCGGGAC -3'

O1L4 5'- CCGGCACGCCTGAGGGACGCTGGTTGTTATCAT-AAATCAGCAGTTTCGGCGCCGTCCCGGGCAACTGC -3

O1L5 5'- CCCTCAGGCGTGCCGGATCGTTTTAGCGGATCC-AAAAGCGGCACCAGCGCGAGCCTTGCG -3'

*FIG. 6B*

O1L6 5'- CCGCTTCGTCTTCGCTTTGCAGGCCCGTAATCG-CAAGGCTCGCGCTGG -3'
O2L1 5'- GAATGCATACGCTCAGAGCGCACTGACCCAGCC-AGCTTCAGTGAGCGGC -3'
O2L2 5'- CGCTGCTAGTACCCGTACACGAGATGGTAATGC-TCTGACCTGGTGAGCCGCTCACTGAAGCTGG -3'
O2L3 5'- GTACGGGTACTAGCAGCGATGTGGGCGGCTATA-ACTATGTGAGCTGGTACCAGCAGCATCCCGG -3'
O2L4 5'- CGCCTGAGGGACGGTTGCTCACATCATAAATCA-TCAGTTTCGGCGCCTTCCCGGGATGCTGCTGGTAC -3'
O2L5 5'- CAACCGTCCCTCAGGCGTGAGCAACCGTTTTAG-CGGATCCAAAAGCGGCAACACCGCGAGCC -3'
O2L6 5'- CCGCTTCGTCTTCCGCTTGCAGGCCGCTAATGG-TCAGGCTCGCGGTGTTGCCG -3'
O3L1 5'- GAATGCATACGCTAGCTATGAACTGACCCAGCC-GCCTTCAGTGAGCG -3'
O3L2 5'- CGCCCAGCGCATCGCCGCTACACGAGATACGCG-CGGTCTGACCTGGTGCAACGCTCACTGAAGGCGGC -3'
O3L3 5'- GGCGATGCGCTGGGCGATAAATACGCGAGCTGG-TACCAGCAGAAACCCGGGCAGGCGC -3'
O3L4 5'- GCGTTCCGGGATGCCTGAGGGACGGTCAGAATC-ATCATAAATCACCAGAACTGGCGCCTGCCCGGGTTTC -3'
O3L5 5'- CAGGCATCCCGGAACGCTTTAGCGGATCCAACA-GCGGCAACACCGCGACCCTGACCATTAGCGG -3'
O3L6 5'- CCGCTTCGTCTTCCGCCTGAGTGCCGCTAATGG-TCAGGGTC -3'
O1246H1 5'- GCTCTTCACCCCTGTTACCAAAGCCCAG-GTGCAATTG -3'
O1AH2 5'- GGCTTTGCAGCTCACTTTCACGCTGCTGCCCGGT-TTTTTCACTTCCGCGCCAGACTGAACCAATTGCACCTGGGC-TTTG -3'

FIG. 6C

O1AH3 5'- GAAAGTGAGCTGCAAAGCCTCCGGAGGCACTTT-
TAGCAGCTATGCGATTAGCTGGGTGCGCCAAGCCCCTGGGCAG
GGTC -3'
O1AH4 5'- GCCCTGAAACTTCTGCGCGTAGTTCGCCGTGCCA-
AAAATCGGAATAATGCCGCCCATCCACTCGAGACCCTGCCC-
AGGGGC -3'
O1AH5 5'- GCGCAGAAGTTTCAGGGCCGGGTGACCATTACC-
GCGGATGAAAGCACCAGCACCGCGTATATGGAACTGAGCAGCC
TGCG -3'
O1ABH6 5'- GCGCGCAATAATACACGGCCGTATCTTCGCT-
ACGCAGGCTGCTCAGTTCC -3'
O1BH2 5'- GGCTTTGCAGCTCACTTTCACGCTCGCGCCCGGT-
TTTTTCACTTCCGCGCCGCTCTGAACCAATTGCACCTGGGC-
TTTG -3'
O1BH3 5'- GAAAGTGAGCTGCAAAGCCTCCGGATATACCTT-
TACCAGCTATTATATGCACTGGGTCCGCCAAGCCCCTGGGCAG
GGTC -3'
O1BH4 5'- GCCCTGAAACTTCTGCGCGTAGTTCGTGCCGCC-
GCTATTCGGGTTAATCCAGCCCATCCACTCGAGACCCTGCCCA
GGGGC -3'
O1BH5 5'- GCGCAGAAGTTTCAGGGCCGGGTGACCATGACC-
CGTGATACCAGCATTAGCACCGCGTATATGGAACTGAGCAGCC
TGCG -3'
O2H2 5'- GGTACAGGTCAGGGTCAGGGTTTGGGTCGGTTT-
CACCAGGGCCGGGCCGCTTTCTTTCAATTGCACCTGGGCTTTG
-3'
O2H3 5'- CTGACCCTGACCTGTACCTTTTCCGGATTTAGC-
CTGTCCACGTCTGGCGTTGGCGTGGGCTGGATTCGCCAGCCGC
CTGGGAAAG -3
O2H4 5'- GCGTTTTCAGGCTGGTGCTATAATACTTATCAT-
CATCCCAATCAATCAGAGCCAGCCACTCGAGGGCTTTCCCAGG
CGGCTGG -3'

*FIG. 6D*

O2H5 5'- GCACCAGCCTGAAAACGCGTCTGACCATTAGCA-
AAGATACTTCGAAAAATCAGGTGGTGCTGACTATGACCAACAT
GG -3'
O2H6 5'- GCGCGCAATAATAGGTGGCCGTATCCACCGGGT-
CCATGTTGGTCATAGTCAGC -3'
O3H1 5'- CGAAGTGCAATTGGTGGAAAGCGGCGGCGGCCT-
GGTGCAACCGGGCGGCAG -3'
O3H2 5'- CATAGCTGCTAAAGGTAAATCCGGAGGCCGCGC-
AGCTCAGACGCAGGCTGCCGCCCGGTTGCAC -3'
O3H3 5'- GATTTACCTTTAGCAGCTATGCGATGAGCTGGG-
TGCGCCAAGCCCCTGGGAAGGGTCTCGAGTGGGTGAG -3'
O3H4 5'- GGCCTTTCACGCTATCCGCATAATAGGTGCTGC-
CGCCGCTACCGCTAATCGCGCTCACCCACTCGAGACCC -3'
O3H5 5'- CGGATAGCGTGAAAGGCCGTTTTACCATTTCAC-
GTGATAATTCGAAAAACACCCTGTATCTGCAAATGAACAG-3'
O3H6 5'- CACGCGCGCAATAATACACGGCCGTATCTTCCG-
CACGCAGGCTGTTCATTTGCAGATACAGG -3'
O4H2 5'- GGTCAGGCTCAGGGTTTCGCTCGGTTTCACCAG-
GCCCGGACCACTTTCTTGCAATTGCACCTGGGCTTTG -3'
O4H3 5'- GAAACCCTGAGCCTGACCTGCACCGTTTCCGGAGG-
CAGCATTAGCAGCTATTATTGGAGCTGGATTCGCCAGCCGC
-3'
O4H4 5'- GATTATAGTTGGTGCTGCCGCTATAATAAATAT-
AGCCAATCCACTCGAGACCCTTCCCAGGCGGCTGGCGAATCCA
G -3'
O4H5 5'- CGGCAGCACCAACTATAATCCGAGCCTGAAAAG-
CCGGGTGACCATTAGCGTTGATACTTCGAAAAACCAGTTTAGC
CTG -3'
O4H6 5'- GCGCGCAATAATACACGGCCGTATCCGCCGCCG-
TCACGCTGCTCAGTTTCAGGCTAAACTGGTTTTTCG -3'

*FIG. 6E*

O5H1 5'- GCTCTTCACCCCTGTTACCAAAGCCGAAGTGCA
ATTG -3'
O5H2 5'- CCTTTGCAGCTAATTTTCAGGCTTTCGCCCGGT-
TTTTTCACTTCCGCGCCGCTCTGAACCAATTGCACTTCGGCTT
TGG -3'
O5H3 5'- CCTGAAAATTAGCTGCAAAGGTTCCGGATATTC-
CTTTACGAGCTATTGGATTGGCTGGGTGCGCCAGATGCCTGG
-3'
O5H4 5'- CGGAGAATAACGGGTATCGCTATCGCCCGGATA-
AATAATGCCCATCCACTCGAGACCCTTCCCAGGCATCTGGCGC
AC -3'
O5H5 5'- CGATACCCGTTATTCTCCGAGCTTTCAGGGCCA-
GGTGACCATTAGCGCGGATAAAAGCATTAGCACCGCGTATCTT
C -3'
O5H6 5'- GCGCGCAATAATACATGGCCGTATCGCTCGCTT-
TCAGGCTGCTCCATTGAAGATACGCGGTGCTAATG -3'
O6H2 5'- GAAATCGCACAGGTCAGGCTCAGGGTTTGGCTC-
GGTTTCACCAGGCCCGGACCAGACTGTTGCAATTGCACCTGG-
GCTTTG -3'
O6H3 5'- GCCTGACCTGTGCGATTTCCGGAGATAGCGTGA-
GCAGCAACAGCGCGGCGTGGAACTGGATTCGCCAGTCTCCTGG
GCG -3'
O6H4 5'- CACCGCATAATCGTTATACCATTTGCTACGATA-
ATAGGTACGGCCCAGCCACTCGAGGCCACGCCCAGGAGACTG
GCG -3'
O6H5 5'- GGTATAACGATTATGCGGTGAGCGTGAAAAGCC-
GGATTACCATCAACCCGGATACTTCGAAAAACCAGTTTAGCCT
GC -3'
O6H6 5'- GCGCGCAATAATACACGGCCGTATCTTCCGGGG-
TCACGCTGTTCAGTTGCAGGCTAAACTGGTTTTTC -3'
OCLK1 5'- GGCTGAAGACGTGGGCGTGTATTATTGCCAGCA-
GCATTATACCACCCCGCCGACCTTTGGCCAGGGTAC -3'

*FIG. 6F*

OCLK2 5'- GCGAAAAATAAACACGCTCGGAGCAGCCACCG-
TACGTTTAATTTCAACTTTCGTACCCTGGCCAAAGGTC -3'
OCLK3 5'- GAGCGTGTTTATTTTTCCGCCGAGCGATGAACA-
ACTGAAAAGCGGCACGGCGAGCGTGGTGTGCCTGCTG -3'
OCLK4 5'- CAGCGCGTTGTCTACTTTCCACTGAACTTTCGC-
TTCACGCGGATAAAAGTTGTTCAGCAGGCACACCACGC -3'
OCLK5 5'- GAAAGTAGACAACGCGCTGCAAAGCGGCAACAG-
CCAGGAAAGCGTGACCGAACAGGATAGCAAAGATAG -3'
OCLK6 5'- GTTTTTCATAATCCGCTTTGCTCAGGGTCAGGG-
TGCTGCTCAGAGAATAGGTGCTATCTTTGCTATCCTGTTCG -
3'
OCLK7 5'- GCAAAGCGGATTATGAAAAACATAAAGTGTATG-
CGTGCGAAGTGACCCATCAAGGTCTGAGCAGCCCGGTG -3'
OCLK8 5'- GGCATGCTTATCAGGCCTCGCCACGATTAAAAG-
ATTTAGTCACCGGGCTGCTCAGAC -3'
OCH1 5'- GGCGTCTAGAGGCCAAGGCACCCTGGTGACGGT-
TAGCTCAGCGTCGAC -3'
OCH2 5'- GTGCTTTTGCTGCTCGGAGCCAGCGGAAACACG-
CTTGGACCTTTGGTCGACGCTGAGCTAACC -3'
OCH3 5'- CTCCGAGCAGCAAAAGCACCAGCGGCGGCACGG-
CTGCCCTGGGCTGCCTGGTTAAAGATTATTTCC -3'
OCH4 5'- CTGGTCAGCGCCCCGCTGTTCCAGCTCACGGTG-
ACTGGTTCCGGGAAATAATCTTTAACCAGGCA -3'
OCH5 5'- AGCGGGGCGCTGACCAGCGGCGTGCATACCTTT-
CCGGCGGTGCTGCAAAGCAGCGGCCTG -3'
OCH6 5'- GTGCCTAAGCTGCTGCTCGGCACGGTCACAACG-
CTGCTCAGGCTATACAGGCCGCTGCTTTGCAG -3'
OCH7 5'- GAGCAGCAGCTTAGGCACTCAGACCTATATTTG-
CAACGTGAACCATAAACCGAGCAACACC -3'
OCH8 5'- GCGCGAATTCGCTTTTCGGTTCCACTTTTTTAT-
CCACTTTGGTGTTGCTCGGTTTATGG -3'

*FIG. 6G*

```
          V  A   A  P  S   V  F  I   F  P  P  S   D  E  Q
  BsiWI
~~~~~~
CGTACGGTGG CTGCTCCGAG CGTGTTTATT TTTCCGCCGA GCGATGAACA
GCATGCCACC GACGAGGCTC GCACAAATAA AAAGGCGGCT CGCTACTTGT

  L  K  S   G  T  A  S   V  V  C   L  L  N   N  F  Y
ACTGAAAAGC GGCACGGCGA GCGTGGTGTG CCTGCTGAAC AACTTTTATC
TGACTTTTCG CCGTGCCGCT CGCACCACAC GGACGACTTG TTGAAAATAG

P  R  E  A   K  V  Q   W  K  V  D   N  A  L   Q  S  G
CGCGTGAAGC GAAAGTTCAG TGGAAAGTAG ACAACGCGCT GCAAAGCGGC
GCGCACTTCG CTTTCAAGTC ACCTTTCATC TGTTGCGCGA CGTTTCGCCG

 N  S  Q  E   S  V  T   E  Q  D   S  K  D  S   T  Y  S
AACAGCCAGG AAAGCGTGAC CGAACAGGAT AGCAAAGATA GCACCTATTC
TTGTCGGTCC TTTCGCACTG GCTTGTCCTA TCGTTTCTAT CGTGGATAAG
```

FIG. 7A

```
L  S  S   T  L  T  L   S  K  A   D  Y  E   K  H  K
TCTGAGCAGC ACCCTGACCC TGAGCAAAGC GGATTATGAA AAACATAAAG
AGACTCGTCG TGGGACTGGG ACTCGTTTCG CCTAATACTT TTTGTATTTC

V  Y  A  C   E  V  T   H  Q  G  L   S  S  P   V  T  K
TGTATGCGTG CGAAGTGACC CATCAAGGTC TGAGCAGCCC GGTGACTAAA
ACATACGCAC GCTTCACTGG GTAGTTCCAG ACTCGTCGGG CCACTGATTT

 S  F  N  R   G  E  A   *
                 StuI         SphI
                ~~~~~~~~     ~~~~~~
TCTTTTAATC GTGGCGAGGC CTGATAAGCA TGC
AGAAAATTAG CACCGCTCCG GACTATTCGT ACG
```

FIG. 7B

```
     A  S   T  K  G   P  S  V  F   P  L  A   P  S  S
 BlpI   SalI
~~~~~~~~~~~~~~~~
GCTCAGCGTC GACCAAAGGT CCAAGCGTGT TTCCGCTGGC TCCGAGCAGC
CGAGTCGCAG CTGGTTTCCA GGTTCGCACA AAGGCGACCG AGGCTCGTCG

 K  S  T  S   G  G  T   A  A  L   G  C  L  V   K  D  Y
AAAAGCACCA GCGGCGGCAC GGCTGCCCTG GGCTGCCTGG TTAAAGATTA
TTTTCGTGGT CGCCGCCGTG CCGACGGGAC CCGACGGACC AATTTCTAAT

  F  P  E   P  V  T  V   S  W  N   S  G  A   L  T  S
TTTCCCGGAA CCAGTCACCG TGAGCTGGAA CAGCGGGGCG CTGACCAGCG
AAAGGGCCTT GGTCAGTGGC ACTCGACCTT GTCGCCCCGC GACTGGTCGC

G  V  H  T   F  P  A   V  L  Q  S   S  G  L   Y  S  L
GCGTGCATAC CTTTCCGGCG GTGCTGCAAA GCAGCGGCCT GTATAGCCTG
CGCACGTATG GAAAGGCCGC CACGACGTTT CGTCGCCGGA CATATCGGAC
```

FIG. 7C

```
 S  S  V  V   T  V  P   S  S  S   L  G  T  Q   T  Y  I
AGCAGCGTTG TGACCGTGCC GAGCAGCAGC TTAGGCACTC AGACCTATAT
TCGTCGCAAC ACTGGCACGG CTCGTCGTCG AATCCGTGAG TCTGGATATA

  C  N  V   N  H  K  P   S  N  T   K  V  D   K  K  V
TTGCAACGTG AACCATAAAC CGAGCAACAC CAAAGTGGAT AAAAAAGTGG
AACGTTGCAC TTGGTATTTG GCTCGTTGTG GTTTCACCTA TTTTTTCACC

E  P  K  S   E  F  *
             EcoRI    HindIII
            ~~~~~~~    ~~~~~~
AACCGAAAAG CGAATTCTGA TAAGCTT
TTGGCTTTTC GCTTAAGACT ATTCGAA
```

FIG. 7D

```
      BbsI
     ~~~~~~~
  1  GAAGACGAAG CGGATTATTA TTGCCAGCAG CATTATACCA CCCCGCCTGT
     CTTCTGCTTC GCCTAATAAT AACGGTCGTC GTAATATGGT GGGGCGGACA

                          HpaI          MscI             DraIII
                        ~~~~~~~~      ~~~~~~~              ~~~
 51  GTTTGGCGGC GGCACGAAGT TAACCGTTCT TGGCCAGCCG AAAGCCGCAC
     CAAACCGCCG CCGTGCTTCA ATTGGCAAGA ACCGGTCGGC TTTCGGCGTG

     DraIII
     ~~~~~~~
101  CGAGTGTGAC GCTGTTTCCG CCGAGCAGCG AAGAATTGCA GGCGAACAAA
     GCTCACACTG CGACAAAGGC GGCTCGTCGC TTCTTAACGT CCGCTTGTTT

151  GCGACCCTGG TGTGCCTGAT TAGCGACTTT TATCCGGGAG CCGTGACAGT
     CGCTGGGACC ACACGGACTA ATCGCTGAAA ATAGGCCCTC GGCACTGTCA
```

FIG. 7F

```
201   GGCCTGGAAG GCAGATAGCA GCCCCGTCAA GGCGGGAGTG GAGACCACCA
      CCGGACCTTC CGTCTATCGT CGGGGCAGTT CCGCCCTCAC CTCTGGTGGT

251   CACCCTCCAA ACAAAGCAAC AACAAGTACG CGGCCAGCAG CTATCTGAGC
      GTGGGAGGTT TGTTTCGTTG TTGTTCATGC GCCGGTCGTC GATAGACTCG

                               RleAI
                              ~~~~~~~
301   CTGACGCCTG AGCAGTGGAA GTCCCACAGA AGCTACAGCT GCCAGGTCAC
      GACTGCGGAC TCGTCACCTT CAGGGTGTCT TCGATGTCGA CGGTCCAGTG

                                                   StuI
                                                  ~~~~~~
```

FIG. 7G

```
351   GCATGAGGGG AGCACCGTGG AAAAAACCGT TGCGCCGACT GAGGCCTGAT
      CGTACTCCCC TCGTGGCACC TTTTTTGGCA ACGCGGCTGA CTCCGGACTA

         SphI
       ~~~~~~
401   AAGCATGC
      TTCGTACG
```

FIG. 7H

M24: assembly PCR

M24-A:

GAAGACAAGCGGATTATTATTGCCAGCAGCATTATACCACCCCGCCTGTGTTTGGCGGCG-
GCACGAAGTTAACCGTTC

M24-B:

CAATTCTTCGCTGCTCGGCGGAAACAGCGTCACACTCGGTGCGGCTTTCGGCTGGCCAA-
GAACGGTTAACTTCGTGCCGC

M24-C:

CGCCGAGCAGCGAAGAATTGCAGGCGAACAAAGCGACCCTGGTGTGCCTGATTAGCGACT-
TTTATCCGGGAGCCGTGACA

*FIG. 7I*

M24-D:

TGTTTGGAGGGTGTGGTGGTCTCCACTCCCGCCTTGACGGGGCTGCTATCTGCCTTCCAG-
GCCACTGTCACGGCTCCCGG

M24-E:

CCACACCCTCCAAACAAAGCAACAACAAGTACGCGGCCAGCAGCTATCTGAGCCTGACGC-
CTGAGCAGTGGAAGTCCCACAGAAGCTACAGCTG

M24-F:

GCATGCTTATCAGGCCTCAGTCGGCGCAACGGTTTTTCCACGGTGCTCCCCTCATGCGT-
GACCTGGCAGCTGTAGCTTC

*FIG. 7J*

```
 M  K  Q  S   T  I  A   L  A  L   L  P  L  L   F  T  P
                                          SapI
                                        ~~~~~~~~~
ATGAAACAAA GCACTATTGC ACTGGCACTC TTACCGTTGC TCTTCACCCC
TACTTTGTTT CGTGATAACG TGACCGTGAG AATGGCAACG AGAAGTGGGG

  V  T  K   A  D  Y  K   D  E  V   Q  L  V   E  S  G
                                   MfeI
                                  ~~~~~~~
TGTTACCAAA GCCGACTACA AAGATGAAGT GCAATTGGTG GAAAGCGGCG
ACAATGGTTT CGGCTGATGT TTCTACTTCA CGTTAACCAC CTTTCGCCGC

G  G  L  V   Q  P  G   G  S  L  R   L  S  C   A  A  S
                                                 BspEI
                                                   ~~~
GCGGCCTGGT GCAACCGGGC GGCAGCCTGC GTCTGAGCTG CGCGGCCTCC
CGCCGGACCA CGTTGGCCCG CCGTCGGACG CAGACTCGAC GCGCCGGAGG

 G  F  T  F   S  S  Y   A  M  S   W  V  R  Q   A  P  G
BspEI                                         BstXI
~~~                                     ~~~~~~~~~~~~~~
GGATTTACCT TTAGCAGCTA TGCGATGAGC TGGGTGCGCC AAGCCCCTGG

CCTAAATGGA AATCGTCGAT ACGCTACTCG ACCCACGCGG TTCGGGGACC
```

*FIG. 8A*

```
K  G  L   E  W  V  S   A  I  S   G  S  G   G  S  T
       XhoI
      ~~~~~~~~
GAAGGGTCTC GAGTGGGTGA GCGCGATTAG CGGTAGCGGC GGCAGCACCT
CTTCCCAGAG CTCACCCACT CGCGCTAATC GCCATCGCCG CCGTCGTGGA

Y  Y  A  D   S  V  K   G  R  F  T   I  S  R   D  N  S
                                      PmlI       NspV
                                     ~~~~~~~~    ~~~~
ATTATGCGGA TAGCGTGAAA GGCCGTTTTA CCATTTCACG TGATAATTCG
TAATACGCCT ATCGCACTTT CCGGCAAAAT GGTAAAGTGC ACTATTAAGC

 K  N  T  L   Y  L  Q   M  N  S   L  R  A  E   D  T  A
NspV                                              EagI
~~                                                ~~~~
AAAAACACCC TGTATCTGCA AATGAACAGC CTGCGTGCGG AAGATACGGC
TTTTTGTGGG ACATAGACGT TTACTTGTCG GACGCACGCC TTCTATGCCG

  V  Y  Y   C  A  R  W   G  G  D   G  F  Y   A  M  D
EagI        BssHII
~~          ~~~~~~~
CGTGTATTAT TGCGCGCGTT GGGGCGGCGA TGGCTTTTAT GCGATGGATT
```

FIG. 8B

```
GCACATAATAACGCGCGCAA CCCCGCCGCT ACCGAAAATA CGCTACCTAA
Y  W  G  Q   G  T  L   V  T  V  S   S  A  G   G  G  S
        StyI                          BlpI
       ~~~~~~~~                      ~~~~~~~~
ATTGGGGCCA AGGCACCCTG GTGACGGTTA GCTCAGCGGG TGGCGGTTCT
TAACCCCGGT TCCGTGGGAC CACTGCCAAT CGAGTCGCCC ACCGCCAAGA

 G  G  G  G   S  G  G   G  G  S   G  G  G  G   S  D  I
                                                 EcoRV
                                                 ~~~~~
GGCGGCGGTG GGAGCGGTGG CGGTGGTTCT GGCGGTGGTG GTTCCGATAT
CCGCCGCCAC CCTCGCCACC GCCACCAAGA CCGCCACCAC CAAGGCTATA

  V  M  T   Q  S  P  L   S  L  P   V  T  P   G  E  P
EcoRV          BanII
~             ~~~~~~~
CGTGATGACC CAGAGCCCAC TGAGCCTGCC AGTGACTCCG GGCGAGCCTG
GCACTACTGG GTCTCGGGTG ACTCGGACGG TCACTGAGGC CCGCTCGGAC

A  S  I  S   C  R  S   S  Q  S  L   L  H  S   N  G  Y
            PstI
           ~~~~~~~
CGAGCATTAG CTGCAGAAGC AGCCAAAGCC TGCTGCATAG CAACGGCTAT
GCTCGTAATC GACGTCTTCG TCGGTTTCGG ACGACGTATC GTTGCCGATA
```

*FIG. 8C*

```
N  Y  L  D   W  Y  L   Q  K  P   G  Q  S  P   Q  L  L
              KpnI           SexAI                AseI
             ~~~~~~~        ~~~~~~~~~              ~~~
AACTATCTGG ATTGGTACCT TCAAAAACCA GGTCAAAGCC CGCAGCTATT
TTGATAGACC TAACCATGGA AGTTTTTGGT CCAGTTTCGG GCGTCGATAA

  I  Y  L   G  S  N  R   A  S  G   V  P  D   R  F  S
AseI                          Eco0109I
~~~                             ~~~~~~~~~
AATTTATCTG GGCAGCAACC GTGCCAGTGG GGTCCCGGAT CGTTTTAGCG
TTAAATAGAC CCGTCGTTGG CACGGTCACC CCAGGGCCTA GCAAAATCGC

G  S  G  S   G  T  D   F  T  L  K   I  S  R   V  E  A
      BamHI
     ~~~~~~~~
GCTCTGGATC CGGCACCGAT TTTACCCTGA AAATTAGCCG TGTGGAAGCT
CGAGACCTAG GCCGTGGCTA AAATGGGACT TTTAATCGGC ACACCTTCGA

 E  D  V  G   V  Y  Y   C  Q  Q   H  Y  T  T   P  P  T
 BbsI
~~~~~~~
GAAGACGTGG GCGTGTATTA TTGCCAGCAG CATTATACCA CCCCGCCGAC
CTTCTGCACC CGCACATAAT AACGGTCGTC GTAATATGGT GGGGCGGCTG
```

FIG. 8D

```
F   G   Q    G   T   K   V    E   I   K    R   T   E    F
    MscI                                   BsiWI EcoRI
   ~~~~~~~                                 ~~~~~~~~~~~~~
CTTTGGCCAG GGTACGAAAG TTGAAATTAA ACGTACGGAA TTC
GAAACCGGTC CCATGCTTTC AACTTTAATT TGCATGCCTT AAG
```

FIG. 8E

| | 92 | 93 | 94 | 95 | 96 | 97 | 98 | 99 | 100 | 100A | 100B | 100C | 100D | 100E | 101 | 102 | 103 |
|---|---|---|---|---|---|---|---|---|---|---|---|---|---|---|---|---|---|
| A | C | A | R | W | G | G | D | G | F | Y | A | - | - | M | D | Y | W |
| B | C | A | R | F | G | K | M | N | Y | - | - | - | - | - | D | Y | W |
| | C | A | R | H | R | T | E | W | H | - | - | - | - | - | D | Y | W |
| | C | A | R | V | R | E | L | Y | H | - | - | - | - | - | D | Y | W |
| | C | A | R | K | F | L | K | A | R | - | - | - | - | - | D | Y | W |
| | C | A | R | W | N | T | T | G | Y | - | - | - | - | - | D | Y | W |
| | C | A | R | I | N | E | A | Q | P | - | - | - | - | - | D | Y | W |
| | C | A | R | T | A | I | T | R | - | - | - | - | - | - | D | Y | W |
| | C | A | R | W | Y | N | R | N | S | - | - | - | - | - | D | Y | W |
| | C | A | R | S | V | G | D | S | K | - | - | - | - | - | D | Y | W |
| | C | A | R | S | K | T | F | A | A | - | - | - | - | - | D | Y | W |
| | C | A | R | V | A | P | Q | Y | D | - | - | - | - | - | D | Y | W |
| | C | A | R | M | Q | S | E | W | M | - | - | - | - | - | D | Y | W |

FIG. 10A

| | | | | | | | | | | | | | | | | | |
|---|---|---|---|---|---|---|---|---|---|---|---|---|---|---|---|---|---|
| C | C | A | R | Y | F | V | H | F | L | Y | T | M | V | M | D | V | W |
| | C | A | R | M | A | L | R | A | S | G | K | Y | I | M | D | V | W |
| | C | A | R | K | N | Q | M | V | F | H | A | R | K | F | D | V | W |
| | C | A | R | T | Q | S | F | W | E | Q | Q | K | V | M | D | Y | W |
| | C | A | R | Y | P | Y | R | S | N | F | F | M | P | M | D | V | W |
| | C | A | R | * | G | S | G | S | E | H | W | S | I | F | D | V | W |
| | C | A | R | R | N | P | W | N | V | N | Y | L | H | F | D | V | W |
| | C | A | R | M | K | P | M | L | N | R | D | G | T | M | D | V | W |
| | C | A | R | K | G | S | E | F | L | E | T | D | V | M | D | Y | W |
| | C | A | R | S | W | T | N | D | K | P | N | F | I | M | D | V | W |
| | C | A | R | Y | A | G | T | T | F | K | Q | G | P | M | D | Y | W |

FIG. 10B

A
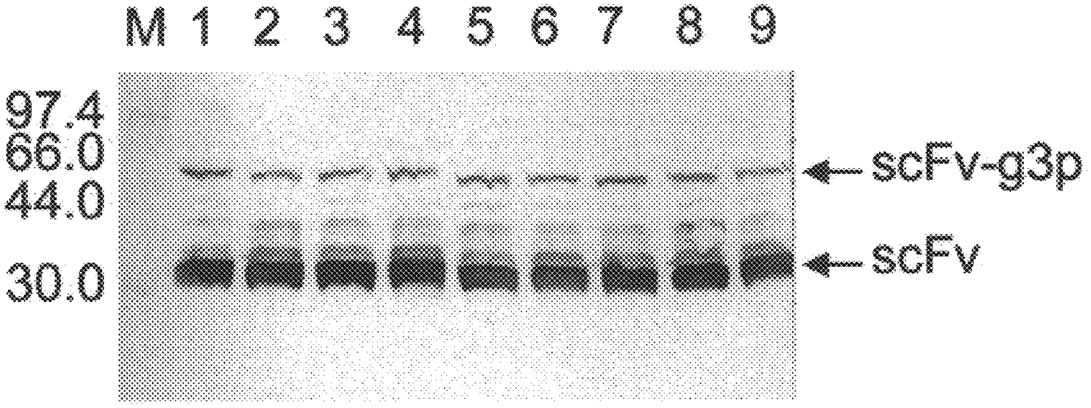
B
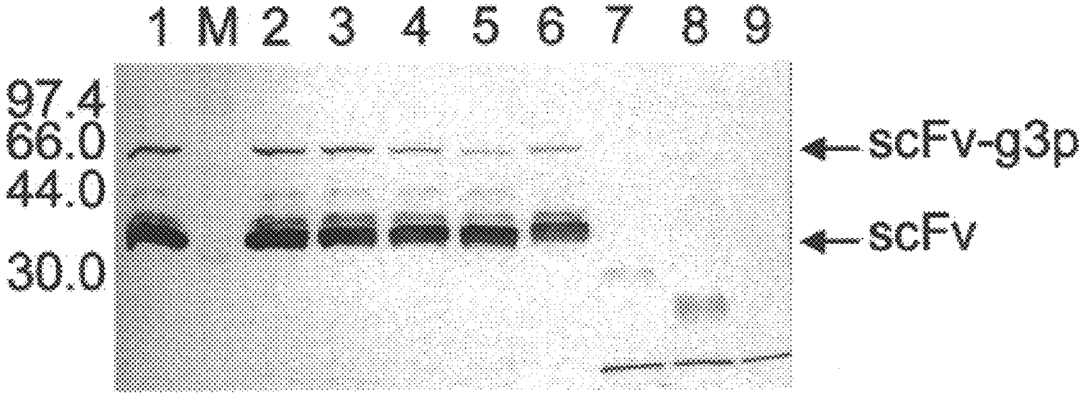
*FIG. 11*

| 92 | 93 | 94 | 95 | 96 | 97 | 98 | 99 | 100 | 100A | 100B | 100C | 100D | 100E | 101 | 102 | 103 | Frequency |
|---|---|---|---|---|---|---|---|---|---|---|---|---|---|---|---|---|---|
| C | A | R | K | R | M | M | Q | N | P | R | F | R | F | D | V | W | 1 |
| C | A | R | R | S | K | Q | K | R | K | M | R | R | F | D | V | W | 3 |
| C | A | R | R | N | G | K | R | H | L | R | H | R | F | D | V | W | 1 |
| C | A | R | R | K | M | R | K | R | I | K | R | R | F | D | V | W | 2 |
| C | A | R | Y | R | K | I | M | K | W | K | N | S | F | D | V | W | 1 |
| C | A | R | L | I | E | V | H | P | S | F | D | Q | M | D | V | W | 1 |
| C | A | R | R | K | P | M | F | L | K | K | A | V | F | D | V | W | 1 |
| C | A | R | R | K | F | H | R | Y | S | T | V | K | F | D | Y | W | 2 |
| C | A | R | R | K | T | M | R | S | R | V | K | Y | F | D | Y | W | 1 |
| C | A | R | K | K | R | S | W | R | R | M | D | R | F | D | V | W | 1 |
| C | A | R | R | N | P | R | R | G | R | M | N | R | F | D | V | W | 1 |
| C | A | R | K | G | K | K | K | F | A | R | P | R | F | D | V | W | 1 |
| C | A | R | R | M | V | H | K | G | K | R | K | I | F | D | V | W | 1 |
| C | A | R | R | K | H | I | T | Y | P | R | K | Q | F | D | V | W | 1 |
| C | A | R | R | W | T | K | R | R | S | F | A | R | F | D | V | W | 1 |
| C | A | R | K | K | L | K | Q | Y | T | F | S | R | F | D | Y | W | 1 |

FIG. 15

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | T | R | P | W | Q | A | T | R | K | G | F | D | V | W | 3 |
| C | A | R | N | Q | W | E | F | K | N | R | R | K | M | D | Y | W | 8 |
| C | A | R | K | R | W | M | W | P | I | G | K | R | F | D | Y | W | 7 |
| C | A | R | Y | S | L | W | R | L | D | E | Y | F | F | D | Y | W | 1 |
| C | A | R | V | P | W | G | D | F | W | S | W | H | M | D | V | W | 1 |
| C | A | R | N | G | L | E | P | R | H | R | K | M | M | D | Y | W | 1 |
| C | A | R | I | M | K | A | P | P | - | - | - | - | - | D | Y | W | 1 |
| C | A | R | R | K | T | W | H | W | F | Y | K | R | M | D | Y | W | 1 |
| C | A | R | W | K | D | M | W | S | Q | V | Y | V | M | D | Y | W | 1 |
| C | A | R | N | K | Q | Q | M | R | F | R | R | F | M | D | Y | W | 5 |
| C | A | R | N | M | L | A | L | S | R | G | K | E | M | D | V | W | 4 |
| C | A | R | N | M | R | L | M | R | M | R | K | N | F | D | V | W | 1 |

FIG. 20

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | Y | I | K | Q | A | K | R | K | L | A | F | D | Y | W | 4 |
| C | A | R | Y | N | R | H | A | W | Q | K | M | Q | F | D | Y | W | 3 |
| C | A | R | Y | V | K | Y | A | R | N | K | M | Q | F | D | Y | W | 2 |
| C | A | R | Y | K | R | G | A | W | M | K | T | M | F | D | V | W | 1 |
| C | A | R | R | K | P | L | R | R | I | M | K | W | F | D | Y | W | 1 |
| C | A | R | Y | R | K | R | A | S | R | Q | M | Q | F | D | Y | W | 1 |

FIG. 21

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | Q | R | Y | R | S | K | I | K | G | H | F | D | V | W | 16 |
| C | A | R | _ | W | R | D | F | N | S | Y | D | P | M | D | Y | W | 1 |
| C | A | R | M | A | D | L | D | N | Y | W | V | Q | F | D | Y | W | 1 |
| C | A | R | L | Q | A | Y | L | K | P | H | H | W | M | D | Y | W | 1 |
| C | A | R | R | L | I | E | Q | A | R | D | H | V | M | D | Y | W | 1 |
| C | A | R | S | W | H | N | S | Q | F | T | Q | S | F | D | V | W | 1 |
| C | A | R | V | D | H | F | Q | T | E | N | E | W | M | D | Y | W | 1 |
| C | A | R | D | W | P | T | L | I | F | W | Y | W | F | D | Y | W | 1 |

FIG. 22

| 92 | 93 | 94 | 95 | 96 | 97 | 98 | 99 | 100 | 100A | 100B | 100C | 100Ca | 100D | 100E | 101 | 102 | 103 | FREQUENCY |
|---|---|---|---|---|---|---|---|---|---|---|---|---|---|---|---|---|---|---|
| C | A | R | G | F | G | F | T | E | - | - | - | - | - | - | D | Y | W | 4 |
| C | A | R | Q | F | D | E | D | S | F | V | R | - | R | F | D | V | W | 4 |
| C | A | R | I | L | K | E | S | S | K | S | R | - | Q | M | D | V | W | 2 |
| C | A | R | E | Q | D | E | Y | G | A | I | R | - | I | M | D | Y | W | 1 |
| C | A | R | N | H | F | E | A | S | W | P | R | R | Q | M | D | V | W | 1 |
| C | A | R | E | N | E | W | V | D | M | I | L | - | D | M | D | Y | W | 2 |
| C | A | R | Q | Y | S | E | T | R | W | V | R | - | K | F | D | Y | W | 1 |
| C | A | R | Q | F | K | E | S | K | T | R | R | - | K | F | D | V | W | 13 |
| C | A | R | K | K | T | Q | Y | V | H | D | W | - | R | M | D | V | W | 3 |
| C | A | R | R | W | R | E | T | K | S | K | R | - | F | F | D | V | W | 1 |
| C | A | R | D | Y | I | M | E | F | - | - | - | - | - | - | D | Y | W | 1 |
| C | A | R | Q | F | E | E | T | K | Q | R | R | - | L | M | D | Y | W | 1 |

*FIG. 23*

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | D | Q | G | F | Y | A | I | D | Y | V | M | D | Y | W | 5 |
| C | A | R | V | F | T | Y | M | Y | N | Y | F | R | F | D | V | W | 1 |
| C | A | R | V | F | F | E | Q | M | E | V | V | R | M | D | V | W | 1 |
| C | A | R | E | K | E | Y | R | L | S | W | S | Q | M | D | Y | W | 1 |
| C | A | R | Y | P | S | R | W | A | P | N | W | Y | M | D | Y | W | 1 |
| C | A | R | D | G | G | F | K | P | L | T | H | F | F | D | V | W | 1 |

FIG. 24

| unique restriction site | Isoschizomers |
|---|---|
| AatII | / |
| AflII | BfrI, BspTI, Bst98I |
| AscI | / |
| AseI | VspI, AsnI, PshBI |
| BamHI | BstI |
| BbeI | EheI, KasI, NarI |
| BbsI | BpuAI, BpiI |
| BglII | / |
| BlpI | Bpu1102I, CelII, BlpI |
| BsaBI | MamI, Bsh1365I, BsrBRI |
| BsiWI | Pfl23II, SplI, SunI |
| BspEI | AccIII, BseAI, BsiMI, Kpn2I, MroI |
| BsrGI | Bsp1407I, SspBI |
| BssHII | PauI |
| BstEII | BstPI, Eco91I, EcoO65I |
| BstXI | / |
| Bsu36I | AocI, CvnI, Eco81I |
| DraIII | / |
| DsmAI |  |
| EagI | BstZI, EclXI, Eco52I, XmaIII |
| Eco57I | / |
| EcoO109I | DraII |
| EcoRI | / |
| EcoRV | Eco32I |
| FseI | / |
| HindIII | / |
| HpaI | / |
| KpnI | Acc65I, Asp718I |
| MluI | / |
| MscI | BalI, MluNI |

*FIG. 25B*

| unique restriction site | Isoschizomers |
|---|---|
| MunI | MfeI |
| NheI | / |
| NsiI | Ppu10I, EcoT22I, Mph1103I |
| NspV | Bsp119I, BstBI, Csp45I, LspI, SfuI |
| PacI | / |
| PmeI | / |
| PmlI | BbrPI, Eco72I, PmaCI |
| Psp5II | PpuMI |
| PstI | / |
| RsrII | (RsriI), CpoI, CspI |
| SanDI | / |
| SapI | / |
| SexAI | / |
| SpeI | / |
| SfiI | / |
| SphI | BbuI, PaeI,NspI |
| StuI | AatI, Eco147I |
| StyI | Eco130I, EcoT14I |
| XbaI | BspLU11II |
| XhoI | PaeR7I |
| XmaI | AvaI, SmaI, Cfr9I, PspAI |

FIG. 25C

| No | module/flanking restriction sites | functional element | sites to be removed | sites to be inserted | template | reference |
|---|---|---|---|---|---|---|
| M1 | AatII-lacp/o-XbaI | lac promotor/operator | 2x VspI (AseI) | AatII | vector pASK30 | Skerra et al. (1991) Bio/Technology 9, 273-278 |
| M2 | BglII-lox-AatII | Cre/lox recombination site | 2x VspI (AseI) | lox, BglII | (synthetic) | Hoess et al. (1986) Nucleic Acids Res. 2287-2300 |
| M3 | XbaI-lox'-SphI | Cre/lox' recombination site | none | lox', SphI | (synthetic) | see M2 |
| M7-I | EcoRI-gIIIlong-HindIII | gIIIp of filamentous phage with N-terminal myctail/amber codon | SphI, BamHI | none | vector pIG10 | Ge et al., (1994) Expressing antibodies in E. coli. In: Antibody engineering: A practical approach. IRL Press, New York, pp 229-266 |

FIG. 26A

| | | | | | | |
|---|---|---|---|---|---|---|
| M7-II | EcoRI-gIIIss-HindIII | truncated gIIIp of filamentous phage with N-terminal Gly-Ser linker | SphI | | vector pIG10 | see M7-I |
| M7-III | EcoRI-gIIIss-HindIII | truncated gIIIp of filamentous phage with N-terminal myctail/amber codon | SphI, BbsI | | vector pIG10 | see M7-I |
| M8 | SphI-lox-HindIII | Cre/lox recombination site | none | lox | (synthetic) | see M3 |
| M9-II | HindIII-lpp-PacI | lpp-terminator | none | PacI, FseI | (synthetic) | see M1 |
| M10-II | PacI/FseI-bla-BsrGI | beta-lactamase/bla (ampR) | VspI, Eco57I, BssSI | PacI, FseI, BsrGI | pASK30 | see M1 |
| M11-II | BsrGI-f1 ori-NheI | origin of single-stranded replication | DraIII (BanII not removed) | BsrGI, NheI | pASK30 | see M1 |
| M11-III | BsrGI-f1 ori-NheI | origin of single-stranded replication | DraIII, BanII | BsrGI, NheI | pASK30 | see M1 |

FIG. 26B

| | | | | | | |
|---|---|---|---|---|---|---|
| M12 | NheI-p15A-BglII | origin of double-stranded replication | BssSI, VspI, NspV | NheI, BglII | pACYC184 | Rose, R.E. (1988) Nucleic Acids Res. 16, 355 |
| M13 | BglII-lox-BglII | Cre/lox recombination site | none | BglII, lox, XmnI | (synthetic) | see M3 |
| M14-Ext2 | BglII-ColEI-NheI | origin of double-stranded replication | Eco57I (BssSI not removed) | BglII, NheI | pUC19 | Yanisch-Peron, C. (1985) Gene 33,103-119 |
| M17 | AatII-cat-BglII | chloramphenicol-acetyltransferase/ cat (camR) | BspEI, MscI, StyI/NcoI | | pACYC184 | Cardoso, M. & Schwarz,S. (1992) J. Appl. Bacteriol.72, 289-293 |
| M19 | XbaI-phoA-EcoRI | signal sequence of phosphatase A | (synthetic) | | (synthetic) | see M1 |
| M20 | XbaI-phoA-FLAG-EcoRI | signal sequence of phosphatase A + FLAG detection tag | (synthetic) | | (synthetic) | Knappik, A & Plückthun, A. (1994) BioTechniques 17, 754-761 |

FIG. 26C

| | | | | | | |
|---|---|---|---|---|---|---|
| M21 | XbaI-stII-SapI | heat-stable enterotoxin II signal sequence | (synthetic) | | (synthetic) | Lee et al. (1983) Infect. Immunol. 264-268 |
| M41 | AflII-lacI-NheI | lac-repressor | BstXI, MluI,BbsI, BanII, BstEII, HpaI, BbeI, VspI | | pASK30 | see M1 |
| M42 | EcoRI-Histail-HindIII | poly-histidine tail | (synthetic) | | (synthetic) | Lindner et al., (1992) Methods: a companion to methods in enzymology 4, 41-56 |

FIG. 26D

```
           HindIII                   PacI                     BsrGI
          ~~~~~~~~               ~~~~~~~~~                   ~~~~~~
  1   ACATGTAAGC TTCCCCCCCC CCTTAATTAA CCCCCCCCCC TGTACACCCC
      TGTACATTCG AAGGGGGGGG GGAATTAATT GGGGGGGGGG ACATGTGGGG

            NheI                 BglII              AatII   XbaI
          ~~~~~~~~              ~~~~~~~            ~~~~~~~~      ~
 51   CCCCCCGCTA GCCCCCCCCC CCAGATCTCC CCCCCCCCGA CGTCCCCCCT
      GGGGGGCGAT CGGGGGGGGG GGTCTAGAGG GGGGGGGGCT GCAGGGGGGA

      XbaI              SphI                   EcoRI AatII
      ~~~~~~           ~~~~~~~~               ~~~~~~~~~~~~~
101   CTAGACCCCC CCCCCGCATG CCCCCCCCCC CGAATTCGAC GTC
      GATCTGGGGG GGGGGCGTAC GGGGGGGGGG GCTTAAGCTG CAG
```

FIG. 27B

```
  1  CAGGTGGCAC TTTTCGGGGA AATGTGCGCG GAACCCCTAT TTGTTTATTT
     GTCCACCGTG AAAAGCCCCT TTACACGCGC CTTGGGGATA AACAAATAAA

 51  TTCTAAATAC ATTCAAATAT GTATCCGCTC ATGAGACAAT AACCCTGATA
     AAGATTTATG TAAGTTTATA CATAGGCGAG TACTCTGTTA TTGGGACTAT

101  AATGCTTCAA TAATATTGAA AAAGGAAGAG TATGAGTATT CAACATTTCC
     TTACGAAGTT ATTATAACTT TTTCCTTCTC ATACTCATAA GTTGTAAAGG

151  GTGTCGCCCT TATTCCCTTT TTTGCGGCAT TTTGCCTTCC TGTTTTTGCT
     CACAGCGGGA ATAAGGGAAA AAACGCCGTA AAACGGAAGG ACAAAAACGA

                                        Eco57I
                                        ~~~~~~~
201  CACCCAGAAA CGCTGGTGAA AGTAAAAGAT GCTGAAGATC AGTTGGGTGC
     GTGGGTCTTT GCGACCACTT TCATTTTCTA CGACTTCTAG TCAACCCACG
                                                     BssSI
                                                         ~

251  ACGAGTGGGT TACATCGAAC TGGATCTCAA CAGCGGTAAG ATCCTTGAGA
     TGCTCACCCA ATGTAGCTTG ACCTAGAGTT GTCGCCATTC TAGGAACTCT
    BssSI
    ~~~~~
```

FIG. 28B

```
                               XmnI
                          ~~~~~~~~~~~~
301  GTTTTCGCCC CGAAGAACGT TTTCCAATGA TGAGCACTTT TAAAGTTCTG
     CAAAAGCGGG GCTTCTTGCA AAAGGTTACT ACTCGTGAAA ATTTCAAGAC

351  CTATGTGGCG CGGTATTATC CCGTATTGAC GCCGGGCAAG AGCAACTCGG
     GATACACCGC GCCATAATAG GGCATAACTG CGGCCCGTTC TCGTTGAGCC

401  TCGCCGCATA CACTATTCTC AGAATGACTT GGTTGAGTAC TCACCAGTCA
     AGCGGCGTAT GTGATAAGAG TCTTACTGAA CCAACTCATG AGTGGTCAGT

451  CAGAAAAGCA TCTTACGGAT GGCATGACAG TAAGAGAATT ATGCAGTGCT
     GTCTTTTCGT AGAATGCCTA CCGTACTGTC ATTCTCTTAA TACGTCACGA

501  GCCATAACCA TGAGTGATAA CACTGCGGCC AACTTACTTC TGACAACGAT
     CGGTATTGGT ACTCACTATT GTGACGCCGG TTGAATGAAG ACTGTTGCTA

551  CGGAGGACCG AAGGAGCTAA CCGCTTTTTT GCACAACATG GGGGATCATG
     GCCTCCTGGC TTCCTCGATT GGCGAAAAAA CGTGTTGTAC CCCCTAGTAC

601  TAACTCGCCT TGATCGTTGG GAACCGGAGC TGAATGAAGC CATACCAAAC
     ATTGAGCGGA ACTAGCAACC CTTGGCCTCG ACTTACTTCG GTATGGTTTG

651  GACGAGCGTG ACACCACGAT GCCTGTAGCA ATGGCAACAA CGTTGCGCAA
```

*FIG. 28C*

```
      CTGCTCGCAC TGTGGTGCTA CGGACATCGT TACCGTTGTT GCAACGCGTT

                                                   AseI
                                                  ~~~~~~
 701  ACTATTAACT GGCGAACTAC TTACTCTAGC TTCCCGGCAA CAATTAATAG
      TGATAATTGA CCGCTTGATG AATGAGATCG AAGGGCCGTT GTTAATTATC

 751  ACTGGATGGA GGCGGATAAA GTTGCAGGAC CACTTCTGCG CTCGGCCCTT
      TGACCTACCT CCGCCTATTT CAACGTCCTG GTGAAGACGC GAGCCGGGAA

 801  CCGGCTGGCT GGTTTATTGC TGATAAATCT GGAGCCGGTG AGCGTGGGTC
      GGCCGACCGA CCAAATAACG ACTATTTAGA CCTCGGCCAC TCGCACCCAG

 851  TCGCGGTATC ATTGCAGCAC TGGGGCCAGA TGGTAAGCCC TCCCGTATCG
      AGCGCCATAG TAACGTCGTG ACCCCGGTCT ACCATTCGGG AGGGCATAGC

 901  TAGTTATCTA CACGACGGGG AGTCAGGCAA CTATGGATGA ACGAAATAGA
      ATCAATAGAT GTGCTGCCCC TCAGTCCGTT GATACCTACT TGCTTTATCT

 951  CAGATCGCTG AGATAGGTGC CTCACTGATT AAGCATTGGT AACTGTCAGA
      GTCTAGCGAC TCTATCCACG GAGTGACTAA TTCGTAACCA TTGACAGTCT

1001  CCAAGTTTAC TCATATATAC TTTAGATTGA TTTAAAACTT CATTTTTAAT
      GGTTCAAATG AGTATATATG AAATCTAACT AAATTTTGAA GTAAAAATTA
```

FIG. 28D

```
1051  TTAAAAGGAT CTAGGTGAAG ATCCTTTTTG ATAATCTCAT GACCAAAATC
      AATTTTCCTA GATCCACTTC TAGGAAAAAC TATTAGAGTA CTGGTTTTAG

1101  CCTTAACGTG AGTTTTCGTT CCACTGAGCG TCAGACCCCG TAGAAAAGAT
      GGAATTGCAC TCAAAAGCAA GGTGACTCGC AGTCTGGGGC ATCTTTTCTA

1151  CAAAGGATCT TCTTGAGATC CTTTTTTTCT GCGCGTAATC TGCTGCTTGC
      GTTTCCTAGA AGAACTCTAG GAAAAAAAGA CGCGCATTAG ACGACGAACG

1201  AAACAAAAAA ACCACCGCTA CCAGCGGTGG TTTGTTTGCC GGATCAAGAG
      TTTGTTTTTT TGGTGGCGAT GGTCGCCACC AAACAAACGG CCTAGTTCTC

1251  CTACCAACTC TTTTTCCGAA GGTAACTGGC TTCAGCAGAG CGCAGATACC
      GATGGTTGAG AAAAAGGCTT CCATTGACCG AAGTCGTCTC GCGTCTATGG
                                   Eco57I
                                   ~~~~~~~~

1301  AAATACTGTC CTTCTAGTGT AGCCGTAGTT AGGCCACCAC TTCAAGAACT
      TTTATGACAG GAAGATCACA TCGGCATCAA TCCGGTGGTG AAGTTCTTGA

1351  CTGTAGCACC GCCTACATAC CTCGCTCTGC TAATCCTGTT ACCAGTGGCT
      GACATCGTGG CGGATGTATG GAGCGAGACG ATTAGGACAA TGGTCACCGA
```

FIG. 28E

```
1401   GCTGCCAGTG GCGATAAGTC GTGTCTTACC GGGTTGGACT CAAGACGATA
        CGACGGTCAC CGCTATTCAG CACAGAATGG CCCAACCTGA GTTCTGCTAT

1451   GTTACCGGAT AAGGCGCAGC GGTCGGGCTG AACGGGGGGT TCGTGCACAC
        CAATGGCCTA TTCCGCGTCG CCAGCCCGAC TTGCCCCCCA AGCACGTGTG

1501   AGCCCAGCTT GGAGCGAACG ACCTACACCG AACTGAGATA CCTACAGCGT
        TCGGGTCGAA CCTCGCTTGC TGGATGTGGC TTGACTCTAT GGATGTCGCA

1551   GAGCTATGAG AAAGCGCCAC GCTTCCCGAA GGGAGAAAGG CGGACAGGTA
        CTCGATACTC TTTCGCGGTG CGAAGGGCTT CCCTCTTTCC GCCTGTCCAT

1601   TCCGGTAAGC GGCAGGGTCG GAACAGGAGA GCGCACGAGG GAGCTTCCAG
        AGGCCATTCG CCGTCCCAGC CTTGTCCTCT CGCGTGCTCC CTCGAAGGTC
                                             BssSI
                                            ~~~~~~~

1651   GGGGAAACGC CTGGTATCTT TATAGTCCTG TCGGGTTTCG CCACCTCTGA
        CCCCTTTGCG GACCATAGAA ATATCAGGAC AGCCCAAAGC GGTGGAGACT

1701   CTTGAGCGTC GATTTTTGTG ATGCTCGTCA GGGGGGCGGA GCCTATGGAA
        GAACTCGCAG CTAAAAACAC TACGAGCAGT CCCCCCGCCT CGGATACCTT

1751   AAACGCCAGC AACGCGGCCT TTTTACGGTT CCTGGCCTTT TGCTGGCCTT
```

FIG. 28F

```
       TTTGCGGTCG TTGCGCCGGA AAAATGCCAA GGACCGGAAA ACGACCGGAA

                  HindIII                PacI            BsrGI
                  ~~~~~~~            ~~~~~~~~~~            ~~~~
1801   TTGCTCACAT GTAAGCTTCC CCCCCCCCTT AATTAACCCC CCCCCCTGTA
       AACGAGTGTA CATTCGAAGG GGGGGGGGAA TTAATTGGGG GGGGGGACAT

       BsrGI       NheI              BglII               AatII
       ~~         ~~~~~~~            ~~~~~~~~           ~~~~~~~
1851   CACCCCCCCC CCGCTAGCCC CCCCCCCCAG ATCTCCCCCC CCCCGACGTC
       GTGGGGGGGG GGCGATCGGG GGGGGGGGTC TAGAGGGGGG GGGGCTGCAG

            XbaI              SphI              EcoRI
          ~~~~~~~~          ~~~~~~~          ~~~~~~~~
1901   CCCCCTCTAG ACCCCCCCCC CGCATGCCCC CCCCCCCGAA TTCACGT
       GGGGGAGATC TGGGGGGGGG GCGTACGGGG GGGGGGGCTT AAGTGCA
```

FIG. 28G

```
        AatII
        ~~~~~~
  1     GACGTCTTAA TGTGAGTTAG CTCACTCATT AGGCACCCCA GGCTTTACAC
        CTGCAGAATT ACACTCAATC GAGTGAGTAA TCCGTGGGGT CCGAAATGTG

 51     TTTATGCTTC CGGCTCGTAT GTTGTGTGGA ATTGTGAGCG GATAACAATT
        AAATACGAAG GCCGAGCATA CAACACACCT TAACACTCGC CTATTGTTAA

                                             XbaI
                                            ~~~~~~
101     TCACACAGGA AACAGCTATG ACCATGATTA CGAATTTCTA GA
        AGTGTGTCCT TTGTCGATAC TGGTACTAAT GCTTAAAGAT CT
```

FIG. 29B

M7-III (ss/myc/TAG)
520 bp

```
       EcoRI
       ~~~~~~
  1    GAATTCGAGC AGAAGCTGAT CTCTGAGGAG GATCTGTAGG GTGGTGGCTC
       CTTAAGCTCG TCTTCGACTA GAGACTCCTC CTAGACATCC CACCACCGAG

 51    TGGTTCCGGT GATTTTGATT ATGAAAAGAT GGCAAACGCT AATAAGGGGG
       ACCAAGGCCA CTAAAACTAA TACTTTTCTA CCGTTTGCGA TTATTCCCCC

101    CTATGACCGA AAATGCCGAT GAAAACGCGC TACAGTCTGA CGCTAAAGGC
       GATACTGGCT TTTACGGCTA CTTTTGCGCG ATGTCAGACT GCGATTTCCG

151    AAACTTGATT CTGTCGCTAC TGATTACGGT GCTGCTATCG ATGGTTTCAT
       TTTGAACTAA GACAGCGATG ACTAATGCCA CGACGATAGC TACCAAAGTA

201    TGGTGACGTT TCCGGCCTTG CTAATGGTAA TGGTGCTACT GGTGATTTTG
       ACCACTGCAA AGGCCGGAAC GATTACCATT ACCACGATGA CCACTAAAAC

251    CTGGCTCTAA TTCCCAAATG GCTCAAGTCG GTGACGGTGA TAATTCACCT
       GACCGAGATT AAGGGTTTAC CGAGTTCAGC CACTGCCACT ATTAAGTGGA

                  XmnI
              ~~~~~~~~~~~~
301    TTAATGAATA ATTTCCGTCA ATATTTACCT TCCCTCCCTC AATCGGTTGA
       AATTACTTAT TAAAGGCAGT TATAAATGGA AGGGAGGGAG TTAGCCAACT
```

FIG. 30B

```
351  ATGTCGCCCT TTTGTCTTTG GCGCTGGTAA ACCATATGAA TTTTCTATTG
     TACAGCGGGA AAACAGAAAC CGCGACCATT TGGTATACTT AAAAGATAAC

401  ATTGTGACAA AATAAACTTA TTCCGTGGTG TCTTTGCGTT TCTTTTATAT
     TAACACTGTT TTATTTGAAT AAGGCACCAC AGAAACGCAA AGAAAATATA

451  GTTGCCACCT TTATGTATGT ATTTTCTACG TTTGCTAACA TACTGCGTAA
     CAACGGTGGA AATACATACA TAAAAGATGC AAACGATTGT ATGACGCATT

                   HindIII
                   ~~~~~~~
501  TAAGGAGTCT TGATAAGCTT
     ATTCCTCAGA ACTATTCGAA
```

FIG. 30C

```
                 HindIII
                 ~~~~~~~
  1   GGGGGGGGGG AAGCTTGACC TGTGAAGTGA AAAATGGCGC AGATTGTGCG
      CCCCCCCCCC TTCGAACTGG ACACTTCACT TTTTACCGCG TCTAACACGC

                             PacI                   FseI
                          ~~~~~~~~~            ~~~~~~~~~~
 51   ACATTTTTTT TGTCTGCCGT TTAATTAAAG GGGGGGGGGG GCCGGCCTGG
      TGTAAAAAAA ACAGACGGCA AATTAATTTC CCCCCCCCCC CGGCCGGACC

            BsrGI
          ~~~~~~~~
101   GGGGGGGTGT ACAGGGGGGG GGG
      CCCCCCCACA TGTCCCCCCC CCC
```

*FIG. 31B*

```
      NheI
     ~~~~~~
  1  GCTAGCACGC GCCCTGTAGC GGCGCATTAA GCGCGGCGGG TGTGGTGGTT
     CGATCGTGCG CGGGACATCG CCGCGTAATT CGCGCCGCCC ACACCACCAA

 51  ACGCGCAGCG TGACCGCTAC ACTTGCCAGC GCCCTAGCGC CCGCTCCTTT
     TGCGCGTCGC ACTGGCGATG TGAACGGTCG CGGGATCGCG GGCGAGGAAA

101  CGCTTTCTTC CCTTCCTTTC TCGCCACGTT CGCCGGCTTT CCCCGTCAAG
     GCGAAAGAAG GGAAGGAAAG AGCGGTGCAA GCGGCCGAAA GGGGCAGTTC

151  CTCTAAATCG GGGCATCCCT TTAGGGTTCC GATTTAGTGC TTTACGGCAC
     GAGATTTAGC CCCGTAGGGA AATCCCAAGG CTAAATCACG AAATGCCGTG

201  CTCGACCCCA AAAAACTTGA TTAGGGTGAT GGTTCTCGTA GTGGGCCATC
     GAGCTGGGGT TTTTTGAACT AATCCCACTA CCAAGAGCAT CACCCGGTAG

251  GCCCTGATAG ACGGTTTTTC GCCCTTTGAC GTTGGAGTCC ACGTTCTTTA
     CGGGACTATC TGCCAAAAAG CGGGAAACTG CAACCTCAGG TGCAAGAAAT

301  ATAGTGGACT CTTGTTCCAA ACTGGAACAA CACTCAACCC TATCTCGGTC
     TATCACCTGA GAACAAGGTT TGACCTTGTT GTGAGTTGGG ATAGAGCCAG

351  TATTCTTTTG ATTTATAAGG GATTTTGCCG ATTTCGGCCT ATTGGTTAAA
```

FIG. 32B

```
     ATAAGAAAAC TAAATATTCC CTAAAACGGC TAAAGCCGGA TAACCAATTT

401  AAATGAGCTG ATTTAACAAA AATTTAACGC GAATTTTAAC AAAATATTAA
     TTTACTCGAC TAAATTGTTT TTAAATTGCG CTTAAAATTG TTTTATAATT

                     BsrGI
                    ~~~~~~
451  CGTTTACAAT TTCATGTACA
     GCAAATGTTA AAGTACATGT
```

FIG. 32C

```
     BglII
     ~~~~~~
  1  AGATCTGACC AAAATCCCTT AACGTGAGTT TTCGTTCCAC TGAGCGTCAG
     TCTAGACTGG TTTTAGGGAA TTGCACTCAA AAGCAAGGTG ACTCGCAGTC

 51  ACCCCGTAGA AAAGATCAAA GGATCTTCTT GAGATCCTTT TTTTCTGCGC
     TGGGGCATCT TTTCTAGTTT CCTAGAAGAA CTCTAGGAAA AAAAGACGCG

101  GTAATCTGCT GCTTGCAAAC AAAAAAACCA CCGCTACCAG CGGTGGTTTG
     CATTAGACGA CGAACGTTTG TTTTTTTGGT GGCGATGGTC GCCACCAAAC

151  TTTGCCGGAT CAAGAGCTAC CAACTCTTTT TCCGAAGGTA ACTGGCTACA
     AAACGGCCTA GTTCTCGATG GTTGAGAAAA AGGCTTCCAT TGACCGATGT

201  GCAGAGCGCA GATACCAAAT ACTGTTCTTC TAGTGTAGCC GTAGTTAGGC
     CGTCTCGCGT CTATGGTTTA TGACAAGAAG ATCACATCGG CATCAATCCG

251  CACCACTTCA AGAACTCTGT AGCACCGCCT ACATACCTCG CTCTGCTAAT
     GTGGTGAAGT TCTTGAGACA TCGTGGCGGA TGTATGGAGC GAGACGATTA

301  CCTGTTACCA GTGGCTGCTG CCAGTGGCGA TAAGTCGTGT CTTACCGGGT
     GGACAATGGT CACCGACGAC GGTCACCGCT ATTCAGCACA GAATGGCCCA

351  TGGACTCAAG ACGATAGTTA CCGGATAAGG CGCAGCGGTC GGGCTGAACG
```

FIG. 33B

```
     ACCTGAGTTC TGCTATCAAT GGCCTATTCC GCGTCGCCAG CCCGACTTGC

401  GGGGGTTCGT GCACACAGCC CAGCTTGGAG CGAACGACCT ACACCGAACT
     CCCCCAAGCA CGTGTGTCGG GTCGAACCTC GCTTGCTGGA TGTGGCTTGA

451  GAGATACCTA CAGCGTGAGC TATGAGAAAG CGCCACGCTT CCCGAAGGGA
     CTCTATGGAT GTCGCACTCG ATACTCTTTC GCGGTGCGAA GGGCTTCCCT

501  GAAAGGCGGA CAGGTATCCG GTAAGCGGCA GGGTCGGAAC AGGAGAGCGC
     CTTTCCGCCT GTCCATAGGC CATTCGCCGT CCCAGCCTTG TCCTCTCGCG
                                                    BssSI
                                                        ~

551  ACGAGGGAGC TTCCAGGGGG AAACGCCTGG TATCTTTATA GTCCTGTCGG
     TGCTCCCTCG AAGGTCCCCC TTTGCGGACC ATAGAAATAT CAGGACAGCC
     BssSI
     ~~~~~

601  GTTTCGCCAC CTCTGACTTG AGCGTCGATT TTTGTGATGC TCGTCAGGGG
     CAAAGCGGTG GAGACTGAAC TCGCAGCTAA AAACACTACG AGCAGTCCCC

651  GGCGGAGCCT ATGGAAAAAC GCCAGCAACG CGGCCTTTTT ACGGTTCCTG
     CCGCCTCGGA TACCTTTTTG CGGTCGTTGC GCCGGAAAAA TGCCAAGGAC
```

FIG. 33C

```
                                              NheI
                                             ~~~~~~
701  GCCTTTTGCT GGCCTTT 'GC TCACATGGCT AGC
     CGGAAAACGA CCGGAAAACG AGTGTACCGA TCG
```

FIG. 33D

```
       AatII
      ~~~~~~
  1   GGGACGTCGG GTGAGGTTCC AACTTTCACC ATAATGAAAT AAGATCACTA
      CCCTGCAGCC CACTCCAAGG TTGAAAGTGG TATTACTTTA TTCTAGTGAT

 51   CCGGGCGTAT TTTTTGAGTT ATCGAGATTT TCAGGAGCTA AGGAAGCTAA
      GGCCCGCATA AAAAACTCAA TAGCTCTAAA AGTCCTCGAT TCCTTCGATT

101   AATGGAGAAA AAAATCACTG GATATACCAC CGTTGATATA TCCCAATGGC
      TTACCTCTTT TTTTAGTGAC CTATATGGTG GCAACTATAT AGGGTTACCG

151   ATCGTAAAGA ACATTTTGAG GCATTTCAGT CAGTTGCTCA ATGTACCTAT
      TAGCATTTCT TGTAAAACTC CGTAAAGTCA GTCAACGAGT TACATGGATA

201   AACCAGACCG TTCAGCTGGA TATTACGGCC TTTTTAAAGA CCGTAAAGAA
      TTGGTCTGGC AAGTCGACCT ATAATGCCGG AAAAATTTCT GGCATTTCTT

251   AAATAAGCAC AAGTTTTATC CGGCCTTTAT TCACATTCTT GCCCGCCTGA
      TTTATTCGTG TTCAAAATAG GCCGGAAATA AGTGTAAGAA CGGGCGGACT

301   TGAATGCTCA CCCGGAGTTC CGTATGGCAA TGAAAGACGG TGAGCTGGTG
      ACTTACGAGT GGGCCTCAAG GCATACCGTT ACTTTCTGCC ACTCGACCAC

351   ATATGGGATA GTGTTCACCC TTGTTACACC GTTTTCCATG AGCAAACTGA
```

FIG. 34B

```
      TATACCCTAT CACAAGTGGG AACAATGTGG CAAAAGGTAC TCGTTTGACT

401   AACGTTTTCA TCGCTCTGGA GTGAATACCA CGACGATTTC CGGCAGTTTC
      TTGCAAAAGT AGCGAGACCT CACTTATGGT GCTGCTAAAG GCCGTCAAAG

451   TACACATATA TTCGCAAGAT GTGGCGTGTT ACGGTGAAAA CCTGGCCTAT
      ATGTGTATAT AAGCGTTCTA CACCGCACAA TGCCACTTTT GGACCGGATA

501   TTCCCTAAAG GGTTTATTGA GAATATGTTT TTCGTCTCAG CCAATCCCTG
      AAGGGATTTC CCAAATAACT CTTATACAAA AAGCAGAGTC GGTTAGGGAC

551   GGTGAGTTTC ACCAGTTTTG ATTTAAACGT AGCCAATATG GACAACTTCT
      CCACTCAAAG TGGTCAAAAC TAAATTTGCA TCGGTTATAC CTGTTGAAGA

601   TCGCCCCCGT TTTCACTATG GGCAAATATT ATACGCAAGG CGACAAGGTG
      AGCGGGGGCA AAAGTGATAC CCGTTTATAA TATGCGTTCC GCTGTTCCAC

651   CTGATGCCGC TGGCGATTCA GGTTCATCAT GCCGTTTGTG ATGGCTTCCA
      GACTACGGCG ACCGCTAAGT CCAAGTAGTA CGGCAAACAC TACCGAAGGT

701   TGTCGGCAGA ATGCTTAATG AATTACAACA GTACTGCGAT GAGTGGCAGG
      ACAGCCGTCT TACGAATTAC TTAATGTTGT CATGACGCTA CTCACCGTCC

751   GCGGGGCGTA ATTTTTTTAA GGCAGTTATT GGGTGCCCTT AAACGCCTGG
```

FIG. 34C

```
     CGCCCCGCAT TAAAAAAATT CCGTCAATAA CCCACGGGAA TTTGCGGACC

          BglII
          ~~~~~~
801  TGCTAGATCT TCC
     ACGATCTAGA AGG
```

FIG. 34D

```
        EcoRI
        ~~~~~
  1     AATTCGAGCA GAAGCTGATC TCTGAGGAGG ATCTGTAGGG TGGTGGCTCT
        TTAAGCTCGT CTTCGACTAG AGACTCCTCC TAGACATCCC ACCACCGAGA

 51     GGTTCCGGTG ATTTTGATTA TGAAAAGATG GCAAACGCTA ATAAGGGGGC
        CCAAGGCCAC TAAAACTAAT ACTTTTCTAC CGTTTGCGAT TATTCCCCCG

101     TATGACCGAA AATGCCGATG AAAACGCGCT ACAGTCTGAC GCTAAAGGCA
        ATACTGGCTT TTACGGCTAC TTTTGCGCGA TGTCAGACTG CGATTTCCGT

151     AACTTGATTC TGTCGCTACT GATTACGGTG CTGCTATCGA TGGTTTCATT
        TTGAACTAAG ACAGCGATGA CTAATGCCAC GACGATAGCT ACCAAAGTAA

201     GGTGACGTTT CCGGCCTTGC TAATGGTAAT GGTGCTACTG GTGATTTTGC
        CCACTGCAAA GGCCGGAACG ATTACCATTA CCACGATGAC CACTAAAACG

251     TGGCTCTAAT TCCCAAATGG CTCAAGTCGG TGACGGTGAT AATTCACCTT
        ACCGAGATTA AGGGTTTACC GAGTTCAGCC ACTGCCACTA TTAAGTGGAA

                  XmnI
             ~~~~~~~~~~~~
301     TAATGAATAA TTTCCGTCAA TATTTACCTT CCCTCCCTCA ATCGGTTGAA
        ATTACTTATT AAAGGCAGTT ATAAATGGAA GGGAGGGAGT TAGCCAACTT
```

FIG. 35B

```
351  TGTCGCCCTT TTGTCTTTGG CGCTGGTAAA CCATATGAAT TTTCTATTGA
     ACAGCGGGAA AACAGAAACC GCGACCATTT GGTATACTTA AAAGATAACT

401  TTGTGACAAA ATAAACTTAT TCCGTGGTGT CTTTGCGTTT CTTTTATATG
     AACACTGTTT TATTTGAATA AGGCACCACA GAAACGCAAA GAAAATATAC

451  TTGCCACCTT TATGTATGTA TTTTCTACGT TTGCTAACAT ACTGCGTAAT
     AACGGTGGAA ATACATACAT AAAAGATGCA AACGATTGTA TGACGCATTA

                HindIII
                ~~~~~~
501  AAGGAGTCTT GATAAGCTTG ACCTGTGAAG TGAAAAATGG CGCAGATTGT
     TTCCTCAGAA CTATTCGAAC TGGACACTTC ACTTTTTACC GCGTCTAACA

                             PacI                 FseI
                           ~~~~~~~~~~           ~~~~~~~~~
551  GCGACATTTT TTTTGTCTGC CGTTTAATTA AAGGGGGGGG GGGGCCGGCC
     CGCTGTAAAA AAAACAGACG GCAAATTAAT TTCCCCCCCC CCCCGGCCGG

              BsrG1
             ~~~~~~
601  TGGGGGGGGG TGTACATGAA ATTGTAAACG TTAATATTTT GTTAAAATTC
     ACCCCCCCCC ACATGTACTT TAACATTTGC AATTATAAAA CAATTTTAAG
```

FIG. 35C

```
651  GCGTTAAATT TTTGTTAAAT CAGCTCATTT TTTAACCAAT AGGCCGAAAT
     CGCAATTTAA AAACAATTTA GTCGAGTAAA AAATTGGTTA TCCGGCTTTA

701  CGGCAAAATC CCTTATAAAT CAAAAGAATA GACCGAGATA GGGTTGAGTG
     GCCGTTTTAG GGAATATTTA GTTTTCTTAT CTGGCTCTAT CCCAACTCAC

751  TTGTTCCAGT TTGGAACAAG AGTCCACTAT TAAAGAACGT GGACTCCAAC
     AACAAGGTCA AACCTTGTTC TCAGGTGATA ATTTCTTGCA CCTGAGGTTG

801  GTCAAAGGGC GAAAAACCGT CTATCAGGGC GATGGCCCAC TACGAGAACC
     CAGTTTCCCG CTTTTTGGCA GATAGTCCCG CTACCGGGTG ATGCTCTTGG

851  ATCACCCTAA TCAAGTTTTT TGGGGTCGAG GTGCCGTAAA GCACTAAATC
     TAGTGGGATT AGTTCAAAAA ACCCCAGCTC CACGGCATTT CGTGATTTAG

                           BanII
                          ~~~~~~~
901  GGAACCCTAA AGGGAGCCCC CGATTTAGAG CTTGACGGGG AAAGCCGGCG
     CCTTGGGATT TCCCTCGGGG GCTAAATCTC GAACTGCCCC TTTCGGCCGC

951  AACGTGGCGA GAAAGGAAGG GAAGAAAGCG AAAGGAGCGG GCGCTAGGGC
     TTGCACCGCT CTTTCCTTCC CTTCTTTCGC TTTCCTCGCC CGCGATCCCG
```

FIG. 35D

```
1001  GCTGGCAAGT GTAGCGGTCA CGCTGCGCGT AACCACCACA CCCGCCGCGC
      CGACCGTTCA CATCGCCAGT GCGACGCGCA TTGGTGGTGT GGGCGGCGCG

                                 NheI
                                ~~~~~~~
1051  TTAATGCGCC GCTACAGGGC GCGTGCTAGC CATGTGAGCA AAAGGCCAGC
      AATTACGCGG CGATGTCCCG CGCACGATCG GTACACTCGT TTTCCGGTCG

1101  AAAAGGCCAG GAACCGTAAA AAGGCCGCGT TGCTGGCGTT TTTCCATAGG
      TTTTCCGGTC CTTGGCATTT TTCCGGCGCA ACGACCGCAA AAAGGTATCC

1151  CTCCGCCCCC CTGACGAGCA TCACAAAAAT CGACGCTCAA GTCAGAGGTG
      GAGGCGGGGG GACTGCTCGT AGTGTTTTTA GCTGCGAGTT CAGTCTCCAC

1201  GCGAAACCCG ACAGGACTAT AAAGATACCA GGCGTTTCCC CCTGGAAGCT
      CGCTTTGGGC TGTCCTGATA TTTCTATGGT CCGCAAAGGG GGACCTTCGA

        BssSI
       ~~~~~~~
1251  CCCTCGTGCG CTCTCCTGTT CCGACCCTGC CGCTTACCGG ATACCTGTCC
      GGGAGCACGC GAGAGGACAA GGCTGGGACG GCGAATGGCC TATGGACAGG

1301  GCCTTTCTCC CTTCGGGAAG CGTGGCGCTT TCTCATAGCT CACGCTGTAG
      CGGAAAGAGG GAAGCCCTTC GCACCGCGAA AGAGTATCGA GTGCGACATC
```

FIG. 35E

```
1351  GTATCTCAGT TCGGTGTAGG TCGTTCGCTC CAAGCTGGGC TGTGTGCACG
      CATAGAGTCA AGCCACATCC AGCAAGCGAG GTTCGACCCG ACACACGTGC

1401  AACCCCCCGT TCAGCCCGAC CGCTGCGCCT TATCCGGTAA CTATCGTCTT
      TTGGGGGGCA AGTCGGGCTG GCGACGCGGA ATAGGCCATT GATAGCAGAA

1451  GAGTCCAACC CGGTAAGACA CGACTTATCG CCACTGGCAG CAGCCACTGG
      CTCAGGTTGG GCCATTCTGT GCTGAATAGC GGTGACCGTC GTCGGTGACC

1501  TAACAGGATT AGCAGAGCGA GGTATGTAGG CGGTGCTACA GAGTTCTTGA
      ATTGTCCTAA TCGTCTCGCT CCATACATCC GCCACGATGT CTCAAGAACT

1551  AGTGGTGGCC TAACTACGGC TACACTAGAA GAACAGTATT TGGTATCTGC
      TCACCACCGG ATTGATGCCG ATGTGATCTT CTTGTCATAA ACCATAGACG

1601  GCTCTGCTGT AGCCAGTTAC CTTCGGAAAA AGAGTTGGTA GCTCTTGATC
      CGAGACGACA TCGGTCAATG GAAGCCTTTT TCTCAACCAT CGAGAACTAG

1651  CGGCAAACAA ACCACCGCTG GTAGCGGTGG TTTTTTTGTT TGCAAGCAGC
      GCCGTTTGTT TGGTGGCGAC CATCGCCACC AAAAAAACAA ACGTTCGTCG

1701  AGATTACGCG CAGAAAAAAA GGATCTCAAG AAGATCCTTT GATCTTTTCT
      TCTAATGCGC GTCTTTTTTT CCTAGAGTTC TTCTAGGAAA CTAGAAAAGA
```

FIG. 35F

```
1751  ACGGGGTCTG ACGCTCAGTG GAACGAAAAC TCACGTTAAG GGATTTTGGT
      TGCCCCAGAC TGCGAGTCAC CTTGCTTTTG AGTGCAATTC CCTAAAACCA

        BglII
       ~~~~~~
1801  CAGATCTAGC ACCAGGCGTT TAAGGGCACC AATAACTGCC TTAAAAAAAT
      GTCTAGATCG TGGTCCGCAA ATTCCCGTGG TTATTGACGG AATTTTTTTA

1851  TACGCCCCGC CCTGCCACTC ATCGCAGTAC TGTTGTAATT CATTAAGCAT
      ATGCGGGGCG GGACGGTGAG TAGCGTCATG ACAACATTAA GTAATTCGTA

1901  TCTGCCGACA TGGAAGCCAT CACAAACGGC ATGATGAACC TGAATCGCCA
      AGACGGCTGT ACCTTCGGTA GTGTTTGCCG TACTACTTGG ACTTAGCGGT

1951  GCGGCATCAG CACCTTGTCG CCTTGCGTAT AATATTTGCC CATAGTGAAA
      CGCCGTAGTC GTGGAACAGC GGAACGCATA TTATAAACGG GTATCACTTT

2001  ACGGGGGCGA AGAAGTTGTC CATATTGGCT ACGTTTAAAT CAAAACTGGT
      TGCCCCCGCT TCTTCAACAG GTATAACCGA TGCAAATTTA GTTTTGACCA

2051  GAAACTCACC CAGGGATTGG CTGAGACGAA AAACATATTC TCAATAAACC
      CTTTGAGTGG GTCCCTAACC GACTCTGCTT TTTGTATAAG AGTTATTTGG
```

FIG. 35G

| | | | | | |
|---|---|---|---|---|---|
| 2101 | CTTTAGGGAA | ATAGGCCAGG | TTTTCACCGT | AACACGCCAC | ATCTTGCGAA |
| | GAAATCCCTT | TATCCGGTCC | AAAAGTGGCA | TTGTGCGGTG | TAGAACGCTT |
| 2151 | TATATGTGTA | GAAACTGCCG | GAAATCGTCG | TGGTATTCAC | TCCAGAGCGA |
| | ATATACACAT | CTTTGACGGC | CTTTAGCAGC | ACCATAAGTG | AGGTCTCGCT |
| 2201 | TGAAAACGTT | TCAGTTTGCT | CATGGAAAAC | GGTGTAACAA | GGGTGAACAC |
| | ACTTTTGCAA | AGTCAAACGA | GTACCTTTTG | CCACATTGTT | CCCACTTGTG |
| 2251 | TATCCCATAT | CACCAGCTCA | CCGTCTTTCA | TTGCCATACG | GAACTCCGGG |
| | ATAGGGTATA | GTGGTCGAGT | GGCAGAAAGT | AACGGTATGC | CTTGAGGCCC |
| 2301 | TGAGCATTCA | TCAGGCGGGC | AAGAATGTGA | ATAAAGGCCG | GATAAAACTT |
| | ACTCGTAAGT | AGTCCGCCCG | TTCTTACACT | TATTTCCGGC | CTATTTTGAA |
| 2351 | GTGCTTATTT | TTCTTTACGG | TCTTTAAAAA | GGCCGTAATA | TCCAGCTGAA |
| | CACGAATAAA | AAGAAATGCC | AGAAATTTTT | CCGGCATTAT | AGGTCGACTT |
| 2401 | CGGTCTGGTT | ATAGGTACAT | TGAGCAACTG | ACTGAAATGC | CTCAAAATGT |
| | GCCAGACCAA | TATCCATGTA | ACTCGTTGAC | TGACTTTACG | GAGTTTTACA |
| 2451 | TCTTTACGAT | GCCATTGGGA | TATATCAACG | GTGGTATATC | CAGTGATTTT |
| | AGAAATGCTA | CGGTAACCCT | ATATAGTTGC | CACCATATAG | GTCACTAAAA |

FIG. 35H

```
2501   TTTCTCCATT TTAGCTTCCT TAGCTCCTGA AAATCTCGAT AACTCAAAAA
       AAAGAGGTAA AATCGAAGGA ATCGAGGACT TTTAGAGCTA TTGAGTTTTT

2551   ATACGCCCGG TAGTGATCTT ATTTCATTAT GGTGAAAGTT GGAACCTCAC
       TATGCGGGCC ATCACTAGAA TAAAGTAATA CCACTTTCAA CCTTGGAGTG

         AatII
       ~~~~~~~
2601   CCGACGTCTA ATGTGAGTTA GCTCACTCAT TAGGCACCCC AGGCTTTACA
       GGCTGCAGAT TACACTCAAT CGAGTGAGTA ATCCGTGGGG TCCGAAATGT

2651   CTTTATGCTT CCGGCTCGTA TGTTGTGTGG AATTGTGAGC GGATAACAAT
       GAAATACGAA GGCCGAGCAT ACAACACACC TTAACACTCG CCTATTGTTA

                                                 XbaI   SphI
                                               ~~~~~~~~~~~~~~
2701   TTCACACAGG AAACAGCTAT GACCATGATT ACGAATTTCT AGAGCATGCG
       AAGTGTGTCC TTTGTCGATA CTGGTACTAA TGCTTAAAGA TCTCGTACGC

       EcoRI

2751   GGGGG
       CCCCC
```

FIG. 35I

M2
173 bp

```
M 2:

     AatII
    ~~~~~~~
  1 GACGTCTTAA TGTGAGTTAG CTCACTCATT AGGCACCCCA GGCTTTACAC
    CTGCAGAATT ACACTCAATC GAGTGAGTAA TCCGTGGGGT CCGAAATGTG

 51 TTTATGCTTC CGGCTCGTAT GTTGTGTGGA ATTGTGAGCG GATAACAATT
    AAATACGAAG GCCGAGCATA CAACACACCT TAACACTCGC CTATTGTTAA

                                          XmnI
                                      ~~~~~~~~~~~
                                   XbaI
                                 ~~~~~~~~
101 TCACACAGGA AACAGCTATG ACCATGTCTA GAATAACTTC GTATAATGTA
    AGTGTGTCCT TTGTCGATAC TGGTACAGAT CTTATTGAAG CATATTACAT

                          SphI
                         ~~~~~~
151 CGCTATACGA AGTTATCGCA TGC
    GCGATATGCT TCAATAGCGT ACG
```

FIG. 35K

M3
47 bp

```
M 3:

     BglII                                                AatII
    ~~~~~~                                                ~~~~~~
1   AGATCTCATA ACTTCGTATA ATGTATGCTA TACGAAGTTA TGACGTC
    TCTAGAGTAT TGAAGCATAT TACATACGAT ATGCTTCAAT ACTGCAG
```

FIG. 35M

M7-I (long)
1255 bp

M 7-I (long):

```
      EcoRI
     ~~~~~~
  1  GAATTCGGTG GTGGTGGATC TGCGTGCGCT GAAACGGTTG AAAGTTGTTT
     CTTAAGCCAC CACCACCTAG ACGCACGCGA CTTTGCCAAC TTTCAACAAA

 51  AGCAAAATCC CATACAGAAA ATTCATTTAC TAACGTCTGG AAAGACGACA
     TCGTTTTAGG GTATGTCTTT TAAGTAAATG ATTGCAGACC TTTCTGCTGT

101  AAACTTTAGA TCGTTACGCT AACTATGAGG GCTGTCTGTG GAATGCTACA
     TTTGAAATCT AGCAATGCGA TTGATACTCC CGACAGACAC CTTACGATGT

151  GGCGTTGTAG TTTGTACTGG TGACGAAACT CAGTGTTACG GTACATGGGT
     CCGCAACATC AAACATGACC ACTGCTTTGA GTCACAATGC CATGTACCCA

201  TCCTATTGGG CTTGCTATCC CTGAAAATGA GGGTGGTGGC TCTGAGGGTG
     AGGATAACCC GAACGATAGG GACTTTTACT CCCACCACCG AGACTCCCAC

251  GCGGTTCTGA GGGTGGCGGT TCTGAGGGTG GCGGTACTAA ACCTCCTGAG
     CGCCAAGACT CCCACCGCCA AGACTCCCAC CGCCATGATT TGGAGGACTC

301  TACGGTGATA CACCTATTCC GGGCTATACT TATATCAACC CTCTCGACGG
     ATGCCACTAT GTGGATAAGG CCCGATATGA ATATAGTTGG GAGAGCTGCC
```

FIG. 35O

```
351  CACTTATCCG CCTGGTACTG AGCAAAACCC CGCTAATCCT AATCCTTCTC
     GTGAATAGGC GGACCATGAC TCGTTTTGGG GCGATTAGGA TTAGGAAGAG

401  TTGAGGAGTC TCAGCCTCTT AATACTTTCA TGTTTCAGAA TAATAGGTTC
     AACTCCTCAG AGTCGGAGAA TTATGAAAGT ACAAAGTCTT ATTATCCAAG

451  CGAAATAGGC AGGGGGCATT AACTGTTTAT ACGGGCACTG TTACTCAAGG
     GCTTTATCCG TCCCCCGTAA TTGACAAATA TGCCCGTGAC AATGAGTTCC

501  CACTGACCCC GTTAAAACTT ATTACCAGTA CACTCCTGTA TCATCAAAAG
     GTGACTGGGG CAATTTTGAA TAATGGTCAT GTGAGGACAT AGTAGTTTTC

551  CCATGTATGA CGCTTACTGG AACGGTAAAT TCAGAGACTG CGCTTTCCAT
     GGTACATACT GCGAATGACC TTGCCATTTA AGTCTCTGAC GCGAAAGGTA

601  TCTGGCTTTA ATGAGGATTT ATTTGTTTGT GAATATCAAG GCCAATCGTC
     AGACCGAAAT TACTCCTAAA TAAACAAACA CTTATAGTTC CGGTTAGCAG

651  TGACCTGCCT CAACCTCCTG TCAATGCTGG CGGCGGCTCT GGTGGTGGTT
     ACTGGACGGA GTTGGAGGAC AGTTACGACC GCCGCCGAGA CCACCACCAA

701  CTGGTGGCGG CTCTGAGGGT GGTGGCTCTG AGGGTGGCGG TTCTGAGGGT
     GACCACCGCC GAGACTCCCA CCACCGAGAC TCCCACCGCC AAGACTCCCA
```

FIG. 35P

```
 751  GGCGGCTCTG AGGGAGGCGG TTCCGGTGGT GGCTCTGGTT CCGGTGATTT
      CCGCCGAGAC TCCCTCCGCC AAGGCCACCA CCGAGACCAA GGCCACTAAA

 801  TGATTATGAA AAGATGGCAA ACGCTAATAA GGGGGCTATG ACCGAAAATG
      ACTAATACTT TTCTACCGTT TGCGATTATT CCCCCGATAC TGGCTTTTAC

 851  CCGATGAAAA CGCGCTACAG TCTGACGCTA AAGGCAAACT TGATTCTGTC
      GGCTACTTTT GCGCGATGTC AGACTGCGAT TTCCGTTTGA ACTAAGACAG

 901  GCTACTGATT ACGGTGCTGC TATCGATGGT TTCATTGGTG ACGTTTCCGG
      CGATGACTAA TGCCACGACG ATAGCTACCA AAGTAACCAC TGCAAAGGCC

 951  CCTTGCTAAT GGTAATGGTG CTACTGGTGA TTTTGCTGGC TCTAATTCCC
      GGAACGATTA CCATTACCAC GATGACCACT AAAACGACCG AGATTAAGGG

                                                  XmnI
                                               ~~~~~~~~~~
1001  AAATGGCTCA AGTCGGTGAA GGTGATAATT CACCTTTAAT GAATAATTTC
      TTTACCGAGT TCAGCCACTT CCACTATTAA GTGGAAATTA CTTATTAAAG

1051  CGTCAATATT TACCTTCCAT CCCTCAATCG GTTGAATGTC GCCCTTTTGT
      GCAGTTATAA ATGGAAGGTA GGGAGTTAGC CAACTTACAG CGGGAAAACA
```

FIG. 35Q

```
1101  CTTTGGCGCT GGTAAACCCT ATGAATTTTC TATTGATTGT GACAAAATAA
      GAAACCGCGA CCATTTGGGA TACTTAAAAG ATAACTAACA CTGTTTTATT

1151  ACTTATTCCG TGGTGTCTTT GCGTTTCTTT TATATGTTGC CACCTTTATG
      TGAATAAGGC ACCACAGAAA CGCAAAGAAA ATATACAACG GTGGAAATAC

                                                  HindIII
                                                        ~
1201  TATGTATTTT CTACGTTTGC TAACATACTG CGTAATAAGG AGTCTTGATA
      ATACATAAAA GATGCAAACG ATTGTATGAC GCATTATTCC TCAGAACTAT

      HindI
      ~~~~
1251  AGCTT
      TCGAA
```

FIG. 35R

M 7-II (ss-TAG):

```
           EcoRI
          ~~~~~~~
  1    CGGGAATTCG GAGGCGGTTC CGGTGGTGGC TCTGGTTCCG GTGATTTTGA
       GCCCTTAAGC CTCCGCCAAG GCCACCACCG AGACCAAGGC CACTAAAACT

 51    TTATGAAAAG ATGGCAAACG CTAATAAGGG GGCTATGACC GAAAATGCCG
       AATACTTTTC TACCGTTTGC GATTATTCCC CCGATACTGG CTTTTACGGC

101    ATGAAAACGC GCTACAGTCT GACGCTAAAG GCAAACTTGA TTCTGTCGCT
       TACTTTTGCG CGATGTCAGA CTGCGATTTC CGTTTGAACT AAGACAGCGA

151    ACTGATTACG GTGCTGCTAT CGATGGTTTC ATTGGTGACG TTTCCGGCCT
       TGACTAATGC CACGACGATA GCTACCAAAG TAACCACTGC AAAGGCCGGA

201    TGCTAATGGT AATGGTGCTA CTGGTGATTT TGCTGGCTCT AATTCCCAAA
       ACGATTACCA TTACCACGAT GACCACTAAA ACGACCGAGA TTAAGGGTTT

                                                  XmnI
                                            ~~~~~~~~~~~~
251    TGGCTCAAGT CGGTGACGGT GATAATTCAC CTTTAATGAA TAATTTCCGT
       ACCGAGTTCA GCCACTGCCA CTATTAAGTG GAAATTACTT ATTAAAGGCA
```

FIG. 35T

```
301   CAATATTTAC CTTCCCTCCC TCAATCGGTT GAATGTCGCC CTTTTGTCTT
      GTTATAAATG GAAGGGAGGG AGTTAGCCAA CTTACAGCGG GAAAACAGAA

351   TGGCGCTGGT AAACCATATG AATTTTCTAT TGATTGTGAC AAAATAAACT
      ACCGCGACCA TTTGGTATAC TTAAAAGATA ACTAACACTG TTTTATTTGA

401   TATTCCGTGG TGTCTTTGCG TTTCTTTTAT ATGTTGCCAC CTTTATGTAT
      ATAAGGCACC ACAGAAACGC AAAGAAAATA TACAACGGTG GAAATACATA

                                                   HindIII
                                                      ~~~~
451   GTATTTTCTA CGTTTGCTAA CATACTGCGT AATAAGGAGT CTTGATAAGC
      CATAAAAGAT GCAAACGATT GTATGACGCA TTATTCCTCA GAACTATTCG

      Hi
      ~
501   TT
      AA
```

FIG. 35U

M8
47 bp

```
M 8:

     SphI                                                HindIII
    ~~~~~~                                                ~~~~~
1   GCATGCCATA ACTTCGTATA ATGTACGCTA TACGAAGTTA TAAGCTT
    CGTACGGTAT TGAAGCATAT TACATGCGAT ATGCTTCAAT ATTCGAA
```

FIG. 35W

```
M 10-II:

          BsrGI
         ~~~~~~~~
  1   GGGGGTGTAC ATTCAAATAT GTATCCGCTC ATGAGACAAT AACCCTGATA
      CCCCCACATG TAAGTTTATA CATAGGCGAG TACTCTGTTA TTGGGACTAT

 51   AATGCTTCAA TAATATTGAA AAAGGAAGAG TATGAGTATT CAACATTTCC
      TTACGAAGTT ATTATAACTT TTTCCTTCTC ATACTCATAA GTTGTAAAGG

101   GTGTCGCCCT TATTCCCTTT TTTGCGGCAT TTTGCCTTCC TGTTTTTGCT
      CACAGCGGGA ATAAGGGAAA AAACGCCGTA AAACGGAAGG ACAAAAACGA

151   CACCCAGAAA CGCTGGTGAA AGTAAAAGAT GCTGAGGATC AGTTGGGTGC
      GTGGGTCTTT GCGACCACTT TCATTTTCTA CGACTCCTAG TCAACCCACG

201   GCGAGTGGGT TACATCGAAC TGGATCTCAA CAGCGGTAAG ATCCTTGAGA
      CGCTCACCCA ATGTAGCTTG ACCTAGAGTT GTCGCCATTC TAGGAACTCT

                     XmnI
                ~~~~~~~~~~~~
251   GTTTTCGCCC CGAAGAACGT TTTCCAATGA TGAGCACTTT TAAAGTTCTG
      CAAAAGCGGG GCTTCTTGCA AAAGGTTACT ACTCGTGAAA ATTTCAAGAC
```

FIG. 35Y

```
301  CTATGTGGCG CGGTATTATC CCGTATTGAC GCCGGGCAAG AGCAACTCGG
     GATACACCGC GCCATAATAG GGCATAACTG CGGCCCGTTC TCGTTGAGCC

351  TCGCCGCATA CACTATTCTC AGAATGACTT GGTTGAGTAC TCACCAGTCA
     AGCGGCGTAT GTGATAAGAG TCTTACTGAA CCAACTCATG AGTGGTCAGT

401  CAGAAAAGCA TCTTACGGAT GGCATGACAG TAAGAGAATT ATGCAGTGCT
     GTCTTTTCGT AGAATGCCTA CCGTACTGTC ATTCTCTTAA TACGTCACGA

451  GCCATAACCA TGAGTGATAA CACTGCGGCC AACTTACTTC TGACAACGAT
     CGGTATTGGT ACTCACTATT GTGACGCCGG TTGAATGAAG ACTGTTGCTA

501  CGGAGGACCG AAGGAGCTAA CCGCTTTTTT GCACAACATG GGGGATCATG
     GCCTCCTGGC TTCCTCGATT GGCGAAAAAA CGTGTTGTAC CCCCTAGTAC

551  TAACTCGCCT TGATCGTTGG GAACCGGAGC TGAATGAAGC CATACCAAAC
     ATTGAGCGGA ACTAGCAACC CTTGGCCTCG ACTTACTTCG GTATGGTTTG

601  GACGAGCGTG ACACCACGAT GCCTGTAGCA ATGGCAACAA CGTTGCGCAA
     CTGCTCGCAC TGTGGTGCTA CGGACATCGT TACCGTTGTT GCAACGCGTT

651  ACTATTAACT GGCGAACTAC TTACTCTAGC TTCCCGGCAA CAGTTAATAG
     TGATAATTGA CCGCTTGATG AATGAGATCG AAGGGCCGTT GTCAATTATC
```

FIG. 35Z

```
 701  ACTGGATGGA GGCGGATAAA GTTGCAGGAC CACTTCTGCG CTCGGCCCTT
      TGACCTACCT CCGCCTATTT CAACGTCCTG GTGAAGACGC GAGCCGGGAA

 751  CCGGCTGGCT GGTTTATTGC TGATAAATCT GGAGCCGGTG AGCGTGGGTC
      GGCCGACCGA CCAAATAACG ACTATTTAGA CCTCGGCCAC TCGCACCCAG

 801  TCGCGGTATC ATTGCAGCAC TGGGGCCAGA TGGTAAGCCC TCCCGTATCG
      AGCGCCATAG TAACGTCGTG ACCCCGGTCT ACCATTCGGG AGGGCATAGC

 851  TAGTTATCTA CACGACGGGG AGTCAGGCAA CTATGGATGA ACGAAATAGA
      ATCAATAGAT GTGCTGCCCC TCAGTCCGTT GATACCTACT TGCTTTATCT

 901  CAGATCGCTG AGATAGGTGC CTCACTGATT AAGCATTGGG TAACTGTCAG
      GTCTAGCGAC TCTATCCACG GAGTGACTAA TTCGTAACCC ATTGACAGTC

 951  ACCAAGTTTA CTCATATATA CTTTAGATTG ATTTAAAACT TCATTTTTAA
      TGGTTCAAAT GAGTATATAT GAAATCTAAC TAAATTTTGA AGTAAAAATT

1001  TTTAAAAGGA TCTAGGTGAA GATCCTTTTT GATAATCTCA TGACCAAAAT
      AAATTTTCCT AGATCCACTT CTAGGAAAAA CTATTAGAGT ACTGGTTTTA

1051  CCCTTAACGT GAGTTTTCGT TCCACTGAGC GTCAGACCCC GTAGAAAAGA
      GGGAATTGCA CTCAAAAGCA AGGTGACTCG CAGTCTGGGG CATCTTTTCT
```

FIG. 35AA

```
                                                      FseI         PacI
                                                   ~~~~~~~~~~         ~~
1101  TCAAAGGATC TTCTTGAGAT CCTTTTTGAT AATGGCCGGC CCCCCCCCTT
      AGTTTCCTAG AAGAACTCTA GGAAAAACTA TTACCGGCCG GGGGGGGGAA

      PacI
      ~~~~~~
1151  AATTAAGGGG GGG
      TTAATTCCCC CCC
```

FIG. 35BB

```
M11-II:

       NheI
     ~~~~~~~
  1  GCTAGCACGC GCCCTGTAGC GGCGCATTAA GCGCGGCGGG TGTGGTGGTT
     CGATCGTGCG CGGGACATCG CCGCGTAATT CGCGCCGCCC ACACCACCAA

 51  ACGCGCAGCG TGACCGCTAC ACTTGCCAGC GCCCTAGCGC CCGCTCCTTT
     TGCGCGTCGC ACTGGCGATG TGAACGGTCG CGGGATCGCG GGCGAGGAAA

101  CGCTTTCTTC CCTTCCTTTC TCGCCACGTT CGCCGGCTTT CCCCGTCAAG
     GCGAAAGAAG GGAAGGAAAG AGCGGTGCAA GCGGCCGAAA GGGGCAGTTC

                  BanII
                 ~~~~~~~
151  CTCTAAATCG GGGGCTCCCT TTAGGGTTCC GATTTAGTGC TTTACGGCAC
     GAGATTTAGC CCCCGAGGGA AATCCCAAGG CTAAATCACG AAATGCCGTG

201  CTCGACCCCA AAAAACTTGA TTAGGGTGAT GGTTCTCGTA GTGGGCCATC
     GAGCTGGGGT TTTTTGAACT AATCCCACTA CCAAGAGCAT CACCCGGTAG

251  GCCCTGATAG ACGGTTTTTC GCCCTTTGAC GTTGGAGTCC ACGTTCTTTA
     CGGGACTATC TGCCAAAAAG CGGGAAACTG CAACCTCAGG TGCAAGAAAT
```

FIG. 35DD

```
301  ATAGTGGACT CTTGTTCCAA ACTGGAACAA CACTCAACCC TATCTCGGTC
     TATCACCTGA GAACAAGGTT TGACCTTGTT GTGAGTTGGG ATAGAGCCAG

351  TATTCTTTTG ATTTATAAGG GATTTTGCCG ATTTCGGCCT ATTGGTTAAA
     ATAAGAAAAC TAAATATTCC CTAAAACGGC TAAAGCCGGA TAACCAATTT

401  AAATGAGCTG ATTTAACAAA AATTTAACGC GAATTTTAAC AAAATATTAA
     TTTACTCGAC TAAATTGTTT TTAAATTGCG CTTAAAATTG TTTTATAATT

                     BsrGI
                    ~~~~~~
451  CGTTTACAAT TTCATGTACA
     GCAAATGTTA AAGTACATGT
```

FIG. 35EE

```
M  12:
      BglII
     ~~~~~~~
  1  AGATCTAATA AGATGATCTT CTTGAGATCG TTTTGGTCTG CGCGTAATCT
     TCTAGATTAT TCTACTAGAA GAACTCTAGC AAAACCAGAC GCGCATTAGA

 51  CTTGCTCTGA AAACGAAAAA ACCGCCTTGC AGGGCGGTTT TTCGTAGGTT
     GAACGAGACT TTTGCTTTTT TGGCGGAACG TCCCGCCAAA AAGCATCCAA

101  CTCTGAGCTA CCAACTCTTT GAACCGAGGT AACTGGCTTG GAGGAGCGCA
     GAGACTCGAT GGTTGAGAAA CTTGGCTCCA TTGACCGAAC CTCCTCGCGT

151  GTCACTAAAA CTTGTCCTTT CAGTTTAGCC TTAACCGGCG CATGACTTCA
     CAGTGATTTT GAACAGGAAA GTCAAATCGG AATTGGCCGC GTACTGAAGT

201  AGACTAACTC CTCTAAATCA ATTACCAGTG GCTGCTGCCA GTGGTGCTTT
     TCTGATTGAG GAGATTTAGT TAATGGTCAC CGACGACGGT CACCACGAAA

251  TGCATGTCTT TCCGGGTTGG ACTCAAGACG ATAGTTACCG GATAAGGCGC
     ACGTACAGAA AGGCCCAACC TGAGTTCTGC TATCAATGGC CTATTCCGCG

301  AGCGGTCGGA CTGAACGGGG GGTTCGTGCA TACAGTCCAG CTTGGAGCGA
     TCGCCAGCCT GACTTGCCCC CCAAGCACGT ATGTCAGGTC GAACCTCGCT
```

*FIG. 35GG*

```
351  ACTGCCTACC CGGAACTGAG TGTCAGGCGT GGAATGAGAC AAACGCGGCC
     TGACGGATGG GCCTTGACTC ACAGTCCGCA CCTTACTCTG TTTGCGCCGG

                       AgeI
                     ~~~~~~~~
401  ATAACAGCGG AATGACACCG GTAAACCGAA AGGCAGGAAC AGGAGAGCGC
     TATTGTCGCC TTACTGTGGC CATTTGGCTT TCCGTCCTTG TCCTCTCGCG

451  AGGAGGGAGC CGCCAGGGGG AAACGCCTGG TATCTTTATA GTCCTGTCGG
     TCCTCCCTCG GCGGTCCCCC TTTGCGGACC ATAGAAATAT CAGGACAGCC

501  GTTTCGCCAC CACTGATTTG AGCGTCAGAT TTCGTGATGC TTGTCAGGGG
     CAAAGCGGTG GTGACTAAAC TCGCAGTCTA AAGCACTACG AACAGTCCCC

551  GGCGGAGCCT ATGGAAAAAC GGCTTTGCCG CGGCCCTCTC ACTTCCCTGT
     CCGCCTCGGA TACCTTTTTG CCGAAACGGC GCCGGGAGAG TGAAGGGACA

601  TAAGTATCTT CCTGGCATCT TCCAGGAAAT CTCCGCCCCG TTCGTAAGCC
     ATTCATAGAA GGACCGTAGA AGGTCCTTTA GAGGCGGGGC AAGCATTCGG

651  ATTTCCGCTC GCCGCAGTCG AACGACCGAG CGTAGCGAGT CAGTGAGCGA
     TAAAGGCGAG CGGCGTCAGC TTGCTGGCTC GCATCGCTCA GTCACTCGCT
```

FIG. 35HH

```
                                                      AgeI
                                                    ~~~~~~~
701  GGAAGCGGAA TATATCCTGT ATCACATATT CTGCTGACGC ACCGGTGCAG
     CCTTCGCCTT ATATAGGACA TAGTGTATAA GACGACTGCG TGGCCACGTC

                                 XmnI
                              ~~~~~~~~~~~
751  CCTTTTTTCT CCTGCCACAT GAAGCACTTC ACTGACACCC TCATCAGTGC
     GGAAAAAAGA GGACGGTGTA CTTCGTGAAG TGACTGTGGG AGTAGTCACG

                                      NheI
                                    ~~~~~~
801  CAACATAGTA AGCCAGTATA CACTCCGCTA GC
     GTTGTATCAT TCGGTCATAT GTGAGGCGAT CG
```

*FIG. 35II*

M 13:

```
     BglII                                              XmnI      BglII
     ~~~~~~                                         ~~~~~~~~~~~~~~~~~~
1    AGATCTCATA ACTTCGTATA ATGTATGCTA TACGAAGTTA TTCAGATCT
     TCTAGAGTAT TGAAGCATAT TACATACGAT ATGCTTCAAT AAGTCTAGA
```

FIG. 35KK

M19
96 bp

```
M 19:

     XbaI   SphI
    ~~~~~~~~~~~~~~~
 1  TCTAGAGCAT GCGTAGGAGA AAATAAAATG AAACAAAGCA CTATTGCACT
    AGATCTCGTA CGCATCCTCT TTTATTTTAC TTTGTTTCGT GATAACGTGA

                   SapI                            EcoRI
                 ~~~~~~~~~                        ~~~~~~
51  GGCACTCTTA CCGTTGCTCT TCACCCCTGT TACCAAAGCC GAATTC
    CCGTGAGAAT GGCAACGAGA AGTGGGGACA ATGGTTTCGG CTTAAG
```

FIG. 35MM

```
M 20:

      XbaI   SphI
     --------------
  1  TCTAGAGCAT GCGTAGGAGA AAATAAAATG AAACAAAGCA CTATTGCACT
     AGATCTCGTA CGCATCCTCT TTTATTTTAC TTTGTTTCGT GATAACGTGA

                      SapI
                    ---------
 51  GGCACTCTTA CCGTTGCTCT TCACCCCTGT TACCAAAGCC GACTACAAAG
     CCGTGAGAAT GGCAACGAGA AGTGGGGACA ATGGTTTCGG CTGATGTTTC

              MunI    EcoRI
             --------------
101  ATGAAGTGCA ATTGGAATTC
     TACTTCACGT TAACCTTAAG
```

FIG. 35OO

M21
96 bp

```
M 21:

      XbaI
     ~~~~~~
 1   TCTAGAGGTT GAGGTGATTT TATGAAAAAG AATATCGCAT TTCTTCTTGC
     AGATCTCCAA CTCCACTAAA ATACTTTTTC TTATAGCGTA AAGAAGAACG

                                       NsiI        EcoRI
                                     ~~~~~~~~    ~~~~~~
51   ATCTATGTTC GTTTTTTCTA TTGCTACAAA TGCATACGCT GAATTC
     TAGATACAAG CAAAAAAGAT AACGATGTTT ACGTATGCGA CTTAAG
```

FIG. 35QQ

```
M 41:

      NheI
     ~~~~~~
  1  GCTAGCATCG AATGGCGCAA AACCTTTCGC GGTATGGCAT GATAGCGCCC
     CGATCGTAGC TTACCGCGTT TTGGAAAGCG CCATACCGTA CTATCGCGGG

 51  GGAAGAGAGT CAATTCAGGG TGGTGAATGT GAAACCAGTA ACGTTATACG
     CCTTCTCTCA GTTAAGTCCC ACCACTTACA CTTTGGTCAT TGCAATATGC

101  ATGTCGCAGA GTATGCCGGT GTCTCTTATC AGACCGTTTC CCGCGTGGTG
     TACAGCGTCT CATACGGCCA CAGAGAATAG TCTGGCAAAG GGCGCACCAC

151  AACCAGGCCA GCCACGTTTC TGCGAAAACG CGGGAAAAAG TGGAAGCGGC
     TTGGTCCGGT CGGTGCAAAG ACGCTTTTGC GCCCTTTTTC ACCTTCGCCG

201  GATGGCGGAG CTGAATTACA TTCCTAACCG CGTGGCACAA CAACTGGCGG
     CTACCGCCTC GACTTAATGT AAGGATTGGC GCACCGTGTT GTTGACCGCC

251  GCAAACAGTC GTTGCTGATT GGCGTTGCCA CCTCCAGTCT GGCCCTGCAC
     CGTTTGTCAG CAACGACTAA CCGCAACGGT GGAGGTCAGA CCGGGACGTG

301  GCGCCGTCGC AAATTGTCGC GGCGATTAAA TCTCGCGCCG ATCAACTGGG
     CGCGGCAGCG TTTAACAGCG CCGCTAATTT AGAGCGCGGC TAGTTGACCC
```

FIG. 35SS

```
351  TGCCAGCGTG GTCGTGTCGA TGGTAGAACG AAGCGGCGTC GAAGCCTGTA
     ACGGTCGCAC CAGCACAGCT ACCATCTTGC TTCGCCGCAG CTTCGGACAT

401  AAGCGGCGGT GCACAATCTT CTCGCGCAAC GTGTCAGTGG GCTGATTATT
     TTCGCCGCCA CGTGTTAGAA GAGCGCGTTG CACAGTCACC CGACTAATAA

451  AACTATCCGC TGGATGACCA GGATGCTATT GCTGTGGAAG CTGCCTGCAC
     TTGATAGGCG ACCTACTGGT CCTACGATAA CGACACCTTC GACGGACGTG

501  TAATGTTCCG GCGTTATTTC TTGATGTCTC TGACCAGACA CCCATCAACA
     ATTACAAGGC CGCAATAAAG AACTACAGAG ACTGGTCTGT GGGTAGTTGT

551  GTATTATTTT CTCCCATGAG GACGGTACGC GACTGGGCGT GGAGCATCTG
     CATAATAAAA GAGGGTACTC CTGCCATGCG CTGACCCGCA CCTCGTAGAC

601  GTCGCATTGG GCCACCAGCA AATCGCGCTG TTAGCTGGCC CATTAAGTTC
     CAGCGTAACC CGGTGGTCGT TTAGCGCGAC AATCGACCGG GTAATTCAAG

651  TGTCTCGGCG CGTCTGCGTC TGGCTGGCTG GCATAAATAT CTCACTCGCA
     ACAGAGCCGC GCAGACGCAG ACCGACCGAC CGTATTTATA GAGTGAGCGT

701  ATCAAATTCA GCCGATAGCG GAACGGGAAG GCGACTGGAG TGCCATGTCC
     TAGTTTAAGT CGGCTATCGC CTTGCCCTTC CGCTGACCTC ACGGTACAGG
```

FIG. 35TT

```
751   GGTTTTCAAC AAACCATGCA AATGCTGAAT GAGGGCATCG TTCCCACTGC
      CCAAAAGTTG TTTGGTACGT TTACGACTTA CTCCCGTAGC AAGGGTGACG

801   GATGCTGGTT GCCAACGATC AGATGGCGCT GGGCGCAATG CGTGCCATTA
      CTACGACCAA CGGTTGCTAG TCTACCGCGA CCCGCGTTAC GCACGGTAAT

851   CCGAGTCCGG GCTGCGCGTT GGTGCGGACA TCTCGGTAGT GGGATACGAC
      GGCTCAGGCC CGACGCGCAA CCACGCCTGT AGAGCCATCA CCCTATGCTG

901   GATACCGAGG ACAGCTCATG TTATATCCCG CCGCTGACCA CCATCAAACA
      CTATGGCTCC TGTCGAGTAC AATATAGGGC GGCGACTGGT GGTAGTTTGT

951   GGATTTTCGC CTGCTGGGGC AAACCAGCGT GGACCGCTTG CTGCAACTCT
      CCTAAAAGCG GACGACCCCG TTTGGTCGCA CCTGGCGAAC GACGTTGAGA

1001  CTCAGGGCCA GGCGGTGAAG GGCAATCAGC TGTTGCCCGT CTCACTGGTG
      GAGTCCCGGT CCGCCACTTC CCGTTAGTCG ACAACGGGCA GAGTGACCAC

1051  AAAAGAAAAA CCACCCTGGC TCCCAATACG CAAACCGCCT CTCCCCGCGC
      TTTTCTTTTT GGTGGGACCG AGGGTTATGC GTTTGGCGGA GAGGGGCGCG

1101  GTTGGCCGAT TCACTGATGC AGCTGGCACG ACAGGTTTCC CGACTGGAAA
      CAACCGGCTA AGTGACTACG TCGACCGTGC TGTCCAAAGG GCTGACCTTT
```

FIG. 35UU

```
1151  GCGGGCAGTG AGGCTACCCG ATAAAAGCGG CTTCCTGACA GGAGGCCGTT
      CGCCCGTCAC TCCGATGGGC TATTTTCGCC GAAGGACTGT CCTCCGGCAA

                          AflII
                         ~~~~~~~
1201  TTGTTTTGCA GCCCACTTAA G
      AACAAAACGT CGGGTGAATT C
```

FIG. 35VV

```
pCALO-1:
     BglII
     ~~~~~~
  1  GATCTAGCAC CAGGCGTTTA AGGGCACCAA TAACTGCCTT AAAAAAATTA
     CTAGATCGTG GTCCGCAAAT TCCCGTGGTT ATTGACGGAA TTTTTTTAAT

 51  CGCCCCGCCC TGCCACTCAT CGCAGTACTG TTGTAATTCA TTAAGCATTC
     GCGGGGCGGG ACGGTGAGTA GCGTCATGAC AACATTAAGT AATTCGTAAG

101  TGCCGACATG GAAGCCATCA CAAACGGCAT GATGAACCTG AATCGCCAGC
     ACGGCTGTAC CTTCGGTAGT GTTTGCCGTA CTACTTGGAC TTAGCGGTCG

151  GGCATCAGCA CCTTGTCGCC TTGCGTATAA TATTTGCCCA TAGTGAAAAC
     CCGTAGTCGT GGAACAGCGG AACGCATATT ATAAACGGGT ATCACTTTTG

201  GGGGGCGAAG AAGTTGTCCA TATTGGCTAC GTTTAAATCA AAACTGGTGA
     CCCCCGCTTC TTCAACAGGT ATAACCGATG CAAATTTAGT TTTGACCACT

251  AACTCACCCA GGGATTGGCT GAGACGAAAA ACATATTCTC AATAAACCCT
     TTGAGTGGGT CCCTAACCGA CTCTGCTTTT TGTATAAGAG TTATTTGGGA

301  TTAGGGAAAT AGGCCAGGTT TTCACCGTAA CACGCCACAT CTTGCGAATA
     AATCCCTTTA TCCGGTCCAA AAGTGGCATT GTGCGGTGTA GAACGCTTAT
```

*FIG. 35XX*

```
351  TATGTGTAGA AACTGCCGGA AATCGTCGTG GTATTCACTC CAGAGCGATG
     ATACACATCT TTGACGGCCT TTAGCAGCAC CATAAGTGAG GTCTCGCTAC

401  AAAACGTTTC AGTTTGCTCA TGGAAAACGG TGTAACAAGG GTGAACACTA
     TTTTGCAAAG TCAAACGAGT ACCTTTTGCC ACATTGTTCC CACTTGTGAT

451  TCCCATATCA CCAGCTCACC GTCTTTCATT GCCATACGGA ACTCCGGGTG
     AGGGTATAGT GGTCGAGTGG CAGAAAGTAA CGGTATGCCT TGAGGCCCAC

501  AGCATTCATC AGGCGGGCAA GAATGTGAAT AAAGGCCGGA TAAAACTTGT
     TCGTAAGTAG TCCGCCCGTT CTTACACTTA TTTCCGGCCT ATTTTGAACA

551  GCTTATTTTT CTTTACGGTC TTTAAAAAGG CCGTAATATC CAGCTGAACG
     CGAATAAAAA GAAATGCCAG AAATTTTTCC GGCATTATAG GTCGACTTGC

601  GTCTGGTTAT AGGTACATTG AGCAACTGAC TGAAATGCCT CAAAATGTTC
     CAGACCAATA TCCATGTAAC TCGTTGACTG ACTTTACGGA GTTTTACAAG

651  TTTACGATGC CATTGGGATA TATCAACGGT GGTATATCCA GTGATTTTTT
     AAATGCTACG GTAACCCTAT ATAGTTGCCA CCATATAGGT CACTAAAAAA

701  TCTCCATTTT AGCTTCCTTA GCTCCTGAAA ATCTCGATAA CTCAAAAAAT
     AGAGGTAAAA TCGAAGGAAT CGAGGACTTT TAGAGCTATT GAGTTTTTTA
```

FIG. 35YY

```
751   ACGCCCGGTA GTGATCTTAT TTCATTATGG TGAAAGTTGG AACCTCACCC
      TGCGGGCCAT CACTAGAATA AAGTAATACC ACTTTCAACC TTGGAGTGGG

       AatII
      ~~~~~~~
801   GACGTCTAAT GTGAGTTAGC TCACTCATTA GGCACCCCAG GCTTTACACT
      CTGCAGATTA CACTCAATCG AGTGAGTAAT CCGTGGGGTC CGAAATGTGA

851   TTATGCTTCC GGCTCGTATG TTGTGTGGAA TTGTGAGCGG ATAACAATTT
      AATACGAAGG CCGAGCATAC AACACACCTT AACACTCGCC TATTGTTAAA

                                           XbaI
                                         ~~~~~~~~
901   CACACAGGAA ACAGCTATGA CCATGATTAC GAATTTCTAG ACCCCCCCCC
      GTGTGTCCTT TGTCGATACT GGTACTAATG CTTAAAGATC TGGGGGGGGG

        SphI                                        HindIII
      ~~~~~~~                                       ~~~~~~~
951   CGCATGCCAT AACTTCGTAT AATGTACGCT ATACGAAGTT ATAAGCTTGA
      GCGTACGGTA TTGAAGCATA TTACATGCGA TATGCTTCAA TATTCGAACT

1001  CCTGTGAAGT GAAAAATGGC GCAGATTGTG CGACATTTTT TTTGTCTGCC
      GGACACTTCA CTTTTTACCG CGTCTAACAC GCTGTAAAAA AAACAGACGG
```

FIG. 35ZZ

```
              PacI                           FseI                          BsrGI
            ~~~~~~~~~                      ~~~~~~~~~                      ~~~~~~~~
1051   GTTTAATTAA  AGGGGGGGGG  GGGCCGGCCT  GGGGGGGGGT  GTACATGAAA
       CAAATTAATT  TCCCCCCCCC  CCCGGCCGGA  CCCCCCCCCA  CATGTACTTT

1101   TTGTAAACGT  TAATATTTTG  TTAAAATTCG  CGTTAAATTT  TTGTTAAATC
       AACATTTGCA  ATTATAAAAC  AATTTTAAGC  GCAATTTAAA  AACAATTTAG

1151   AGCTCATTTT  TTAACCAATA  GGCCGAAATC  GGCAAAATCC  CTTATAAATC
       TCGAGTAAAA  AATTGGTTAT  CCGGCTTTAG  CCGTTTTAGG  GAATATTTAG

1201   AAAAGAATAG  ACCGAGATAG  GGTTGAGTGT  TGTTCCAGTT  TGGAACAAGA
       TTTTCTTATC  TGGCTCTATC  CCAACTCACA  ACAAGGTCAA  ACCTTGTTCT

1251   GTCCACTATT  AAAGAACGTG  GACTCCAACG  TCAAAGGGCG  AAAAACCGTC
       CAGGTGATAA  TTTCTTGCAC  CTGAGGTTGC  AGTTTCCCGC  TTTTTGGCAG

1301   TATCAGGGCG  ATGGCCCACT  ACGAGAACCA  TCACCCTAAT  CAAGTTTTTT
       ATAGTCCCGC  TACCGGGTGA  TGCTCTTGGT  AGTGGGATTA  GTTCAAAAAA

                                                             BanII
                                                            ~~~~~~
1351   GGGGTCGAGG  TGCCGTAAAG  CACTAAATCG  GAACCCTAAA  GGGAGCCCCC
       CCCCAGCTCC  ACGGCATTTC  GTGATTTAGC  CTTGGGATTT  CCCTCGGGGG
```

FIG. 35AAA

```
1401  GATTTAGAGC TTGACGGGGA AAGCCGGCGA ACGTGGCGAG AAAGGAAGGG
      CTAAATCTCG AACTGCCCCT TTCGGCCGCT TGCACCGCTC TTTCCTTCCC

1451  AAGAAAGCGA AAGGAGCGGG CGCTAGGGCG CTGGCAAGTG TAGCGGTCAC
      TTCTTTCGCT TTCCTCGCCC GCGATCCCGC GACCGTTCAC ATCGCCAGTG

1501  GCTGCGCGTA ACCACCACAC CCGCCGCGCT TAATGCGCCG CTACAGGGCG
      CGACGCGCAT TGGTGGTGTG GGCGGCGCGA ATTACGCGGC GATGTCCCGC

         NheI
        ~~~~~~~
1551  CGTGCTAGCG GAGTGTATAC TGGCTTACTA TGTTGGCACT GATGAGGGTG
      GCACGATCGC CTCACATATG ACCGAATGAT ACAACCGTGA CTACTCCCAC

             XmnI                                  AgeI
        ~~~~~~~~~~~~                             ~~~~~~~~
1601  TCAGTGAAGT GCTTCATGTG GCAGGAGAAA AAAGGCTGCA CCGGTGCGTC
      AGTCACTTCA CGAAGTACAC CGTCCTCTTT TTTCCGACGT GGCCACGCAG

1651  AGCAGAATAT GTGATACAGG ATATATTCCG CTTCCTCGCT CACTGACTCG
      TCGTCTTATA CACTATGTCC TATATAAGGC GAAGGAGCGA GTGACTGAGC

1701  CTACGCTCGG TCGTTCGACT GCGGCGAGCG GAAATGGCTT ACGAACGGGG
```

FIG. 35BBB

```
     GATGCGAGCC AGCAAGCTGA CGCCGCTCGC CTTTACCGAA TGCTTGCCCC

1751 CGGAGATTTC CTGGAAGATG CCAGGAAGAT ACTTAACAGG GAAGTGAGAG
     GCCTCTAAAG GACCTTCTAC GGTCCTTCTA TGAATTGTCC CTTCACTCTC

1801 GGCCGCGGCA AAGCCGTTTT TCCATAGGCT CCGCCCCCCT GACAAGCATC
     CCGGCGCCGT TTCGGCAAAA AGGTATCCGA GGCGGGGGGA CTGTTCGTAG

1851 ACGAAATCTG ACGCTCAAAT CAGTGGTGGC GAAACCCGAC AGGACTATAA
     TGCTTTAGAC TGCGAGTTTA GTCACCACCG CTTTGGGCTG TCCTGATATT

1901 AGATACCAGG CGTTTCCCCC TGGCGGCTCC CTCCTGCGCT CTCCTGTTCC
     TCTATGGTCC GCAAAGGGGG ACCGCCGAGG GAGGACGCGA GAGGACAAGG

                  AgeI
                 ~~~~~~
1951 TGCCTTTCGG TTTACCGGTG TCATTCCGCT GTTATGGCCG CGTTTGTCTC
     ACGGAAAGCC AAATGGCCAC AGTAAGGCGA CAATACCGGC GCAAACAGAG

2001 ATTCCACGCC TGACACTCAG TTCCGGGTAG GCAGTTCGCT CCAAGCTGGA
     TAAGGTGCGG ACTGTGAGTC AAGGCCCATC CGTCAAGCGA GGTTCGACCT

2051 CTGTATGCAC GAACCCCCCG TTCAGTCCGA CCGCTGCGCC TTATCCGGTA
     GACATACGTG CTTGGGGGGC AAGTCAGGCT GGCGACGCGG AATAGGCCAT
```

FIG. 35CCC

```
2101  ACTATCGTCT TGAGTCCAAC CCGGAAAGAC ATGCAAAAGC ACCACTGGCA
      TGATAGCAGA ACTCAGGTTG GGCCTTTCTG TACGTTTTCG TGGTGACCGT

2151  GCAGCCACTG GTAATTGATT TAGAGGAGTT AGTCTTGAAG TCATGCGCCG
      CGTCGGTGAC CATTAACTAA ATCTCCTCAA TCAGAACTTC AGTACGCGGC

2201  GTTAAGGCTA AACTGAAAGG ACAAGTTTTA GTGACTGCGC TCCTCCAAGC
      CAATTCCGAT TTGACTTTCC TGTTCAAAAT CACTGACGCG AGGAGGTTCG

2251  CAGTTACCTC GGTTCAAAGA GTTGGTAGCT CAGAGAACCT ACGAAAAACC
      GTCAATGGAG CCAAGTTTCT CAACCATCGA GTCTCTTGGA TGCTTTTTGG

2301  GCCCTGCAAG GCGGTTTTTT CGTTTTCAGA GCAAGAGATT ACGCGCAGAC
      CGGGACGTTC CGCCAAAAAA GCAAAAGTCT CGTTCTCTAA TGCGCGTCTG

                                BglII
                                    ~
2351  CAAAACGATC TCAAGAAGAT CATCTTATTA
      GTTTTGCTAG AGTTCTTCTA GTAGAATAAT
```

FIG. 35DDD

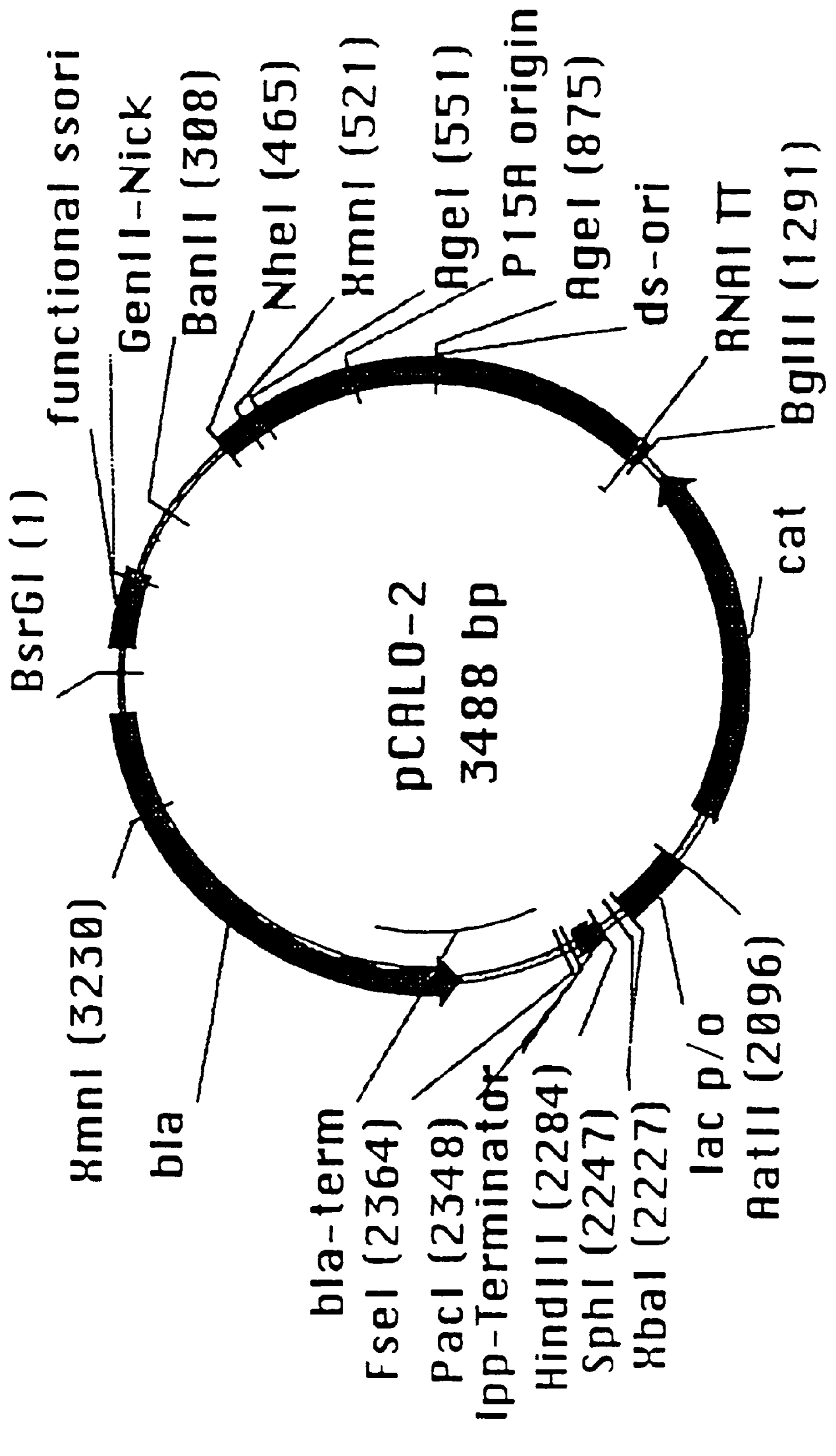
FIG. 35EEE

```
pCALO-2:
    BsrGI
    ~~~~~~
  1 GTACATGAAA TTGTAAACGT TAATATTTTG TTAAAATTCG CGTTAAATTT
    CATGTACTTT AACATTTGCA ATTATAAAAC AATTTTAAGC GCAATTTAAA

 51 TTGTTAAATC AGCTCATTTT TTAACCAATA GGCCGAAATC GGCAAAATCC
    AACAATTTAG TCGAGTAAAA AATTGGTTAT CCGGCTTTAG CCGTTTTAGG

101 CTTATAAATC AAAAGAATAG ACCGAGATAG GGTTGAGTGT TGTTCCAGTT
    GAATATTTAG TTTTCTTATC TGGCTCTATC CCAACTCACA ACAAGGTCAA

151 TGGAACAAGA GTCCACTATT AAAGAACGTG GACTCCAACG TCAAAGGGCG
    ACCTTGTTCT CAGGTGATAA TTTCTTGCAC CTGAGGTTGC AGTTTCCCGC

201 AAAAACCGTC TATCAGGGCG ATGGCCCACT ACGAGAACCA TCACCCTAAT
    TTTTTGGCAG ATAGTCCCGC TACCGGGTGA TGCTCTTGGT AGTGGGATTA

251 CAAGTTTTTT GGGGTCGAGG TGCCGTAAAG CACTAAATCG GAACCCTAAA
    GTTCAAAAAA CCCCAGCTCC ACGGCATTTC GTGATTTAGC CTTGGGATTT

        BanII
       ~~~~~~~
301 GGGAGCCCCC GATTTAGAGC TTGACGGGGA AAGCCGGCGA ACGTGGCGAG
```

FIG. 35FFF

```
       CCCTCGGGGG CTAAATCTCG AACTGCCCCT TTCGGCCGCT TGCACCGCTC

351    AAAGGAAGGG AAGAAAGCGA AAGGAGCGGG CGCTAGGGCG CTGGCAAGTG
       TTTCCTTCCC TTCTTTCGCT TTCCTCGCCC GCGATCCCGC GACCGTTCAC

401    TAGCGGTCAC GCTGCGCGTA ACCACCACAC CCGCCGCGCT TAATGCGCCG
       ATCGCCAGTG CGACGCGCAT TGGTGGTGTG GGCGGCGCGA ATTACGCGGC

                    NheI
                  ~~~~~~
451    CTACAGGGCG CGTGCTAGCG GAGTGTATAC TGGCTTACTA TGTTGGCACT
       GATGTCCCGC GCACGATCGC CTCACATATG ACCGAATGAT ACAACCGTGA

                        XmnI                              AgeI
                     ~~~~~~~~~~~~                            ~
501    GATGAGGGTG TCAGTGAAGT GCTTCATGTG GCAGGAGAAA AAAGGCTGCA
       CTACTCCCAC AGTCACTTCA CGAAGTACAC CGTCCTCTTT TTTCCGACGT

       AgeI
       ~~~~~
551    CCGGTGCGTC AGCAGAATAT GTGATACAGG ATATATTCCG CTTCCTCGCT
       GGCCACGCAG TCGTCTTATA CACTATGTCC TATATAAGGC GAAGGAGCGA

601    CACTGACTCG CTACGCTCGG TCGTTCGACT GCGGCGAGCG GAAATGGCTT
```

FIG. 35GGG

```
      GTGACTGAGC GATGCGAGCC AGCAAGCTGA CGCCGCTCGC CTTTACCGAA

651   ACGAACGGGG CGGAGATTTC CTGGAAGATG CCAGGAAGAT ACTTAACAGG
      TGCTTGCCCC GCCTCTAAAG GACCTTCTAC GGTCCTTCTA TGAATTGTCC

701   GAAGTGAGAG GGCCGCGGCA AAGCCGTTTT TCCATAGGCT CCGCCCCCCT
      CTTCACTCTC CCGGCGCCGT TTCGGCAAAA AGGTATCCGA GGCGGGGGGA

751   GACAAGCATC ACGAAATCTG ACGCTCAAAT CAGTGGTGGC GAAACCCGAC
      CTGTTCGTAG TGCTTTAGAC TGCGAGTTTA GTCACCACCG CTTTGGGCTG

801   AGGACTATAA AGATACCAGG CGTTTCCCCC TGGCGGCTCC CTCCTGCGCT
      TCCTGATATT TCTATGGTCC GCAAAGGGGG ACCGCCGAGG GAGGACGCGA

                                 AgeI
                                ~~~~~~
851   CTCCTGTTCC TGCCTTTCGG TTTACCGGTG TCATTCCGCT GTTATGGCCG
      GAGGACAAGG ACGGAAAGCC AAATGGCCAC AGTAAGGCGA CAATACCGGC

901   CGTTTGTCTC ATTCCACGCC TGACACTCAG TTCCGGGTAG GCAGTTCGCT
      GCAAACAGAG TAAGGTGCGG ACTGTGAGTC AAGGCCCATC CGTCAAGCGA

951   CCAAGCTGGA CTGTATGCAC GAACCCCCCG TTCAGTCCGA CCGCTGCGCC
      GGTTCGACCT GACATACGTG CTTGGGGGGC AAGTCAGGCT GGCGACGCGG
```

*FIG. 35HHH*

```
1001  TTATCCGGTA ACTATCGTCT TGAGTCCAAC CCGGAAAGAC ATGCAAAAGC
      AATAGGCCAT TGATAGCAGA ACTCAGGTTG GGCCTTTCTG TACGTTTTCG

1051  ACCACTGGCA GCAGCCACTG GTAATTGATT TAGAGGAGTT AGTCTTGAAG
      TGGTGACCGT CGTCGGTGAC CATTAACTAA ATCTCCTCAA TCAGAACTTC

1101  TCATGCGCCG GTTAAGGCTA AACTGAAAGG ACAAGTTTTA GTGACTGCGC
      AGTACGCGGC CAATTCCGAT TTGACTTTCC TGTTCAAAAT CACTGACGCG

1151  TCCTCCAAGC CAGTTACCTC GGTTCAAAGA GTTGGTAGCT CAGAGAACCT
      AGGAGGTTCG GTCAATGGAG CCAAGTTTCT CAACCATCGA GTCTCTTGGA

1201  ACGAAAAACC GCCCTGCAAG GCGGTTTTTT CGTTTTCAGA GCAAGAGATT
      TGCTTTTTGG CGGGACGTTC CGCCAAAAAA GCAAAAGTCT CGTTCTCTAA

                                                BglII
                                              ~~~~~~~~
1251  ACGCGCAGAC CAAAACGATC TCAAGAAGAT CATCTTATTA GATCTAGCAC
      TGCGCGTCTG GTTTTGCTAG AGTTCTTCTA GTAGAATAAT CTAGATCGTG

1301  CAGGCGTTTA AGGGCACCAA TAACTGCCTT AAAAAAATTA CGCCCCGCCC
      GTCCGCAAAT TCCCGTGGTT ATTGACGGAA TTTTTTTAAT GCGGGGCGGG
```

FIG. 35III

```
1351  TGCCACTCAT CGCAGTACTG TTGTAATTCA TTAAGCATTC TGCCGACATG
      ACGGTGAGTA GCGTCATGAC AACATTAAGT AATTCGTAAG ACGGCTGTAC

1401  GAAGCCATCA CAAACGGCAT GATGAACCTG AATCGCCAGC GGCATCAGCA
      CTTCGGTAGT GTTTGCCGTA CTACTTGGAC TTAGCGGTCG CCGTAGTCGT

1451  CCTTGTCGCC TTGCGTATAA TATTTGCCCA TAGTGAAAAC GGGGGCGAAG
      GGAACAGCGG AACGCATATT ATAAACGGGT ATCACTTTTG CCCCCGCTTC

1501  AAGTTGTCCA TATTGGCTAC GTTTAAATCA AAACTGGTGA AACTCACCCA
      TTCAACAGGT ATAACCGATG CAAATTTAGT TTTGACCACT TTGAGTGGGT

1551  GGGATTGGCT GAGACGAAAA ACATATTCTC AATAAACCCT TTAGGGAAAT
      CCCTAACCGA CTCTGCTTTT TGTATAAGAG TTATTTGGGA AATCCCTTTA

1601  AGGCCAGGTT TTCACCGTAA CACGCCACAT CTTGCGAATA TATGTGTAGA
      TCCGGTCCAA AAGTGGCATT GTGCGGTGTA GAACGCTTAT ATACACATCT

1651  AACTGCCGGA AATCGTCGTG GTATTCACTC CAGAGCGATG AAAACGTTTC
      TTGACGGCCT TTAGCAGCAC CATAAGTGAG GTCTCGCTAC TTTTGCAAAG

1701  AGTTTGCTCA TGGAAAACGG TGTAACAAGG GTGAACACTA TCCCATATCA
      TCAAACGAGT ACCTTTTGCC ACATTGTTCC CACTTGTGAT AGGGTATAGT
```

FIG. 35JJJ

```
1751  CCAGCTCACC GTCTTTCATT GCCATACGGA ACTCCGGGTG AGCATTCATC
      GGTCGAGTGG CAGAAAGTAA CGGTATGCCT TGAGGCCCAC TCGTAAGTAG

1801  AGGCGGGCAA GAATGTGAAT AAAGGCCGGA TAAAACTTGT GCTTATTTTT
      TCCGCCCGTT CTTACACTTA TTTCCGGCCT ATTTTGAACA CGAATAAAAA

1851  CTTTACGGTC TTTAAAAAGG CCGTAATATC CAGCTGAACG GTCTGGTTAT
      GAAATGCCAG AAATTTTTCC GGCATTATAG GTCGACTTGC CAGACCAATA

1901  AGGTACATTG AGCAACTGAC TGAAATGCCT CAAAATGTTC TTTACGATGC
      TCCATGTAAC TCGTTGACTG ACTTTACGGA GTTTTACAAG AAATGCTACG

1951  CATTGGGATA TATCAACGGT GGTATATCCA GTGATTTTTT TCTCCATTTT
      GTAACCCTAT ATAGTTGCCA CCATATAGGT CACTAAAAAA AGAGGTAAAA

2001  AGCTTCCTTA GCTCCTGAAA ATCTCGATAA CTCAAAAAAT ACGCCCGGTA
      TCGAAGGAAT CGAGGACTTT TAGAGCTATT GAGTTTTTTA TGCGGGCCAT

                                                AatII
                                               ~~~~~~
2051  GTGATCTTAT TTCATTATGG TGAAAGTTGG AACCTCACCC GACGTCTAAT
      CACTAGAATA AAGTAATACC ACTTTCAACC TTGGAGTGGG CTGCAGATTA

2101  GTGAGTTAGC TCACTCATTA GGCACCCCAG GCTTTACACT TTATGCTTCC
```

*FIG. 35KKK*

```
     CACTCAATCG AGTGAGTAAT CCGTGGGGTC CGAAATGTGA AATACGAAGG

2151 GGCTCGTATG TTGTGTGGAA TTGTGAGCGG ATAACAATTT CACACAGGAA
     CCGAGCATAC AACACACCTT AACACTCGCC TATTGTTAAA GTGTGTCCTT

                                XbaI               SphI
                              ~~~~~~~~            ~~~~~~~
2201 ACAGCTATGA CCATGATTAC GAATTTCTAG ACCCCCCCCC CGCATGCCAT
     TGTCGATACT GGTACTAATG CTTAAAGATC TGGGGGGGGG GCGTACGGTA

                                         HindIII
                                         ~~~~~~
2251 AACTTCGTAT AATGTACGCT ATACGAAGTT ATAAGCTTGA CCTGTGAAGT
     TTGAAGCATA TTACATGCGA TATGCTTCAA TATTCGAACT GGACACTTCA

                                                     PacI
                                                  ~~~~~~~~~
2301 GAAAAATGGC GCAGATTGTG CGACATTTTT TTTGTCTGCC GTTTAATTAA
     CTTTTTACCG CGTCTAACAC GCTGTAAAAA AAACAGACGG CAAATTAATT

         FseI
      ~~~~~~~~~~
2351 GGGGGGGGGC CGGCCATTAT CAAAAAGGAT CTCAAGAAGA TCCTTTGATC
     CCCCCCCCCG GCCGGTAATA GTTTTTCCTA GAGTTCTTCT AGGAAACTAG
```

FIG. 35LLL

```
2401  TTTTCTACGG GGTCTGACGC TCAGTGGAAC GAAAACTCAC GTTAAGGGAT
      AAAAGATGCC CCAGACTGCG AGTCACCTTG CTTTTGAGTG CAATTCCCTA

2451  TTTGGTCATG AGATTATCAA AAAGGATCTT CACCTAGATC CTTTTAAATT
      AAACCAGTAC TCTAATAGTT TTTCCTAGAA GTGGATCTAG GAAAATTTAA

2501  AAAAATGAAG TTTTAAATCA ATCTAAAGTA TATATGAGTA AACTTGGTCT
      TTTTTACTTC AAAATTTAGT TAGATTTCAT ATATACTCAT TTGAACCAGA

2551  GACAGTTACC CAATGCTTAA TCAGTGAGGC ACCTATCTCA GCGATCTGTC
      CTGTCAATGG GTTACGAATT AGTCACTCCG TGGATAGAGT CGCTAGACAG

2601  TATTTCGTTC ATCCATAGTT GCCTGACTCC CCGTCGTGTA GATAACTACG
      ATAAAGCAAG TAGGTATCAA CGGACTGAGG GGCAGCACAT CTATTGATGC

2651  ATACGGGAGG GCTTACCATC TGGCCCCAGT GCTGCAATGA TACCGCGAGA
      TATGCCCTCC CGAATGGTAG ACCGGGGTCA CGACGTTACT ATGGCGCTCT

2701  CCCACGCTCA CCGGCTCCAG ATTTATCAGC AATAAACCAG CCAGCCGGAA
      GGGTGCGAGT GGCCGAGGTC TAAATAGTCG TTATTTGGTC GGTCGGCCTT

2751  GGGCCGAGCG CAGAAGTGGT CCTGCAACTT TATCCGCCTC CATCCAGTCT
      CCCGGCTCGC GTCTTCACCA GGACGTTGAA ATAGGCGGAG GTAGGTCAGA
```

FIG. 35MMM

```
2801  ATTAACTGTT GCCGGGAAGC TAGAGTAAGT AGTTCGCCAG TTAATAGTTT
      TAATTGACAA CGGCCCTTCG ATCTCATTCA TCAAGCGGTC AATTATCAAA

2851  GCGCAACGTT GTTGCCATTG CTACAGGCAT CGTGGTGTCA CGCTCGTCGT
      CGCGTTGCAA CAACGGTAAC GATGTCCGTA GCACCACAGT GCGAGCAGCA

2901  TTGGTATGGC TTCATTCAGC TCCGGTTCCC AACGATCAAG GCGAGTTACA
      AACCATACCG AAGTAAGTCG AGGCCAAGGG TTGCTAGTTC CGCTCAATGT

2951  TGATCCCCCA TGTTGTGCAA AAAAGCGGTT AGCTCCTTCG GTCCTCCGAT
      ACTAGGGGGT ACAACACGTT TTTTCGCCAA TCGAGGAAGC CAGGAGGCTA

3001  CGTTGTCAGA AGTAAGTTGG CCGCAGTGTT ATCACTCATG GTTATGGCAG
      GCAACAGTCT TCATTCAACC GGCGTCACAA TAGTGAGTAC CAATACCGTC

3051  CACTGCATAA TTCTCTTACT GTCATGCCAT CCGTAAGATG CTTTTCTGTG
      GTGACGTATT AAGAGAATGA CAGTACGGTA GGCATTCTAC GAAAAGACAC

3101  ACTGGTGAGT ACTCAACCAA GTCATTCTGA GAATAGTGTA TGCGGCGACC
      TGACCACTCA TGAGTTGGTT CAGTAAGACT CTTATCACAT ACGCCGCTGG

3151  GAGTTGCTCT TGCCCGGCGT CAATACGGGA TAATACCGCG CCACATAGCA
      CTCAACGAGA ACGGGCCGCA GTTATGCCCT ATTATGGCGC GGTGTATCGT
```

*FIG. 35NNN*

```
                                         XmnI
                                     ~~~~~~~~~~~~~
3201  GAACTTTAAA AGTGCTCATC ATTGGAAAAC GTTCTTCGGG GCGAAAACTC
      CTTGAAATTT TCACGAGTAG TAACCTTTTG CAAGAAGCCC CGCTTTTGAG

3251  TCAAGGATCT TACCGCTGTT GAGATCCAGT TCGATGTAAC CCACTCGCGC
      AGTTCCTAGA ATGGCGACAA CTCTAGGTCA AGCTACATTG GGTGAGCGCG

3301  ACCCAACTGA TCCTCAGCAT CTTTTACTTT CACCAGCGTT TCTGGGTGAG
      TGGGTTGACT AGGAGTCGTA GAAAATGAAA GTGGTCGCAA AGACCCACTC

3351  CAAAAACAGG AAGGCAAAAT GCCGCAAAAA AGGGAATAAG GGCGACACGG
      GTTTTTGTCC TTCCGTTTTA CGGCGTTTTT TCCCTTATTC CCGCTGTGCC

3401  AAATGTTGAA TACTCATACT CTTCCTTTTT CAATATTATT GAAGCATTTA
      TTTACAACTT ATGAGTATGA GAAGGAAAAA GTTATAATAA CTTCGTAAAT

                                           BsrGI

3451  TCAGGGTTAT TGTCTCATGA GCGGATACAT ATTTGAAT
      AGTCCCAATA ACAGAGTACT CGCCTATGTA TAAACTTA
```

FIG. 35OOO

Figure 35A:
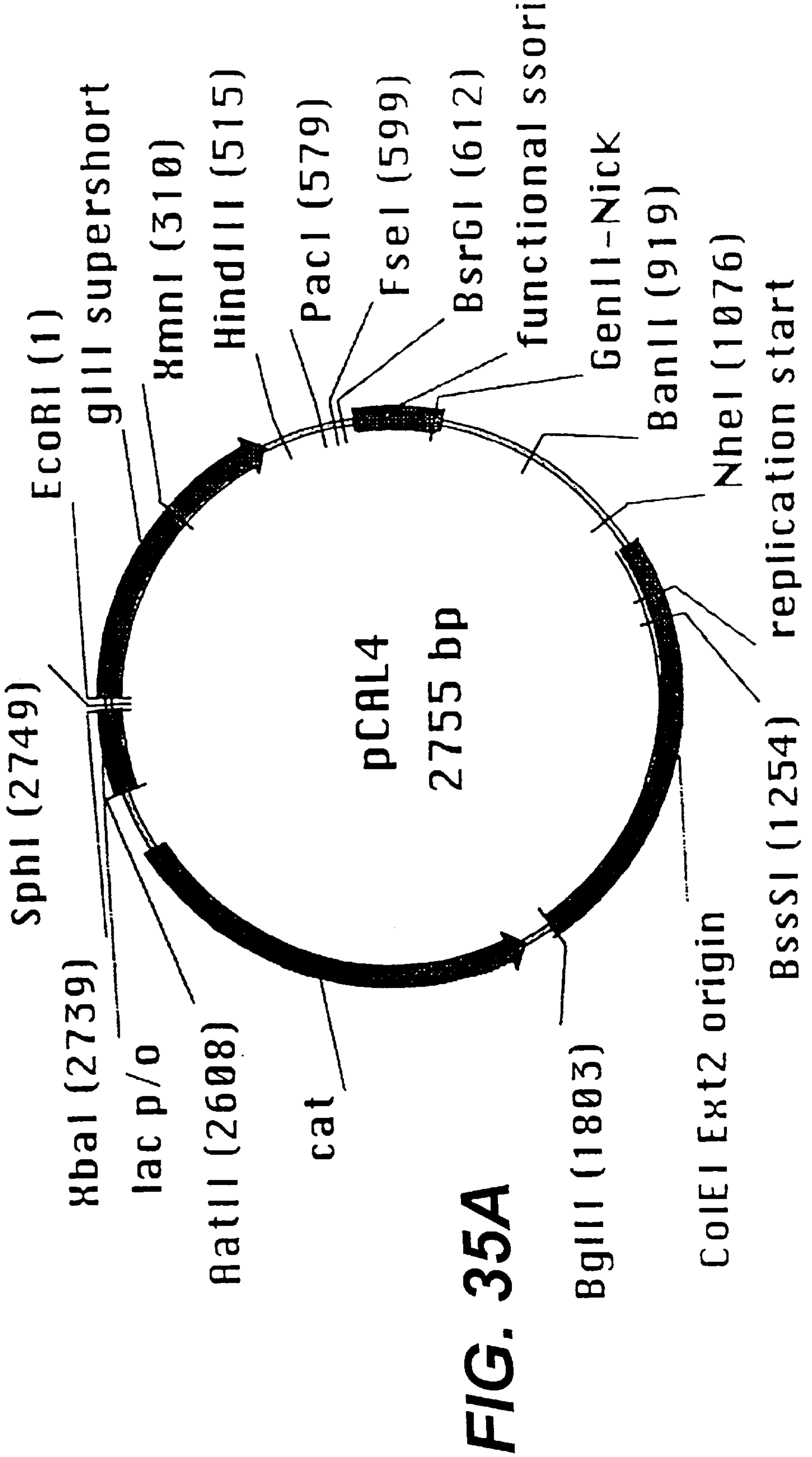
Figure 35J:
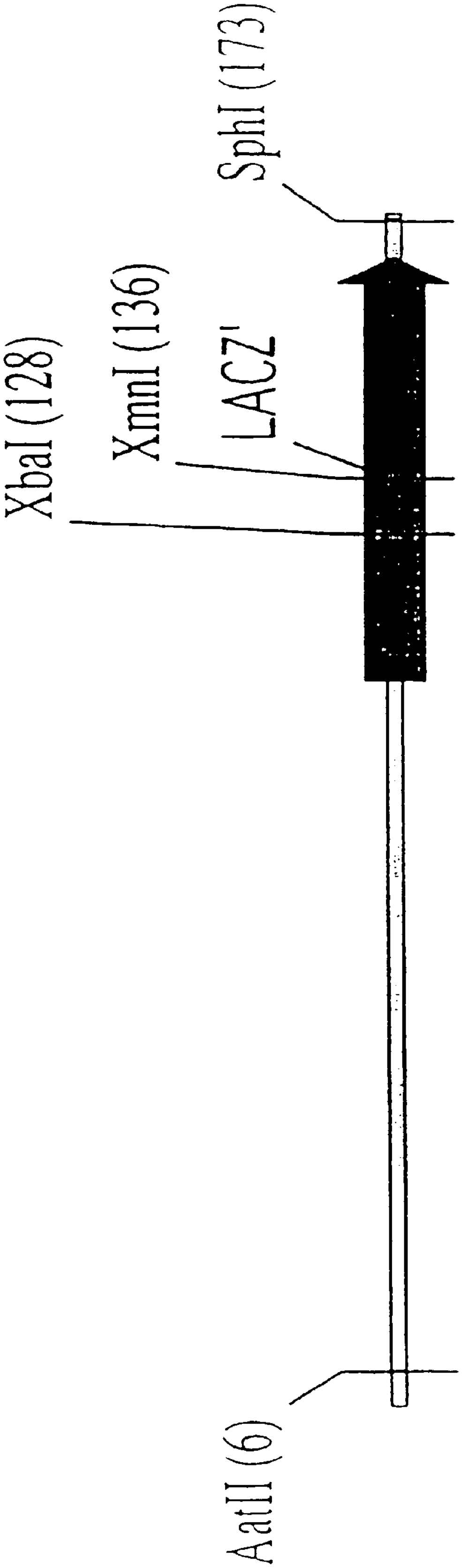
Figure 35L:
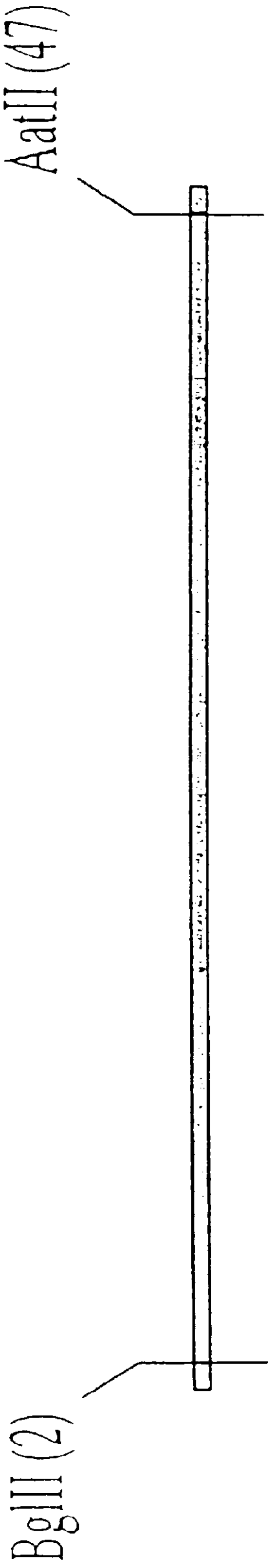
Figure 35N:
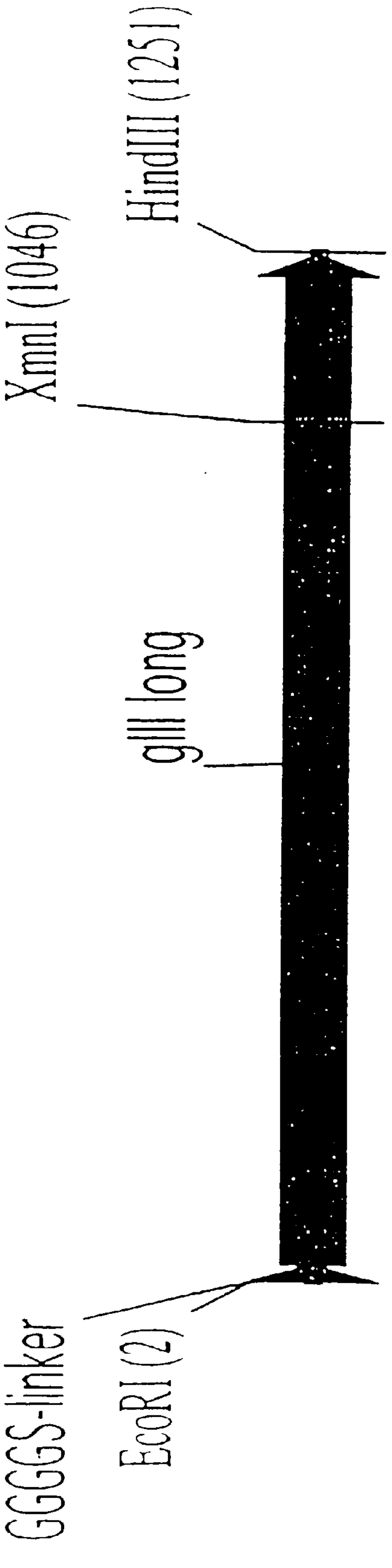
Figure 35S:
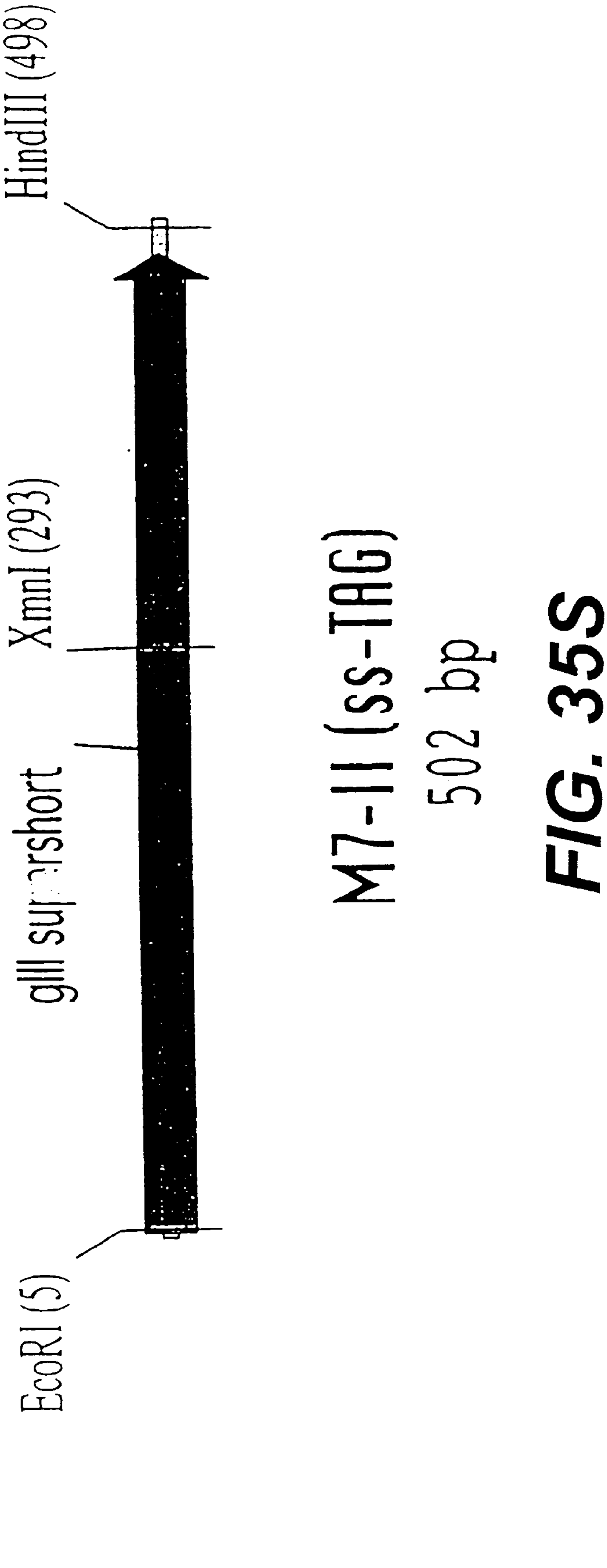
Figure 35V:
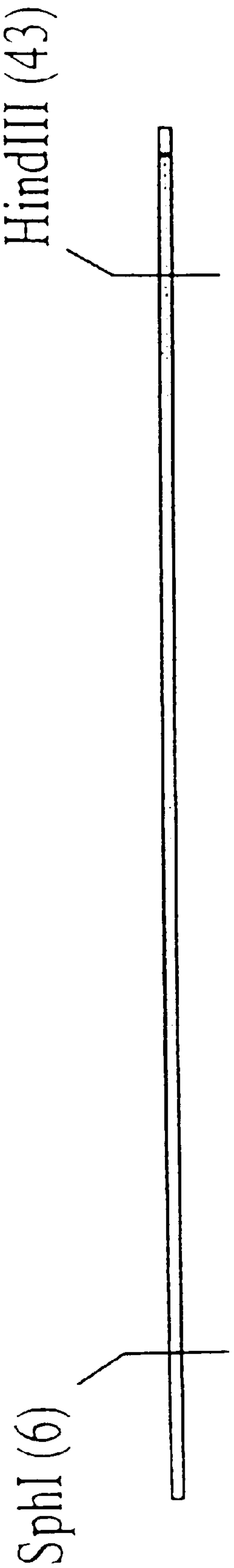
Figure 35X:
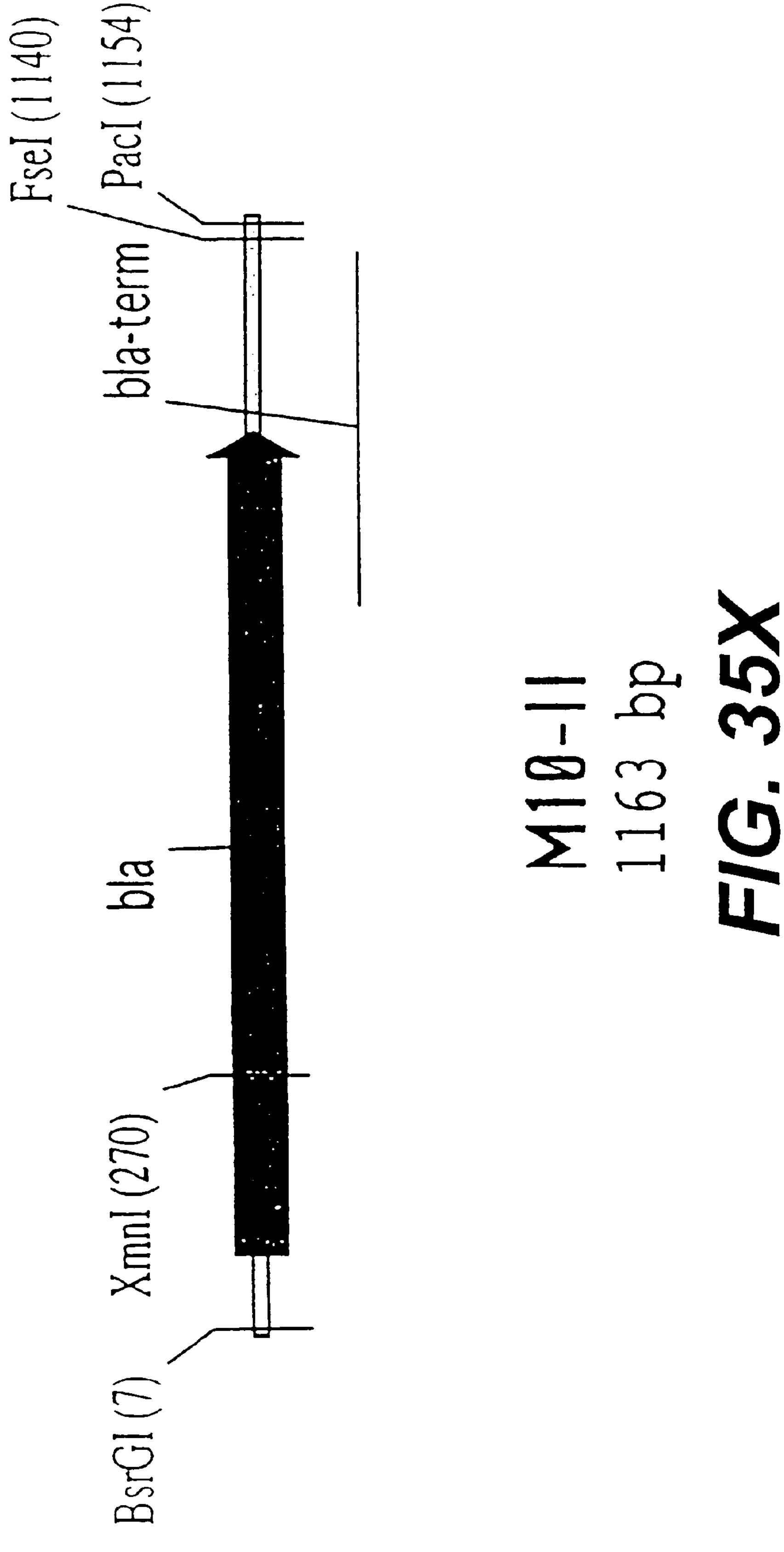
Figure 35C:
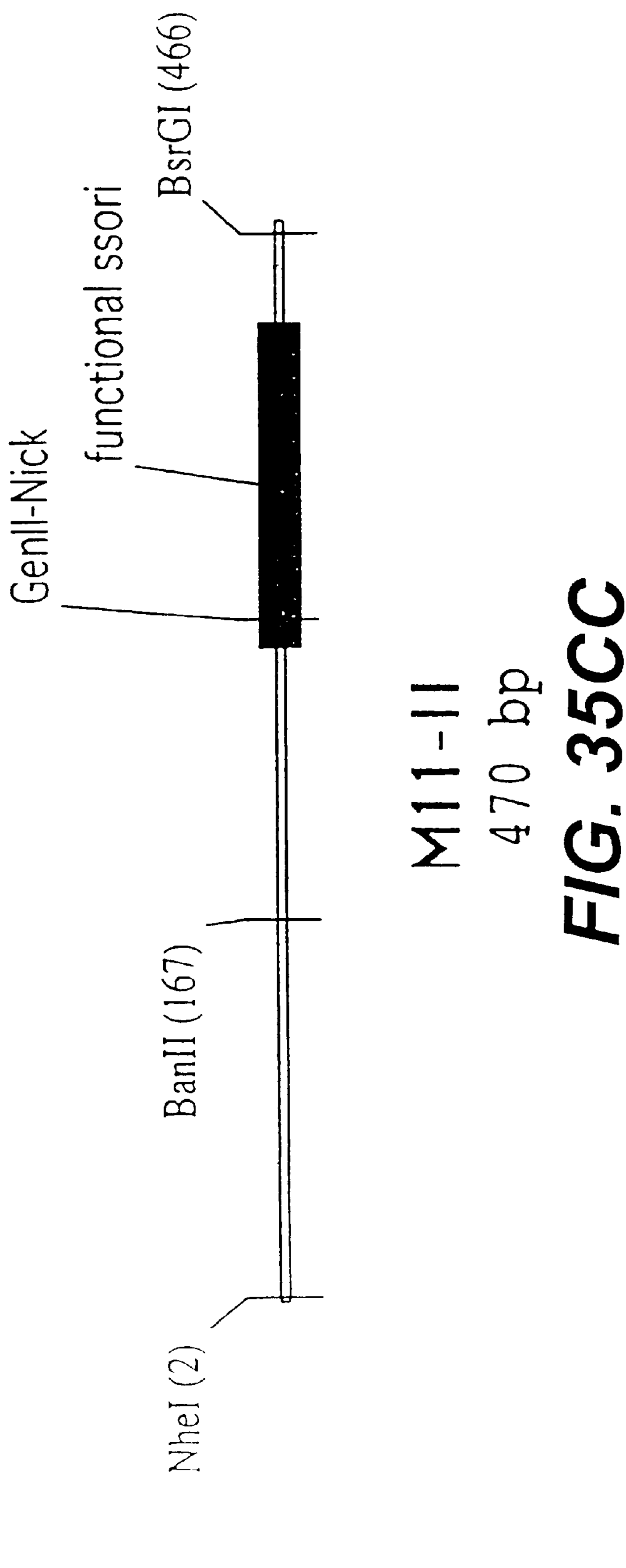
Figure 35F:
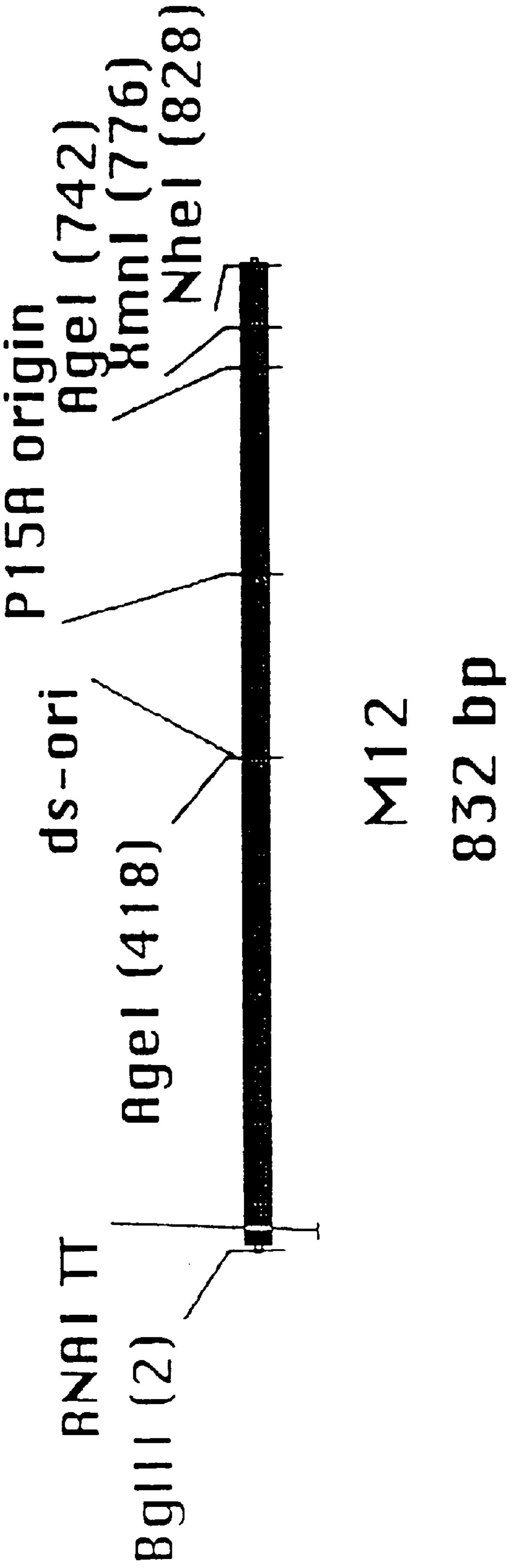
Figure 35J:
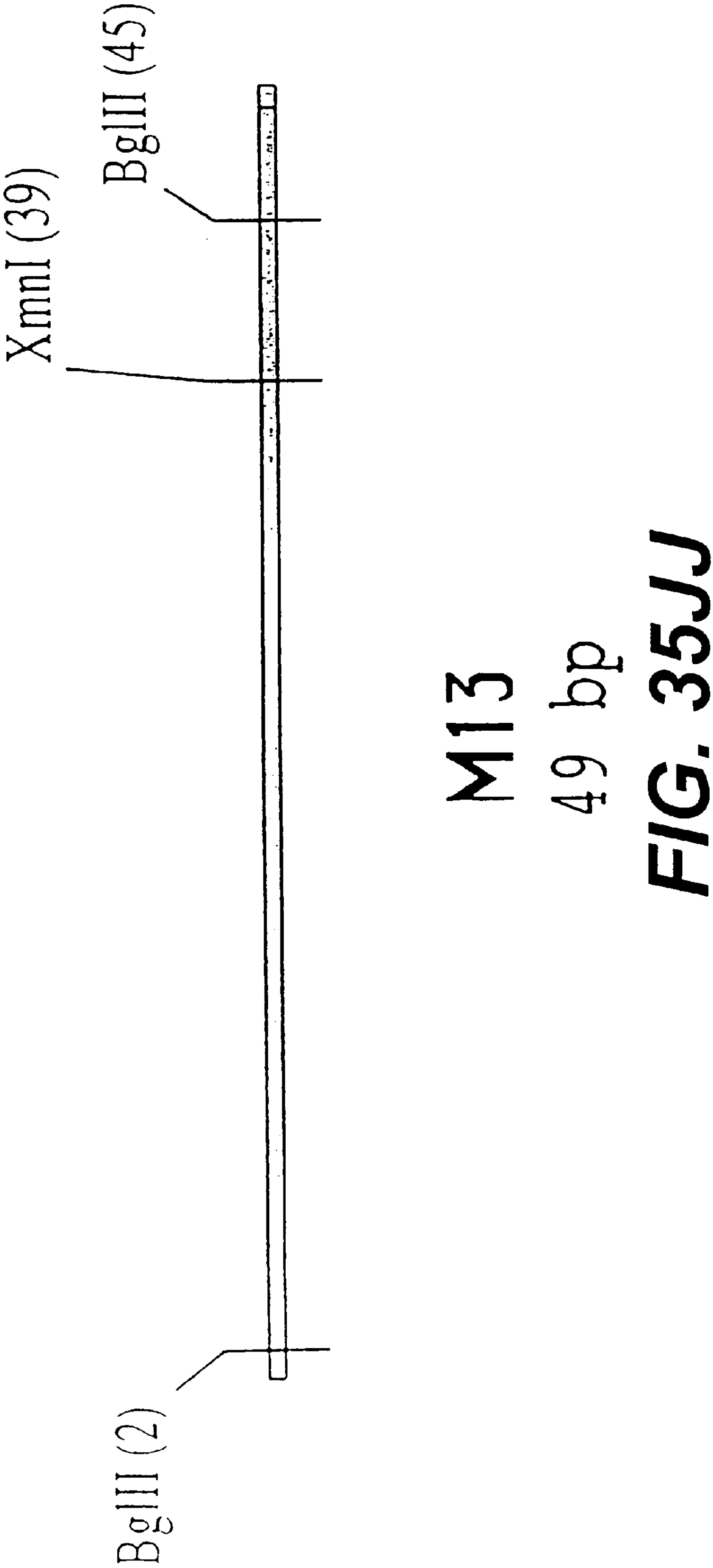
Figure 35L:
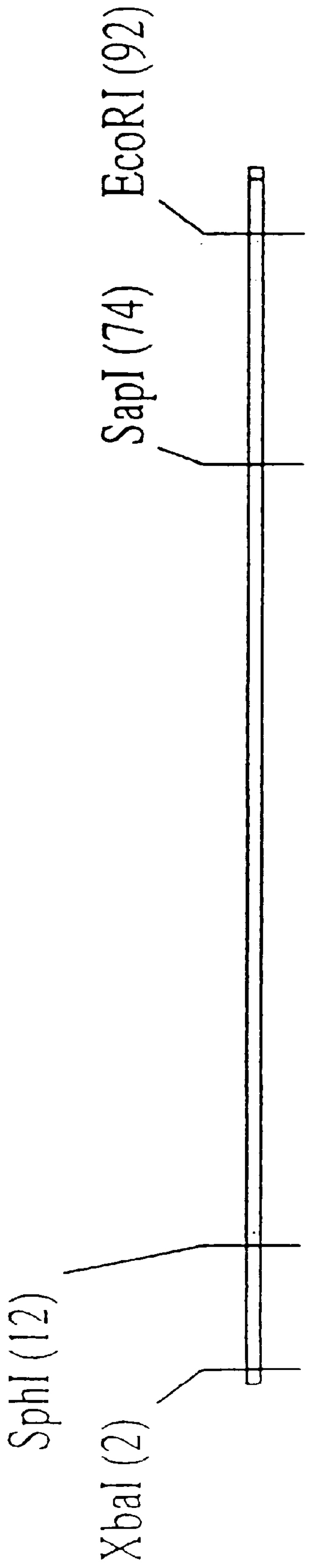
Figure 35N:
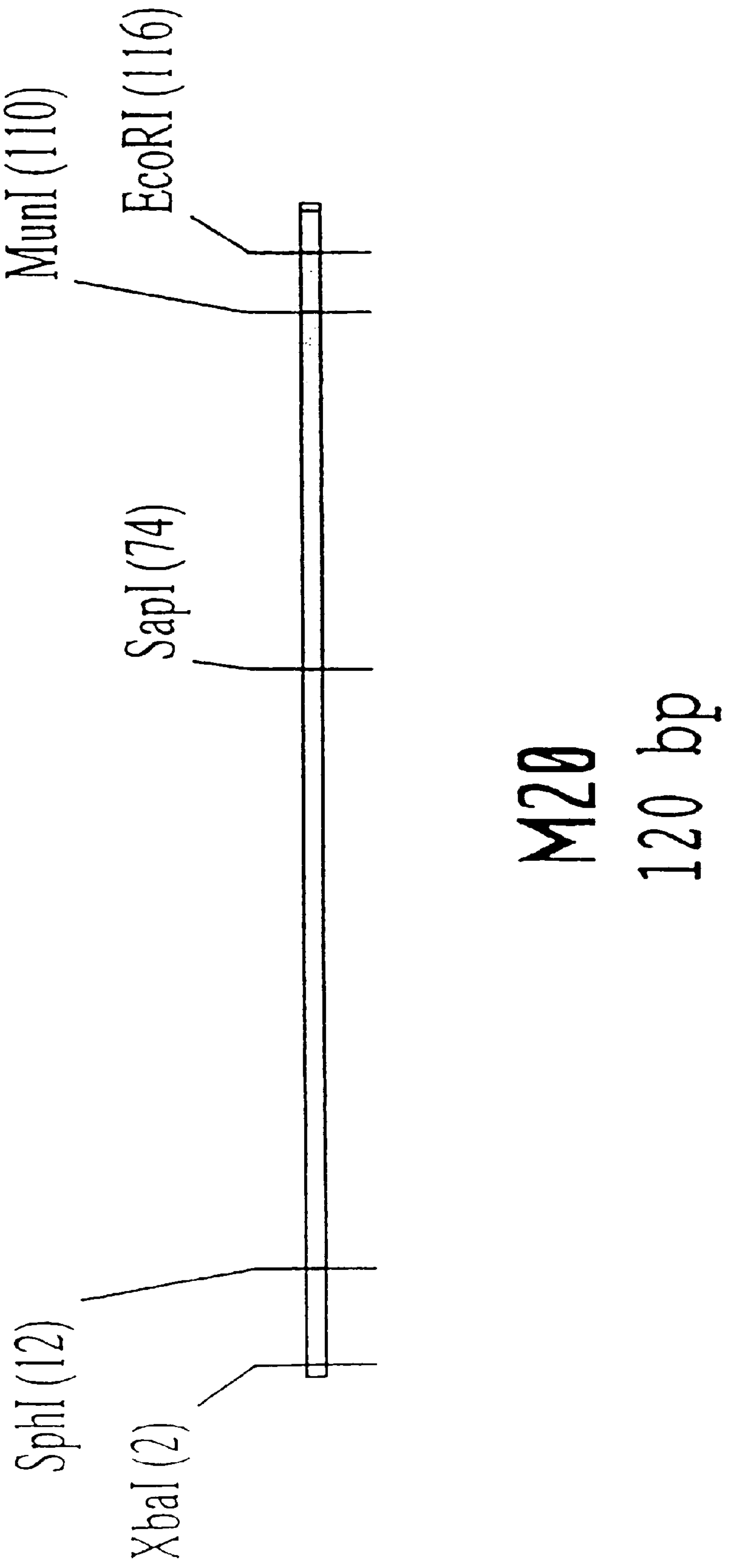
Figure 35P:
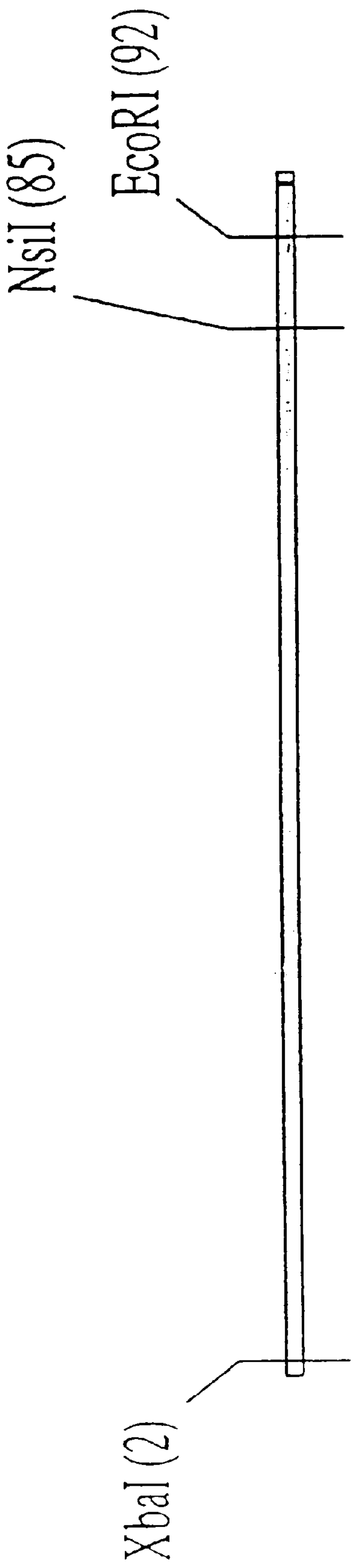
Figure 35R:
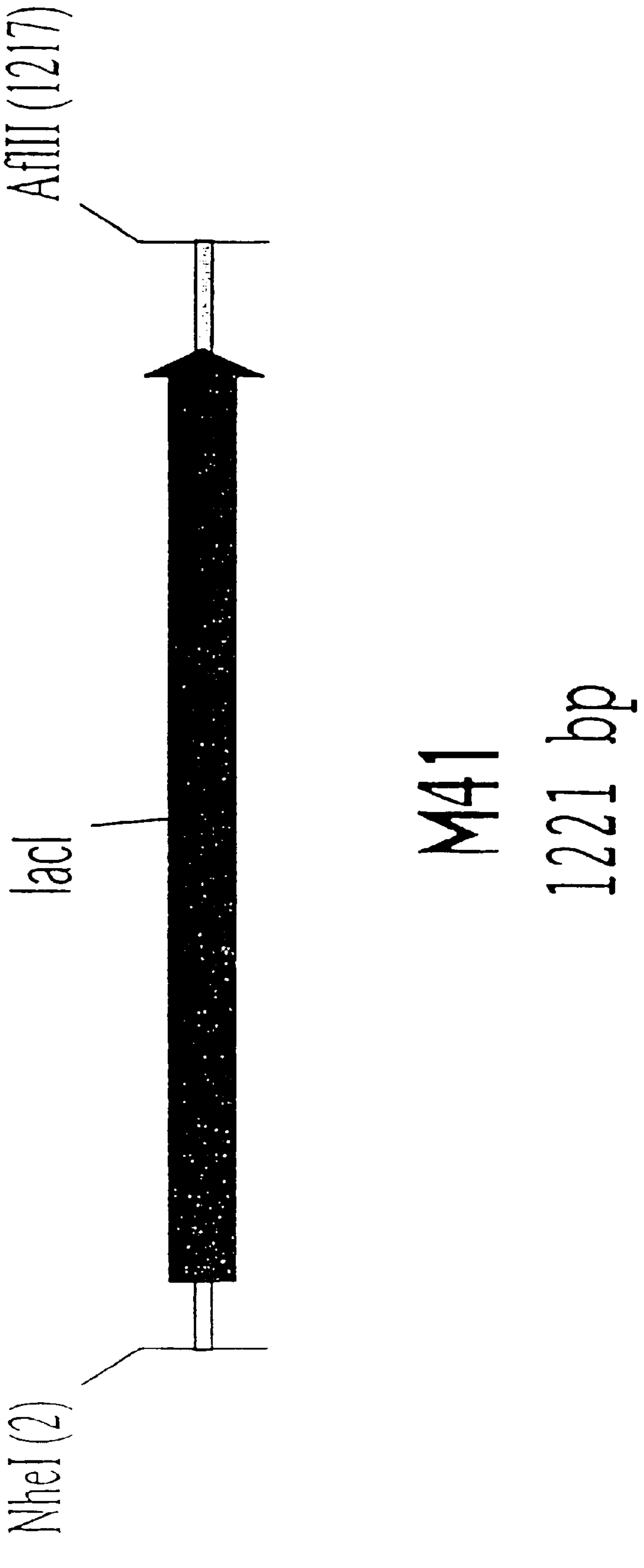
Figure 35W:
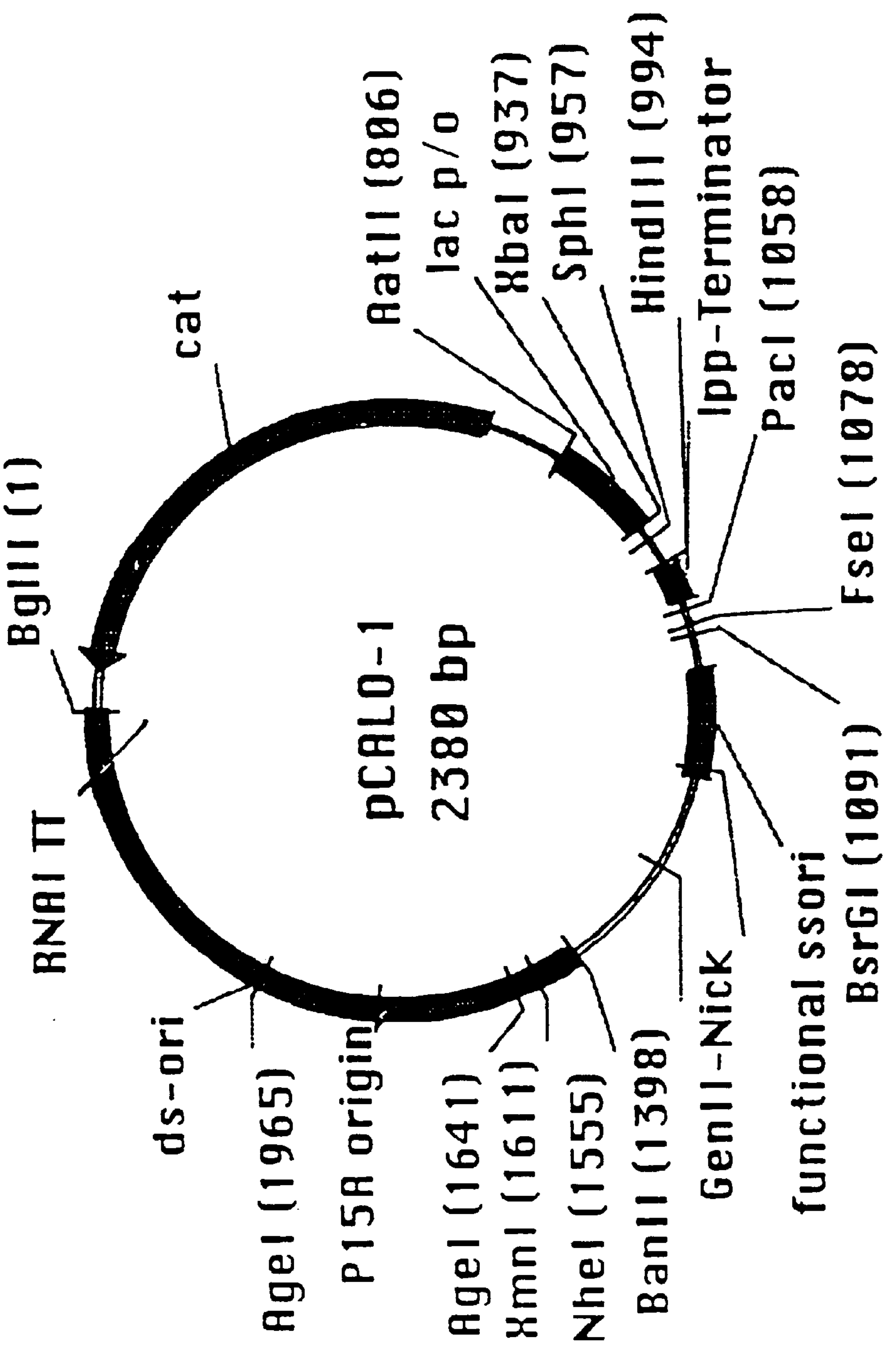

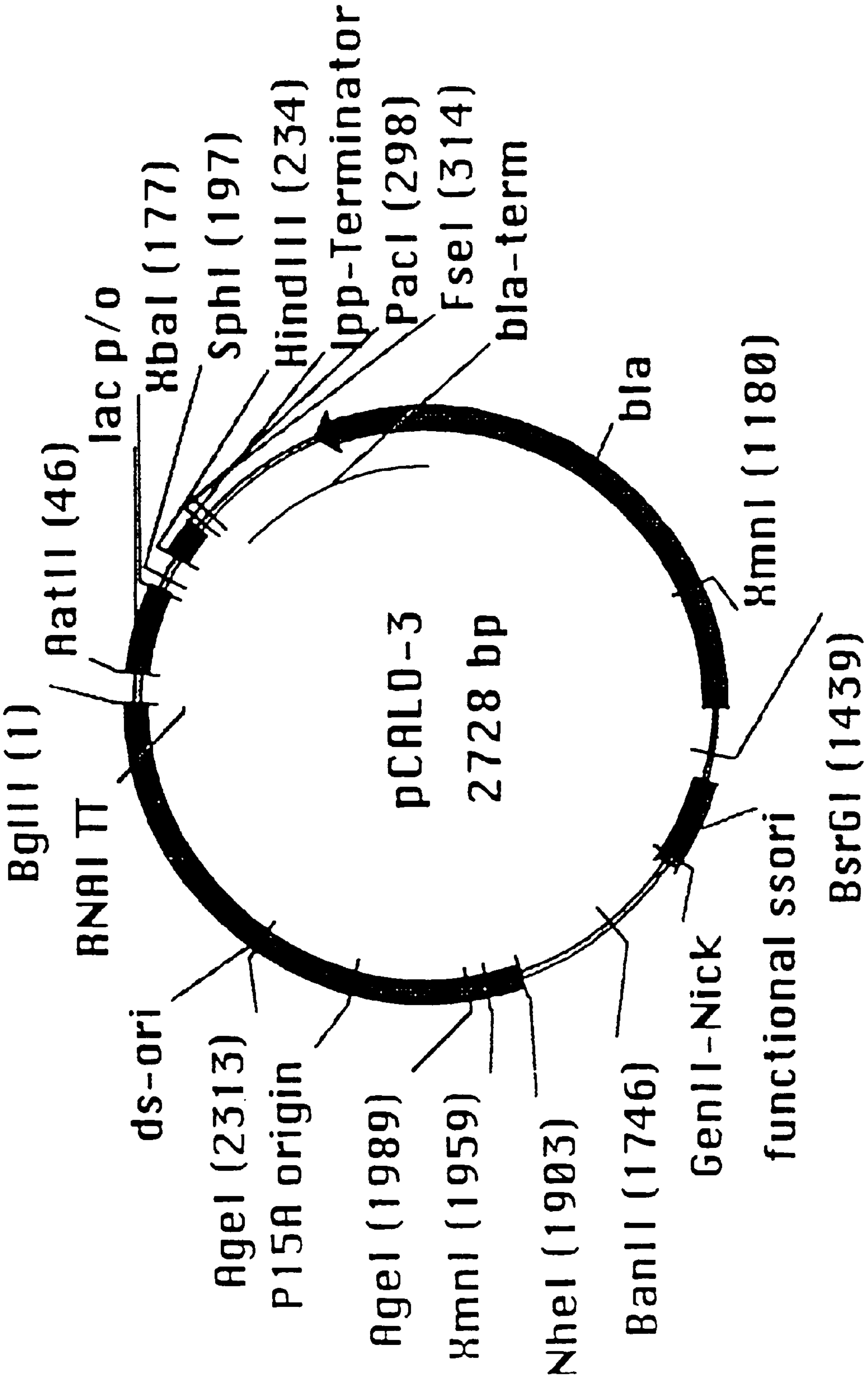
*FIG. 35PPP*

```
pCALO-3:
      BglII                                                   AatII
      ~~~~~~                                                 ~~~~~~~
  1   GATCTCATAA CTTCGTATAA TGTATGCTAT ACGAAGTTAT GACGTCTAAT
      CTAGAGTATT GAAGCATATT ACATACGATA TGCTTCAATA CTGCAGATTA

 51   GTGAGTTAGC TCACTCATTA GGCACCCCAG GCTTTACACT TTATGCTTCC
      CACTCAATCG AGTGAGTAAT CCGTGGGGTC CGAAATGTGA AATACGAAGG

101   GGCTCGTATG TTGTGTGGAA TTGTGAGCGG ATAACAATTT CACACAGGAA
      CCGAGCATAC AACACACCTT AACACTCGCC TATTGTTAAA GTGTGTCCTT

                                   XbaI                 SphI
                                 ~~~~~~~~             ~~~~~~~
151   ACAGCTATGA CCATGATTAC GAATTTCTAG ACCCCCCCCC CGCATGCCAT
      TGTCGATACT GGTACTAATG CTTAAAGATC TGGGGGGGGG GCGTACGGTA

                                          HindIII
                                          ~~~~~~~
201   AACTTCGTAT AATGTACGCT ATACGAAGTT ATAAGCTTGA CCTGTGAAGT
      TTGAAGCATA TTACATGCGA TATGCTTCAA TATTCGAACT GGACACTTCA

                                                        PacI
```

FIG. 35QQQ

```
                                                   ~~~~~~~~~
251  GAAAAATGGC GCAGATTGTG CGACATTTTT TTTGTCTGCC GTTTAATTAA
     CTTTTTACCG CGTCTAACAC GCTGTAAAAA AAACAGACGG CAAATTAATT

                 FseI
               ~~~~~~~~~~
301  GGGGGGGGGC CGGCCATTAT CAAAAAGGAT CTCAAGAAGA TCCTTTGATC
     CCCCCCCCCG GCCGGTAATA GTTTTTCCTA GAGTTCTTCT AGGAAACTAG

351  TTTTCTACGG GGTCTGACGC TCAGTGGAAC GAAAACTCAC GTTAAGGGAT
     AAAAGATGCC CCAGACTGCG AGTCACCTTG CTTTTGAGTG CAATTCCCTA

401  TTTGGTCATG AGATTATCAA AAAGGATCTT CACCTAGATC CTTTTAAATT
     AAACCAGTAC TCTAATAGTT TTTCCTAGAA GTGGATCTAG GAAAATTTAA

451  AAAAATGAAG TTTTAAATCA ATCTAAAGTA TATATGAGTA AACTTGGTCT
     TTTTTACTTC AAAATTTAGT TAGATTTCAT ATATACTCAT TTGAACCAGA

501  GACAGTTACC CAATGCTTAA TCAGTGAGGC ACCTATCTCA GCGATCTGTC
     CTGTCAATGG GTTACGAATT AGTCACTCCG TGGATAGAGT CGCTAGACAG

551  TATTTCGTTC ATCCATAGTT GCCTGACTCC CCGTCGTGTA GATAACTACG
     ATAAAGCAAG TAGGTATCAA CGGACTGAGG GGCAGCACAT CTATTGATGC
```

FIG. 35RRR

```
601  ATACGGGAGG GCTTACCATC TGGCCCCAGT GCTGCAATGA TACCGCGAGA
     TATGCCCTCC CGAATGGTAG ACCGGGGTCA CGACGTTACT ATGGCGCTCT

651  CCCACGCTCA CCGGCTCCAG ATTTATCAGC AATAAACCAG CCAGCCGGAA
     GGGTGCGAGT GGCCGAGGTC TAAATAGTCG TTATTTGGTC GGTCGGCCTT

701  GGGCCGAGCG CAGAAGTGGT CCTGCAACTT TATCCGCCTC CATCCAGTCT
     CCCGGCTCGC GTCTTCACCA GGACGTTGAA ATAGGCGGAG GTAGGTCAGA

751  ATTAACTGTT GCCGGGAAGC TAGAGTAAGT AGTTCGCCAG TTAATAGTTT
     TAATTGACAA CGGCCCTTCG ATCTCATTCA TCAAGCGGTC AATTATCAAA

801  GCGCAACGTT GTTGCCATTG CTACAGGCAT CGTGGTGTCA CGCTCGTCGT
     CGCGTTGCAA CAACGGTAAC GATGTCCGTA GCACCACAGT GCGAGCAGCA

851  TTGGTATGGC TTCATTCAGC TCCGGTTCCC AACGATCAAG GCGAGTTACA
     AACCATACCG AAGTAAGTCG AGGCCAAGGG TTGCTAGTTC CGCTCAATGT

901  TGATCCCCCA TGTTGTGCAA AAAAGCGGTT AGCTCCTTCG GTCCTCCGAT
     ACTAGGGGGT ACAACACGTT TTTTCGCCAA TCGAGGAAGC CAGGAGGCTA

951  CGTTGTCAGA AGTAAGTTGG CCGCAGTGTT ATCACTCATG GTTATGGCAG
     GCAACAGTCT TCATTCAACC GGCGTCACAA TAGTGAGTAC CAATACCGTC
```

*FIG. 35SSS*

```
1001  CACTGCATAA TTCTCTTACT GTCATGCCAT CCGTAAGATG CTTTTCTGTG
      GTGACGTATT AAGAGAATGA CAGTACGGTA GGCATTCTAC GAAAAGACAC

1051  ACTGGTGAGT ACTCAACCAA GTCATTCTGA GAATAGTGTA TGCGGCGACC
      TGACCACTCA TGAGTTGGTT CAGTAAGACT CTTATCACAT ACGCCGCTGG

1101  GAGTTGCTCT TGCCCGGCGT CAATACGGGA TAATACCGCG CCACATAGCA
      CTCAACGAGA ACGGGCCGCA GTTATGCCCT ATTATGGCGC GGTGTATCGT

                                 XmnI
                             ~~~~~~~~~~~~
1151  GAACTTTAAA AGTGCTCATC ATTGGAAAAC GTTCTTCGGG GCGAAAACTC
      CTTGAAATTT TCACGAGTAG TAACCTTTTG CAAGAAGCCC CGCTTTTGAG

1201  TCAAGGATCT TACCGCTGTT GAGATCCAGT TCGATGTAAC CCACTCGCGC
      AGTTCCTAGA ATGGCGACAA CTCTAGGTCA AGCTACATTG GGTGAGCGCG

1251  ACCCAACTGA TCCTCAGCAT CTTTTACTTT CACCAGCGTT TCTGGGTGAG
      TGGGTTGACT AGGAGTCGTA GAAAATGAAA GTGGTCGCAA AGACCCACTC

1301  CAAAAACAGG AAGGCAAAAT GCCGCAAAAA AGGGAATAAG GGCGACACGG
      GTTTTTGTCC TTCCGTTTTA CGGCGTTTTT TCCCTTATTC CCGCTGTGCC

1351  AAATGTTGAA TACTCATACT CTTCCTTTTT CAATATTATT GAAGCATTTA
```

FIG. 35TTT

```
          TTTACAACTT ATGAGTATGA GAAGGAAAAA GTTATAATAA CTTCGTAAAT

                                                    BsrGI
                                                   ~~~~~~~~
1401      TCAGGGTTAT TGTCTCATGA GCGGATACAT ATTTGAATGT ACATGAAATT
          AGTCCCAATA ACAGAGTACT CGCCTATGTA TAAACTTACA TGTACTTTAA

1451      GTAAACGTTA ATATTTTGTT AAAATTCGCG TTAAATTTTT GTTAAATCAG
          CATTTGCAAT TATAAAACAA TTTTAAGCGC AATTTAAAAA CAATTTAGTC

1501      CTCATTTTTT AACCAATAGG CCGAAATCGG CAAAATCCCT TATAAATCAA
          GAGTAAAAAA TTGGTTATCC GGCTTTAGCC GTTTTAGGGA ATATTTAGTT

1551      AAGAATAGAC CGAGATAGGG TTGAGTGTTG TTCCAGTTTG GAACAAGAGT
          TTCTTATCTG GCTCTATCCC AACTCACAAC AAGGTCAAAC CTTGTTCTCA

1601      CCACTATTAA AGAACGTGGA CTCCAACGTC AAAGGGCGAA AAACCGTCTA
          GGTGATAATT TCTTGCACCT GAGGTTGCAG TTTCCCGCTT TTTGGCAGAT

1651      TCAGGGCGAT GGCCCACTAC GAGAACCATC ACCCTAATCA AGTTTTTTGG
          AGTCCCGCTA CCGGGTGATG CTCTTGGTAG TGGGATTAGT TCAAAAAACC

                                                      BanII
                                                     ~~~~~~
```

FIG. 35UUU

```
1701  GGTCGAGGTG CCGTAAAGCA CTAAATCGGA ACCCTAAAGG GAGCCCCCGA
      CCAGCTCCAC GGCATTTCGT GATTTAGCCT TGGGATTTCC CTCGGGGGCT

1751  TTTAGAGCTT GACGGGGAAA GCCGGCGAAC GTGGCGAGAA AGGAAGGGAA
      AAATCTCGAA CTGCCCCTTT CGGCCGCTTG CACCGCTCTT TCCTTCCCTT

1801  GAAAGCGAAA GGAGCGGGCG CTAGGGCGCT GGCAAGTGTA GCGGTCACGC
      CTTTCGCTTT CCTCGCCCGC GATCCCGCGA CCGTTCACAT CGCCAGTGCG

1851  TGCGCGTAAC CACCACACCC GCCGCGCTTA ATGCGCCGCT ACAGGGCGCG
      ACGCGCATTG GTGGTGTGGG CGGCGCGAAT TACGCGGCGA TGTCCCGCGC

        NheI
       ~~~~~~
1901  TGCTAGCGGA GTGTATACTG GCTTACTATG TTGGCACTGA TGAGGGTGTC
      ACGATCGCCT CACATATGAC CGAATGATAC AACCGTGACT ACTCCCACAG

            XmnI                             AgeI
        ~~~~~~~~~~~~                       ~~~~~~~
1951  AGTGAAGTGC TTCATGTGGC AGGAGAAAAA AGGCTGCACC GGTGCGTCAG
      TCACTTCACG AAGTACACCG TCCTCTTTTT TCCGACGTGG CCACGCAGTC

2001  CAGAATATGT GATACAGGAT ATATTCCGCT TCCTCGCTCA CTGACTCGCT
      GTCTTATACA CTATGTCCTA TATAAGGCGA AGGAGCGAGT GACTGAGCGA
```

FIG. 35VVV

```
2051  ACGCTCGGTC GTTCGACTGC GGCGAGCGGA AATGGCTTAC GAACGGGGCG
      TGCGAGCCAG CAAGCTGACG CCGCTCGCCT TTACCGAATG CTTGCCCCGC

2101  GAGATTTCCT GGAAGATGCC AGGAAGATAC TTAACAGGGA AGTGAGAGGG
      CTCTAAAGGA CCTTCTACGG TCCTTCTATG AATTGTCCCT TCACTCTCCC

2151  CCGCGGCAAA GCCGTTTTTC CATAGGCTCC GCCCCCCTGA CAAGCATCAC
      GGCGCCGTTT CGGCAAAAAG GTATCCGAGG CGGGGGGACT GTTCGTAGTG

2201  GAAATCTGAC GCTCAAATCA GTGGTGGCGA AACCCGACAG GACTATAAAG
      CTTTAGACTG CGAGTTTAGT CACCACCGCT TTGGGCTGTC CTGATATTTC

2251  ATACCAGGCG TTTCCCCCTG GCGGCTCCCT CCTGCGCTCT CCTGTTCCTG
      TATGGTCCGC AAAGGGGGAC CGCCGAGGGA GGACGCGAGA GGACAAGGAC

                 AgeI
                ~~~~~~~
2301  CCTTTCGGTT TACCGGTGTC ATTCCGCTGT TATGGCCGCG TTTGTCTCAT
      GGAAAGCCAA ATGGCCACAG TAAGGCGACA ATACCGGCGC AAACAGAGTA

2351  TCCACGCCTG ACACTCAGTT CCGGGTAGGC AGTTCGCTCC AAGCTGGACT
      AGGTGCGGAC TGTGAGTCAA GGCCCATCCG TCAAGCGAGG TTCGACCTGA
```

FIG. 35WWW

```
2401  GTATGCACGA ACCCCCCGTT CAGTCCGACC GCTGCGCCTT ATCCGGTAAC
      CATACGTGCT TGGGGGGCAA GTCAGGCTGG CGACGCGGAA TAGGCCATTG

2451  TATCGTCTTG AGTCCAACCC GGAAAGACAT GCAAAAGCAC CACTGGCAGC
      ATAGCAGAAC TCAGGTTGGG CCTTTCTGTA CGTTTTCGTG GTGACCGTCG

2501  AGCCACTGGT AATTGATTTA GAGGAGTTAG TCTTGAAGTC ATGCGCCGGT
      TCGGTGACCA TTAACTAAAT CTCCTCAATC AGAACTTCAG TACGCGGCCA

2551  TAAGGCTAAA CTGAAAGGAC AAGTTTTAGT GACTGCGCTC CTCCAAGCCA
      ATTCCGATTT GACTTTCCTG TTCAAAATCA CTGACGCGAG GAGGTTCGGT

2601  GTTACCTCGG TTCAAAGAGT TGGTAGCTCA GAGAACCTAC GAAAAACCGC
      CAATGGAGCC AAGTTTCTCA ACCATCGAGT CTCTTGGATG CTTTTTGGCG

2651  CCTGCAAGGC GGTTTTTTCG TTTTCAGAGC AAGAGATTAC GCGCAGACCA
      GGACGTTCCG CCAAAAAAGC AAAAGTCTCG TTCTCTAATG CGCGTCTGGT

                                BglII

2701  AAACGATCTC AAGAAGATCA TCTTATTA
      TTTGCTAGAG TTCTTCTAGT AGAATAAT
```

FIG. 35XXX

M1: PCR using template

NoVspAatII: TAGACGTC

M2: synthesis

BloxA-A: TATGAGATCTCATAACTTCGTATAATGTACGCTATACG-
AAGTTAT

BloxA-B: TAATAACTTCGTATAGCATACATTATACGAAGTTATG-
AGATCTCA

M3: PCR, NoVspAatII as second oligo

XloxS-muta: CATTTTTTGCCCTCGTTATCTACGCATGCGATAACTTCGTA-
TAGCGTACATTATACGAAGTTATTCTAGACATGGTCATAGCTGTTTCCTG

M7-I: PCR gIIINEW-fow: GGGGGGAATTCGGTGGTGGTGGATCTGCGTGCGCTG-
AAACGGTTGAAAGTTG gIIINEW-rev: CCCCCCCAAGCTTATCAAGACTCCTTATTACG

M7-II: PCR gIIIss-fow: GGGGGGGGAATTCGGAGGCGGTTCCGGTGGTGGC

M7-III: PCR gIIIsupernew-fow: GGGGGGGGAATTCGAGCAGAAGCTGATCTCT-
GAGGAGGATCTGTAGGGTGGTGGCTCTGGTTCCGGTGATTTTG

FIG. 35YYY

M8: synthesis lox514-A: CCATAACTTCGTATAATGTACGCTATACGAAGTTATA lox514-B: AGCTTATAACTTCGTATAGCGTACATTATACGAAGT-TATGGCATG M9II: synthesis M9II-fow: AGCTTGACCTGTGAAGTGAAAAATGGCGCAGATT-GTGCGACATTTTTTTGTCTGCCGTTTAATTAAAGGGGGGGT M9II-rev: GTACACCCCCCCCAGGCCGGCCCCCCCCCCCTTTAA-TTAAACGGCAGACAAAAAAATGTCGCACAATCTGCG M10II: assembly PCR with template bla-fow: GGGGGGGTGTACATTCAAATATGTATCCGCTCATG bla-seq4: GGGTTACATCGAACTGGATCTC bla1-muta: CCAGTTCGATGTAACCCACTCGCGCACCCAACTGATC-CTCAGCATCTTTTACTTTCACC blaII-muta: ACTCTAGCTTCCCGGCAACAGTTAATAGACTGGATG-GAGGCGG bla-NEW: CTGTTGCCGGGAAGCTAGAGTAAG bla-rev: CCCCCCCTTAATTAAGGGGGGGGGCCGGCCATTATCAAA-AAGGATCTCAAGAAGATCC M11II/III: PCR, site-directed mutagenesis

FIG. 35ZZZ f1-fow: GGGGGGGGCTAGCACGCGCCCTGTAGCGGCGCATTAA f1-rev: CCCCCCCTGTACATGAAATTGTAAACGTTAATATTTTG f1-t133.muta: GGGCGATGGCCCACTACGAGAACCATCACCCTAATC M12: assembly PCR using template p15-fow: GGGGGGAGATCTAATAAGATGATCTTCTTGAG p15-NEWI: GAGTTGGTAGCTCAGAGAACCTACGAAAAACCGCCCTG-CAAGGCG p15-NEWII: GTAGGTTCTCTGAGCTACCAACTC p15-NEWIII: GTTTCCCCCTGGCGGCTCCCTCCTGCGCTCTCCTGTTCCT-GCC p15-NEWIV: AGGAGGGAGCCGCCAGGGGGAAAC p15-rev: GACATCAGCGCTAGCGGAGTGTATAC M13: synthesis BloxXB-A: GATCTCATAACTTCGTATAATGTATGCTATACGAAGTTA-TTCA BloxXB-B: GATCTGAATAACTTCGTATAGCATACATTATACGAAGTTA-TGAGA M14-Ext2: PCR, site-directed mutagenesis ColEXT2-fow: GGGGGGGAGATCTGACCAAAATCCCTTAACGTGAG Col-mutaI: GGTATCTGCGCTCTGCTGTAGCCAGTTACCTTCGG

*FIG. 35AAAA*

Col-rev: CCCCCCCGCTAGCCATGTGAGCAAAAGGCCAGCAA

M17: assembly PCR using template

CAT-1: GGGACGTCGGGTGAGGTTCCAAC

CAT-2: CCATACGGAACTCCGGGTGAGCATTCATC

CAT-3: CCGGAGTTCCGTATGG

CAT-4: ACGTTTAAATCAAAACTGG

CAT-5: CCAGTTTTGATTTAAACGTAGCCAATATGGACAACTTCTTC-GCCCCCGTTTTCACTATGGGCAAATATT

CAT-6: GGAAGATCTAGCACCAGGCGTTTAAG

M41: assembly PCR using template

LAC1: GAGGCCGGCCATCGAATGGCGCAAAAC

LAC2: CGCGTACCGTCCTCATGGGAGAAAATAATAC

LAC3: CCATGAGGACGGTACGCGACTGGGCGTGGAGCATCTGGTCGCA-TTGGGTCACCAGCAAATCCGCTGTTAGCTGGCCCATTAAG

LAC4: GTCAGCGGCGGGATATAACATGAGCTGTCCTCGGTATCGTCG

LAC5: GTTATATCCCGCCGCTGACCACCATCAAAC

LAC6: CATCAGTGAATCGGCCAACGCGCGGGGAGAGGCGGTTTGCGT4TTG-GGAGCCAGGGTGGTTTTTC

LAC7: GGTTAATTAACCTCACTGCCCGCTTTCCAGTCGGGAAACCTGTCGTGCC-AGCTGCATCAGTGAATCGGCCAAC

M41-MCS-fow: CTAGACTAGTGTTTAAACCGGACCGGGGGGGGGCTT-AAGGGGGGGGGGGG

FIG. 35BBBB

M41-MCS-rev: CTAGCCCCCCCCCCCTTAAGCCCCCCCCCGGTCCGGT-TTAAACACTAGT

M41-fow: CTAGACTAGTGTTTAAACCGGACCGGGGGGGGGCTTAA-GGGGGGGGGGG

M41-rev: CCCCCCCTTAAGTGGGCTGCAAAACAAAACGGCCTCC-TGTCAGGAAGCCGCTTTTATCGGGTAGCCTCACTGCCCGCTTTCC

M41-A2: GTTGTTGTGCCACGCGGTTAGGAATGTAATTCAGCTCCGC

M41-B1: AACCGCGTGGCACAACAAC

M41-B2: CTTCGTTCTACCATCGACACGACCACGCTGGCACCCAGTTG

M41-C1: GTGTCGATGGTAGAACGAAG

M41-CII: CCACAGCAATAGCATCCTGGTCATCCAGCGGATAGTT-AATAATCAGCCCACTGACACGTTGCGCGAG

M41-DI: GACCAGGATGCTATTGCTGTGG

M41-DII: CAGCGCGATTTGCTGGTGGCCCAATGCGACCAGATGC

M41-EI: CACCAGCAAATCGCGCTG

M41-EII: CCCGGACTCGGTAATGGCACGCATTGCGCCCAGCGCC

M41-FI: GCCATTACCGAGTCCGGG

M42: synthesis

Eco-H5-Hind-fow: AATTCCACCATCATCACCATTGACGTCTA

Eco-H5-Hind-rev: AGCTTAGACGTCAATGGTGATGATGGTGG

FIG. 35CCCC

```
                                                       StyI
                                                      ~~~~~~
                                                         Psp5II
                                                         ~~~~~~~~
       MluI      Bsu36I              BstXI           EcoO109I
       ~~~~~     ~~~~~~~~~   ~~~~~~~~~~~~~~~          ~~~~~~~~
           HpaI        BstEII              MscI             BsiWI NspV
          ~~~~~~~      ~~~~~~~~         ~~~~~~~~         ~~~~~~~~~~~~~~
126   CGCGTTAACC TCAGGTGACC AAGCCCCTGG CCAAGGTCCC GTACGTTCGA
      GCGCAATTGG AGTCCACTGG TTCGGGGACC GGTTCCAGGG CATGCAAGCT

                 PmlI
                ~~~~~~
      NspVBsaBI          BamHI   KpnI       FseI
      ~~~~~~~~~~~~~     ~~~~~~~~~~~~~~~ ~~~~~~~~~~
176   AGATTACCAT CACGTGGATC CGGTACCAGG CCGGCCATTA TCAAAAAGGA
      TCTAATGGTA GTGCACCTAG GCCATGGTCC GGCCGGTAAT AGTTTTTCCT

226   TCTCAAGAAG ATCCTTTGAT CTTTTCTACG GGGTCTGACG CTCAGTGGAA
      AGAGTTCTTC TAGGAAACTA GAAAAGATGC CCCAGACTGC GAGTCACCTT

276   CGAAAACTCA CGTTAAGGGA TTTTGGTCAT GAGATTATCA AAAAGGATCT
      GCTTTTGAGT GCAATTCCCT AAAACCAGTA CTCTAATAGT TTTTCCTAGA
```

FIG. 36B

```
326  TCACCTAGAT CCTTTTAAAT TAAAAATGAA GTTTTAAATC AATCTAAAGT
     AGTGGATCTA GGAAAATTTA ATTTTTACTT CAAAATTTAG TTAGATTTCA

376  ATATATGAGT AAACTTGGTC TGACAGTTAC CAATGCTTAA TCAGTGAGGC
     TATATACTCA TTTGAACCAG ACTGTCAATG GTTACGAATT AGTCACTCCG

426  ACCTATCTCA GCGATCTGTC TATTTCGTTC ATCCATAGTT GCCTGACTCC
     TGGATAGAGT CGCTAGACAG ATAAAGCAAG TAGGTATCAA CGGACTGAGG

476  CCGTCGTGTA GATAACTACG ATACGGGAGG GCTTACCATC TGGCCCCAGT
     GGCAGCACAT CTATTGATGC TATGCCCTCC CGAATGGTAG ACCGGGGTCA

526  GCTGCAATGA TACCGCGAGA CCCACGCTCA CCGGCTCCAG ATTTATCAGC
     CGACGTTACT ATGGCGCTCT GGGTGCGAGT GGCCGAGGTC TAAATAGTCG

576  AATAAACCAG CCAGCCGGAA GGGCCGAGCG CAGAAGTGGT CCTGCAACTT
     TTATTTGGTC GGTCGGCCTT CCCGGCTCGC GTCTTCACCA GGACGTTGAA

626  TATCCGCCTC CATCCAGTCT ATTAACTGTT GCCGGGAAGC TAGAGTAAGT
     ATAGGCGGAG GTAGGTCAGA TAATTGACAA CGGCCCTTCG ATCTCATTCA

676  AGTTCGCCAG TTAATAGTTT GCGCAACGTT GTTGCCATTG CTACAGGCAT
     TCAAGCGGTC AATTATCAAA CGCGTTGCAA CAACGGTAAC GATGTCCGTA
```

FIG. 36C

```
726   CGTGGTGTCA CGCTCGTCGT TTGGTATGGC TTCATTCAGC TCCGGTTCCC
      GCACCACAGT GCGAGCAGCA AACCATACCG AAGTAAGTCG AGGCCAAGGG

776   AACGATCAAG GCGAGTTACA TGATCCCCCA TGTTGTGCAA AAAAGCGGTT
      TTGCTAGTTC CGCTCAATGT ACTAGGGGGT ACAACACGTT TTTTCGCCAA

826   AGCTCCTTCG GTCCTCCGAT CGTTGTCAGA AGTAAGTTGG CCGCAGTGTT
      TCGAGGAAGC CAGGAGGCTA GCAACAGTCT TCATTCAACC GGCGTCACAA

876   ATCACTCATG GTTATGGCAG CACTGCATAA TTCTCTTACT GTCATGCCAT
      TAGTGAGTAC CAATACCGTC GTGACGTATT AAGAGAATGA CAGTACGGTA

926   CCGTAAGATG CTTTTCTGTG ACTGGTGAGT ACTCAACCAA GTCATTCTGA
      GGCATTCTAC GAAAAGACAC TGACCACTCA TGAGTTGGTT CAGTAAGACT

976   GAATAGTGTA TGCGGCGACC GAGTTGCTCT TGCCCGGCGT CAATACGGGA
      CTTATCACAT ACGCCGCTGG CTCAACGAGA ACGGGCCGCA GTTATGCCCT

1026  TAATACCGCG CCACATAGCA GAACTTTAAA AGTGCTCATC ATTGGAAAAC
      ATTATGGCGC GGTGTATCGT CTTGAAATTT TCACGAGTAG TAACCTTTTG

1076  GTTCTTCGGG GCGAAAACTC TCAAGGATCT TACCGCTGTT GAGATCCAGT
      CAAGAAGCCC CGCTTTTGAG AGTTCCTAGA ATGGCGACAA CTCTAGGTCA
```

FIG. 36D

```
1126  TCGATGTAAC CCACTCGTGC ACCCAACTGA TCTTCAGCAT CTTTTACTTT
      AGCTACATTG GGTGAGCACG TGGGTTGACT AGAAGTCGTA GAAAATGAAA
                   BssSI                 Eco57I
                  ~~~~~~~               ~~~~~~~

1176  CACCAGCGTT TCTGGGTGAG CAAAAACAGG AAGGCAAAAT GCCGCAAAAA
      GTGGTCGCAA AGACCCACTC GTTTTTGTCC TTCCGTTTTA CGGCGTTTTT

1226  AGGGAATAAG GGCGACACGG AAATGTTGAA TACTCATACT CTTCCTTTTT
      TCCCTTATTC CCGCTGTGCC TTTACAACTT ATGAGTATGA GAAGGAAAAA

1276  CAATATTATT GAAGCATTTA TCAGGGTTAT TGTCTCATGA GCGGATACAT
      GTTATAATAA CTTCGTAAAT AGTCCCAATA ACAGAGTACT CGCCTATGTA

                                 PstI                 XhoI
                               ~~~~~~~~              ~~~~~~
                   EagI    BssSI          BbeI  AseI     BssHII
                  ~~~~~~~~~~~~~~        ~~~~~~~~~~~~~~        ~
1326  ATTTGAATGT ACTCGGCCGC ACGAGCTGCA GGCGCCATTA ATGGCTCGAG
      TAAACTTACA TGAGCCGGCG TGCTCGACGT CCGCGGTAAT TACCGAGCTC

      BssHII                 BspEI BsrGI
      ~~~~~                ~~~~~~~~~~~~~~
```

FIG. 36E

```
1376   CGCGCTTCAG CGCTTTGTCT TCCGGATGTA CATGAAATT
       GCGCGAAGTC GCGAAACAGA AGGCCTACAT GTACTTTAA
           Eco57I        BbsI
           ~~~~~~~     ~~~~~~~~
```

FIG. 36F

```
                         1               10
O_K3L_5   5'- G C C T G C A A G C G G A A G A C
                                      ┌─────────┐
                                      │  BbsI   │
                                      └─────────┘
                                         E     D
Vk1 & Vk3 5'- G C C T G C A A G C G G A A G A C

                                         E     D
Vk2       5'- G C C T G C A A G C G G A A G A C

                                         E     D
Vk4       5'- G C C T G C A A G C G G A A G A C
```

50                              60

3'- G G A

T
                G                                             A C C T

T
                G                                             A C C T
                                                                    T
                G                                             A C C T

| G C T |       |       | G C T |       | G C T |
|-------|-------|-------|-------|-------|-------|
| G A T | G A T | G A T | G A T |       | G A T |
| G A G |       |       | G A G |       | G A G |
| T T T |       |       | T T T |       | T T T |
| G G T | G G T | G G T | G G T |       | G G T |
| C A T |       |       | C A T |       | C A T |
| A T T |       |       | A T T |       | A T T |
| A A G |       |       | A A G |       | A A G |
| C T T |       |       | C T T |       | C T T |
| A T G |       |       | A T G |       | A T G |
| A A T | A A T | A A T | A A T |       | A A T |
|       |       |       | C C T | C C T | C C T |
| C A G |       |       | C A G |       | C A G |
| C G T |       |       | C G T |       | C G T |
| T C T | T C T | T C T | T C T | T C T | T C T |
| A C T |       |       | A C T |       | A C T |
| G T T |       |       | G T T |       | G T T |
| T G G |       |       | T G G |       | T G G |
| T A T | T A T |       | T A T |       | T A T |
| 50% Y |       |       |       | 80% P |       |

FIG. 37C

```
                               70                    80  81
                               ↓                     ↓   ↓
             A A C C G G T A A G C T T T C G G  -5' O_K3L_3
                ┌─────────┐
                │  MscI   │
             F     G    Q
             T ┌─T G G C A┐T T C G A A A G C  C  -3'
               └─────────┘

             F     G    Q
             T ┌─T G G C A┐T T C G A A A G C  C  -3'
               └─────────┘
             F     G    Q
             T ┌─T G G C A┐T T C G A A A G C  C  -3'
               └─────────┘
```

```
1                 10                  20
                      E     D     E     A     D
5'- C C T G C A A G C G [G A A G A C] G A A G C G G A T T -
```

FIG. 38A

|   | 30 | | | | | 40 | | | 50 | |
|---|---|---|---|---|---|---|---|---|---|---|
| | Y | Y | C | Q | S | | D | | | |
| -A T T | A T T | G C C | A G A | G C | | | G A C | | | |

|   |   |   |   |   |
|---|---|---|---|---|
| A |   |   | G C T | G C T - |
| C |   |   |   |   |
| D |   |   | G A T | G A T |
| E |   |   | G A G | G A G |
| F |   |   | T T T | T T T |
| G |   |   | G G T | G G T |
| H |   |   | C A T | C A T |
| I |   |   | A T T | A T T |
| K |   |   | A A G | A A G |
| L |   |   | C T T | C T T |
| M |   |   | A T G | A T G |
| N |   |   | A A T | A A T |
| P |   |   | C C T | C C T |
| Q |   |   | C A G | C A G |
| R | C G T |   | C G T | C G T |
| S |   |   | T C T | T C T |
| T |   |   | A C T | A C T |
| V |   |   | G T T | G T T |
| W | T G G |   |   |   |
| Y | T A T |   | T A T | T A T |
|   | 3 | 1 | 18 | 18 |
|   | 3 | 1 | 18 | 18 |
|   | 3 | 1 | 18 | 18 |

60 70 80

G G G T K L

GGCGGCGGCACGAAGTTA

| | | gap | gap | | |
|---|---|---|---|---|---|
| - | GCT | GCT | GCT | GCT | |
| | GAT | GAT | GAT | GAT | |
| | GAG | GAG | GAG | GAG | |
| | TTT | TTT | TTT | TTT | |
| | GGT | GGT | GGT | GGT | |
| | CAT | CAT | CAT | CAT | |
| | ATT | ATT | ATT | ATT | |
| | AAG | AAG | AAG | AAG | |
| | CTT | CTT | CTT | CTT | |
| | ATG | ATG | ATG | ATG | |
| | AAT | AAT | AAT | AAT | |
| | CCT | CCT | CCT | CCT | |
| | CAG | CAG | CAG | CAG | |
| | CGT | CGT | CGT | CGT | |
| | TCT | TCT | TCT | TCT | |
| | ACT | ACT | ACT | ACT | |
| | GTT | GTT | GTT | GTT | |
| | | | | TGG | |
| | TAT | TAT | TAT | TAT | Variability |
| | 18 | | | 19 | 3.32E+05 |
| | 18 | 18 | | 19 | 5.98E+06 |
| | 18 | 18 | 18 | 19 | 1.08E+08 |

FIG. 38C

| % soluble | κ1 | κ2 | κ3 | κ4 | λ1 | λ2 | λ3 |
|---|---|---|---|---|---|---|---|
| H1A | 61% | 58% | 52% | 42% | 90% | 61% | 60% |
| H1B | 39% | 48% | 66% | 48% | 47% | 39% | 36% |
| H2 | 47% | 57% | 46% | 49% | 37% | 36% | 45% |
| H3 | 85% | 67% | 76% | 61% | 80% | 71% | 83% |
| H4 | 69% | 52% | 51% | 44% | 45% | 33% | 42% |
| H5 | 49% | 49% | 46% | 67% | 54% | 46% | 47% |
| H6 | 90% | 58% | 54% | 47% | 45% | 50% | 51% |

| Total amount compared to H3κ2 | κ1 | κ2 | κ3 | κ4 | λ1 | λ2 | λ3 |
|---|---|---|---|---|---|---|---|
| H1A | 289% | 94% | 166% | 272% | 20% | 150% | 78% |
| H1B | 219% | 122% | 89% | 139% | 117% | 158% | 101% |
| H2 | 186% | 223% | 208% | 182% | 126% | 60% | 97% |
| H3 | 50% | | 71% | 54% | 59% | 130% | 47% |
| H4 | 37% | 55% | 60% | 77% | 195% | 107% | 251% |
| H5 | 98% | 201% | 167% | 83% | 93% | 128% | 115% |
| H6 | 65% | 117% | 89% | 109% | 299% | 215% | 278% |

FIG. 40A

| Soluble amount compared to H3κ2 | κ1 | κ2 | κ3 | κ4 | λ1 | λ2 | λ3 |
|---|---|---|---|---|---|---|---|
| H1A | 191% | 88% | 121% | 122% | 26% | 211% | 76% |
| H1B | 124% | 95% | 83% | 107% | 79% | 142% | 59% |
| H2 | 126% | 204% | 139% | 130% | 66% | 50% | 70% |
| H3 | 63% | - | 81% | 49% | 69% | 143% | 61% |
| H4 | 40% | 47% | 49% | 54% | 95% | 55% | 125% |
| H5 | 69% | 158% | 116% | 80% | 72% | 84% | 84% |
| H6 | 85% | 122% | 87% | 77% | 162% | 162% | 212% |

| | McPC |
|---|---|
| soluble | 38% |
| %H3k2 total | 117% |
| %H3k2 soluble | 69% |

FIG. 40B

SEQUENCE LISTING

```
(1) GENERAL INFORMATION:

   (iii) NUMBER OF SEQUENCES: 373


(2) INFORMATION FOR SEQ ID NO: 1:

     (i) SEQUENCE CHARACTERISTICS:
          (A) LENGTH: 20 amino acids
          (B) TYPE: amino acid
          (C) STRANDEDNESS:
          (D) TOPOLOGY: linear

    (ii) MOLECULE TYPE: protein

    (xi) SEQUENCE DESCRIPTION: SEQ ID NO: 1:

Ala Gly Gly Gly Ser Gly Gly Gly Gly Ser Gly Gly Gly Gly Ser Gly
1               5                   10                  15
```

-continued

```
Gly Gly Gly Ser
            20

(2) INFORMATION FOR SEQ ID NO: 2:

     (i) SEQUENCE CHARACTERISTICS:
          (A) LENGTH: 82 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "synthetic oligonucleotide"

    (xi) SEQUENCE DESCRIPTION: SEQ ID NO: 2:

TCAGCGGGTG GCGGTTCTGG CGGCGGTGGG AGCGGTGGCG GTGGTTCTGG CGGTGGTGGT     60

TCCGATATCG GTCCACGTAC GG                                              82


(2) INFORMATION FOR SEQ ID NO: 3:

     (i) SEQUENCE CHARACTERISTICS:
          (A) LENGTH: 83 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "synthetic oligonucleotide"

    (xi) SEQUENCE DESCRIPTION: SEQ ID NO: 3:

AATTCCGTAC GTGGACCGAT ATCGGAACCA CCACCGCCAG AACCACCGCC ACCGCTCCCA     60

CCGCCGCCAG AACCGCCACC CGC                                             83


(2) INFORMATION FOR SEQ ID NO: 4:

     (i) SEQUENCE CHARACTERISTICS:
          (A) LENGTH: 69 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "synthetic oligonucleotide
               library"

    (ix) FEATURE:
          (A) NAME/KEY: misc_feature
          (B) LOCATION:28..45
          (D) OTHER INFORMATION:/product= "6 random codons by
               trinucleotide mutagenesis (19aa, no Cys)"

    (xi) SEQUENCE DESCRIPTION: SEQ ID NO: 4:

GATACGGCCG TGTATTATTG CGCGCGTNNK NNKNNKNNKN NKNNKGATTA TTGGGGCCAA     60

GGCACCCTG                                                             69


(2) INFORMATION FOR SEQ ID NO: 5:

     (i) SEQUENCE CHARACTERISTICS:
          (A) LENGTH: 84 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "synthetic oligonucleotide
               library"

    (ix) FEATURE:
```

-continued (A) NAME/KEY: misc_feature
(B) LOCATION:28..57
(D) OTHER INFORMATION:/product= "10 random codons by trinucleotide mutagenesis (19aa, no Cys)"

(ix) FEATURE:
(A) NAME/KEY: misc_feature
(B) LOCATION:58..60
(D) OTHER INFORMATION:/product= "random codon by trinucleotide mutagenesis (TTT/ATG)"

(ix) FEATURE:
(A) NAME/KEY: misc_feature
(B) LOCATION:64..66
(D) OTHER INFORMATION:/product= "random codon by trinucleotide mutagenesis (GTT/TAT)"

(xi) SEQUENCE DESCRIPTION: SEQ ID NO: 5:

GATACGGCCG TGTATTATTG CGCGCGTNNK NNKNNKNNKN NKNNKNNKNN KNNKNNKWTK 60

GATKWTTGGG GCCAAGGCAC CCTG 84

(2) INFORMATION FOR SEQ ID NO: 6:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 6:

GATACGGCCG TGTATTATTG C 21

(2) INFORMATION FOR SEQ ID NO: 7:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 7:

CAGGGTGCCT TGGCCCC 17

(2) INFORMATION FOR SEQ ID NO: 8:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 8:

GCAGAAGGCG AACGTCC 17

(2) INFORMATION FOR SEQ ID NO: 9:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

(ix) FEATURE:
(A) NAME/KEY: misc_feature
(B) LOCATION:39..41
(D) OTHER INFORMATION:/product= "random codon (mixture of GCT, CGT, CAT, TCT, TAT)"

(ix) FEATURE:
(A) NAME/KEY: misc_feature
(B) LOCATION:42..53
(D) OTHER INFORMATION:/product= "random codons by trinucleotide mutagenesis (19 aa, no Cys)"

(ix) FEATURE:
(A) NAME/KEY: misc_feature
(B) LOCATION:57..59
(D) OTHER INFORMATION:/product= "random codon by trinucleotide mutagenesis (19 aa, no Cys)"

(xi) SEQUENCE DESCRIPTION: SEQ ID NO: 9:

TGGAAGCTGA AGACGTGGGC GTGTATTATT GCCAGCAGBV TNNKNNKNNK NNKCCGNNKT 60

TTGGCCAGGG TACGAAAGTT 80

(2) INFORMATION FOR SEQ ID NO: 10:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 10:

AACTTTCGTA CCCTGGCC 18

(2) INFORMATION FOR SEQ ID NO: 11:

(i) SEQUENCE CHARACTERISTICS:
(A) LENGTH: 108 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

(ix) FEATURE:
(A) NAME/KEY: misc_feature
(B) LOCATION:21..23
(D) OTHER INFORMATION:/product= "random codon by trinucleotide mutagenesis (19aa, no Cys)"

(ix) FEATURE:
(A) NAME/KEY: misc_feature
(B) LOCATION:27..35
(D) OTHER INFORMATION:/product= "random codons by trinucleotide mutagenesis (19 aa, no Cys)"

(ix) FEATURE:
(A) NAME/KEY: misc_feature
(B) LOCATION:36..41
(D) OTHER INFORMATION:/product= "random codons by mixed monomers (A/G A/C/G T)"

(ix) FEATURE:
(A) NAME/KEY: misc_feature
(B) LOCATION:42..44

-continued (D) OTHER INFORMATION:/product= "random codon by trinucleotide mutagenesis (19aa, no Cys)"

(ix) FEATURE:
(A) NAME/KEY: misc_feature
(B) LOCATION:48..50
(D) OTHER INFORMATION:/product= "random codon by trinucleotide mutagenesis (19aa, no Cys)"

(xi) SEQUENCE DESCRIPTION: SEQ ID NO: 11:

AGGGTCTCGA GTGGGTGAGC NNKATTNNKN NKNNKRVTRV TNNKACCNNK TATGCGGATA 60

GCGTGAAAGG CCGTTTTACC ATTTCACGTG ATAATTCGAA AAACACCA 108

(2) INFORMATION FOR SEQ ID NO: 12:

(i) SEQUENCE CHARACTERISTICS:
(A) LENGTH: 105 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

(ix) FEATURE:
(A) NAME/KEY: misc_feature
(B) LOCATION:21..23
(D) OTHER INFORMATION:/product= "random codon by trinucleotide mutagenesis (19aa, no Cys)"

(ix) FEATURE:
(A) NAME/KEY: misc_feature
(B) LOCATION:27..32
(D) OTHER INFORMATION:/product= "random codons by trinucleotide mutagenesis (19aa, no Cys)"

(ix) FEATURE:
(A) NAME/KEY: misc_feature
(B) LOCATION:33..38
(D) OTHER INFORMATION:/product= "random codons by mixed monomers (A/G A/C/G T)"

(ix) FEATURE:
(A) NAME/KEY: misc_feature
(B) LOCATION:39..41
(D) OTHER INFORMATION:/product= "random codon by trinucleotide mutagenesis (19aa, no Cys)"

(ix) FEATURE:
(A) NAME/KEY: misc_feature
(B) LOCATION:45..47
(D) OTHER INFORMATION:/product= "random codon by trinucleotide mutagenesis (19aa, no Cys)"

(xi) SEQUENCE DESCRIPTION: SEQ ID NO: 12:

AGGGTCTCGA GTGGGTGAGC NNKATTNNKN NKRVTRVTNN KACCNNKTAT GCGGATAGCG 60

TGAAAGGCCG TTTTACCATT TCACGTGATA ATTCGAAAAA CACCA 105

(2) INFORMATION FOR SEQ ID NO: 13:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 13:

TGGTGTTTTT CGAATTATCA 20

-continued (2) INFORMATION FOR SEQ ID NO: 14:

(i) SEQUENCE CHARACTERISTICS:
(A) LENGTH: 108 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 14:

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys Arg
            100                 105
```

(2) INFORMATION FOR SEQ ID NO: 15:

(i) SEQUENCE CHARACTERISTICS:
(A) LENGTH: 113 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 15:

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg
```

(2) INFORMATION FOR SEQ ID NO: 16:

(i) SEQUENCE CHARACTERISTICS:
(A) LENGTH: 109 amino acids
(B) TYPE: amino acid
(C) STRANDEDNESS:
(D) TOPOLOGY: linear -continued (ii) MOLECULE TYPE: protein (xi) SEQUENCE DESCRIPTION: SEQ ID NO: 16:

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Tyr Thr Phe Gly Gln Gly Thr Lys Val Glu Ile Lys Arg
            100                 105
```

(2) INFORMATION FOR SEQ ID NO: 17:

(i) SEQUENCE CHARACTERISTICS:
(A) LENGTH: 114 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 17:

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys Arg
```

(2) INFORMATION FOR SEQ ID NO: 18:

(i) SEQUENCE CHARACTERISTICS:
(A) LENGTH: 112 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 18:

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn Asn
```

-continued

```
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ala Thr Trp Asp Asp Ser Leu
                85                  90                  95

Ser Gly Val Val Phe Gly Gly Gly Thr Lys Leu Thr Val Leu Gly Gln
            100                 105                 110
```

(2) INFORMATION FOR SEQ ID NO: 19:

(i) SEQUENCE CHARACTERISTICS:
(A) LENGTH: 112 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 19:

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Ser Thr Val Val Phe Gly Gly Gly Thr Lys Leu Thr Val Leu Gly Gln
            100                 105                 110
```

(2) INFORMATION FOR SEQ ID NO: 20:

(i) SEQUENCE CHARACTERISTICS:
(A) LENGTH: 108 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 20:

```
Tyr Glu Leu Thr Gln Pro Pro Ser Val Ser Val Ala Pro Gly Gln Thr
1               5                   10                  15

Ala Arg Ile Thr Cys Ser Gly Asp Ser Leu Gly Ser Lys Tyr Ala Ser
            20                  25                  30

Trp Tyr Gln Gln Lys Pro Gly Gln Ala Pro Val Leu Val Ile Tyr Asp
        35                  40                  45

Asp Asn Lys Arg Pro Ser Gly Ile Pro Glu Arg Phe Ser Gly Ser Asn
    50                  55                  60

Ser Gly Asn Thr Ala Thr Leu Thr Ile Ser Gly Val Gln Ala Glu Asp
65                  70                  75                  80
```

-continued

```
Glu Ala Asp Tyr Tyr Cys Gln Ser Trp Asp Ser Ser Gly Asn Val Val
                85                  90                  95

Phe Gly Gly Gly Thr Lys Leu Thr Val Leu Gly Gln
            100                 105
```

(2) INFORMATION FOR SEQ ID NO: 21:

(i) SEQUENCE CHARACTERISTICS:
(A) LENGTH: 119 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 21:

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Gly Tyr Cys Ser Gly Phe Asp Tyr Trp Gly Gln Gly
            100                 105                 110

Thr Leu Val Thr Val Ser Ser
        115
```

(2) INFORMATION FOR SEQ ID NO: 22:

(i) SEQUENCE CHARACTERISTICS:
(A) LENGTH: 117 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 22:

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Asp Gly Gly Phe Asp Tyr Trp Gly Gln Gly Thr Leu
            100                 105                 110

Val Thr Val Ser Ser
        115
```

-continued (2) INFORMATION FOR SEQ ID NO: 23:

(i) SEQUENCE CHARACTERISTICS:
(A) LENGTH: 120 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 23:

```
Glx Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Asp Trp Asp Asp Asp Lys Tyr Tyr Ser Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile His Asn Ile Gly Glu Ala Phe Asp Val Trp Gly Gln
            100                 105                 110

Gly Thr Leu Val Thr Val Ser Ser
        115                 120
```

(2) INFORMATION FOR SEQ ID NO: 24:

(i) SEQUENCE CHARACTERISTICS:
(A) LENGTH: 117 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 24:

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Val Ile Ser Tyr Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ser Gly Asp Tyr Trp Gly Gln Gly Thr Leu
            100                 105                 110

Val Thr Val Ser Ser
        115
```

(2) INFORMATION FOR SEQ ID NO: 25:

(i) SEQUENCE CHARACTERISTICS:

-continued (A) LENGTH: 118 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 25:

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Glu Ile Tyr His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Gly Gly Gly Val Phe Asp Tyr Trp Gly Gln Gly Thr
            100                 105                 110

Leu Val Thr Val Ser Ser
        115
```

(2) INFORMATION FOR SEQ ID NO: 26:

(i) SEQUENCE CHARACTERISTICS:
(A) LENGTH: 119 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 26:

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Gly Gly Gly Tyr Tyr Phe Asp Tyr Trp Gly Gln Gly
            100                 105                 110

Thr Leu Val Thr Val Ser Ser
        115
```

(2) INFORMATION FOR SEQ ID NO: 27:

(i) SEQUENCE CHARACTERISTICS:
(A) LENGTH: 119 amino acids
(B) TYPE: amino acid
(C) STRANDEDNESS:
(D) TOPOLOGY: linear -continued (ii) MOLECULE TYPE: protein (xi) SEQUENCE DESCRIPTION: SEQ ID NO: 27:

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Phe Asp Val Trp Gly Gln Gly
            100                 105                 110

Thr Leu Val Thr Val Ser Ser
        115
```

(2) INFORMATION FOR SEQ ID NO: 28:

(i) SEQUENCE CHARACTERISTICS:
(A) LENGTH: 109 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 28:

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105
```

(2) INFORMATION FOR SEQ ID NO: 29:

(i) SEQUENCE CHARACTERISTICS:
(A) LENGTH: 114 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 29:

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
```

-continued

```
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln His
                85                  90                  95

Tyr Thr Thr Pro Pro Thr Phe Gly Gln Gly Thr Lys Val Glu Ile Lys
            100                 105                 110

Arg Thr
```

(2) INFORMATION FOR SEQ ID NO: 30:

(i) SEQUENCE CHARACTERISTICS:
(A) LENGTH: 110 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 30:

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln His Tyr Thr Thr Pro
                85                  90                  95

Pro Thr Phe Gly Gln Gly Thr Lys Val Glu Ile Lys Arg Thr
            100                 105                 110
```

(2) INFORMATION FOR SEQ ID NO: 31:

(i) SEQUENCE CHARACTERISTICS:
(A) LENGTH: 115 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 31:

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
```

-continued

```
65                  70                  75                  80

Ile Ser Ser Leu Gln Ala Glu Asp Val Ala Val Tyr Tyr Cys Gln Gln
                85                  90                  95

His Tyr Thr Thr Pro Pro Thr Phe Gly Gln Gly Thr Lys Val Glu Ile
            100                 105                 110

Lys Arg Thr
        115
```

(2) INFORMATION FOR SEQ ID NO: 32:

(i) SEQUENCE CHARACTERISTICS:
(A) LENGTH: 109 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 32:

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Gln His Tyr Thr Thr Pro
                85                  90                  95

Pro Val Phe Gly Gly Gly Thr Lys Leu Thr Val Leu Gly
            100                 105
```

(2) INFORMATION FOR SEQ ID NO: 33:

(i) SEQUENCE CHARACTERISTICS:
(A) LENGTH: 110 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 33:

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Gln His Tyr Thr Thr
                85                  90                  95

Pro Pro Val Phe Gly Gly Gly Thr Lys Leu Thr Val Leu Gly
            100                 105                 110
```

-continued (2) INFORMATION FOR SEQ ID NO: 34:

(i) SEQUENCE CHARACTERISTICS:
(A) LENGTH: 107 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 34:

```
Ser Tyr Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Gln His Tyr Thr Thr Pro Pro Val
                85                  90                  95

Phe Gly Gly Gly Thr Lys Leu Thr Val Leu Gly
            100                 105
```

(2) INFORMATION FOR SEQ ID NO: 35:

(i) SEQUENCE CHARACTERISTICS:
(A) LENGTH: 120 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 35:

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 36:

(i) SEQUENCE CHARACTERISTICS:
(A) LENGTH: 120 amino acids
(B) TYPE: amino acid
(C) STRANDEDNESS:
(D) TOPOLOGY: linear -continued (ii) MOLECULE TYPE: protein (xi) SEQUENCE DESCRIPTION: SEQ ID NO: 36:

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 37:

(i) SEQUENCE CHARACTERISTICS:
(A) LENGTH: 121 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 37:

```
Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Trp Gly Gly Asp Gly Phe Tyr Ala Met Asp Tyr Trp Gly
            100                 105                 110

Gln Gly Thr Leu Val Thr Val Ser Ser
        115                 120
```

(2) INFORMATION FOR SEQ ID NO: 38:

(i) SEQUENCE CHARACTERISTICS:
(A) LENGTH: 120 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 38:

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 39:

(i) SEQUENCE CHARACTERISTICS:
(A) LENGTH: 119 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 39:

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Gly Asp Gly Phe Tyr Ala Met Asp Tyr Trp Gly Gln Gly
            100                 105                 110

Thr Leu Val Thr Val Ser Ser
        115
```

(2) INFORMATION FOR SEQ ID NO: 40:

(i) SEQUENCE CHARACTERISTICS:
(A) LENGTH: 120 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 40:

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30
```

-continued

```
Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 41:

(i) SEQUENCE CHARACTERISTICS:
(A) LENGTH: 123 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO: 41:

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser
        115                 120
```

(2) INFORMATION FOR SEQ ID NO: 42:

(i) SEQUENCE CHARACTERISTICS:
(A) LENGTH: 327 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..327
(D) OTHER INFORMATION:/product= "V kappa 1"

(xi) SEQUENCE DESCRIPTION: SEQ ID NO: 42:

```
GAT ATC CAG ATG ACC CAG AGC CCG TCT AGC CTG AGC GCG AGC GTG GGT       48
Asp Ile Gln Met Thr Gln Ser Pro Ser Ser Leu Ser Ala Ser Val Gly
  1               5                  10                  15
```

-continued

```
GAT CGT GTG ACC ATT ACC TGC AGA GCG AGC CAG GGC ATT AGC AGC TAT        96
Asp Arg Val Thr Ile Thr Cys Arg Ala Ser Gln Gly Ile Ser Ser Tyr
             20                  25                  30

CTG GCG TGG TAC CAG CAG AAA CCA GGT AAA GCA CCG AAA CTA TTA ATT       144
Leu Ala Trp Tyr Gln Gln Lys Pro Gly Lys Ala Pro Lys Leu Leu Ile
         35                  40                  45

TAT GCA GCC AGC AGC TTG CAA AGC GGG GTC CCG TCC CGT TTT AGC GGC       192
Tyr Ala Ala Ser Ser Leu Gln Ser Gly Val Pro Ser Arg Phe Ser Gly
     50                  55                  60

TCT GGA TCC GGC ACT GAT TTT ACC CTG ACC ATT AGC AGC CTG CAA CCT       240
Ser Gly Ser Gly Thr Asp Phe Thr Leu Thr Ile Ser Ser Leu Gln Pro
 65                  70                  75                  80

GAA GAC TTT GCG ACC TAT TAT TGC CAG CAG CAT TAT ACC ACC CCG CCG       288
Glu Asp Phe Ala Thr Tyr Tyr Cys Gln Gln His Tyr Thr Thr Pro Pro
                 85                  90                  95

ACC TTT GGC CAG GGT ACG AAA GTT GAA ATT AAA CGT ACG                   327
Thr Phe Gly Gln Gly Thr Lys Val Glu Ile Lys Arg Thr
            100                 105
```

(2) INFORMATION FOR SEQ ID NO: 43:

(i) SEQUENCE CHARACTERISTICS:
(A) LENGTH: 109 amino acids
(B) TYPE: amino acid
(D) TOPOLOGY: linear (ii) MOLECULE TYPE: protein (xi) SEQUENCE DESCRIPTION: SEQ ID NO: 43:

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr
            100                 105
```

(2) INFORMATION FOR SEQ ID NO: 44:

(i) SEQUENCE CHARACTERISTICS:
(A) LENGTH: 342 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..342
(D) OTHER INFORMATION:/product= "V kappa 2"

(xi) SEQUENCE DESCRIPTION: SEQ ID NO: 44:

```
GAT ATC GTG ATG ACC CAG AGC CCA CTG AGC CTG CCA GTG ACT CCG GGC        48
Asp Ile Val Met Thr Gln Ser Pro Leu Ser Leu Pro Val Thr Pro Gly
110                 115                 120                 125
```

-continued

```
GAG CCT GCG AGC ATT AGC TGC AGA AGC AGC CAA AGC CTG CTG CAT AGC        96
Glu Pro Ala Ser Ile Ser Cys Arg Ser Ser Gln Ser Leu Leu His Ser
                130                 135                 140

AAC GGC TAT AAC TAT CTG GAT TGG TAC CTT CAA AAA CCA GGT CAA AGC       144
Asn Gly Tyr Asn Tyr Leu Asp Trp Tyr Leu Gln Lys Pro Gly Gln Ser
            145                 150                 155

CCG CAG CTA TTA ATT TAT CTG GGC AGC AAC CGT GCC AGT GGG GTC CCG       192
Pro Gln Leu Leu Ile Tyr Leu Gly Ser Asn Arg Ala Ser Gly Val Pro
        160                 165                 170

GAT CGT TTT AGC GGC TCT GGA TCC GGC ACC GAT TTT ACC CTG AAA ATT       240
Asp Arg Phe Ser Gly Ser Gly Ser Gly Thr Asp Phe Thr Leu Lys Ile
    175                 180                 185

AGC CGT GTG GAA GCT GAA GAC GTG GGC GTG TAT TAT TGC CAG CAG CAT       288
Ser Arg Val Glu Ala Glu Asp Val Gly Val Tyr Tyr Cys Gln Gln His
190                 195                 200                 205

TAT ACC ACC CCG CCG ACC TTT GGC CAG GGT ACG AAA GTT GAA ATT AAA       336
Tyr Thr Thr Pro Pro Thr Phe Gly Gln Gly Thr Lys Val Glu Ile Lys
                210                 215                 220

CGT ACG                                                               342
Arg Thr
```

(2) INFORMATION FOR SEQ ID NO: 45:

(i) SEQUENCE CHARACTERISTICS:
(A) LENGTH: 114 amino acids
(B) TYPE: amino acid
(D) TOPOLOGY: linear (ii) MOLECULE TYPE: protein (xi) SEQUENCE DESCRIPTION: SEQ ID NO: 45:

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln His
                 85                  90                  95

Tyr Thr Thr Pro Pro Thr Phe Gly Gln Gly Thr Lys Val Glu Ile Lys
            100                 105                 110

Arg Thr
```

(2) INFORMATION FOR SEQ ID NO: 46:

(i) SEQUENCE CHARACTERISTICS:
(A) LENGTH: 330 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..330
(D) OTHER INFORMATION:/product= "V kappa 3"

-continued (xi) SEQUENCE DESCRIPTION: SEQ ID NO: 46:

```
GAT ATC GTG CTG ACC CAG AGC CCG GCG ACC CTG AGC CTG TCT CCG GGC       48
Asp Ile Val Leu Thr Gln Ser Pro Ala Thr Leu Ser Leu Ser Pro Gly
115                 120                 125                 130

GAA CGT GCG ACC CTG AGC TGC AGA GCG AGC CAG AGC GTG AGC AGC AGC       96
Glu Arg Ala Thr Leu Ser Cys Arg Ala Ser Gln Ser Val Ser Ser Ser
                135                 140                 145

TAT CTG GCG TGG TAC CAG CAG AAA CCA GGT CAA GCA CCG CGT CTA TTA      144
Tyr Leu Ala Trp Tyr Gln Gln Lys Pro Gly Gln Ala Pro Arg Leu Leu
            150                 155                 160

ATT TAT GGC GCG AGC AGC CGT GCA ACT GGG GTC CCG GCG CGT TTT AGC      192
Ile Tyr Gly Ala Ser Ser Arg Ala Thr Gly Val Pro Ala Arg Phe Ser
        165                 170                 175

GGC TCT GGA TCC GGC ACG GAT TTT ACC CTG ACC ATT AGC AGC CTG GAA      240
Gly Ser Gly Ser Gly Thr Asp Phe Thr Leu Thr Ile Ser Ser Leu Glu
    180                 185                 190

CCT GAA GAC TTT GCG GTG TAT TAT TGC CAG CAG CAT TAT ACC ACC CCG      288
Pro Glu Asp Phe Ala Val Tyr Tyr Cys Gln Gln His Tyr Thr Thr Pro
195                 200                 205                 210

CCG ACC TTT GGC CAG GGT ACG AAA GTT GAA ATT AAA CGT ACG              330
Pro Thr Phe Gly Gln Gly Thr Lys Val Glu Ile Lys Arg Thr
                215                 220
```

(2) INFORMATION FOR SEQ ID NO: 47:

(i) SEQUENCE CHARACTERISTICS:
(A) LENGTH: 110 amino acids
(B) TYPE: amino acid
(D) TOPOLOGY: linear (ii) MOLECULE TYPE: protein (xi) SEQUENCE DESCRIPTION: SEQ ID NO: 47:

```
Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln His Tyr Thr Thr Pro
                 85                  90                  95

Pro Thr Phe Gly Gln Gly Thr Lys Val Glu Ile Lys Arg Thr
            100                 105                 110
```

(2) INFORMATION FOR SEQ ID NO: 48:

(i) SEQUENCE CHARACTERISTICS:
(A) LENGTH: 345 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..345

-continued (D) OTHER INFORMATION:/product= "V kappa 4"

(xi) SEQUENCE DESCRIPTION: SEQ ID NO: 48:

```
GAT ATC GTG ATG ACC CAG AGC CCG GAT AGC CTG GCG GTG AGC CTG GGC       48
Asp Ile Val Met Thr Gln Ser Pro Asp Ser Leu Ala Val Ser Leu Gly
            115                 120                 125

GAA CGT GCG ACC ATT AAC TGC AGA AGC AGC CAG AGC GTG CTG TAT AGC       96
Glu Arg Ala Thr Ile Asn Cys Arg Ser Ser Gln Ser Val Leu Tyr Ser
        130                 135                 140

AGC AAC AAC AAA AAC TAT CTG GCG TGG TAC CAG CAG AAA CCA GGT CAG      144
Ser Asn Asn Lys Asn Tyr Leu Ala Trp Tyr Gln Gln Lys Pro Gly Gln
    145                 150                 155

CCG CCG AAA CTA TTA ATT TAT TGG GCA TCC ACC CGT GAA AGC GGG GTC      192
Pro Pro Lys Leu Leu Ile Tyr Trp Ala Ser Thr Arg Glu Ser Gly Val
160                 165                 170

CCG GAT CGT TTT AGC GGC TCT GGA TCC GGC ACT GAT TTT ACC CTG ACC      240
Pro Asp Arg Phe Ser Gly Ser Gly Ser Gly Thr Asp Phe Thr Leu Thr
175                 180                 185                 190

ATT TCG TCC CTG CAA GCT GAA GAC GTG GCG GTG TAT TAT TGC CAG CAG      288
Ile Ser Ser Leu Gln Ala Glu Asp Val Ala Val Tyr Tyr Cys Gln Gln
            195                 200                 205

CAT TAT ACC ACC CCG CCG ACC TTT GGC CAG GGT ACG AAA GTT GAA ATT      336
His Tyr Thr Thr Pro Pro Thr Phe Gly Gln Gly Thr Lys Val Glu Ile
        210                 215                 220

AAA CGT ACG                                                          345
Lys Arg Thr
    225
```

(2) INFORMATION FOR SEQ ID NO: 49:

(i) SEQUENCE CHARACTERISTICS:
(A) LENGTH: 115 amino acids
(B) TYPE: amino acid
(D) TOPOLOGY: linear (ii) MOLECULE TYPE: protein (xi) SEQUENCE DESCRIPTION: SEQ ID NO: 49:

```
Asp Ile Val Met Thr Gln Ser Pro Asp Ser Leu Ala Val Ser Leu Gly
  1               5                  10                  15

Glu Arg Ala Thr Ile Asn Cys Arg Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Thr Thr Pro Pro Thr Phe Gly Gln Gly Thr Lys Val Glu Ile
            100                 105                 110

Lys Arg Thr
        115
```

(2) INFORMATION FOR SEQ ID NO: 50:

(i) SEQUENCE CHARACTERISTICS:
(A) LENGTH: 327 base pairs
(B) TYPE: nucleic acid
(C) STRANDEDNESS: double -continued (D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..327
(D) OTHER INFORMATION:/product= "V lambda 1"

(xi) SEQUENCE DESCRIPTION: SEQ ID NO: 50:

```
CAG AGC GTG CTG ACC CAG CCG CCT TCA GTG AGT GGC GCA CCA GGT CAG       48
Gln Ser Val Leu Thr Gln Pro Pro Ser Val Ser Gly Ala Pro Gly Gln
                120                 125                 130

CGT GTG ACC ATC TCG TGT AGC GGC AGC AGC AGC AAC ATT GGC AGC AAC       96
Arg Val Thr Ile Ser Cys Ser Gly Ser Ser Ser Asn Ile Gly Ser Asn
            135                 140                 145

TAT GTG AGC TGG TAC CAG CAG TTG CCC GGG ACG GCG CCG AAA CTG CTG      144
Tyr Val Ser Trp Tyr Gln Gln Leu Pro Gly Thr Ala Pro Lys Leu Leu
        150                 155                 160

ATT TAT GAT AAC AAC CAG CGT CCC TCA GGC GTG CCG GAT CGT TTT AGC      192
Ile Tyr Asp Asn Asn Gln Arg Pro Ser Gly Val Pro Asp Arg Phe Ser
    165                 170                 175

GGA TCC AAA AGC GGC ACC AGC GCG AGC CTT GCG ATT ACG GGC CTG CAA      240
Gly Ser Lys Ser Gly Thr Ser Ala Ser Leu Ala Ile Thr Gly Leu Gln
180                 185                 190                 195

AGC GAA GAC GAA GCG GAT TAT TAT TGC CAG CAG CAT TAT ACC ACC CCG      288
Ser Glu Asp Glu Ala Asp Tyr Tyr Cys Gln Gln His Tyr Thr Thr Pro
                200                 205                 210

CCT GTG TTT GGC GGC GGC ACG AAG TTA ACC GTT CTT GGC                  327
Pro Val Phe Gly Gly Gly Thr Lys Leu Thr Val Leu Gly
            215                 220
```

(2) INFORMATION FOR SEQ ID NO: 51:

(i) SEQUENCE CHARACTERISTICS:
(A) LENGTH: 109 amino acids
(B) TYPE: amino acid
(D) TOPOLOGY: linear (ii) MOLECULE TYPE: protein (xi) SEQUENCE DESCRIPTION: SEQ ID NO: 51:

```
Gln Ser Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
             20                  25                  30

Tyr Val Ser Trp Tyr Gln Gln Leu Pro Gly Thr Ala Pro Lys Leu Leu
         35                  40                  45

Ile Tyr Asp Asn Asn Gln Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Gln His Tyr Thr Thr Pro
                 85                  90                  95

Pro Val Phe Gly Gly Gly Thr Lys Leu Thr Val Leu Gly
            100                 105
```

(2) INFORMATION FOR SEQ ID NO: 52:

(i) SEQUENCE CHARACTERISTICS:
(A) LENGTH: 330 base pairs
(B) TYPE: nucleic acid

-continued

```
(C) STRANDEDNESS: double
(D) TOPOLOGY: linear

(ii) MOLECULE TYPE: other nucleic acid
(A) DESCRIPTION: /desc = "synthetic gene"

(ix) FEATURE:
(A) NAME/KEY: CDS
(B) LOCATION:1..330
(D) OTHER INFORMATION:/product= "V lambda 2"

(xi) SEQUENCE DESCRIPTION: SEQ ID NO: 52:

CAG AGC GCA CTG ACC CAG CCA GCT TCA GTG AGC GGC TCA CCA GGT CAG       48
Gln Ser Ala Leu Thr Gln Pro Ala Ser Val Ser Gly Ser Pro Gly Gln
110                 115                 120                 125

AGC ATT ACC ATC TCG TGT ACG GGT ACT AGC AGC GAT GTG GGC GGC TAT       96
Ser Ile Thr Ile Ser Cys Thr Gly Thr Ser Ser Asp Val Gly Gly Tyr
                130                 135                 140

AAC TAT GTG AGC TGG TAC CAG CAG CAT CCC GGG AAG GCG CCG AAA CTG      144
Asn Tyr Val Ser Trp Tyr Gln Gln His Pro Gly Lys Ala Pro Lys Leu
            145                 150                 155

ATG ATT TAT GAT GTG AGC AAC CGT CCC TCA GGC GTG AGC AAC CGT TTT      192
Met Ile Tyr Asp Val Ser Asn Arg Pro Ser Gly Val Ser Asn Arg Phe
        160                 165                 170

AGC GGA TCC AAA AGC GGC AAC ACC GCG AGC CTG ACC ATT AGC GGC CTG      240
Ser Gly Ser Lys Ser Gly Asn Thr Ala Ser Leu Thr Ile Ser Gly Leu
    175                 180                 185

CAA GCG GAA GAC GAA GCG GAT TAT TAT TGC CAG CAG CAT TAT ACC ACC      288
Gln Ala Glu Asp Glu Ala Asp Tyr Tyr Cys Gln Gln His Tyr Thr Thr
190                 195                 200                 205

CCG CCT GTG TTT GGC GGC GGC ACG AAG TTA ACC GTT CTT GGC              330
Pro Pro Val Phe Gly Gly Gly Thr Lys Leu Thr Val Leu Gly
                210                 215


(2) INFORMATION FOR SEQ ID NO: 53:

(i) SEQUENCE CHARACTERISTICS:
(A) LENGTH: 110 amino acids
(B) TYPE: amino acid
(D) TOPOLOGY: linear

(ii) MOLECULE TYPE: protein

(xi) SEQUENCE DESCRIPTION: SEQ ID NO: 53:

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Gln His Tyr Thr Thr
                85                  90                  95

Pro Pro Val Phe Gly Gly Gly Thr Lys Leu Thr Val Leu Gly
            100                 105                 110


(2) INFORMATION FOR SEQ ID NO: 54:

(i) SEQUENCE CHARACTERISTICS:
(A) LENGTH: 321 base pairs
```

-continued (B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..321
(D) OTHER INFORMATION:/product= "V lambda 3"

(xi) SEQUENCE DESCRIPTION: SEQ ID NO: 54:

```
AGC TAT GAA CTG ACC CAG CCG CCT TCA GTG AGC GTT GCA CCA GGT CAG       48
Ser Tyr Glu Leu Thr Gln Pro Pro Ser Val Ser Val Ala Pro Gly Gln
            115                 120                 125

ACC GCG CGT ATC TCG TGT AGC GGC GAT GCG CTG GGC GAT AAA TAC GCG       96
Thr Ala Arg Ile Ser Cys Ser Gly Asp Ala Leu Gly Asp Lys Tyr Ala
            130                 135                 140

AGC TGG TAC CAG CAG AAA CCC GGG CAG GCG CCA GTT CTG GTG ATT TAT      144
Ser Trp Tyr Gln Gln Lys Pro Gly Gln Ala Pro Val Leu Val Ile Tyr
        145                 150                 155

GAT GAT TCT GAC CGT CCC TCA GGC ATC CCG GAA CGC TTT AGC GGA TCC      192
Asp Asp Ser Asp Arg Pro Ser Gly Ile Pro Glu Arg Phe Ser Gly Ser
    160                 165                 170

AAC AGC GGC AAC ACC GCG ACC CTG ACC ATT AGC GGC ACT CAG GCG GAA      240
Asn Ser Gly Asn Thr Ala Thr Leu Thr Ile Ser Gly Thr Gln Ala Glu
175                 180                 185                 190

GAC GAA GCG GAT TAT TAT TGC CAG CAG CAT TAT ACC ACC CCG CCT GTG      288
Asp Glu Ala Asp Tyr Tyr Cys Gln Gln His Tyr Thr Thr Pro Pro Val
                195                 200                 205

TTT GGC GGC GGC ACG AAG TTA ACC GTT CTT GGC                          321
Phe Gly Gly Gly Thr Lys Leu Thr Val Leu Gly
            210                 215
```

(2) INFORMATION FOR SEQ ID NO: 55:

(i) SEQUENCE CHARACTERISTICS:
(A) LENGTH: 107 amino acids
(B) TYPE: amino acid
(D) TOPOLOGY: linear (ii) MOLECULE TYPE: protein (xi) SEQUENCE DESCRIPTION: SEQ ID NO: 55:

```
Ser Tyr Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
             20                  25                  30

Ser Trp Tyr Gln Gln Lys Pro Gly Gln Ala Pro Val Leu Val Ile Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Gln His Tyr Thr Thr Pro Pro Val
                 85                  90                  95

Phe Gly Gly Gly Thr Lys Leu Thr Val Leu Gly
            100                 105
```

(2) INFORMATION FOR SEQ ID NO: 56:

(i) SEQUENCE CHARACTERISTICS:

-continued (A) LENGTH: 361 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..360
(D) OTHER INFORMATION:/product= "VH1A"

(xi) SEQUENCE DESCRIPTION: SEQ ID NO: 56:

```
CAG GTG CAA TTG GTT CAG TCT GGC GCG GAA GTG AAA AAA CCG GGC AGC       48
Gln Val Gln Leu Val Gln Ser Gly Ala Glu Val Lys Lys Pro Gly Ser
        110                 115                 120

AGC GTG AAA GTG AGC TGC AAA GCC TCC GGA GGC ACT TTT AGC AGC TAT       96
Ser Val Lys Val Ser Cys Lys Ala Ser Gly Gly Thr Phe Ser Ser Tyr
    125                 130                 135

GCG ATT AGC TGG GTG CGC CAA GCC CCT GGG CAG GGT CTC GAG TGG ATG      144
Ala Ile Ser Trp Val Arg Gln Ala Pro Gly Gln Gly Leu Glu Trp Met
140                 145                 150                 155

GGC GGC ATT ATT CCG ATT TTT GGC ACG GCG AAC TAC GCG CAG AAG TTT      192
Gly Gly Ile Ile Pro Ile Phe Gly Thr Ala Asn Tyr Ala Gln Lys Phe
                160                 165                 170

CAG GGC CGG GTG ACC ATT ACC GCG GAT GAA AGC ACC AGC ACC GCG TAT      240
Gln Gly Arg Val Thr Ile Thr Ala Asp Glu Ser Thr Ser Thr Ala Tyr
            175                 180                 185

ATG GAA CTG AGC AGC CTG CGT AGC GAA GAT ACG GCC GTG TAT TAT TGC      288
Met Glu Leu Ser Ser Leu Arg Ser Glu Asp Thr Ala Val Tyr Tyr Cys
        190                 195                 200

GCG CGT TGG GGC GGC GAT GGC TTT TAT GCG ATG GAT TAT TGG GGC CAA      336
Ala Arg Trp Gly Gly Asp Gly Phe Tyr Ala Met Asp Tyr Trp Gly Gln
    205                 210                 215

GGC ACC CTG GTG ACG GTT AGC TCA G                                    361
Gly Thr Leu Val Thr Val Ser Ser
220                 225
```

(2) INFORMATION FOR SEQ ID NO: 57:

(i) SEQUENCE CHARACTERISTICS:
(A) LENGTH: 120 amino acids
(B) TYPE: amino acid
(D) TOPOLOGY: linear (ii) MOLECULE TYPE: protein (xi) SEQUENCE DESCRIPTION: SEQ ID NO: 57:

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Gly Asp Gly Phe Tyr Ala Met Asp Tyr Trp Gly Gln
            100                 105                 110
```

-continued

```
Gly Thr Leu Val Thr Val Ser Ser
        115                 120
```

(2) INFORMATION FOR SEQ ID NO: 58:

(i) SEQUENCE CHARACTERISTICS:
(A) LENGTH: 361 base pairs
(B) TYPE: nucleic acid
(C) STRANDEDNESS: double
(D) TOPOLOGY: linear (ii) MOLECULE TYPE: other nucleic acid
(A) DESCRIPTION: /desc = “synthetic gene”

(ix) FEATURE:
(A) NAME/KEY: CDS
(B) LOCATION:1..360
(D) OTHER INFORMATION:/product= “VH1B”

(xi) SEQUENCE DESCRIPTION: SEQ ID NO: 58:

```
CAG GTG CAA TTG GTT CAG AGC GGC GCG GAA GTG AAA AAA CCG GGC GCG       48
Gln Val Gln Leu Val Gln Ser Gly Ala Glu Val Lys Lys Pro Gly Ala
                125                 130                 135

AGC GTG AAA GTG AGC TGC AAA GCC TCC GGA TAT ACC TTT ACC AGC TAT       96
Ser Val Lys Val Ser Cys Lys Ala Ser Gly Tyr Thr Phe Thr Ser Tyr
            140                 145                 150

TAT ATG CAC TGG GTC CGC CAA GCC CCT GGG CAG GGT CTC GAG TGG ATG      144
Tyr Met His Trp Val Arg Gln Ala Pro Gly Gln Gly Leu Glu Trp Met
        155                 160                 165

GGC TGG ATT AAC CCG AAT AGC GGC GGC ACG AAC TAC GCG CAG AAG TTT      192
Gly Trp Ile Asn Pro Asn Ser Gly Gly Thr Asn Tyr Ala Gln Lys Phe
    170                 175                 180

CAG GGC CGG GTG ACC ATG ACC CGT GAT ACC AGC ATT AGC ACC GCG TAT      240
Gln Gly Arg Val Thr Met Thr Arg Asp Thr Ser Ile Ser Thr Ala Tyr
185                 190                 195                 200

ATG GAA CTG AGC AGC CTG CGT AGC GAA GAT ACG GCC GTG TAT TAT TGC      288
Met Glu Leu Ser Ser Leu Arg Ser Glu Asp Thr Ala Val Tyr Tyr Cys
                205                 210                 215

GCG CGT TGG GGC GGC GAT GGC TTT TAT GCG ATG GAT TAT TGG GGC CAA      336
Ala Arg Trp Gly Gly Asp Gly Phe Tyr Ala Met Asp Tyr Trp Gly Gln
            220                 225                 230

GGC ACC CTG GTG ACG GTT AGC TCA G                                    361
Gly Thr Leu Val Thr Val Ser Ser
        235                 240
```

(2) INFORMATION FOR SEQ ID NO: 59:

(i) SEQUENCE CHARACTERISTICS:
(A) LENGTH: 120 amino acids
(B) TYPE: amino acid
(D) TOPOLOGY: linear (ii) MOLECULE TYPE: protein (xi) SEQUENCE DESCRIPTION: SEQ ID NO: 59:

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60
```

-continued

```
Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 60:

(i) SEQUENCE CHARACTERISTICS:
(A) LENGTH: 364 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..363
(D) OTHER INFORMATION:/product= "VH2"

(xi) SEQUENCE DESCRIPTION: SEQ ID NO: 60:

```
CAG GTG CAA TTG AAA GAA AGC GGC CCG GCC CTG GTG AAA CCG ACC CAA       48
Gln Val Gln Leu Lys Glu Ser Gly Pro Ala Leu Val Lys Pro Thr Gln
                125                 130                 135

ACC CTG ACC CTG ACC TGT ACC TTT TCC GGA TTT AGC CTG TCC ACG TCT       96
Thr Leu Thr Leu Thr Cys Thr Phe Ser Gly Phe Ser Leu Ser Thr Ser
            140                 145                 150

GGC GTT GGC GTG GGC TGG ATT CGC CAG CCG CCT GGG AAA GCC CTC GAG      144
Gly Val Gly Val Gly Trp Ile Arg Gln Pro Pro Gly Lys Ala Leu Glu
        155                 160                 165

TGG CTG GCT CTG ATT GAT TGG GAT GAT GAT AAG TAT TAT AGC ACC AGC      192
Trp Leu Ala Leu Ile Asp Trp Asp Asp Asp Lys Tyr Tyr Ser Thr Ser
    170                 175                 180

CTG AAA ACG CGT CTG ACC ATT AGC AAA GAT ACT TCG AAA AAT CAG GTG      240
Leu Lys Thr Arg Leu Thr Ile Ser Lys Asp Thr Ser Lys Asn Gln Val
185                 190                 195                 200

GTG CTG ACT ATG ACC AAC ATG GAC CCG GTG GAT ACG GCC ACC TAT TAT      288
Val Leu Thr Met Thr Asn Met Asp Pro Val Asp Thr Ala Thr Tyr Tyr
                205                 210                 215

TGC GCG CGT TGG GGC GGC GAT GGC TTT TAT GCG ATG GAT TAT TGG GGC      336
Cys Ala Arg Trp Gly Gly Asp Gly Phe Tyr Ala Met Asp Tyr Trp Gly
            220                 225                 230

CAA GGC ACC CTG GTG ACG GTT AGC TCA G                                364
Gln Gly Thr Leu Val Thr Val Ser Ser
        235                 240
```

(2) INFORMATION FOR SEQ ID NO: 61:

(i) SEQUENCE CHARACTERISTICS:
(A) LENGTH: 121 amino acids
(B) TYPE: amino acid
(D) TOPOLOGY: linear (ii) MOLECULE TYPE: protein (xi) SEQUENCE DESCRIPTION: SEQ ID NO: 61:

```
Gln Val Gln Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
```

-continued

```
            20                  25                  30

Gly Val Gly Val Gly Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Trp Gly Gly Asp Gly Phe Tyr Ala Met Asp Tyr Trp Gly
            100                 105                 110

Gln Gly Thr Leu Val Thr Val Ser Ser
        115                 120
```

(2) INFORMATION FOR SEQ ID NO: 62:

(i) SEQUENCE CHARACTERISTICS:
(A) LENGTH: 361 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..360
(D) OTHER INFORMATION:/product= "VH3"

(xi) SEQUENCE DESCRIPTION: SEQ ID NO: 62:

```
GAA GTG CAA TTG GTG GAA AGC GGC GGC GGC CTG GTG CAA CCG GGC GGC       48
Glu Val Gln Leu Val Glu Ser Gly Gly Gly Leu Val Gln Pro Gly Gly
            125                 130                 135

AGC CTG CGT CTG AGC TGC GCG GCC TCC GGA TTT ACC TTT AGC AGC TAT       96
Ser Leu Arg Leu Ser Cys Ala Ala Ser Gly Phe Thr Phe Ser Ser Tyr
        140                 145                 150

GCG ATG AGC TGG GTG CGC CAA GCC CCT GGG AAG GGT CTC GAG TGG GTG      144
Ala Met Ser Trp Val Arg Gln Ala Pro Gly Lys Gly Leu Glu Trp Val
    155                 160                 165

AGC GCG ATT AGC GGT AGC GGC GGC AGC ACC TAT TAT GCG GAT AGC GTG      192
Ser Ala Ile Ser Gly Ser Gly Gly Ser Thr Tyr Tyr Ala Asp Ser Val
170                 175                 180                 185

AAA GGC CGT TTT ACC ATT TCA CGT GAT AAT TCG AAA AAC ACC CTG TAT      240
Lys Gly Arg Phe Thr Ile Ser Arg Asp Asn Ser Lys Asn Thr Leu Tyr
                190                 195                 200

CTG CAA ATG AAC AGC CTG CGT GCG GAA GAT ACG GCC GTG TAT TAT TGC      288
Leu Gln Met Asn Ser Leu Arg Ala Glu Asp Thr Ala Val Tyr Tyr Cys
            205                 210                 215

GCG CGT TGG GGC GGC GAT GGC TTT TAT GCG ATG GAT TAT TGG GGC CAA      336
Ala Arg Trp Gly Gly Asp Gly Phe Tyr Ala Met Asp Tyr Trp Gly Gln
        220                 225                 230

GGC ACC CTG GTG ACG GTT AGC TCA G                                    361
Gly Thr Leu Val Thr Val Ser Ser
    235                 240
```

(2) INFORMATION FOR SEQ ID NO: 63:

(i) SEQUENCE CHARACTERISTICS:
(A) LENGTH: 120 amino acids
(B) TYPE: amino acid
(D) TOPOLOGY: linear -continued (ii) MOLECULE TYPE: protein (xi) SEQUENCE DESCRIPTION: SEQ ID NO: 63:

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 64:

(i) SEQUENCE CHARACTERISTICS:
(A) LENGTH: 358 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..357
(D) OTHER INFORMATION:/product= "VH4"

(xi) SEQUENCE DESCRIPTION: SEQ ID NO: 64:

```
CAG GTG CAA TTG CAA GAA AGT GGT CCG GGC CTG GTG AAA CCG AGC GAA       48
Gln Val Gln Leu Gln Glu Ser Gly Pro Gly Leu Val Lys Pro Ser Glu
                125                 130                 135

ACC CTG AGC CTG ACC TGC ACC GTT TCC GGA GGC AGC ATT AGC AGC TAT       96
Thr Leu Ser Leu Thr Cys Thr Val Ser Gly Gly Ser Ile Ser Ser Tyr
            140                 145                 150

TAT TGG AGC TGG ATT CGC CAG CCG CCT GGG AAG GGT CTC GAG TGG ATT      144
Tyr Trp Ser Trp Ile Arg Gln Pro Pro Gly Lys Gly Leu Glu Trp Ile
        155                 160                 165

GGC TAT ATT TAT TAT AGC GGC AGC ACC AAC TAT AAT CCG AGC CTG AAA      192
Gly Tyr Ile Tyr Tyr Ser Gly Ser Thr Asn Tyr Asn Pro Ser Leu Lys
    170                 175                 180

AGC CGG GTG ACC ATT AGC GTT GAT ACT TCG AAA AAC CAG TTT AGC CTG      240
Ser Arg Val Thr Ile Ser Val Asp Thr Ser Lys Asn Gln Phe Ser Leu
185                 190                 195                 200

AAA CTG AGC AGC GTG ACG GCG GCG GAT ACG GCC GTG TAT TAT TGC GCG      288
Lys Leu Ser Ser Val Thr Ala Ala Asp Thr Ala Val Tyr Tyr Cys Ala
                205                 210                 215

CGT TGG GGC GGC GAT GGC TTT TAT GCG ATG GAT TAT TGG GGC CAA GGC      336
Arg Trp Gly Gly Asp Gly Phe Tyr Ala Met Asp Tyr Trp Gly Gln Gly
            220                 225                 230

ACC CTG GTG ACG GTT AGC TCA G                                        358
Thr Leu Val Thr Val Ser Ser
        235
```

```
(2) INFORMATION FOR SEQ ID NO: 65:

     (i) SEQUENCE CHARACTERISTICS:
          (A) LENGTH: 119 amino acids
          (B) TYPE: amino acid
          (D) TOPOLOGY: linear

    (ii) MOLECULE TYPE: protein

    (xi) SEQUENCE DESCRIPTION: SEQ ID NO: 65:

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Trp Gly Gly Asp Gly Phe Tyr Ala Met Asp Tyr Trp Gly Gln Gly
            100                 105                 110

Thr Leu Val Thr Val Ser Ser
        115


(2) INFORMATION FOR SEQ ID NO: 66:

     (i) SEQUENCE CHARACTERISTICS:
          (A) LENGTH: 361 base pairs
          (B) TYPE: nucleic acid
          (C) STRANDEDNESS: double
          (D) TOPOLOGY: linear

    (ii) MOLECULE TYPE: other nucleic acid
          (A) DESCRIPTION:   /desc = "synthetic gene"

    (ix) FEATURE:
          (A) NAME/KEY: CDS
          (B) LOCATION:1..360
          (D) OTHER INFORMATION:/product= "VH5"

    (xi) SEQUENCE DESCRIPTION: SEQ ID NO: 66:

GAA GTG CAA TTG GTT CAG AGC GGC GCG GAA GTG AAA AAA CCG GGC GAA       48
Glu Val Gln Leu Val Gln Ser Gly Ala Glu Val Lys Lys Pro Gly Glu
120                 125                 130                 135

AGC CTG AAA ATT AGC TGC AAA GGT TCC GGA TAT TCC TTT ACG AGC TAT       96
Ser Leu Lys Ile Ser Cys Lys Gly Ser Gly Tyr Ser Phe Thr Ser Tyr
                140                 145                 150

TGG ATT GGC TGG GTG CGC CAG ATG CCT GGG AAG GGT CTC GAG TGG ATG      144
Trp Ile Gly Trp Val Arg Gln Met Pro Gly Lys Gly Leu Glu Trp Met
            155                 160                 165

GGC ATT ATT TAT CCG GGC GAT AGC GAT ACC CGT TAT TCT CCG AGC TTT      192
Gly Ile Ile Tyr Pro Gly Asp Ser Asp Thr Arg Tyr Ser Pro Ser Phe
        170                 175                 180

CAG GGC CAG GTG ACC ATT AGC GCG GAT AAA AGC ATT AGC ACC GCG TAT      240
Gln Gly Gln Val Thr Ile Ser Ala Asp Lys Ser Ile Ser Thr Ala Tyr
    185                 190                 195

CTT CAA TGG AGC AGC CTG AAA GCG AGC GAT ACG GCC ATG TAT TAT TGC      288
Leu Gln Trp Ser Ser Leu Lys Ala Ser Asp Thr Ala Met Tyr Tyr Cys
200                 205                 210                 215
```

-continued

```
GCG CGT TGG GGC GGC GAT GGC TTT TAT GCG ATG GAT TAT TGG GGC CAA       336
Ala Arg Trp Gly Gly Asp Gly Phe Tyr Ala Met Asp Tyr Trp Gly Gln
                220                 225                 230

GGC ACC CTG GTG ACG GTT AGC TCA G                                     361
Gly Thr Leu Val Thr Val Ser Ser
            235
```

(2) INFORMATION FOR SEQ ID NO: 67:

(i) SEQUENCE CHARACTERISTICS:
(A) LENGTH: 120 amino acids
(B) TYPE: amino acid
(D) TOPOLOGY: linear (ii) MOLECULE TYPE: protein (xi) SEQUENCE DESCRIPTION: SEQ ID NO: 67:

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

(2) INFORMATION FOR SEQ ID NO: 68:

(i) SEQUENCE CHARACTERISTICS:
(A) LENGTH: 370 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..369
(D) OTHER INFORMATION:/product= "VH6"

(xi) SEQUENCE DESCRIPTION: SEQ ID NO: 68:

```
CAG GTG CAA TTG CAA CAG TCT GGT CCG GGC CTG GTG AAA CCG AGC CAA        48
Gln Val Gln Leu Gln Gln Ser Gly Pro Gly Leu Val Lys Pro Ser Gln
                125                 130                 135

ACC CTG AGC CTG ACC TGT GCG ATT TCC GGA GAT AGC GTG AGC AGC AAC        96
Thr Leu Ser Leu Thr Cys Ala Ile Ser Gly Asp Ser Val Ser Ser Asn
            140                 145                 150

AGC GCG GCG TGG AAC TGG ATT CGC CAG TCT CCT GGG CGT GGC CTC GAG       144
Ser Ala Ala Trp Asn Trp Ile Arg Gln Ser Pro Gly Arg Gly Leu Glu
        155                 160                 165

TGG CTG GGC CGT ACC TAT TAT CGT AGC AAA TGG TAT AAC GAT TAT GCG       192
Trp Leu Gly Arg Thr Tyr Tyr Arg Ser Lys Trp Tyr Asn Asp Tyr Ala
    170                 175                 180
```

-continued

```
GTG AGC GTG AAA AGC CGG ATT ACC ATC AAC CCG GAT ACT TCG AAA AAC      240
Val Ser Val Lys Ser Arg Ile Thr Ile Asn Pro Asp Thr Ser Lys Asn
185                 190                 195                 200

CAG TTT AGC CTG CAA CTG AAC AGC GTG ACC CCG GAA GAT ACG GCC GTG      288
Gln Phe Ser Leu Gln Leu Asn Ser Val Thr Pro Glu Asp Thr Ala Val
                205                 210                 215

TAT TAT TGC GCG CGT TGG GGC GGC GAT GGC TTT TAT GCG ATG GAT TAT      336
Tyr Tyr Cys Ala Arg Trp Gly Gly Asp Gly Phe Tyr Ala Met Asp Tyr
            220                 225                 230

TGG GGC CAA GGC ACC CTG GTG ACG GTT AGC TCA G                        370
Trp Gly Gln Gly Thr Leu Val Thr Val Ser Ser
        235                 240
```

(2) INFORMATION FOR SEQ ID NO: 69:

(i) SEQUENCE CHARACTERISTICS:
(A) LENGTH: 123 amino acids
(B) TYPE: amino acid
(D) TOPOLOGY: linear (ii) MOLECULE TYPE: protein (xi) SEQUENCE DESCRIPTION: SEQ ID NO: 69:

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser
        115                 120
```

(2) INFORMATION FOR SEQ ID NO: 70:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 70:

```
GAATGCATAC GCTGATATCC AGATGACCCA GAGCCCGTCT AGCCTGAGC                 49
```

(2) INFORMATION FOR SEQ ID NO: 71:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

-continued (xi) SEQUENCE DESCRIPTION: SEQ ID NO: 71:

CGCTCTGCAG GTAATGGTCA CACGATCACC CACGCTCGCG CTCAGGCTAG ACGGGC 56

(2) INFORMATION FOR SEQ ID NO: 72:

(i) SEQUENCE CHARACTERISTICS:
(A) LENGTH: 58 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 72:

GACCATTACC TGCAGAGCGA GCCAGGGCAT TAGCAGCTAT CTGGCGTGGT ACCAGCAG 58

(2) INFORMATION FOR SEQ ID NO: 73:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 73:

CTTTGCAAGC TGCTGGCTGC ATAAATTAAT AGTTTCGGTG CTTTACCTGG TTTCTGCTGG 60

TACCACGCCA G 71

(2) INFORMATION FOR SEQ ID NO: 74:

(i) SEQUENCE CHARACTERISTICS:
(A) LENGTH: 67 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 74:

CAGCCAGCAG CTTGCAAAGC GGGGTCCCGT CCCGTTTTAG CGGCTCTGGA TCCGGCACTG 60

ATTTTAC 67

(2) INFORMATION FOR SEQ ID NO: 75:

(i) SEQUENCE CHARACTERISTICS:
(A) LENGTH: 67 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 75:

GATAATAGGT CGCAAAGTCT TCAGGTTGCA GGCTGCTAAT GGTCAGGGTA AAATCAGTGC 60

CGGATCC 67

(2) INFORMATION FOR SEQ ID NO: 76:

(i) SEQUENCE CHARACTERISTICS:

-continued (A) LENGTH: 54 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 76:

CGATATCGTG ATGACCCAGA GCCCACTGAG CCTGCCAGTG ACTCCGGGCG AGCC 54

(2) INFORMATION FOR SEQ ID NO: 77:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 77:

GCCGTTGCTA TGCAGCAGGC TTTGGCTGCT TCTGCAGCTA ATGCTCGCAG GCTCGCCCGG 60

AGTCAC 66

(2) INFORMATION FOR SEQ ID NO: 78:

(i) SEQUENCE CHARACTERISTICS:
(A) LENGTH: 62 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 78:

CTGCTGCATA GCAACGGCTA TAACTATCTG GATTGGTACC TTCAAAAACC AGGTCAAAGC 60

CC 62

(2) INFORMATION FOR SEQ ID NO: 79:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 79:

CGATCCGGGA CCCCACTGGC ACGGTTGCTG CCCAGATAAA TTAATAGCTG CGGGCTTTGA 60

CCTGGTTTTT G 71

(2) INFORMATION FOR SEQ ID NO: 80:

(i) SEQUENCE CHARACTERISTICS:
(A) LENGTH: 69 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 80:

-continued

AGTGGGGTCC CGGATCGTTT TAGCGGCTCT GGATCCGGCA CCGATTTTAC CCTGAAAATT 60

AGCCGTGTG 69

(2) INFORMATION FOR SEQ ID NO: 81:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 81:

CCATGCAATA ATACACGCCC ACGTCTTCAG CTTCCACACG GCTAATTTTC AGGG 54

(2) INFORMATION FOR SEQ ID NO: 82:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 82:

GAATGCATAC GCTGATATCG TGCTGACCCA GAGCCCGG 38

(2) INFORMATION FOR SEQ ID NO: 83:

(i) SEQUENCE CHARACTERISTICS:
(A) LENGTH: 67 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 83:

CGCTCTGCAG CTCAGGGTCG CACGTTCGCC CGGAGACAGG CTCAGGGTCG CCGGGCTCTG 60

GGTCAGC 67

(2) INFORMATION FOR SEQ ID NO: 84:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 84:

CCCTGAGCTG CAGAGCGAGC CAGAGCGTGA GCAGCAGCTA TCTGGCGTGG TACCAG 56

(2) INFORMATION FOR SEQ ID NO: 85:

(i) SEQUENCE CHARACTERISTICS:
(A) LENGTH: 72 base pairs
(B) TYPE: nucleic acid
(C) STRANDEDNESS: single
(D) TOPOLOGY: linear -continued (ii) MOLECULE TYPE: other nucleic acid
(A) DESCRIPTION: /desc = "synthetic oligonucleotide"

(xi) SEQUENCE DESCRIPTION: SEQ ID NO: 85:

GCACGGCTGC TCGCGCCATA AATTAATAGA CGCGGTGCTT GACCTGGTTT CTGCTGGTAC 60

CACGCCAGAT AG 72

(2) INFORMATION FOR SEQ ID NO: 86:

(i) SEQUENCE CHARACTERISTICS:
(A) LENGTH: 67 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 86:

GCGCGAGCAG CCGTGCAACT GGGGTCCCGG CGCGTTTTAG CGGCTCTGGA TCCGGCACGG 60

ATTTTAC 67

(2) INFORMATION FOR SEQ ID NO: 87:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 87:

GATAATACAC CGCAAAGTCT TCAGGTTCCA GGCTGCTAAT GGTCAGGGTA AAATCCGTGC 60

CGGATC 66

(2) INFORMATION FOR SEQ ID NO: 88:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 88:

GAATGCATAC GCTGATATCG TGATGACCCA GAGCCCGGAT AGCCTGGCG 49

(2) INFORMATION FOR SEQ ID NO: 89:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 89:

GCTTCTGCAG TTAATGGTCG CACGTTCGCC CAGGCTCACC GCCAGGCTAT CCGGGC 56

-continued (2) INFORMATION FOR SEQ ID NO: 90:

(i) SEQUENCE CHARACTERISTICS:
(A) LENGTH: 74 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 90:

CGACCATTAA CTGCAGAAGC AGCCAGAGCG TGCTGTATAG CAGCAACAAC AAAAACTATC 60

TGGCGTGGTA CCAG 74

(2) INFORMATION FOR SEQ ID NO: 91:

(i) SEQUENCE CHARACTERISTICS:
(A) LENGTH: 63 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 91:

GATGCCCAAT AAATTAATAG TTTCGGCGGC TGACCTGGTT TCTGCTGGTA CCACGCCAGA 60

TAG 63

(2) INFORMATION FOR SEQ ID NO: 92:

(i) SEQUENCE CHARACTERISTICS:
(A) LENGTH: 74 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 92:

AAACTATTAA TTTATTGGGC ATCCACCCGT GAAAGCGGGG TCCCGGATCG TTTTAGCGGC 60

TCTGGATCCG GCAC 74

(2) INFORMATION FOR SEQ ID NO: 93:

(i) SEQUENCE CHARACTERISTICS:
(A) LENGTH: 73 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 93:

GATAATACAC CGCCACGTCT TCAGCTTGCA GGGACGAAAT GGTCAGGGTA AAATCAGTGC 60

CGGATCCAGA GCC 73

(2) INFORMATION FOR SEQ ID NO: 94:

(i) SEQUENCE CHARACTERISTICS:
(A) LENGTH: 48 base pairs
(B) TYPE: nucleic acid
(C) STRANDEDNESS: single
(D) TOPOLOGY: linear -continued (ii) MOLECULE TYPE: other nucleic acid
(A) DESCRIPTION: /desc = "synthetic oligonucleotide"

(xi) SEQUENCE DESCRIPTION: SEQ ID NO: 94:

GAATGCATAC GCTCAGAGCG TGCTGACCCA GCCGCCTTCA GTGAGTGG 48

(2) INFORMATION FOR SEQ ID NO: 95:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 95:

CAATGTTGCT GCTGCTGCCG CTACACGAGA TGGTCACACG CTGACCTGGT GCGCCACTCA 60

CTGAAGGCGG C 71

(2) INFORMATION FOR SEQ ID NO: 96:

(i) SEQUENCE CHARACTERISTICS:
(A) LENGTH: 59 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 96:

GGCAGCAGCA GCAACATTGG CAGCAACTAT GTGAGCTGGT ACCAGCAGTT GCCCGGGAC 59

(2) INFORMATION FOR SEQ ID NO: 97:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 97:

CCGGCACGCC TGAGGGACGC TGGTTGTTAT CATAAATCAG CAGTTTCGGC GCCGTCCCGG 60

GCAACTGC 68

(2) INFORMATION FOR SEQ ID NO: 98:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 98:

CCCTCAGGCG TGCCGGATCG TTTTAGCGGA TCCAAAAGCG GCACCAGCGC GAGCCTTGCG 60

(2) INFORMATION FOR SEQ ID NO: 99:

-continued (i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 99:

CCGCTTCGTC TTCGCTTTGC AGGCCCGTAA TCGCAAGGCT CGCGCTGG 48

(2) INFORMATION FOR SEQ ID NO: 100:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 100:

GAATGCATAC GCTCAGAGCG CACTGACCCA GCCAGCTTCA GTGAGCGGC 49

(2) INFORMATION FOR SEQ ID NO: 101:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 101:

CGCTGCTAGT ACCCGTACAC GAGATGGTAA TGCTCTGACC TGGTGAGCCG CTCACTGAAG 60

CTGG 64

(2) INFORMATION FOR SEQ ID NO: 102:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 102:

GTACGGGTAC TAGCAGCGAT GTGGGCGGCT ATAACTATGT GAGCTGGTAC CAGCAGCATC 60

CCGG 64

(2) INFORMATION FOR SEQ ID NO: 103:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 103:

-continued

```
CGCCTGAGGG ACGGTTGCTC ACATCATAAA TCATCAGTTT CGGCGCCTTC CCGGGATGCT     60

GCTGGTAC                                                              68


(2) INFORMATION FOR SEQ ID NO: 104:

     (i) SEQUENCE CHARACTERISTICS:
          (A) LENGTH: 62 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "synthetic oligonucleotide"

    (xi) SEQUENCE DESCRIPTION: SEQ ID NO: 104:

CAACCGTCCC TCAGGCGTGA GCAACCGTTT TAGCGGATCC AAAAGCGGCA ACACCGCGAG     60

CC                                                                    62


(2) INFORMATION FOR SEQ ID NO: 105:

     (i) SEQUENCE CHARACTERISTICS:
          (A) LENGTH: 53 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "synthetic oligonucleotide"

    (xi) SEQUENCE DESCRIPTION: SEQ ID NO: 105:

CCGCTTCGTC TTCCGCTTGC AGGCCGCTAA TGGTCAGGCT CGCGGTGTTG CCG            53


(2) INFORMATION FOR SEQ ID NO: 106:

     (i) SEQUENCE CHARACTERISTICS:
          (A) LENGTH: 47 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "synthetic oligonucleotide"

    (xi) SEQUENCE DESCRIPTION: SEQ ID NO: 106:

GAATGCATAC GCTAGCTATG AACTGACCCA GCCGCCTTCA GTGAGCG                   47


(2) INFORMATION FOR SEQ ID NO: 107:

     (i) SEQUENCE CHARACTERISTICS:
          (A) LENGTH: 68 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION:  /desc = "synthetic oligonucleotide"

    (xi) SEQUENCE DESCRIPTION: SEQ ID NO: 107:

CGCCCAGCGC ATCGCCGCTA CACGAGATAC GCGCGGTCTG ACCTGGTGCA ACGCTCACTG     60

AAGGCGGC                                                              68


(2) INFORMATION FOR SEQ ID NO: 108:

     (i) SEQUENCE CHARACTERISTICS:
          (A) LENGTH: 58 base pairs
          (B) TYPE: nucleic acid
          (C) STRANDEDNESS: single
```

-continued (D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 108:

GGCGATGCGC TGGGCGATAA ATACGCGAGC TGGTACCAGC AGAAACCCGG GCAGGCGC 58

(2) INFORMATION FOR SEQ ID NO: 109:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 109:

GCGTTCCGGG ATGCCTGAGG GACGGTCAGA ATCATCATAA ATCACCAGAA CTGGCGCCTG 60

CCCGGGTTTC 70

(2) INFORMATION FOR SEQ ID NO: 110:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 110:

CAGGCATCCC GGAACGCTTT AGCGGATCCA ACAGCGGCAA CACCGCGACC CTGACCATTA 60

GCGG 64

(2) INFORMATION FOR SEQ ID NO: 111:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 111:

CCGCTTCGTC TTCCGCCTGA GTGCCGCTAA TGGTCAGGGT C 41

(2) INFORMATION FOR SEQ ID NO: 112:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 112:

GCTCTTCACC CCTGTTACCA AAGCCCAGGT GCAATTG 37

(2) INFORMATION FOR SEQ ID NO: 113:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 113:

GGCTTTGCAG CTCACTTTCA CGCTGCTGCC CGGTTTTTTC ACTTCCGCGC CAGACTGAAC 60

CAATTGCACC TGGGCTTTG 79

(2) INFORMATION FOR SEQ ID NO: 114:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 114:

GAAAGTGAGC TGCAAAGCCT CCGGAGGCAC TTTTAGCAGC TATGCGATTA GCTGGGTGCG 60

CCAAGCCCCT GGGCAGGGTC 80

(2) INFORMATION FOR SEQ ID NO: 115:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 115:

GCCCTGAAAC TTCTGCGCGT AGTTCGCCGT GCCAAAAATC GGAATAATGC CGCCCATCCA 60

CTCGAGACCC TGCCCAGGGG C 81

(2) INFORMATION FOR SEQ ID NO: 116:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 116:

GCGCAGAAGT TTCAGGGCCG GGTGACCATT ACCGCGGATG AAAGCACCAG CACCGCGTAT 60

ATGGAACTGA GCAGCCTGCG 80

(2) INFORMATION FOR SEQ ID NO: 117:

(i) SEQUENCE CHARACTERISTICS:
(A) LENGTH: 50 base pairs
(B) TYPE: nucleic acid
(C) STRANDEDNESS: single
(D) TOPOLOGY: linear -continued (ii) MOLECULE TYPE: other nucleic acid
(A) DESCRIPTION: /desc = “synthetic oligonucleotide”

(xi) SEQUENCE DESCRIPTION: SEQ ID NO: 117:

GCGCGCAATA ATACACGGCC GTATCTTCGC TACGCAGGCT GCTCAGTTCC 50

(2) INFORMATION FOR SEQ ID NO: 118:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “synthetic oligonucleotide”

(xi) SEQUENCE DESCRIPTION: SEQ ID NO: 118:

GGCTTTGCAG CTCACTTTCA CGCTCGCGCC CGGTTTTTTC ACTTCCGCGC CGCTCTGAAC 60

CAATTGCACC TGGGCTTTG 79

(2) INFORMATION FOR SEQ ID NO: 119:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “synthetic oligonucleotide”

(xi) SEQUENCE DESCRIPTION: SEQ ID NO: 119:

GAAAGTGAGC TGCAAAGCCT CCGGATATAC CTTTACCAGC TATTATATGC ACTGGGTCCG 60

CCAAGCCCCT GGGCAGGGTC 80

(2) INFORMATION FOR SEQ ID NO: 120:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “synthetic oligonucleotide”

(xi) SEQUENCE DESCRIPTION: SEQ ID NO: 120:

GCCCTGAAAC TTCTGCGCGT AGTTCGTGCC GCCGCTATTC GGGTTAATCC AGCCCATCCA 60

CTCGAGACCC TGCCCAGGGG C 81

(2) INFORMATION FOR SEQ ID NO: 121:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “synthetic oligonucleotide”

(xi) SEQUENCE DESCRIPTION: SEQ ID NO: 121:

GCGCAGAAGT TTCAGGGCCG GGTGACCATG ACCCGTGATA CCAGCATTAG CACCGCGTAT 60

ATGGAACTGA GCAGCCTGCG 80

(2) INFORMATION FOR SEQ ID NO: 122:

(i) SEQUENCE CHARACTERISTICS:
(A) LENGTH: 76 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 122:

GGTACAGGTC AGGGTCAGGG TTTGGGTCGG TTTCACCAGG GCCGGGCCGC TTTCTTTCAA 60

TTGCACCTGG GCTTTG 76

(2) INFORMATION FOR SEQ ID NO: 123:

(i) SEQUENCE CHARACTERISTICS:
(A) LENGTH: 85 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 123:

CTGACCCTGA CCTGTACCTT TTCCGGATTT AGCCTGTCCA CGTCTGGCGT TGGCGTGGGC 60

TGGATTCGCC AGCCGCCTGG GAAAG 85

(2) INFORMATION FOR SEQ ID NO: 124:

(i) SEQUENCE CHARACTERISTICS:
(A) LENGTH: 83 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 124:

GCGTTTTCAG GCTGGTGCTA TAATACTTAT CATCATCCCA ATCAATCAGA GCCAGCCACT 60

CGAGGGCTTT CCCAGGCGGC TGG 83

(2) INFORMATION FOR SEQ ID NO: 125:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 125:

GCACCAGCCT GAAAACGCGT CTGACCATTA GCAAAGATAC TTCGAAAAAT CAGGTGGTGC 60

TGACTATGAC CAACATGG 78

(2) INFORMATION FOR SEQ ID NO: 126:

(i) SEQUENCE CHARACTERISTICS:
(A) LENGTH: 53 base pairs
(B) TYPE: nucleic acid
(C) STRANDEDNESS: single -continued (D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 126:

GCGCGCAATA ATAGGTGGCC GTATCCACCG GGTCCATGTT GGTCATAGTC AGC 53

(2) INFORMATION FOR SEQ ID NO: 127:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 127:

CGAAGTGCAA TTGGTGGAAA GCGGCGGCGG CCTGGTGCAA CCGGGCGGCA G 51

(2) INFORMATION FOR SEQ ID NO: 128:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 128:

CATAGCTGCT AAAGGTAAAT CCGGAGGCCG CGCAGCTCAG ACGCAGGCTG CCGCCCGGTT 60

GCAC 64

(2) INFORMATION FOR SEQ ID NO: 129:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 129:

GATTTACCTT TAGCAGCTAT GCGATGAGCT GGGTGCGCCA AGCCCCTGGG AAGGGTCTCG 60

AGTGGGTGAG 70

(2) INFORMATION FOR SEQ ID NO: 130:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 130:

GGCCTTTCAC GCTATCCGCA TAATAGGTGC TGCCGCCGCT ACCGCTAATC GCGCTCACCC 60

ACTCGAGACC C 71

-continued (2) INFORMATION FOR SEQ ID NO: 131:

(i) SEQUENCE CHARACTERISTICS:
(A) LENGTH: 73 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 131:

CGGATAGCGT GAAAGGCCGT TTTACCATTT CACGTGATAA TTCGAAAAAC ACCCTGTATC 60

TGCAAATGAA CAG 73

(2) INFORMATION FOR SEQ ID NO: 132:

(i) SEQUENCE CHARACTERISTICS:
(A) LENGTH: 62 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 132:

CACGCGCGCA ATAATACACG GCCGTATCTT CCGCACGCAG GCTGTTCATT TGCAGATACA 60

GG 62

(2) INFORMATION FOR SEQ ID NO: 133:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 133:

GGTCAGGCTC AGGGTTTCGC TCGGTTTCAC CAGGCCCGGA CCACTTTCTT GCAATTGCAC 60

CTGGGCTTTG 70

(2) INFORMATION FOR SEQ ID NO: 134:

(i) SEQUENCE CHARACTERISTICS:
(A) LENGTH: 76 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 134:

GAAACCCTGA GCCTGACCTG CACCGTTTCC GGAGGCAGCA TTAGCAGCTA TTATTGGAGC 60

TGGATTCGCC AGCCGC 76

(2) INFORMATION FOR SEQ ID NO: 135:

(i) SEQUENCE CHARACTERISTICS:
(A) LENGTH: 77 base pairs
(B) TYPE: nucleic acid
(C) STRANDEDNESS: single -continued (D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 135:

GATTATAGTT GGTGCTGCCG CTATAATAAA TATAGCCAAT CCACTCGAGA CCCTTCCCAG 60

GCGGCTGGCG AATCCAG 77

(2) INFORMATION FOR SEQ ID NO: 136:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 136:

CGGCAGCACC AACTATAATC CGAGCCTGAA AAGCCGGGTG ACCATTAGCG TTGATACTTC 60

GAAAAACCAG TTTAGCCTG 79

(2) INFORMATION FOR SEQ ID NO: 137:

(i) SEQUENCE CHARACTERISTICS:
(A) LENGTH: 69 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 137:

GCGCGCAATA ATACACGGCC GTATCCGCCG CCGTCACGCT GCTCAGTTTC AGGCTAAACT 60

GGTTTTTCG 69

(2) INFORMATION FOR SEQ ID NO: 138:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 138:

GCTCTTCACC CCTGTTACCA AAGCCGAAGT GCAATTG 37

(2) INFORMATION FOR SEQ ID NO: 139:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 139:

CCTTTGCAGC TAATTTTCAG GCTTTCGCCC GGTTTTTTCA CTTCCGCGCC GCTCTGAACC 60

-continued

AATTGCACTT CGGCTTTGG 79

(2) INFORMATION FOR SEQ ID NO: 140:

(i) SEQUENCE CHARACTERISTICS:
(A) LENGTH: 75 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 140:

CCTGAAAATT AGCTGCAAAG GTTCCGGATA TTCCTTTACG AGCTATTGGA TTGGCTGGGT 60

GCGCCAGATG CCTGG 75

(2) INFORMATION FOR SEQ ID NO: 141:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 141:

CGGAGAATAA CGGGTATCGC TATCGCCCGG ATAAATAATG CCCATCCACT CGAGACCCTT 60

CCCAGGCATC TGGCGCAC 78

(2) INFORMATION FOR SEQ ID NO: 142:

(i) SEQUENCE CHARACTERISTICS:
(A) LENGTH: 77 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 142:

CGATACCCGT TATTCTCCGA GCTTTCAGGG CCAGGTGACC ATTAGCGCGG ATAAAAGCAT 60

TAGCACCGCG TATCTTC 77

(2) INFORMATION FOR SEQ ID NO: 143:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 143:

GCGCGCAATA ATACATGGCC GTATCGCTCG CTTTCAGGCT GCTCCATTGA AGATACGCGG 60

TGCTAATG 68

(2) INFORMATION FOR SEQ ID NO: 144:

(i) SEQUENCE CHARACTERISTICS:
(A) LENGTH: 81 base pairs

-continued (B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 144:

GAAATCGCAC AGGTCAGGCT CAGGGTTTGG CTCGGTTTCA CCAGGCCCGG ACCAGACTGT 60

TGCAATTGCA CCTGGGCTTT G 81

(2) INFORMATION FOR SEQ ID NO: 145:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 145:

GCCTGACCTG TGCGATTTCC GGAGATAGCG TGAGCAGCAA CAGCGCGGCG TGGAACTGGA 60

TTCGCCAGTC TCCTGGGCG 79

(2) INFORMATION FOR SEQ ID NO: 146:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 146:

CACCGCATAA TCGTTATACC ATTTGCTACG ATAATAGGTA CGGCCCAGCC ACTCGAGGCC 60

ACGCCCAGGA GACTGGCG 78

(2) INFORMATION FOR SEQ ID NO: 147:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 147:

GGTATAACGA TTATGCGGTG AGCGTGAAAA GCCGGATTAC CATCAACCCG GATACTTCGA 60

AAAACCAGTT TAGCCTGC 78

(2) INFORMATION FOR SEQ ID NO: 148:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

-continued (xi) SEQUENCE DESCRIPTION: SEQ ID NO: 148:

GCGCGCAATA ATACACGGCC GTATCTTCCG GGGTCACGCT GTTCAGTTGC AGGCTAAACT 60

GGTTTTTC 68

(2) INFORMATION FOR SEQ ID NO: 149:

(i) SEQUENCE CHARACTERISTICS:
(A) LENGTH: 69 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 149:

GGCTGAAGAC GTGGGCGTGT ATTATTGCCA GCAGCATTAT ACCACCCCGC CGACCTTTGG 60

CCAGGGTAC 69

(2) INFORMATION FOR SEQ ID NO: 150:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 150:

GCGGAAAAAT AAACACGCTC GGAGCAGCCA CCGTACGTTT AATTTCAACT TTCGTACCCT 60

GGCCAAAGGT C 71

(2) INFORMATION FOR SEQ ID NO: 151:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 151:

GAGCGTGTTT ATTTTTCCGC CGAGCGATGA ACAACTGAAA AGCGGCACGG CGAGCGTGGT 60

GTGCCTGCTG 70

(2) INFORMATION FOR SEQ ID NO: 152:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 152:

CAGCGCGTTG TCTACTTTCC ACTGAACTTT CGCTTCACGC GGATAAAAGT TGTTCAGCAG 60

GCACACCACG C 71

-continued (2) INFORMATION FOR SEQ ID NO: 153:

(i) SEQUENCE CHARACTERISTICS:
(A) LENGTH: 69 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 153:

GAAAGTAGAC AACGCGCTGC AAAGCGGCAA CAGCCAGGAA AGCGTGACCG AACAGGATAG 60

CAAAGATAG 69

(2) INFORMATION FOR SEQ ID NO: 154:

(i) SEQUENCE CHARACTERISTICS:
(A) LENGTH: 74 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 154:

GTTTTTCATA ATCCGCTTTG CTCAGGGTCA GGGTGCTGCT CAGAGAATAG GTGCTATCTT 60

TGCTATCCTG TTCG 74

(2) INFORMATION FOR SEQ ID NO: 155:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 155:

GCAAAGCGGA TTATGAAAAA CATAAAGTGT ATGCGTGCGA AGTGACCCAT CAAGGTCTGA 60

GCAGCCCGGT G 71

(2) INFORMATION FOR SEQ ID NO: 156:

(i) SEQUENCE CHARACTERISTICS:
(A) LENGTH: 57 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 156:

GGCATGCTTA TCAGGCCTCG CCACGATTAA AAGATTTAGT CACCGGGCTG CTCAGAC 57

(2) INFORMATION FOR SEQ ID NO: 157:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: other nucleic acid -continued (A) DESCRIPTION: /desc = "synthetic oligonucleotide"

(xi) SEQUENCE DESCRIPTION: SEQ ID NO: 157:

GGCGTCTAGA GGCCAAGGCA CCCTGGTGAC GGTTAGCTCA GCGTCGAC 48

(2) INFORMATION FOR SEQ ID NO: 158:

(i) SEQUENCE CHARACTERISTICS:
(A) LENGTH: 63 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 158:

GTGCTTTTGC TGCTCGGAGC CAGCGGAAAC ACGCTTGGAC CTTTGGTCGA CGCTGAGCTA 60

ACC 63

(2) INFORMATION FOR SEQ ID NO: 159:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 159:

CTCCGAGCAG CAAAAGCACC AGCGGCGGCA CGGCTGCCCT GGGCTGCCTG GTTAAAGATT 60

ATTTCC 66

(2) INFORMATION FOR SEQ ID NO: 160:

(i) SEQUENCE CHARACTERISTICS:
(A) LENGTH: 65 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 160:

CTGGTCAGCG CCCCGCTGTT CCAGCTCACG GTGACTGGTT CCGGGAAATA ATCTTTAACC 60

AGGCA 65

(2) INFORMATION FOR SEQ ID NO: 161:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 161:

AGCGGGGCGC TGACCAGCGG CGTGCATACC TTTCCGGCGG TGCTGCAAAG CAGCGGCCTG 60

(2) INFORMATION FOR SEQ ID NO: 162:

-continued (i) SEQUENCE CHARACTERISTICS:
(A) LENGTH: 65 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 162:

```
GTGCCTAAGC TGCTGCTCGG CACGGTCACA ACGCTGCTCA GGCTATACAG GCCGCTGCTT     60

TGCAG                                                                 65
```

(2) INFORMATION FOR SEQ ID NO: 163:

(i) SEQUENCE CHARACTERISTICS:
(A) LENGTH: 61 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 163:

```
GAGCAGCAGC TTAGGCACTC AGACCTATAT TTGCAACGTG AACCATAAAC CGAGCAACAC     60

C                                                                     61
```

(2) INFORMATION FOR SEQ ID NO: 164:

(i) SEQUENCE CHARACTERISTICS:
(A) LENGTH: 59 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 164:

```
GCGCGAATTC GCTTTTCGGT TCCACTTTTT TATCCACTTT GGTGTTGCTC GGTTTATGG      59
```

(2) INFORMATION FOR SEQ ID NO: 165:

(i) SEQUENCE CHARACTERISTICS:
(A) LENGTH: 333 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:7..321
(D) OTHER INFORMATION:/product= "C kappa"

(xi) SEQUENCE DESCRIPTION: SEQ ID NO: 165:

```
CGTACG GTG GCT GCT CCG AGC GTG TTT ATT TTT CCG CCG AGC GAT GAA        48
       Val Ala Ala Pro Ser Val Phe Ile Phe Pro Pro Ser Asp Glu
           125                 130                 135

CAA CTG AAA AGC GGC ACG GCG AGC GTG GTG TGC CTG CTG AAC AAC TTT       96
Gln Leu Lys Ser Gly Thr Ala Ser Val Val Cys Leu Leu Asn Asn Phe
        140                 145                 150

TAT CCG CGT GAA GCG AAA GTT CAG TGG AAA GTA GAC AAC GCG CTG CAA      144
Tyr Pro Arg Glu Ala Lys Val Gln Trp Lys Val Asp Asn Ala Leu Gln
    155                 160                 165
```

-continued

```
AGC GGC AAC AGC CAG GAA AGC GTG ACC GAA CAG GAT AGC AAA GAT AGC      192
Ser Gly Asn Ser Gln Glu Ser Val Thr Glu Gln Asp Ser Lys Asp Ser
170                 175                 180                 185

ACC TAT TCT CTG AGC AGC ACC CTG ACC CTG AGC AAA GCG GAT TAT GAA      240
Thr Tyr Ser Leu Ser Ser Thr Leu Thr Leu Ser Lys Ala Asp Tyr Glu
                190                 195                 200

AAA CAT AAA GTG TAT GCG TGC GAA GTG ACC CAT CAA GGT CTG AGC AGC      288
Lys His Lys Val Tyr Ala Cys Glu Val Thr His Gln Gly Leu Ser Ser
            205                 210                 215

CCG GTG ACT AAA TCT TTT AAT CGT GGC GAG GCC TGATAAGCAT GC            333
Pro Val Thr Lys Ser Phe Asn Arg Gly Glu Ala
        220                 225
```

(2) INFORMATION FOR SEQ ID NO: 166:

(i) SEQUENCE CHARACTERISTICS:
(A) LENGTH: 105 amino acids
(B) TYPE: amino acid
(D) TOPOLOGY: linear (ii) MOLECULE TYPE: protein (xi) SEQUENCE DESCRIPTION: SEQ ID NO: 166:

```
Val Ala Ala Pro Ser Val Phe Ile Phe Pro Pro Ser Asp Glu Gln Leu
  1               5                  10                  15

Lys Ser Gly Thr Ala Ser Val Val Cys Leu Leu Asn Asn Phe Tyr Pro
             20                  25                  30

Arg Glu Ala Lys Val Gln Trp Lys Val Asp Asn Ala Leu Gln Ser Gly
         35                  40                  45

Asn Ser Gln Glu Ser Val Thr Glu Gln Asp Ser Lys Asp Ser Thr Tyr
     50                  55                  60

Ser Leu Ser Ser Thr Leu Thr Leu Ser Lys Ala Asp Tyr Glu Lys His
 65                  70                  75                  80

Lys Val Tyr Ala Cys Glu Val Thr His Gln Gly Leu Ser Ser Pro Val
                 85                  90                  95

Thr Lys Ser Phe Asn Arg Gly Glu Ala
            100                 105
```

(2) INFORMATION FOR SEQ ID NO: 167:

(i) SEQUENCE CHARACTERISTICS:
(A) LENGTH: 327 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:6..317
(D) OTHER INFORMATION:/product= "CH1"

(xi) SEQUENCE DESCRIPTION: SEQ ID NO: 167:

```
GCTCA GCG TCG ACC AAA GGT CCA AGC GTG TTT CCG CTG GCT CCG AGC         47
      Ala Ser Thr Lys Gly Pro Ser Val Phe Pro Leu Ala Pro Ser
                      110                 115

AGC AAA AGC ACC AGC GGC GGC ACG GCT GCC CTG GGC TGC CTG GTT AAA       95
Ser Lys Ser Thr Ser Gly Gly Thr Ala Ala Leu Gly Cys Leu Val Lys
120                 125                 130                 135

GAT TAT TTC CCG GAA CCA GTC ACC GTG AGC TGG AAC AGC GGG GCG CTG      143
Asp Tyr Phe Pro Glu Pro Val Thr Val Ser Trp Asn Ser Gly Ala Leu
```

-continued

```
            140                 145                 150

ACC AGC GGC GTG CAT ACC TTT CCG GCG GTG CTG CAA AGC AGC GGC CTG       191
Thr Ser Gly Val His Thr Phe Pro Ala Val Leu Gln Ser Ser Gly Leu
            155                 160                 165

TAT AGC CTG AGC AGC GTT GTG ACC GTG CCG AGC AGC AGC TTA GGC ACT       239
Tyr Ser Leu Ser Ser Val Val Thr Val Pro Ser Ser Ser Leu Gly Thr
        170                 175                 180

CAG ACC TAT ATT TGC AAC GTG AAC CAT AAA CCG AGC AAC ACC AAA GTG       287
Gln Thr Tyr Ile Cys Asn Val Asn His Lys Pro Ser Asn Thr Lys Val
    185                 190                 195

GAT AAA AAA GTG GAA CCG AAA AGC GAA TTC TGATAAGCTT                    327
Asp Lys Lys Val Glu Pro Lys Ser Glu Phe
200                 205
```

(2) INFORMATION FOR SEQ ID NO: 168:

(i) SEQUENCE CHARACTERISTICS:
(A) LENGTH: 104 amino acids
(B) TYPE: amino acid
(D) TOPOLOGY: linear (ii) MOLECULE TYPE: protein (xi) SEQUENCE DESCRIPTION: SEQ ID NO: 168:

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Glu Phe
            100
```

(2) INFORMATION FOR SEQ ID NO: 169:

(i) SEQUENCE CHARACTERISTICS:
(A) LENGTH: 408 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:85..396
(D) OTHER INFORMATION:/product= "C lambda"

(xi) SEQUENCE DESCRIPTION: SEQ ID NO: 169:

```
GAAGACGAAG CGGATTATTA TTGCCAGCAG CATTATACCA CCCCGCCTGT GTTTGGCGGC      60

GGCACGAAGT TAACCGTTCT TGGC CAG CCG AAA GCC GCA CCG AGT GTG ACG       111
                           Gln Pro Lys Ala Ala Pro Ser Val Thr
                           105                 110

CTG TTT CCG CCG AGC AGC GAA GAA TTG CAG GCG AAC AAA GCG ACC CTG       159
Leu Phe Pro Pro Ser Ser Glu Glu Leu Gln Ala Asn Lys Ala Thr Leu
    115                 120                 125
```

-continued

```
GTG TGC CTG ATT AGC GAC TTT TAT CCG GGA GCC GTG ACA GTG GCC TGG      207
Val Cys Leu Ile Ser Asp Phe Tyr Pro Gly Ala Val Thr Val Ala Trp
130                 135                 140                 145

AAG GCA GAT AGC AGC CCC GTC AAG GCG GGA GTG GAG ACC ACC ACA CCC      255
Lys Ala Asp Ser Ser Pro Val Lys Ala Gly Val Glu Thr Thr Thr Pro
                150                 155                 160

TCC AAA CAA AGC AAC AAC AAG TAC GCG GCC AGC AGC TAT CTG AGC CTG      303
Ser Lys Gln Ser Asn Asn Lys Tyr Ala Ala Ser Ser Tyr Leu Ser Leu
            165                 170                 175

ACG CCT GAG CAG TGG AAG TCC CAC AGA AGC TAC AGC TGC CAG GTC ACG      351
Thr Pro Glu Gln Trp Lys Ser His Arg Ser Tyr Ser Cys Gln Val Thr
        180                 185                 190

CAT GAG GGG AGC ACC GTG GAA AAA ACC GTT GCG CCG ACT GAG GCC          396
His Glu Gly Ser Thr Val Glu Lys Thr Val Ala Pro Thr Glu Ala
    195                 200                 205

TGATAAGCAT GC                                                        408
```

(2) INFORMATION FOR SEQ ID NO: 170:

(i) SEQUENCE CHARACTERISTICS:
(A) LENGTH: 104 amino acids
(B) TYPE: amino acid
(D) TOPOLOGY: linear (ii) MOLECULE TYPE: protein (xi) SEQUENCE DESCRIPTION: SEQ ID NO: 170:

```
Gln Pro Lys Ala Ala Pro Ser Val Thr Leu Phe Pro Pro Ser Ser Glu
  1               5                  10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
     50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                85                  90                  95

Lys Thr Val Ala Pro Thr Glu Ala
            100
```

(2) INFORMATION FOR SEQ ID NO: 171:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 171:

```
GAAGACAAGC GGATTATTAT TGCCAGCAGC ATTATACCAC CCCGCCTGTG TTTGGCGGCG     60

GCACGAAGTT AACCGTTC                                                   78
```

(2) INFORMATION FOR SEQ ID NO: 172:

(i) SEQUENCE CHARACTERISTICS:
(A) LENGTH: 80 base pairs

-continued (B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 172:

CAATTCTTCG CTGCTCGGCG GAAACAGCGT CACACTCGGT GCGGCTTTCG GCTGGCCAAG 60

AACGGTTAAC TTCGTGCCGC 80

(2) INFORMATION FOR SEQ ID NO: 173:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 173:

CGCCGAGCAG CGAAGAATTG CAGGCGAACA AAGCGACCCT GGTGTGCCTG ATTAGCGACT 60

TTTATCCGGG AGCCGTGACA 80

(2) INFORMATION FOR SEQ ID NO: 174:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 174:

TGTTTGGAGG GTGTGGTGGT CTCCACTCCC GCCTTGACGG GGCTGCTATC TGCCTTCCAG 60

GCCACTGTCA CGGCTCCCGG 80

(2) INFORMATION FOR SEQ ID NO: 175:

(i) SEQUENCE CHARACTERISTICS:
(A) LENGTH: 94 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 175:

CCACACCCTC CAAACAAAGC AACAACAAGT ACGCGGCCAG CAGCTATCTG AGCCTGACGC 60

CTGAGCAGTG GAAGTCCCAC AGAAGCTACA GCTG 94

(2) INFORMATION FOR SEQ ID NO: 176:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

-continued (xi) SEQUENCE DESCRIPTION: SEQ ID NO: 176:

```
GCATGCTTAT CAGGCCTCAG TCGGCGCAAC GGTTTTTTCC ACGGTGCTCC CCTCATGCGT     60

GACCTGGCAG CTGTAGCTTC                                                 80
```

(2) INFORMATION FOR SEQ ID NO: 177:

(i) SEQUENCE CHARACTERISTICS:
(A) LENGTH: 843 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene"

(ix) FEATURE:
(A) NAME/KEY: CDS
(B) LOCATION:1..843
(D) OTHER INFORMATION:/product= "VH3-Vk2"

(xi) SEQUENCE DESCRIPTION: SEQ ID NO: 177:

```
ATG AAA CAA AGC ACT ATT GCA CTG GCA CTC TTA CCG TTG CTC TTC ACC       48
Met Lys Gln Ser Thr Ile Ala Leu Ala Leu Leu Pro Leu Leu Phe Thr
105                 110                 115                 120

CCT GTT ACC AAA GCC GAC TAC AAA GAT GAA GTG CAA TTG GTG GAA AGC       96
Pro Val Thr Lys Ala Asp Tyr Lys Asp Glu Val Gln Leu Val Glu Ser
                125                 130                 135

GGC GGC GGC CTG GTG CAA CCG GGC GGC AGC CTG CGT CTG AGC TGC GCG      144
Gly Gly Gly Leu Val Gln Pro Gly Gly Ser Leu Arg Leu Ser Cys Ala
            140                 145                 150

GCC TCC GGA TTT ACC TTT AGC AGC TAT GCG ATG AGC TGG GTG CGC CAA      192
Ala Ser Gly Phe Thr Phe Ser Ser Tyr Ala Met Ser Trp Val Arg Gln
        155                 160                 165

GCC CCT GGG AAG GGT CTC GAG TGG GTG AGC GCG ATT AGC GGT AGC GGC      240
Ala Pro Gly Lys Gly Leu Glu Trp Val Ser Ala Ile Ser Gly Ser Gly
    170                 175                 180

GGC AGC ACC TAT TAT GCG GAT AGC GTG AAA GGC CGT TTT ACC ATT TCA      288
Gly Ser Thr Tyr Tyr Ala Asp Ser Val Lys Gly Arg Phe Thr Ile Ser
185                 190                 195                 200

CGT GAT AAT TCG AAA AAC ACC CTG TAT CTG CAA ATG AAC AGC CTG CGT      336
Arg Asp Asn Ser Lys Asn Thr Leu Tyr Leu Gln Met Asn Ser Leu Arg
                205                 210                 215

GCG GAA GAT ACG GCC GTG TAT TAT TGC GCG CGT TGG GGC GGC GAT GGC      384
Ala Glu Asp Thr Ala Val Tyr Tyr Cys Ala Arg Trp Gly Gly Asp Gly
            220                 225                 230

TTT TAT GCG ATG GAT TAT TGG GGC CAA GGC ACC CTG GTG ACG GTT AGC      432
Phe Tyr Ala Met Asp Tyr Trp Gly Gln Gly Thr Leu Val Thr Val Ser
        235                 240                 245

TCA GCG GGT GGC GGT TCT GGC GGC GGT GGG AGC GGT GGC GGT GGT TCT      480
Ser Ala Gly Gly Gly Ser Gly Gly Gly Gly Ser Gly Gly Gly Gly Ser
    250                 255                 260

GGC GGT GGT GGT TCC GAT ATC GTG ATG ACC CAG AGC CCA CTG AGC CTG      528
Gly Gly Gly Gly Ser Asp Ile Val Met Thr Gln Ser Pro Leu Ser Leu
265                 270                 275                 280

CCA GTG ACT CCG GGC GAG CCT GCG AGC ATT AGC TGC AGA AGC AGC CAA      576
Pro Val Thr Pro Gly Glu Pro Ala Ser Ile Ser Cys Arg Ser Ser Gln
                285                 290                 295

AGC CTG CTG CAT AGC AAC GGC TAT AAC TAT CTG GAT TGG TAC CTT CAA      624
Ser Leu Leu His Ser Asn Gly Tyr Asn Tyr Leu Asp Trp Tyr Leu Gln
            300                 305                 310

AAA CCA GGT CAA AGC CCG CAG CTA TTA ATT TAT CTG GGC AGC AAC CGT      672
Lys Pro Gly Gln Ser Pro Gln Leu Leu Ile Tyr Leu Gly Ser Asn Arg
```

-continued

```
        315                 320                 325

GCC AGT GGG GTC CCG GAT CGT TTT AGC GGC TCT GGA TCC GGC ACC GAT      720
Ala Ser Gly Val Pro Asp Arg Phe Ser Gly Ser Gly Ser Gly Thr Asp
    330                 335                 340

TTT ACC CTG AAA ATT AGC CGT GTG GAA GCT GAA GAC GTG GGC GTG TAT      768
Phe Thr Leu Lys Ile Ser Arg Val Glu Ala Glu Asp Val Gly Val Tyr
345                 350                 355                 360

TAT TGC CAG CAG CAT TAT ACC ACC CCG CCG ACC TTT GGC CAG GGT ACG      816
Tyr Cys Gln Gln His Tyr Thr Thr Pro Pro Thr Phe Gly Gln Gly Thr
                365                 370                 375

AAA GTT GAA ATT AAA CGT ACG GAA TTC                                  843
Lys Val Glu Ile Lys Arg Thr Glu Phe
            380                 385
```

(2) INFORMATION FOR SEQ ID NO: 178:

(i) SEQUENCE CHARACTERISTICS:
(A) LENGTH: 281 amino acids
(B) TYPE: amino acid
(D) TOPOLOGY: linear (ii) MOLECULE TYPE: protein (xi) SEQUENCE DESCRIPTION: SEQ ID NO: 178:

```
Met Lys Gln Ser Thr Ile Ala Leu Ala Leu Leu Pro Leu Leu Phe Thr
  1               5                  10                  15

Pro Val Thr Lys Ala Asp Tyr Lys Asp Glu Val Gln Leu Val Glu Ser
             20                  25                  30

Gly Gly Gly Leu Val Gln Pro Gly Gly Ser Leu Arg Leu Ser Cys Ala
        35                  40                  45

Ala Ser Gly Phe Thr Phe Ser Ser Tyr Ala Met Ser Trp Val Arg Gln
    50                  55                  60

Ala Pro Gly Lys Gly Leu Glu Trp Val Ser Ala Ile Ser Gly Ser Gly
 65                  70                  75                  80

Gly Ser Thr Tyr Tyr Ala Asp Ser Val Lys Gly Arg Phe Thr Ile Ser
                 85                  90                  95

Arg Asp Asn Ser Lys Asn Thr Leu Tyr Leu Gln Met Asn Ser Leu Arg
            100                 105                 110

Ala Glu Asp Thr Ala Val Tyr Tyr Cys Ala Arg Trp Gly Gly Asp Gly
        115                 120                 125

Phe Tyr Ala Met Asp Tyr Trp Gly Gln Gly Thr Leu Val Thr Val Ser
    130                 135                 140

Ser Ala Gly Gly Gly Ser Gly Gly Gly Gly Ser Gly Gly Gly Gly Ser
145                 150                 155                 160

Gly Gly Gly Gly Ser Asp Ile Val Met Thr Gln Ser Pro Leu Ser Leu
                165                 170                 175

Pro Val Thr Pro Gly Glu Pro Ala Ser Ile Ser Cys Arg Ser Ser Gln
            180                 185                 190

Ser Leu Leu His Ser Asn Gly Tyr Asn Tyr Leu Asp Trp Tyr Leu Gln
        195                 200                 205

Lys Pro Gly Gln Ser Pro Gln Leu Leu Ile Tyr Leu Gly Ser Asn Arg
    210                 215                 220

Ala Ser Gly Val Pro Asp Arg Phe Ser Gly Ser Gly Ser Gly Thr Asp
225                 230                 235                 240

Phe Thr Leu Lys Ile Ser Arg Val Glu Ala Glu Asp Val Gly Val Tyr
                245                 250                 255

Tyr Cys Gln Gln His Tyr Thr Thr Pro Pro Thr Phe Gly Gln Gly Thr
```

-continued

```
            260                 265                 270

Lys Val Glu Ile Lys Arg Thr Glu Phe
        275                 280
```

(2) INFORMATION FOR SEQ ID NO: 179:

(i) SEQUENCE CHARACTERISTICS:
(A) LENGTH: 15 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 179:

```
Cys Ala Arg Trp Gly Gly Asp Gly Phe Tyr Ala Met Asp Tyr Trp
1               5                   10                  15
```

(2) INFORMATION FOR SEQ ID NO: 180:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 180:

```
Cys Ala Arg Phe Gly Lys Met Asn Tyr Asp Tyr Trp
1               5                   10
```

(2) INFORMATION FOR SEQ ID NO: 181:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 181:

```
Cys Ala Arg His Arg Thr Glu Trp His Asp Tyr Trp
1               5                   10
```

(2) INFORMATION FOR SEQ ID NO: 182:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 182:

```
Cys Ala Arg Val Arg Glu Leu Tyr His Asp Tyr Trp
1               5                   10
```

(2) INFORMATION FOR SEQ ID NO: 183:

-continued (i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 183:

Cys Ala Arg Lys Phe Leu Lys Ala Arg Asp Tyr Trp
1 5 10

(2) INFORMATION FOR SEQ ID NO: 184:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 184:

Cys Ala Arg Trp Asn Thr Thr Gly Tyr Asp Tyr Trp
1 5 10

(2) INFORMATION FOR SEQ ID NO: 185:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 185:

Cys Ala Arg Ile Asn Glu Ala Gln Pro Asp Tyr Trp
1 5 10

(2) INFORMATION FOR SEQ ID NO: 186:

(i) SEQUENCE CHARACTERISTICS:
(A) LENGTH: 11 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 186:

Cys Ala Arg Thr Ala Ile Thr Arg Asp Tyr Trp
1 5 10

(2) INFORMATION FOR SEQ ID NO: 187:

(i) SEQUENCE CHARACTERISTICS:
(A) LENGTH: 12 amino acids
(B) TYPE: amino acid
(C) STRANDEDNESS:
(D) TOPOLOGY: linear -continued (ii) MOLECULE TYPE: protein (v) FRAGMENT TYPE: internal (xi) SEQUENCE DESCRIPTION: SEQ ID NO: 187:

Cys Ala Arg Trp Tyr Asn Arg Asn Ser Asp Tyr Trp
1 5 10

(2) INFORMATION FOR SEQ ID NO: 188:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 188:

Cys Ala Arg Ser Val Gly Asp Ser Lys Asp Tyr Trp
1 5 10

(2) INFORMATION FOR SEQ ID NO: 189:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 189:

Cys Ala Arg Ser Lys Thr Phe Ala Ala Asp Tyr Trp
1 5 10

(2) INFORMATION FOR SEQ ID NO: 190:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 190:

Cys Ala Arg Val Ala Pro Gln Tyr Asp Asp Tyr Trp
1 5 10

(2) INFORMATION FOR SEQ ID NO: 191:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 191:

Cys Ala Arg Met Gln Ser Glu Trp Met Asp Tyr Trp

-continued 1 5 10

(2) INFORMATION FOR SEQ ID NO: 192:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 192:

Cys Ala Arg Tyr Phe Val His Phe Leu Tyr Thr Met Val Met Asp Val
1 5 10 15

Trp (2) INFORMATION FOR SEQ ID NO: 193:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 193:

Cys Ala Arg Met Ala Leu Arg Ala Ser Gly Lys Tyr Ile Met Asp Val
1 5 10 15

Trp (2) INFORMATION FOR SEQ ID NO: 194:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 194:

Cys Ala Arg Lys Asn Gln Met Val Phe His Ala Arg Lys Phe Asp Val
1 5 10 15

Trp (2) INFORMATION FOR SEQ ID NO: 195:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 195:

Cys Ala Arg Thr Gln Ser Phe Trp Glu Gln Gln Lys Val Met Asp Tyr
1 5 10 15

-continued

Trp (2) INFORMATION FOR SEQ ID NO: 196:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 196:

```
Cys Ala Arg Tyr Pro Tyr Arg Ser Asn Phe Phe Met Pro Met Asp Val
1               5                   10                  15

Trp
```

(2) INFORMATION FOR SEQ ID NO: 197:

(i) SEQUENCE CHARACTERISTICS:
(A) LENGTH: 16 amino acids
(B) TYPE: amino acid
(C) STRANDEDNESS:
(D) TOPOLOGY: linear (ii) MOLECULE TYPE: protein (v) FRAGMENT TYPE: internal (ix) FEATURE:
(A) NAME/KEY: Modified-site
(B) LOCATION:3..4
(D) OTHER INFORMATION:/product= "see Figure 10C"
/label= R*G
/note= "* denotes codon with one-base deletion, causes shift of reading fr..."

(xi) SEQUENCE DESCRIPTION: SEQ ID NO: 197:

```
Cys Ala Arg Gly Ser Gly Ser Glu His Trp Ser Ile Phe Asp Val Trp
1               5                   10                  15
```

(2) INFORMATION FOR SEQ ID NO: 198:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 198:

```
Cys Ala Arg Arg Asn Pro Trp Asn Val Asn Tyr Leu His Phe Asp Val
1               5                   10                  15

Trp
```

(2) INFORMATION FOR SEQ ID NO: 199:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein -continued (v) FRAGMENT TYPE: internal (xi) SEQUENCE DESCRIPTION: SEQ ID NO: 199:

```
Cys Ala Arg Met Lys Pro Met Leu Asn Arg Asp Gly Thr Met Asp Val
1               5                   10                  15

Trp
```

(2) INFORMATION FOR SEQ ID NO: 200:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 200:

```
Cys Ala Arg Lys Gly Ser Glu Phe Leu Glu Thr Asp Val Met Asp Tyr
1               5                   10                  15

Trp
```

(2) INFORMATION FOR SEQ ID NO: 201:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 201:

```
Cys Ala Arg Ser Trp Thr Asn Asp Lys Pro Asn Phe Ile Met Asp Val
1               5                   10                  15

Trp
```

(2) INFORMATION FOR SEQ ID NO: 202:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 202:

```
Cys Ala Arg Tyr Ala Gly Thr Thr Phe Lys Gln Gly Pro Met Asp Tyr
1               5                   10                  15

Trp
```

(2) INFORMATION FOR SEQ ID NO: 203:

(i) SEQUENCE CHARACTERISTICS:
(A) LENGTH: 17 amino acids
(B) TYPE: amino acid
(C) STRANDEDNESS:
(D) TOPOLOGY: linear -continued (ii) MOLECULE TYPE: protein (v) FRAGMENT TYPE: internal (xi) SEQUENCE DESCRIPTION: SEQ ID NO: 203:

```
Cys Ala Arg Lys Arg Met Met Gln Asn Pro Arg Phe Arg Phe Asp Val
1               5                   10                  15

Trp
```

(2) INFORMATION FOR SEQ ID NO: 204:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 204:

```
Cys Ala Arg Arg Ser Lys Gln Lys Arg Lys Met Arg Arg Phe Asp Val
1               5                   10                  15

Trp
```

(2) INFORMATION FOR SEQ ID NO: 205:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 205:

```
Cys Ala Arg Arg Asn Gly Lys Arg His Leu Arg His Arg Phe Asp Val
1               5                   10                  15

Trp
```

(2) INFORMATION FOR SEQ ID NO: 206:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 206:

```
Cys Ala Arg Arg Lys Met Arg Lys Arg Ile Lys Arg Arg Phe Asp Val
1               5                   10                  15

Trp
```

(2) INFORMATION FOR SEQ ID NO: 207:

(i) SEQUENCE CHARACTERISTICS:
(A) LENGTH: 17 amino acids
(B) TYPE: amino acid
(C) STRANDEDNESS:
(D) TOPOLOGY: linear -continued (ii) MOLECULE TYPE: protein (v) FRAGMENT TYPE: internal (xi) SEQUENCE DESCRIPTION: SEQ ID NO: 207:

Cys Ala Arg Tyr Arg Lys Ile Met Lys Trp Lys Asn Ser Phe Asp Val
1 5 10 15

Trp (2) INFORMATION FOR SEQ ID NO: 208:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 208:

Cys Ala Arg Leu Ile Glu Val His Pro Ser Phe Asp Gln Met Asp Val
1 5 10 15

Trp (2) INFORMATION FOR SEQ ID NO: 209:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 209:

Cys Ala Arg Arg Lys Pro Met Phe Leu Lys Lys Ala Val Phe Asp Val
1 5 10 15

Trp (2) INFORMATION FOR SEQ ID NO: 210:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 210:

Cys Ala Arg Arg Lys Phe His Arg Tyr Ser Thr Val Lys Phe Asp Tyr
1 5 10 15

Trp (2) INFORMATION FOR SEQ ID NO: 211:

(i) SEQUENCE CHARACTERISTICS:
(A) LENGTH: 17 amino acids
(B) TYPE: amino acid
(C) STRANDEDNESS:

-continued (D) TOPOLOGY: linear (ii) MOLECULE TYPE: protein (v) FRAGMENT TYPE: internal (xi) SEQUENCE DESCRIPTION: SEQ ID NO: 211:

Cys Ala Arg Arg Lys Thr Met Arg Ser Arg Val Lys Tyr Phe Asp Tyr
1 5 10 15

Trp (2) INFORMATION FOR SEQ ID NO: 212:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 212:

Cys Ala Arg Lys Lys Arg Ser Trp Arg Arg Met Asp Arg Phe Asp Val
1 5 10 15

Trp (2) INFORMATION FOR SEQ ID NO: 213:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 213:

Cys Ala Arg Arg Asn Pro Arg Arg Gly Arg Met Asn Arg Phe Asp Val
1 5 10 15

Trp (2) INFORMATION FOR SEQ ID NO: 214:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 214:

Cys Ala Arg Lys Gly Lys Lys Lys Phe Ala Arg Pro Arg Phe Asp Val
1 5 10 15

Trp (2) INFORMATION FOR SEQ ID NO: 215:

(i) SEQUENCE CHARACTERISTICS:
(A) LENGTH: 17 amino acids
(B) TYPE: amino acid

-continued (C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 215:

```
Cys Ala Arg Arg Met Val His Lys Gly Lys Arg Lys Ile Phe Asp Val
1               5                   10                  15

Trp
```

(2) INFORMATION FOR SEQ ID NO: 216:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 216:

```
Cys Ala Arg Arg Lys His Ile Thr Tyr Pro Arg Lys Gln Phe Asp Val
1               5                   10                  15

Trp
```

(2) INFORMATION FOR SEQ ID NO: 217:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 217:

```
Cys Ala Arg Arg Trp Thr Lys Arg Arg Ser Phe Ala Arg Phe Asp Val
1               5                   10                  15

Trp
```

(2) INFORMATION FOR SEQ ID NO: 218:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 218:

```
Cys Ala Arg Lys Lys Leu Lys Gln Tyr Thr Phe Ser Arg Phe Asp Tyr
1               5                   10                  15

Trp
```

(2) INFORMATION FOR SEQ ID NO: 219:

(i) SEQUENCE CHARACTERISTICS:
(A) LENGTH: 17 amino acids

-continued (B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 219:

Cys Ala Arg Thr Arg Pro Trp Gln Ala Thr Arg Lys Gly Phe Asp Val
1 5 10 15

Trp (2) INFORMATION FOR SEQ ID NO: 220:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 220:

Cys Ala Arg Asn Gln Trp Glu Phe Lys Asn Arg Arg Lys Met Asp Tyr
1 5 10 15

Trp (2) INFORMATION FOR SEQ ID NO: 221:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 221:

Cys Ala Arg Lys Arg Trp Met Trp Pro Ile Gly Lys Arg Phe Asp Tyr
1 5 10 15

Trp (2) INFORMATION FOR SEQ ID NO: 222:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 222:

Cys Ala Arg Tyr Ser Leu Trp Arg Leu Asp Glu Tyr Phe Phe Asp Tyr
1 5 10 15

Trp (2) INFORMATION FOR SEQ ID NO: 223:

(i) SEQUENCE CHARACTERISTICS:

-continued (A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 223:

```
Cys Ala Arg Val Pro Trp Gly Asp Phe Trp Ser Trp His Met Asp Val
1               5                   10                  15

Trp
```

(2) INFORMATION FOR SEQ ID NO: 224:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 224:

```
Cys Ala Arg Asn Gly Leu Glu Pro Arg His Arg Lys Met Met Asp Tyr
1               5                   10                  15

Trp
```

(2) INFORMATION FOR SEQ ID NO: 225:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 225:

```
Cys Ala Arg Ile Met Lys Ala Pro Pro Asp Tyr Trp
1               5                   10
```

(2) INFORMATION FOR SEQ ID NO: 226:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 226:

```
Cys Ala Arg Arg Lys Thr Trp His Trp Phe Tyr Lys Arg Met Asp Tyr
1               5                   10                  15

Trp
```

(2) INFORMATION FOR SEQ ID NO: 227:

(i) SEQUENCE CHARACTERISTICS:
(A) LENGTH: 17 amino acids

-continued (B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 227:

Cys Ala Arg Trp Lys Asp Met Trp Ser Gln Val Tyr Val Met Asp Tyr
1 5 10 15

Trp (2) INFORMATION FOR SEQ ID NO: 228:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 228:

Cys Ala Arg Asn Lys Gln Gln Met Arg Phe Arg Arg Phe Met Asp Tyr
1 5 10 15

Trp (2) INFORMATION FOR SEQ ID NO: 229:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 229:

Cys Ala Arg Asn Met Leu Ala Leu Ser Arg Gly Lys Glu Met Asp Val
1 5 10 15

Trp (2) INFORMATION FOR SEQ ID NO: 230:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 230:

Cys Ala Arg Asn Met Arg Leu Met Arg Met Arg Lys Asn Phe Asp Val
1 5 10 15

Trp (2) INFORMATION FOR SEQ ID NO: 231:

(i) SEQUENCE CHARACTERISTICS:

-continued (A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 231:

Cys Ala Arg Tyr Ile Lys Gln Ala Lys Arg Lys Leu Ala Phe Asp Tyr
1 5 10 15

Trp (2) INFORMATION FOR SEQ ID NO: 232:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 232:

Cys Ala Arg Tyr Asn Arg His Ala Trp Gln Lys Met Gln Phe Asp Tyr
1 5 10 15

Trp (2) INFORMATION FOR SEQ ID NO: 233:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 233:

Cys Ala Arg Tyr Val Lys Tyr Ala Arg Asn Lys Met Gln Phe Asp Tyr
1 5 10 15

Trp (2) INFORMATION FOR SEQ ID NO: 234:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 234:

Cys Ala Arg Tyr Lys Arg Gly Ala Trp Met Lys Thr Met Phe Asp Val
1 5 10 15

Trp (2) INFORMATION FOR SEQ ID NO: 235:

-continued (i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 235:

```
Cys Ala Arg Arg Lys Pro Leu Arg Arg Ile Met Lys Trp Phe Asp Tyr
1               5                   10                  15

Trp
```

(2) INFORMATION FOR SEQ ID NO: 236:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 236:

```
Cys Ala Arg Tyr Arg Lys Arg Ala Ser Arg Gln Met Gln Phe Asp Tyr
1               5                   10                  15

Trp
```

(2) INFORMATION FOR SEQ ID NO: 237:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 237:

```
Cys Ala Arg Gln Arg Tyr Arg Ser Lys Ile Lys Gly His Phe Asp Val
1               5                   10                  15

Trp
```

(2) INFORMATION FOR SEQ ID NO: 238:

(i) SEQUENCE CHARACTERISTICS:
(A) LENGTH: 16 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 238:

```
Cys Ala Arg Trp Arg Asp Phe Asn Ser Tyr Asp Pro Met Asp Tyr Trp
1               5                   10                  15
```

(2) INFORMATION FOR SEQ ID NO: 239:

(i) SEQUENCE CHARACTERISTICS:

(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 239:

```
Cys Ala Arg Met Ala Asp Leu Asp Asn Tyr Trp Val Gln Phe Asp Tyr
1               5                   10                  15

Trp
```

(2) INFORMATION FOR SEQ ID NO: 240:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 240:

```
Cys Ala Arg Leu Gln Ala Tyr Leu Lys Pro His His Trp Met Asp Tyr
1               5                   10                  15

Trp
```

(2) INFORMATION FOR SEQ ID NO: 241:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 241:

```
Cys Ala Arg Arg Leu Ile Glu Gln Ala Arg Asp His Val Met Asp Tyr
1               5                   10                  15

Trp
```

(2) INFORMATION FOR SEQ ID NO: 242:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 242:

```
Cys Ala Arg Ser Trp His Asn Ser Gln Phe Thr Gln Ser Phe Asp Val
1               5                   10                  15

Trp
```

(2) INFORMATION FOR SEQ ID NO: 243:

-continued (i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 243:

```
Cys Ala Arg Val Asp His Phe Gln Thr Glu Asn Glu Trp Met Asp Tyr
1               5                   10                  15

Trp
```

(2) INFORMATION FOR SEQ ID NO: 244:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 244:

```
Cys Ala Arg Asp Trp Pro Thr Leu Ile Phe Trp Tyr Trp Phe Asp Tyr
1               5                   10                  15

Trp
```

(2) INFORMATION FOR SEQ ID NO: 245:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 245:

```
Cys Ala Arg Gly Phe Gly Phe Thr Glu Asp Tyr Trp
1               5                   10
```

(2) INFORMATION FOR SEQ ID NO: 246:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 246:

```
Cys Ala Arg Gln Phe Asp Glu Asp Ser Phe Val Arg Arg Phe Asp Val
1               5                   10                  15

Trp
```

(2) INFORMATION FOR SEQ ID NO: 247:

(i) SEQUENCE CHARACTERISTICS:

-continued (A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 247:

```
Cys Ala Arg Ile Leu Lys Glu Ser Ser Lys Ser Arg Gln Met Asp Val
1               5                   10                  15

Trp
```

(2) INFORMATION FOR SEQ ID NO: 248:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 248:

```
Cys Ala Arg Glu Gln Asp Glu Tyr Gly Ala Ile Arg Ile Met Asp Tyr
1               5                   10                  15

Trp
```

(2) INFORMATION FOR SEQ ID NO: 249:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 249:

```
Cys Ala Arg Asn His Phe Glu Ala Ser Trp Pro Arg Arg Gln Met Asp
1               5                   10                  15

Val Trp
```

(2) INFORMATION FOR SEQ ID NO: 250:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 250:

```
Cys Ala Arg Glu Asn Glu Trp Val Asp Met Ile Leu Asp Met Asp Tyr
1               5                   10                  15

Trp
```

(2) INFORMATION FOR SEQ ID NO: 251:

-continued (i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 251:

Cys Ala Arg Gln Tyr Ser Glu Thr Arg Trp Val Arg Lys Phe Asp Tyr
1 5 10 15

Trp (2) INFORMATION FOR SEQ ID NO: 252:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 252:

Cys Ala Arg Gln Phe Lys Glu Ser Lys Thr Arg Arg Lys Phe Asp Val
1 5 10 15

Trp (2) INFORMATION FOR SEQ ID NO: 253:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 253:

Cys Ala Arg Lys Lys Thr Gln Tyr Val His Asp Trp Arg Met Asp Val
1 5 10 15

Trp (2) INFORMATION FOR SEQ ID NO: 254:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 254:

Cys Ala Arg Arg Trp Arg Glu Thr Lys Ser Lys Arg Phe Phe Asp Val
1 5 10 15

Trp (2) INFORMATION FOR SEQ ID NO: 255:

-continued (i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 255:

```
Cys Ala Arg Asp Tyr Ile Met Glu Phe Asp Tyr Trp
1               5                   10
```

(2) INFORMATION FOR SEQ ID NO: 256:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 256:

```
Cys Ala Arg Gln Phe Glu Glu Thr Lys Gln Arg Arg Leu Met Asp Tyr
1               5                   10                  15

Trp
```

(2) INFORMATION FOR SEQ ID NO: 257:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 257:

```
Cys Ala Arg Asp Gln Gly Phe Tyr Ala Ile Asp Tyr Val Met Asp Tyr
1               5                   10                  15

Trp
```

(2) INFORMATION FOR SEQ ID NO: 258:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 258:

```
Cys Ala Arg Val Phe Thr Tyr Met Tyr Asn Tyr Phe Arg Phe Asp Val
1               5                   10                  15

Trp
```

(2) INFORMATION FOR SEQ ID NO: 259:

-continued (i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 259:

Cys Ala Arg Val Phe Phe Glu Gln Met Glu Val Val Arg Met Asp Val
1 5 10 15

Trp (2) INFORMATION FOR SEQ ID NO: 260:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 260:

Cys Ala Arg Glu Lys Glu Tyr Arg Leu Ser Trp Ser Gln Met Asp Tyr
1 5 10 15

Trp (2) INFORMATION FOR SEQ ID NO: 261:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 261:

Cys Ala Arg Tyr Pro Ser Arg Trp Ala Pro Asn Trp Tyr Met Asp Tyr
1 5 10 15

Trp (2) INFORMATION FOR SEQ ID NO: 262:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: protein (v) FRAGMENT TYPE: internal (xi) SEQUENCE DESCRIPTION: SEQ ID NO: 262:

Cys Ala Arg Asp Gly Gly Phe Lys Pro Leu Thr His Phe Phe Asp Val
1 5 10 15

Trp (2) INFORMATION FOR SEQ ID NO: 263:

-continued

```
     (i) SEQUENCE CHARACTERISTICS:
          (A) LENGTH: 143 base pairs
          (B) TYPE: nucleic acid
          (C) STRANDEDNESS: double
          (D) TOPOLOGY: linear

    (ii) MOLECULE TYPE: other nucleic acid
          (A) DESCRIPTION:   /desc = "synthetic DNA cassette"

    (xi) SEQUENCE DESCRIPTION: SEQ ID NO: 263:

ACATGTAAGC TTCCCCCCCC CCTTAATTAA CCCCCCCCCC TGTACACCCC CCCCCCGCTA     60

GCCCCCCCCC CCAGATCTCC CCCCCCCCGA CGTCCCCCCT CTAGACCCCC CCCCCGCATG    120

CCCCCCCCCC CGAATTCGAC GTC                                            143


(2) INFORMATION FOR SEQ ID NO: 264:

     (i) SEQUENCE CHARACTERISTICS:
          (A) LENGTH: 1947 base pairs
          (B) TYPE: nucleic acid
          (C) STRANDEDNESS: double
          (D) TOPOLOGY: circular

    (ii) MOLECULE TYPE: other nucleic acid
          (A) DESCRIPTION:   /desc = "synthetic vector"

    (ix) FEATURE:
          (A) NAME/KEY: CDS
          (B) LOCATION:132..989
          (D) OTHER INFORMATION:/product= "Amp resistance"

    (xi) SEQUENCE DESCRIPTION: SEQ ID NO: 264:

CAGGTGGCAC TTTTCGGGGA AATGTGCGCG GAACCCCTAT TTGTTTATTT TTCTAAATAC     60

ATTCAAATAT GTATCCGCTC ATGAGACAAT AACCCTGATA AATGCTTCAA TAATATTGAA    120

AAAGGAAGAG T ATG AGT ATT CAA CAT TTC CGT GTC GCC CTT ATT CCC TTT     170
             Met Ser Ile Gln His Phe Arg Val Ala Leu Ile Pro Phe
                         285                 290

TTT GCG GCA TTT TGC CTT CCT GTT TTT GCT CAC CCA GAA ACG CTG GTG     218
Phe Ala Ala Phe Cys Leu Pro Val Phe Ala His Pro Glu Thr Leu Val
295                 300                 305                 310

AAA GTA AAA GAT GCT GAA GAT CAG TTG GGT GCA CGA GTG GGT TAC ATC     266
Lys Val Lys Asp Ala Glu Asp Gln Leu Gly Ala Arg Val Gly Tyr Ile
                315                 320                 325

GAA CTG GAT CTC AAC AGC GGT AAG ATC CTT GAG AGT TTT CGC CCC GAA     314
Glu Leu Asp Leu Asn Ser Gly Lys Ile Leu Glu Ser Phe Arg Pro Glu
            330                 335                 340

GAA CGT TTT CCA ATG ATG AGC ACT TTT AAA GTT CTG CTA TGT GGC GCG     362
Glu Arg Phe Pro Met Met Ser Thr Phe Lys Val Leu Leu Cys Gly Ala
        345                 350                 355

GTA TTA TCC CGT ATT GAC GCC GGG CAA GAG CAA CTC GGT CGC CGC ATA     410
Val Leu Ser Arg Ile Asp Ala Gly Gln Glu Gln Leu Gly Arg Arg Ile
    360                 365                 370

CAC TAT TCT CAG AAT GAC TTG GTT GAG TAC TCA CCA GTC ACA GAA AAG     458
His Tyr Ser Gln Asn Asp Leu Val Glu Tyr Ser Pro Val Thr Glu Lys
375                 380                 385                 390

CAT CTT ACG GAT GGC ATG ACA GTA AGA GAA TTA TGC AGT GCT GCC ATA     506
His Leu Thr Asp Gly Met Thr Val Arg Glu Leu Cys Ser Ala Ala Ile
                395                 400                 405

ACC ATG AGT GAT AAC ACT GCG GCC AAC TTA CTT CTG ACA ACG ATC GGA     554
Thr Met Ser Asp Asn Thr Ala Ala Asn Leu Leu Leu Thr Thr Ile Gly
            410                 415                 420

GGA CCG AAG GAG CTA ACC GCT TTT TTG CAC AAC ATG GGG GAT CAT GTA     602
Gly Pro Lys Glu Leu Thr Ala Phe Leu His Asn Met Gly Asp His Val
```

-continued

```
        425                 430                 435

ACT CGC CTT GAT CGT TGG GAA CCG GAG CTG AAT GAA GCC ATA CCA AAC       650
Thr Arg Leu Asp Arg Trp Glu Pro Glu Leu Asn Glu Ala Ile Pro Asn
    440                 445                 450

GAC GAG CGT GAC ACC ACG ATG CCT GTA GCA ATG GCA ACA ACG TTG CGC       698
Asp Glu Arg Asp Thr Thr Met Pro Val Ala Met Ala Thr Thr Leu Arg
455                 460                 465                 470

AAA CTA TTA ACT GGC GAA CTA CTT ACT CTA GCT TCC CGG CAA CAA TTA       746
Lys Leu Leu Thr Gly Glu Leu Leu Thr Leu Ala Ser Arg Gln Gln Leu
                475                 480                 485

ATA GAC TGG ATG GAG GCG GAT AAA GTT GCA GGA CCA CTT CTG CGC TCG       794
Ile Asp Trp Met Glu Ala Asp Lys Val Ala Gly Pro Leu Leu Arg Ser
            490                 495                 500

GCC CTT CCG GCT GGC TGG TTT ATT GCT GAT AAA TCT GGA GCC GGT GAG       842
Ala Leu Pro Ala Gly Trp Phe Ile Ala Asp Lys Ser Gly Ala Gly Glu
        505                 510                 515

CGT GGG TCT CGC GGT ATC ATT GCA GCA CTG GGG CCA GAT GGT AAG CCC       890
Arg Gly Ser Arg Gly Ile Ile Ala Ala Leu Gly Pro Asp Gly Lys Pro
    520                 525                 530

TCC CGT ATC GTA GTT ATC TAC ACG ACG GGG AGT CAG GCA ACT ATG GAT       938
Ser Arg Ile Val Val Ile Tyr Thr Thr Gly Ser Gln Ala Thr Met Asp
535                 540                 545                 550

GAA CGA AAT AGA CAG ATC GCT GAG ATA GGT GCC TCA CTG ATT AAG CAT       986
Glu Arg Asn Arg Gln Ile Ala Glu Ile Gly Ala Ser Leu Ile Lys His
                555                 560                 565

TGG TAACTGTCAG ACCAAGTTTA CTCATATATA CTTTAGATTG ATTTAAAACT          1039
Trp

TCATTTTTAA TTTAAAAGGA TCTAGGTGAA GATCCTTTTT GATAATCTCA TGACCAAAAT   1099

CCCTTAACGT GAGTTTTCGT TCCACTGAGC GTCAGACCCC GTAGAAAAGA TCAAAGGATC   1159

TTCTTGAGAT CCTTTTTTTC TGCGCGTAAT CTGCTGCTTG CAAACAAAAA AACCACCGCT   1219

ACCAGCGGTG GTTTGTTTGC CGGATCAAGA GCTACCAACT CTTTTTCCGA AGGTAACTGG   1279

CTTCAGCAGA GCGCAGATAC CAAATACTGT CCTTCTAGTG TAGCCGTAGT TAGGCCACCA   1339

CTTCAAGAAC TCTGTAGCAC CGCCTACATA CCTCGCTCTG CTAATCCTGT TACCAGTGGC   1399

TGCTGCCAGT GGCGATAAGT CGTGTCTTAC CGGGTTGGAC TCAAGACGAT AGTTACCGGA   1459

TAAGGCGCAG CGGTCGGGCT GAACGGGGGG TTCGTGCACA CAGCCCAGCT TGGAGCGAAC   1519

GACCTACACC GAACTGAGAT ACCTACAGCG TGAGCTATGA GAAAGCGCCA CGCTTCCCGA   1579

AGGGAGAAAG GCGGACAGGT ATCCGGTAAG CGGCAGGGTC GGAACAGGAG AGCGCACGAG   1639

GGAGCTTCCA GGGGGAAACG CCTGGTATCT TTATAGTCCT GTCGGGTTTC GCCACCTCTG   1699

ACTTGAGCGT CGATTTTTGT GATGCTCGTC AGGGGGGCGG AGCCTATGGA AAAACGCCAG   1759

CAACGCGGCC TTTTTACGGT TCCTGGCCTT TTGCTGGCCT TTTGCTCACA TGTAAGCTTC   1819

CCCCCCCCCT TAATTAACCC CCCCCCCTGT ACACCCCCCC CCCGCTAGCC CCCCCCCCCA   1879

GATCTCCCCC CCCCCGACGT CCCCCCTCTA GACCCCCCCC CCGCATGCCC CCCCCCCCGA   1939

ATTCACGT                                                            1947
```

(2) INFORMATION FOR SEQ ID NO: 265:

(i) SEQUENCE CHARACTERISTICS:
(A) LENGTH: 286 amino acids
(B) TYPE: amino acid
(D) TOPOLOGY: linear (ii) MOLECULE TYPE: protein -continued (xi) SEQUENCE DESCRIPTION: SEQ ID NO: 265:

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

(2) INFORMATION FOR SEQ ID NO: 266:

(i) SEQUENCE CHARACTERISTICS:
(A) LENGTH: 142 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 266:

```
GACGTCTTAA TGTGAGTTAG CTCACTCATT AGGCACCCCA GGCTTTACAC TTTATGCTTC     60

CGGCTCGTAT GTTGTGTGGA ATTGTGAGCG GATAACAATT TCACACAGGA AACAGCTATG    120

ACCATGATTA CGAATTTCTA GA                                             142
```

(2) INFORMATION FOR SEQ ID NO: 267:

-continued

```
     (i) SEQUENCE CHARACTERISTICS:
          (A) LENGTH: 520 base pairs
          (B) TYPE: nucleic acid
          (C) STRANDEDNESS: double
          (D) TOPOLOGY: linear

    (ii) MOLECULE TYPE: other nucleic acid
          (A) DESCRIPTION:  /desc = "synthetic gene cassette"

    (ix) FEATURE:
          (A) NAME/KEY: CDS
          (B) LOCATION:1..510
          (D) OTHER INFORMATION:/product= "gIIIp ss with myc-tag,
               amber codon"

    (xi) SEQUENCE DESCRIPTION: SEQ ID NO: 267:

GAA TTC GAG CAG AAG CTG ATC TCT GAG GAG GAT CTG TAG GGT GGT GGC       48
Glu Phe Glu Gln Lys Leu Ile Ser Glu Glu Asp Leu  *  Gly Gly Gly
            290                 295                 300

TCT GGT TCC GGT GAT TTT GAT TAT GAA AAG ATG GCA AAC GCT AAT AAG       96
Ser Gly Ser Gly Asp Phe Asp Tyr Glu Lys Met Ala Asn Ala Asn Lys
        305                 310                 315

GGG GCT ATG ACC GAA AAT GCC GAT GAA AAC GCG CTA CAG TCT GAC GCT      144
Gly Ala Met Thr Glu Asn Ala Asp Glu Asn Ala Leu Gln Ser Asp Ala
    320                 325                 330

AAA GGC AAA CTT GAT TCT GTC GCT ACT GAT TAC GGT GCT GCT ATC GAT      192
Lys Gly Lys Leu Asp Ser Val Ala Thr Asp Tyr Gly Ala Ala Ile Asp
335                 340                 345                 350

GGT TTC ATT GGT GAC GTT TCC GGC CTT GCT AAT GGT AAT GGT GCT ACT      240
Gly Phe Ile Gly Asp Val Ser Gly Leu Ala Asn Gly Asn Gly Ala Thr
                355                 360                 365

GGT GAT TTT GCT GGC TCT AAT TCC CAA ATG GCT CAA GTC GGT GAC GGT      288
Gly Asp Phe Ala Gly Ser Asn Ser Gln Met Ala Gln Val Gly Asp Gly
            370                 375                 380

GAT AAT TCA CCT TTA ATG AAT AAT TTC CGT CAA TAT TTA CCT TCC CTC      336
Asp Asn Ser Pro Leu Met Asn Asn Phe Arg Gln Tyr Leu Pro Ser Leu
        385                 390                 395

CCT CAA TCG GTT GAA TGT CGC CCT TTT GTC TTT GGC GCT GGT AAA CCA      384
Pro Gln Ser Val Glu Cys Arg Pro Phe Val Phe Gly Ala Gly Lys Pro
    400                 405                 410

TAT GAA TTT TCT ATT GAT TGT GAC AAA ATA AAC TTA TTC CGT GGT GTC      432
Tyr Glu Phe Ser Ile Asp Cys Asp Lys Ile Asn Leu Phe Arg Gly Val
415                 420                 425                 430

TTT GCG TTT CTT TTA TAT GTT GCC ACC TTT ATG TAT GTA TTT TCT ACG      480
Phe Ala Phe Leu Leu Tyr Val Ala Thr Phe Met Tyr Val Phe Ser Thr
                435                 440                 445

TTT GCT AAC ATA CTG CGT AAT AAG GAG TCT TGATAAGCTT                   520
Phe Ala Asn Ile Leu Arg Asn Lys Glu Ser
            450                 455


(2) INFORMATION FOR SEQ ID NO: 268:

     (i) SEQUENCE CHARACTERISTICS:
          (A) LENGTH: 12 amino acids
          (B) TYPE: amino acid
          (D) TOPOLOGY: linear

    (ii) MOLECULE TYPE: protein

    (xi) SEQUENCE DESCRIPTION: SEQ ID NO: 268:

Glu Phe Glu Gln Lys Leu Ile Ser Glu Glu Asp Leu
  1               5                  10


(2) INFORMATION FOR SEQ ID NO: 269:
```

-continued (i) SEQUENCE CHARACTERISTICS:
(A) LENGTH: 123 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 269:

```
GGGGGGGGGG AAGCTTGACC TGTGAAGTGA AAAATGGCGC AGATTGTGCG ACATTTTTTT     60

TGTCTGCCGT TTAATTAAAG GGGGGGGGGG GCCGGCCTGG GGGGGGGTGT ACAGGGGGGG    120

GGG                                                                  123
```

(2) INFORMATION FOR SEQ ID NO: 270:

(i) SEQUENCE CHARACTERISTICS:
(A) LENGTH: 470 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 270:

```
GCTAGCACGC GCCCTGTAGC GGCGCATTAA GCGCGGCGGG TGTGGTGGTT ACGCGCAGCG     60

TGACCGCTAC ACTTGCCAGC GCCCTAGCGC CCGCTCCTTT CGCTTTCTTC CCTTCCTTTC    120

TCGCCACGTT CGCCGGCTTT CCCCGTCAAG CTCTAAATCG GGCATCCCT TTAGGGTTCC    180

GATTTAGTGC TTTACGGCAC CTCGACCCCA AAAAACTTGA TTAGGGTGAT GGTTCTCGTA    240

GTGGGCCATC GCCCTGATAG ACGGTTTTTC GCCCTTTGAC GTTGGAGTCC ACGTTCTTTA    300

ATAGTGGACT CTTGTTCCAA ACTGGAACAA CACTCAACCC TATCTCGGTC TATTCTTTTG    360

ATTTATAAGG GATTTTGCCG ATTTCGGCCT ATTGGTTAAA AAATGAGCTG ATTTAACAAA    420

AATTTAACGC GAATTTTAAC AAAATATTAA CGTTTACAAT TTCATGTACA               470
```

(2) INFORMATION FOR SEQ ID NO: 271:

(i) SEQUENCE CHARACTERISTICS:
(A) LENGTH: 733 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 271:

```
AGATCTGACC AAAATCCCTT AACGTGAGTT TTCGTTCCAC TGAGCGTCAG ACCCCGTAGA     60

AAAGATCAAA GGATCTTCTT GAGATCCTTT TTTTCTGCGC GTAATCTGCT GCTTGCAAAC    120

AAAAAAACCA CCGCTACCAG CGGTGGTTTG TTTGCCGGAT CAAGAGCTAC CAACTCTTTT    180

TCCGAAGGTA ACTGGCTACA GCAGAGCGCA GATACCAAAT ACTGTTCTTC TAGTGTAGCC    240

GTAGTTAGGC CACCACTTCA AGAACTCTGT AGCACCGCCT ACATACCTCG CTCTGCTAAT    300

CCTGTTACCA GTGGCTGCTG CCAGTGGCGA TAAGTCGTGT CTTACCGGGT TGGACTCAAG    360

ACGATAGTTA CCGGATAAGG CGCAGCGGTC GGGCTGAACG GGGGGTTCGT GCACACAGCC    420

CAGCTTGGAG CGAACGACCT ACACCGAACT GAGATACCTA CAGCGTGAGC TATGAGAAAG    480

CGCCACGCTT CCCGAAGGGA GAAAGGCGGA CAGGTATCCG GTAAGCGGCA GGGTCGGAAC    540
```

-continued

```
AGGAGAGCGC ACGAGGGAGC TTCCAGGGGG AAACGCCTGG TATCTTTATA GTCCTGTCGG    600

GTTTCGCCAC CTCTGACTTG AGCGTCGATT TTTGTGATGC TCGTCAGGGG GGCGGAGCCT    660

ATGGAAAAAC GCCAGCAACG CGGCCTTTTT ACGGTTCCTG GCCTTTTGCT GGCCTTTTGC    720

TCACATGGCT AGC                                                       733
```

(2) INFORMATION FOR SEQ ID NO: 272:

(i) SEQUENCE CHARACTERISTICS:
(A) LENGTH: 813 base pairs
(B) TYPE: nucleic acid
(C) STRANDEDNESS: double
(D) TOPOLOGY: linear (ii) MOLECULE TYPE: other nucleic acid
(A) DESCRIPTION: /desc = “synthetic gene cassette”

(ix) FEATURE:
(A) NAME/KEY: CDS
(B) LOCATION:102..758
(D) OTHER INFORMATION:/product= “cat resistance”

(xi) SEQUENCE DESCRIPTION: SEQ ID NO: 272:

```
GGGACGTCGG GTGAGGTTCC AACTTTCACC ATAATGAAAT AAGATCACTA CCGGGCGTAT     60

TTTTTGAGTT ATCGAGATTT TCAGGAGCTA AGGAAGCTAA A ATG GAG AAA AAA       113
                                              Met Glu Lys Lys

ATC ACT GGA TAT ACC ACC GTT GAT ATA TCC CAA TGG CAT CGT AAA GAA     161
Ile Thr Gly Tyr Thr Thr Val Asp Ile Ser Gln Trp His Arg Lys Glu
175                 180                 185                 190

CAT TTT GAG GCA TTT CAG TCA GTT GCT CAA TGT ACC TAT AAC CAG ACC     209
His Phe Glu Ala Phe Gln Ser Val Ala Gln Cys Thr Tyr Asn Gln Thr
                195                 200                 205

GTT CAG CTG GAT ATT ACG GCC TTT TTA AAG ACC GTA AAG AAA AAT AAG     257
Val Gln Leu Asp Ile Thr Ala Phe Leu Lys Thr Val Lys Lys Asn Lys
            210                 215                 220

CAC AAG TTT TAT CCG GCC TTT ATT CAC ATT CTT GCC CGC CTG ATG AAT     305
His Lys Phe Tyr Pro Ala Phe Ile His Ile Leu Ala Arg Leu Met Asn
        225                 230                 235

GCT CAC CCG GAG TTC CGT ATG GCA ATG AAA GAC GGT GAG CTG GTG ATA     353
Ala His Pro Glu Phe Arg Met Ala Met Lys Asp Gly Glu Leu Val Ile
    240                 245                 250

TGG GAT AGT GTT CAC CCT TGT TAC ACC GTT TTC CAT GAG CAA ACT GAA     401
Trp Asp Ser Val His Pro Cys Tyr Thr Val Phe His Glu Gln Thr Glu
255                 260                 265                 270

ACG TTT TCA TCG CTC TGG AGT GAA TAC CAC GAC GAT TTC CGG CAG TTT     449
Thr Phe Ser Ser Leu Trp Ser Glu Tyr His Asp Asp Phe Arg Gln Phe
                275                 280                 285

CTA CAC ATA TAT TCG CAA GAT GTG GCG TGT TAC GGT GAA AAC CTG GCC     497
Leu His Ile Tyr Ser Gln Asp Val Ala Cys Tyr Gly Glu Asn Leu Ala
            290                 295                 300

TAT TTC CCT AAA GGG TTT ATT GAG AAT ATG TTT TTC GTC TCA GCC AAT     545
Tyr Phe Pro Lys Gly Phe Ile Glu Asn Met Phe Phe Val Ser Ala Asn
        305                 310                 315

CCC TGG GTG AGT TTC ACC AGT TTT GAT TTA AAC GTA GCC AAT ATG GAC     593
Pro Trp Val Ser Phe Thr Ser Phe Asp Leu Asn Val Ala Asn Met Asp
    320                 325                 330

AAC TTC TTC GCC CCC GTT TTC ACT ATG GGC AAA TAT TAT ACG CAA GGC     641
Asn Phe Phe Ala Pro Val Phe Thr Met Gly Lys Tyr Tyr Thr Gln Gly
335                 340                 345                 350

GAC AAG GTG CTG ATG CCG CTG GCG ATT CAG GTT CAT CAT GCC GTT TGT     689
Asp Lys Val Leu Met Pro Leu Ala Ile Gln Val His His Ala Val Cys
                355                 360                 365
```

-continued

```
GAT GGC TTC CAT GTC GGC AGA ATG CTT AAT GAA TTA CAA CAG TAC TGC       737
Asp Gly Phe His Val Gly Arg Met Leu Asn Glu Leu Gln Gln Tyr Cys
            370                 375                 380

GAT GAG TGG CAG GGC GGG GCG TAATTTTTTT AAGGCAGTTA TTGGGTGCCC          788
Asp Glu Trp Gln Gly Gly Ala
        385

TTAAACGCCT GGTGCTAGAT CTTCC                                           813
```

(2) INFORMATION FOR SEQ ID NO: 273:

(i) SEQUENCE CHARACTERISTICS:
(A) LENGTH: 219 amino acids
(B) TYPE: amino acid
(D) TOPOLOGY: linear (ii) MOLECULE TYPE: protein (xi) SEQUENCE DESCRIPTION: SEQ ID NO: 273:

```
Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

(2) INFORMATION FOR SEQ ID NO: 274:

(i) SEQUENCE CHARACTERISTICS:
(A) LENGTH: 2755 base pairs
(B) TYPE: nucleic acid
(C) STRANDEDNESS: double
(D) TOPOLOGY: circular (ii) MOLECULE TYPE: other nucleic acid
(A) DESCRIPTION: /desc = “synthetic vector”

(ix) FEATURE:
(A) NAME/KEY: CDS

-continued

```
        (B) LOCATION:3..509
        (D) OTHER INFORMATION:/product= "gIIIp ss, myc tag, amber
             codon"

    (ix) FEATURE:
        (A) NAME/KEY: CDS
        (B) LOCATION:complement (1853..2509)
        (D) OTHER INFORMATION:/product= "cat resistance"

    (xi) SEQUENCE DESCRIPTION: SEQ ID NO: 274:

AA TTC GAG CAG AAG CTG ATC TCT GAG GAG GAT CTG TAG GGT GGT GGC        47
   Phe Glu Gln Lys Leu Ile Ser Glu Glu Asp Leu  *  Gly Gly Gly
   220                225                 230

TCT GGT TCC GGT GAT TTT GAT TAT GAA AAG ATG GCA AAC GCT AAT AAG       95
Ser Gly Ser Gly Asp Phe Asp Tyr Glu Lys Met Ala Asn Ala Asn Lys
235                 240                 245                 250

GGG GCT ATG ACC GAA AAT GCC GAT GAA AAC GCG CTA CAG TCT GAC GCT      143
Gly Ala Met Thr Glu Asn Ala Asp Glu Asn Ala Leu Gln Ser Asp Ala
                255                 260                 265

AAA GGC AAA CTT GAT TCT GTC GCT ACT GAT TAC GGT GCT GCT ATC GAT      191
Lys Gly Lys Leu Asp Ser Val Ala Thr Asp Tyr Gly Ala Ala Ile Asp
            270                 275                 280

GGT TTC ATT GGT GAC GTT TCC GGC CTT GCT AAT GGT AAT GGT GCT ACT      239
Gly Phe Ile Gly Asp Val Ser Gly Leu Ala Asn Gly Asn Gly Ala Thr
        285                 290                 295

GGT GAT TTT GCT GGC TCT AAT TCC CAA ATG GCT CAA GTC GGT GAC GGT      287
Gly Asp Phe Ala Gly Ser Asn Ser Gln Met Ala Gln Val Gly Asp Gly
    300                 305                 310

GAT AAT TCA CCT TTA ATG AAT AAT TTC CGT CAA TAT TTA CCT TCC CTC      335
Asp Asn Ser Pro Leu Met Asn Asn Phe Arg Gln Tyr Leu Pro Ser Leu
315                 320                 325                 330

CCT CAA TCG GTT GAA TGT CGC CCT TTT GTC TTT GGC GCT GGT AAA CCA      383
Pro Gln Ser Val Glu Cys Arg Pro Phe Val Phe Gly Ala Gly Lys Pro
                335                 340                 345

TAT GAA TTT TCT ATT GAT TGT GAC AAA ATA AAC TTA TTC CGT GGT GTC      431
Tyr Glu Phe Ser Ile Asp Cys Asp Lys Ile Asn Leu Phe Arg Gly Val
            350                 355                 360

TTT GCG TTT CTT TTA TAT GTT GCC ACC TTT ATG TAT GTA TTT TCT ACG      479
Phe Ala Phe Leu Leu Tyr Val Ala Thr Phe Met Tyr Val Phe Ser Thr
        365                 370                 375

TTT GCT AAC ATA CTG CGT AAT AAG GAG TCT TGATAAGCTT GACCTGTGAA        529
Phe Ala Asn Ile Leu Arg Asn Lys Glu Ser
    380                 385

GTGAAAAATG GCGCAGATTG TGCGACATTT TTTTTGTCTG CCGTTTAATT AAAGGGGGGG    589

GGGGGCCGGC CTGGGGGGGG GTGTACATGA AATTGTAAAC GTTAATATTT TGTTAAAATT    649

CGCGTTAAAT TTTTGTTAAA TCAGCTCATT TTTTAACCAA TAGGCCGAAA TCGGCAAAAT    709

CCCTTATAAA TCAAAAGAAT AGACCGAGAT AGGGTTGAGT GTTGTTCCAG TTTGGAACAA    769

GAGTCCACTA TTAAAGAACG TGGACTCCAA CGTCAAAGGG CGAAAAACCG TCTATCAGGG    829

CGATGGCCCA CTACGAGAAC CATCACCCTA ATCAAGTTTT TTGGGGTCGA GGTGCCGTAA    889

AGCACTAAAT CGGAACCCTA AAGGGAGCCC CCGATTTAGA GCTTGACGGG GAAAGCCGGC    949

GAACGTGGCG AGAAAGGAAG GGAAGAAAGC GAAAGGAGCG GGCGCTAGGG CGCTGGCAAG   1009

TGTAGCGGTC ACGCTGCGCG TAACCACCAC ACCCGCCGCG CTTAATGCGC CGCTACAGGG   1069

CGCGTGCTAG CCATGTGAGC AAAAGGCCAG CAAAAGGCCA GGAACCGTAA AAAGGCCGCG   1129

TTGCTGGCGT TTTTCCATAG GCTCCGCCCC CCTGACGAGC ATCACAAAAA TCGACGCTCA   1189

AGTCAGAGGT GGCGAAACCC GACAGGACTA TAAAGATACC AGGCGTTTCC CCCTGGAAGC   1249
```

-continued

```
TCCCTCGTGC GCTCTCCTGT TCCGACCCTG CCGCTTACCG GATACCTGTC CGCCTTTCTC   1309

CCTTCGGGAA GCGTGGCGCT TTCTCATAGC TCACGCTGTA GGTATCTCAG TTCGGTGTAG   1369

GTCGTTCGCT CCAAGCTGGG CTGTGTGCAC GAACCCCCCG TTCAGCCCGA CCGCTGCGCC   1429

TTATCCGGTA ACTATCGTCT TGAGTCCAAC CCGGTAAGAC ACGACTTATC GCCACTGGCA   1489

GCAGCCACTG GTAACAGGAT TAGCAGAGCG AGGTATGTAG GCGGTGCTAC AGAGTTCTTG   1549

AAGTGGTGGC CTAACTACGG CTACACTAGA AGAACAGTAT TTGGTATCTG CGCTCTGCTG   1609

TAGCCAGTTA CCTTCGGAAA AAGAGTTGGT AGCTCTTGAT CCGGCAAACA AACCACCGCT   1669

GGTAGCGGTG GTTTTTTTGT TTGCAAGCAG CAGATTACGC GCAGAAAAAA AGGATCTCAA   1729

GAAGATCCTT TGATCTTTTC TACGGGGTCT GACGCTCAGT GGAACGAAAA CTCACGTTAA   1789

GGGATTTTGG TCAGATCTAG CACCAGGCGT TTAAGGGCAC CAATAACTGC CTTAAAAAAA   1849

TTACGCCCCG CCCTGCCACT CATCGCAGTA CTGTTGTAAT TCATTAAGCA TTCTGCCGAC   1909

ATGGAAGCCA TCACAAACGG CATGATGAAC CTGAATCGCC AGCGGCATCA GCACCTTGTC   1969

GCCTTGCGTA TAATATTTGC CCATAGTGAA AACGGGGGCG AAGAAGTTGT CCATATTGGC   2029

TACGTTTAAA TCAAAACTGG TGAAACTCAC CCAGGGATTG GCTGAGACGA AAAACATATT   2089

CTCAATAAAC CCTTTAGGGA AATAGGCCAG GTTTTCACCG TAACACGCCA CATCTTGCGA   2149

ATATATGTGT AGAAACTGCC GGAAATCGTC GTGGTATTCA CTCCAGAGCG ATGAAAACGT   2209

TTCAGTTTGC TCATGGAAAA CGGTGTAACA AGGGTGAACA CTATCCCATA TCACCAGCTC   2269

ACCGTCTTTC ATTGCCATAC GGAACTCCGG GTGAGCATTC ATCAGGCGGG CAAGAATGTG   2329

AATAAAGGCC GGATAAAACT TGTGCTTATT TTTCTTTACG GTCTTTAAAA AGGCCGTAAT   2389

ATCCAGCTGA ACGGTCTGGT TATAGGTACA TTGAGCAACT GACTGAAATG CCTCAAAATG   2449

TTCTTTACGA TGCCATTGGG ATATATCAAC GGTGGTATAT CCAGTGATTT TTTTCTCCAT   2509

TTTAGCTTCC TTAGCTCCTG AAAATCTCGA TAACTCAAAA AATACGCCCG GTAGTGATCT   2569

TATTTCATTA TGGTGAAAGT TGGAACCTCA CCCGACGTCT AATGTGAGTT AGCTCACTCA   2629

TTAGGCACCC CAGGCTTTAC ACTTTATGCT TCCGGCTCGT ATGTTGTGTG GAATTGTGAG   2689

CGGATAACAA TTTCACACAG GAAACAGCTA TGACCATGAT TACGAATTTC TAGAGCATGC   2749

GGGGGG                                                              2755
```

(2) INFORMATION FOR SEQ ID NO: 275:

(i) SEQUENCE CHARACTERISTICS:
(A) LENGTH: 11 amino acids
(B) TYPE: amino acid
(D) TOPOLOGY: linear (ii) MOLECULE TYPE: protein (xi) SEQUENCE DESCRIPTION: SEQ ID NO: 275:

```
Phe Glu Gln Lys Leu Ile Ser Glu Glu Asp Leu
  1               5                  10
```

(2) INFORMATION FOR SEQ ID NO: 276:

(i) SEQUENCE CHARACTERISTICS:
(A) LENGTH: 219 amino acids
(B) TYPE: amino acid
(D) TOPOLOGY: linear (ii) MOLECULE TYPE: protein (xi) SEQUENCE DESCRIPTION: SEQ ID NO: 276:

-continued

```
Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

(2) INFORMATION FOR SEQ ID NO: 277:

(i) SEQUENCE CHARACTERISTICS:
(A) LENGTH: 173 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 277:

```
GACGTCTTAA TGTGAGTTAG CTCACTCATT AGGCACCCCA GGCTTTACAC TTTATGCTTC     60

CGGCTCGTAT GTTGTGTGGA ATTGTGAGCG GATAACAATT TCACACAGGA AACAGCTATG    120

ACCATGTCTA GAATAACTTC GTATAATGTA CGCTATACGA AGTTATCGCA TGC           173
```

(2) INFORMATION FOR SEQ ID NO: 278:

(i) SEQUENCE CHARACTERISTICS:
(A) LENGTH: 47 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 278:

```
AGATCTCATA ACTTCGTATA ATGTATGCTA TACGAAGTTA TGACGTC                   47
```

-continued (2) INFORMATION FOR SEQ ID NO: 279:

(i) SEQUENCE CHARACTERISTICS:
(A) LENGTH: 1255 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene cassette"

(ix) FEATURE:
(A) NAME/KEY: CDS
(B) LOCATION:1..1245
(D) OTHER INFORMATION:/product= "gIIIp, GGGGS linker"

(xi) SEQUENCE DESCRIPTION: SEQ ID NO: 279:

```
GAA TTC GGT GGT GGT GGA TCT GCG TGC GCT GAA ACG GTT GAA AGT TGT       48
Glu Phe Gly Gly Gly Gly Ser Ala Cys Ala Glu Thr Val Glu Ser Cys
220                 225                 230                 235

TTA GCA AAA TCC CAT ACA GAA AAT TCA TTT ACT AAC GTC TGG AAA GAC       96
Leu Ala Lys Ser His Thr Glu Asn Ser Phe Thr Asn Val Trp Lys Asp
                240                 245                 250

GAC AAA ACT TTA GAT CGT TAC GCT AAC TAT GAG GGC TGT CTG TGG AAT      144
Asp Lys Thr Leu Asp Arg Tyr Ala Asn Tyr Glu Gly Cys Leu Trp Asn
            255                 260                 265

GCT ACA GGC GTT GTA GTT TGT ACT GGT GAC GAA ACT CAG TGT TAC GGT      192
Ala Thr Gly Val Val Val Cys Thr Gly Asp Glu Thr Gln Cys Tyr Gly
        270                 275                 280

ACA TGG GTT CCT ATT GGG CTT GCT ATC CCT GAA AAT GAG GGT GGT GGC      240
Thr Trp Val Pro Ile Gly Leu Ala Ile Pro Glu Asn Glu Gly Gly Gly
    285                 290                 295

TCT GAG GGT GGC GGT TCT GAG GGT GGC GGT TCT GAG GGT GGC GGT ACT      288
Ser Glu Gly Gly Gly Ser Glu Gly Gly Gly Ser Glu Gly Gly Gly Thr
300                 305                 310                 315

AAA CCT CCT GAG TAC GGT GAT ACA CCT ATT CCG GGC TAT ACT TAT ATC      336
Lys Pro Pro Glu Tyr Gly Asp Thr Pro Ile Pro Gly Tyr Thr Tyr Ile
                320                 325                 330

AAC CCT CTC GAC GGC ACT TAT CCG CCT GGT ACT GAG CAA AAC CCC GCT      384
Asn Pro Leu Asp Gly Thr Tyr Pro Pro Gly Thr Glu Gln Asn Pro Ala
            335                 340                 345

AAT CCT AAT CCT TCT CTT GAG GAG TCT CAG CCT CTT AAT ACT TTC ATG      432
Asn Pro Asn Pro Ser Leu Glu Glu Ser Gln Pro Leu Asn Thr Phe Met
        350                 355                 360

TTT CAG AAT AAT AGG TTC CGA AAT AGG CAG GGG GCA TTA ACT GTT TAT      480
Phe Gln Asn Asn Arg Phe Arg Asn Arg Gln Gly Ala Leu Thr Val Tyr
    365                 370                 375

ACG GGC ACT GTT ACT CAA GGC ACT GAC CCC GTT AAA ACT TAT TAC CAG      528
Thr Gly Thr Val Thr Gln Gly Thr Asp Pro Val Lys Thr Tyr Tyr Gln
380                 385                 390                 395

TAC ACT CCT GTA TCA TCA AAA GCC ATG TAT GAC GCT TAC TGG AAC GGT      576
Tyr Thr Pro Val Ser Ser Lys Ala Met Tyr Asp Ala Tyr Trp Asn Gly
                400                 405                 410

AAA TTC AGA GAC TGC GCT TTC CAT TCT GGC TTT AAT GAG GAT TTA TTT      624
Lys Phe Arg Asp Cys Ala Phe His Ser Gly Phe Asn Glu Asp Leu Phe
            415                 420                 425

GTT TGT GAA TAT CAA GGC CAA TCG TCT GAC CTG CCT CAA CCT CCT GTC      672
Val Cys Glu Tyr Gln Gly Gln Ser Ser Asp Leu Pro Gln Pro Pro Val
        430                 435                 440

AAT GCT GGC GGC GGC TCT GGT GGT GGT TCT GGT GGC GGC TCT GAG GGT      720
Asn Ala Gly Gly Gly Ser Gly Gly Gly Ser Gly Gly Gly Ser Glu Gly
    445                 450                 455

GGT GGC TCT GAG GGT GGC GGT TCT GAG GGT GGC GGC TCT GAG GGA GGC      768
```

-continued

```
Gly Gly Ser Glu Gly Gly Gly Ser Glu Gly Gly Gly Ser Glu Gly Gly
460                 465                 470                 475

GGT TCC GGT GGT GGC TCT GGT TCC GGT GAT TTT GAT TAT GAA AAG ATG      816
Gly Ser Gly Gly Gly Ser Gly Ser Gly Asp Phe Asp Tyr Glu Lys Met
                480                 485                 490

GCA AAC GCT AAT AAG GGG GCT ATG ACC GAA AAT GCC GAT GAA AAC GCG      864
Ala Asn Ala Asn Lys Gly Ala Met Thr Glu Asn Ala Asp Glu Asn Ala
            495                 500                 505

CTA CAG TCT GAC GCT AAA GGC AAA CTT GAT TCT GTC GCT ACT GAT TAC      912
Leu Gln Ser Asp Ala Lys Gly Lys Leu Asp Ser Val Ala Thr Asp Tyr
        510                 515                 520

GGT GCT GCT ATC GAT GGT TTC ATT GGT GAC GTT TCC GGC CTT GCT AAT      960
Gly Ala Ala Ile Asp Gly Phe Ile Gly Asp Val Ser Gly Leu Ala Asn
    525                 530                 535

GGT AAT GGT GCT ACT GGT GAT TTT GCT GGC TCT AAT TCC CAA ATG GCT     1008
Gly Asn Gly Ala Thr Gly Asp Phe Ala Gly Ser Asn Ser Gln Met Ala
540                 545                 550                 555

CAA GTC GGT GAA GGT GAT AAT TCA CCT TTA ATG AAT AAT TTC CGT CAA     1056
Gln Val Gly Glu Gly Asp Asn Ser Pro Leu Met Asn Asn Phe Arg Gln
                560                 565                 570

TAT TTA CCT TCC ATC CCT CAA TCG GTT GAA TGT CGC CCT TTT GTC TTT     1104
Tyr Leu Pro Ser Ile Pro Gln Ser Val Glu Cys Arg Pro Phe Val Phe
            575                 580                 585

GGC GCT GGT AAA CCC TAT GAA TTT TCT ATT GAT TGT GAC AAA ATA AAC     1152
Gly Ala Gly Lys Pro Tyr Glu Phe Ser Ile Asp Cys Asp Lys Ile Asn
        590                 595                 600

TTA TTC CGT GGT GTC TTT GCG TTT CTT TTA TAT GTT GCC ACC TTT ATG     1200
Leu Phe Arg Gly Val Phe Ala Phe Leu Leu Tyr Val Ala Thr Phe Met
    605                 610                 615

TAT GTA TTT TCT ACG TTT GCT AAC ATA CTG CGT AAT AAG GAG TCT         1245
Tyr Val Phe Ser Thr Phe Ala Asn Ile Leu Arg Asn Lys Glu Ser
620                 625                 630

TGATAAGCTT                                                          1255
```

(2) INFORMATION FOR SEQ ID NO: 280:

(i) SEQUENCE CHARACTERISTICS:
(A) LENGTH: 415 amino acids
(B) TYPE: amino acid
(D) TOPOLOGY: linear (ii) MOLECULE TYPE: protein (xi) SEQUENCE DESCRIPTION: SEQ ID NO: 280:

```
Glu Phe Gly Gly Gly Gly Ser Ala Cys Ala Glu Thr Val Glu Ser Cys
  1               5                  10                  15

Leu Ala Lys Ser His Thr Glu Asn Ser Phe Thr Asn Val Trp Lys Asp
            20                  25                  30

Asp Lys Thr Leu Asp Arg Tyr Ala Asn Tyr Glu Gly Cys Leu Trp Asn
        35                  40                  45

Ala Thr Gly Val Val Val Cys Thr Gly Asp Glu Thr Gln Cys Tyr Gly
    50                  55                  60

Thr Trp Val Pro Ile Gly Leu Ala Ile Pro Glu Asn Glu Gly Gly Gly
 65                  70                  75                  80

Ser Glu Gly Gly Gly Ser Glu Gly Gly Gly Ser Glu Gly Gly Gly Thr
                85                  90                  95

Lys Pro Pro Glu Tyr Gly Asp Thr Pro Ile Pro Gly Tyr Thr Tyr Ile
            100                 105                 110

Asn Pro Leu Asp Gly Thr Tyr Pro Pro Gly Thr Glu Gln Asn Pro Ala
```

-continued

```
        115                 120                 125

Asn Pro Asn Pro Ser Leu Glu Glu Ser Gln Pro Leu Asn Thr Phe Met
    130                 135                 140

Phe Gln Asn Asn Arg Phe Arg Asn Arg Gln Gly Ala Leu Thr Val Tyr
145                 150                 155                 160

Thr Gly Thr Val Thr Gln Gly Thr Asp Pro Val Lys Thr Tyr Tyr Gln
                165                 170                 175

Tyr Thr Pro Val Ser Ser Lys Ala Met Tyr Asp Ala Tyr Trp Asn Gly
            180                 185                 190

Lys Phe Arg Asp Cys Ala Phe His Ser Gly Phe Asn Glu Asp Leu Phe
        195                 200                 205

Val Cys Glu Tyr Gln Gly Gln Ser Ser Asp Leu Pro Gln Pro Pro Val
    210                 215                 220

Asn Ala Gly Gly Gly Ser Gly Gly Gly Ser Gly Gly Gly Ser Glu Gly
225                 230                 235                 240

Gly Gly Ser Glu Gly Gly Gly Ser Glu Gly Gly Gly Ser Glu Gly Gly
                245                 250                 255

Gly Ser Gly Gly Gly Ser Gly Ser Gly Asp Phe Asp Tyr Glu Lys Met
            260                 265                 270

Ala Asn Ala Asn Lys Gly Ala Met Thr Glu Asn Ala Asp Glu Asn Ala
        275                 280                 285

Leu Gln Ser Asp Ala Lys Gly Lys Leu Asp Ser Val Ala Thr Asp Tyr
    290                 295                 300

Gly Ala Ala Ile Asp Gly Phe Ile Gly Asp Val Ser Gly Leu Ala Asn
305                 310                 315                 320

Gly Asn Gly Ala Thr Gly Asp Phe Ala Gly Ser Asn Ser Gln Met Ala
                325                 330                 335

Gln Val Gly Glu Gly Asp Asn Ser Pro Leu Met Asn Asn Phe Arg Gln
            340                 345                 350

Tyr Leu Pro Ser Ile Pro Gln Ser Val Glu Cys Arg Pro Phe Val Phe
        355                 360                 365

Gly Ala Gly Lys Pro Tyr Glu Phe Ser Ile Asp Cys Asp Lys Ile Asn
    370                 375                 380

Leu Phe Arg Gly Val Phe Ala Phe Leu Leu Tyr Val Ala Thr Phe Met
385                 390                 395                 400

Tyr Val Phe Ser Thr Phe Ala Asn Ile Leu Arg Asn Lys Glu Ser
                405                 410                 415
```

(2) INFORMATION FOR SEQ ID NO: 281:

(i) SEQUENCE CHARACTERISTICS:
(A) LENGTH: 502 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene cassette"

(ix) FEATURE:
(A) NAME/KEY: CDS
(B) LOCATION:4..492
(D) OTHER INFORMATION:/product= "gIIIp ss"

(xi) SEQUENCE DESCRIPTION: SEQ ID NO: 281:

```
CGG GAA TTC GGA GGC GGT TCC GGT GGT GGC TCT GGT TCC GGT GAT TTT       48
    Glu Phe Gly Gly Gly Ser Gly Gly Gly Ser Gly Ser Gly Asp Phe
                    420                 425                 430
```

-continued

```
GAT TAT GAA AAG ATG GCA AAC GCT AAT AAG GGG GCT ATG ACC GAA AAT        96
Asp Tyr Glu Lys Met Ala Asn Ala Asn Lys Gly Ala Met Thr Glu Asn
                435                 440                 445

GCC GAT GAA AAC GCG CTA CAG TCT GAC GCT AAA GGC AAA CTT GAT TCT       144
Ala Asp Glu Asn Ala Leu Gln Ser Asp Ala Lys Gly Lys Leu Asp Ser
            450                 455                 460

GTC GCT ACT GAT TAC GGT GCT GCT ATC GAT GGT TTC ATT GGT GAC GTT       192
Val Ala Thr Asp Tyr Gly Ala Ala Ile Asp Gly Phe Ile Gly Asp Val
        465                 470                 475

TCC GGC CTT GCT AAT GGT AAT GGT GCT ACT GGT GAT TTT GCT GGC TCT       240
Ser Gly Leu Ala Asn Gly Asn Gly Ala Thr Gly Asp Phe Ala Gly Ser
    480                 485                 490

AAT TCC CAA ATG GCT CAA GTC GGT GAC GGT GAT AAT TCA CCT TTA ATG       288
Asn Ser Gln Met Ala Gln Val Gly Asp Gly Asp Asn Ser Pro Leu Met
495                 500                 505                 510

AAT AAT TTC CGT CAA TAT TTA CCT TCC CTC CCT CAA TCG GTT GAA TGT       336
Asn Asn Phe Arg Gln Tyr Leu Pro Ser Leu Pro Gln Ser Val Glu Cys
                515                 520                 525

CGC CCT TTT GTC TTT GGC GCT GGT AAA CCA TAT GAA TTT TCT ATT GAT       384
Arg Pro Phe Val Phe Gly Ala Gly Lys Pro Tyr Glu Phe Ser Ile Asp
            530                 535                 540

TGT GAC AAA ATA AAC TTA TTC CGT GGT GTC TTT GCG TTT CTT TTA TAT       432
Cys Asp Lys Ile Asn Leu Phe Arg Gly Val Phe Ala Phe Leu Leu Tyr
        545                 550                 555

GTT GCC ACC TTT ATG TAT GTA TTT TCT ACG TTT GCT AAC ATA CTG CGT       480
Val Ala Thr Phe Met Tyr Val Phe Ser Thr Phe Ala Asn Ile Leu Arg
    560                 565                 570

AAT AAG GAG TCT TGATAAGCTT                                            502
Asn Lys Glu Ser
575
```

(2) INFORMATION FOR SEQ ID NO: 282:

(i) SEQUENCE CHARACTERISTICS:
(A) LENGTH: 163 amino acids
(B) TYPE: amino acid
(D) TOPOLOGY: linear (ii) MOLECULE TYPE: protein (xi) SEQUENCE DESCRIPTION: SEQ ID NO: 282:

```
Glu Phe Gly Gly Gly Ser Gly Gly Gly Ser Gly Ser Gly Asp Phe Asp
  1               5                  10                  15

Tyr Glu Lys Met Ala Asn Ala Asn Lys Gly Ala Met Thr Glu Asn Ala
             20                  25                  30

Asp Glu Asn Ala Leu Gln Ser Asp Ala Lys Gly Lys Leu Asp Ser Val
         35                  40                  45

Ala Thr Asp Tyr Gly Ala Ala Ile Asp Gly Phe Ile Gly Asp Val Ser
     50                  55                  60

Gly Leu Ala Asn Gly Asn Gly Ala Thr Gly Asp Phe Ala Gly Ser Asn
 65                  70                  75                  80

Ser Gln Met Ala Gln Val Gly Asp Gly Asp Asn Ser Pro Leu Met Asn
                 85                  90                  95

Asn Phe Arg Gln Tyr Leu Pro Ser Leu Pro Gln Ser Val Glu Cys Arg
            100                 105                 110

Pro Phe Val Phe Gly Ala Gly Lys Pro Tyr Glu Phe Ser Ile Asp Cys
        115                 120                 125

Asp Lys Ile Asn Leu Phe Arg Gly Val Phe Ala Phe Leu Leu Tyr Val
    130                 135                 140
```

-continued

```
Ala Thr Phe Met Tyr Val Phe Ser Thr Phe Ala Asn Ile Leu Arg Asn
145                 150                 155                 160

Lys Glu Ser
```

(2) INFORMATION FOR SEQ ID NO: 283:

(i) SEQUENCE CHARACTERISTICS:
(A) LENGTH: 47 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 283:

```
GCATGCCATA ACTTCGTATA ATGTACGCTA TACGAAGTTA TAAGCTT                47
```

(2) INFORMATION FOR SEQ ID NO: 284:

(i) SEQUENCE CHARACTERISTICS:
(A) LENGTH: 1163 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene cassette"

(ix) FEATURE:
(A) NAME/KEY: CDS
(B) LOCATION:82..978
(D) OTHER INFORMATION:/product= "bla resistance"

(xi) SEQUENCE DESCRIPTION: SEQ ID NO: 284:

```
GGGGGTGTAC ATTCAAATAT GTATCCGCTC ATGAGACAAT AACCCTGATA AATGCTTCAA     60

TAATATTGAA AAAGGAAGAG T ATG AGT ATT CAA CAT TTC CGT GTC GCC CTT      111
                        Met Ser Ile Gln His Phe Arg Val Ala Leu
                                165                 170

ATT CCC TTT TTT GCG GCA TTT TGC CTT CCT GTT TTT GCT CAC CCA GAA      159
Ile Pro Phe Phe Ala Ala Phe Cys Leu Pro Val Phe Ala His Pro Glu
    175                 180                 185

ACG CTG GTG AAA GTA AAA GAT GCT GAG GAT CAG TTG GGT GCG CGA GTG      207
Thr Leu Val Lys Val Lys Asp Ala Glu Asp Gln Leu Gly Ala Arg Val
190                 195                 200                 205

GGT TAC ATC GAA CTG GAT CTC AAC AGC GGT AAG ATC CTT GAG AGT TTT      255
Gly Tyr Ile Glu Leu Asp Leu Asn Ser Gly Lys Ile Leu Glu Ser Phe
                210                 215                 220

CGC CCC GAA GAA CGT TTT CCA ATG ATG AGC ACT TTT AAA GTT CTG CTA      303
Arg Pro Glu Glu Arg Phe Pro Met Met Ser Thr Phe Lys Val Leu Leu
            225                 230                 235

TGT GGC GCG GTA TTA TCC CGT ATT GAC GCC GGG CAA GAG CAA CTC GGT      351
Cys Gly Ala Val Leu Ser Arg Ile Asp Ala Gly Gln Glu Gln Leu Gly
        240                 245                 250

CGC CGC ATA CAC TAT TCT CAG AAT GAC TTG GTT GAG TAC TCA CCA GTC      399
Arg Arg Ile His Tyr Ser Gln Asn Asp Leu Val Glu Tyr Ser Pro Val
    255                 260                 265

ACA GAA AAG CAT CTT ACG GAT GGC ATG ACA GTA AGA GAA TTA TGC AGT      447
Thr Glu Lys His Leu Thr Asp Gly Met Thr Val Arg Glu Leu Cys Ser
270                 275                 280                 285

GCT GCC ATA ACC ATG AGT GAT AAC ACT GCG GCC AAC TTA CTT CTG ACA      495
Ala Ala Ile Thr Met Ser Asp Asn Thr Ala Ala Asn Leu Leu Leu Thr
                290                 295                 300

ACG ATC GGA GGA CCG AAG GAG CTA ACC GCT TTT TTG CAC AAC ATG GGG      543
```

-continued

```
Thr Ile Gly Gly Pro Lys Glu Leu Thr Ala Phe Leu His Asn Met Gly
            305                 310                 315

GAT CAT GTA ACT CGC CTT GAT CGT TGG GAA CCG GAG CTG AAT GAA GCC      591
Asp His Val Thr Arg Leu Asp Arg Trp Glu Pro Glu Leu Asn Glu Ala
        320                 325                 330

ATA CCA AAC GAC GAG CGT GAC ACC ACG ATG CCT GTA GCA ATG GCA ACA      639
Ile Pro Asn Asp Glu Arg Asp Thr Thr Met Pro Val Ala Met Ala Thr
    335                 340                 345

ACG TTG CGC AAA CTA TTA ACT GGC GAA CTA CTT ACT CTA GCT TCC CGG      687
Thr Leu Arg Lys Leu Leu Thr Gly Glu Leu Leu Thr Leu Ala Ser Arg
350                 355                 360                 365

CAA CAG TTA ATA GAC TGG ATG GAG GCG GAT AAA GTT GCA GGA CCA CTT      735
Gln Gln Leu Ile Asp Trp Met Glu Ala Asp Lys Val Ala Gly Pro Leu
                370                 375                 380

CTG CGC TCG GCC CTT CCG GCT GGC TGG TTT ATT GCT GAT AAA TCT GGA      783
Leu Arg Ser Ala Leu Pro Ala Gly Trp Phe Ile Ala Asp Lys Ser Gly
            385                 390                 395

GCC GGT GAG CGT GGG TCT CGC GGT ATC ATT GCA GCA CTG GGG CCA GAT      831
Ala Gly Glu Arg Gly Ser Arg Gly Ile Ile Ala Ala Leu Gly Pro Asp
        400                 405                 410

GGT AAG CCC TCC CGT ATC GTA GTT ATC TAC ACG ACG GGG AGT CAG GCA      879
Gly Lys Pro Ser Arg Ile Val Val Ile Tyr Thr Thr Gly Ser Gln Ala
    415                 420                 425

ACT ATG GAT GAA CGA AAT AGA CAG ATC GCT GAG ATA GGT GCC TCA CTG      927
Thr Met Asp Glu Arg Asn Arg Gln Ile Ala Glu Ile Gly Ala Ser Leu
430                 435                 440                 445

ATT AAG CAT TGG GTA ACT GTC AGA CCA AGT TTA CTC ATA TAT ACT TTA      975
Ile Lys His Trp Val Thr Val Arg Pro Ser Leu Leu Ile Tyr Thr Leu
                450                 455                 460

GAT TGATTTAAAA CTTCATTTTT AATTTAAAAG GATCTAGGTG AAGATCCTTT          1028
Asp

TTGATAATCT CATGACCAAA ATCCCTTAAC GTGAGTTTTC GTTCCACTGA GCGTCAGACC   1088

CCGTAGAAAA GATCAAAGGA TCTTCTTGAG ATCCTTTTTG ATAATGGCCG GCCCCCCCCC   1148

TTAATTAAGG GGGGG                                                    1163
```

(2) INFORMATION FOR SEQ ID NO: 285:

(i) SEQUENCE CHARACTERISTICS:
(A) LENGTH: 299 amino acids
(B) TYPE: amino acid
(D) TOPOLOGY: linear (ii) MOLECULE TYPE: protein (xi) SEQUENCE DESCRIPTION: SEQ ID NO: 285:

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
```

-continued

```
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285

Val Arg Pro Ser Leu Leu Ile Tyr Thr Leu Asp
    290                 295
```

(2) INFORMATION FOR SEQ ID NO: 286:

(i) SEQUENCE CHARACTERISTICS:
(A) LENGTH: 470 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 286:

```
GCTAGCACGC GCCCTGTAGC GGCGCATTAA GCGCGGCGGG TGTGGTGGTT ACGCGCAGCG      60

TGACCGCTAC ACTTGCCAGC GCCCTAGCGC CCGCTCCTTT CGCTTTCTTC CCTTCCTTTC     120

TCGCCACGTT CGCCGGCTTT CCCCGTCAAG CTCTAAATCG GGGGCTCCCT TTAGGGTTCC     180

GATTTAGTGC TTTACGGCAC CTCGACCCCA AAAAACTTGA TTAGGGTGAT GGTTCTCGTA     240

GTGGGCCATC GCCCTGATAG ACGGTTTTTC GCCCTTTGAC GTTGGAGTCC ACGTTCTTTA     300

ATAGTGGACT CTTGTTCCAA ACTGGAACAA CACTCAACCC TATCTCGGTC TATTCTTTTG     360

ATTTATAAGG GATTTTGCCG ATTTCGGCCT ATTGGTTAAA AAATGAGCTG ATTTAACAAA     420

AATTTAACGC GAATTTTAAC AAAATATTAA CGTTTACAAT TTCATGTACA                470
```

(2) INFORMATION FOR SEQ ID NO: 287:

(i) SEQUENCE CHARACTERISTICS:
(A) LENGTH: 832 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

-continued (xi) SEQUENCE DESCRIPTION: SEQ ID NO: 287:

AGATCTAATA AGATGATCTT CTTGAGATCG TTTTGGTCTG CGCGTAATCT CTTGCTCTGA 60

AAACGAAAAA ACCGCCTTGC AGGGCGGTTT TTCGTAGGTT CTCTGAGCTA CCAACTCTTT 120

GAACCGAGGT AACTGGCTTG GAGGAGCGCA GTCACTAAAA CTTGTCCTTT CAGTTTAGCC 180

TTAACCGGCG CATGACTTCA AGACTAACTC CTCTAAATCA ATTACCAGTG GCTGCTGCCA 240

GTGGTGCTTT TGCATGTCTT TCCGGGTTGG ACTCAAGACG ATAGTTACCG GATAAGGCGC 300

AGCGGTCGGA CTGAACGGGG GGTTCGTGCA TACAGTCCAG CTTGGAGCGA ACTGCCTACC 360

CGGAACTGAG TGTCAGGCGT GGAATGAGAC AAACGCGGCC ATAACAGCGG AATGACACCG 420

GTAAACCGAA AGGCAGGAAC AGGAGAGCGC AGGAGGGAGC CGCCAGGGGG AAACGCCTGG 480

TATCTTTATA GTCCTGTCGG GTTTCGCCAC CACTGATTTG AGCGTCAGAT TTCGTGATGC 540

TTGTCAGGGG GGCGGAGCCT ATGGAAAAAC GGCTTTGCCG CGGCCCTCTC ACTTCCCTGT 600

TAAGTATCTT CCTGGCATCT TCCAGGAAAT CTCCGCCCCG TTCGTAAGCC ATTTCCGCTC 660

GCCGCAGTCG AACGACCGAG CGTAGCGAGT CAGTGAGCGA GGAAGCGGAA TATATCCTGT 720

ATCACATATT CTGCTGACGC ACCGGTGCAG CCTTTTTTCT CCTGCCACAT GAAGCACTTC 780

ACTGACACCC TCATCAGTGC CAACATAGTA AGCCAGTATA CACTCCGCTA GC 832

(2) INFORMATION FOR SEQ ID NO: 288:

(i) SEQUENCE CHARACTERISTICS:
(A) LENGTH: 49 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 288:

AGATCTCATA ACTTCGTATA ATGTATGCTA TACGAAGTTA TTCAGATCT 49

(2) INFORMATION FOR SEQ ID NO: 289:

(i) SEQUENCE CHARACTERISTICS:
(A) LENGTH: 96 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 289:

TCTAGAGCAT GCGTAGGAGA AAATAAAATG AAACAAAGCA CTATTGCACT GGCACTCTTA 60

CCGTTGCTCT TCACCCCTGT TACCAAAGCC GAATTC 96

(2) INFORMATION FOR SEQ ID NO: 290:

(i) SEQUENCE CHARACTERISTICS:
(A) LENGTH: 120 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 290:

-continued

```
TCTAGAGCAT GCGTAGGAGA AAATAAAATG AAACAAAGCA CTATTGCACT GGCACTCTTA      60

CCGTTGCTCT TCACCCCTGT TACCAAAGCC GACTACAAAG ATGAAGTGCA ATTGGAATTC     120
```

(2) INFORMATION FOR SEQ ID NO: 291:

(i) SEQUENCE CHARACTERISTICS:
(A) LENGTH: 96 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic DNA cassette"

(xi) SEQUENCE DESCRIPTION: SEQ ID NO: 291:

```
TCTAGAGGTT GAGGTGATTT TATGAAAAAG AATATCGCAT TTCTTCTTGC ATCTATGTTC      60

GTTTTTTCTA TTGCTACAAA TGCATACGCT GAATTC                                96
```

(2) INFORMATION FOR SEQ ID NO: 292:

(i) SEQUENCE CHARACTERISTICS:
(A) LENGTH: 1221 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene cassette"

(ix) FEATURE:
(A) NAME/KEY: CDS
(B) LOCATION:79..1158
(D) OTHER INFORMATION:/product= "lacI"

(xi) SEQUENCE DESCRIPTION: SEQ ID NO: 292:

```
GCTAGCATCG AATGGCGCAA AACCTTTCGC GGTATGGCAT GATAGCGCCC GGAAGAGAGT      60

CAATTCAGGG TGGTGAAT GTG AAA CCA GTA ACG TTA TAC GAT GTC GCA GAG      111
                    Val Lys Pro Val Thr Leu Tyr Asp Val Ala Glu
                    300                 305                 310

TAT GCC GGT GTC TCT TAT CAG ACC GTT TCC CGC GTG GTG AAC CAG GCC      159
Tyr Ala Gly Val Ser Tyr Gln Thr Val Ser Arg Val Val Asn Gln Ala
            315                 320                 325

AGC CAC GTT TCT GCG AAA ACG CGG GAA AAA GTG GAA GCG GCG ATG GCG      207
Ser His Val Ser Ala Lys Thr Arg Glu Lys Val Glu Ala Ala Met Ala
        330                 335                 340

GAG CTG AAT TAC ATT CCT AAC CGC GTG GCA CAA CAA CTG GCG GGC AAA      255
Glu Leu Asn Tyr Ile Pro Asn Arg Val Ala Gln Gln Leu Ala Gly Lys
    345                 350                 355

CAG TCG TTG CTG ATT GGC GTT GCC ACC TCC AGT CTG GCC CTG CAC GCG      303
Gln Ser Leu Leu Ile Gly Val Ala Thr Ser Ser Leu Ala Leu His Ala
360                 365                 370

CCG TCG CAA ATT GTC GCG GCG ATT AAA TCT CGC GCC GAT CAA CTG GGT      351
Pro Ser Gln Ile Val Ala Ala Ile Lys Ser Arg Ala Asp Gln Leu Gly
375                 380                 385                 390

GCC AGC GTG GTC GTG TCG ATG GTA GAA CGA AGC GGC GTC GAA GCC TGT      399
Ala Ser Val Val Val Ser Met Val Glu Arg Ser Gly Val Glu Ala Cys
            395                 400                 405

AAA GCG GCG GTG CAC AAT CTT CTC GCG CAA CGT GTC AGT GGG CTG ATT      447
Lys Ala Ala Val His Asn Leu Leu Ala Gln Arg Val Ser Gly Leu Ile
        410                 415                 420

ATT AAC TAT CCG CTG GAT GAC CAG GAT GCT ATT GCT GTG GAA GCT GCC      495
Ile Asn Tyr Pro Leu Asp Asp Gln Asp Ala Ile Ala Val Glu Ala Ala
    425                 430                 435
```

-continued

```
TGC ACT AAT GTT CCG GCG TTA TTT CTT GAT GTC TCT GAC CAG ACA CCC      543
Cys Thr Asn Val Pro Ala Leu Phe Leu Asp Val Ser Asp Gln Thr Pro
    440                 445                 450

ATC AAC AGT ATT ATT TTC TCC CAT GAG GAC GGT ACG CGA CTG GGC GTG      591
Ile Asn Ser Ile Ile Phe Ser His Glu Asp Gly Thr Arg Leu Gly Val
455                 460                 465                 470

GAG CAT CTG GTC GCA TTG GGC CAC CAG CAA ATC GCG CTG TTA GCT GGC      639
Glu His Leu Val Ala Leu Gly His Gln Gln Ile Ala Leu Leu Ala Gly
                475                 480                 485

CCA TTA AGT TCT GTC TCG GCG CGT CTG CGT CTG GCT GGC TGG CAT AAA      687
Pro Leu Ser Ser Val Ser Ala Arg Leu Arg Leu Ala Gly Trp His Lys
            490                 495                 500

TAT CTC ACT CGC AAT CAA ATT CAG CCG ATA GCG GAA CGG GAA GGC GAC      735
Tyr Leu Thr Arg Asn Gln Ile Gln Pro Ile Ala Glu Arg Glu Gly Asp
        505                 510                 515

TGG AGT GCC ATG TCC GGT TTT CAA CAA ACC ATG CAA ATG CTG AAT GAG      783
Trp Ser Ala Met Ser Gly Phe Gln Gln Thr Met Gln Met Leu Asn Glu
    520                 525                 530

GGC ATC GTT CCC ACT GCG ATG CTG GTT GCC AAC GAT CAG ATG GCG CTG      831
Gly Ile Val Pro Thr Ala Met Leu Val Ala Asn Asp Gln Met Ala Leu
535                 540                 545                 550

GGC GCA ATG CGT GCC ATT ACC GAG TCC GGG CTG CGC GTT GGT GCG GAC      879
Gly Ala Met Arg Ala Ile Thr Glu Ser Gly Leu Arg Val Gly Ala Asp
                555                 560                 565

ATC TCG GTA GTG GGA TAC GAC GAT ACC GAG GAC AGC TCA TGT TAT ATC      927
Ile Ser Val Val Gly Tyr Asp Asp Thr Glu Asp Ser Ser Cys Tyr Ile
            570                 575                 580

CCG CCG CTG ACC ACC ATC AAA CAG GAT TTT CGC CTG CTG GGG CAA ACC      975
Pro Pro Leu Thr Thr Ile Lys Gln Asp Phe Arg Leu Leu Gly Gln Thr
        585                 590                 595

AGC GTG GAC CGC TTG CTG CAA CTC TCT CAG GGC CAG GCG GTG AAG GGC     1023
Ser Val Asp Arg Leu Leu Gln Leu Ser Gln Gly Gln Ala Val Lys Gly
    600                 605                 610

AAT CAG CTG TTG CCC GTC TCA CTG GTG AAA AGA AAA ACC ACC CTG GCT     1071
Asn Gln Leu Leu Pro Val Ser Leu Val Lys Arg Lys Thr Thr Leu Ala
615                 620                 625                 630

CCC AAT ACG CAA ACC GCC TCT CCC CGC GCG TTG GCC GAT TCA CTG ATG     1119
Pro Asn Thr Gln Thr Ala Ser Pro Arg Ala Leu Ala Asp Ser Leu Met
                635                 640                 645

CAG CTG GCA CGA CAG GTT TCC CGA CTG GAA AGC GGG CAG TGAGGCTACC     1168
Gln Leu Ala Arg Gln Val Ser Arg Leu Glu Ser Gly Gln
            650                 655

CGATAAAAGC GGCTTCCTGA CAGGAGGCCG TTTTGTTTTG CAGCCCACTT AAG          1221
```

(2) INFORMATION FOR SEQ ID NO: 293:

(i) SEQUENCE CHARACTERISTICS:
(A) LENGTH: 360 amino acids
(B) TYPE: amino acid
(D) TOPOLOGY: linear (ii) MOLECULE TYPE: protein (xi) SEQUENCE DESCRIPTION: SEQ ID NO: 293:

```
Val Lys Pro Val Thr Leu Tyr Asp Val Ala Glu Tyr Ala Gly Val Ser
  1               5                  10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45
```

-continued

```
Pro Asn Arg Val Ala Gln Gln Leu Ala Gly Lys Gln Ser Leu Leu Ile
     50                  55                  60

Gly Val Ala Thr Ser Ser Leu Ala Leu His Ala Pro Ser Gln Ile Val
 65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360
```

(2) INFORMATION FOR SEQ ID NO: 294:

(i) SEQUENCE CHARACTERISTICS:
(A) LENGTH: 2380 base pairs
(B) TYPE: nucleic acid
(C) STRANDEDNESS: double
(D) TOPOLOGY: circular (ii) MOLECULE TYPE: other nucleic acid
(A) DESCRIPTION: /desc = “synthetic vector”

(ix) FEATURE:
(A) NAME/KEY: CDS
(B) LOCATION:complement (51..707)
(D) OTHER INFORMATION:/product= “cat resistance”

(xi) SEQUENCE DESCRIPTION: SEQ ID NO: 294:

-continued

```
GATCTAGCAC CAGGCGTTTA AGGGCACCAA TAACTGCCTT AAAAAAATTA CGCCCCGCCC     60
TGCCACTCAT CGCAGTACTG TTGTAATTCA TTAAGCATTC TGCCGACATG GAAGCCATCA    120
CAAACGGCAT GATGAACCTG AATCGCCAGC GGCATCAGCA CCTTGTCGCC TTGCGTATAA    180
TATTTGCCCA TAGTGAAAAC GGGGGCGAAG AAGTTGTCCA TATTGGCTAC GTTTAAATCA    240
AAACTGGTGA AACTCACCCA GGGATTGGCT GAGACGAAAA ACATATTCTC AATAAACCCT    300
TTAGGGAAAT AGGCCAGGTT TTCACCGTAA CACGCCACAT CTTGCGAATA TATGTGTAGA    360
AACTGCCGGA AATCGTCGTG GTATTCACTC CAGAGCGATG AAAACGTTTC AGTTTGCTCA    420
TGGAAAACGG TGTAACAAGG GTGAACACTA TCCCATATCA CCAGCTCACC GTCTTTCATT    480
GCCATACGGA ACTCCGGGTG AGCATTCATC AGGCGGGCAA GAATGTGAAT AAAGGCCGGA    540
TAAAACTTGT GCTTATTTTT CTTTACGGTC TTTAAAAAGG CCGTAATATC CAGCTGAACG    600
GTCTGGTTAT AGGTACATTG AGCAACTGAC TGAAATGCCT CAAAATGTTC TTTACGATGC    660
CATTGGGATA TATCAACGGT GGTATATCCA GTGATTTTTT TCTCCATTTT AGCTTCCTTA    720
GCTCCTGAAA ATCTCGATAA CTCAAAAAAT ACGCCCGGTA GTGATCTTAT TTCATTATGG    780
TGAAAGTTGG AACCTCACCC GACGTCTAAT GTGAGTTAGC TCACTCATTA GGCACCCCAG    840
GCTTTACACT TTATGCTTCC GGCTCGTATG TTGTGTGGAA TTGTGAGCGG ATAACAATTT    900
CACACAGGAA ACAGCTATGA CCATGATTAC GAATTTCTAG ACCCCCCCCC CGCATGCCAT    960
AACTTCGTAT AATGTACGCT ATACGAAGTT ATAAGCTTGA CCTGTGAAGT GAAAAATGGC   1020
GCAGATTGTG CGACATTTTT TTTGTCTGCC GTTTAATTAA AGGGGGGGGG GGGCCGGCCT   1080
GGGGGGGGGT GTACATGAAA TTGTAAACGT TAATATTTTG TTAAAATTCG CGTTAAATTT   1140
TTGTTAAATC AGCTCATTTT TTAACCAATA GGCCGAAATC GGCAAAATCC CTTATAAATC   1200
AAAAGAATAG ACCGAGATAG GGTTGAGTGT TGTTCCAGTT TGGAACAAGA GTCCACTATT   1260
AAAGAACGTG GACTCCAACG TCAAAGGGCG AAAAACCGTC TATCAGGGCG ATGGCCCACT   1320
ACGAGAACCA TCACCCTAAT CAAGTTTTTT GGGGTCGAGG TGCCGTAAAG CACTAAATCG   1380
GAACCCTAAA GGGAGCCCCC GATTTAGAGC TTGACGGGGA AAGCCGGCGA ACGTGGCGAG   1440
AAAGGAAGGG AAGAAAGCGA AAGGAGCGGG CGCTAGGGCG CTGGCAAGTG TAGCGGTCAC   1500
GCTGCGCGTA ACCACCACAC CCGCCGCGCT TAATGCGCCG CTACAGGGCG CGTGCTAGCG   1560
GAGTGTATAC TGGCTTACTA TGTTGGCACT GATGAGGGTG TCAGTGAAGT GCTTCATGTG   1620
GCAGGAGAAA AAAGGCTGCA CCGGTGCGTC AGCAGAATAT GTGATACAGG ATATATTCCG   1680
CTTCCTCGCT CACTGACTCG CTACGCTCGG TCGTTCGACT GCGGCGAGCG GAAATGGCTT   1740
ACGAACGGGG CGGAGATTTC CTGGAAGATG CCAGGAAGAT ACTTAACAGG GAAGTGAGAG   1800
GGCCGCGGCA AAGCCGTTTT TCCATAGGCT CCGCCCCCCT GACAAGCATC ACGAAATCTG   1860
ACGCTCAAAT CAGTGGTGGC GAAACCCGAC AGGACTATAA AGATACCAGG CGTTTCCCCC   1920
TGGCGGCTCC CTCCTGCGCT CTCCTGTTCC TGCCTTTCGG TTTACCGGTG TCATTCCGCT   1980
GTTATGGCCG CGTTTGTCTC ATTCCACGCC TGACACTCAG TTCCGGGTAG GCAGTTCGCT   2040
CCAAGCTGGA CTGTATGCAC GAACCCCCCG TTCAGTCCGA CCGCTGCGCC TTATCCGGTA   2100
ACTATCGTCT TGAGTCCAAC CCGGAAAGAC ATGCAAAAGC ACCACTGGCA GCAGCCACTG   2160
GTAATTGATT TAGAGGAGTT AGTCTTGAAG TCATGCGCCG GTTAAGGCTA AACTGAAAGG   2220
ACAAGTTTTA GTGACTGCGC TCCTCCAAGC CAGTTACCTC GGTTCAAAGA GTTGGTAGCT   2280
CAGAGAACCT ACGAAAAACC GCCCTGCAAG GCGGTTTTTT CGTTTTCAGA GCAAGAGATT   2340
ACGCGCAGAC CAAAACGATC TCAAGAAGAT CATCTTATTA                         2380
```

(2) INFORMATION FOR SEQ ID NO: 295:

(i) SEQUENCE CHARACTERISTICS:
(A) LENGTH: 219 amino acids
(B) TYPE: amino acid
(D) TOPOLOGY: linear (ii) MOLECULE TYPE: protein (xi) SEQUENCE DESCRIPTION: SEQ ID NO: 295:

```
Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

(2) INFORMATION FOR SEQ ID NO: 296:

(i) SEQUENCE CHARACTERISTICS:
(A) LENGTH: 3488 base pairs
(B) TYPE: nucleic acid
(C) STRANDEDNESS: double
(D) TOPOLOGY: circular (ii) MOLECULE TYPE: other nucleic acid
(A) DESCRIPTION: /desc = “synthetic vector”

(ix) FEATURE:
(A) NAME/KEY: CDS
(B) LOCATION:complement (1341..1997)
(D) OTHER INFORMATION:/product= “cat resistance”

(ix) FEATURE:
(A) NAME/KEY: CDS
(B) LOCATION:complement (2521..3417)
(D) OTHER INFORMATION:/product= “bla resistance”

(xi) SEQUENCE DESCRIPTION: SEQ ID NO: 296:

-continued

```
GTACATGAAA TTGTAAACGT TAATATTTTG TTAAAATTCG CGTTAAATTT TTGTTAAATC     60
AGCTCATTTT TTAACCAATA GGCCGAAATC GGCAAAATCC CTTATAAATC AAAAGAATAG    120
ACCGAGATAG GGTTGAGTGT TGTTCCAGTT TGGAACAAGA GTCCACTATT AAAGAACGTG    180
GACTCCAACG TCAAAGGGCG AAAAACCGTC TATCAGGGCG ATGGCCCACT ACGAGAACCA    240
TCACCCTAAT CAAGTTTTTT GGGGTCGAGG TGCCGTAAAG CACTAAATCG GAACCCTAAA    300
GGGAGCCCCC GATTTAGAGC TTGACGGGGA AAGCCGGCGA ACGTGGCGAG AAAGGAAGGG    360
AAGAAAGCGA AAGGAGCGGG CGCTAGGGCG CTGGCAAGTG TAGCGGTCAC GCTGCGCGTA    420
ACCACCACAC CCGCCGCGCT TAATGCGCCG CTACAGGGCG CGTGCTAGCG GAGTGTATAC    480
TGGCTTACTA TGTTGGCACT GATGAGGGTG TCAGTGAAGT GCTTCATGTG GCAGGAGAAA    540
AAAGGCTGCA CCGGTGCGTC AGCAGAATAT GTGATACAGG ATATATTCCG CTTCCTCGCT    600
CACTGACTCG CTACGCTCGG TCGTTCGACT GCGGCGAGCG GAAATGGCTT ACGAACGGGG    660
CGGAGATTTC CTGGAAGATG CCAGGAAGAT ACTTAACAGG GAAGTGAGAG GGCCGCGGCA    720
AAGCCGTTTT TCCATAGGCT CCGCCCCCCT GACAAGCATC ACGAAATCTG ACGCTCAAAT    780
CAGTGGTGGC GAAACCCGAC AGGACTATAA AGATACCAGG CGTTTCCCCC TGGCGGCTCC    840
CTCCTGCGCT CTCCTGTTCC TGCCTTTCGG TTTACCGGTG TCATTCCGCT GTTATGGCCG    900
CGTTTGTCTC ATTCCACGCC TGACACTCAG TTCCGGGTAG GCAGTTCGCT CCAAGCTGGA    960
CTGTATGCAC GAACCCCCCG TTCAGTCCGA CCGCTGCGCC TTATCCGGTA ACTATCGTCT   1020
TGAGTCCAAC CCGGAAAGAC ATGCAAAAGC ACCACTGGCA GCAGCCACTG GTAATTGATT   1080
TAGAGGAGTT AGTCTTGAAG TCATGCGCCG GTTAAGGCTA AACTGAAAGG ACAAGTTTTA   1140
GTGACTGCGC TCCTCCAAGC CAGTTACCTC GGTTCAAAGA GTTGGTAGCT CAGAGAACCT   1200
ACGAAAAACC GCCCTGCAAG GCGGTTTTTT CGTTTTCAGA GCAAGAGATT ACGCGCAGAC   1260
CAAAACGATC TCAAGAAGAT CATCTTATTA GATCTAGCAC CAGGCGTTTA AGGGCACCAA   1320
TAACTGCCTT AAAAAAATTA CGCCCCGCCC TGCCACTCAT CGCAGTACTG TTGTAATTCA   1380
TTAAGCATTC TGCCGACATG GAAGCCATCA CAAACGGCAT GATGAACCTG AATCGCCAGC   1440
GGCATCAGCA CCTTGTCGCC TTGCGTATAA TATTTGCCCA TAGTGAAAAC GGGGGCGAAG   1500
AAGTTGTCCA TATTGGCTAC GTTTAAATCA AAACTGGTGA AACTCACCCA GGGATTGGCT   1560
GAGACGAAAA ACATATTCTC AATAAACCCT TTAGGGAAAT AGGCCAGGTT TTCACCGTAA   1620
CACGCCACAT CTTGCGAATA TATGTGTAGA AACTGCCGGA AATCGTCGTG GTATTCACTC   1680
CAGAGCGATG AAAACGTTTC AGTTTGCTCA TGGAAAACGG TGTAACAAGG GTGAACACTA   1740
TCCCATATCA CCAGCTCACC GTCTTTCATT GCCATACGGA ACTCCGGGTG AGCATTCATC   1800
AGGCGGGCAA GAATGTGAAT AAAGGCCGGA TAAAACTTGT GCTTATTTTT CTTTACGGTC   1860
TTTAAAAAGG CCGTAATATC CAGCTGAACG GTCTGGTTAT AGGTACATTG AGCAACTGAC   1920
TGAAATGCCT CAAAATGTTC TTTACGATGC CATTGGGATA TATCAACGGT GGTATATCCA   1980
GTGATTTTTT TCTCCATTTT AGCTTCCTTA GCTCCTGAAA ATCTCGATAA CTCAAAAAAT   2040
ACGCCCGGTA GTGATCTTAT TTCATTATGG TGAAAGTTGG AACCTCACCC GACGTCTAAT   2100
GTGAGTTAGC TCACTCATTA GGCACCCCAG GCTTTACACT TTATGCTTCC GGCTCGTATG   2160
TTGTGTGGAA TTGTGAGCGG ATAACAATTT CACACAGGAA ACAGCTATGA CCATGATTAC   2220
GAATTTCTAG ACCCCCCCCC CGCATGCCAT AACTTCGTAT AATGTACGCT ATACGAAGTT   2280
ATAAGCTTGA CCTGTGAAGT GAAAAATGGC GCAGATTGTG CGACATTTTT TTTGTCTGCC   2340
GTTTAATTAA GGGGGGGGGC CGGCCATTAT CAAAAAGGAT CTCAAGAAGA TCCTTTGATC   2400
```

-continued

```
TTTTCTACGG GGTCTGACGC TCAGTGGAAC GAAAACTCAC GTTAAGGGAT TTTGGTCATG   2460

AGATTATCAA AAAGGATCTT CACCTAGATC CTTTTAAATT AAAAATGAAG TTTTAAATCA   2520

ATCTAAAGTA TATATGAGTA AACTTGGTCT GACAGTTACC CAATGCTTAA TCAGTGAGGC   2580

ACCTATCTCA GCGATCTGTC TATTTCGTTC ATCCATAGTT GCCTGACTCC CCGTCGTGTA   2640

GATAACTACG ATACGGGAGG GCTTACCATC TGGCCCCAGT GCTGCAATGA TACCGCGAGA   2700

CCCACGCTCA CCGGCTCCAG ATTTATCAGC AATAAACCAG CCAGCCGGAA GGGCCGAGCG   2760

CAGAAGTGGT CCTGCAACTT TATCCGCCTC CATCCAGTCT ATTAACTGTT GCCGGGAAGC   2820

TAGAGTAAGT AGTTCGCCAG TTAATAGTTT GCGCAACGTT GTTGCCATTG CTACAGGCAT   2880

CGTGGTGTCA CGCTCGTCGT TTGGTATGGC TTCATTCAGC TCCGGTTCCC AACGATCAAG   2940

GCGAGTTACA TGATCCCCCA TGTTGTGCAA AAAAGCGGTT AGCTCCTTCG GTCCTCCGAT   3000

CGTTGTCAGA AGTAAGTTGG CCGCAGTGTT ATCACTCATG GTTATGGCAG CACTGCATAA   3060

TTCTCTTACT GTCATGCCAT CCGTAAGATG CTTTTCTGTG ACTGGTGAGT ACTCAACCAA   3120

GTCATTCTGA GAATAGTGTA TGCGGCGACC GAGTTGCTCT TGCCCGGCGT CAATACGGGA   3180

TAATACCGCG CCACATAGCA GAACTTTAAA AGTGCTCATC ATTGGAAAAC GTTCTTCGGG   3240

GCGAAAACTC TCAAGGATCT TACCGCTGTT GAGATCCAGT TCGATGTAAC CCACTCGCGC   3300

ACCCAACTGA TCCTCAGCAT CTTTTACTTT CACCAGCGTT TCTGGGTGAG CAAAAACAGG   3360

AAGGCAAAAT GCCGCAAAAA AGGGAATAAG GGCGACACGG AAATGTTGAA TACTCATACT   3420

CTTCCTTTTT CAATATTATT GAAGCATTTA TCAGGGTTAT TGTCTCATGA GCGGATACAT   3480

ATTTGAAT                                                            3488
```

(2) INFORMATION FOR SEQ ID NO: 297:

(i) SEQUENCE CHARACTERISTICS:
(A) LENGTH: 219 amino acids
(B) TYPE: amino acid
(D) TOPOLOGY: linear (ii) MOLECULE TYPE: protein (xi) SEQUENCE DESCRIPTION: SEQ ID NO: 297:

```
Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
```

-continued

```
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

(2) INFORMATION FOR SEQ ID NO: 298:

(i) SEQUENCE CHARACTERISTICS:
(A) LENGTH: 299 amino acids
(B) TYPE: amino acid
(D) TOPOLOGY: linear (ii) MOLECULE TYPE: protein (xi) SEQUENCE DESCRIPTION: SEQ ID NO: 298:

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285
```

-continued

```
Val Arg Pro Ser Leu Leu Ile Tyr Thr Leu Asp
    290                 295
```

(2) INFORMATION FOR SEQ ID NO: 299:

(i) SEQUENCE CHARACTERISTICS:
(A) LENGTH: 2728 base pairs
(B) TYPE: nucleic acid
(C) STRANDEDNESS: double
(D) TOPOLOGY: circular (ii) MOLECULE TYPE: other nucleic acid
(A) DESCRIPTION: /desc = "synthetic vector"

(ix) FEATURE:
(A) NAME/KEY: CDS
(B) LOCATION:complement (471..1367)
(D) OTHER INFORMATION:/product= "bla resistance"

(xi) SEQUENCE DESCRIPTION: SEQ ID NO: 299:

```
GATCTCATAA CTTCGTATAA TGTATGCTAT ACGAAGTTAT GACGTCTAAT GTGAGTTAGC     60

TCACTCATTA GGCACCCCAG GCTTTACACT TTATGCTTCC GGCTCGTATG TTGTGTGGAA    120

TTGTGAGCGG ATAACAATTT CACACAGGAA ACAGCTATGA CCATGATTAC GAATTTCTAG    180

ACCCCCCCCC CGCATGCCAT AACTTCGTAT AATGTACGCT ATACGAAGTT ATAAGCTTGA    240

CCTGTGAAGT GAAAAATGGC GCAGATTGTG CGACATTTTT TTTGTCTGCC GTTTAATTAA    300

GGGGGGGGGC CGGCCATTAT CAAAAAGGAT CTCAAGAAGA TCCTTTGATC TTTTCTACGG    360

GGTCTGACGC TCAGTGGAAC GAAAACTCAC GTTAAGGGAT TTTGGTCATG AGATTATCAA    420

AAAGGATCTT CACCTAGATC CTTTTAAATT AAAAATGAAG TTTTAAATCA ATCTAAAGTA    480

TATATGAGTA AACTTGGTCT GACAGTTACC CAATGCTTAA TCAGTGAGGC ACCTATCTCA    540

GCGATCTGTC TATTTCGTTC ATCCATAGTT GCCTGACTCC CCGTCGTGTA GATAACTACG    600

ATACGGGAGG GCTTACCATC TGGCCCCAGT GCTGCAATGA TACCGCGAGA CCCACGCTCA    660

CCGGCTCCAG ATTTATCAGC AATAAACCAG CCAGCCGGAA GGGCCGAGCG CAGAAGTGGT    720

CCTGCAACTT TATCCGCCTC CATCCAGTCT ATTAACTGTT GCCGGGAAGC TAGAGTAAGT    780

AGTTCGCCAG TTAATAGTTT GCGCAACGTT GTTGCCATTG CTACAGGCAT CGTGGTGTCA    840

CGCTCGTCGT TTGGTATGGC TTCATTCAGC TCCGGTTCCC AACGATCAAG GCGAGTTACA    900

TGATCCCCCA TGTTGTGCAA AAAAGCGGTT AGCTCCTTCG GTCCTCCGAT CGTTGTCAGA    960

AGTAAGTTGG CCGCAGTGTT ATCACTCATG GTTATGGCAG CACTGCATAA TTCTCTTACT   1020

GTCATGCCAT CCGTAAGATG CTTTTCTGTG ACTGGTGAGT ACTCAACCAA GTCATTCTGA   1080

GAATAGTGTA TGCGGCGACC GAGTTGCTCT TGCCCGGCGT CAATACGGGA TAATACCGCG   1140

CCACATAGCA GAACTTTAAA AGTGCTCATC ATTGGAAAAC GTTCTTCGGG GCGAAAACTC   1200

TCAAGGATCT TACCGCTGTT GAGATCCAGT TCGATGTAAC CCACTCGCGC ACCCAACTGA   1260

TCCTCAGCAT CTTTTACTTT CACCAGCGTT TCTGGGTGAG CAAAAACAGG AAGGCAAAAT   1320

GCCGCAAAAA AGGGAATAAG GGCGACACGG AAATGTTGAA TACTCATACT CTTCCTTTTT   1380

CAATATTATT GAAGCATTTA TCAGGGTTAT TGTCTCATGA GCGGATACAT ATTTGAATGT   1440

ACATGAAATT GTAAACGTTA ATATTTTGTT AAAATTCGCG TTAAATTTTT GTTAAATCAG   1500

CTCATTTTTT AACCAATAGG CCGAAATCGG CAAAATCCCT TATAAATCAA AAGAATAGAC   1560

CGAGATAGGG TTGAGTGTTG TTCCAGTTTG GAACAAGAGT CCACTATTAA AGAACGTGGA   1620

CTCCAACGTC AAAGGGCGAA AAACCGTCTA TCAGGGCGAT GGCCCACTAC GAGAACCATC   1680
```

-continued

```
ACCCTAATCA AGTTTTTTGG GGTCGAGGTG CCGTAAAGCA CTAAATCGGA ACCCTAAAGG   1740

GAGCCCCCGA TTTAGAGCTT GACGGGGAAA GCCGGCGAAC GTGGCGAGAA AGGAAGGGAA   1800

GAAAGCGAAA GGAGCGGGCG CTAGGGCGCT GGCAAGTGTA GCGGTCACGC TGCGCGTAAC   1860

CACCACACCC GCCGCGCTTA ATGCGCCGCT ACAGGGCGCG TGCTAGCGGA GTGTATACTG   1920

GCTTACTATG TTGGCACTGA TGAGGGTGTC AGTGAAGTGC TTCATGTGGC AGGAGAAAAA   1980

AGGCTGCACC GGTGCGTCAG CAGAATATGT GATACAGGAT ATATTCCGCT TCCTCGCTCA   2040

CTGACTCGCT ACGCTCGGTC GTTCGACTGC GGCGAGCGGA AATGGCTTAC GAACGGGGCG   2100

GAGATTTCCT GGAAGATGCC AGGAAGATAC TTAACAGGGA AGTGAGAGGG CCGCGGCAAA   2160

GCCGTTTTTC CATAGGCTCC GCCCCCCTGA CAAGCATCAC GAAATCTGAC GCTCAAATCA   2220

GTGGTGGCGA AACCCGACAG GACTATAAAG ATACCAGGCG TTTCCCCCTG GCGGCTCCCT   2280

CCTGCGCTCT CCTGTTCCTG CCTTTCGGTT TACCGGTGTC ATTCCGCTGT TATGGCCGCG   2340

TTTGTCTCAT TCCACGCCTG ACACTCAGTT CCGGGTAGGC AGTTCGCTCC AAGCTGGACT   2400

GTATGCACGA ACCCCCCGTT CAGTCCGACC GCTGCGCCTT ATCCGGTAAC TATCGTCTTG   2460

AGTCCAACCC GGAAAGACAT GCAAAAGCAC CACTGGCAGC AGCCACTGGT AATTGATTTA   2520

GAGGAGTTAG TCTTGAAGTC ATGCGCCGGT TAAGGCTAAA CTGAAAGGAC AAGTTTTAGT   2580

GACTGCGCTC CTCCAAGCCA GTTACCTCGG TTCAAAGAGT TGGTAGCTCA GAGAACCTAC   2640

GAAAAACCGC CCTGCAAGGC GGTTTTTTCG TTTTCAGAGC AAGAGATTAC GCGCAGACCA   2700

AAACGATCTC AAGAAGATCA TCTTATTA                                      2728
```

(2) INFORMATION FOR SEQ ID NO: 300:

(i) SEQUENCE CHARACTERISTICS:
(A) LENGTH: 299 amino acids
(B) TYPE: amino acid
(D) TOPOLOGY: linear (ii) MOLECULE TYPE: protein (xi) SEQUENCE DESCRIPTION: SEQ ID NO: 300:

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
```

-continued

```
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285

Val Arg Pro Ser Leu Leu Ile Tyr Thr Leu Asp
    290                 295
```

(2) INFORMATION FOR SEQ ID NO: 301:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 301:

TATGAGATCT CATAACTTCG TATAATGTAC GCTATACGAA GTTAT 45

(2) INFORMATION FOR SEQ ID NO: 302:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 302:

TAATAACTTC GTATAGCATA CATTATACGA AGTTATGAGA TCTCA 45

(2) INFORMATION FOR SEQ ID NO: 303:

(i) SEQUENCE CHARACTERISTICS:
(A) LENGTH: 91 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 303:

CATTTTTTGC CCTCGTTATC TACGCATGCG ATAACTTCGT ATAGCGTACA TTATACGAAG 60

TTATTCTAGA CATGGTCATA GCTGTTTCCT G 91

(2) INFORMATION FOR SEQ ID NO: 304:

-continued (i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 304:

GGGGGGAATT CGGTGGTGGT GGATCTGCGT GCGCTGAAAC GGTTGAAAGT TG 52

(2) INFORMATION FOR SEQ ID NO: 305:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 305:

CCCCCCCAAG CTTATCAAGA CTCCTTATTA CG 32

(2) INFORMATION FOR SEQ ID NO: 306:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 306:

GGGGGGGGAA TTCGGAGGCG GTTCCGGTGG TGGC 34

(2) INFORMATION FOR SEQ ID NO: 307:

(i) SEQUENCE CHARACTERISTICS:
(A) LENGTH: 74 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 307:

GGGGGGGGAA TTCGAGCAGA AGCTGATCTC TGAGGAGGAT CTGTAGGGTG GTGGCTCTGG 60

TTCCGGTGAT TTTG 74

(2) INFORMATION FOR SEQ ID NO: 308:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 308:

CCATAACTTC GTATAATGTA CGCTATACGA AGTTATA 37

(2) INFORMATION FOR SEQ ID NO: 309:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 309:

AGCTTATAAC TTCGTATAGC GTACATTATA CGAAGTTATG GCATG 45

(2) INFORMATION FOR SEQ ID NO: 310:

(i) SEQUENCE CHARACTERISTICS:
(A) LENGTH: 76 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 310:

AGCTTGACCT GTGAAGTGAA AAATGGCGCA GATTGTGCGA CATTTTTTTT GTCTGCCGTT 60

TAATTAAAGG GGGGGT 76

(2) INFORMATION FOR SEQ ID NO: 311:

(i) SEQUENCE CHARACTERISTICS:
(A) LENGTH: 75 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 311:

GTACACCCCC CCCCAGGCCG GCCCCCCCCC CCCTTTAATT AAACGGCAGA CAAAAAAAAT 60

GTCGCACAAT CTGCG 75

(2) INFORMATION FOR SEQ ID NO: 312:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 312:

GGGGGGGTGT ACATTCAAAT ATGTATCCGC TCATG 35

(2) INFORMATION FOR SEQ ID NO: 313:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

-continued (xi) SEQUENCE DESCRIPTION: SEQ ID NO: 313:

GGGTTACATC GAACTGGATC TC 22

(2) INFORMATION FOR SEQ ID NO: 314:

(i) SEQUENCE CHARACTERISTICS:
(A) LENGTH: 59 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 314:

CCAGTTCGAT GTAACCCACT CGCGCACCCA ACTGATCCTC AGCATCTTTT ACTTTCACC 59

(2) INFORMATION FOR SEQ ID NO: 315:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 315:

ACTCTAGCTT CCCGGCAACA GTTAATAGAC TGGATGGAGG CGG 43

(2) INFORMATION FOR SEQ ID NO: 316:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 316:

CTGTTGCCGG GAAGCTAGAG TAAG 24

(2) INFORMATION FOR SEQ ID NO: 317:

(i) SEQUENCE CHARACTERISTICS:
(A) LENGTH: 58 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 317:

CCCCCCCTTA ATTAAGGGGG GGGGCCGGCC ATTATCAAAA AGGATCTCAA GAAGATCC 58

(2) INFORMATION FOR SEQ ID NO: 318:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: other nucleic acid -continued (A) DESCRIPTION: /desc = "synthetic oligonucleotide"

(xi) SEQUENCE DESCRIPTION: SEQ ID NO: 318:

GGGGGGGGCT AGCACGCGCC CTGTAGCGGC GCATTAA 37

(2) INFORMATION FOR SEQ ID NO: 319:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 319:

CCCCCCCTGT ACATGAAATT GTAAACGTTA ATATTTTG 38

(2) INFORMATION FOR SEQ ID NO: 320:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 320:

GGGCGATGGC CCACTACGAG AACCATCACC CTAATC 36

(2) INFORMATION FOR SEQ ID NO: 321:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 321:

GGGGGGAGAT CTAATAAGAT GATCTTCTTG AG 32

(2) INFORMATION FOR SEQ ID NO: 322:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 322:

GAGTTGGTAG CTCAGAGAAC CTACGAAAAA CCGCCCTGCA AGGCG 45

(2) INFORMATION FOR SEQ ID NO: 323:

(i) SEQUENCE CHARACTERISTICS:
(A) LENGTH: 24 base pairs
(B) TYPE: nucleic acid
(C) STRANDEDNESS: single
(D) TOPOLOGY: linear -continued (ii) MOLECULE TYPE: other nucleic acid
(A) DESCRIPTION: /desc = "synthetic oligonucleotide"

(xi) SEQUENCE DESCRIPTION: SEQ ID NO: 323:

GTAGGTTCTC TGAGCTACCA ACTC 24

(2) INFORMATION FOR SEQ ID NO: 324:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 324:

GTTTCCCCCT GGCGGCTCCC TCCTGCGCTC TCCTGTTCCT GCC 43

(2) INFORMATION FOR SEQ ID NO: 325:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 325:

AGGAGGGAGC CGCCAGGGGG AAAC 24

(2) INFORMATION FOR SEQ ID NO: 326:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 326:

GACATCAGCG CTAGCGGAGT GTATAC 26

(2) INFORMATION FOR SEQ ID NO: 327:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 327:

GATCTCATAA CTTCGTATAA TGTATGCTAT ACGAAGTTAT TCA 43

(2) INFORMATION FOR SEQ ID NO: 328:

(i) SEQUENCE CHARACTERISTICS:
(A) LENGTH: 45 base pairs
(B) TYPE: nucleic acid
(C) STRANDEDNESS: single
(D) TOPOLOGY: linear -continued (ii) MOLECULE TYPE: other nucleic acid
(A) DESCRIPTION: /desc = "synthetic oligonucleotide"

(xi) SEQUENCE DESCRIPTION: SEQ ID NO: 328:

GATCTGAATA ACTTCGTATA GCATACATTA TACGAAGTTA TGAGA 45

(2) INFORMATION FOR SEQ ID NO: 329:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 329:

GGGGGGGAGA TCTGACCAAA ATCCCTTAAC GTGAG 35

(2) INFORMATION FOR SEQ ID NO: 330:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 330:

GGTATCTGCG CTCTGCTGTA GCCAGTTACC TTCGG 35

(2) INFORMATION FOR SEQ ID NO: 331:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 331:

CCCCCCCGCT AGCCATGTGA GCAAAAGGCC AGCAA 35

(2) INFORMATION FOR SEQ ID NO: 332:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 332:

GGGACGTCGG GTGAGGTTCC AAC 23

(2) INFORMATION FOR SEQ ID NO: 333:

(i) SEQUENCE CHARACTERISTICS:
(A) LENGTH: 29 base pairs
(B) TYPE: nucleic acid
(C) STRANDEDNESS: single -continued (D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 333:

CCATACGGAA CTCCGGGTGA GCATTCATC 29

(2) INFORMATION FOR SEQ ID NO: 334:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 334:

CCGGAGTTCC GTATGG 16

(2) INFORMATION FOR SEQ ID NO: 335:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 335:

ACGTTTAAAT CAAAACTGG 19

(2) INFORMATION FOR SEQ ID NO: 336:

(i) SEQUENCE CHARACTERISTICS:
(A) LENGTH: 69 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 336:

CCAGTTTTGA TTTAAACGTA GCCAATATGG ACAACTTCTT CGCCCCCGTT TTCACTATGG 60

GCAAATATT 69

(2) INFORMATION FOR SEQ ID NO: 337:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 337:

GGAAGATCTA GCACCAGGCG TTTAAG 26

(2) INFORMATION FOR SEQ ID NO: 338:

(i) SEQUENCE CHARACTERISTICS:

-continued (A) LENGTH: 27 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 338:

GAGGCCGGCC ATCGAATGGC GCAAAAC 27

(2) INFORMATION FOR SEQ ID NO: 339:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 339:

CGCGTACCGT CCTCATGGGA GAAAATAATA C 31

(2) INFORMATION FOR SEQ ID NO: 340:

(i) SEQUENCE CHARACTERISTICS:
(A) LENGTH: 83 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 340:

CCATGAGGAC GGTACGCGAC TGGGCGTGGA GCATCTGGTC GCATTGGGTC ACCAGCAAAT 60

CCGCTGTTAG CTGGCCCATT AAG 83

(2) INFORMATION FOR SEQ ID NO: 341:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 341:

GTCAGCGGCG GGATATAACA TGAGCTGTCC TCGGTATCGT CG 42

(2) INFORMATION FOR SEQ ID NO: 342:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 342:

GTTATATCCC GCCGCTGACC ACCATCAAAC 30

-continued (2) INFORMATION FOR SEQ ID NO: 343:

(i) SEQUENCE CHARACTERISTICS:
(A) LENGTH: 65 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(ix) FEATURE:
(A) NAME/KEY: conflict
(B) LOCATION:replace(42..44, "")
(D) OTHER INFORMATION:/note= "in Fig.35b, M41, LAC6: T4T; but see Fig.35a, M41: LAC6 pos.1055-1119 on complementary strand, 1076 to 1078: TAT"

(xi) SEQUENCE DESCRIPTION: SEQ ID NO: 343:

CATCAGTGAA TCGGCCAACG CGCGGGGAGA GGCGGTTTGC GTATTGGGAG CCAGGGTGGT 60

TTTTC 65

(2) INFORMATION FOR SEQ ID NO: 344:

(i) SEQUENCE CHARACTERISTICS:
(A) LENGTH: 73 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 344:

GGTTAATTAA CCTCACTGCC CGCTTTCCAG TCGGGAAACC TGTCGTGCCA GCTGCATCAG 60

TGAATCGGCC AAC 73

(2) INFORMATION FOR SEQ ID NO: 345:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 345:

CTAGACTAGT GTTTAAACCG GACCGGGGGG GGGCTTAAGG GGGGGGGGGG 50

(2) INFORMATION FOR SEQ ID NO: 346:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 346:

CTAGCCCCCC CCCCCCTTAA GCCCCCCCCC GGTCCGGTTT AAACACTAGT 50

(2) INFORMATION FOR SEQ ID NO: 347:

(i) SEQUENCE CHARACTERISTICS:
(A) LENGTH: 50 base pairs

-continued (B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 347:

CTAGACTAGT GTTTAAACCG GACCGGGGGG GGGCTTAAGG GGGGGGGGGG 50

(2) INFORMATION FOR SEQ ID NO: 348:

(i) SEQUENCE CHARACTERISTICS:
(A) LENGTH: 82 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 348:

CCCCCCCTTA AGTGGGCTGC AAAACAAAAC GGCCTCCTGT CAGGAAGCCG CTTTTATCGG 60

GTAGCCTCAC TGCCCGCTTT CC 82

(2) INFORMATION FOR SEQ ID NO: 349:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 349:

GTTGTTGTGC CACGCGGTTA GGAATGTAAT TCAGCTCCGC 40

(2) INFORMATION FOR SEQ ID NO: 350:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 350:

AACCGCGTGG CACAACAAC 19

(2) INFORMATION FOR SEQ ID NO: 351:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 351:

CTTCGTTCTA CCATCGACAC GACCACGCTG GCACCCAGTT G 41

(2) INFORMATION FOR SEQ ID NO: 352:

-continued (i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 352:

GTGTCGATGG TAGAACGAAG 20

(2) INFORMATION FOR SEQ ID NO: 353:

(i) SEQUENCE CHARACTERISTICS:
(A) LENGTH: 67 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 353:

CCACAGCAAT AGCATCCTGG TCATCCAGCG GATAGTTAAT AATCAGCCCA CTGACACGTT 60

GCGCGAG 67

(2) INFORMATION FOR SEQ ID NO: 354:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 354:

GACCAGGATG CTATTGCTGT GG 22

(2) INFORMATION FOR SEQ ID NO: 355:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 355:

CAGCGCGATT TGCTGGTGGC CCAATGCGAC CAGATGC 37

(2) INFORMATION FOR SEQ ID NO: 356:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 356:

CACCAGCAAA TCGCGCTG 18

-continued (2) INFORMATION FOR SEQ ID NO: 357:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 357:

CCCGGACTCG GTAATGGCAC GCATTGCGCC CAGCGCC 37

(2) INFORMATION FOR SEQ ID NO: 358:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 358:

GCCATTACCG AGTCCGGG 18

(2) INFORMATION FOR SEQ ID NO: 359:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 359:

AATTCCACCA TCATCACCAT TGACGTCTA 29

(2) INFORMATION FOR SEQ ID NO: 360:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 360:

AGCTTAGACG TCAATGGTGA TGATGGTGG 29

(2) INFORMATION FOR SEQ ID NO: 361:

(i) SEQUENCE CHARACTERISTICS:
(A) LENGTH: 1289 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "synthetic gene cassette"

(ix) FEATURE:
(A) NAME/KEY: CDS

-continued (B) LOCATION:complement (280..1137)
(D) OTHER INFORMATION:/product= "bla resistance"

(xi) SEQUENCE DESCRIPTION: SEQ ID NO: 361:

```
CGCGTTAACC TCAGGTGACC AAGCCCCTGG CCAAGGTCCC GTACGTTCGA AGATTACCAT     60
CACGTGGATC CGGTACCAGG CCGGCCATTA TCAAAAAGGA TCTCAAGAAG ATCCTTTGAT    120
CTTTTCTACG GGGTCTGACG CTCAGTGGAA CGAAAACTCA CGTTAAGGGA TTTTGGTCAT    180
GAGATTATCA AAAAGGATCT TCACCTAGAT CCTTTTAAAT TAAAAATGAA GTTTTAAATC    240
AATCTAAAGT ATATATGAGT AAACTTGGTC TGACAGTTAC CAATGCTTAA TCAGTGAGGC    300
ACCTATCTCA GCGATCTGTC TATTTCGTTC ATCCATAGTT GCCTGACTCC CCGTCGTGTA    360
GATAACTACG ATACGGGAGG GCTTACCATC TGGCCCCAGT GCTGCAATGA TACCGCGAGA    420
CCCACGCTCA CCGGCTCCAG ATTTATCAGC AATAAACCAG CCAGCCGGAA GGGCCGAGCG    480
CAGAAGTGGT CCTGCAACTT TATCCGCCTC CATCCAGTCT ATTAACTGTT GCCGGGAAGC    540
TAGAGTAAGT AGTTCGCCAG TTAATAGTTT GCGCAACGTT GTTGCCATTG CTACAGGCAT    600
CGTGGTGTCA CGCTCGTCGT TTGGTATGGC TTCATTCAGC TCCGGTTCCC AACGATCAAG    660
GCGAGTTACA TGATCCCCCA TGTTGTGCAA AAAAGCGGTT AGCTCCTTCG GTCCTCCGAT    720
CGTTGTCAGA AGTAAGTTGG CCGCAGTGTT ATCACTCATG GTTATGGCAG CACTGCATAA    780
TTCTCTTACT GTCATGCCAT CCGTAAGATG CTTTTCTGTG ACTGGTGAGT ACTCAACCAA    840
GTCATTCTGA GAATAGTGTA TGCGGCGACC GAGTTGCTCT TGCCCGGCGT CAATACGGGA    900
TAATACCGCG CCACATAGCA GAACTTTAAA AGTGCTCATC ATTGGAAAAC GTTCTTCGGG    960
GCGAAAACTC TCAAGGATCT TACCGCTGTT GAGATCCAGT TCGATGTAAC CCACTCGTGC   1020
ACCCAACTGA TCTTCAGCAT CTTTTACTTT CACCAGCGTT TCTGGGTGAG CAAAAACAGG   1080
AAGGCAAAAT GCCGCAAAAA AGGGAATAAG GGCGACACGG AAATGTTGAA TACTCATACT   1140
CTTCCTTTTT CAATATTATT GAAGCATTTA TCAGGGTTAT TGTCTCATGA GCGGATACAT   1200
ATTTGAATGT ACTCGGCCGC ACGAGCTGCA GGCGCCATTA ATGGCTCGAG CGCGCTTCAG   1260
CGCTTTGTCT TCCGGATGTA CATGAAATT                                     1289
```

(2) INFORMATION FOR SEQ ID NO: 362:

(i) SEQUENCE CHARACTERISTICS:
(A) LENGTH: 286 amino acids
(B) TYPE: amino acid
(D) TOPOLOGY: linear (ii) MOLECULE TYPE: protein (xi) SEQUENCE DESCRIPTION: SEQ ID NO: 362:

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95
```

-continued

```
Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

(2) INFORMATION FOR SEQ ID NO: 363:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 363:

GCCCTGCAAG CGGAAGAC 18

(2) INFORMATION FOR SEQ ID NO: 364:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 364:

GGCTTTCGAA TGGCCAAAGG 20

(2) INFORMATION FOR SEQ ID NO: 365:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

-continued (ix) FEATURE:
(A) NAME/KEY: misc_feature
(B) LOCATION:25..27
(D) OTHER INFORMATION:/product= "random codon by trinucleotide mutagenesis (ACT/GTT)"

(ix) FEATURE:
(A) NAME/KEY: misc_feature
(B) LOCATION:37..39
(D) OTHER INFORMATION:/product= "random codon by trinucleotides (TTT,CAT,CTT,ATG,CAG)"

(ix) FEATURE:
(A) NAME/KEY: misc_feature
(B) LOCATION:43..45
(D) OTHER INFORMATION:/product= "random codon by trinucleotides (18 codons, no Pro, no Cys)"

(ix) FEATURE:
(A) NAME/KEY: misc_feature
(B) LOCATION:46..48
(D) OTHER INFORMATION:/product= "random codon by trinucleotides (GAT, GGT, AAT, TCT, TAT)"

(ix) FEATURE:
(A) NAME/KEY: misc_feature
(B) LOCATION:49..51
(D) OTHER INFORMATION:/product= "random codon by trinucleotides (GAT, GGT, AAT, TCT)"

(ix) FEATURE:
(A) NAME/KEY: misc_feature
(B) LOCATION:52..54
(D) OTHER INFORMATION:/product= "random codon by trinucleotide mutagenesis (19aa, no Cys)"

(ix) FEATURE:
(A) NAME/KEY: misc_feature
(B) LOCATION:55..57
(D) OTHER INFORMATION:/product= "random codon by trinucleotides (CCT/TCT)"

(ix) FEATURE:
(A) NAME/KEY: misc_feature
(B) LOCATION:58..60
(D) OTHER INFORMATION:/product= "random codon by trinucleotide mutagenesis (19 aa, no Cys)"

(xi) SEQUENCE DESCRIPTION: SEQ ID NO: 365:

GCCCTGCAAG CGGAAGACTT TGCGRYTTAT TATTGCHWKC AGNNKDVTDV TNNKYCTNNK 60

ACCTTTGGCC ATTCGAAAGC C 81

(2) INFORMATION FOR SEQ ID NO: 366:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

(ix) FEATURE:
(A) NAME/KEY: misc_feature
(B) LOCATION:37..39
(D) OTHER INFORMATION:/product= "random codon by trinucleotides (TTT,CAT,CTT,ATG,CAG)"

(ix) FEATURE:
(A) NAME/KEY: misc_feature
(B) LOCATION:43..45
(D) OTHER INFORMATION:/product= "random codon by trinucleotides (18 codons, no Pro, no Cys)"

(ix) FEATURE:
(A) NAME/KEY: misc_feature
(B) LOCATION:46..48
(D) OTHER INFORMATION:/product= "random codon by trinucleotides (GAT, GGT, AAT, TCT, TAT)"

(ix) FEATURE:
(A) NAME/KEY: misc_feature
(B) LOCATION:49..51
(D) OTHER INFORMATION:/product= "random codon by trinucleotides (GAT, GGT, AAT, TCT)"

(ix) FEATURE:
(A) NAME/KEY: misc_feature
(B) LOCATION:52..54
(D) OTHER INFORMATION:/product= "random codon by trinucleotide mutagenesis (19aa, no Cys)"

(ix) FEATURE:
(A) NAME/KEY: misc_feature
(B) LOCATION:55..57
(D) OTHER INFORMATION:/product= "random codon by trinucleotides (CCT/TCT)"

(ix) FEATURE:
(A) NAME/KEY: misc_feature
(B) LOCATION:58..60
(D) OTHER INFORMATION:/product= "random codon by trinucleotide mutagenesis (19 aa, no Cys)"

(xi) SEQUENCE DESCRIPTION: SEQ ID NO: 366:

GCCCTGCAAG CGGAAGACGT GGGCGTGTAT TATTGCHWKC AGNNKDVTDV TNNKYCTNNK 60

ACCTTTGGCC ATTCGAAAGC C 81

(2) INFORMATION FOR SEQ ID NO: 367:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

(ix) FEATURE:
(A) NAME/KEY: misc_feature
(B) LOCATION:37..39
(D) OTHER INFORMATION:/product= "random codon by trinucleotides (TTT,CAT,CTT,ATG,CAG)"

(ix) FEATURE:
(A) NAME/KEY: misc_feature
(B) LOCATION:43..45
(D) OTHER INFORMATION:/product= "random codon by trinucleotides (18 codons, no Pro, no Cys)"

(ix) FEATURE:
(A) NAME/KEY: misc_feature
(B) LOCATION:46..48
(D) OTHER INFORMATION:/product= "random codon by trinucleotides (GAT, GGT, AAT, TCT, TAT)"

(ix) FEATURE:
(A) NAME/KEY: misc_feature
(B) LOCATION:49..51
(D) OTHER INFORMATION:/product= "random codon by trinucleotides (GAT, GGT, AAT, TCT)"

(ix) FEATURE:
(A) NAME/KEY: misc_feature
(B) LOCATION:52..54
(D) OTHER INFORMATION:/product= "random codon by trinucleotide mutagenesis (19aa, no Cys)"

-continued (ix) FEATURE:
(A) NAME/KEY: misc_feature
(B) LOCATION:55..57
(D) OTHER INFORMATION:/product= "random codon by trinucleotides (CCT/TCT)"

(ix) FEATURE:
(A) NAME/KEY: misc_feature
(B) LOCATION:58..60
(D) OTHER INFORMATION:/product= "random codon by trinucleotide mutagenesis (19 aa, no Cys)"

(xi) SEQUENCE DESCRIPTION: SEQ ID NO: 367:

GCCCTGCAAG CGGAAGACGT GGCGGTGTAT TATTGCHWKC AGNNKDVTDV TNNKYCTNNK 60

ACCTTTGGCC ATTCGAAAGC C 81

(2) INFORMATION FOR SEQ ID NO: 368:

(i) SEQUENCE CHARACTERISTICS:
(A) LENGTH: 108 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

(ix) FEATURE:
(A) NAME/KEY: misc_feature
(B) LOCATION:41..43
(D) OTHER INFORMATION:/product= "random codon by trinucleotides (CGT, TGG, TAT)"

(ix) FEATURE:
(A) NAME/KEY: misc_feature
(B) LOCATION:47..61
(D) OTHER INFORMATION:/product= "random codons by trinucleotides (18 aa, no Trp, no Cys)"

(ix) FEATURE:
(A) NAME/KEY: misc_feature
(B) LOCATION:62..64
(D) OTHER INFORMATION:/product= "random codon by trinucleotide mutagenesis (19aa, no Cys)"

(xi) SEQUENCE DESCRIPTION: SEQ ID NO: 368:

CCTGCAAGCG GAAGACGAAG CGGATTATTA TTGCCAGAGC YRKGACNNKN NKNNKNNKNN 60

KNNKGGCGGC GGCACGAAGT TAACCGTTCT TGGCCAGGAA TTCGAGCC 108

(2) INFORMATION FOR SEQ ID NO: 369:

(i) SEQUENCE CHARACTERISTICS:
(A) LENGTH: 105 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

(ix) FEATURE:
(A) NAME/KEY: misc_feature
(B) LOCATION:41..43
(D) OTHER INFORMATION:/product= "random codon by trinucleotides (CGT, TGG, TAT)"

(ix) FEATURE:
(A) NAME/KEY: misc_feature
(B) LOCATION:47..58
(D) OTHER INFORMATION:/product= "random codons by -continued trinucleotides (18 aa, no Trp, no Cys)"

(ix) FEATURE:
(A) NAME/KEY: misc_feature
(B) LOCATION:59..61
(D) OTHER INFORMATION:/product= "random codon by trinucleotide mutagenesis (19aa, no Cys)"

(xi) SEQUENCE DESCRIPTION: SEQ ID NO: 369:

CCTGCAAGCG GAAGACGAAG CGGATTATTA TTGCCAGAGC YRKGACNNKN NKNNKNNKNN 60

KGGCGGCGGC ACGAAGTTAA CCGTTCTTGG CCAGGAATTC GAGCC 105

(2) INFORMATION FOR SEQ ID NO: 370:

(i) SEQUENCE CHARACTERISTICS:
(A) LENGTH: 102 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide library"

(ix) FEATURE:
(A) NAME/KEY: misc_feature
(B) LOCATION:41..43
(D) OTHER INFORMATION:/product= "random codon by trinucleotides (CGT, TGG, TAT)"

(ix) FEATURE:
(A) NAME/KEY: misc_feature
(B) LOCATION:47..55
(D) OTHER INFORMATION:/product= "random codons by trinucleotides (18 aa, no Trp, no Cys)"

(ix) FEATURE:
(A) NAME/KEY: misc_feature
(B) LOCATION:56..58
(D) OTHER INFORMATION:/product= "random codon by trinucleotide mutagenesis (19aa, no Cys)"

(xi) SEQUENCE DESCRIPTION: SEQ ID NO: 370:

CCTGCAAGCG GAAGACGAAG CGGATTATTA TTGCCAGAGC YRKGACNNKN NKNNKNNKGG 60

CGGCGGCACG AAGTTAACCG TTCTTGGCCA GGAATTCGAG CC 102

(2) INFORMATION FOR SEQ ID NO: 371:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(xi) SEQUENCE DESCRIPTION: SEQ ID NO: 371:

GGCTCGAATT CCTGGCC 17

(2) INFORMATION FOR SEQ ID NO: 372:

(i) SEQUENCE CHARACTERISTICS:
(A) LENGTH: 157 amino acids
(B) TYPE: amino acid
(D) TOPOLOGY: linear (ii) MOLECULE TYPE: protein (xi) SEQUENCE DESCRIPTION: SEQ ID NO: 372:

-continued

```
Gly Gly Gly Ser Gly Ser Gly Asp Phe Asp Tyr Glu Lys Met Ala Asn
  1               5                  10                  15

Ala Asn Lys Gly Ala Met Thr Glu Asn Ala Asp Glu Asn Ala Leu Gln
             20                  25                  30

Ser Asp Ala Lys Gly Lys Leu Asp Ser Val Ala Thr Asp Tyr Gly Ala
         35                  40                  45

Ala Ile Asp Gly Phe Ile Gly Asp Val Ser Gly Leu Ala Asn Gly Asn
     50                  55                  60

Gly Ala Thr Gly Asp Phe Ala Gly Ser Asn Ser Gln Met Ala Gln Val
 65                  70                  75                  80

Gly Asp Gly Asp Asn Ser Pro Leu Met Asn Asn Phe Arg Gln Tyr Leu
                 85                  90                  95

Pro Ser Leu Pro Gln Ser Val Glu Cys Arg Pro Phe Val Phe Gly Ala
            100                 105                 110

Gly Lys Pro Tyr Glu Phe Ser Ile Asp Cys Asp Lys Ile Asn Leu Phe
        115                 120                 125

Arg Gly Val Phe Ala Phe Leu Leu Tyr Val Ala Thr Phe Met Tyr Val
    130                 135                 140

Phe Ser Thr Phe Ala Asn Ile Leu Arg Asn Lys Glu Ser
145                 150                 155
```

(2) INFORMATION FOR SEQ ID NO: 373:

(i) SEQUENCE CHARACTERISTICS:
(A) LENGTH: 157 amino acids
(B) TYPE: amino acid
(D) TOPOLOGY: linear (ii) MOLECULE TYPE: protein (xi) SEQUENCE DESCRIPTION: SEQ ID NO: 373:

```
Gly Gly Gly Ser Gly Ser Gly Asp Phe Asp Tyr Glu Lys Met Ala Asn
  1               5                  10                  15

Ala Asn Lys Gly Ala Met Thr Glu Asn Ala Asp Glu Asn Ala Leu Gln
             20                  25                  30

Ser Asp Ala Lys Gly Lys Leu Asp Ser Val Ala Thr Asp Tyr Gly Ala
         35                  40                  45

Ala Ile Asp Gly Phe Ile Gly Asp Val Ser Gly Leu Ala Asn Gly Asn
     50                  55                  60

Gly Ala Thr Gly Asp Phe Ala Gly Ser Asn Ser Gln Met Ala Gln Val
 65                  70                  75                  80

Gly Asp Gly Asp Asn Ser Pro Leu Met Asn Asn Phe Arg Gln Tyr Leu
                 85                  90                  95

Pro Ser Leu Pro Gln Ser Val Glu Cys Arg Pro Phe Val Phe Gly Ala
            100                 105                 110

Gly Lys Pro Tyr Glu Phe Ser Ile Asp Cys Asp Lys Ile Asn Leu Phe
        115                 120                 125

Arg Gly Val Phe Ala Phe Leu Leu Tyr Val Ala Thr Phe Met Tyr Val
    130                 135                 140

Phe Ser Thr Phe Ala Asn Ile Leu Arg Asn Lys Glu Ser
145                 150                 155
```

PROTEIN/(POLY)PEPTIDE LIBRARIES

This application is a continuation of international application number PCT/EP96/03647, filed Aug. 19, 1996.

FIELD OF THE INVENTION

The present invention relates to synthetic DNA sequences which encode one or more collections of homologous proteins/(poly)peptides, and methods for generating and applying libraries of these DNA sequences. In particular, the invention relates to the preparation of a library of human-derived antibody genes by the use of synthetic consensus sequences which cover the structural repertoire of antibodies encoded in the human genome. Furthermore, the invention relates to the use of a single consensus antibody gene as a universal framework for highly diverse antibody libraries.

BACKGROUND TO THE INVENTION

All current recombinant methods which use libraries of proteins/(poly)peptides, e.g. antibodies, to screen for members with desired properties, e.g. binding a given ligand, do not provide the possibility to improve the desired properties of the members in an easy and rapid manner. Usually a library is created either by inserting a random oligonucleotide sequence into one or more DNA sequences cloned from an organism, or a family of DNA sequences is cloned and used as the library. The library is then screened, e.g. using phage display, for members which show the desired property. The sequences of one or more of these resulting molecules are then determined. There is no general procedure available to improve these molecules further on.

Winter (EP 0368 684 B1) has provided a method for amplifying (by PCR), cloning, and expressing antibody variable region genes. Starting with these genes he was able to create libraries of functional antibody fragments by randomizing the CDR3 of the heavy and/or the light chain. This process is functionally equivalent to the natural process of VJ and VDJ recombination which occurs during the development of B-cells in the immune system.

However the Winter invention does not provide a method for optimizing the binding affinities of antibody fragments further on, a process which would be functionally equivalent to the naturally occurring phenomenon of "affinity maturation", which is provided by the present invention. Furthermore, the Winter invention does not provide for artificial variable region genes, which represent a whole family of structurally similar natural genes, and which can be assembled from synthetic DNA oligonucleotides. Additionally, Winter does not enable the combinatorial assembly of portions of antibody variable regions, a feature which is provided by the present invention. Furthermore, this approach has the disadvantage that the genes of all antibodies obtained in the screening procedure have to be completely sequenced, since, except for the PCR priming regions, no additional sequence information about the library members is available. This is time and labor intensive and potentially leads to sequencing errors.

The teaching of Winter as well as other approaches have tried to create large antibody libraries having high diversity in the complementarity determining regions (CDRs) as well as in the frameworks to be able to find antibodies against as many different antigens as possible. It has been suggested that a single universal framework may be useful to build antibody libraries, but no approach has yet been successful.

Another problem lies in the production of reagents derived from antibodies. Small antibody fragments show exciting promise for use as therapeutic agents, diagnostic reagents, and for biochemical research. Thus, they are needed in large amounts, and the expression of antibody fragments, e.g. Fv, single-chain Fv (scFv), or Fab in the periplasm of *E. coli* (Skerra & Plückthun, 1988; Better et al., 1988) is now used routinely in many laboratories. Expression yields vary widely, however. While some fragments yield up to several mg of functional, soluble protein per liter and OD of culture broth in shake flask culture (Carter et al., 1992, Plückthun et al. 1996), other fragments may almost exclusively lead to insoluble material, often found in so-called inclusion bodies. Functional protein may be obtained from the latter in modest yields by a laborious and time-consuming refolding process. The factors influencing antibody expression levels are still only poorly understood. Folding efficiency and stability of the antibody fragments, protease lability and toxicity of the expressed proteins to the host cells often severely limit actual production levels, and several attempts have been tried to increase expression yields. For example, Knappik & Plückthun (1995) could show that expression yield depends on the antibody sequence. They identified key residues in the antibody framework which influence expression yields dramatically. Similarly, Ullrich et al. (1995) found that point mutations in the CDRs can increase the yields in periplasmic antibody fragment expression. Nevertheless, these strategies are only applicable to a few antibodies. Since the Winter invention uses existing repertoires of antibodies, no influence on expressibility of the genes is possible.

Furthermore, the findings of Knappik & Plückthun and Ullrich demonstrate that the knowledge about antibodies, especially about folding and expression is still increasing. The Winter invention does not allow to incorporate such improvements into the library design.

The expressibility of the genes is important for the library quality as well, since the screening procedure relies in most cases on the display of the gene product on a phage surface, and efficient display relies on at least moderate expression of the gene.

These disadvantages of the existing methodologies are overcome by the present invention, which is applicable for all collections of homologous proteins. It has the following novel and useful features illustrated in the following by antibodies as an example:

Artificial antibodies and fragments thereof can be constructed based on known antibody sequences, which reflect the structural properties of a whole group of homologous antibody genes. Therefore it is possible to reduce the number of different genes without any loss in the structural repertoire. This approach leads to a limited set of artificial genes, which can be synthesized de novo, thereby allowing introduction of cleavage sites and removing unwanted cleavages sites. Furthermore, this approach enables (i), adapting the codon usage of the genes to that of highly expressed genes in any desired host cell and (ii), analyzing all possible pairs of antibody light (L) and heavy (H) chains in terms of interaction preference, antigen preference or recombinant expression titer, which is virtually impossible using the complete collection of antibody genes of an organism and all combinations thereof.

The use of a limited set of completely synthetic genes makes it possible to create cleavage sites at the boundaries of encoded structural sub-elements. Therefore, each gene is built up from modules which represent structural sub-elements on the protein/(poly)peptide level. In the case of antibodies, the modules consist of "framework" and "CDR"

modules. By creating separate framework and CDR modules, different combinatorial assembly possibilities are enabled. Moreover, if two or more artificial genes carry identical pairs of cleavage sites at the boundaries of each of the genetic sub-elements, pre-built libraries of sub-elements can be inserted in these genes simultaneously, without any additional information related to any particular gene sequence. This strategy enables rapid optimization of, for example, antibody affinity, since DNA cassettes encoding libraries of genetic sub-elements can be (i), pre-built, stored and reused and (ii), inserted in any of these sequences at the right position without knowing the actual sequence or having to determine the sequence of the individual library member.

Additionally, new information about amino acid residues important for binding, stability, or solubility and expression could be integrated into the library design by replacing existing modules with modules modified according to the new observations.

The limited number of consensus sequences used for creating the library allows to speed up the identification of binding antibodies after screening. After having identified the underlying consensus gene sequence, which could be done by sequencing or by using fingerprint restriction sites, just those part(s) comprising the random sequence(s) have to be determined. This reduces the probability of sequencing errors and of false-positive results.

The above mentioned cleavage sites can be used only if they are unique in the vector system where the artificial genes have been inserted. As a result, the vector has to be modified to contain none of these cleavage sites. The construction of a vector consisting of basic elements like resistance gene and origin of replication, where cleavage sites have been removed, is of general interest for many cloning attempts. Additionally, these vector(s) could be part of a kit comprising the above mentioned artificial genes and pre-built libraries.

The collection of artificial genes can be used for a rapid humanization procedure of non-human antibodies, preferably of rodent antibodies. First, the amino acid sequence of the non-human, preferably rodent antibody is compared with the amino acid sequences encoded by the collection of artificial genes to determine the most homologous light and heavy framework regions. These genes are then used for insertion of the genetic sub-elements encoding the CDRs of the non-human, preferably rodent antibody.

Surprisingly, it has been found that with a combination of only one consensus sequence for each of the light and heavy chains of a scFv fragment an antibody repertoire could be created yielding antibodies against virtually every antigen. Therefore, one aspect of the present invention is the use of a single consensus sequence as a universal framework for the creation of useful (poly)peptide libraries and antibody consensus sequences useful therefor.

LEGENDS TO FIGURES AND TABLES

FIG. 1: Flow chart outlining the process of construction of a synthetic human antibody library based on consensus sequences.

FIG. 2: Alignment of consensus sequences designed for each subgroup (amino acid residues are shown with their standard one-letter abbreviation). (A) (SEQ ID NOS 28–31, respectively) kappa sequences, (B) (SEQ ID NOS 32–34, respectively) lambda sequences and (C) (SEQ ID NOS 35–41, respectively), heavy chain sequences. The positions are numbered according to Kabat (1991). In order to maximize homology in the alignment, gaps (–) have been introduced in the sequence at certain positions.

FIG. 3: Gene sequences (SEQ ID NOS 42, 44, 46 and 48, respectively) of the synthetic V kappa consensus genes. The corresponding amino acid sequences (SEQ ID NOS 43, 45, 47 and 49 respectively) (see FIG. 2) as well as the unique cleavage sites are also shown.

FIG. 4: Gene sequences (SEQ ID NOS 50, 52 and 54 respectively) of the synthetic V lambda consensus genes. The corresponding amino acid sequences (SEQ ID NOS 51, 53 and 55 respectively) (see FIG. 2) as well as the unique cleavage sites are also shown.

FIG. 5: Gene sequences (SEQ ID NOS 56, 58, 60, 62, 64, 66 and 68 respectively) of the synthetic V heavy chain consensus genes. The corresponding amino acid sequences (SEQ ID NOS 57, 59, 61, 63, 65, 67 and 69 respectively) (see FIG. 2) as well as the unique cleavage sites are also shown.

FIG. 6: Oligonucleotides (SEQ ID NOS 70–164, respectively) used for construction of the consensus genes. The oligos are named according to the corresponding consensus gene, e.g. the gene Vk1 was constructed using the six oligonucleotides O1K1 to O1K6. The oligonucleotides used for synthesizing the genes encoding the constant domains Ck (OCLK1 to 8) and CH1 (OCH1 to 8) are also shown.

Figure 7E:
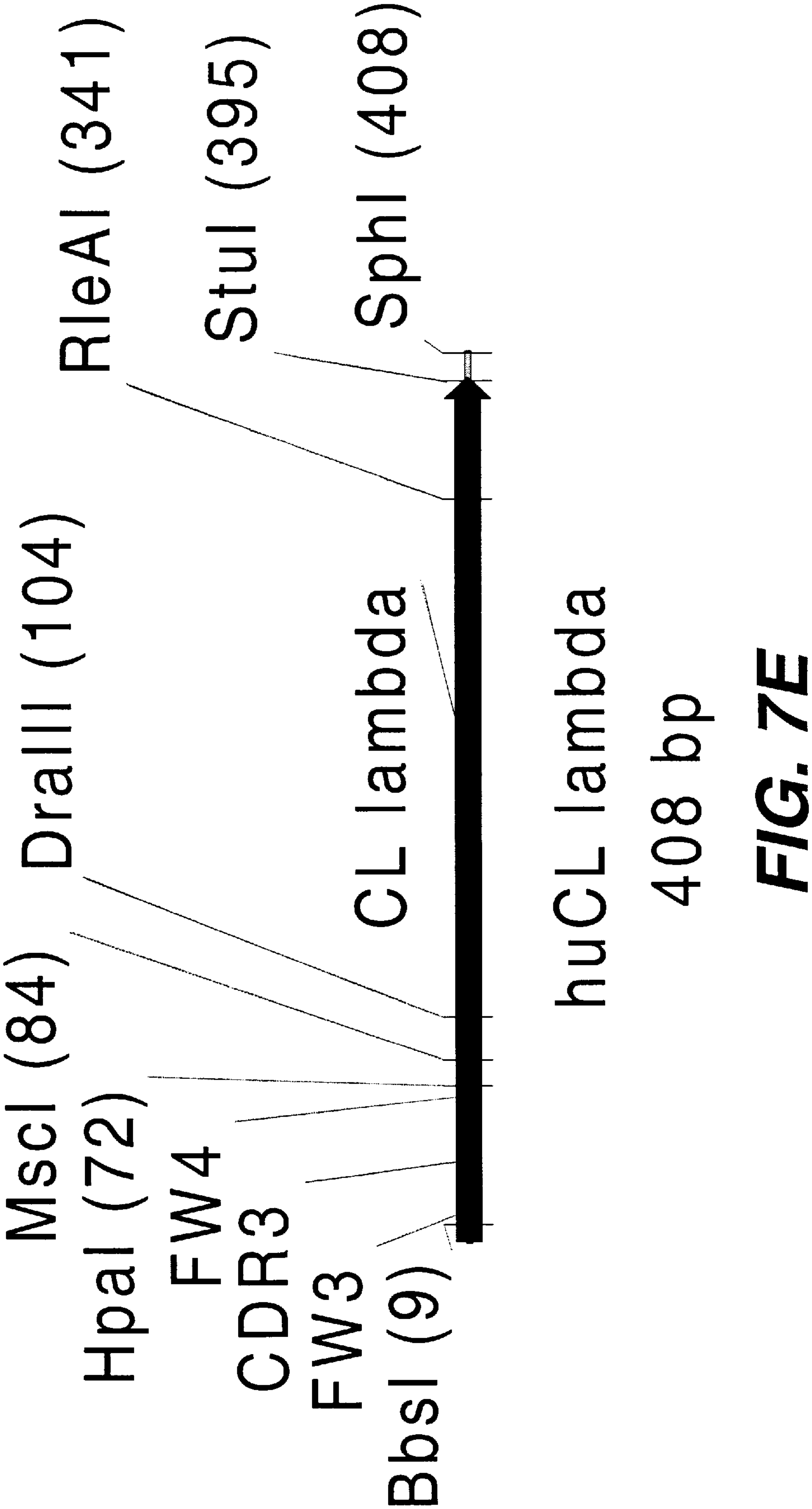

FIGS. 7A/B: Sequences of the synthetic genes (SEQ ID NOS 165 and 167 respectively) encoding the constant domains Ck (A) and CH1 (B). The corresponding amino acid sequences (SEQ ID NOS 166 and 168 respectively) as well as unique cleavage sites introduced in these genes are also shown.

FIG. 7C: Functional map and sequence (SEQ ID NOS 169–170 respectively) of module M24 comprising the synthetic Cl gene segment (huCL lambda).

FIG. 7D: Oligonucleotides (SEQ ID NOS 171–176 respectively) used for synthesis of module M24.

FIG. 8: Sequence (SEQ ID NOS 177–178 respectively) and restriction map of the synthetic gene encoding the consensus single-chain fragment VH3-Vk2. The signal sequence (amino acids 1 to 21) was derived from the *E. coli* phoA gene (Skerra & Plückthun, 1988). Between the phoA signal sequence and the VH3 domain, a short sequence stretch encoding 4 amino acid residues (amino acid 22 to 25) has been inserted in order to allow detection of the single-chain fragment in Western blot or ELISA using the monoclonal antibody M1 (Knappik & Plückthun, 1994). The last 6 basepairs of the sequence were introduced for cloning purposes (EcoRI site).

Figure 9:
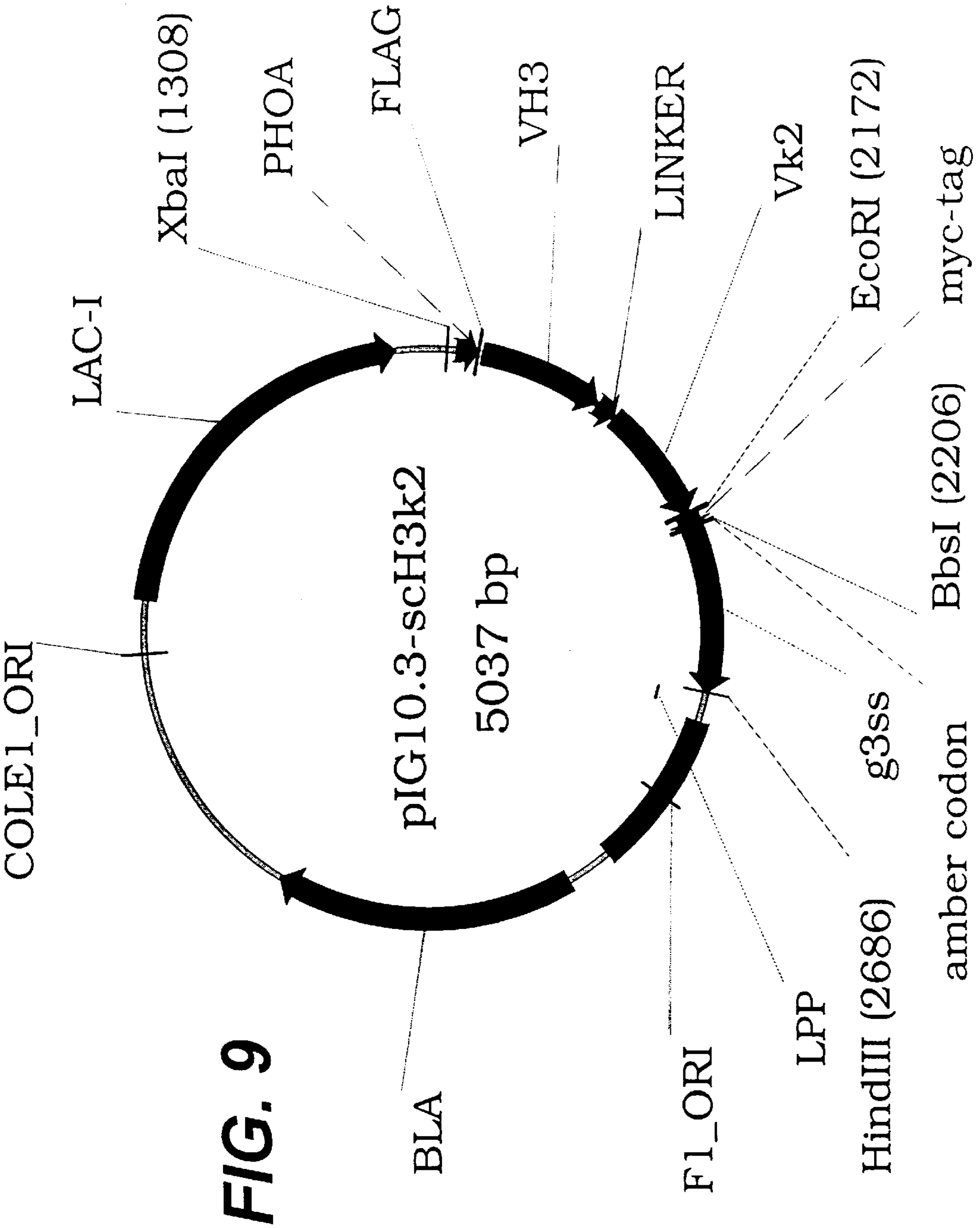

FIG. 9: Plasmid map of the vector pIG10.3 used for phage display of the H3k2 scFv fragment. The vector is derived from pIG10 and contains the gene for the lac operon repressor, lacl, the artificial operon encoding the H3k2-gene3ss fusion under control of the lac promoter, the lpp terminator of transcription, the single-strand replication origin of the *E. coli* phage f1 (F1_ORI), a gene encoding β-lactamase (bla) and the ColEI derived origin of replication.

FIG. 10: Sequencing results of independent clones from the initial library, translated into the corresponding amino acid sequences. (A) (SEQ ID NO: 179) Amino acid sequence of the VH3 consensus heavy chain CDR3 (position 93 to 102, Kabat numbering). (B) (SEQ ID NOS 180–191 respectively) Amino acid sequences of 12 clones of the 10-mer library. (C) (SEQ ID NOS 192–202 respectively) Amino acid sequences of 11 clones of the 15-mer library, *: single base deletion.

FIG. 11: Expression test of individual library members. (A) Expression of 9 independent clones of the 10-mer library. (B) Expression of 9 independent clones of the 15-mer library. The lane designated with M contains the size marker. Both the gp3-scFv fusion and the scFv monomer are indicated.

Figure 12:
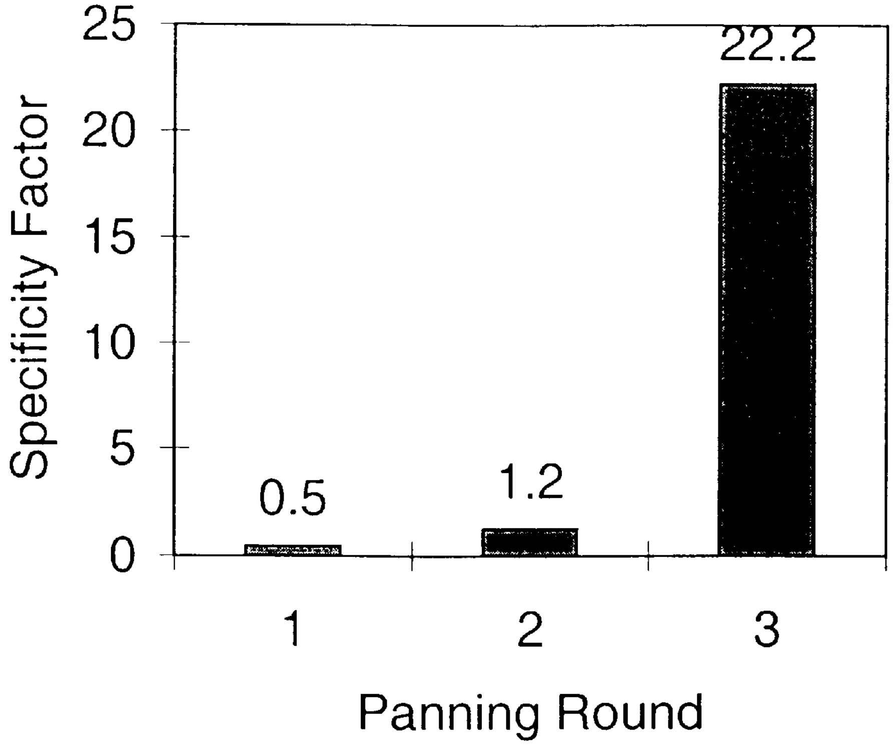

FIG. 12: Enrichment of specific phage antibodies during the panning against FITC-BSA. The initial as well as the subsequent fluorescein-specific sub-libraries were panned against the blocking buffer and the ratio of the phage eluted from the FITC-BSA coated well vs. that from the powder milk coated well from each panning round is presented as the "specificity factor".

Figure 13:
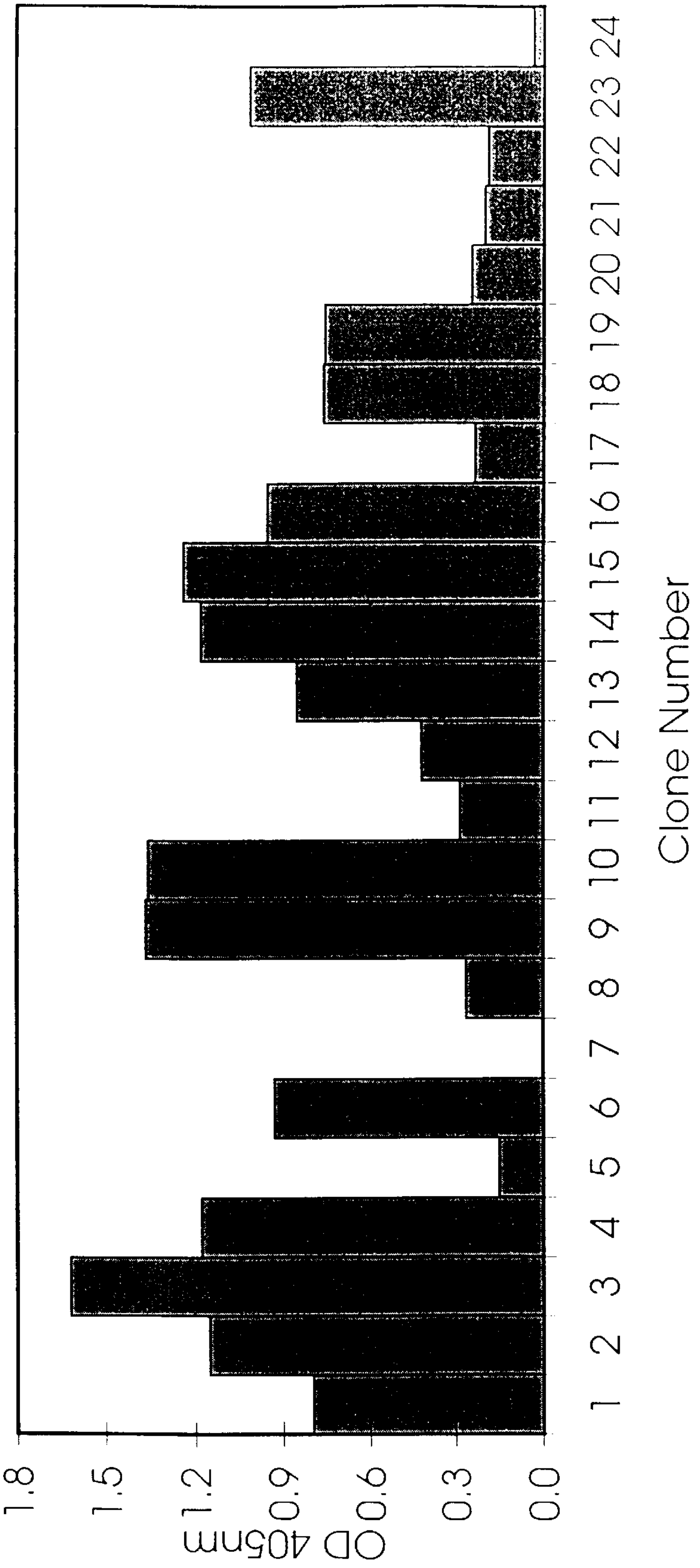

FIG. 13: Phage ELISA of 24 independent clones after the third round of panning tested for binding on FITC-BSA.

Figure 14:
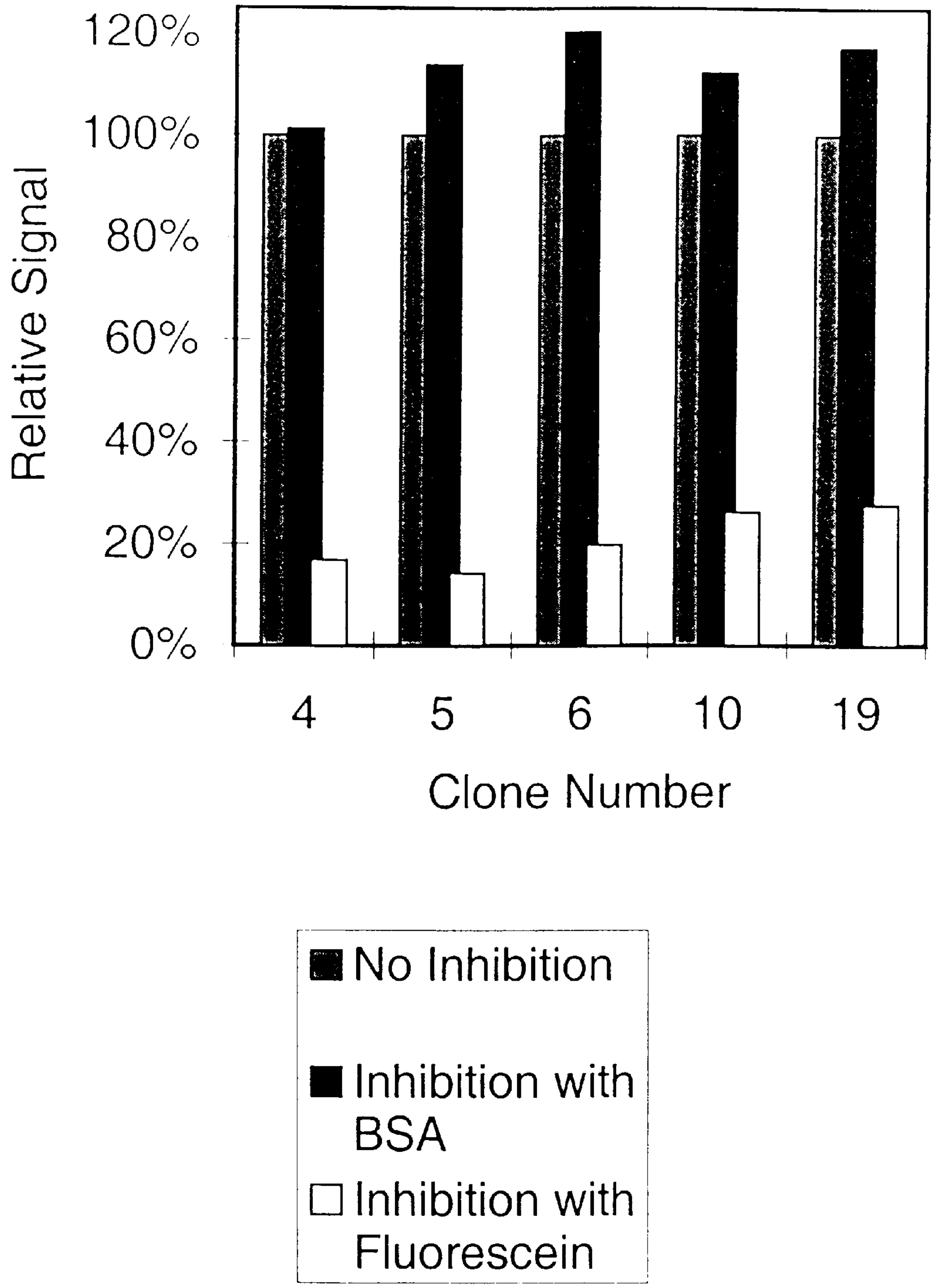

FIG. 14: Competition ELISA of selected FITC-BSA binding clones. The ELISA signals ($OD_{405\ nm}$) of scFv binding without inhibition are taken as 100%.

FIG. 15: Sequencing results of the heavy chain CDR3s of independent clones after 3 rounds of panning against FITC-BSA, translated into the corresponding amino acid sequences (SEQ ID NOS 203–218 respectively) (position 93 to 102, Kabat numbering).

Figure 16:
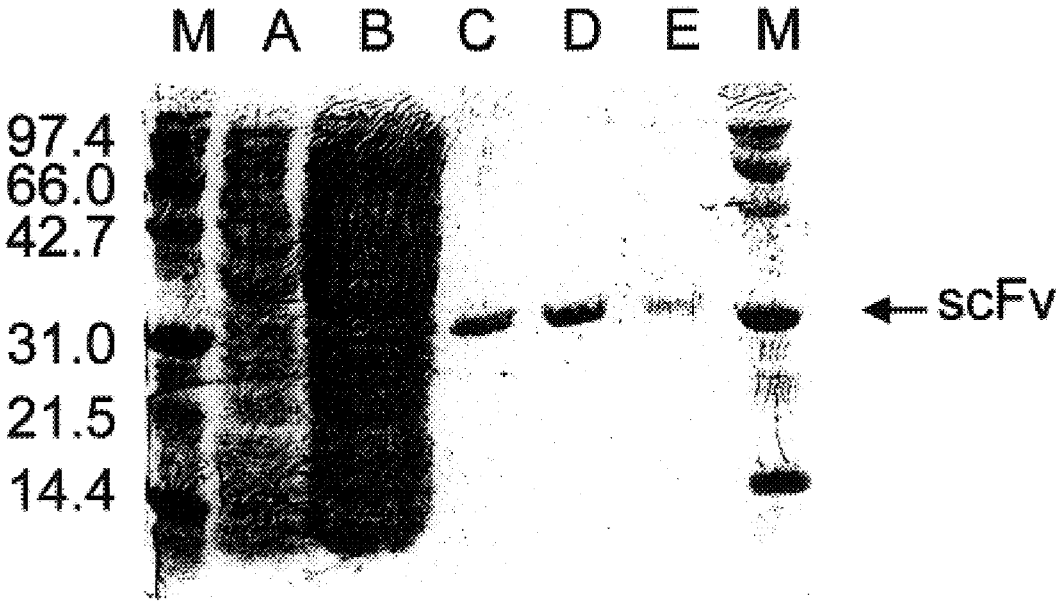

FIG. 16: Coomassie-Blue stained SDS-PAGE of the purified anti-fluorescein scFv fragments: M: molecular weight marker, A: total soluble cell extract after induction, B: fraction of the flow-through, C, D and E: purified scFv fragments 1HA-3E4, 1HA-3E5 and 1HA-3E10, respectively.

Figure 17:
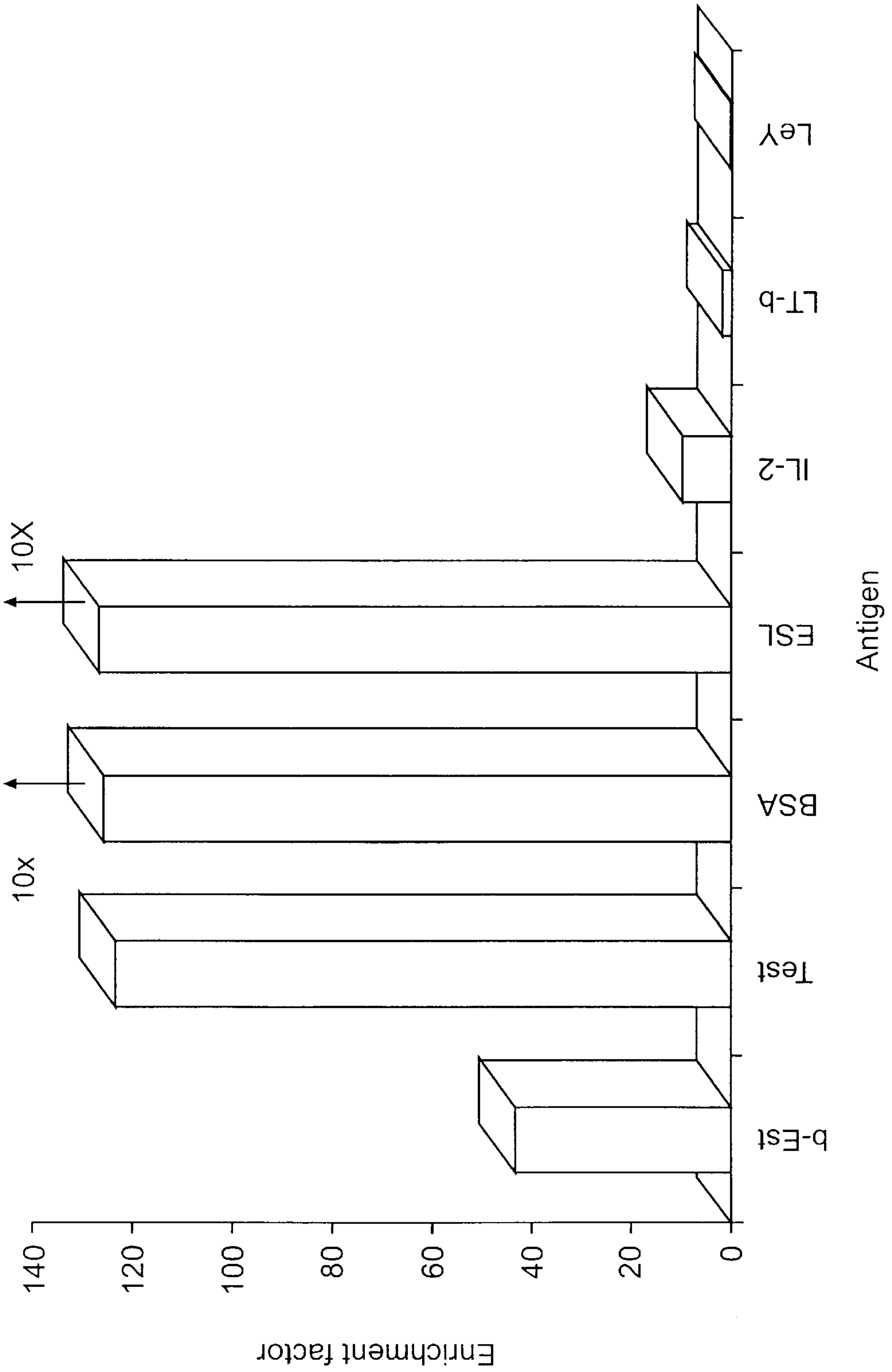

FIG. 17: Enrichment of specific phage antibodies during the panning against β-estradiol-BSA, testosterone-BSA, BSA, ESL-1, interleukin-2, lymphotoxin-β, and LeY-BSA after three rounds of panning.

Figure 18:
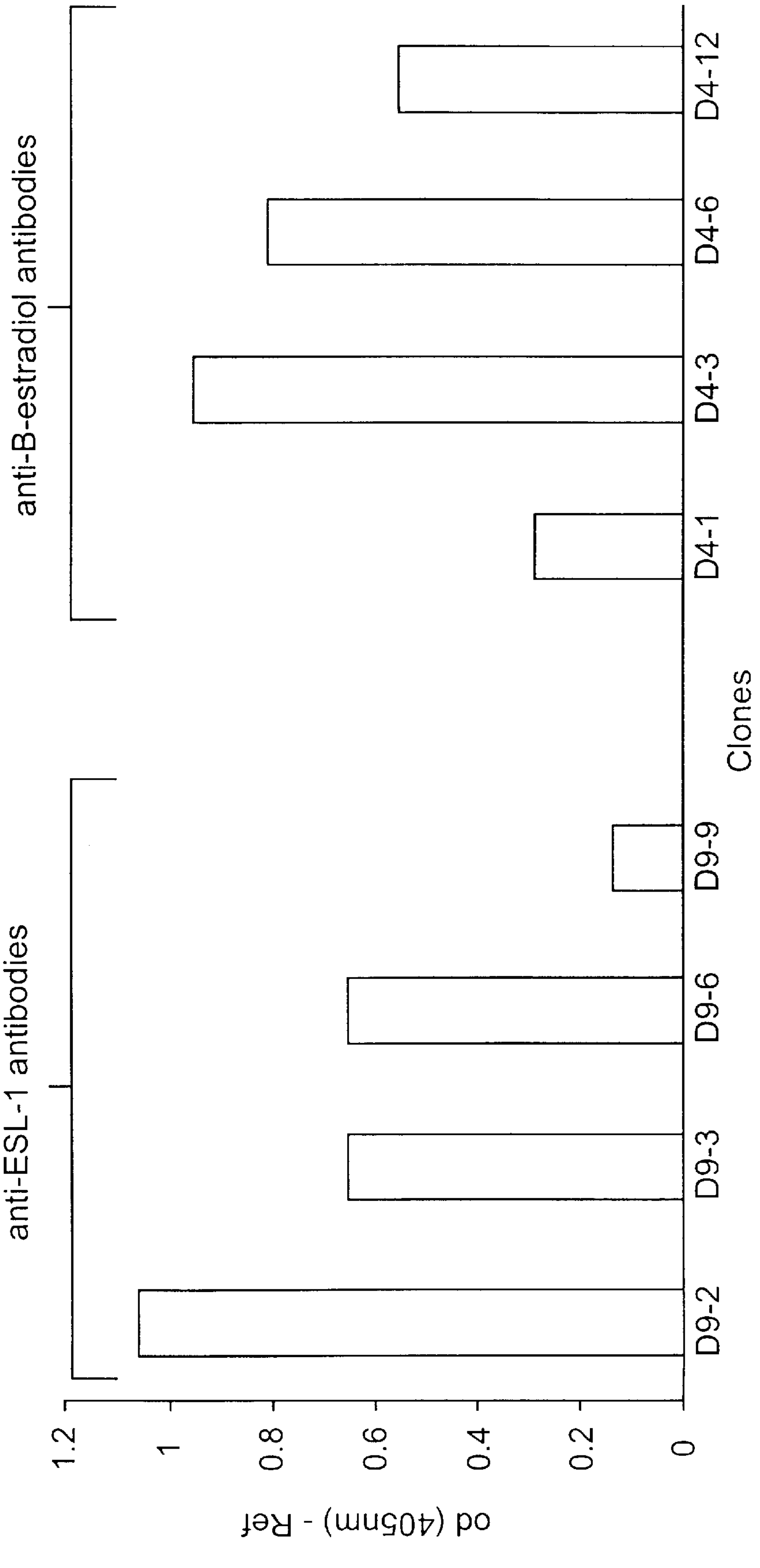

FIG. 18: ELISA of selected ESL-1 and β-estradiol binding clones.

Figure 19:
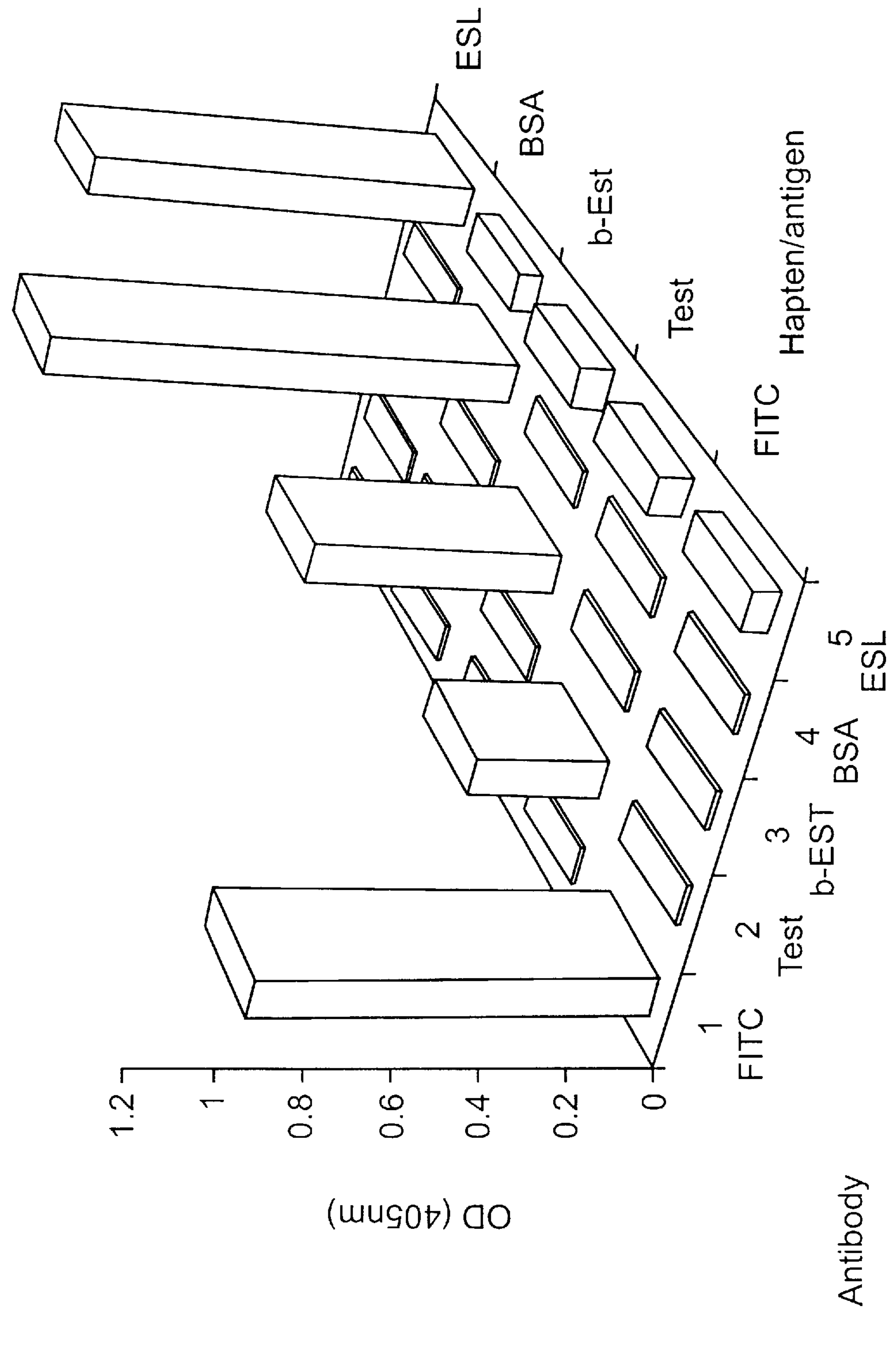

FIG. 19: Selectivity and cross-reactivity of HuCAL antibodies: in the diagonal specific binding of HuCAL antibodies can be seen, off-diagonal signals show non-specific cross-reactivity.

FIG. 20: Sequencing results of the heavy chain CDR3s of independent clones after 3 rounds of panning against β-estradiol-BSA, translated into the corresponding amino acid sequences (SEQ ID NOS 219–230 respectively) (position 93 to 102, Kabat numbering). One clone is derived from the 10mer library.

FIG. 21: Sequencing results of the heavy chain CDR3s of independent clones after 3 rounds of panning against testosterone-BSA, translated into the corresponding amino acid sequences (SEQ ID NOS 231–236 respectively) (position 93 to 102, Kabat numbering).

FIG. 22: Sequencing results of the heavy chain CDR3s of independent clones after 3 rounds of panning against lymphotoxin-β, translated into the corresponding amino acid sequences (SEQ ID NOS 237–244 respectively) (position 93 to 102, Kabat numbering). One clone comprises a 14mer CDR, presumably introduced by incomplete coupling of the trinucleotide mixture during oligonucleotide synthesis.

FIG. 23: Sequencing results of the heavy chain CDR3s of independent clones after 3 rounds of panning against ESL-1, translated into the corresponding amino acid sequences (SEQ ID NOS 245–256 respectively) (position 93 to 102, Kabat numbering). Two clones are derived from the 10mer library. One clone comprises a 16mer CDR, presumably introduced by chain elongation during oligonucleotide synthesis using trinucleotides.

FIG. 24: Sequencing results of the heavy chain CDR3s of independent clones after 3 rounds of panning against BSA, translated into the corresponding amino acid sequences (SEQ ID NOS 257–262 respectively) (position 93 to 102, Kabat numbering).

FIG. 25: Schematic representation of the modular pCAL vector system.

Figure 25A:
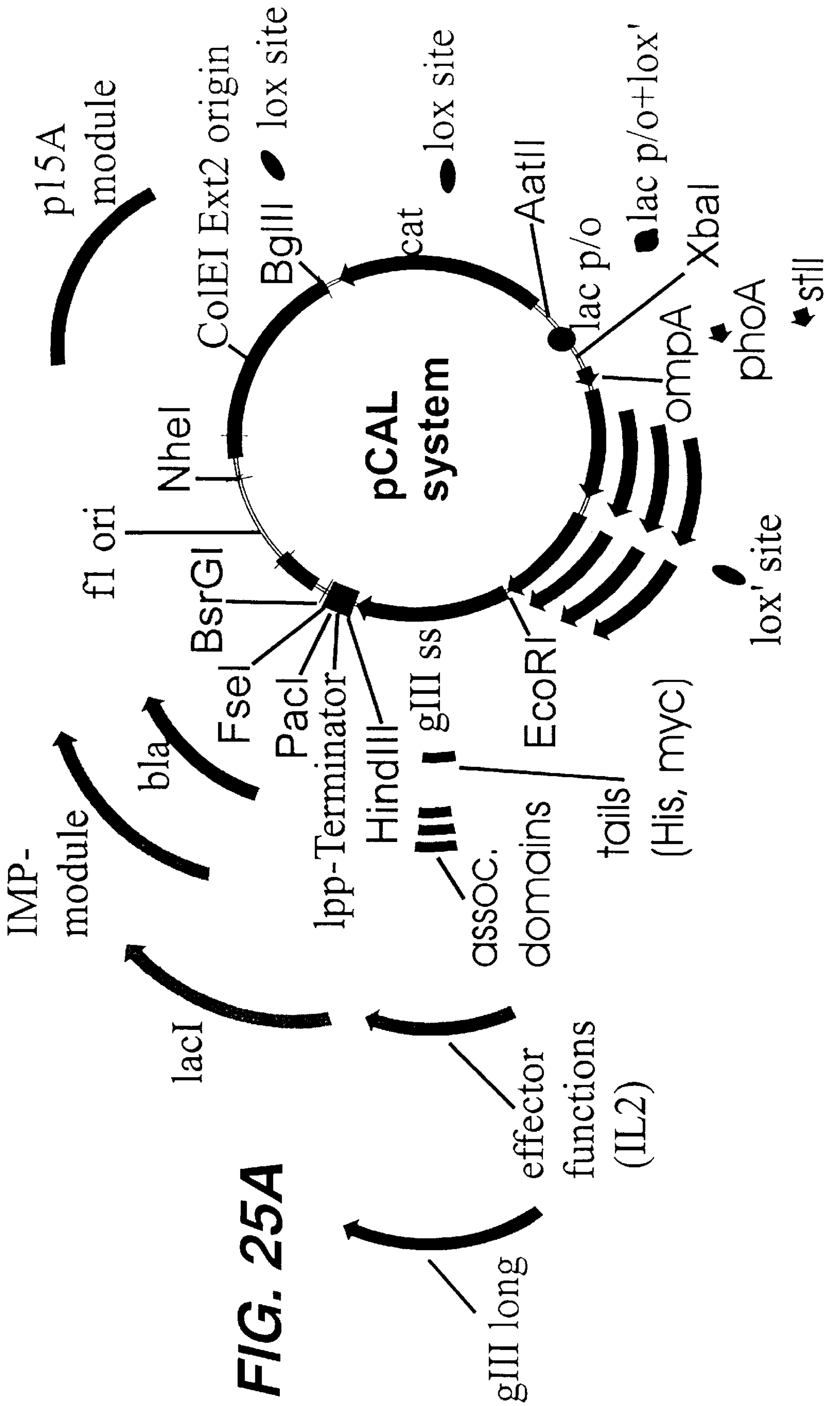

FIG. 25*a*: List of restriction sites already used in or suitable for the modular HuCAL genes and pCAL vector system.

FIG. 26: List of the modular vector elements for the pCAL vector series: shown are only those restriction sites which are part of the modular system.

Figure 27A:
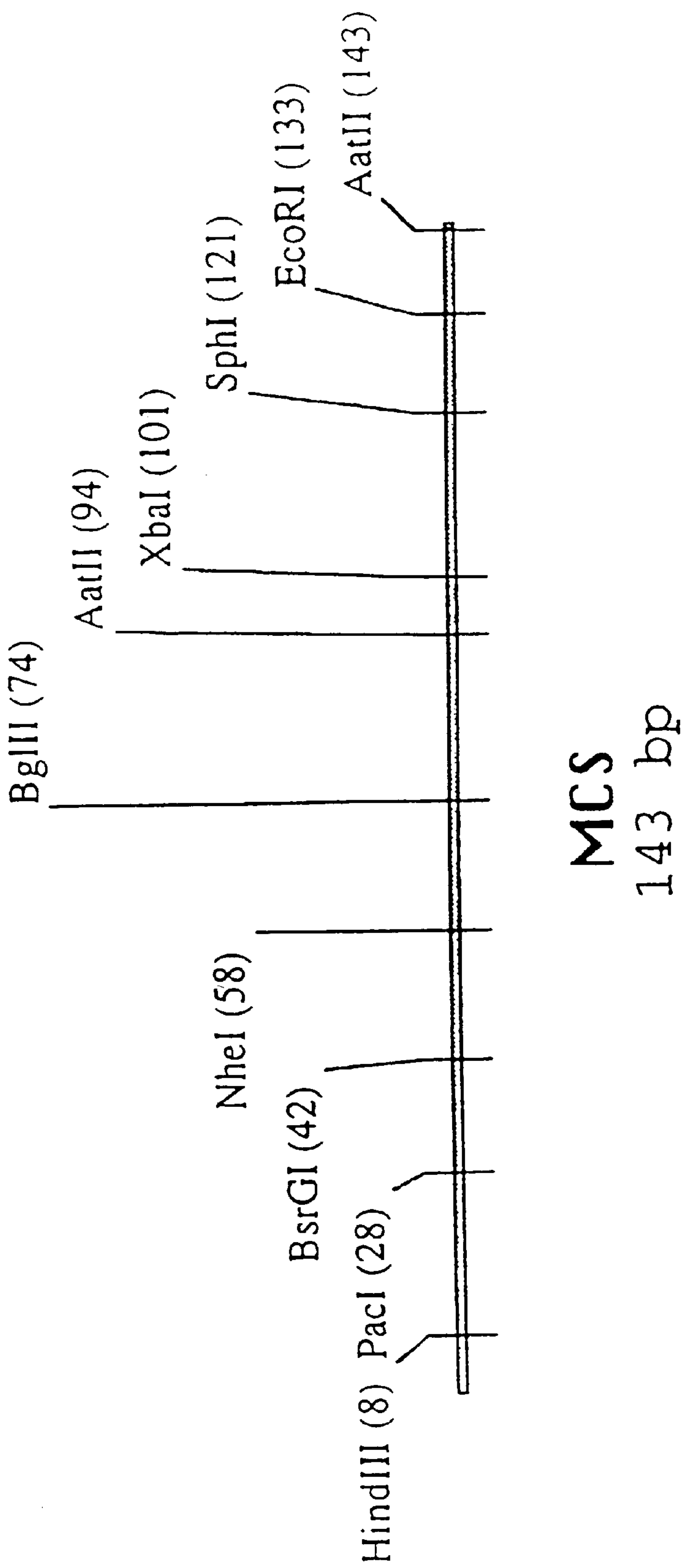

FIG. 27: Functional map and sequence (SEQ ID NO: 263) of the multi-cloning site module (MCS)

Figure 28A:
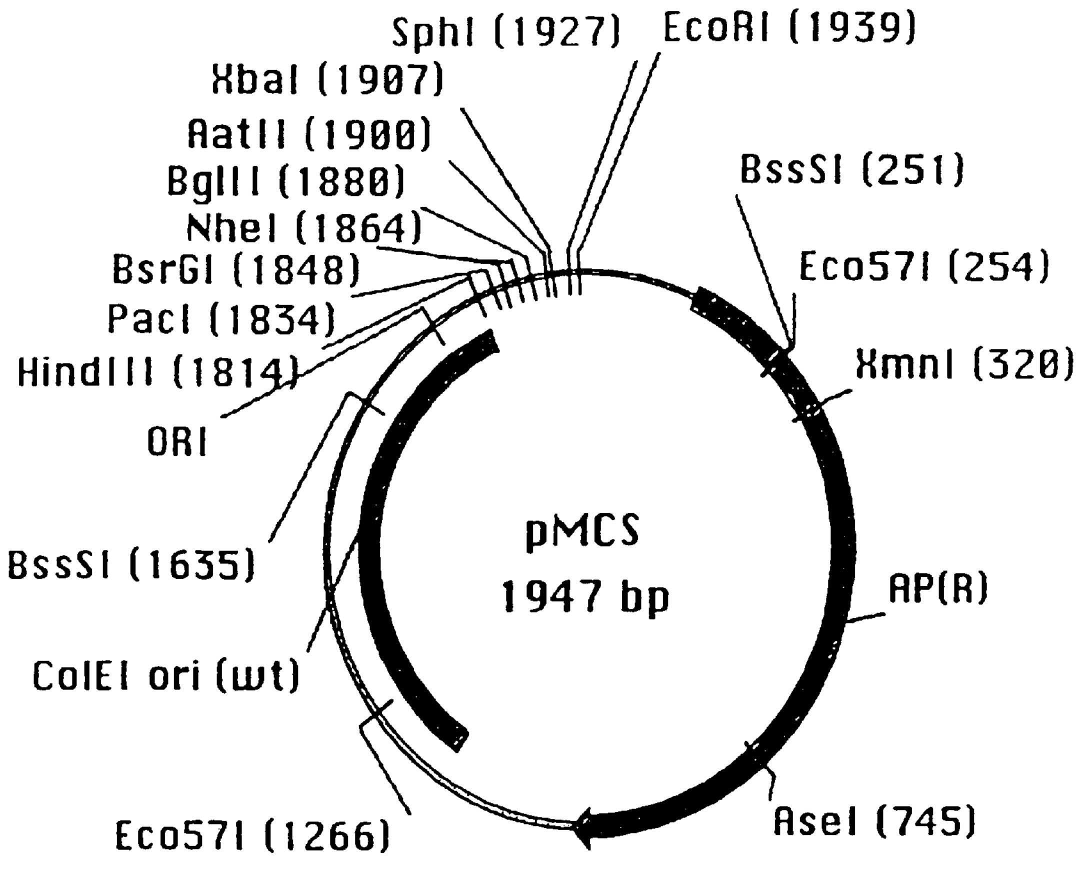

FIG. 28: Functional map and sequence (SEQ ID NOS 264–265 respectively) of the pMCS cloning vector series.

Figure 29A:
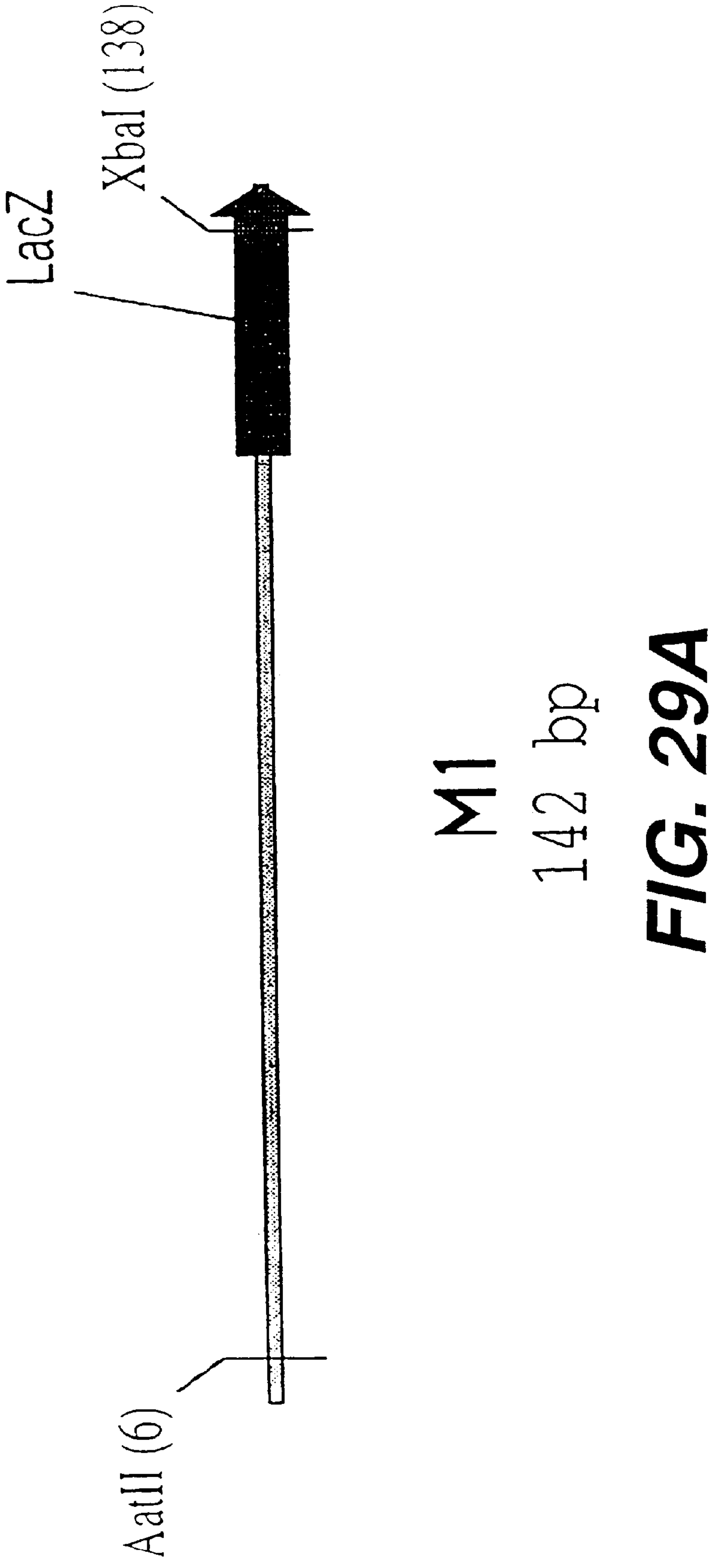

FIG. 29: Functional map and sequence (SEQ ID NO: 266) of the pCAL module M1 (see FIG. 26).

Figure 30A:
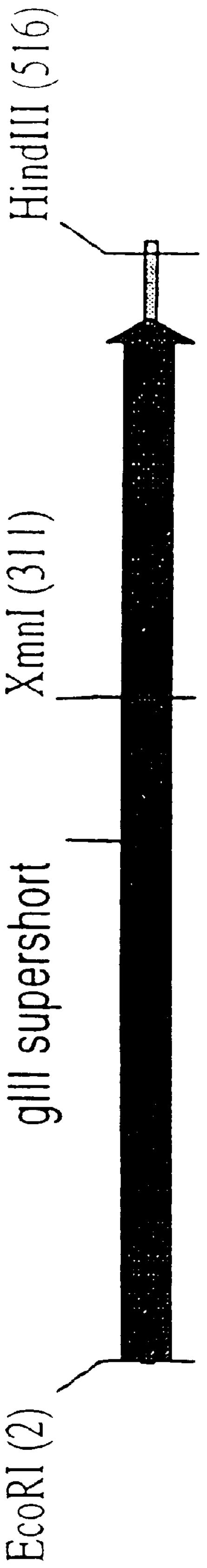

FIG. 30: Functional map and sequence (SEQ ID NOS 267–268 respectively) of the pCAL module M7-III (see FIG. 26).

Figure 31A:
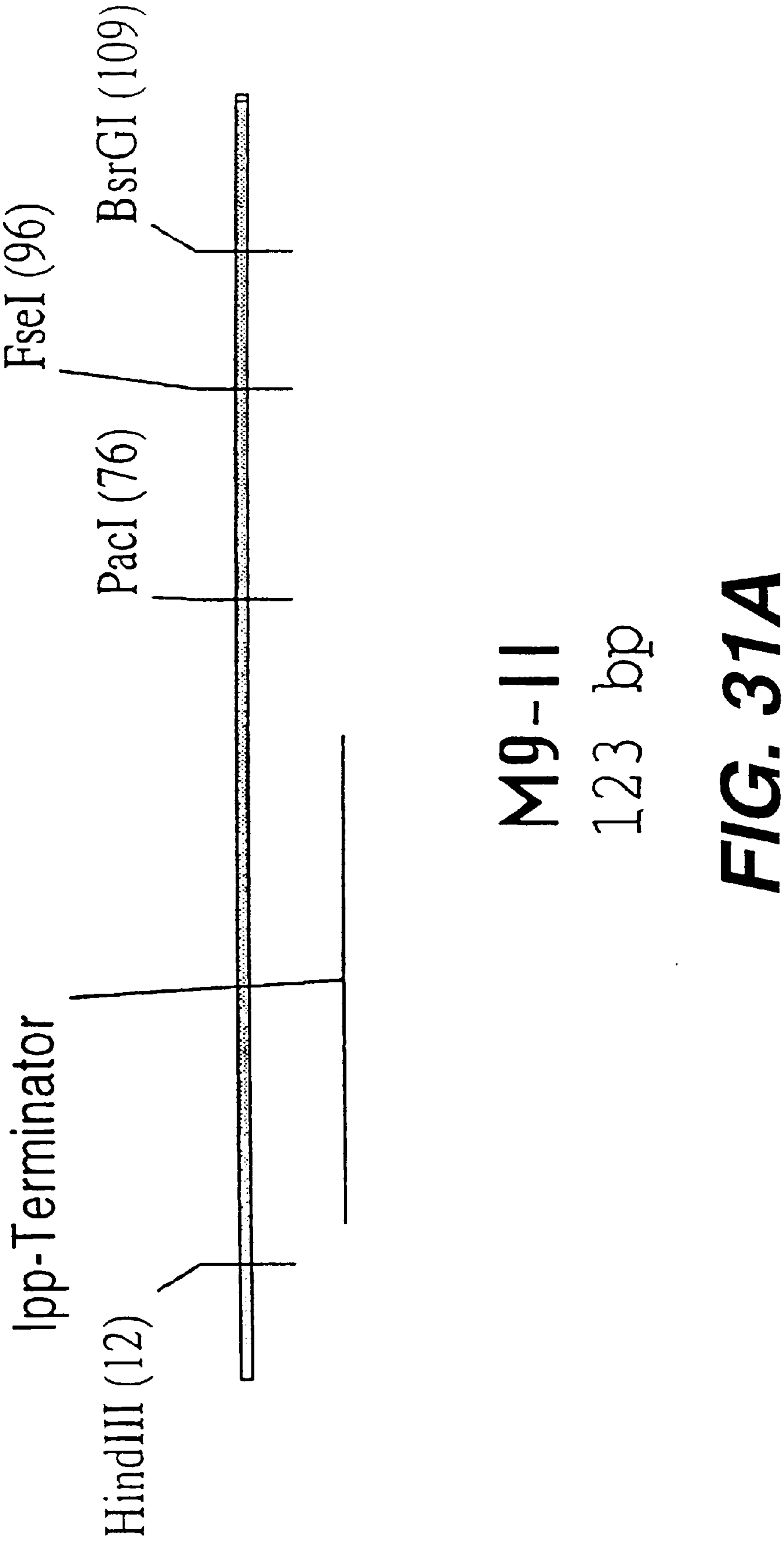

FIG. 31: Functional map and sequence (SEQ ID NO: 269) of the pCAL module M9-II (see FIG. 26).

Figure 32A:
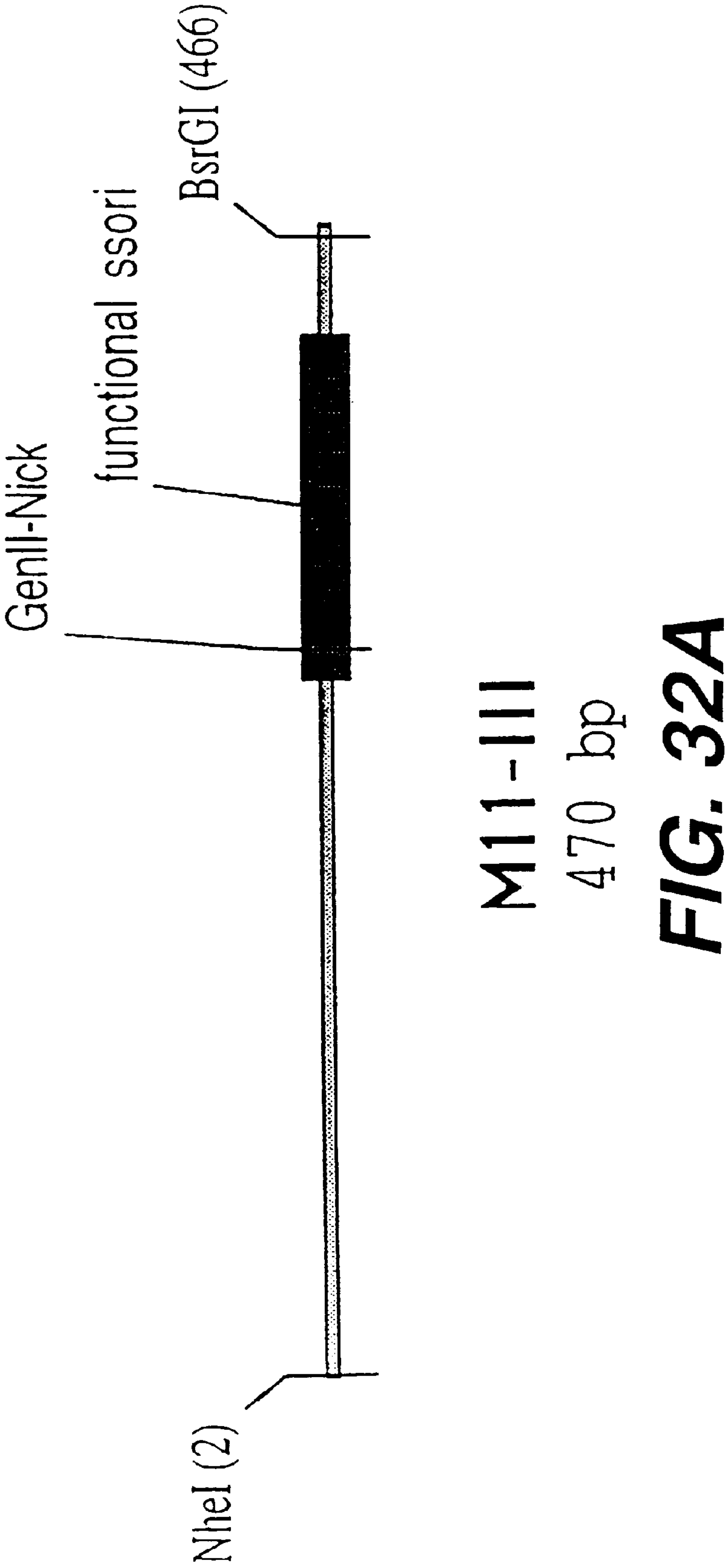

FIG. 32: Functional map and sequence (SEQ ID NO: 270) of the pCAL module M11-II (see FIG. 26).

Figure 33A:
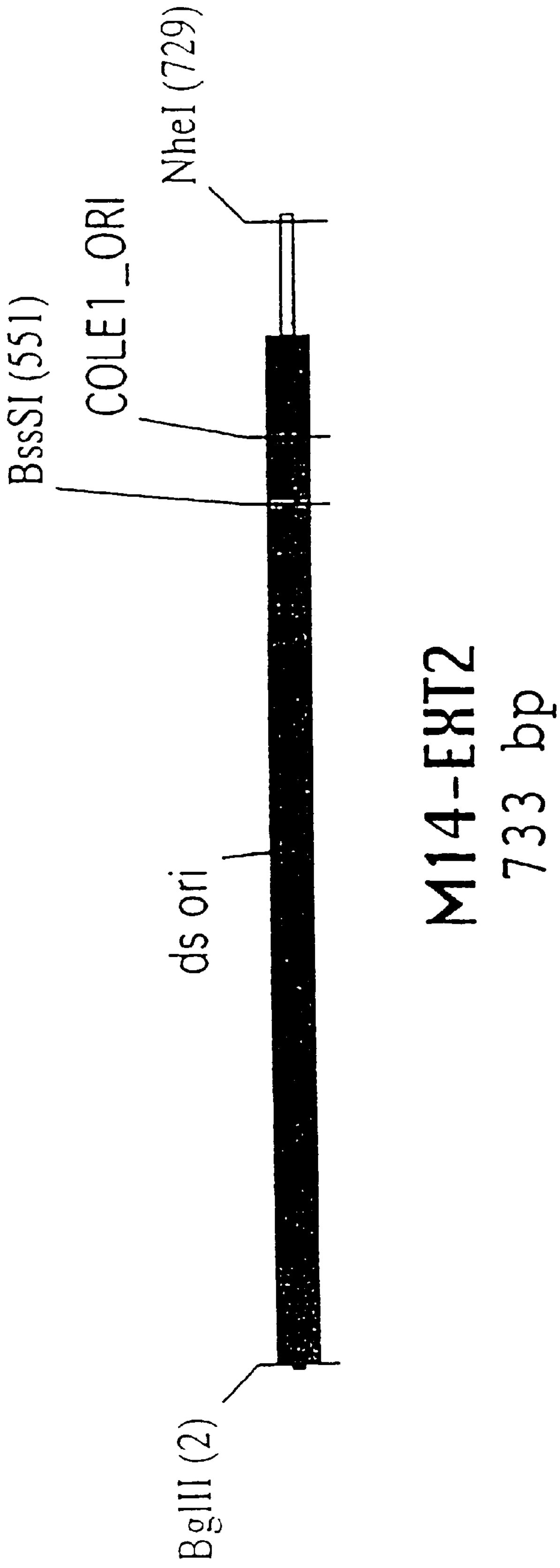

FIG. 33: Functional map and sequence (SEQ ID NO: 271) of the pCAL module M14-Ext2 (see FIG. 26).

Figure 34A:
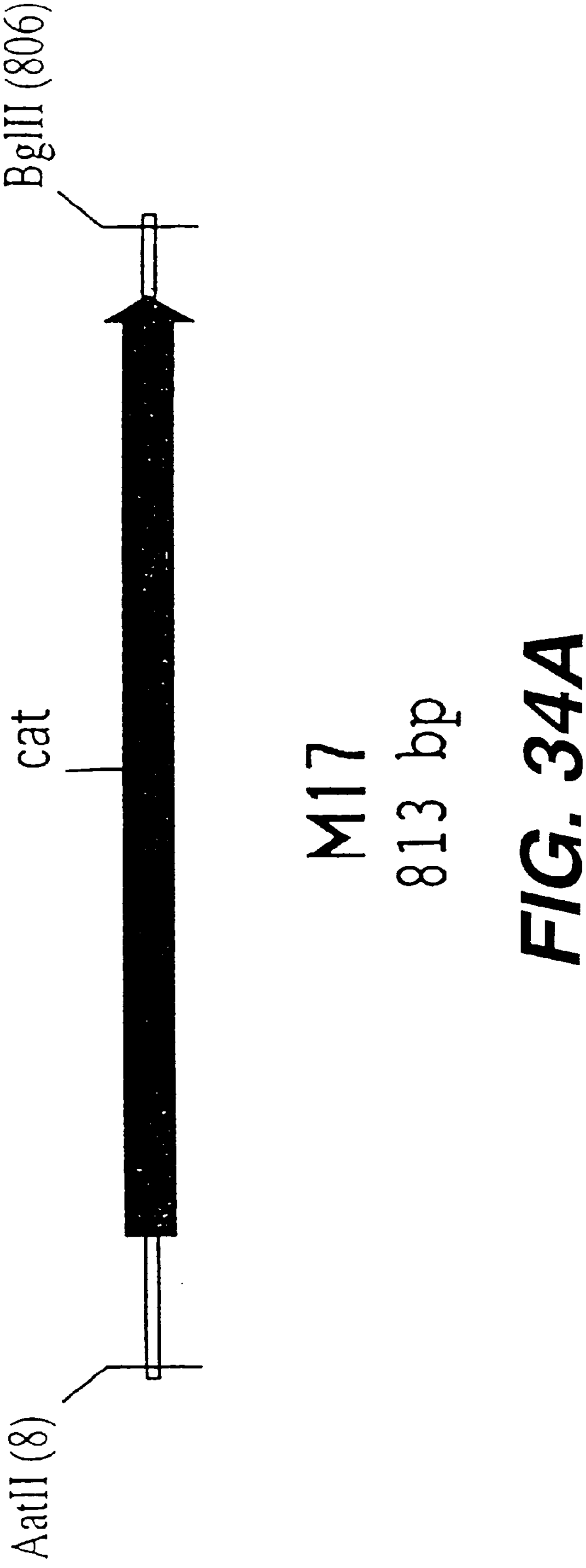
Figure 34D:
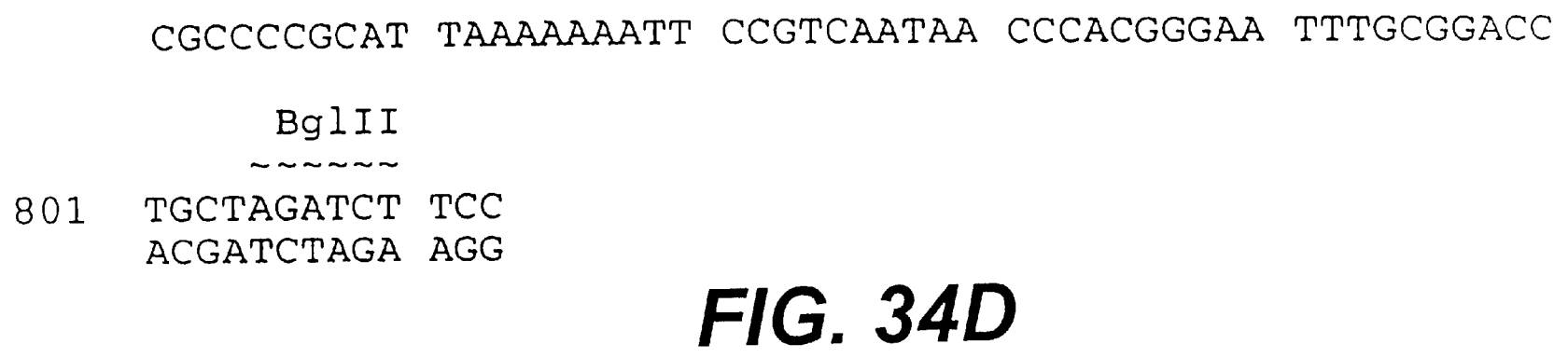

FIG. 34: Functional map and sequence (SEQ ID NOS 272–273 respectively) of the pCAL module M17 (see FIG. 26).

FIG. 35: Functional map and sequence (SEQ ID NOS 274–276 respectively) of the modular vector pCAL4.

FIG. 35*a*: Functional maps and sequences (SEQ ID NOS 277–300 respectively) of additional pCAL modules (M2, M3, M7I, M7II, M8, M10II, M11II, M12, M13, M19, M20, M21, M41) and of low-copy number plasmid vectors (pCALO1 to pCALO3).

FIG. 35*b*: List of oligonucleotides and primers (SEQ ID NOS 301–360 respectively) used for synthesis of pCAL vector modules.

Figure 36A:
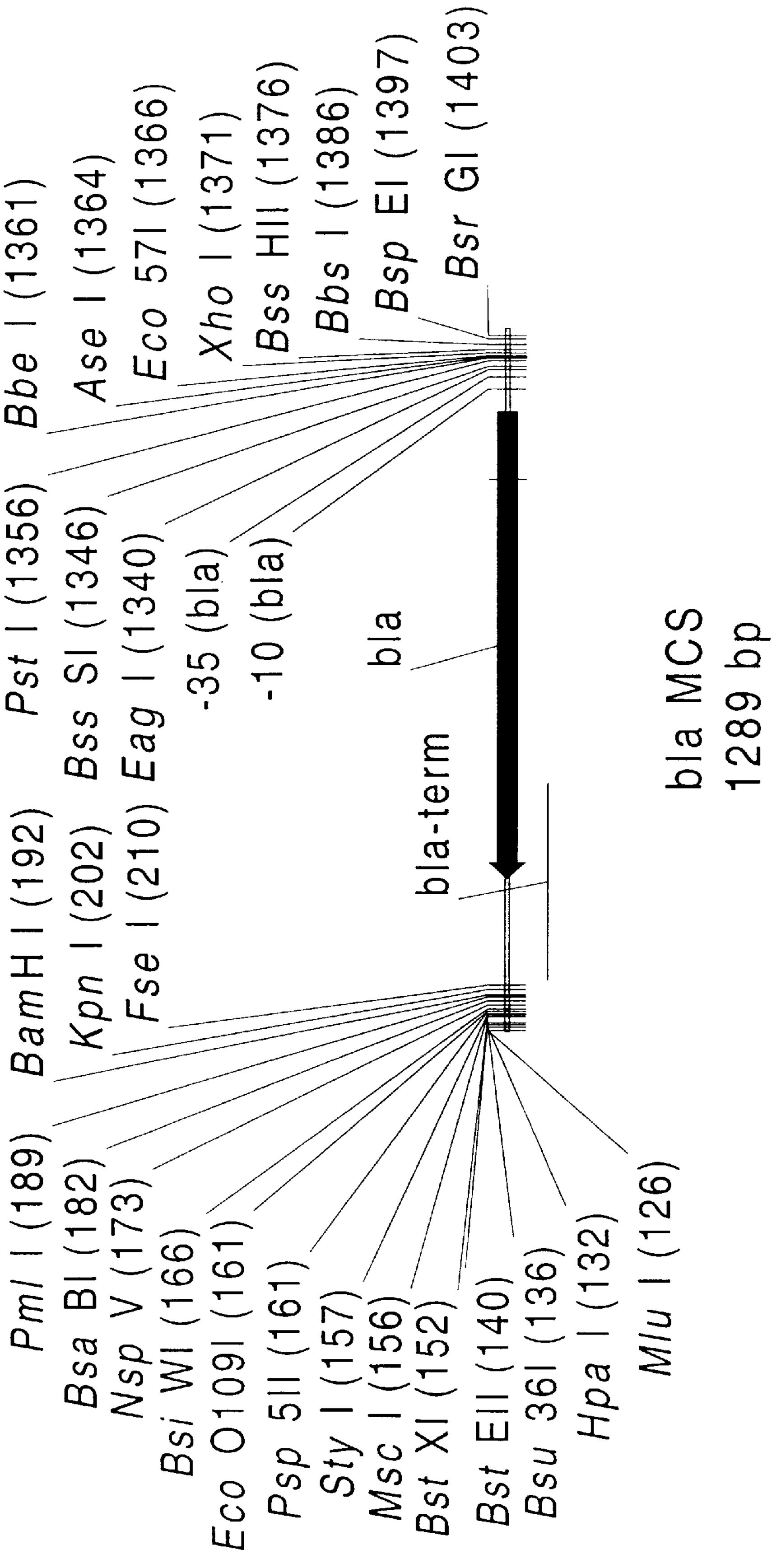
Figure 36F:
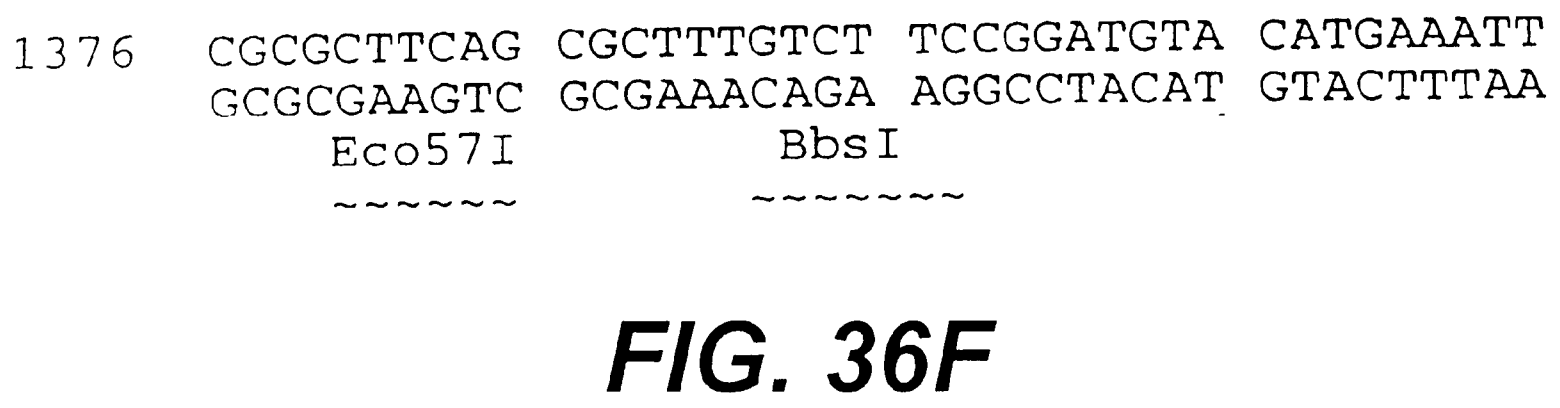

FIG. 36: Functional map and sequence (SEQ ID NOS 361–362 respectively) of the β-lactamase cassette for replacement of CDRs for CDR library cloning.

Figure 37A:
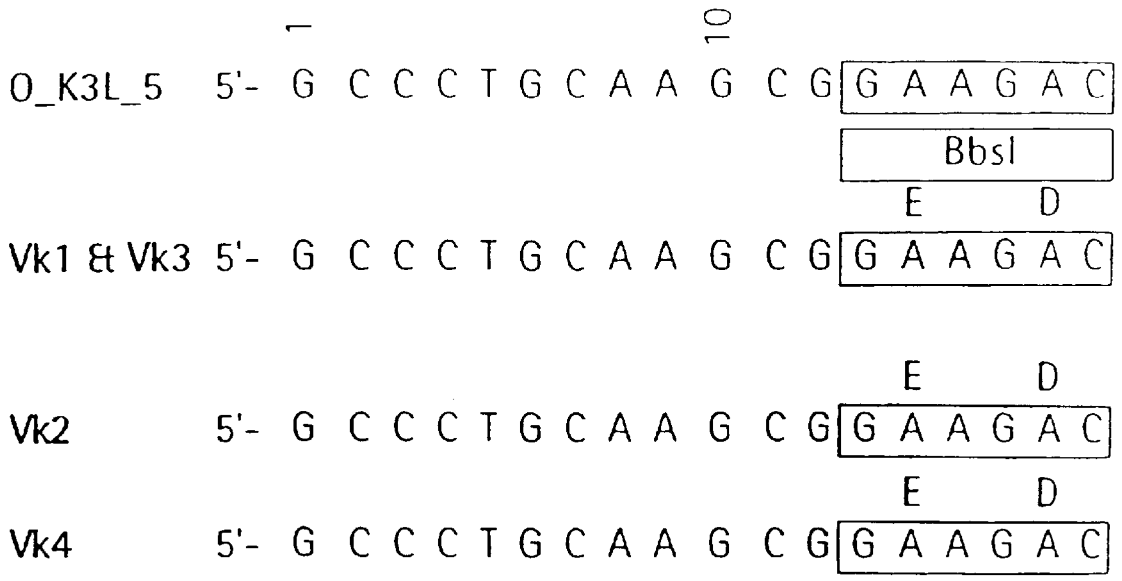
Figure 37B:
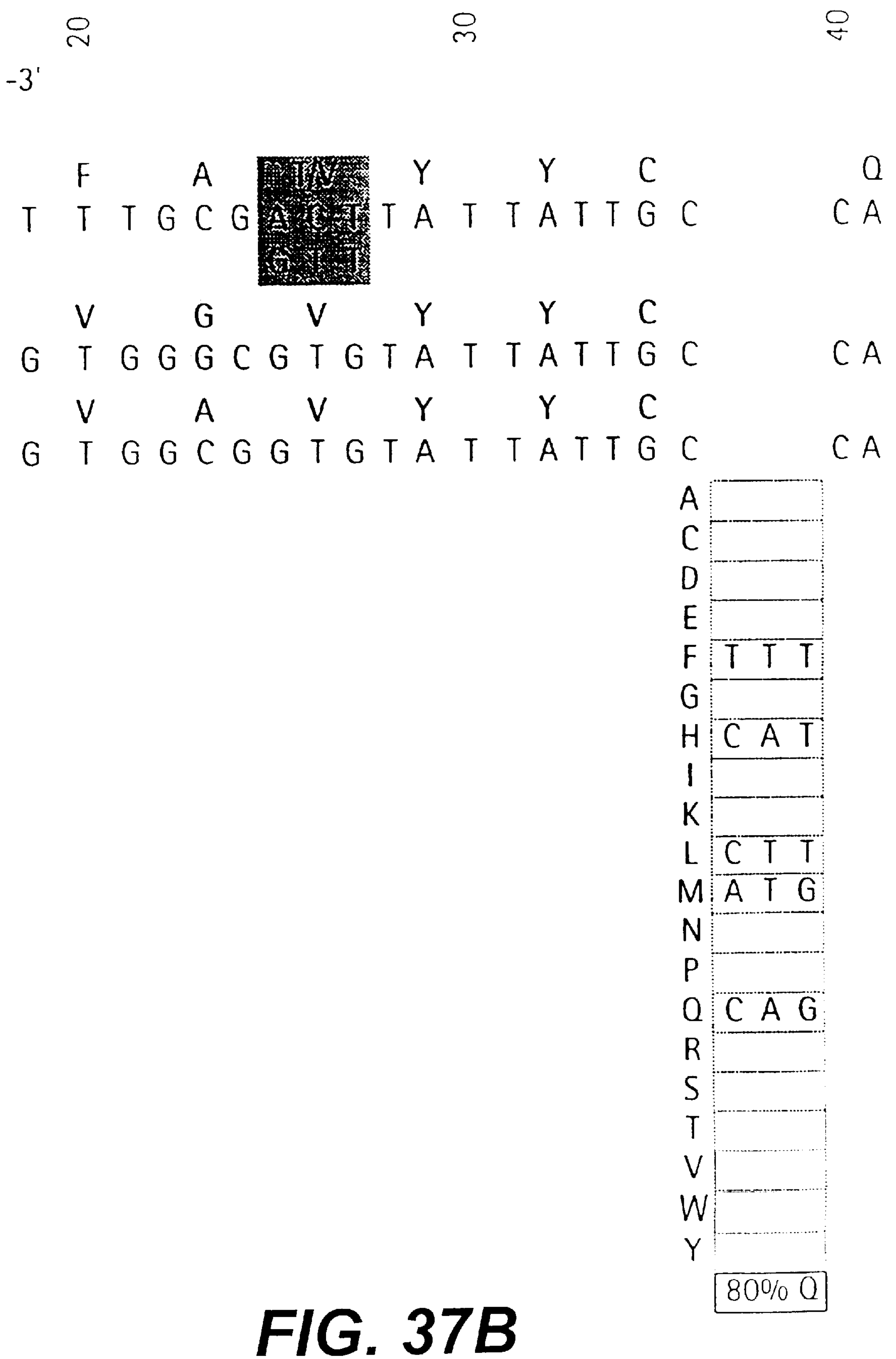
Figure 37D:
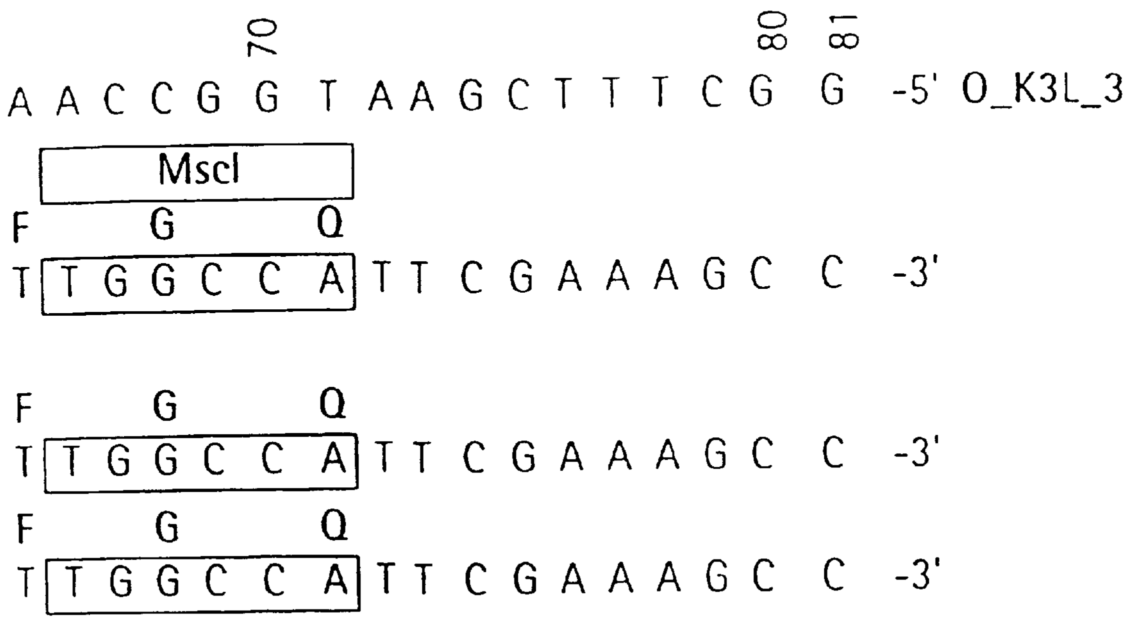

FIG. 37: Oligo and primer (SEQ ID NOS 363–367 respectively) design for Vk CDR3 libraries.

Figure 38B:
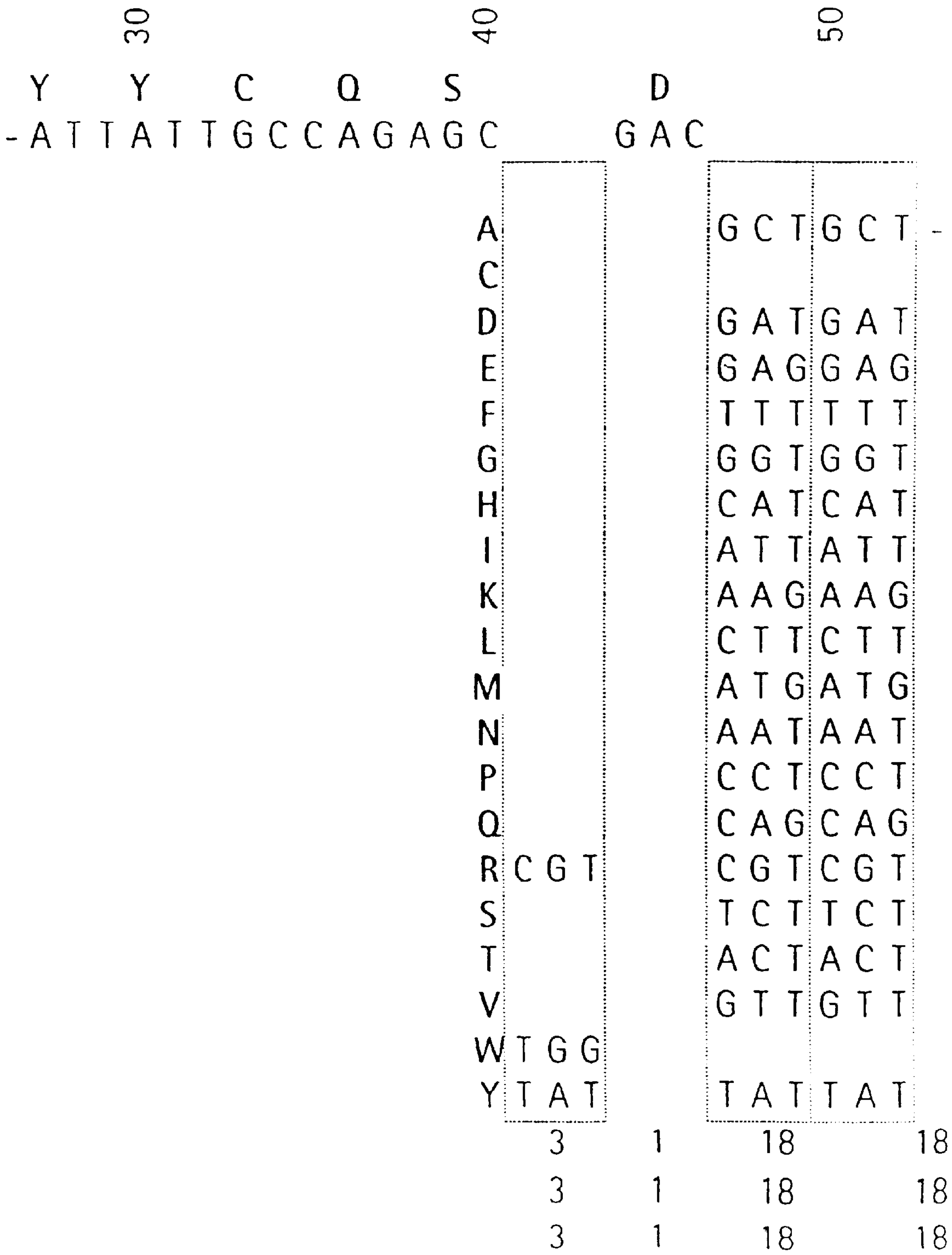
Figure 38D:
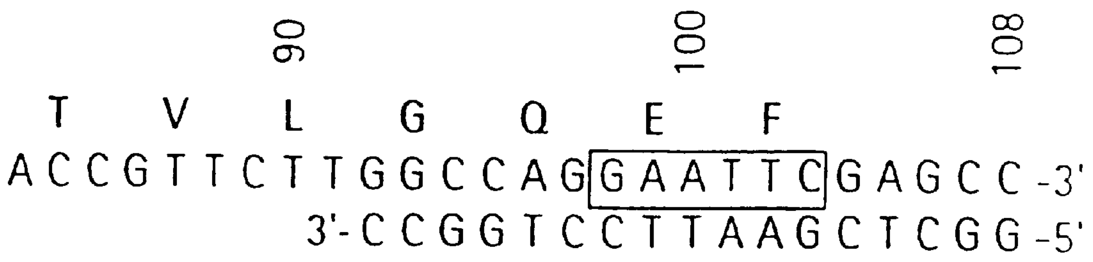

FIG. 38: Oligo and primer (SEQ ID NOS 368–371 respectively) design for Vl CDR3 libraries.

Figure 39:
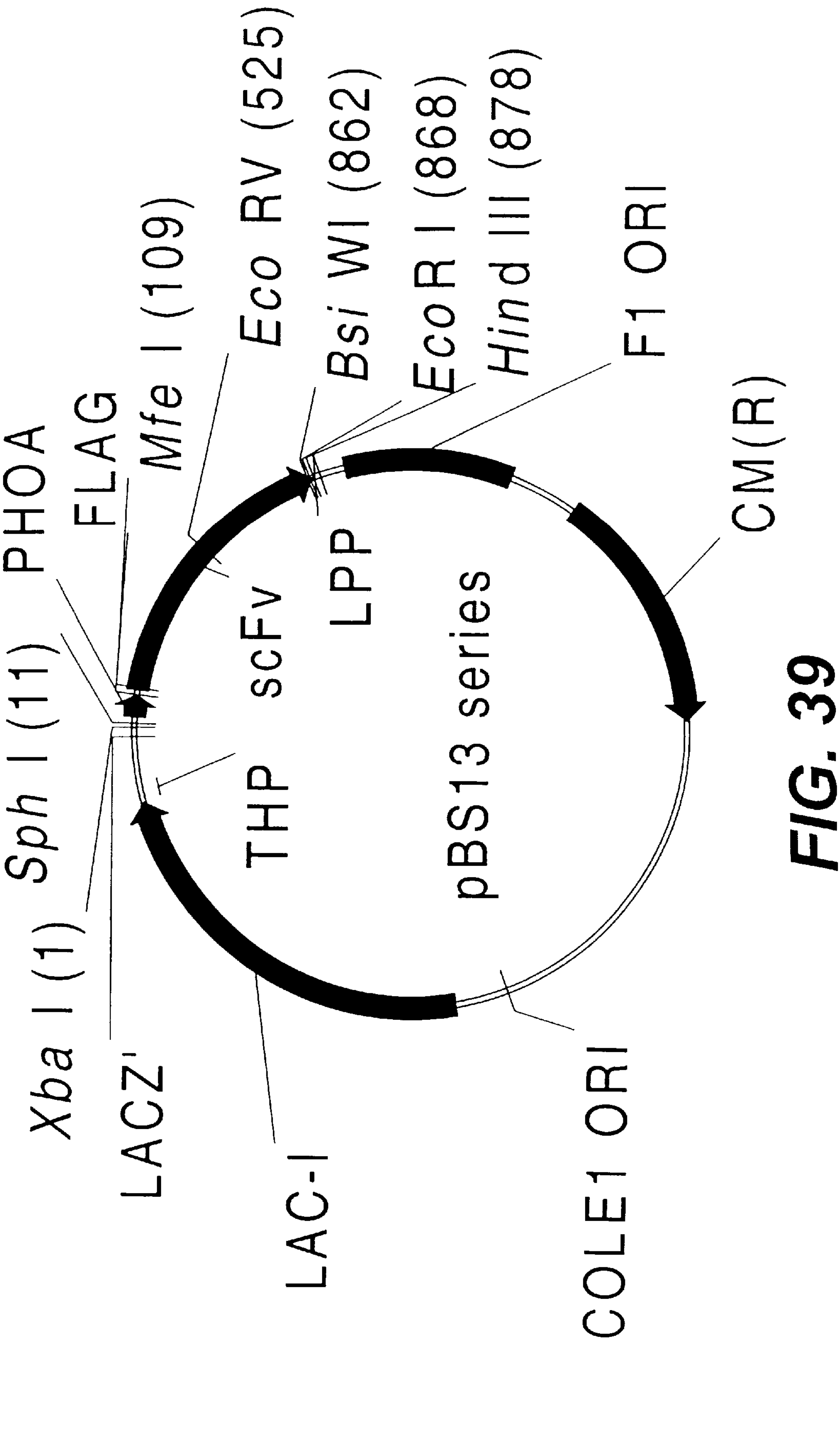

FIG. 39: Functional map of the pBS13 expression vector series.

FIG. 40: Expression of all 49 HuCAL scFvs obtained by combining each of the 7 VH genes with each of the 7 VL genes (pBS13, 30° C.): Values are given for the percentage of soluble vs. insoluble material, the total and the soluble amount compared to the combination H3k2, which was set to 100%. In addition, the corresponding values for the McPC603 scFv are given.

Table 1: Summary of human immunoglobulin germline sequences used for computing the germline membership of rearranged sequences. (A) kappa sequences, (B) lambda sequences and (C), heavy chain sequences. (1) The germline name used in the various calculations, (2) the references number for the corresponding sequence (see appendix for sequence related citations), (3) the family where each sequence belongs to and (4), the various names found in literature for germline genes with identical amino acid sequences.

Table 2: Rearranged human sequences used for the calculation of consensus sequences. (A) kappa sequences, (B) lambda sequences and (C), heavy chain sequences. The table summarized the name of the sequence (1), the length of the sequence in amino acids (2), the germline family (3) as well as the computed germline counterpart (4). The number of amino acid exchanges between the rearranged sequence and the germlne sequence is tabulated in (5), and the percentage of different amino acids is given in (6). Column (7) gives the references number for the corresponding sequence (see appendix for sequence related citations).

Table 3: Assignment of rearranged V sequences to their germline counterparts. (A) kappa sequences, (B) lambda sequences and (C), heavy chain sequences. The germlne genes are tabulated according to their family (1), and the number of rearranged genes found for every germline gene is given in (2).

Table 4: Computation of the consensus sequence of the rearranged V kappa sequences. (A) (SEQ ID NO: 14), V kappa subgroup 1, (B) (SEQ ID NO: 15), V kappa subgroup 2, (C) (SEQ ID NO: 16), V kappa subgroup 3 and (D) (SEQ ID NO: 17), V kappa subgroup 4. The number of each amino acid found at each position is tabulated together with the statistical analysis of the data. (1) Amino acids are given with their standard one-letter abbreviations (and B means D or N, Z means E or Q and X means any amino acid). The statistical analysis summarizes the number of sequences found at each position (2), the number of occurrences of the most common amino acid (3), the amino acid residue which is most common at this position (4), the relative frequency of the occurrence of the most common amino acid (5) and the number of different amino acids found at each position (6).

Table 5: Computation of the consensus sequence of the rearranged V lambda sequences. (A) (SEQ ID NO: 18), V lambda subgroup 1, (B) (SEQ ID NO: 19), V lambda subgroup 2, and (C) (SEQ ID NO: 20), V lambda subgroup 3. The number of each amino acid found at each position is tabulated together with the statistical analysis of the data. Abbreviations are the same as in Table 4.

Table 6: Computation of the consensus sequence of the rearranged V heavy chain sequences. (A) (SEQ ID NO: 21), V heavy chain subgroup 1A, (B) (SEQ ID NO: 22), V heavy chain subgroup 1B, (C) (SEQ ID NO: 23), V heavy chain subgroup 2, (D) (SEQ ID NO: 24), V heavy chain subgroup 3, (E) (SEQ ID NO: 25), V heavy chain subgroup 4, (F) (SEQ ID NO: 26), V heavy chain subgroup 5, and (G) (SEQ ID NO: 27), V heavy chain subgroup 6. The number of each amino acid found at each position is tabulated together with the statistical analysis of the data. Abbreviations are the same as in Table 4.

DETAILED DESCRIPTION OF THE INVENTION

The present invention enables the creation of useful libraries of (poly)peptides. In a first embodiment, the invention provides for a method of setting up nucleic acid sequences suitable for the creation of said libraries. In a first step, a collection of at least three homologous proteins is identified and then analyzed. Therefore, a database of the protein sequences is established where the protein sequences are aligned to each other. The database is used to define subgroups of protein sequences which show a high degree of similarity in both the sequence and, if information is available, in the structural arrangement. For each of the subgroups a (poly)peptide sequence comprising at least one consensus sequence is deduced which represents the members of this subgroup; the complete collection of (poly) peptide sequences represent therefore the complete structural repertoire of the collection of homologous proteins. These artificial (poly)peptide sequences are then analyzed, if possible, according to their structural properties to identify unfavorable interactions between amino acids within said (poly)peptide sequences or between said or other (poly) peptide sequences, for example, in multimeric proteins. Such interactions are then removed by changing the consensus sequence accordingly. The (poly)peptide sequences are then analyzed to identify sub-elements such as domains, loops, helices or CDRs. The amino acid sequence is backtranslated into a corresponding coding nucleic acid sequence which is adapted to the codon usage of the host planned for expressing said nucleic acid sequences. A set of cleavage sites is set up in a way that each of the sub-sequences encoding the sub-elements identified as described above, is flanked by two sites which do not occur a second time within the nucleic acid sequence. This can be achieved by either identifying a cleavage site already flanking a sub-sequence of by changing one or more nucleotides to create the cleavage site, and by removing that site from the remaining part of the gene. The cleavage sites should be common to all corresponding sub-elements or sub-sequences, thus creating a fully modular arrangement of the sub-sequences in the nucleic acid sequence and of the sub-elements in the corresponding (poly)peptide.

In a further embodiment, the invention provides for a method which sets up two or more sets of (poly)peptides, where for each set the method as described above is performed, and where the cleavage sites are not only unique within each set but also between any two sets. This method can be applied for the creation of (poly)peptide libraries comprising for example two a-helical domains from two different proteins, where said library is screened for novel hetero-association domains.

In yet a further embodiment, at least two of the sets as described above, are derived from the same collection of proteins or at least a part of it. This describes libraries comprising for example, but not limited to, two domains from antibodies such as VH and VL, or two extracellular loops of transmembrane receptors.

In another embodiment, the nucleic acid sequences set up as described above, are synthesized. This can be achieved by any one of several methods well known to the practitioner skilled in the art, for example, by total gene synthesis or by PCR-based approaches.

In one embodiment, the nucleic acid sequences are cloned into a vector. The vector could be a sequencing vector, an expression vector or a display (e.g. phage display) vector, which are well known to those skilled in the art. Any vector could comprise one nucleic acid sequence, or two or more nucleic sequences, either in different or the same operon. In the last case, they could either be cloned separately or as contiguous sequences.

In one embodiment, the removal of unfavorable interactions as described above, leads to enhanced expression of the modified (poly)peptides.

In a preferred embodiment, one or more sub-sequences of the nucleic acid sequences are replaced by different sequences. This can be achieved by excising the sub-sequences using the conditions suitable for cleaving the cleavage sites adjacent to or at the end of the sub-sequence, for example, by using a restriction enzyme at the corresponding restriction site under the conditions well known to those skilled in the art, and replacing the sub-sequence by a different sequence compatible with the cleaved nucleic acid sequence. In a further preferred embodiment, the different sequences replacing the initial sub-sequence(s) are genomic or rearranged genomic sequences, for example in grafting CDRs from non-human antibodies onto consensus antibody sequences for rapid humanization of non-human antibodies. In the most preferred embodiment, the different sequences are random sequences, thus replacing the sub-sequence by a collection of sequences to introduce variability and to create a library. The random sequences can be assembled in various ways, for example by using a mixture of mononucleotides or preferably a mixture of trinucleotides (Virnekäs et al., 1994) during automated oligonucleotide synthesis, by error-prone PCR or by other methods well known to the practitioner in the art. The random sequences may be completely randomized or biased towards or against certain codons according to the amino acid distribution at certain positions in known protein sequences. Additionally, the collection of random sub-sequences may comprise different numbers of codons, giving rise to a collection of sub-elements having different lengths.

In another embodiment, the invention provides for the expression of the nucleic acid sequences from a suitable vector and under suitable conditions well known to those skilled in the art.

In a further preferred embodiment, the (poly)peptides expressed from said nucleic acid sequences are screened and, optionally, optimized. Screening may be performed by using one of the methods well known to the practitioner in the art, such as phage-display, selectively infective phage, polysome technology to screen for binding, assay systems for enzymatic activity or protein stability. (Poly)peptides having the desired property can be identified by sequencing of the corresponding nucleic acid sequence or by amino acid sequencing or mass spectrometry. In the case of subsequent optimization, the nucleic acid sequences encoding the initially selected (poly)peptides can optionally be used without sequencing. Optimization is performed by repeating the replacement of sub-sequences by different sequences, preferably by random sequences, and the screening step one or more times.

The desired property the (poly)peptides are screened for is preferably, but not exclusively, selected from the group of optimized affinity or specificity for a target molecule, optimized enzymatic activity, optimized expression yields, optimized stability and optimized solubility.

In one embodiment, the cleavage sites flanking the sub-sequences are sites recognized and cleaved by restriction enzymes, with recognition and cleavage sequences being either identical or different, the restricted sites either having blunt or sticky ends.

The length of the sub-elements is preferably, but not exclusively ranging between 1 amino acid, such as one residue in the active site of an enzyme or a structure-determining residue, and 150 amino acids, as for whole protein domains. Most preferably, the length ranges between 3 and 25 amino acids, such as most commonly found in CDR loops of antibodies.

The nucleic acid sequences could be RNA or, preferably, DNA.

In one embodiment, the (poly)peptides have an amino acid pattern characteristic of a particular species. This can for example be achieved by deducing the consensus sequences from a collection of homologous proteins of just one species, most preferably from a collection of human proteins. Since the (poly)peptides comprising consensus sequences are artificial, they have to be compared to the protein sequence(s) having the closest similarity to ensure the presence of said characteristic amino acid pattern.

In one embodiment, the invention provides for the creation of libraries of (poly)peptides comprising at least part of members or derivatives of the immunoglobulin superfamily, preferably of member or derivatives of the immnoglobulins. Most preferably, the invention provides for the creation of libraries of human antibodies, wherein said (poly)peptides are or are derived from heavy or light chain variable regions wherein said structural sub-elements are framework regions (FR) 1, 2, 3, or 4 or complementary determining regions (CDR) 1, 2, or 3. In a first step, a database of published antibody sequences of human origin is established where the antibody sequences are aligned to each other. The database is used to define subgroups of antibody sequences which show a high degree of similarity in both the sequence and the canonical fold of CDR loops (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed e.g. by total gene synthesis or by the use of synthetic genetic subunits. These genetic subunits correspond to structural sub-elements on the (poly)peptide level. On the DNA level, these genetic subunits are defined by cleavage sites at the start and the end of each of the sub-elements, which are unique in the vector system. All genes which are members of the collection of consensus sequences are constructed such that they contain a similar pattern of corresponding genetic sub-sequences. Most preferably, said (poly)peptides are or are derived from the HuCAL consensus genes: Vk1, Vk2, Vk3, Vk4, Vl1, Vl2, Vl3, VH1A, VH1B, VH2, VH3, VH4, VH5, VH6, Ck, Cl, CH1 or any combination of said HuCAL consensus genes.

This collection of DNA molecules can then be used to create libraries of antibodies or antibody fragments, preferably Fv, disulphide-linked Fv, single-chain Fv (scFv), or Fab fragments, which may be used as sources of specificities against new target antigens. Moreover, the affinity of the antibodies can be optimized using pre-built library cassettes and a general procedure. The invention provides a method for identifying one or more genes encoding one or more antibody fragments which binds to a target, comprising the steps of expressing the antibody fragments, and then screening them to isolate one or more antibody fragments which bind to a given target molecule. Preferably, an scFv fragment library comprising the combination of HuCAL VH3 and HuCAL Vκ2 consensus genes and at least a random sub-sequence encoding the heavy chain CDR3 sub-element is screened for binding antibodies. If necessary, the modular design of the genes can then be used to excise from the genes encoding the antibody fragments one or more genetic sub-sequences encoding structural sub-elements, and replacing them by one or more second sub-sequences encoding structural sub-elements. The expression and screening steps can then be repeated until an antibody having the desired affinity is generated.

Particularly preferred is a method in which one or more of the genetic subunits (e.g. the CDRs) are replaced by a random collection of sequences (the library) using the said cleavage sites. Since these cleavage sites are (i) unique in the vector system and (ii) common to all consensus genes, the same (pre-built) library can be inserted into all artificial antibody genes. The resulting library is then screened against any chosen antigen. Binding antibodies are selected, collected and used as starting material for the next library. Here, one or more of the remaining genetic subunits are randomized as described above.

A further embodiment of the present invention relates to fusion proteins by providing for a DNA sequence which encodes both the (poly)peptide, as described above, as well as an additional moiety. Particularly preferred are moieties which have a useful therapeutic function. For example, the additional moiety may be a toxin molecule which is able to kill cells (Vitetta et al., 1993). There are numerous examples of such toxins, well known to the one skilled in the art, such as the bacterial toxins Pseudomonas exotoxin A, and diphtheria toxin, as well as the plant toxins ricin, abrin, modeccin, saporin, and gelonin. By fusing such a toxin for example to an antibody fragment, the toxin can be targeted to, for example, diseased cells, and thereby have a beneficial therapeutic effect. Alternatively, the additional moiety may be a cytokine, such as IL-2 (Rosenberg & Lotze, 1986), which has a particular effect (in this case a T-cell proliferative effect) on a family of cells. In a further embodiment, the additional moiety may confer on its (poly)peptide partner a means of detection and/or purification. For example, the fusion protein could comprise the modified antibody fragment and an enzyme commonly used for detection purposes, such as alkaline phosphatase (Blake et al., 1984). There are numerous other moieties which can be used as detection or purification tags, which are well known to the practitioner skilled in the art. Particularly preferred are peptides comprising at least five histidine residues (Hochuli et al., 1988), which are able to bind to metal ions, and can therefore be used for the purification of the protein to which they are fused (Lindner et al., 1992). Also provided for by the invention are additional moieties such as the commonly used C-myc and FLAG tags (Hopp et al., 1988; Knappik & Pl ückthun, 1994).

By engineering one or more fused additional domains, antibody fragments or any other (poly)peptide can be assembled into larger molecules which also fall under the scope of the present invention. For example, mini-antibodies (Pack, 1994) are dimers comprising two antibody fragments, each fused to a self-associating dimerization domain. Dimerization domains which are particularly preferred include those derived from a leucine zipper (Pack & Pl ückthun, 1992) or helix-turn-helix motif (Pack et al., 1993).

All of the above embodiments of the present invention can be effected using standard techniques of molecular biology known to anyone skilled in the art.

In a further embodiment, the random collection of sub-sequences (the library) is inserted into a singular nucleic acid sequence encoding one (poly)peptide, thus creating a (poly)peptide library based on one universal framework. Preferably a random collection of CDR sub-sequences is inserted into a universal antibody framework, for example into the HuCAL H3k2 single-chain Fv fragment described above.

In further embodiments, the invention provides for nucleic acid sequence(s), vector(s) containing the nucleic acid sequence(s), host cell(s) containing the vector(s), and (poly)peptides, obtainable according to the methods described above.

In a further preferred embodiment, the invention provides for modular vector systems being compatible with the modular nucleic acid sequences encoding the (poly) peptides. The modules of the vectors are flanked by restriction sites unique within the vector system and essentially unique with respect to the restriction sites incorporated into the nucleic acid sequences encoding the (poly)peptides, except for example the restriction sites necessary for cloning the nucleic acid sequences into the vector. The list of vector modules comprises origins of single-stranded replication, origins of double-stranded replication for high- and low copy number plasmids, promotor/operator, repressor or terminator elements, resistance genes, potential recombination sites, gene III for display on filamentous phages, signal sequences, purification and detection tags, and sequences of additional moieties. The vectors are preferably, but not exclusively, expression vectors or vectors suitable for expression and screening of libraries.

In another embodiment, the invention provides for a kit, comprising one or more of the list of nucleic acid sequence (s), recombinant vector(s), (poly)peptide(s), and vector(s) according to the methods described above, and suitable host cell(s) for producing the (poly)peptide(s).

In a preferred embodiment, the invention provides for the creation of libraries of human antibodies. In a first step, a database of published antibody sequences of human origin is established. The database is used to define subgroups of antibody sequences which show a high degree of similarity in both the sequence and the canonical fold (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed by the use of synthetic genetic subunits. These genetic subunits correspond to structural sub-elements on the protein level. On the DNA level, these genetic subunits are defined by cleavage sites at the start and the end of each of the subelements, which are unique in the vector system. All genes which are members of the collection of consensus sequences are constructed such that they contain a similar pattern of said genetic subunits.

This collection of DNA molecules can then be used to create libraries of antibodies which may be used as sources of specificities against new target antigens. Moreover, the affinity of the antibodies can be optimised using pre-built library cassettes and a general procedure. The invention provides a method for identifying one or more genes encoding one or more antibody fragments which binds to a target, comprising the steps of expressing the antibody fragments, and then screening them to isolate one or more antibody fragments which bind to a given target molecule. If necessary, the modular design of the genes can then be used to excise from the genes encoding the antibody fragments one or more genetic sub-sequences encoding structural sub-elements, and replacing them by one or more second sub-sequences encoding structural sub-elements. The expression and screening steps can then be repeated until an antibody having the desired affinity is generated.

Particularly preferred is a method in which one or more of the genetic subunits (e.g. the CDR's) are replaced by a random collection of sequences (the library) using the said cleavage sites. Since these cleavage sites are (i) unique in the vector system and (ii) common to all consensus genes, the same (pre-built) library can be inserted into all artificial antibody genes. The resulting library is then screened against any chosen antigen. Binding antibodies are eluted, collected and used as starting material for the next library. Here, one or more of the remaining genetic subunits are randomized as described above.

DEFINITIONS

Protein

The term protein comprises monomeric polypeptide chains as well as homo- or heteromultimeric complexes of two or more polypeptide chains connected either by covalent interactions (such as disulphide bonds) or by non-covalent interactions (such as hydrophobic or electrostatic interactions).

Analysis of Homologous Proteins

The amino acid sequences of three or more proteins are aligned to each other (allowing for introduction of gaps) in a way which maximizes the correspondence between identical or similar amino acid residues at all positions. These aligned sequences are termed homologous if the percentage of the sum of identical and/or similar residues exceeds a defined threshold. This threshold is commonly regarded by those skilled in the art as being exceeded when at least 15% of the amino acids in the aligned genes are identical, and at least 30% are similar. Examples for families of homologous proteins are: immunoglobulin superfamily, scavenger receptor superfamily, fibronectin superfamilies (e.g. type II and III), complement control protein superfamily, cytokine receptor superfamily, cystine knot proteins, tyrosine kinases, and numerous other examples well known to one of ordinary skill in the art.

Consensus Sequence

Using a matrix of at least three aligned amino acid sequences, and allowing for gaps in the alignment, it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

Removing Unfavorable Interactions

The consensus sequence is per se in most cases artificial and has to be analyzed in order to change amino acid residues which, for example, would prevent the resulting molecule to adapt a functional tertiary structure or which would block the interaction with other (poly)peptide chains in multimeric complexes. This can be done either by (i) building a three-dimensional model of the consensus sequence using known related structures as a template, and identifying amino acid residues within the model which may interact unfavorably with each other, or (ii) analyzing the matrix of aligned amino acid sequences in order to detect combinations of amino acid residues within the sequences which frequently occur together in one sequence and are therefore likely to interact with each other. These probable interaction-pairs are then tabulated and the consensus is compared with these "interaction maps". Missing or wrong interactions in the consensus are repaired accordingly by introducing appropriate changes in amino acids which minimize unfavorable interactions.

Identification of Structural Sub-elements

Structural sub-elements are stretches of amino acid residues within a protein/(poly)peptide which correspond to a defined structural or functional part of the molecule. These can be loops (e.g. CDR loops of an antibody) or any other secondary or functional structure within the protein/(poly) peptide (domains, a-helices, β-sheets, framework regions of antibodies, etc.). A structural sub-element can be identified using known structures of similar or homologous (poly) peptides, or by using the above mentioned matrices of aligned amino acid sequences. Here the variability at each position is the basis for determining stretches of amino acid residues which belong to a structural sub-element (e.g. hypervariable regions of an antibody).

Sub-sequence

A sub-sequence is defined as a genetic module which is flanked by unique cleavage sites and encodes at least one structural sub-element. It is not necessarily identical to a structural sub-element.

Cleavage Site

A short DNA sequence which is used as a specific target for a reagent which cleaves DNA in a sequence-specific manner (e.g. restriction endonucleases).

Compatible Cleavage Sites

Cleavage sites are compatible with each other, if they can be efficiently ligated without modification and, preferably, also without adding an adapter molecule.

Unique Cleavage Sites

A cleavage site is defined as unique if it occurs only once in a vector containing at least one of the genes of interest, or if a vector containing at least one of the genes of interest could be treated in a way that only one of the cleavage sites could be used by the cleaving agent.

Corresponding (Poly)peptide Sequences

Sequences deduced from the same part of one group of homologous proteins are called corresponding (poly)peptide sequences.

Common Cleavage Sites

A cleavage site in at least two corresponding sequences, which occurs at the same functional position (i.e. which flanks a defined sub-sequence), which can be hydrolyzed by the same cleavage tool and which yields identical compatible ends is termed a common cleavage site.

Excising Genetic Sub-sequences

A method which uses the unique cleavage sites and the corresponding cleavage reagents to cleave the target DNA at the specified positions in order to isolate, remove or replace the genetic sub-sequence flanked by these unique cleavage sites.

Exchanging Genetic Sub-sequences

A method by which an existing sub-sequence is removed using the flanking cleavage sites of this sub-sequence, and a new sub-sequence or a collection of sub-sequences, which contain ends compatible with the cleavage sites thus created, is inserted.

Expression of Genes

The term expression refers to in vivo or in vitro processes, by which the information of a gene is transcribed into mRNA and then translated into a protein/(poly)peptide. Thus, the term expression refers to a process which occurs inside cells, by which the information of a gene is transcribed into mRNA and then into a protein. The term expression also includes all events of post-translational modification and transport, which are necessary for the (poly)peptide to be functional.

Screening of Protein/(poly)peptide Libraries

Any method which allows isolation of one or more proteins/(poly)peptides having a desired property from other proteins/(poly)peptides within a library.

Amino Acid Pattern Characteristic for a Species

A (poly)peptide sequence is assumed to exhibit an amino acid pattern characteristic for a species if it is deduced from a collection of homologous proteins from just this species.

Immunoglobulin Superfamily (IgSF)

The IgSF is a family of proteins comprising domains being characterized by the immunoglobulin fold. The IgSF comprises for example T-cell receptors and the immunoglobulins (antibodies).

Antibody Framework

A framework of an antibody variable domain is defined by Kabat et al. (1991) as the part of the variable domain which serves as a scaffold for the antigen binding loops of this variable domain.

Antibody CDR

The CDRs (complementarity determining regions) of an antibody consist of the antigen binding loops, as defined by Kabat et al. (1991). Each of the two variable domains of an antibody Fv fragment contain three CDRs.

HuCAL

Acronym for Human Combinatorial Antibody Library. Antibody Library based on modular consensus genes according to the invention (see Example 1).

Antibody Fragment

Any portion of an antibody which has a particular function, e.g. binding of antigen. Usually, antibody fragments are smaller than whole antibodies. Examples are Fv, disulphide-linked Fv, single-chain Fv (scFv), or Fab fragments. Additionally, antibody fragments are often engineered to include new functions or properties.

Universal Framework

One single framework which can be used to create the full variability of functions, specificities or properties which is originally sustained by a large collection of different frameworks, is called universal framework.

Binding of an Antibody to its Target

The process which leads to a tight and specific association between an antibody and a corresponding molecule or ligand is called binding. A molecule or ligand or any part of a molecukle or ligand which is recognized by an antibody is called the target.

Replacing Genetic Sub-sequences

A method by which an existing sub-sequence is removed using the flanking cleavage sites of this sub-sequence, and a new sub-sequence or collection of sub-sequences, which contains ends compatible with the cleavage sites thus created, is inserted.

Assembling of Genetic Sequences

Any process which is used to combine synthetic or natural genetic sequences in a specific manner in order to get longer genetic sequences which contain at least parts of the used synthetic or natural genetic sequences.

EXAMPLES

Example 1

Design of a Synthetic Human Combinatorial Antibody Library (HuCAL)

The following example describes the design of a fully synthetic human combinatorial antibody library (HuCAL), based on consensus sequences of the human immunoglobulin repertoire, and the synthesis of the consensus genes. The general procedure is outlined in FIG. 1.

1.1 Sequence Database 1.1.1 Collection and Alignment of Human Immunoglobulin Sequences In a first step, sequences of variable domains of human immunoglobulins have been collected and divided into three sub bases: V heavy chain (VH), V kappa (Vk) and V lambda (Vl). For each sequence, the gene sequence was then translated into the corresponding amino acid sequence. Subsequently, all amino acid sequences were aligned according to Kabat et al. (1991). In the case of Vl sequences, the numbering system of Chuchana et al. (1990) was used. Each of the three main databases was then divided into two further sub bases: the first sub base contained all sequences derived from rearranged V genes, where more than 70 positions of the sequence were known. The second sub base contained all germlne gene segments (without the D- and J-minigenes; pseudogenes with internal stop codons were also removed). In all cases, where germlne sequences with identical amino acid sequence but different names were found, only one sequence was used (see Table 1). The final databases of rearranged sequences contained 386, 149 and 674 entries for Vk, Vl and VH, respectively. The final databases of germlne sequences contained 48, 26 and 141 entries for Vk, Vl and VH, respectively.

1.1.2 Assignment of Sequences to Subgroups

The sequences in the three germline databases where then grouped according to sequence homology (see also Tomlinson et al., 1992, Williams & Winter, 1993, and Cox et al., 1994). In the case of Vk, 7 families could be established. Vl was divided into 8 families and VH into 6 families. The VH germlne genes of the VH7 family (Van Dijk et al., 1993) were grouped into the VH1 family, since the genes of the two families are highly homologous. Each family contained different numbers of germlne genes, varying from 1 (for example VH6) to 47 (VH3).

1.2 Analysis of Sequences 1.2.1 Computation of Germline Membership

For each of the 1209 amino acid sequences in the databases of rearranged genes, the nearest germline counterpart, i.e. the germline sequence with the smallest number of amino acid differences was then calculated. After the germline counterpart was found, the number of somatic mutations which occurred in the rearranged gene and which led to amino acid exchanges could be tabulated. In 140 cases, the germlne counterpart could not be calculated exactly, because more than one germlne gene was found with an identical number of amino acid exchanges. These rearranged sequences were removed from the database. In a few cases, the number of amino acid exchanges was found to be unusually large (>20 for VL and >25 for VH), indicating either heavily mutated rearranged genes or derivation from germlne genes not present in the database. Since it was not possible to distinguish between these two possibilities, these sequences were also removed from the database. Finally, 12 rearranged sequences were removed from the database because they were found to have very unusual CDR lengths and composition or unusual amino acids at canonical positions (see below). In summary, 1023 rearranged sequences out of 1209 (85%) could be clearly assigned to their germline counterparts (see Table 2).

After this calculation, every rearranged gene could be arranged in one of the families established for the germline genes. Now the usage of each germline gene, i.e. the number of rearranged genes which originate from each germlne gene, could be calculated (see Table 2). It was found that the usage was strongly biased towards a subset of germlne genes, whereas most of the germline genes were not present as rearranged genes in the database and therefore apparently not used in the immune system (Table 3). This observation had already been reported in the case of Vk (Cox, et al., 1994). All germlne gene families, where no or only very few rearranged counterparts could be assigned, were removed from the database, leaving 4 Vk, 3 Vl, and 6 VH families.

1.2.2 Analysis of CDR Conformations

The conformation of the antigen binding loops of antibody molecules, the CDRs, is strongly dependent on both the length of the CDRs and the amino acid residues located at the so-called canonical positions (Chothia & Lesk, 1987). It has been found that only a few canonical structures exist, which determine the structural repertoire of the immunoglobulin variable domains (Chothia et al., 1989). The canonical amino acid positions can be found in CDR as well as framework regions. The 13 used germline families defined above (7 VL and 6 VH) were now analyzed for their canonical structures in order to define the structural repertoire encoded in these families.

In 3 of the 4 Vk families (Vk1, 2 and 4), one different type of CDR1 conformation could be defined for every family. The family Vk3 showed two types of CDR1 conformation: one type which was identical to Vk1 and one type only found in Vk3. All Vk CDR2s used the same type of canonical structure. The CDR3 conformation is not encoded in the germline gene segments. Therefore, the 4 Vk families defined by sequence homology and usage corresponded also to 4 types of canonical structures found in Vk germline genes.

The 3 Vl families defined above showed 3 types of CDR1 conformation, each family with one unique type. The Vl1 family contained 2 different CDR1 lengths (13 and 14 amino acids), but identical canonical residues, and it is thought that both lengths adopt the same canonical conformation (Chothia & Lesk, 1987). In the CDR2 of the used Vl germlines, only one canonical conformation exists, and the CDR3 conformation is not encoded in the germline gene segments. Therefore, the 3 Vl families defined by sequence homology and usage corresponded also to 3 types of canonical structures.

The structural repertoire of the human VH sequences was analyzed in detail by Chothia et al., 1992. In total, 3 conformations of CDR1 (H1-1, H1-2 and H1-3) and 6 conformations of CDR2 (H2-1, H2-2, H2-3, H2-4, H2-5 and H2-x) could be defined Since the CDR3 is encoded in the D- and J-minigene segments, no particular canonical residues are defined for this CDR.

All the members of the VH1 family defined above contained the CDR1 conformation H1-1, but differed in their CDR2 conformation: the H2-2 conformation was found in 6 germline genes, whereas the conformation H2-3 was found in 8 germline genes. Since the two types of CDR2 conformations are defined by different types of amino acid at the framework position 72, the VH1 family was divided into two subfamilies:

VH1A with CDR2 conformation H2-2 and VH1B with the conformation H2-3. The members of the VH2 family all had the conformations H1-3 and H2-1 in CDR1 and CDR2, respectively. The CDR1 conformation of the VH3 members was found in all cases to be H1-1, but 4 different types were found in CDR2 (H2-1, H2-3, H2-4 and H2-x). In these CDR2 conformations, the canonical framework residue 71 is always defined by an arginine. Therefore, it was not necessary to divide the VH3 family into subfamilies, since the 4 types of CDR2 conformations were defined solely by the CDR2 itself. The same was true for the VH4 family. Here, all 3 types of CDR1 conformations were found, but since the CDR1 conformation was defined by the CDR itself (the canonical framework residue 26 was found to be glycine in all cases), no subdivisions were necessary. The CDR2 conformation of the VH4 members was found to be H2-1 in all cases. All members of the VH5 family were found to have the conformation H1-1 and H2-2, respectively. The single germline gene of the VH6 family had the conformations H1-3 and H2-5 in CDR1 and CDR2, respectively.

In summary, all possible CDR conformations of the Vk and Vl genes were present in the 7 families defined by sequence comparison. From the 12 different CDR conformations found in the used VH germline genes, 7 could be covered by dividing the family VH1 into two subfamilies, thereby creating 7 VH families. The remaining 5 CDR conformations (3 in the VH3 and 2 in the VH4 family) were defined by the CDRs themselves and could be created during the construction of CDR libraries. Therefore, the structural repertoire of the used human V genes could be covered by 49 (7×7) different frameworks.

1.2.3 Computation of Consensus Sequences

The 14 databases of rearranged sequences (4 Vk, 3 Vl and 7 VH) were used to compute the HuCAL consensus sequences of each subgroup (4 HuCAL-Vk, 3 HuCAL-Vl, 7 HuCAL-VH, see Table 4, 5 and 6). This was done by counting the number of amino acid residues used at each position (position variability) and subsequently identifying the amino acid residue most frequently used at each position. By using the rearranged sequences instead of the used germline sequences for the calculation of the consensus, the consensus was weighted according to the frequency of usage. Additionally, frequently mutated and highly conserved positions could be identified. The consensus sequences were cross-checked with the consensus of the germline families to see whether the rearranged sequences were biased at certain positions towards amino acid residues which do not occur in the collected germline sequences, but this was found not to be the case. Subsequently, the number of differences of each of the 14 consensus sequences to each of the germline sequences found in each specific family was calculated. The overall deviation from the most homologous germline sequence was found to be 2.4 amino acid residues (s.d.=2.7), ensuring that the "artificial" consensus sequences can still be considered as truly human sequences as far as immunogenicity is concerned.

1.3 Structural Analysis

So far, only sequence information was used to design the consensus sequences. Since it was possible that during the calculation certain artificial combinations of amino acid residues have been created, which are located far away in the sequence but have contacts to each other in the three dimensional structure, leading to destabilized or even misfolded frameworks, the 14 consensus sequences were analyzed according to their structural properties.

It was rationalized that all rearranged sequences present in the database correspond to functional and therefore correctly folded antibody molecules. Hence, the most homologous rearranged sequence was calculated for each consensus sequence. The positions where the consensus differed from the rearranged sequence were identified as potential "artificial residues" and inspected.

The inspection itself was done in two directions. First, the local sequence stretch around each potentially "artificial residue" was compared with the corresponding stretch of all the rearranged sequences. If this stretch was found to be truly artificial, i.e. never occurred in any of the rearranged sequences, the critical residue was converted into the second most common amino acid found at this position and analyzed again. Second, the potentially "artificial residues" were analyzed for their long range interactions. This was done by collecting all available structures of human antibody variable domains from the corresponding PDB files and calculating for every structure the number and type of interactions each amino acid residue established to each side-chain. These "interaction maps" were used to analyze the probable side-chain/side-chain interactions of the potentially "artificial residues". As a result of this analysis, the following residues were exchanged (given is the name of the gene, the position according to Kabat's numbering scheme, the amino acid found at this position as the most abundant one and the amino acid which was used instead):

VH2: $S_{65}T$

Vk1: $N_{34}A$,

Vk3: $G_9A$, $D_{60}A$, $R_{77}S$

Vl3: $V_{78}T$ 1.4 Design of CDR Sequences

The process described above provided the complete consensus sequences derived solely from the databases of rearranged sequences. It was rationalized that the CDR1 and CDR2 regions should be taken from the databases of used germline sequences, since the CDRs of rearranged and mutated sequences are biased towards their particular antigens. Moreover, the germline CDR sequences are known to allow binding to a variety of antigens in the primary immune response, where only CDR3 is varied. Therefore, the consensus CDRs obtained from the calculations described above were replaced by germlne CDRs in the case of VH and Vk. In the case of Vl, a few amino acid exchanges were introduced in some of the chosen germline CDRs in order to avoid possible protease cleavage sites as well as possible structural constraints.

The CDRs of following germlne genes have been chosen:

| HuCAL gene | CDR1 | CDR2 |
| --- | --- | --- |
| HuCAL-VH1A | VH1-12-1 | VH1-12-1 |
| HuCAL-VH1B | VH1-13-16 | VH1-13-6, -7, -8, -9 |
| HuCAL-VH2 | VH2-31-10, -11, -12, -13 | VH2-31-3, -4 |
| HuCAL-VH3 | VH3-13-8, -9, -10 | VH3-13-8, -9, -10 |
| HuCAL-VH4 | VH4-11-7 to -14 | VH4-11-8, -9, -11, -12, -14, -16 VH4-31-17, -18, -19, -20 |
| HuCAL-VH5 | VH5-12-1, -2 | VH5-12-1, -2 |
| HuCAL-VH6 | VH6-35-1 | VH6-35-1 |
| HuCAL-Vk1 | Vk1-14, -15 | Vk1-2, -3, -4, -5, -7, -8, -12, -13, -18, -19 |
| HuCAL-Vk2 | Vk2-6 | Vk2-6 |
| HuCAL-Vk3 | Vk3-1, -4 | Vk3-4 |
| HuCAL-Vk4 | Vk4-1 | Vk4-1 |
| HuCAL-Vl1 | HUMLV117, DPL5 | DPL5 |
| HuCAL-Vl2 | DPL11, DPL12 | DPL12 |
| HuCAL-Vl3 | DPL23 | HUMLV318 |

In the case of the CDR3s, any sequence could be chosen since these CDRs were planned to be the first to be replaced by oligonucleotide libraries. In order to study the expression and folding behavior of the consensus sequences in *E. coli*, it would be useful to have all sequences with the same CDR3, since the influence of the CDR3s on the folding behavior would then be identical in all cases. The dummy sequences QQHYTTPP (see, for instance, positions 89–96 of SEQ ID NO: 28 and positions 88–95 of SEQ ID NO: 34) and ARWGGDGFYAMDY (positions 97–109 of SEQ ID NOS 35 & 36) were selected for the VL chains (kappa and lambda) and for the VH chains, respectively. These sequences are known to be compatible with antibody folding in *E. coli* (Carter et al., 1992).

1.5 Gene Design

The final outcome of the process described above was a collection of 14 HuCAL amino acid sequences, which represent the frequently used structural antibody repertoire of the human immune system (see FIG. 2). These sequences were back-translated into DNA sequences. In a first step, the back-translation was done using only codons which are known to be frequently used in *E. coli*. These gene sequences were then used for creating a database of all possible restriction endonuclease sites, which could be introduced without changing the corresponding amino acid sequences. Using this database, cleavage sites were selected which were located at the flanking regions of all sub-elements of the genes (CDRs and framework regions) and which could be introduced in all HuCAL VH, Vk or Vl genes simultaneously at the same position. In a few cases it was not possible to find cleavage sites for all genes of a subgroup. When this happened, the amino acid sequence was changed, if this was possible according to the available sequence and structural information. This exchange was then analyzed again as described above. In total, the following 6 amino acid residues were exchanged during this design (given is the name of the gene, the position according to Kabat's numbering scheme, the amino acid found at this position as the most abundant one and the amino acid which was used instead):

VH2: $T_3Q$

VH6: $S_{42}G$

Vk3: $E_1D$, $I_{58}V$

Vk4: $K_{24}R$

Vl3: $T_{22}S$

In one case (5'-end of VH framework 3) it was not possible to identify a single cleavage site for all 7 VH genes. Two different type of cleavage sites were used instead: BstEII for HuCAL VH1A, VH1B, VH4 and VH5, and NspV for HuCAL VH2, VH3, VH4 and VH6.

Several restriction endonuclease sites were identified, which were not located at the flanking regions of the sub-elements but which could be introduced in every gene of a given group without changing the amino acid sequence. These cleavage sites were also introduced in order to make the system more flexible for further improvements. Finally, all but one remaining restriction endonuclease sites were removed in every gene sequence. The single cleavage site, which was not removed was different in all genes of a subgroup and could be therefore used as a "fingerprint" site to ease the identification of the different genes by restriction digest. The designed genes, together with the corresponding amino acid sequences and the group-specific restriction endonuclease sites are shown in FIGS. 3, 4 and 5, respectively.

1.6 Gene Synthesis and Cloning

The consensus genes were synthesized using the method described by Prodromou & Pearl, 1992, using the oligonucleotides shown in FIG. 6. Gene segments encoding the human constant domains Ck, Cl and CH1 were also synthesized, based on sequence information given by Kabat et al., 1991 (see FIG. 6 and FIG. 7). Since for both the CDR3 and the framework 4 gene segments identical sequences were chosen in all HuCAL Vk, Vl and VH genes, respectively, this part was constructed only once, together with the corresponding gene segments encoding the constant domains. The PCR products were cloned into pCR-Script KS(+) (Stratagene, Inc.) or pZErO-1 (Invitrogen, Inc.) and verified by sequencing.

Example 2

Cloning and Testing of a HuCAL-Based Antibody Library

A combination of two of the synthetic consensus genes was chosen after construction to test whether binding antibody fragments can be isolated from a library based on these two consensus frameworks. The two genes were cloned as a single-chain Fv (scFv) fragment, and a VH-CDR3 library was inserted. In order to test the library for the presence of functional antibody molecules, a selection procedure was carried out using the small hapten fluorescein bound to BSA (FITC-BSA) as antigen.

2.1 Cloning of the HuCAL VH3-Vk2 scFv Fragment

In order to test the design of the consensus genes, one randomly chosen combination of synthetic light and heavy gene (HuCAL-Vk2 and HuCAL-VH3) was used for the construction of a single-chain antibody (scFv) fragment. Briefly, the gene segments encoding the VH3 consensus gene and the CH1 gene segment including the CDR3—framework 4 region, as well as the Vk2 consensus gene and the Ck gene segment including the CDR3—framework 4 region were assembled yielding the gene for the VH3-CH1 Fd fragment and the gene encoding the Vk2-Ck light chain, respectively. The CH1 gene segment was then replaced by an oligonucleotide (SEQ ID NOS 2 & 3, respectively) cassette encoding a 20-mer peptide linker (SEQ ID NO: 1) with the sequence AGGGSGGGGSGGGGSGGGGS. The two oligonucleotides encoding this linker were 5'-TCAGCGGGTGGCGGTTCTGGCGGCGGTGGGAGC GGTGGCGGTGGTTCTGGCGGTGGTGGT-TCCGATATC GGTCCACGTACGG-3' and 5'-AATTCCGTACGTGGACCGATATCGGAACCACCAC CGCCAGAACCACCGCCACCGCTCCCAC-CGCCGCCA GAACCGCCACCCGC-3', respectively. Finally, the HuCAL-Vk2 gene was inserted via EcoRV and BsiWI into the plasmid encoding the HuCAL-VH3-linker fusion, leading to the final gene HuCAL-VH3-Vk2, which encoded the two consensus sequences in the single-chain format VH-linker-VL. The complete coding sequence is shown in FIG. 8.

2.2 Construction of a Monovalent Phage-display Phagemid Vector pIG10.3

Phagemid pIG10.3 (FIG. 9) was constructed in order to create a phage-display system (Winter et al., 1994) for the H3k2 scFv gene. Briefly, the EcoRI/HindIII restriction fragment in the phagemid vector pIG10 (Ge et al., 1995) was replaced by the c-myc followed by an amber codon (which encodes an glutamate in the amber-suppresser strain XL1 Blue and a stop codon in the non-suppresser strain JM83) and a truncated version of the gene III (fusion junction at codon 249, see Lowman et al., 1991) through PCR mutagenesis.

2.3 Construction of H-CDR3 Libraries

Heavy chain CDR3 libraries of two lengths (10 and 15 amino acids) were constructed using trinucleotide codon containing oligonucleotides (Virnekäs et al., 1994) as templates and the oligonucleotides complementing the flanking regions as primers. To concentrate only on the CDR3 structures that appear most often in functional antibodies, we kept the salt-bridge of $R_{H94}$ and $D_{H101}$ in the CDR3 loop. For the 15-mer library, both phenylalanine and methionine were introduced at position 100 since these two residues were found to occur quite often in human CDR3s of this length (not shown). For the same reason, valine and tyrosine were introduced at position 102. All other randomized positions contained codons for all amino acids except cystein, which was not used in the trinucleotide mixture.

The CDR3 libraries of lengths 10 and 15 were generated from the PCR fragments using oligonucleotide templates (SEQ ID NOS 4 & 5, respectively) O3HCDR103T (5'-GATACGGCCGTGTATTATTGCGCGCGT $(TRI)_6$GATTATTGGGGCCAAGGCACCCTG-3') and O3H CDR153T (5'-GATACGGCCGTGTATTATTGCGCGCGT $(TRI)_{10}$(TT T/ATG)GAT(GTT/TAT)TGGGGCCAAGGCACCCTG-3'), and primers (SEQ ID NOS 6 & 7, respectively) O3HCDR35 (5'-GATACGGCCGTGTATTATTGC-3') and O3HCDR33 (5'-CAGGGTGCCTTGGCCCC-3'), where TRI are trinucleotide mixtures representing all amino acids without cystein, (TTT/ATG) and (GTT/TAT) are trinucleotide mixtures encoding the amino acids phenylalanine/methionine and valine/tyrosine, respectively. The potential diversity of these libraries was $4.7\times10^7$ and $3.4\times10^{10}$ for 10-mer and 15-mer library, respectively. The library cassettes were first synthesized from PCR amplification of the oligo templates in the presence of both primers: 25 pmol of the oligo template O3HCDR103T or O3HCDR153T, 50 pmol each of the primers O3HCDR35 and O3HCDR33, 20 nmol of dNTP, 10× buffer and 2.5 units of Pfu DNA polymerase (Stratagene) in a total volume of 100 ml for 30 cycles (1 minute at 92° C., 1 minute at 62° C. and 1 minute at 72° C.). A hot-start procedure was used. The resulting mixtures were phenol-extracted, ethanol-precipitated and digested overnight with EagI and StyI. The vector pIG10.3-scH3k2cat, where the EagI-StyI fragment in the vector pIG10.3-scH3k2 encoding the H-CDR3 was replaced by the chloramphenicol acetyltransferase gene (cat) flanked with these two sites, was similarly digested. The digested vector (35 μg) was gel-purified and ligated with 100 μg of the library cassette overnight at 16° C. The ligation mixtures were isopropanol precipitated, air-dried and the pellets were redissolved in 100 ml of ddH2O. The ligation was mixed with 1 ml of freshly prepared electrocompetent XL1 Blue on ice. 20 rounds of electroporation were performed and the transformants were diluted in SOC medium, shaken at 37° C. for 30 minutes and plated out on large LB plates (Amp/Tet/Glucose) at 37° C. for 6–9 hrs. The number of transformants (library size) was $3.2\times10^7$ and $2.3\times10^7$ for the 10-mer and the 15-mer library, respectively. The colonies were suspended in 2×YT medium (Amp/Tet/Glucose) and stored as glycerol culture.

In order to test the quality of the initial library, phagemids from 24 independent colonies (12 from the 10-mer and 12 from the 15-mer library, respectively) were isolated and analyzed by restriction digestion and sequencing. The restriction analysis of the 24 phagemids indicated the presence of intact vector in all cases. Sequence analysis of these clones (see FIG. 10) indicated that 22 out of 24 contained a functional sequence in their heavy chain CDR3 regions. 1 out of 12 clones of the 10-mer library had a CDR3 of length 9 instead of 10, and 2 out of 12 clones of the 15-mer library had no open reading frame, thereby leading to a non-functional scFv; one of these two clones contained two consecutive inserts, but out of frame (data not shown). All codons introduced were presented in an even distribution.

Expression levels of individual library members were also measured. Briefly, 9 clones from each library were grown in 2×YT medium containing Amp/Tet/0.5% glucose at 37° C. overnight. Next day, the cultures were diluted into fresh medium with Amp/Tet. At an $OD_{600\ nm}$ of 0.4, the cultures were induced with 1 mM of IPTG and shaken at RT overnight. Then the cell pellets were suspended in 1 ml of PBS buffer+1 mM of EDTA. The suspensions were sonicated and the supernatants were separated on an SDS-PAGE under reducing conditions, blotted on nylon membrane and detected with anti-FLAG M1 antibody (see FIG. 11). From the nine clones of the 10-mer library, all express the scFv fragments. Moreover, the gene III/scFv fusion proteins were present in all cases. Among the nine clones from the 15-mer library analyzed, 6/9 (67%) led to the expression of both scFv and the gene III/scFv fusion proteins. More importantly, all clones expressing the scFvs and gene III/scFv fusions gave rise to about the same level of expression.

2.4 Biopanning

Phages displaying the antibody libraries were prepared using standard protocols. Phages derived from the 10-mer library were mixed with phages from the 15-mer library in a ratio of 20:1 ($1\times10^{10}$ cfu/well of the 10-mer and $5\times10^8$ cfu/well of the 15-mer phages, respectively). Subsequently, the phage solution was used for panning in ELISA plates (Maxisorp, Nunc) coated with FITC-BSA (Sigma) at concentration of 100 μg/ml in PBS at 4° C. overnight. The antigen-coated wells were blocked with 3% powder milk in PBS and the phage solutions in 1% powder milk were added to each well and the plate was shaken at RT for 1 hr. The wells were then washed with PBST and PBS (4 times each with shaking at RT for 5 minutes). The bound phages were eluted with 0.1 M triethylamine (TEA) at RT for 10 minutes. The eluted phage solutions were immediately neutralized with ½ the volume of 1 M Tris.Cl, pH 7.6. Eluted phage solutions (ca. 450 μl) were used to infect 5 ml of XL1 Blue cells at 37° C. for 30 min. The infected cultures were then plated out on large LB plates (Amp/Tet/Glucose) and allowed to grow at 37° C. until the colonies were visible. The colonies were suspended in 2×YT medium and the glycerol cultures were made as above described. This panning round was repeated twice, and in the third round elution was carried out with addition of fluorescein in a concentration of 100 μg/ml in PBS. The enrichment of specific phage antibodies was monitored by panning the initial as well as the subsequent fluorescein-specific sub-libraries against the blocking buffer (FIG. 12). Antibodies with specificity against fluorescein were isolated after 3 rounds of panning.

2.5 ELISA Measurements

One of the criteria for the successful biopanning is the isolation of individual phage clones that bind to the targeted antigen or hapten. We undertook the isolation of anti-FITC phage antibody clones and characterized them first in a phage ELISA format. After the 3rd round of biopanning (see above), 24 phagemid containing clones were used to inoculate 100 μl of 2×YT medium (Amp/Tet/Glucose) in an ELISA plate (Nunc), which was subsequently shaken at 37° C. for 5 hrs. 100 μl of 2×YT medium (Amp/Tet/1 mM IPTG) were added and shaking was continued for 30 minutes. A further 100 μl of 2×YT medium (Amp/Tet) containing the helper phage ($1\times10^9$ cfu/well) was added and shaking was done at RT for 3 hrs. After addition of kanamycin to select for successful helper phage infection, the shaking was continued overnight. The plates were then centrifuged and the supernatants were pipetted directly into ELISA wells coated with 100 μl FITC-BSA (100 μg/ml) and blocked with milk powder. Washing was performed similarly as during the panning procedure and the bound phages were detected with anti-M13 antibody-POD conjugate (Pharmacia) using soluble POD substrate (Boehringer-Mannheim). Of the 24 clones screened against FITC-BSA, 22 were active in the ELISA (FIG. 13). The initial libraries of similar titer gave rise to no detectable signal.

Specificity for fluorescein was measured in a competitive ELISA. Periplasmic fractions of five FITC specific scFvs were prepared as described above. Western blotting indicated that all clones expressed about the same amount of scFv fragment (data not shown). ELISA was performed as described above, but additionally, the periplasmic fractions were incubated 30 min at RT either with buffer (no inhibition), with 10 mg/ml BSA (inhibition with BSA) or with 10 mg/ml fluorescein (inhibition with fluorescein) before adding to the well. Binding scFv fragment was detected using the anti-FLAG antibody M1. The ELISA signal could only be inhibited, when soluble fluorescein was added, indicating binding of the scFvs was specific for fluorescein (FIG. 14).

2.6 Sequence Analysis

The heavy chain CDR3 region of 20 clones were sequenced in order to estimate the sequence diversity of fluorescein binding antibodies in the library (FIG. 15). In total, 16 of 20 sequences (80%) were different, showing that the constructed library contained a highly diverse repertoire of fluorescein binders. The CDR3s showed no particular sequence homology, but contained on average 4 arginine residues. This bias towards arginine in fluorescein binding antibodies had already been described by Barbas et al., 1992.

2.7 Production

*E. coli* JM83 was transformed with phagemid DNA of 3 selected clones and cultured in 0.5 L 2×YT medium. Induction was carried out with 1 mM IPTG at $OD_{600\ nm}$=0.4 and growth was continued with vigorous shaking at RT overnight. The cells were harvested and pellets were suspended in PBS buffer and sonicated. The supernatants were separated from the cell debris via centrifugation and purified via the BioLogic system (Bio-Rad) by with a POROS®MC 20 column (IMAC, PerSeptive Biosystems, Inc.) coupled with an ion-exchange chromatography column. The ion-exchange column was one of the POROS®HS, CM or HQ or PI 20 (PerSeptive Biosystems, Inc.) depended on the theoretical pI of the scFv being purified. The pH of all the buffers was adjusted to one unit lower or higher than the pI of the scFv being purified throughout. The sample was loaded onto the first IMAC column, washed with 7 column volumes of 20 mM sodium phosphate, 1 M NaCl and 10 mM imidazole. This washing was followed by 7 column volumes of 20 mM sodium phosphate and 10 mM imidazole. Then 3 column volumes of an imidazole gradient (10 to 250 mM) were applied and the eluent was connected directly to the ion-exchanger. Nine column volumes of isocratic washing with 250 mM imidazole was followed by 15 column volumes of 250 mM to 100 mM and 7 column volumes of an imidazole/NaCl gradient (100 to 10 mM imidazole, 0 to 1 M NaCl). The flow rate was 5 ml/min. The purity of scFv fragments was checked by SDS-PAGE Coomassie staining (FIG. 16). The concentration of the fragments was determined from the absorbance at 280 nm using the theoretically determined extinction coefficient (Gill & von Hippel, 1989). The scFv fragments could be purified to homogeneity (see FIG. 16). The yield of purified fragments ranged from 5 to 10 mg/L/OD.

Example 3

HuCAL H3k2 Library Against a Collection of Antigens

In order to test the library used in Example 2 further, a new selection procedure was carried out using a variety of antigens comprising β-estradiol, testosterone, Lewis-Y epitope (LeY), interleukin-2 (IL-2), lymphotoxin-β (LT-β), E-selectin ligand-1 (ESL-1), and BSA.

3.1 Biopanning

The library and all procedures were identical to those described in Example 2. The ELISA plates were coated with β-estradiol-BSA (100 μg/ml), testosterone-BSA (100 μg/ml), LeY-BSA (20 μg/ml) IL-2 (20 μg/ml), ESL-1 (20 μg/ml) and BSA (100 μg/ml), LT-β (denatured protein, 20 μg/ml). In the first two rounds, bound phages were eluted with 0.1 M triethylamine (TEA) at RT for 10 minutes. In the case of BSA, elution after three rounds of panning was carried out with addition of BSA in a concentration of 100 μg/ml in PBS. In the case of the other antigens, third round elution was done with 0.1 M triethylamine. In all cases except LeY, enrichment of binding phages could be seen (FIG. 17). Moreover, a repetition of the biopanning experiment using only the 15-mer library resulted in the enrichment of LeY-binding phages as well (data not shown).

3.2. ELISA Measurements

Clones binding to β-estradiol, testosterone, LeY, LT-β, ESL-1 and BSA were further analyzed and characterized as described in Example 2 for FITC. ELISA data for anti-β-estradiol and anti-ESL-1 antibodies are shown in FIG. 18. In one experiment, selectivity and cross-reactivity of binding scFv fragments were tested. For this purpose, an ELISA plate was coated with FITC, testosterone, β-estradiol, BSA, and ESL-1, with 5 wells for each antigen arranged in 5 rows, and 5 antibodies, one against each of the antigens, were screened against each of the antigens. FIG. 19 shows the specific binding of the antibodies to the antigen it was selected for, and the low cross-reactivity with the other four antigens.

3.3 Sequence Analysis

The sequencing data of several clones against β-estradiol (34 clones), testosterone (12 clones), LT-β (23 clones), ESL-1 (34 clones), and BSA (10 clones) are given in FIGS. 20 to 24.

Example 4

Vector Construction

To be able to take advantage of the modularity of the consensus gene repertoire, a vector system had to be constructed which could be used in phage display screening of HuCAL libraries and subsequent optimization procedures. Therefore, all necessary vector elements such as origins of single-stranded or double-stranded replication, promotor/operator, repressor or terminator elements, resistance genes, potential recombination sites, gene III for display on filamentous phages, signal sequences, or detection tags had to be made compatible with the restriction site pattern of the modular consensus genes. FIG. 25 shows a schematic representation of the pCAL vector system and the arrangement of vector modules and restriction sites therein. FIG. 25*a* shows a list of all restriction sites which are already incorporated into the consensus genes or the vector elements as part of the modular system or which are not yet present in the whole system. The latter could be used in a later stage for the introduction of or within new modules.

4.1 Vector Modules

A series of vector modules was constructed where the restriction sites flanking the gene sub-elements of the HuCAL genes were removed, the vector modules themselves being flanked by unique restriction sites. These modules were constructed either by gene synthesis or by mutagenesis of templates. Mutagenesis was done by add-on PCR, by site-directed mutagenesis (Kunkel et al., 1991) or multisite oligonucleotide-mediated mutagenesis (Sutherland et al., 1995; Perlak, 1990) using a PCR-based assembly method.

FIG. 26 contains a list of the modules constructed. Instead of the terminator module M9 (HindIII-Ipp-PacI), a larger cassette M9II was prepared to introduce FseI as additional restriction site. M9II can be cloned via HindIII/BsrGI.

All vector modules were characterized by restriction analysis and sequencing. In the case of module M11-II, sequencing of the module revealed a two-base difference in positions 164/65 compared to the sequence database of the template. These two different bases (CA→GC) created an additional BanII site. Since the same two-base difference occurs in the f1 origin of other bacteriophages, it can be assumed that the two-base difference was present in the template and not created by mutagenesis during cloning. This BanII site was removed by site-directed mutagenesis, leading to module M11-III. The BssSI site of module M14 could initially not be removed without impact on the function of the ColE1 origin, therefore M14-Ext2 was used for cloning of the first pCAL vector series. FIGS. 29 to 34 are showing the functional maps and sequences of the modules used for assembly of the modular vector pCAL4 (see below). The functional maps and sequences of additional modules can be found in FIG. 35*a*. FIG. 35*b* contains a list of oligonucleotides and primers used for the synthesis of the modules.

4.2 Cloning Vector pMCS

To be able to assemble the individual vector modules, a cloning vector pMCS containing a specific multi-cloning site (MCS) was constructed. First, an MCS cassette (FIG. 27) was made by gene synthesis. This cassette contains all those restriction sites in the order necessary for the sequential introduction of all vector modules and can be cloned via the 5'-HindIII site and a four base overhang at the 3'-end compatible with an AatII site. The vector pMCS (FIG. 28) was constructed by digesting pUC19 with AatII and HindIII, isolating the 2174 base pair fragment containing the bla gene and the ColE1 origin, and ligating the MCS cassette.

4.3 Cloning of Modular Vector pCAL4

This was cloned step by step by restriction digest of pMCS and subsequent ligation of the modules M1 (via AatII/XbaI), M7III (via EcoRI/HindIII), and M9II (via HindIII/BsrGI), and M11-II (via BsrGI/NheI). Finally, the bla gene was replaced by the cat gene module M17 (via AatII/BglII), and the wild type ColE1 origin by module M14-Ext2 (via BglII/NheI). FIG. 35 is showing the functional map and the sequence of pCAL4.

4.4 Cloning of Low-copy Number Plasmid Vectors pCALO

A series of low-copy number plasmid vectors was constructed in a similar way using the p15A module M12 instead of the ColE1 module M14-Ext2. FIG. 35*a* is showing the functional maps and sequences of the vectors pCALO1 to pCALO3.

Example 5

Construction of a HuCAL scFv Library 5.1. Cloning of All 49 HuCAL scFv Fragments All 49 combinations of the 7 HuCAL-VH and 7 HuCAL-VL consensus genes were assembled as described for the HuCAL VH3-Vk2 scFv in Example 2 and inserted into the vector pBS12, a modified version of the pLisc series of antibody expression vectors (Skerra et al., 1991).

5.2 Construction of a CDR Cloning Cassette

For replacement of CDRs, a universal β-lactamase cloning cassette was constructed having a multi-cloning site at the 5'-end as well as at the 3'-end. The 5'-multi-cloning site comprises all restriction sites adjacent to the 5'-end of the HuCAL VH and VL CDRs, the 3'-multi-cloning site comprises all restriction sites adjacent to the 3' end of the HuCAL VH and VL CDRs. Both 5'- and 3'-multi-cloning site were prepared as cassettes via add-on PCR using synthetic oligonucleotides as 5'- and 3'-primers using wild type β-lactamase gene as template. FIG. 36 shows the functional map and the sequence of the cassette bla-MCS.

5.3. Preparation of VL-CDR3 Library Cassettes

The VL-CDR3 libraries comprising 7 random positions were generated from the PCR fragments using oligonucleotide templates Vk1&Vk3, Vk2 and Vk4 and primers O_K3L_5 and O_K3L_3 (FIG. 37) for the Vk genes, and Vl and primers (SEQ ID NO: 8) O_L3L_5 (5'-GCAGAAGGCGAACGTCC-3') and O_L3LA_3 (FIG. 38) for the Vl genes. Construction of the cassettes was performed as described in Example 2.3.

5.4 Cloning of HuCAL scFv Genes With VL-CDR3 Libraries

Each of the 49 single-chains was subcloned into pCAL4 via XbaI/EcoRI and the VL-CDR3 replaced by the β-lactamase cloning cassette via BbsI/MscI, which was then replaced by the corresponding VL-CDR3 library cassette synthesized as described above. This CDR replacement is described in detail in Example 2.3 where the cat gene was used.

5.5 Preparation of VH-CDR3 Library Cassette

The VH-CDR3 libraries were designed and synthesized as described in Example 2.3.

5.6 Cloning of HuCAL scFv Genes With VL- and VH-CDR3 Libraries

Each of the 49 single-chain VL-CDR3 libraries was digested with BssHII/StyI to replace VH-CDR3. The "dummy" cassette digested with BssHII/StyI was inserted, and was then replaced by a corresponding VH-CDR3 library cassette synthesized as described above.

Example 6

Expression Tests

Expression and toxicity studies were performed using the scFv format VH-linker-VL. All 49 combinations of the 7 HuCAL-VH and 7 HuCAL-VL consensus genes assembled as described in Example 5 were inserted into the vector pBS13, a modified version of the pLisc series of antibody expression vectors (Skerra et al., 1991). A map of this vector is shown in FIG. 39.

*E. coli* JM83 was transformed 49 times with each of the vectors and stored as glycerol stock. Between 4 and 6 clones were tested simultaneously, always including the clone H3k2, which was used as internal control throughout. As additional control, the McPC603 scFv fragment (Knappik & Plückthun, 1995) in pBS13 was expressed under identical conditions. Two days before the expression test was performed, the clones were cultivated on LB plates containing 30 μg/ml chloramphenicol and 60 mM glucose. Using this plates an 3 ml culture (LB medium containing 90 μg chloramphenicol and 60 mM glucose) was inoculated overnight at 37 ° C. Next day the overnight culture was used to inoculate 30 ml LB medium containing chloramphenicol (30 μg/ml). The starting $OD_{600\ nm}$ was adjusted to 0.2 and a growth temperature of 30° C. was used. The physiology of the cells was monitored by measuring every 30 minutes for 8 to 9 hours the optical density at 600 nm. After the culture reached an $OD_{600\ nm}$ of 0.5, antibody expression was induced by adding IPTG to a final concentration of 1 mM. A 5 ml aliquot of the culture was removed after 2 h of induction in order to analyze the antibody expression. The cells were lysed and the soluble and insoluble fractions of the crude extract were separated as described in Knappik & Plückthun, 1995. The fractions were assayed by reducing SDS-PAGE with the samples normalized to identical optical densities. After blotting and immunostaining using the α-FLAG antibody M1 as the first antibody (see Ge et al., 1994) and an Fc-specific anti-mouse antiserum conjugated to alkaline phosphatase as the second antibody, the lanes were scanned and the intensities of the bands of the expected size (appr. 30 kDa) were quantified densitometrically and tabulated relative to the control antibody (see FIG. 40).

Example 7

Optimization of Fluorescein Binders 7.1. Construction of L-CDR3 and H-CDR2 Library Cassettes A L-CDR3 library cassette was prepared from the oligonucleotide (SEQ ID NO: 9) template CDR3L (5'-TGGAAGCTGAAGACGTGGGCGTGTATTATTGCCAGCAG(TR5)$(TRI)_4$CCG(TRI)TTTGGCCAGGGTACGAAAGTT-3') and primer (SEQ ID NO: 10) 5'-AATTTCGTACCCTGGCC-3' for synthesis of the complementary strand, where (TRI) was a trinucleotide mixture representing all amino acids except Cys, (TR5) comprised a trinucleotide mixture representing the 5 codons for Ala, Arg, His, Ser, and Tyr.

A H-CDR2 library cassette was prepared from the oligonucleotide template CDRsH (SEQ ID NOS 11 & 12, respectively) (5'-AGGGTCTCGAGTGGGTGAGC(TRI)ATT$(TRI)_{2-3}(6)_2$(TRI)ACC(TRI)TATGCGGATAGCGTGAAAGGCCGTTTTACCATTTCACGTGATAATTCGAAAAACACCA-3'), and primer (SEQ ID NO: 13) 5'-TGGTGTTTTTCGAATTATCA-3' for synthesis of the complementary strand, where (TRI) was a trinucleotide mixture representing all amino acids except Cys, (6) comprised the incorporation of (A/G) (A/C/G) T, resulting in the formation of 6 codons for Ala, Asn, Asp, Gly, Ser, and Thr, and the length distribution being obtained by performing one substoichiometric coupling of the (TRI) mixture during synthesis, omitting the capping step normally used in DNA synthesis.

DNA synthesis was performed on a 40 nmole scale, oligos were dissolved in TE buffer, purified via gel filtration using spin columns (S-200), and the DNA concentration determined by OD measurement at 260 nm (OD 1.0=40 μg/ml).

10 nmole of the oligonucleotide templates and 12 nmole of the corresponding primers were mixed and annealed at 80° C. for 1 min, and slowly cooled down to 37° C. within 20 to 30 min. The fill-in reaction was performed for 2 h at 37° C. using Klenow polymerase (2.0 μl) and 250 nmole of each dNTP. The excess of dNTPs was removed by gel filtration using Nick-Spin columns (Pharmacia), and the double-stranded DNA digested with Bbsl/Mscl (L-CDR3), or Xhol/Sful (H-CDR2) over night at 37° C. The cassettes were purified via Nick-Spin columns (Pharmacia), the concentration determined by OD measurement, and the cassettes aliquoted (15 pmole) for being stored at −80° C.

7.2 Library Cloning

DNA was prepared from the collection of FITC binding clones obtained in Example 2 (approx. $10^4$ to clones). The collection of scFv fragments was isolated via Xbal/EcoRI digest. The vector pCAL4 (100 fmole, 10 μg) described in Example 4.3 was similarly digested with Xbal/EcoRI, gel-purified and ligated with 300 fmole of the scFv fragment collection over night at 16° C. The ligation mixture was isopropanol precipitated, air-dried, and the pellets were redissolved in 100 μl of dd $H_2O$. The ligation mixture was mixed with 1 ml of freshly prepared electrocompetent SCS 101 cells (for optimization of L-CDR3), or XL1 Blue cells (for optimization of H-CDR2) on ice. One round of electroporation was performed and the transformants were eluted in SOC medium, shaken at 37° C. for 30 minutes, and an aliquot plated out on LB plates (Amp/Tet/Glucose) at 37° C. for 6–9 hrs. The number of transformants was $5\times10^4$.

Vector DNA (100 μg) was isolated and digested (sequence and restriction map of scH3k2 see FIG. 8) with Bbsl/Mscl for optimization of L-CDR3, or Xhol/NspV for optimization of H-CDR2. 10 μg of purified vector fragments (5 pmole) were ligated with 15 pmole of the L-CDR3 or H-CDR2 library cassettes over night at 16° C. The ligation mixtures were isopropanol precipitated, air-dried, and the pellets were redissolved in 100 μl of dd $H_2O$. The ligation mixtures, were mixed with 1 ml of freshly prepared electrocompetent XL1 Blue cells on ice. Electroporation was performed and the transformants were eluted in SOC medium and shaken at 37° C. for 30 minutes. An aliquot was plated out on LB plates (Amp/Tet/Glucose) at 37° C. for 6–9 hrs. The number of transformants (library size) was greater than $10^8$ for both libraries. The libraries were stored as glycerol cultures.

7.3. Biopanning

This was performed as described for the initial H3k2 H-CDR3 library in Example 2.1. Optimized scFvs binding to FITC could be characterized and analyzed as described in Example 2.2 and 2.3, and further rounds of optimization could be made if necessary.

REFERENCES

Barbas III, C. F., Bain, J. D., Hoekstra, D. M. & Lerner, R. A., PNAS 89, 4457–4461 (1992).

Better, M., Chang, P., Robinson, R. & Horwitz, A. H., Science 240, 1041–1043 (1988).

Blake, M. S., Johnston, K. H., Russel-Jones, G. J. & Gotschlich, E. C., Anal. Biochem. 136, 175–179 (1984).

Carter, P., Kelly, R. F., Rodrigues, M. L., Snedecor, B., Covrrubias, M., Velligan, M. D., Wong, W. L. T ., Rowland, A. M., Kotts, C. E., Carver, M. E., Yang, M., Bourell, J. H., Shepard, H. M. & Henner, D., Bio/Technology 10, 163–167 (1992).

Chothia, C. & Lesk, A. M., J. Biol. Chem. 196, 910–917 (1987).

Chothia, C., Lesk, A. M., Gherardi, E., Tomlinson, I. A., Walter, G., Marks, J. D., Llewelyn, M. B. & Winter, G., J. Mol. Biol. 227, 799–817 (1992).

Chothia, C., Lesk, A. M., Tramontano, A., Levitt, M., Smith-Gill, S. J., Air, G., Sheriff, S., Padlan, E. A., Davies, D., Tulip, W. R., Colman, P. M., Spinelli, S., Alzari, P. M. & Poljak, R. J., Nature 342, 877–883 (1989).

Chuchana, P., Blancher, A., Brockly, F., Alexandre, D., Lefranc, G. & Lefranc, M.-P., Eur. J. Immunol. 20, 1317–1325 (1990).

Cox, J. P. L., Tomlinson, I. M. & Winter, G., Eur. J. Immunol. 24, 827–836 (1994).

Ge, L., Knappik, A., Pack, P., Freund, C. & Plückthun, A., In: Antibody Engineering. Borrebaeck, C. A. K. (Ed.). p.229–266 (1995), Oxford University Press, New York, Oxford.)

Gill, S. C. & von Hippel, P. H., Anal. Biochem. 182, 319.326 (1989).

Hochuli, E., Bannwarth, W., Döbeli, H., Gentz, R. & Stüber, D., Bio/Technology 6, 1321–1325 (1988).

Hopp, T. P., Prickett, K. S., Price, V. L., Libby, R. T., March, C. J., Cerretti, D. P., Urdal, D. L. & Conlon, P. J. Bio/Technology 6, 1204–1210 (1988).

Kabat, E. A., Wu, T. T., Perry, H. M., Gottesmann, K. S. & Foeller, C., Sequences of proteins of immunological interest, NIH publication 91–3242 (1991).

Knappik, A. & Plückthun, A., Biotechniques 17, 754–761 (1994).

Knappik, A. & Plückthun, A., Protein Engineering 8, 81–89 (1995).

Kunkel, T. A., Bebenek, K. & McClary, J., Methods in Enzymol. 204, 125–39 (1991).

Lindner, P., Guth, B., Wülfing, C., Krebber, C., Steipe, B., M üller, F. & Plückthun, A., Methods: A Companion to Methods Enzymol. 4, 41–56 (1992).

Lowman, H. B., Bass, S. H., Simpson, N. and Wells, J. A., Biochemistry 30, 10832–10838(1991).

Pack, P. & Plückthun, A., Biochemistry 31, 1579–1584 (1992).

Pack, P., Kujau, M., Schroeckh, V., Knüpfer, U., Wenderoth, R., Riesenberg D. & Plückthun, A., Bio/Technology 11, 1271–1277 (1993).

Pack, P., Ph.D. thesis, Ludwig-Maximilians-Universität M ünchen (1994).

Periak, F. J., Nuc. Acids Res. 18, 7457–7458 (1990).

Plückthun, A., Krebber, A., Krebber, C., Horn, U., Knüpfer, U., Wenderoth, R., Nieba, L., Proba, K. & Riesenberg, D., A practical approach. Antibody Engineering (Ed. J. McCafferty). IRL Press, Oxford, pp. 203–252 (1996).

Prodromou, C. & Pearl, L. H., Protein Engineering 5, 827–829 (1992).

Rosenberg, S. A. & Lotze, M. T., Ann. Rev. Immunol. 4, 681–709 (1986).

Skerra, A. & Plückthun, A., Science 240, 1038–1041 (1988).

Skerra, A., Pfitzinger, I. & Plückthun, A., Bio/Technology9, 273–278 (1991).

Sutherland, L., Davidson, J., Glass, L. L., & Jacobs, H. T., BioTechniques 18, 458–464, 1995.

Tomlinson, I. M., Walter, G., Marks, J. D., Llewelyn, M. B. & Winter, G., J. Mol. Biol. 227, 776–798 (1992).

Ullrich, H. D., Patten, P. A., Yang, P. L., Romesberg, F. E. & Schultz, P. G., Proc. Natl. Acad. Sci. USA 92, 11907–11911 (1995).

Van Dijk, K. W., Mortari, F., Kirkham, P. M., Schroeder Jr., H. W. & Milner, E. C. B., Eur. J. Immunol. 23, 832–839 (1993).

Virnekäs, B., Ge, L., Plückthun, A., Schneider, K. C., Wellnhofer, G. & Moroney, S. E., Nucleic Acids Research 22, 5600–5607 (1994).

Vitetta, E. S., Thorpe, P. E. & Uhr, J., Immunol. Today 14, 253–259 (1993).

Williams, S. C. & Winter, G., Eur. J. Immunol. 23, 1456–1461 (1993).

Winter, G., Griffiths, A. D., Hawkins, R. E. & Hoogenboom, H. R., Ann. Rev. Immunol. 12, 433–455 (1994).

TABLE 1A

Human kappa germline gene segments

| Used Name[1] | Reference[2] | Family[3] | Germline genes[4] |
|---|---|---|---|
| Vk1-1 | 9 | 1 | 08; 018; DPK1 |
| Vk1-2 | 1 | 1 | L14; DPK2 |
| Vk1-3 | 2 | 1 | L15(1); HK101; HK146; HK189 |
| Vk1-4 | 9 | 1 | L11 |
| Vk1-5 | 2 | 1 | A30 |
| Vk1-6 | 1 | 1 | LFVK5 |
| Vk1-7 | 1 | 1 | LFVK431 |
| Vk1-8 | 1 | 1 | L1; HK137 |
| Vk1-9 | 1 | 1 | A20; DPK4 |
| Vk1-10 | 1 | 1 | L18; Va" |
| Vk1-11 | 1 | 1 | L4; L18; Va'; V4a |
| Vk1-12 | 2 | 1 | L5; L19(1); Vb; Vb4; DPK5; L19(2); Vb"; DPK6 |
| Vk1-13 | 2 | 1 | L15(2); HK134; HK166; DPK7 |
| Vk1-14 | 8 | 1 | L8; Vd; DPK8 |
| Vk1-15 | 8 | 1 | L9; Ve |
| Vk1-16 | 1 | 1 | L12(1); HK102; V1 |
| Vk1-17 | 2 | 1 | L12(2) |
| Vk1-18 | 1 | 1 | 012a(V3b) |
| Vk1-19 | 6 | 1 | 02; 012; DPK9 |
| Vk1-20 | 2 | 1 | L24; Ve"; V13; DPK10 |
| Vk1-21 | 1 | 1 | 04; 014 |
| Vk1-22 | 2 | 1 | L22 |
| Vk1-23 | 2 | 1 | L23 |
| Vk2-1 | 1 | 2 | A2; DPK12 |
| Vk2-2 | 6 | 2 | 01; 011(1); DPK13 |
| Vk2-3 | 6 | 2 | 012(2); V3a |
| Vk2-4 | 2 | 2 | L13 |
| Vk2-5 | 1 | 2 | DPK14 |
| Vk2-6 | 4 | 2 | A3; A19; DPK15 |
| Vk2-7 | 4 | 2 | A29; DPK27 |
| Vk2-8 | 4 | 2 | A13 |
| Vk2-9 | 1 | 2 | A23 |
| Vk2-10 | 4 | 2 | A7; DPK17 |
| Vk2-11 | 4 | 2 | A17; DPK18 |
| Vk2-12 | 4 | 2 | A1; DPK19 |
| Vk3-1 | 11 | 3 | A11; humkv305; DPK20 |
| Vk3-2 | 1 | 3 | L20; Vg" |
| Vk3-3 | 2 | 3 | L2; L1G; humkv328; humkv328h2; humkv328h5; DPK21 |
| Vk3-4 | 11 | 3 | A27; humkv325; VkRF; DPK22 |
| Vk3-5 | 2 | 3 | L25; DPK23 |
| Vk3-6 | 2 | 3 | L10(1) |
| Vk3-7 | 7 | 3 | L10(2) |
| Vk3-8 | 7 | 3 | L6; Vg |
| Vk4-1 | 3 | 4 | B3; VkIV; DPK24 |

TABLE 1A-continued

| Human kappa germline gene segments | | | |
|---|---|---|---|
| Used Name[1] | Reference[2] | Family[3] | Germline genes[4] |
| Vk5-1 | 10 | 5 | B2; EV15 |
| Vk6-1 | 12 | 6 | A14; DPK25 |
| Vk6-2 | 12 | 6 | A10; A26; DPK26 |
| Vk7-1 | 5 | 7 | B1 |

TABLE 1B

| Human lambda germline gene segments | | | |
|---|---|---|---|
| Used Name[1] | Reference[2] | Family[3] | Germline genes[4] |
| DPL1 | 1 | 1 | |
| DPL2 | 1 | 1 | HUMLV1L1 |
| DPL3 | 1 | 1 | HUMLV122 |
| DPL4 | 1 | 1 | VLAMBDA 1.1 |
| HUMLV117 | 2 | 1 | |
| DPL5 | 1 | 1 | HUMLV117D |
| DPL6 | 1 | 1 | |
| DPL7 | 1 | 1 | IGLV1S2 |
| DPL8 | 1 | 1 | HUMLV1042 |
| DPL9 | 1 | 1 | HUMLV101 |
| DPL10 | 1 | 2 | |
| VLAMBDA 2.1 | 3 | 2 | |
| DPL11 | 1 | 2 | |
| DPL12 | 1 | 2 | |
| DPL13 | 1 | 2 | |
| DPL14 | 1 | 2 | |
| DPL16 | 1 | 3 | Humlv418; IGLV3S1 |
| DPL23 | 1 | 3 | VI III.1 |
| Humlv318 | 4 | 3 | |
| DPL18 | 1 | 7 | 4A; HUMIGLVA |
| DPL19 | 1 | 7 | |
| DPL21 | 1 | 8 | VL8.1 |
| HUMLV801 | 5 | 8 | |
| DPL22 | 1 | 9 | |
| DPL24 | 1 | unassigned | VLAMBDA N.2 |
| qVLX-4.4 | 6 | 10 | |

TABLE 1C

| Human heavy chain germline gene segments | | | |
|---|---|---|---|
| Used Name[1] | Reference[2] | Family[3] | Germline genes[4] |
| VH1-12-1 | 19 | 1 | DP10; DA-2; DA-6 |
| VH1-12-8 | 22 | 1 | RR.VH1.2 |
| VH1-12-2 | 6 | 1 | hv1263 |
| VH1-12-9 | 7 | 1 | YAC-7; RR.VH1.1; 1-69 |
| VH1-12-3 | 19 | 1 | DP3 |
| VH1-12-4 | 19 | 1 | DP21; 4d275a; VH7a |
| VH1-12-5 | 18 | 1 | I-4.1b; V1-4.1b |
| VH1-12-6 | 21 | 1 | 1D37; VH7b; 7-81; YAC-10 |
| VH1-12-7 | 19 | 1 | DP14; VH1GRR; V1-18 |
| VH1-13-1 | 10 | 1 | 71-5; DP2 |
| VH1-13-2 | 10 | 1 | E3-10 |
| VH1-13-3 | 19 | 1 | DP1 |
| VH1-13-4 | 12 | 1 | V35 |
| VH1-13-5 | 8 | 1 | V1-2b |
| VH1-13-6 | 18 | 1 | I-2; DP75 |
| VH1-13-7 | 21 | 1 | V1-2 |
| VH1-13-8 | 19 | 1 | DP8 |
| VH1-13-9 | 3 | 1 | 1-1 |
| VH1-13-10 | 19 | 1 | DP12 |
| VH1-13-11 | 15 | 1 | V13C |
| VH1-13-12 | 18 | 1 | I-3b; DP25; V1-3b |
| VH1-13-13 | 3 | 1 | 1-92 |
| VH1-13-14 | 18 | 1 | I-3; V1-3 |
| VH1-13-15 | 19 | 1 | DP15; V1-8 |
| VH1-13-16 | 3 | 1 | 21-2; 3-1; DP7; V1-46 |
| VH1-13-17 | 16 | 1 | HG3 |

TABLE 1C-continued

| Human heavy chain germline gene segments | | | |
|---|---|---|---|
| Used Name[1] | Reference[2] | Family[3] | Germline genes[4] |
| VH1-13-18 | 19 | 1 | DP4; 7-2; V1-45 |
| VH1-13-19 | 27 | 1 | COS 5 |
| VH1-1X-1 | 19 | 1 | DP5; 1-24P |
| VH2-21-1 | 18 | 2 | II-5b |
| VH2-31-1 | 2 | 2 | VH2S12-1 |
| VH2-31-2 | 2 | 2 | VH2S12-7 |
| VH2-31-3 | 2 | 2 | VH2S12-9; DP27 |
| VH2-31-4 | 2 | 2 | VH2S12-10 |
| VH2-31-5 | 14 | 2 | V2-26; DP26; 2-26 |
| VH2-31-6 | 15 | 2 | VF2-26 |
| VH2-31-7 | 19 | 2 | DP28; DA-7 |
| VH2-31-14 | 7 | 2 | YAC-3; 2-70 |
| VH2-31-8 | 2 | 2 | VH2S12-5 |
| VH2-31-9 | 2 | 2 | VH2S12-12 |
| VH2-31-10 | 18 | 2 | II-5; V2-5 |
| VH2-31-11 | 2 | 2 | VH2S12-2; VH2S12-8 |
| VH2-31-12 | 2 | 2 | VH2S12-4; VH2S12-6 |
| VH2-31-13 | 2 | 2 | VH2S12-14 |
| VH3-11-1 | 13 | 3 | v65-2; DP44 |
| VH3-11-2 | 19 | 3 | DP45 |
| VH3-11-3 | 3 | 3 | 13-2; DP48 |
| VH3-11-4 | 19 | 3 | DP52 |
| VH3-11-5 | 14 | 3 | v3-13 |
| VH3-11-6 | 19 | 3 | DP42 |
| VH3-11-7 | 3 | 3 | 8-1B; YAC-5; 3-66 |
| VH3-11-8 | 14 | 3 | V3-53 |
| VH3-13-1 | 3 | 3 | 22-2B; DP35; V3-11 |
| VH3-13-5 | 19 | 3 | DP59; VH19; V3-35 |
| VH3-13-6 | 25 | 3 | f1-p1; DP61 |
| VH3-13-7 | 19 | 3 | DP46; GL-SJ2; COS 8; hv3005; hv3005f3; 3d21b; 56p1 |
| VH3-13-8 | 24 | 3 | VH26 |
| VH3-13-9 | 5 | 3 | vh26c |
| VH3-13-10 | 19 | 3 | DP47; VH26; 3-23 |
| VH3-13-11 | 3 | 3 | 1-91 |
| VH3-13-12 | 19 | 3 | DP58 |
| VH3-13-13 | 3 | 3 | 1-9III; DP49; 3-30; 3d28.1 |
| VH3-13-14 | 24 | 3 | 3019B9; DP50; 3-33; 3d277 |
| VH3-13-15 | 27 | 3 | COS 3 |
| VH3-13-16 | 19 | 3 | DP51 |
| VH3-13-17 | 16 | 3 | H11 |
| VH3-13-18 | 19 | 3 | DP53; COS 6; 3-74; DA-8 |
| VH3-13-19 | 19 | 3 | DP54; VH3-11; V3-7 |
| VH3-13-20 | 14 | 3 | V3-64; YAC-6 |
| VH3-13-21 | 14 | 3 | V3-48 |
| VH3-13-22 | 14 | 3 | V3-43; DP33 |
| VH3-13-23 | 14 | 3 | V3-33 |
| VH3-13-24 | 14 | 3 | V3-21; DP77 |
| VH3-13-25 | 14 | 3 | V3-20; DP32 |
| VH3-13-26 | 14 | 3 | V3-9; DP31 |
| VH3-14-1 | 3 | 3 | 12-2; DP29; 3-72; DA-3 |
| VH3-14-4 | 7 | 3 | YAC-9; 3-73; MTGL |
| VH3-14-2 | 4 | 3 | VHD26 |
| VH3-14-3 | 19 | 3 | DP30 |
| VH3-1X-1 | 1 | 3 | LSG8.1; LSG9.1; LSG10.1; HUM12IGVH; HUM13IGVH |
| VH3-1X-2 | 1 | 3 | LSG11.1; HUM4IGVH |
| VH3-1X-3 | 3 | 3 | 9-1; DP38; LSG7.1; RCG1.1; LSG1.1; LSG3.1; LSG5.1; HUM15IGVH; HUM2IGVH; HUM9IGVH |
| VH3-1X-4 | 1 | 3 | LSG4.1 |
| VH3-1X-5 | 1 | 3 | LSG2.1 |
| VH3-1X-6 | 1 | 3 | LSG6.1; HUM10IGVH |
| VH3-1X-7 | 18 | 3 | 3-15; V3-15 |
| VH3-1X-8 | 1 | 3 | LSG12.1; HUM5IGVH |
| VH3-1X-9 | 14 | 3 | V3-49 |
| VH4-11-1 | 22 | 4 | Tou-VH4.21 |
| VH4-11-2 | 17 | 4 | VH4.21; DP63; VH5; 4d76; V4-34 |
| VH4-11-3 | 23 | 4 | 4.44 |
| VH4-11-4 | 23 | 4 | 4.44.3 |
| VH4-11-5 | 23 | 4 | 4.36 |
| VH4-11-6 | 23 | 4 | 4.37 |
| VH4-11-7 | 18 | 4 | IV-4; 4.35; V4-4 |
| VH4-11-8 | 17 | 4 | VH4.11; 3d197d; DP71; 58p2 |

TABLE 1C-continued

Human heavy chain germline gene segments

| Used Name[1] | Reference[2] | Family[3] | Germline genes[4] |
|---|---|---|---|
| VH4-11-9 | 20 | 4 | H7 |
| VH4-11-10 | 20 | 4 | H8 |
| VH4-11-11 | 20 | 4 | H9 |
| VH4-11-12 | 17 | 4 | VH4.16 |
| VH4-11-13 | 23 | 4 | 4.38 |
| VH4-11-14 | 17 | 4 | VH4.15 |
| VH4-11-15 | 11 | 4 | 58 |
| VH4-11-16 | 10 | 4 | 71-4; V4-59 |
| VH4-21-1 | 11 | 4 | 11 |
| VH4-21-2 | 17 | 4 | VH4.17; VH4.23; 4d255; 4.40; DP69 |
| VH4-21-3 | 17 | 4 | VH4.19; 79; V4-4b |
| VH4-21-4 | 19 | 4 | DP70; 4d68; 4.41 |
| VH4-21-5 | 19 | 4 | DP67; VH4-4B |
| VH4-21-6 | 17 | 4 | VH4.22; VHSP; VH-JA |
| VH4-21-7 | 17 | 4 | VH4.13; 1-9II; 12G-1; 3d28d; 4.42; DP68; 4-28 |
| VH4-21-8 | 26 | 4 | hv4005; 3d24d |
| VH4-21-9 | 17 | 4 | VH4.14 |
| VH4-31-1 | 23 | 4 | 4.34; 3d230d; DP78 |
| VH4-31-2 | 23 | 4 | 4.34.2 |
| VH4-31-3 | 19 | 4 | DP64; 3d216d |
| VH4-31-4 | 19 | 4 | DP65; 4-31; 3d277d |
| VH4-31-5 | 23 | 4 | 4.33; 3d75d |
| VH4-31-6 | 20 | 4 | H10 |
| VH4-31-7 | 20 | 4 | H11 |
| VH4-31-8 | 23 | 4 | 4.31 |
| VH4-31-9 | 23 | 4 | 4.32 |
| VH4-31-10 | 20 | 4 | 3d277d |
| VH4-31-11 | 20 | 4 | 3d216d |
| VH4-31-12 | 20 | 4 | 3d279d |
| VH4-31-13 | 17 | 4 | VH4.18; 4d154; DP79 |
| VH4-31-14 | 8 | 4 | V4-39 |
| VH4-31-15 | 11 | 4 | 2-1; DP79 |
| VH4-31-16 | 23 | 4 | 4.30 |
| VH4-31-17 | 17 | 4 | VH4.12 |
| VH4-31-18 | 10 | 4 | 71-2; DP66 |
| VH4-31-19 | 23 | 4 | 4.39 |
| VH4-31-20 | 8 | 4 | V4-61 |
| VH5-12-1 | 9 | 5 | VH251; DP73; VHVCW; 51-R1; VHVLB; VHVCH,VHVTT; VHVAU; VHVBLK; VhAU; V5-51 |
| VH5-12-2 | 17 | 5 | VHVJB |
| VH5-12-3 | 3 | 5 | 1-v; DP80; 5-78 |
| VH5-12-4 | 9 | 5 | VH32; VHVRC; VHVMW; 5-2R1 |
| VH6-35-1 | 4 | 6 | VHVI; VH6; VHVIIS; VHVITE; VHVIJB; VHVICH; VHVICW; VHVIBLK; VHVIMW; DP74; 6-1G1; V6-1 |

TABLE 2A rearranged human kappa sequences

| Name[1] | aa[2] | Computed family[3] | Germline gene[4] | Diff. to germline[5] | % diff. to germline[6] | Reference |
|---|---|---|---|---|---|---|
| III-3R | 108 | 1 | O8 | 1 | 1.1% | 70 |
| No.86 | 109 | 1 | O8 | 3 | 3.2% | 80 |
| AU | 108 | 1 | O8 | 6 | 6.3% | 103 |
| ROY | 108 | 1 | O8 | 6 | 6.3% | 43 |
| IC4 | 108 | 1 | O8 | 6 | 6.3% | 70 |
| HIV-B26 | 106 | 1 | O8 | 3 | 3.2% | 8 |
| GRI | 108 | 1 | O8 | 8 | 8.4% | 30 |
| AG | 106 | 1 | O8 | 8 | 8.6% | 116 |
| REI | 108 | 1 | O8 | 9 | 9.5% | 86 |
| CLL PATIENT 16 | 88 | 1 | O8 | 2 | 2.3% | 122 |
| CLL PATIENT 14 | 87 | 1 | O8 | 2 | 2.3% | 122 |
| CLL PATIENT 15 | 88 | 1 | O8 | 2 | 2.3% | 122 |

TABLE 2A-continued rearranged human kappa sequences

| Name[1] | aa[2] | Computed family[3] | Germline gene[4] | Diff. to germline[5] | % diff. to germline[6] | Reference |
|---|---|---|---|---|---|---|
| GM4672 | 108 | 1 | O8 | 11 | 11.6% | 24 |
| HUM.YFC51.1 | 108 | 1 | O8 | 12 | 12.6% | 110 |
| LAY | 108 | 1 | O8 | 12 | 12.6% | 48 |
| HIV-b13 | 106 | 1 | O8 | 9 | 9.7% | 8 |
| MAL-NaCl | 108 | 1 | O8 | 13 | 13.7% | 102 |
| STRAb SA-1A | 108 | 1 | O2 | 0 | 0.0% | 120 |
| HuVHCAMP | 108 | 1 | O8 | 13 | 13.7% | 100 |
| CRO | 108 | 1 | O2 | 10 | 10.5% | 30 |
| Am107 | 108 | 1 | O2 | 12 | 12.6% | 108 |
| WALKER | 107 | 1 | O2 | 4 | 4.2% | 57 |
| III-2R | 109 | 1 | A20 | 0 | 0.0% | 70 |
| FOG1-A4 | 107 | 1 | A20 | 4 | 4.2% | 41 |
| HK137 | 95 | 1 | L1 | 0 | 0.0% | 10 |
| CEA4-8A | 107 | 1 | O2 | 7 | 7.4% | 41 |
| Va' | 95 | 1 | L4 | 0 | 0.0% | 90 |
| TR1.21 | 108 | 1 | O2 | 4 | 4.2% | 92 |
| HAU | 108 | 1 | O2 | 6 | 6.3% | 123 |
| HK102 | 95 | 1 | L12(1) | 0 | 0.0% | 9 |
| H20C3K | 108 | 1 | L12(2) | 3 | 3.2% | 125 |
| CHEB | 108 | 1 | O2 | 7 | 7.4% | 5 |
| HK134 | 95 | 1 | L15(2) | 0 | 0.0% | 10 |
| TEL9 | 108 | 1 | O2 | 9 | 9.5% | 73 |
| TR1.32 | 103 | 1 | O2 | 3 | 3.2% | 92 |
| RF-KES1 | 97 | 1 | A20 | 4 | 4.2% | 121 |
| WES | 108 | 1 | L5 | 10 | 10.5% | 61 |
| DILp1 | 95 | 1 | O4 | 1 | 1.1% | 70 |
| SA-4B | 107 | 1 | L12(2) | 8 | 8.4% | 120 |
| HK101 | 95 | 1 | L15(1) | 0 | 0.0% | 9 |
| TR1.23 | 108 | 1 | O2 | 5 | 5.3% | 92 |
| HF2-1/17 | 108 | 1 | A30 | 0 | 0.0% | 4 |
| 2E7 | 108 | 1 | A30 | 1 | 1.1% | 62 |
| 33.C9 | 107 | 1 | L12(2) | 7 | 7.4% | 126 |
| 3D6 | 105 | 1 | L12(2) | 2 | 2.1% | 34 |
| I-2a | 108 | 1 | L8 | 8 | 8.4% | 70 |
| RF-KL1 | 97 | 1 | L8 | 4 | 4.2% | 121 |
| TNF-E7 | 108 | 1 | A30 | 9 | 9.5% | 41 |
| TR1.22 | 108 | 1 | O2 | 7 | 7.4% | 92 |
| HIV-B35 | 106 | 1 | O2 | 2 | 2.2% | 8 |
| HIV-b22 | 106 | 1 | O2 | 2 | 2.2% | 8 |
| HIV-b27 | 106 | 1 | O2 | 2 | 2.2% | 8 |
| HIV-B8 | 107 | 1 | O2 | 10 | 10.8% | 8 |
| HIV-b8 | 107 | 1 | O2 | 10 | 10.8% | 8 |
| RF-SJ5 | 95 | 1 | A30 | 5 | 5.3% | 113 |
| GAL(I) | 108 | 1 | A30 | 6 | 6.3% | 64 |
| R3.5H5G | 108 | 1 | O2 | 6 | 6.3% | 70 |
| HIV-b14 | 106 | 1 | A20 | 2 | 2.2% | 8 |
| TNF-E1 | 105 | 1 | L5 | 8 | 8.4% | 41 |
| WEA | 108 | 1 | A30 | 8 | 8.4% | 37 |
| EU | 108 | 1 | L12(2) | 5 | 5.3% | 40 |
| FOG1-G8 | 108 | 1 | L8 | 11 | 11.6% | 41 |
| 1X7RG1 | 108 | 1 | L1 | 8 | 8.4% | 70 |
| BLI | 108 | 1 | L8 | 3 | 3.2% | 72 |
| KUE | 108 | 1 | L12(2) | 11 | 11.6% | 32 |
| LUNm01 | 108 | 1 | L12(2) | 10 | 10.5% | 6 |
| HIV-b1 | 106 | 1 | A20 | 4 | 4.3% | 8 |
| HIV-s4 | 103 | 1 | O2 | 2 | 2.2% | 8 |
| CAR | 107 | 1 | L12(2) | 11 | 11.7% | 79 |
| BR | 107 | 1 | L12(2) | 11 | 11.6% | 50 |
| CLL PATIENT 10 | 88 | 1 | O2 | 0 | 0.0% | 122 |
| CLL PATIENT 12 | 88 | 1 | O2 | 0 | 0.0% | 122 |
| KING | 108 | 1 | L12(2) | 12 | 12.6% | 30 |
| V13 | 95 | 1 | L24 | 0 | 0.0% | 46 |
| CLL PATIENT 11 | 87 | 1 | O2 | 0 | 0.0% | 122 |
| CLL PATIENT 13 | 87 | 1 | O2 | 0 | 0.00% | 122 |
| CLL PATIENT 9 | 88 | 1 | O12 | 1 | 1.1% | 122 |
| HIV-B2 | 106 | 1 | A20 | 9 | 9.7% | 8 |
| HIV-b2 | 106 | 1 | A20 | 9 | 9.7% | 8 |
| CLL PATIENT 5 | 88 | 1 | A20 | 1 | 1.1% | 122 |
| CLL PATIENT 1 | 88 | 1 | L8 | 2 | 2.3% | 122 |
| CLL PATIENT 2 | 88 | 1 | L8 | 0 | 0.0% | 122 |
| CLL PATIENT 7 | 88 | 1 | L5 | 0 | 0.0% | 122 |
| CLL PATIENT 8 | 88 | 1 | L5 | 0 | 0.0% | 122 |

TABLE 2A-continued rearranged human kappa sequences

| Name[1] | aa[2] | Computed family[3] | Germline gene[4] | Diff. to germline[5] | % diff. to germline[6] | Reference |
|---|---|---|---|---|---|---|
| HIV-b5 | 105 | 1 | L5 | 11 | 12.0% | 8 |
| CLL PATIENT 3 | 87 | 1 | L8 | 1 | 1.1% | 122 |
| CLL PATIENT 4 | 88 | 1 | L9 | 0 | 0.0% | 122 |
| CLL PATIENT 18 | 85 | 1 | L9 | 6 | 7.1% | 122 |
| CLL PATIENT 17 | 86 | 1 | L12(2) | 7 | 8.1% | 122 |
| HIV-b20 | 107 | 3 | A27 | 11 | 11.7% | 8 |
| 2C12 | 108 | 1 | L12(2) | 20 | 21.1% | 68 |
| 1B11 | 108 | 1 | L12(2) | 20 | 21.1% | 68 |
| 1H1 | 108 | 1 | L12(2) | 21 | 22.1% | G8 |
| 2A12 | 108 | 1 | L12(2) | 21 | 22.1% | 68 |
| CUR | 109 | 3 | A27 | 0 | 0.0% | 66 |
| GLO | 109 | 3 | A27 | 0 | 0.0% | 16 |
| RF-TS1 | 96 | 3 | A27 | 0 | 0.0% | 121 |
| GAR' | 109 | 3 | A27 | 0 | 0.0% | 67 |
| FLO | 109 | 3 | A27 | 0 | 0.0% | 66 |
| PIE | 109 | 3 | A27 | 0 | 0.0% | 91 |
| HAH 14.1 | 109 | 3 | A27 | 1 | 1.0% | 51 |
| HAH 14.2 | 109 | 3 | A27 | 1 | 1.0% | 51 |
| HAH 16.1 | 109 | 3 | A27 | 1 | 1.0% | 51 |
| NOV | 109 | 3 | A27 | 1 | 1.0% | 52 |
| 33.F12 | 108 | 3 | A27 | 1 | 1.0% | 126 |
| 8E10 | 110 | 3 | A27 | 1 | 1.0% | 25 |
| TH3 | 109 | 3 | A27 | 1 | 1.0% | 25 |
| HIC (R) | 108 | 3 | A27 | 0 | 0.0% | 51 |
| SON | 110 | 3 | A27 | 1 | 1.0% | 67 |
| PAY | 109 | 3 | A27 | 1 | 1.0% | 66 |
| GOT | 109 | 3 | A27 | 1 | 1.0% | 67 |
| mAbA6H4C5 | 109 | 3 | A27 | 1 | 1.0% | 12 |
| BOR' | 109 | 3 | A27 | 2 | 2.1% | 84 |
| RF-SJ3 | 96 | 3 | A27 | 2 | 2.1% | 121 |
| SIE | 109 | 3 | A27 | 2 | 2.1% | 15 |
| ESC | 109 | 3 | A27 | 2 | 2.1% | 98 |
| HEW' | 110 | 3 | A27 | 2 | 2.1% | 98 |
| YES8c | 109 | 3 | A27 | 3 | 3.1% | 33 |
| TI | 109 | 3 | A27 | 3 | 3.1% | 114 |
| mAb113 | 109 | 3 | A27 | 3 | 3.1% | 71 |
| HEW | 107 | 3 | A27 | 0 | 0.0% | 94 |
| BRO | 106 | 3 | A27 | 0 | 0.0% | 94 |
| ROB | 106 | 3 | A27 | 0 | 0.0% | 94 |
| NG9 | 96 | 3 | A27 | 4 | 4.2% | 11 |
| NEU | 109 | 3 | A27 | 4 | 4.2% | 66 |
| WOL | 109 | 3 | A27 | 4 | 4.2% | 2 |
| 35G6 | 109 | 3 | A27 | 4 | 4.2% | 59 |
| RF-SJ4 | 109 | 3 | A11 | 0 | 0.0% | 88 |
| KAS | 109 | 3 | A27 | 4 | 4.2% | 84 |
| BRA | 106 | 3 | A27 | 1 | 1.1% | 94 |
| HAH | 106 | 3 | A27 | 1 | 1.1% | 94 |
| HIC | 105 | 3 | A27 | 0 | 0.0% | 94 |
| FS-2 | 109 | 3 | A27 | 6 | 6.3% | 87 |
| JH' | 107 | 3 | A27 | 6 | 6.3% | 38 |
| EV1-15 | 109 | 3 | A27 | 6 | 6.3% | 83 |
| SCA | 108 | 3 | A27 | 6 | 6.3% | 65 |
| mAb112 | 109 | 3 | A27 | 6 | 6.3% | 71 |
| SIC | 103 | 3 | A27 | 3 | 3.3% | 94 |
| SA-4A | 109 | 3 | A27 | 6 | 6.3% | 120 |
| SER | 108 | 3 | A27 | 6 | 6.3% | 98 |
| GOL' | 109 | 3 | A27 | 7 | 7.3% | 82 |
| B5G10K | 105 | 3 | A27 | 9 | 9.7% | 125 |
| HG2B10K | 110 | 3 | A27 | 9 | 9.4% | 125 |
| Taykv322 | 105 | 3 | A27 | 5 | 5.4% | 52 |
| CLL PATIENT 24 | 89 | 3 | A27 | 1 | 1.1% | 122 |
| HIV-b24 | 107 | 3 | A27 | 7 | 7.4% | 8 |
| HIV-b6 | 107 | 3 | A27 | 7 | 7.4% | 8 |
| Taykv310 | 99 | 3 | A27 | 1 | 1.1% | 52 |
| KA3D1 | 108 | 3 | L6 | 0 | 0.0% | 85 |
| 19.E7 | 107 | 3 | L6 | 0 | 0.0% | 126 |
| rsv6L | 109 | 3 | A27 | 12 | 12.5% | 7 |
| Taykv320 | 98 | 3 | A27 | 1 | 1.2% | 52 |
| Vh | 96 | 3 | L10(2) | 0 | 0.0% | 89 |
| LS8 | 108 | 3 | L6 | 1 | 1.1% | 109 |
| LS1 | 108 | 3 | L6 | 1 | 1.1% | 109 |
| LS2S3-3 | 107 | 3 | L6 | 2 | 2.1% | 99 |

TABLE 2A-continued rearranged human kappa sequences

| Name[1] | aa[2] | Computed family[3] | Germline gene[4] | Diff. to germline[5] | % diff. to germline[6] | Reference |
|---|---|---|---|---|---|---|
| LS2 | 108 | 3 | L6 | 1 | 1.1% | 109 |
| LS7 | 108 | 3 | L6 | 1 | 1.1% | 109 |
| LS2S3-4d | 107 | 3 | L6 | 2 | 2.1% | 99 |
| LS2S3-4a | 107 | 3 | L6 | 2 | 2.1% | 99 |
| LS4 | 108 | 3 | L6 | 1 | 1.1% | 109 |
| LS6 | 108 | 3 | L6 | 1 | 1.1% | 109 |
| LS2S3-10a | 107 | 3 | L6 | 2 | 2.1% | 99 |
| LS2S3-8c | 107 | 3 | L6 | 2 | 2.1% | 99 |
| LS5 | 108 | 3 | L6 | 1 | 1.1% | 109 |
| LS2S3-5 | 107 | 3 | L6 | 3 | 3.2% | 99 |
| LUNm03 | 109 | 3 | A27 | 13 | 13.5% | 6 |
| IARC/BL41 | 108 | 3 | A27 | 13 | 13.7% | 55 |
| slkv22 | 99 | 3 | A27 | 3 | 3.5% | 13 |
| POP | 108 | 3 | L6 | 4 | 4.2% | 111 |
| LS2S3-10b | 107 | 3 | L6 | 3 | 3.2% | 99 |
| LS2S3-8f | 107 | 3 | L6 | 3 | 3.2% | 99 |
| LS2S3-12 | 107 | 3 | L6 | 3 | 3.2% | 99 |
| HIV-B30 | 107 | 3 | A27 | 11 | 11.7% | 8 |
| HIV-B20 | 107 | 3 | A27 | 11 | 11.7% | 8 |
| HIV-b3 | 108 | 3 | A27 | 11 | 11.7% | 8 |
| HIV-s6 | 104 | 3 | A27 | 9 | 9.9% | 8 |
| YSE | 107 | 3 | L2/L16 | 1 | 1.1% | 72 |
| POM | 109 | 3 | L2/L16 | 9 | 9.4% | 53 |
| Humkv328 | 95 | 3 | L2/L16 | 1 | 1.1% | 19 |
| CLL | 109 | 3 | L2/L16 | 3 | 3.2% | 47 |
| LES | 96 | 3 | L2/L16 | 3 | 3.2% | 38 |
| HIV-s5 | 104 | 3 | A27 | 11 | 12.1% | 8 |
| HIV-s7 | 104 | 3 | A27 | 11 | 12.1% | 8 |
| slkv1 | 99 | 3 | A27 | 7 | 8.1% | 13 |
| Humka31es | 95 | 3 | L2/L16 | 4 | 4.2% | 18 |
| slkv12 | 101 | 3 | A27 | 8 | 9.2% | 13 |
| RF-TS2 | 95 | 3 | L2/L16 | 3 | 3.2% | 121 |
| II-1 | 109 | 3 | L2/L16 | 4 | 4.2% | 70 |
| HIV-s3 | 105 | 3 | A27 | 13 | 14.3% | 8 |
| RF-TMC1 | 96 | 3 | L6 | 10 | 10.5% | 121 |
| GER | 109 | 3 | L2/L16 | 7 | 7.4% | 75 |
| GF4/1.1 | 109 | 3 | L2/L16 | 8 | 8.4% | 36 |
| mAb114 | 109 | 3 | L2/L16 | 6 | 6.3% | 71 |
| HIV-loop13 | 109 | 3 | L2/L16 | 7 | 7.4% | 8 |
| bkv16 | 86 | 3 | L6 | 1 | 1.2% | 13 |
| CLL PATIENT 29 | 86 | 3 | L6 | 1 | 1.2% | 122 |
| slkv9 | 98 | 3 | L6 | 3 | 3.5% | 13 |
| bkv17 | 99 | 3 | L6 | 1 | 1.2% | 13 |
| slkv14 | 99 | 3 | L6 | 1 | 1.2% | 13 |
| slkv16 | 101 | 3 | L6 | 2 | 2.3% | 13 |
| bkv33 | 101 | 3 | L6 | 4 | 4.7% | 13 |
| slkv15 | 99 | 3 | L6 | 2 | 2.3% | 13 |
| bkv6 | 100 | 3 | L6 | 3 | 3.5% | 13 |
| R6B8K | 108 | 3 | L2/L16 | 12 | 12.6% | 125 |
| AL 700 | 107 | 3 | L2/L16 | 9 | 9.5% | 117 |
| slkv11 | 100 | 3 | L2/L16 | 3 | 3.5% | 13 |
| slkv4 | 97 | 3 | L6 | 4 | 4.8% | 13 |
| CLL PATIENT 26 | 87 | 3 | L2/L16 | 1 | 1.1% | 122 |
| AL Se124 | 103 | 3 | L2/L16 | 9 | 9.5% | 117 |
| slkv13 | 100 | 3 | L2/L16 | 6 | 7.0% | 13 |
| bkv7 | 100 | 3 | L2/L16 | 5 | 5.8% | 13 |
| bkv22 | 100 | 3 | L2/L16 | 6 | 7.0% | 13 |
| CLL PATIENT 27 | 84 | 3 | L2/L16 | 0 | 0.0% | 122 |
| bkv35 | 100 | 3 | L6 | 8 | 9.3% | 13 |
| CLL PATIENT 25 | 87 | 3 | L2/L16 | 4 | 4.6% | 122 |
| slkv3 | 86 | 3 | L2/L16 | 7 | 8.1% | 13 |
| slkv7 | 99 | 3 | O2 | 7 | 8.1% | 13 |
| HuFd79 | 111 | 3 | L2/L16 | 24 | 24.2% | 21 |
| RAD | 99 | 3 | A27 | 9 | 10.3% | 78 |
| CLL PATIENT 28 | 83 | 3 | L2/L16 | 4 | 4.8% | 122 |
| REE | 104 | 3 | L2/L16 | 25 | 27.2% | 95 |
| FR4 | 99 | 3 | A27 | 8 | 9.2% | 77 |
| MD3.3 | 92 | 3 | L6 | 1 | 1.3% | 54 |
| MD3.1 | 92 | 3 | L6 | 0 | 0.0% | 54 |
| GA3.6 | 92 | 3 | L6 | 2 | 2.6% | 54 |
| M3.5N | 92 | 3 | L6 | 3 | 3.8% | 54 |
| WEI' | 82 | 3 | A27 | 0 | 0.0% | 65 |

TABLE 2A-continued rearranged human kappa sequences

| Name[1] | aa[2] | Computed family[3] | Germline gene[4] | Diff. to germline[5] | % diff. to germline[6] | Reference |
|---|---|---|---|---|---|---|
| MD3.4 | 92 | 3 | L2/L16 | 1 | 1.3% | 54 |
| MD3.2 | 91 | 3 | L6 | 3 | 3.8% | 54 |
| VER | 97 | 3 | A27 | 19 | 22.4% | 20 |
| CLL PATIENT 30 | 78 | 3 | L6 | 3 | 3.8% | 122 |
| M3.1N | 92 | 3 | L2/L16 | 1 | 1.3% | 54 |
| MD3.6 | 91 | 3 | L2/L16 | 0 | 0.0% | 54 |
| MD3.8 | 91 | 3 | L2/L16 | 0 | 0.0% | 54 |
| GA3.4 | 92 | 3 | L6 | 7 | 9.0% | 54 |
| M3.6N | 92 | 3 | A27 | 0 | 0.0% | 54 |
| MD3.10 | 92 | 3 | A27 | 0 | 0.0% | 54 |
| MD3.13 | 91 | 3 | A27 | 0 | 0.0% | 54 |
| MD3.7 | 93 | 3 | A27 | 0 | 0.0% | 54 |
| MD3.9 | 93 | 3 | A27 | 0 | 0.0% | 54 |
| GA3.1 | 93 | 3 | A27 | 6 | 7.6% | 54 |
| bkv32 | 101 | 3 | A27 | 5 | 5.7% | 13 |
| GA3.5 | 93 | 3 | A27 | 5 | 6.3% | 54 |
| GA3.7 | 92 | 3 | A27 | 7 | 8.9% | 54 |
| MD3.12 | 92 | 3 | A27 | 2 | 2.5% | 54 |
| M3.2N | 90 | 3 | L6 | 6 | 7.8% | 54 |
| MD3.5 | 92 | 3 | A27 | 1 | 1.3% | 54 |
| M3.4N | 91 | 3 | L2/L16 | 8 | 1.3% | 54 |
| M3.8N | 91 | 3 | L2/L16 | 7 | 9.0% | 54 |
| M3.7N | 92 | 3 | A27 | 3 | 3.8% | 54 |
| GA3.2 | 92 | 3 | A27 | 9 | 11.4% | 54 |
| GA3.8 | 93 | 3 | A27 | 4 | 5.1% | 54 |
| GA3.3 | 92 | 3 | A27 | 8 | 10.1% | 54 |
| M3.3N | 92 | 3 | A27 | 5 | 6.3% | 54 |
| B6 | 83 | 3 | A27 | 8 | 11.3% | 78 |
| E29.1 KAPPA | 78 | 3 | L2/L16 | 0 | 0.0% | 22 |
| SCW | 108 | 1 | O8 | 12 | 12.6% | 31 |
| REI-based CAMPATH-9 | 107 | 1 | O8 | 14 | 14.7% | 39 |
| RZ | 107 | 1 | O8 | 14 | 14.7% | 50 |
| BI | 108 | 1 | O8 | 14 | 14.7% | 14 |
| AND | 107 | 1 | O2 | 13 | 13.7% | 69 |
| 2A4 | 109 | 1 | O2 | 12 | 12.6% | 23 |
| KA | 108 | 1 | O8 | 19 | 20.0% | 107 |
| MEV | 109 | 1 | O2 | 14 | 14.7% | 29 |
| DEE | 106 | 1 | O2 | 13 | 14.0% | 76 |
| OU(IOC) | 108 | 1 | O2 | 18 | 18.9% | 60 |
| HuRSV19VK | 111 | 1 | O8 | 21 | 21.0% | 115 |
| SP2 | 108 | 1 | O2 | 17 | 17.9% | 93 |
| 8J26 | 99 | 1 | O8 | 21 | 24.1% | 1 |
| NI | 112 | 1 | O8 | 24 | 24.2% | 106 |
| BMA 0310EUCIV2 | 106 | 1 | L12(1) | 21 | 22.3% | 105 |
| CLL PATIENT 6 | 71 | 1 | A20 | 0 | 0.0% | 122 |
| BJ19 | 85 | 1 | O8 | 16 | 21.9% | 1 |
| GM 607 | 113 | 2 | A3 | 0 | 0.0% | 58 |
| R5A3K | 114 | 2 | A3 | 1 | 1.0% | 125 |
| RIC8K | 114 | 2 | A3 | 1 | 1.0% | 125 |
| VK2.R149 | 113 | 2 | A3 | 2 | 2.0% | 118 |
| TR1.6 | 109 | 2 | A3 | 4 | 4.0% | 92 |
| TR1.37 | 104 | 2 | A3 | 5 | 5.0% | 92 |
| FS-1 | 113 | 2 | A3 | 6 | 6.0% | 87 |
| TR1.8 | 110 | 2 | A3 | 6 | 6.0% | 92 |
| NIM | 113 | 2 | A3 | 8 | 8.0% | 28 |
| Inc | 112 | 2 | A3 | 11 | 11.0% | 35 |
| TEW | 107 | 2 | A3 | 6 | 6.4% | 96 |
| CUM | 114 | 2 | 01 | 7 | 6.9% | 44 |
| HRF1 | 71 | 2 | A3 | 4 | 5.6% | 124 |
| CLL PATIENT 19 | 87 | 2 | A3 | 0 | 0.0% | 122 |
| CLL PATIENT 20 | 87 | 2 | A3 | 0 | 0.0% | 122 |
| MIL | 112 | 2 | A3 | 16 | 16.2% | 26 |
| FR | 113 | 2 | A3 | 20 | 20.0% | 101 |
| MAL-Urine | 83 | 1 | O2 | 6 | 8.6% | 102 |
| Taykv306 | 73 | 3 | A27 | 1 | 1.6% | 52 |
| Taykv312 | 75 | 3 | A27 | 1 | 1.6% | 52 |
| HIV-b29 | 93 | 3 | A27 | 14 | 17.5% | 8 |
| 1-185-37 | 110 | 3 | A27 | 0 | 0.0% | 119 |
| 1-187-29 | 110 | 3 | A27 | 0 | 0.0% | 119 |
| TT117 | 110 | 3 | A27 | 9 | 9.4% | 63 |

TABLE 2A-continued rearranged human kappa sequences

| Name[1] | aa[2] | Computed family[3] | Germline gene[4] | Diff. to germline[5] | % diff. to germline[6] | Reference |
|---|---|---|---|---|---|---|
| HW-loop8 | 108 | 3 | A27 | 16 | 16.8% | 8 |
| rsv23L | 108 | 3 | A27 | 16 | 16.8% | 7 |
| HIV-b7 | 107 | 3 | A27 | 14 | 14.9% | 8 |
| HIV-b11 | 107 | 3 | A27 | 15 | 16.0% | 8 |
| HIV-LC1 | 107 | 3 | A27 | 19 | 20.2% | 8 |
| HIV-LC7 | 107 | 3 | A27 | 20 | 21.3% | 8 |
| HIV-LC22 | 107 | 3 | A27 | 21 | 22.3% | 8 |
| HIV-LC13 | 107 | 3 | A27 | 21 | 22.3% | 8 |
| HIV-LC3 | 107 | 3 | A27 | 21 | 22.3% | 8 |
| HIV-LC5 | 107 | 3 | A27 | 21 | 22.3% | 8 |
| HIV-LC28 | 107 | 3 | A27 | 21 | 22.3% | 8 |
| HIV-b4 | 107 | 3 | A27 | 22 | 23.4% | 8 |
| CLL PATIENT 31 | 87 | 3 | A27 | 15 | 17.2% | 122 |
| HIV-loop2 | 108 | 3 | L2/L16 | 17 | 17.9% | 8 |
| HIV-loop35 | 108 | 3 | L2/L16 | 17 | 17.9% | 8 |
| HIV-LC11 | 107 | 3 | A27 | 23 | 24.5% | 8 |
| HIV-LC24 | 107 | 3 | A27 | 23 | 24.5% | 8 |
| HIV-b12 | 107 | 3 | A27 | 24 | 25.5% | 8 |
| HIV-LC25 | 107 | 3 | A27 | 24 | 25.5% | 8 |
| HIV-b21 | 107 | 3 | A27 | 24 | 25.5% | 8 |
| HIV-LC26 | 107 | 3 | A27 | 26 | 27.7% | 8 |
| G3D10K | 108 | 1 | L12(2) | 12 | 12.6% | 125 |
| TT125 | 108 | 1 | L5 | 8 | 8.4% | 63 |
| HIV-s2 | 103 | 3 | A27 | 28 | 31.1% | 8 |
| 265-695 | 108 | 1 | L5 | 7 | 7.4% | 3 |
| 2-115-19 | 108 | 1 | A30 | 2 | 2.1% | 119 |
| rsv13L | 107 | 1 | O2 | 20 | 21.1% | 7 |
| HIV-b18 | 106 | 1 | O2 | 14 | 15.1% | 8 |
| RF-KL5 | 98 | 3 | L6 | 36 | 36.7% | 97 |
| ZM1-1 | 113 | 2 | A17 | 7 | 7.0% | 3 |
| HIV-s8 | 103 | 1 | O8 | 16 | 17.8% | 8 |
| K-EV15 | 95 | 5 | B2 | 0 | 0.0% | 112 |
| RF-TS3 | 100 | 2 | A23 | 0 | 0.0% | 121 |
| HF-21/28 | 111 | 2 | A17 | 1 | 1.0% | 17 |
| RPMI6410 | 113 | 2 | A17 | 1 | 1.0% | 42 |
| JC11 | 113 | 2 | A17 | 1 | 1.0% | 49 |
| O-81 | 114 | 2 | A17 | 5 | 5.0% | 45 |
| FK-001 | 113 | 4 | B3 | 0 | 0.0% | 81 |
| CD5 + .28 | 101 | 4 | B3 | 1 | 1.0% | 27 |
| LEN | 114 | 4 | B3 | 1 | 1.0% | 104 |
| UC | 114 | 4 | B3 | 1 | 1.0% | 111 |
| CD5 + .5 | 101 | 4 | B3 | 1 | 1.0% | 27 |
| CD5 + .26 | 101 | 4 | B3 | 1 | 1.0% | 27 |
| CD5 + .12 | 101 | 4 | B3 | 2 | 2.0% | 27 |
| CD5 + .23 | 101 | 4 | B3 | 2 | 2.0% | 27 |
| CD5 + .7 | 101 | 4 | B3 | 2 | 2.0% | 27 |
| VJI | 113 | 4 | B3 | 3 | 3.0% | 56 |
| LOC | 113 | 4 | B3 | 3 | 3.0% | 72 |
| MAL | 113 | 4 | B3 | 3 | 3.0% | 72 |
| CD5 + .6 | 101 | 4 | B3 | 3 | 3.0% | 27 |
| H2F | 113 | 4 | B3 | 3 | 3.0% | 70 |
| PB17IV | 114 | 4 | B3 | 4 | 4.0% | 74 |
| CD5 + .27 | 101 | 4 | B3 | 4 | 4.0% | 27 |
| CD5 + .9 | 101 | 4 | B3 | 4 | 4.0% | 27 |
| CD5 − .28 | 101 | 4 | B3 | 5 | 5.0% | 27 |
| CD5 − .26 | 101 | 4 | B3 | 6 | 5.9% | 27 |
| CD5 + .24 | 101 | 4 | B3 | 6 | 5.9% | 27 |
| CD4 + .10 | 101 | 4 | B3 | 6 | 5.9% | 27 |
| CD5 − .19 | 101 | 4 | B3 | 6 | 5.9% | 27 |
| CD5 − .18 | 101 | 4 | B3 | 7 | 6.9% | 27 |
| CD5 − .16 | 101 | 4 | B3 | 8 | 7.9% | 27 |
| CD5 − .24 | 101 | 4 | B3 | 8 | 7.9% | 27 |
| CD5 − .17 | 101 | 4 | B3 | 10 | 9.9% | 27 |
| MD4.1 | 92 | 4 | B3 | 0 | 0.0% | 54 |
| MD4.4 | 92 | 4 | B3 | 0 | 0.0% | 54 |
| MD4.5 | 92 | 4 | B3 | 0 | 0.0% | 54 |
| MD4.6 | 92 | 4 | B3 | 0 | 0.0% | 54 |
| MD4.7 | 92 | 4 | B3 | 0 | 0.0% | 54 |
| MD4.2 | 92 | 4 | B3 | 1 | 1.3% | 54 |
| MD4.3 | 92 | 4 | B3 | 5 | 6.3% | 54 |

TABLE 2A-continued rearranged human kappa sequences

| Name[1] | aa[2] | Computed family[3] | Germline gene[4] | Diff. to germline[5] | % diff. to germline[6] | Reference |
|---|---|---|---|---|---|---|
| CLL PATIENT 22 | 87 | 2 | A17 | 2 | 2.3% | 122 |
| CLL PATIENT 23 | 84 | 2 | A17 | 2 | 2.4% | 122 |

TABLE 2B rearranged human lambda sequences

| Name[1] | aa[2] | Computed family[3] | Germline gene[4] | Diff. to germline[5] | % diff. to germline[6] | Reference[7] |
|---|---|---|---|---|---|---|
| WAH | 110 | 1 | DPL3 | 7 | 7% | 68 |
| 1B9/F2 | 112 | 1 | DPL3 | 7 | 7% | 9 |
| DIA | 112 | 1 | DPL2 | 7 | 7% | 36 |
| mAb67 | 89 | 1 | DPL3 | 0 | 0% | 29 |
| HiH2 | 110 | 1 | DPL3 | 12 | 11% | 3 |
| NIG-77 | 112 | 1 | DPL2 | 9 | 9% | 72 |
| OKA | 112 | 1 | DPL2 | 7 | 7% | 84 |
| KOL | 112 | 1 | DPL2 | 12 | 11% | 40 |
| T2:C5 | 111 | 1 | DPL5 | 0 | 0% | 6 |
| T2:C14 | 110 | 1 | DPL5 | 0 | 0% | 6 |
| PR-TS1 | 110 | 1 | DPL5 | 0 | 0% | 55 |
| 4G12 | 111 | 1 | DPL5 | 1 | 1% | 35 |
| KIM46L | 112 | 1 | HUMLV117 | 0 | 0% | 8 |
| Fog-B | 111 | 1 | DPL5 | 3 | 3% | 31 |
| 9F2L | 111 | 1 | DPL5 | 3 | 3% | 79 |
| mAb111 | 110 | 1 | DPL5 | 3 | 3% | 48 |
| PHOX15 | 111 | 1 | DPL5 | 4 | 4% | 49 |
| BL2 | 111 | 1 | DPL5 | 4 | 4% | 74 |
| NIG-64 | 111 | 1 | DPL5 | 4 | 4% | 72 |
| RF-SJ2 | 100 | 1 | DPL5 | 6 | 6% | 78 |
| AL EZI | 112 | 1 | DPL5 | 7 | 7% | 41 |
| ZIM | 112 | 1 | HUMLV117 | 7 | 7% | 18 |
| RF-SJ1 | 100 | 1 | DPL5 | 9 | 9% | 78 |
| IGLV1.1 | 98 | 1 | DPL4 | 0 | 0% | 1 |
| NEW | 112 | 1 | HUMLV117 | 11 | 10% | 42 |
| CB-201 | 87 | 1 | DPL2 | 1 | 1% | 62 |
| MEM | 109 | 1 | DPL2 | 6 | 6% | 50 |
| H210 | 111 | 2 | DPL10 | 4 | 4% | 45 |
| NOV | 110 | 2 | DPL10 | 8 | 8% | 25 |
| NEI | 111 | 2 | DPL10 | 8 | 8% | 24 |
| AL MC | 110 | 2 | DPL11 | 6 | 6% | 28 |
| MES | 112 | 2 | DPL11 | 8 | 8% | 84 |
| FOG1-A3 | 111 | 2 | DPL11 | 9 | 9% | 27 |
| AL NOV | 112 | 2 | DPL11 | 7 | 7% | 28 |
| HMST-1 | 110 | 2 | DPL11 | 4 | 4% | 82 |
| HBW4-1 | 108 | 2 | DPL12 | 9 | 9% | 52 |
| WH | 110 | 2 | DPL11 | 11 | 11% | 34 |
| 11-50 | 110 | 2 | DPL11 | 7 | 7% | 82 |
| HBp2 | 110 | 2 | DPL12 | 8 | 8% | 3 |
| NIG-84 | 113 | 2 | DPL11 | 12 | 11% | 73 |
| VIL | 112 | 2 | DPL11 | 9 | 9% | 58 |
| TRO | 111 | 2 | DPL12 | 10 | 10% | 61 |
| ES492 | 108 | 2 | DPL11 | 15 | 15% | 76 |
| mAb216 | 89 | 2 | DPL12 | 1 | 1% | 7 |
| BSA3 | 109 | 3 | DPL16 | 0 | 0% | 49 |
| THY-29 | 110 | 3 | DPL16 | 0 | 0% | 27 |
| PR-TS2 | 108 | 3 | DPL16 | 0 | 0% | 55 |
| E29.1 LAMBDA | 107 | 3 | DPL16 | 1 | 1% | 13 |
| mAb63 | 109 | 3 | DPL16 | 2 | 2% | 29 |
| TEL14 | 110 | 3 | DPL16 | 6 | 6% | 49 |
| 6H-3C4 | 108 | 3 | DPL16 | 7 | 7% | 39 |
| SH | 109 | 3 | DPL16 | 7 | 7% | 70 |
| AL GIL | 109 | 3 | DPL16 | 8 | 8% | 23 |
| H6-3C4 | 108 | 3 | DPL16 | 8 | 8% | 83 |
| V-lambda-2.DS | 111 | 2 | DPL11 | 3 | 3% | 15 |
| 8.12 ID | 110 | 2 | DPL11 | 3 | 3% | 81 |
| DSC | 111 | 2 | DPL11 | 3 | 3% | 56 |

TABLE 2B-continued rearranged human lambda sequences

| Name[1] | aa[2] | Computed family[3] | Germline gene[4] | Diff. to germline[5] | % diff. to germline[6] | Reference[7] |
|---|---|---|---|---|---|---|
| PV11 | 110 | 2 | DPL11 | 1 | 1% | 56 |
| 33.H11 | 110 | 2 | DPL11 | 4 | 4% | 81 |
| AS17 | 111 | 2 | DPL11 | 7 | 7% | 56 |
| SD6 | 110 | 2 | DPL11 | 7 | 7% | 56 |
| K53 | 110 | 2 | DPL11 | 9 | 9% | 56 |
| PV6 | 110 | 2 | DPL12 | 5 | 5% | 56 |
| NGD9 | 110 | 2 | DPL11 | 7 | 7% | 56 |
| MUC1-1 | 111 | 2 | DPL11 | 11 | 10% | 27 |
| A30c | 111 | 2 | DPL10 | 6 | 6% | 56 |
| KS6 | 110 | 2 | DPL12 | 6 | 6% | 56 |
| TEL13 | 111 | 2 | DPL11 | 11 | 10% | 49 |
| AS7 | 110 | 2 | DPL12 | 6 | 6% | 56 |
| MCG | 112 | 2 | DPL12 | 12 | 11% | 20 |
| U266L | 110 | 2 | DPL12 | 13 | 12% | 77 |
| PR-SJ2 | 110 | 2 | DPL12 | 14 | 13% | 55 |
| BOH | 112 | 2 | DPL12 | 11 | 10% | 37 |
| TOG | 111 | 2 | DPL11 | 19 | 18% | 53 |
| TEL16 | 111 | 2 | DPL11 | 19 | 18% | 49 |
| No. 13 | 110 | 2 | DPL10 | 14 | 13% | 52 |
| BO | 112 | 2 | DPL12 | 18 | 17% | 80 |
| WIN | 112 | 2 | DPL12 | 17 | 16% | 11 |
| BUR | 104 | 2 | DPL12 | 15 | 15% | 46 |
| NIG-58 | 110 | 2 | DPL12 | 20 | 19% | 69 |
| WEIR | 112 | 2 | DPL11 | 26 | 25% | 21 |
| THY-32 | 111 | 1 | DPL8 | 8 | 8% | 27 |
| TNF-H9G1 | 111 | 1 | DPL8 | 9 | 9% | 27 |
| mAb61 | 111 | 1 | DPL3 | 1 | 1% | 29 |
| LV1L1 | 98 | 1 | DPL2 | 0 | 0% | 54 |
| HA | 113 | 1 | DPL3 | 14 | 13% | 63 |
| LA1L1 | 111 | 1 | DPL2 | 3 | 3% | 54 |
| RHE | 112 | 1 | DPL1 | 17 | 16% | 22 |
| K1B12L | 113 | 1 | DPL8 | 17 | 16% | 79 |
| LOC | 113 | 1 | DPL2 | 15 | 14% | 84 |
| NIG-51 | 112 | 1 | DPL2 | 12 | 11% | 67 |
| NEWM | 104 | 1 | DPL8 | 23 | 22% | 10 |
| MD3-4 | 106 | 3 | DPL23 | 14 | 13% | 4 |
| COX | 112 | 1 | DPL2 | 13 | 12% | 84 |
| HiH10 | 106 | 3 | DPL23 | 13 | 12% | 3 |
| VOR | 112 | 1 | DPL2 | 16 | 15% | 16 |
| AL POL | 113 | 1 | DPL2 | 16 | 15% | 57 |
| CD4-74 | 111 | 1 | DPL2 | 19 | 18% | 27 |
| AMYLOID MOL | 102 | 3 | DPL23 | 15 | 15% | 30 |
| OST577 | 108 | 3 | Humlv318 | 10 | 10% | 4 |
| NIG-48 | 113 | 1 | DPL3 | 42 | 40% | 66 |
| CARR | 108 | 3 | DPL23 | 18 | 17% | 19 |
| mAb60 | 108 | 3 | DPL23 | 14 | 13% | 29 |
| NIG-68 | 99 | 3 | DPL23 | 25 | 26% | 32 |
| KERN | 107 | 3 | DPL23 | 26 | 25% | 59 |
| ANT | 106 | 3 | DPL23 | 17 | 16% | 19 |
| LEE | 110 | 3 | DPL23 | 18 | 17% | 85 |
| CLE | 94 | 3 | DPL23 | 17 | 17% | 19 |
| VL8 | 98 | 8 | DPL21 | 0 | 0% | 81 |
| MOT | 110 | 3 | Humlv318 | 23 | 22% | 38 |
| GAR | 108 | 3 | DPL23 | 26 | 25% | 33 |
| 32.B9 | 98 | 8 | DPL21 | 5 | 5% | 81 |
| PUG | 108 | 3 | Humlv318 | 24 | 23% | 19 |
| T1 | 115 | 8 | HUMLV801 | 52 | 50% | 6 |
| PF-TS7 | 96 | 7 | DPL18 | 4 | 4% | 60 |
| YM-1 | 116 | 8 | HUMLV801 | 51 | 49% | 75 |
| K6H6 | 112 | 8 | HUMLV801 | 20 | 19% | 44 |
| K5C7 | 112 | 8 | HUMLV801 | 20 | 19% | 44 |
| K5B8 | 112 | 8 | HUMLV801 | 20 | 19% | 44 |
| K5G5 | 112 | 8 | HUMLV801 | 20 | 19% | 44 |
| K4B8 | 112 | 8 | HUMLV801 | 19 | 18% | 44 |
| K6F5 | 112 | 8 | HUMLV801 | 17 | 16% | 44 |
| HIL | 108 | 3 | DPL23 | 22 | 21% | 47 |
| KIR | 109 | 3 | DPL23 | 20 | 19% | 19 |
| CAP | 109 | 3 | DPL23 | 19 | 18% | 84 |
| 1B8 | 110 | 3 | DPL23 | 22 | 21% | 43 |
| SHO | 108 | 3 | DPL23 | 19 | 18% | 19 |
| HAN | 108 | 3 | DPL23 | 20 | 19% | 19 |
| cML23 | 96 | 3 | DPL23 | 3 | 3% | 12 |

TABLE 2B-continued rearranged human lambda sequences

| Name[1] | aa[2] | Computed family[3] | Germline gene[4] | Diff. to germline[5] | % diff. to germline[6] | Reference[7] |
|---|---|---|---|---|---|---|
| PR-SJ1 | 96 | 3 | DPL23 | 7 | 7% | 55 |
| BAU | 107 | 3 | DPL23 | 9 | 9% | 5 |
| TEX | 99 | 3 | DPL23 | 8 | 8% | 19 |
| X(PET) | 107 | 3 | DPL23 | 9 | 9% | 51 |
| DOY | 106 | 3 | DPL23 | 9 | 9% | 19 |
| COT | 106 | 3 | DPL23 | 13 | 12% | 19 |
| Pag-1 | 111 | 3 | Humlv318 | 5 | 5% | 31 |
| DIS | 107 | 3 | Humlv318 | 2 | 2% | 19 |
| WIT | 108 | 3 | Humlv318 | 7 | 7% | 19 |
| I.RH | 108 | 3 | Humlv318 | 12 | 11% | 19 |
| S1-1 | 108 | 3 | Humlv318 | 12 | 11% | 52 |
| DEL | 108 | 3 | Humlv318 | 14 | 13% | 17 |
| TYR | 108 | 3 | Humlv318 | 11 | 10% | 19 |
| J.RH | 109 | 3 | Humlv318 | 13 | 12% | 19 |
| THO | 112 | 2 | DPL13 | 38 | 36% | 26 |
| LBV | 113 | 1 | DPL3 | 38 | 36% | 2 |
| WLT | 112 | 1 | DPL3 | 33 | 31% | 14 |
| SUT | 112 | 2 | DPL12 | 37 | 35% | 65 |

TABLE 2C rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| 21/28 | 119 | 1 | VH1-13-12 | 0 | 0.0% | 31 |
| 8E10 | 123 | 1 | VH1-13-12 | 0 | 0.0% | 31 |
| MUC1-1 | 118 | 1 | VH1-13-6 | 4 | 4.1% | 42 |
| gF1 | 98 | 1 | VH1-13-12 | 10 | 10.2% | 75 |
| VHGL 1.2 | 98 | 1 | VH1-13-6 | 2 | 2.0% | 26 |
| HV1L1 | 98 | 1 | VH1-13-6 | 0 | 0.0% | 81 |
| RF-TS7 | 104 | 1 | VH1-13-6 | 3 | 3.1% | 96 |
| E55 1.A15 | 106 | 1 | VH1-13-15 | 1 | 1.0% | 26 |
| HA1L1 | 126 | 1 | VH1-13-6 | 7 | 7.1% | 81 |
| UC | 123 | 1 | VH1-13-6 | 5 | 5.1% | 115 |
| WIL2 | 123 | 1 | VH1-13-6 | 6 | 6.1% | 55 |
| R3.5H5G | 122 | 1 | VH1-13-6 | 10 | 10.2% | 70 |
| N89P2 | 123 | 1 | VH1-13-16 | 11 | 11.2% | 77 |
| mAb113 | 126 | 1 | VH1-13-6 | 10 | 10.2% | 71 |
| LS2S3-3 | 125 | 1 | VH1-12-7 | 5 | 5.1% | 98 |
| LS2S3-12a | 125 | 1 | VH1-12-7 | 5 | 5.1% | 98 |
| LS2S3-5 | 125 | 1 | VH1-12-7 | 5 | 5.1% | 98 |
| LS2S3-12e | 125 | 1 | VH1-12-7 | 5 | 5.1% | 98 |
| LS2S3-4 | 125 | 1 | VH1-12-7 | 5 | 5.1% | 98 |
| LS2S3-10 | 125 | 1 | VH1-12-7 | 5 | 5.1% | 98 |
| LS2S3-12d | 125 | 1 | VH1-12-7 | 6 | 6.1% | 98 |
| LS2S3-8 | 125 | 1 | VH1-12-7 | 5 | 5.1% | 98 |
| LS2 | 125 | 1 | VH1-12-7 | 6 | 6.1% | 113 |
| LS4 | 105 | 1 | VH1-12-7 | 6 | 6.1% | 113 |
| LS5 | 125 | 1 | VH1-12-7 | 6 | 6.1% | 113 |
| LS1 | 125 | 1 | VH1-12-7 | 6 | 6.1% | 113 |
| LS6 | 125 | 1 | VH1-12-7 | 6 | 6.1% | 113 |
| LS8 | 125 | 1 | VH1-12-7 | 7 | 7.1% | 113 |
| THY-29 | 122 | 1 | VH1-12-7 | 0 | 0.0% | 42 |
| 1B9/F2 | 122 | 1 | VH1-12-7 | 10 | 10.2% | 21 |
| 51P1 | 122 | 1 | VH1-12-1 | 0 | 0.0% | 105 |
| NEI | 127 | 1 | VH1-12-1 | 0 | 0.0% | 55 |
| AND | 127 | 1 | VH1-12-1 | 0 | 0.0% | 55 |
| L7 | 127 | 1 | VH1-12-1 | 0 | 0.0% | 54 |
| L22 | 124 | 1 | VH1-12-1 | 0 | 0.0% | 54 |
| L24 | 127 | 1 | VH1-12-1 | 0 | 0.0% | 54 |
| L26 | 116 | 1 | VH1-12-1 | 0 | 0.0% | 54 |
| L33 | 119 | 1 | VH1-12-1 | 0 | 0.0% | 54 |
| L34 | 117 | 1 | VH1-12-1 | 0 | 0.0% | 54 |
| L36 | 118 | 1 | VH1-12-1 | 0 | 0.0% | 54 |
| L39 | 120 | 1 | VH1-12-1 | 0 | 0.0% | 54 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| L41 | 120 | 1 | VH1-12-1 | 0 | 0.0% | 54 |
| L42 | 125 | 1 | VH1-12-1 | 0 | 0.0% | 54 |
| VHGL 1.8 | 101 | 1 | VH1-12-1 | 0 | 0.0% | 26 |
| 783c | 127 | 1 | VH1-12-1 | 0 | 0.0% | 22 |
| X17115 | 127 | 1 | VH1-12-1 | 0 | 0.0% | 37 |
| L25 | 124 | 1 | VH1-12-1 | 0 | 0.0% | 54 |
| L17 | 120 | 1 | VH1-12-1 | 1 | 1.0% | 54 |
| L30 | 127 | 1 | VH1-12-1 | 1 | 1.0% | 54 |
| L37 | 120 | 1 | VH1-12-1 | 1 | 1.0% | 54 |
| TNF-E7 | 116 | 1 | VH1-12-1 | 2 | 2.0% | 42 |
| mAb111 | 122 | 1 | VH1-12-1 | 7 | 7.1% | 71 |
| III-2R | 122 | 1 | VH1-12-9 | 3 | 3.1% | 70 |
| KAS | 121 | 1 | VH1-12-1 | 7 | 7.1% | 79 |
| YES8c | 122 | 1 | VH1-12-1 | 8 | 8.2% | 34 |
| RF-TS1 | 123 | 1 | VH1-12-1 | 8 | 8.2% | 82 |
| BOR' | 121 | 1 | VH1-12-8 | 7 | 7.1% | 79 |
| VHGL 1.9 | 101 | 1 | VH1-12-1 | 8 | 8.2% | 26 |
| mAb410.30F305 | 117 | 1 | VH1-12-9 | 5 | 5.1% | 52 |
| EV1-15 | 127 | i | VH1-12-8 | 10 | 10.2% | 78 |
| mAb112 | 122 | 1 | VH1-12-1 | 11 | 11.2% | 71 |
| EU | 117 | 1 | VH1-12-1 | 11 | 11.2% | 28 |
| H210 | 127 | 1 | VH1-12-1 | 12 | 12.2% | 66 |
| TRANSGENE | 104 | 1 | VH1-12-1 | 0 | 0.0% | 111 |
| CLL2-1 | 93 | 1 | VH1-12-1 | 0 | 0.0% | 30 |
| CLL10 13-3 | 97 | 1 | VH1-12-1 | 0 | 0.0% | 29 |
| LS7 | 99 | 1 | VH1-12-7 | 4 | 4.1% | 113 |
| ALL7-1 | 87 | 1 | VH1-12-7 | 0 | 0.0% | 30 |
| CLL3-1 | 91 | 1 | VH1-12-7 | 1 | 1.0% | 30 |
| ALL56-1 | 85 | 1 | VH1-13-8 | 0 | 0.0% | 30 |
| ALL1-1 | 87 | 1 | VH1-13-6 | 1 | 1.0% | 30 |
| ALL4-1 | 94 | 1 | VH1-13-8 | 0 | 0.0% | 30 |
| ALL56 15-4 | 85 | 1 | VH1-13-8 | 5 | 5.1% | 29 |
| CLL4-1 | 88 | 1 | VH1-13-1 | 1 | 1.0% | 30 |
| Au92.1 | 98 | 1 | VH1-12-5 | 0 | 0.0% | 49 |
| RF-TS3 | 120 | 1 | VH1-12-5 | 1 | 1.0% | 82 |
| Au4.1 | 98 | 1 | VH1-12-5 | 1 | 1.0% | 49 |
| HP1 | 121 | 1 | VH1-13-6 | 13 | 13.3% | 110 |
| BLI | 127 | 1 | VH1-13-15 | 5 | 5.1% | 72 |
| No.13 | 127 | 1 | VH1-12-2 | 19 | 19.4% | 76 |
| TR1.23 | 122 | 1 | VH1-13-2 | 23 | 23.5% | 88 |
| S1-1 | 125 | 1 | VH1-12-2 | 18 | 18.4% | 76 |
| TR1.10 | 119 | 1 | VH1-13-12 | 14 | 14.3% | 88 |
| E55 1.A2 | 102 | 1 | VH1-13-15 | 3 | 3.1% | 26 |
| SP2 | 119 | 1 | VH1-13-6 | 15 | 15.3% | 89 |
| TNF-H9G1 | 111 | 1 | VH1-13-18 | 2 | 2.0% | 42 |
| G3D10H | 127 | 1 | VH1-13-16 | 19 | 19.4% | 127 |
| TR1.9 | 118 | 1 | VH1-13-12 | 14 | 14.3% | 88 |
| TR1.8 | 121 | 1 | VH1-12-1 | 24 | 24.5% | 88 |
| LUNm01 | 127 | 1 | VH1-13-6 | 22 | 22.4% | 9 |
| K1B12H | 127 | 1 | VH1-12-7 | 23 | 23.5% | 127 |
| L3B2 | 99 | 1 | VH1-13-6 | 2 | 2.0% | 46 |
| ss2 | 100 | 1 | VH1-13-6 | 2 | 2.0% | 46 |
| No.86 | 124 | 1 | VH1-12-1 | 20 | 20.4% | 76 |
| TR1.6 | 124 | 1 | VH1-12-1 | 19 | 19.4% | 88 |
| ss7 | 99 | 1 | VH1-12-7 | 3 | 3.1% | 46 |
| s5B7 | 102 | 1 | VH1-12-1 | 0 | 0.0% | 46 |
| s6A3 | 97 | 1 | VH1-12-1 | 0 | 0.0% | 46 |
| ss6 | 99 | 1 | VH1-12-1 | 0 | 0.0% | 46 |
| L2H7 | 103 | 1 | VH1-13-12 | 0 | 0.0% | 46 |
| s6BG8 | 93 | 1 | VH1-13-12 | 0 | 0.0% | 46 |
| s6C9 | 107 | 1 | VH1-13-12 | 0 | 0.0% | 46 |
| HIV-b4 | 124 | 1 | VH1-13-12 | 21 | 21.4% | 12 |
| HIV-b12 | 124 | 1 | VH1-13-12 | 21 | 21.4% | 12 |
| L3G5 | 98 | 1 | VH1-13-6 | 1 | 1.0% | 46 |
| 22 | 115 | 1 | VH1-13-6 | 11 | 11.2% | 118 |
| L2A12 | 99 | 1 | VH1-13-15 | 3 | 3.1% | 46 |
| PHOX15 | 124 | 1 | VH1-12-7 | 20 | 20.4% | 73 |
| LUNm03 | 127 | 1 | VH1-1X-1 | 18 | 18.4% | 9 |
| CEA4-8A | 129 | 1 | VH1-12-7 | 1 | 1.0% | 42 |
| M60 | 121 | 2 | VH2-31-3 | 3 | 3.0% | 103 |
| HiH10 | 127 | 2 | VH2-31-5 | 9 | 9.0% | 4 |
| COR | 119 | 2 | VH2-31-2 | 11 | 11.0% | 91 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| 2-115-19 | 124 | 2 | VH2-31-11 | 8 | 8.1% | 124 |
| OU | 125 | 2 | VH2-31-14 | 20 | 25.6% | 92 |
| HE | 120 | 2 | VH2-31-13 | 19 | 19.0% | 27 |
| CLL33 40-1 | 78 | 2 | VH2-31-5 | 2 | 2.0% | 29 |
| E55 3.9 | 88 | 3 | VH3-11-5 | 7 | 7.2% | 26 |
| MTFC3 | 125 | 3 | VH3-14-4 | 21 | 21.0% | 131 |
| MTFC11 | 125 | 3 | VH3-14-4 | 21 | 21.0% | 131 |
| MTFJ1 | 114 | 3 | VH3-14-4 | 21 | 21.0% | 131 |
| MTFJ2 | 114 | 3 | VH3-14-4 | 21 | 21.0% | 131 |
| MTFUJ4 | 100 | 3 | VH3-14-4 | 21 | 21.0% | 131 |
| MTFUJ5 | 100 | 3 | VH3-14-4 | 21 | 21.0% | 131 |
| MTFUJ2 | 100 | 3 | VH3-14-4 | 22 | 22.0% | 131 |
| MTFC8 | 125 | 3 | VH3-14-4 | 23 | 23.0% | 131 |
| TD e Vq | 113 | 3 | VH3-14-4 | 0 | 0.0% | 16 |
| rMTF | 114 | 3 | VH3-14-4 | 5 | 5.0% | 131 |
| MTFUJ6 | 100 | 3 | VH3-14-4 | 10 | 10.0% | 131 |
| RF-KES | 107 | 3 | VH3-14-4 | 9 | 9.0% | 85 |
| N51P8 | 126 | 3 | VH3-14-1 | 9 | 9.0% | 77 |
| TEI | 119 | 3 | VH3-13-8 | 21 | 21.4% | 20 |
| 33.H11 | 115 | 3 | VH3-13-19 | 10 | 10.2% | 129 |
| SB1/D8 | 101 | 3 | VH3-1X-8 | 14 | 14.0% | 2 |
| 38P1 | 119 | 3 | VH3-11-3 | 0 | 0.0% | 104 |
| BRO'IGM | 119 | 3 | VH3-11-3 | 13 | 13.4% | 19 |
| NIE | 119 | 3 | VH3-13-7 | 15 | 15.3% | 87 |
| 3D6 | 126 | 3 | VH3-13-26 | 5 | 5.1% | 35 |
| ZM1-1 | 112 | 3 | VH3-11-3 | 8 | 8.2% | 5 |
| E55 3.15 | 110 | 3 | VH3-13-26 | 0 | 0.0% | 26 |
| gF9 | 108 | 3 | VH3-13-8 | 15 | 15.3% | 75 |
| THY-32 | 120 | 3 | VH3-13-26 | 3 | 3.1% | 42 |
| RF-KL5 | 100 | 3 | VH3-13-26 | 5 | 5.1% | 96 |
| OST577 | 122 | 3 | VH3-13-13 | 6 | 6.1% | 5 |
| BO | 113 | 3 | VH3-13-19 | 15 | 15.3% | 10 |
| TT125 | 121 | 3 | VH3-13-10 | 15 | 15.3% | 64 |
| 2-115-58 | 127 | 3 | VH3-13-10 | 11 | 11.2% | 124 |
| KOL | 126 | 3 | VH3-13-14 | 16 | 16.3% | 102 |
| mAb60 | 118 | 3 | VH3-13-17 | 14 | 14.3% | 45 |
| RF-AN | 106 | 3 | VH3-13-26 | 8 | 8.2% | 85 |
| BUT | 115 | 3 | VH3-11-6 | 13 | 13.4% | 119 |
| KOL-based CAMPATH-9 | 118 | 3 | VH3-13-13 | 16 | 16.3% | 41 |
| B1 | 119 | 3 | VH3-13-19 | 13 | 13.3% | 53 |
| N98P1 | 127 | 3 | VH3-13-1 | 13 | 13.3% | 77 |
| TT117 | 107 | 3 | VH3-13-10 | 12 | 12.2% | 64 |
| WEA | 114 | 3 | VH3-13-12 | 15 | 15.3% | 40 |
| HIL | 120 | 3 | VH3-13-14 | 14 | 14.3% | 23 |
| s5A10 | 97 | 3 | VH3-13-14 | 0 | 0.0% | 46 |
| s5D11 | 98 | 3 | VH3-13-7 | 0 | 0.0% | 46 |
| s6C8 | 100 | 3 | VH3-13-7 | 0 | 0.0% | 46 |
| s6H12 | 98 | 3 | VH3-13-7 | 0 | 0.0% | 46 |
| VH10.7 | 119 | 3 | VH3-13-14 | 16 | 16.3% | 128 |
| HIV-loop2 | 126 | 3 | VH3-13-7 | 16 | 16.3% | 12 |
| HIV-loop35 | 126 | 3 | VH3-13-7 | 16 | 16.3% | 12 |
| TRO | 122 | 3 | VH3-13-1 | 13 | 13.3% | 61 |
| SA-4B | 123 | 3 | VH3-13-1 | 15 | 15.3% | 125 |
| L2B5 | 98 | 3 | VH3-13-13 | 0 | 0.0% | 46 |
| s6E11 | 95 | 3 | VH3-13-13 | 0 | 0.0% | 46 |
| s6H7 | 100 | 3 | VH3-13-13 | 0 | 0.0% | 46 |
| ss1 | 102 | 3 | VH3-13-13 | 0 | 0.0% | 46 |
| ss8 | 94 | 3 | VH3-13-13 | 0 | 0.0% | 46 |
| DOB | 120 | 3 | VH3-13-26 | 21 | 21.4% | 116 |
| THY-33 | 115 | 3 | VH3-13-15 | 20 | 20.4% | 42 |
| NOV | 118 | 3 | VH3-13-19 | 14 | 14.3% | 38 |
| rsv13H | 120 | 3 | VH3-13-24 | 20 | 20.4% | 11 |
| L3G11 | 98 | 3 | VH3-13-20 | 2 | 2.0% | 46 |
| L2E8 | 99 | 3 | VH3-13-19 | 0 | 0.0% | 46 |
| L2D10 | 101 | 3 | VH3-13-10 | 0 | 1.0% | 46 |
| L2E7 | 98 | 3 | VH3-13-10 | 1 | 1.0% | 46 |
| L3A10 | 100 | 3 | VH3-13-24 | 0 | 0.0% | 46 |
| L2E5 | 97 | 3 | VH3-13-2 | 1 | 1.0% | 46 |
| BUR | 119 | 3 | VH3-13-7 | 21 | 21.4% | 67 |
| s4D5 | 107 | 3 | VH3-11-3 | 1 | 1.0% | 46 |
| 19 | 116 | 3 | VH3-13-16 | 4 | 4.1% | 118 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| s5D4 | 99 | 3 | VH3-13-1 | 0 | 0.0% | 46 |
| s6A8 | 100 | 3 | VH3-13-1 | 0 | 0.0% | 46 |
| HIV-loopl3 | 123 | 3 | VH3-13-12 | 17 | 17.3% | 12 |
| TR1.32 | 112 | 3 | VH3-11-8 | 18 | 18.6% | 88 |
| L2B10 | 97 | 3 | VH3-11-3 | 1 | 1.0% | 46 |
| TR1.5 | 114 | 3 | VH3-11-8 | 21 | 21.6% | 88 |
| s6H9 | 101 | 3 | VH3-13-25 | 0 | 0.0% | 46 |
| 8 | 112 | 3 | VH3-13-1 | 6 | 6.1% | 118 |
| 23 | 115 | 3 | VH3-13-1 | 6 | 6.1% | 118 |
| 7 | 115 | 3 | VH3-13-1 | 4 | 4.1% | 118 |
| TR1.3 | 120 | 3 | VH3-1l-8 | 20 | 20.6% | 88 |
| 18/2 | 125 | 3 | VH3-13-10 | 0 | 0.0% | 32 |
| 18/9 | 125 | 3 | VH3-13-10 | 0 | 0.0% | 31 |
| 30P1 | 119 | 3 | VH3-13-10 | 0 | 0.0% | 106 |
| HF2-1/17 | 125 | 3 | VH3-13-10 | 0 | 0.0% | 8 |
| A77 | 109 | 3 | VH3-13-10 | 0 | 0.0% | 44 |
| B19.7 | 108 | 3 | VH3-13-10 | 0 | 0.0% | 44 |
| M43 | 119 | 3 | VH3-13-10 | 0 | 0.0% | 103 |
| 1/17 | 125 | 3 | VH3-13-10 | 0 | 0.0% | 31 |
| 18/17 | 125 | 3 | VH3-13-10 | 0 | 0.0% | 31 |
| E54 3.4 | 109 | 3 | VH3-13-10 | 0 | 0.0% | 26 |
| LAMBDA-VH26 | 98 | 3 | VH3-13-10 | 1 | 1.0% | 95 |
| E54 3.8 | 111 | 3 | VH3-13-10 | 1 | 1.0% | 26 |
| GL16 | 106 | 3 | VH3-13-10 | 1 | 1.0% | 44 |
| 4G12 | 125 | 3 | VH3-13-10 | 1 | 1.0% | 56 |
| A73 | 106 | 3 | VH3-13-10 | 2 | 2.0% | 44 |
| AL1.3 | 111 | 3 | VH3-13-10 | 3 | 3.1% | 117 |
| 3.A290 | 118 | 3 | VH3-13-10 | 2 | 2.0% | 108 |
| Ab18 | 127 | 3 | VH3-13-8 | 2 | 2.0% | 100 |
| E54 3.3 | 105 | 3 | VH3-13-10 | 3 | 3.1% | 26 |
| 35G6 | 121 | 3 | VH3-13-10 | 3 | 3.1% | 57 |
| A95 | 107 | 3 | VH3-13-10 | 5 | 5.1% | 44 |
| Ab25 | 128 | 3 | VH3-13-10 | 5 | 5.1% | 100 |
| N87 | 126 | 3 | VH3-13-10 | 4 | 4.1% | 77 |
| ED8.4 | 99 | 3 | VH3-13-10 | 6 | 6.1% | 2 |
| RF-KL1 | 122 | 3 | VH3-13-10 | 6 | 6.1% | 82 |
| AL1.1 | 112 | 3 | VH3-13-10 | 2 | 2.0% | 117 |
| AL3.11 | 102 | 3 | VH3-13-10 | 1 | 1.0% | 117 |
| 32.B9 | 127 | 3 | VH3-13-8 | 6 | 6.1% | 129 |
| TK1 | 109 | 3 | VH3-13-10 | 2 | 2.0% | 117 |
| POP | 123 | 3 | VH3-13-10 | 8 | 8.2% | 115 |
| 9F2H | 127 | 3 | VH3-13-10 | 9 | 9.2% | 127 |
| VD | 115 | 3 | VH3-13-10 | 9 | 9.2% | 10 |
| Vh38Cl.10 | 121 | 3 | VH3-13-10 | 8 | 8.2% | 74 |
| Vh38Cl.9 | 121 | 3 | VH3-13-10 | 8 | 8.2% | 74 |
| Vh38Cl.8 | 121 | 3 | VH3-13-10 | 8 | 8.2% | 74 |
| 63P1 | 120 | 3 | VH3-11-8 | 0 | 0.0% | 104 |
| 60P2 | 117 | 3 | VH3-11-8 | 0 | 0.0% | 104 |
| AL3.5 | 90 | 3 | VH3-13-10 | 2 | 2.0% | 117 |
| GF4/1.1 | 123 | 3 | VH3-13-10 | 10 | 10.2% | 39 |
| Ab21 | 126 | 3 | VH3-13-10 | 12 | 12.2% | 100 |
| TD d Vp | 118 | 3 | VH3-13-17 | 2 | 2.0% | 16 |
| Vh38Cl.4 | 119 | 3 | VH3-13-10 | 8 | 8.2% | 74 |
| Vh38Cl.5 | 119 | 3 | VH3-13-10 | 8 | 8.2% | 74 |
| AL3.4 | 104 | 3 | VH3-13-10 | 1 | 1.0% | 117 |
| FOG1-A3 | 115 | 3 | VH3-13-19 | 2 | 2.0% | 42 |
| HA3D1 | 117 | 3 | VH3-13-21 | 1 | 1.0% | 81 |
| E54 3.2 | 112 | 3 | VH3-13-24 | 0 | 0.0% | 26 |
| mAb52 | 128 | 3 | VH3-13-12 | 2 | 2.0% | 51 |
| mAb53 | 128 | 3 | VH3-13-12 | 2 | 2.0% | 51 |
| mAb56 | 128 | 3 | VH3-13-12 | 2 | 2.0% | 51 |
| mAb57 | 128 | 3 | VH3-13-12 | 2 | 2.0% | 51 |
| mAb58 | 128 | 3 | VH3-13-12 | 2 | 2.0% | 51 |
| mAb59 | 128 | 3 | VH3-13-12 | 2 | 2.0% | 51 |
| mAb105 | 128 | 3 | VH3-13-12 | 2 | 2.0% | 51 |
| mAb107 | 128 | 3 | VH3-13-12 | 2 | 2.0% | 51 |
| E55 3.14 | 110 | 3 | VH3-13-19 | 0 | 0.0% | 26 |
| F13-28 | 106 | 3 | VH3-13-19 | 1 | 1.0% | 94 |
| mAb55 | 127 | 3 | VH3-13-18 | 4 | 4.1% | 51 |
| YSE | 117 | 3 | VH3-13-24 | 6 | 6.1% | 72 |
| E55 3.23 | 106 | 3 | VH3-13-19 | 2 | 2.0% | 26 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| RF-TS5 | 101 | 3 | VH3-13-1 | 3 | 3.1% | 85 |
| N42P5 | 124 | 3 | VH3-13-2 | 7 | 7.1% | 77 |
| FOG1-H6 | 110 | 3 | VH3-13-16 | 7 | 7.1% | 42 |
| O-81 | 115 | 3 | VH3-13-19 | 11 | 11.2% | 47 |
| HIV-s8 | 122 | 3 | VH3-13-12 | 11 | 11.2% | 12 |
| mAb114 | 125 | 3 | VH3-13-19 | 12 | 12.2% | 71 |
| 33.F12 | 116 | 3 | VH3-13-2 | 4 | 4.1% | 129 |
| 4B4 | 119 | 3 | VH3-1X-3 | 0 | 0.0% | 101 |
| M26 | 123 | 3 | VH3-1X-3 | 0 | 0.0% | 103 |
| VHGL 3.1 | 100 | 3 | VH3-1X-3 | 0 | 0.0% | 26 |
| E55 3.13 | 113 | 3 | VH3-1X-3 | 1 | 1.0% | 26 |
| SB5/D6 | 101 | 3 | VH3-1X-6 | 3 | 3.0% | 2 |
| RAY4 | 101 | 3 | VH3-1X-6 | 3 | 3.0% | 2 |
| 82-D V-D | 106 | 3 | VH3-1X-3 | 5 | 5.0% | 112 |
| MAL | 129 | 3 | VH3-1X-3 | 5 | 5.0% | 72 |
| LOC | 123 | 3 | VH3-1X-6 | 5 | 5.0% | 72 |
| LSF2 | 101 | 3 | VH3-1X-6 | 11 | 11.0% | 2 |
| HIB RC3 | 100 | 3 | VH3-1X-6 | 11 | 11.0% | 1 |
| 56P1 | 119 | 3 | VH3-13-7 | 0 | 0.0% | 104 |
| M72 | 122 | 3 | VH3-13-7 | 0 | 0.0% | 103 |
| M74 | 121 | 3 | VH3-13-7 | 0 | 0.0% | 103 |
| E54 3.5 | 105 | 3 | VH3-13-7 | 0 | 0.0% | 26 |
| 2E7 | 123 | 3 | VH3-13-7 | 0 | 0.0% | 63 |
| 2P1 | 117 | 3 | VH3-13-7 | 0 | 0.0% | 104 |
| RF-SJ2 | 127 | 3 | VH3-13-7 | 1 | 1.0% | 83 |
| PR-TS1 | 114 | 3 | VH3-13-7 | 1 | 1.0% | 85 |
| KIM46H | 127 | 3 | VH3-3-13 | 0 | 0.0% | 18 |
| E55 3.6 | 108 | 3 | VH3-13-7 | 2 | 2.0% | 26 |
| E55 3.10 | 107 | 3 | VH3-13-13 | 1 | 1.0% | 26 |
| 3.B6 | 114 | 3 | VH3-13-13 | 1 | 1.0% | 108 |
| E54 3.6 | 110 | 3 | VH3-13-13 | 1 | 1.0% | 26 |
| FL2-2 | 114 | 3 | VH3-13-13 | 1 | 1.0% | 80 |
| RF-SJ3 | 112 | 3 | VH3-13-7 | 2 | 2.0% | 85 |
| E55 3.5 | 105 | 3 | VH3-13-14 | 1 | 1.0% | 26 |
| BSA3 | 121 | 3 | VH3-13-13 | 1 | 1.0% | 73 |
| HMST-1 | 119 | 3 | VH3-13-7 | 3 | 3.1% | 130 |
| RF-TS2 | 126 | 3 | VH3-13-13 | 4 | 4.1% | 82 |
| E55 3.12 | 109 | 3 | VH3-13-15 | 0 | 0.0% | 26 |
| 19.E7 | 126 | 3 | VH3-13-14 | 3 | 3.1% | 129 |
| 11-50 | 119 | 3 | VH3-13-13 | 6 | 6.1% | 130 |
| E29.1 | 120 | 3 | VH3-13-15 | 2 | 2.0% | 25 |
| E55 3.16 | 108 | 3 | VH3-13-7 | 6 | 6.1% | 26 |
| TNF-E1 | 117 | 3 | VH3-13-7 | 7 | 7.1% | 42 |
| RF-SJ1 | 127 | 3 | VH3-13-13 | 6 | 6.1% | 83 |
| FOG1-A4 | 116 | 3 | VH3-13-7 | 8 | 8.2% | 42 |
| TNF-A1 | 117 | 3 | VH3-13-15 | 4 | 4.1% | 42 |
| PR-SJ2 | 107 | 3 | VH3-13-14 | 8 | 8.2% | 85 |
| HN.14 | 124 | 3 | VH3-13-13 | 10 | 10.2% | 33 |
| CAM' | 121 | 3 | VH3-13-7 | 12 | 12.2% | 65 |
| HIV-B8 | 125 | 3 | VH3-13-7 | 9 | 9.2% | 12 |
| HIV-b27 | 125 | 3 | VH3-13-7 | 9 | 9.2% | 12 |
| HIV-b8 | 125 | 3 | VH3-13-7 | 9 | 9.2% | 12 |
| HIV-s4 | 125 | 3 | VH3-13-7 | 9 | 9.2% | 12 |
| HIV-B26 | 125 | 3 | VH3-13-7 | 9 | 9.2% | 12 |
| HIV-B35 | 125 | 3 | VH3-13-7 | 10 | 10.2% | 12 |
| HIV-b18 | 125 | 3 | VH3-13-7 | 10 | 10.2% | 12 |
| HIV-b22 | 125 | 3 | VH3-13-7 | 11 | 11.2% | 12 |
| HIV-b13 | 125 | 3 | VH3-13-7 | 12 | 12.2% | 12 |
| 333 | 117 | 3 | VH3-14-4 | 24 | 24.0% | 24 |
| 1H1 | 120 | 3 | VH3-14-4 | 24 | 24.0% | 24 |
| 1B11 | 120 | 3 | VH3-14-4 | 23 | 23.0% | 24 |
| CLL30 2-3 | 86 | 3 | VH3-13-19 | 1 | 1.0% | 29 |
| GA | 110 | 3 | VH3-13-7 | 19 | 19.4% | 36 |
| JeB | 99 | 3 | VH3-13-14 | 3 | 3.1% | 7 |
| GAL | 110 | 3 | VH3-13-19 | 10 | 10.2% | 126 |
| K6H6 | 119 | 3 | VH3-1X-6 | 18 | 18.0% | 60 |
| K4B8 | 119 | 3 | VH3-1X-6 | 1B | 18.0% | 60 |
| K5B8 | 119 | 3 | VH3-1X-6 | 18 | 18.0% | 60 |
| K5C7 | 119 | 3 | VH3-1X-6 | 19 | 19.0% | 60 |
| K5G5 | 119 | 3 | VH3-1X-6 | 19 | 19.0% | 60 |
| K6F5 | 119 | 3 | VH3-1X-6 | 19 | 19.0% | 60 |
| AL3.16 | 98 | 3 | VH3-13-10 | 1 | 1.0% | 117 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| N86P2 | 98 | 3 | VH3-13-10 | 3 | 3.1% | 77 |
| N54P6 | 95 | 3 | VH3-13-16 | 7 | 7.1% | 77 |
| LAMBDA HT112-1 | 126 | 4 | VH4-11-2 | 0 | 0.0% | 3 |
| HY18 | 121 | 4 | VH4-11-2 | 0 | 0.0% | 43 |
| mAb63 | 126 | 4 | VH4-11-2 | 0 | 0.0% | 45 |
| FS-3 | 105 | 4 | VH4-11-2 | 0 | 0.0% | 86 |
| FS-5 | 111 | 4 | VH4-11-2 | 0 | 0.0% | 86 |
| FS-7 | 107 | 4 | VH4-11-2 | 0 | 0.0% | 86 |
| FS-8 | 110 | 4 | VH4-11-2 | 0 | 0.0% | 86 |
| PR-TS2 | 105 | 4 | VH4-11-2 | 0 | 0.0% | 85 |
| RF-TMC | 102 | 4 | VH4-11-2 | 0 | 0.0% | 85 |
| mAb216 | 122 | 4 | VH4-11-2 | 1 | 1.0% | 15 |
| mAb410.7.F91 | 122 | 4 | VH4-11-2 | 1 | 1.0% | 52 |
| mAbA6H4C5 | 124 | 4 | VH4-11-2 | 1 | 1.0% | 15 |
| Ab44 | 127 | 4 | VH4-11-2 | 2 | 2.1% | 100 |
| 6H-3C4 | 124 | 4 | VH4-11-2 | 3 | 3.1% | 59 |
| FS-6 | 108 | 4 | VH4-11-2 | 6 | 6.2% | 86 |
| FS-2 | 114 | 4 | VH4-11-2 | 6 | 6.2% | 84 |
| HIG1 | 126 | 4 | VH4-11-2 | 7 | 7.2% | 62 |
| FS-4 | 105 | 4 | VH4-11-2 | 8 | 8.2% | 86 |
| SA-4A | 123 | 4 | VH4-11-2 | 9 | 9.3% | 125 |
| LES-C | 119 | 4 | VH4-11-2 | 10 | 10.3% | 99 |
| DI | 78 | 4 | VH4-11-9 | 16 | 16.5% | 58 |
| Ab26 | 126 | 4 | VH4-31-4 | 8 | 8.1% | 100 |
| TS2 | 124 | 4 | VH4-31-12 | 15 | 15.2% | 110 |
| 265-695 | 115 | 4 | VH4-11-7 | 16 | 16.5% | 5 |
| WAH | 129 | 4 | VH4-31-13 | 19 | 19.2% | 93 |
| 268-D | 122 | 4 | VH4-11-8 | 22 | 22.7% | 6 |
| 58P2 | 118 | 4 | VH4-11-8 | 0 | 0.0% | 104 |
| mAb67 | 128 | 4 | VH4-21-4 | 1 | 1.0% | 45 |
| 4.L39 | 115 | 4 | VH4-11-8 | 2 | 2.1% | 108 |
| mF7 | 111 | 4 | VH4-31-13 | 3 | 3.0% | 75 |
| 33.C9 | 122 | 4 | VH4-21-5 | 7 | 7.1% | 129 |
| Pag-1 | 124 | 4 | VH4-11-16 | 5 | 5.2% | 50 |
| B3 | 123 | 4 | VH4-21-3 | 8 | 8.2% | 53 |
| IC4 | 120 | 4 | VH4-11-8 | 6 | 6.2% | 70 |
| C6B2 | 127 | 4 | VH4-31-12 | 4 | 4.0% | 48 |
| N78 | 118 | 4 | VH4-11-9 | 11 | 11.3% | 77 |
| B2 | 109 | 4 | VH4-11-8 | 12 | 12.4% | 53 |
| WRD2 | 123 | 4 | VH4-11-12 | 6 | 6.2% | 90 |
| mAb426.4.2F20 | 126 | 4 | VH4-11-8 | 2 | 2.1% | 52 |
| E54 4.58 | 115 | 4 | VH4-11-8 | 1 | 1.0% | 26 |
| WRD6 | 123 | 4 | VH4-11-12 | 10 | 10.3% | 90 |
| mAb426.12.3F1.4 | 122 | 4 | VH4-11-9 | 4 | 4.1% | 52 |
| E54 4.2 | 108 | 4 | VH4-21-6 | 2 | 2.0% | 26 |
| WIL | 127 | 4 | VH4-31-13 | 0 | 0.0% | 90 |
| COF | 126 | 4 | VH4-31-13 | 0 | 0.0% | 90 |
| LAR | 122 | 4 | VH4-31-13 | 2 | 2.0% | 90 |
| WAT | 125 | 4 | VH4-31-13 | 4 | 4.0% | 90 |
| mAb61 | 123 | 4 | VH4-31-13 | 5 | 5.1% | 45 |
| WAG | 127 | 4 | VH4-31-4 | 0 | 0.0% | 90 |
| RF-SJ4 | 108 | 4 | VH4-31-12 | 2 | 2.0% | 85 |
| E54 4.4 | 110 | 4 | VH4-11-7 | 0 | 0.0% | 26 |
| E55 4.A1 | 108 | 4 | VH4-11-7 | 0 | 0.0% | 26 |
| PR-SJ1 | 103 | 4 | VH4-11-7 | 1 | 1.0% | 85 |
| E54 4.23 | 111 | 4 | VH4-11-7 | 1 | 1.0% | 26 |
| CLL7 7-2 | 97 | 4 | VH4-11-12 | 0 | 0.0% | 29 |
| 37P1 | 95 | 4 | VH4-11-12 | 0 | 0.0% | 104 |
| ALL52 30-2 | 91 | 4 | VH4-31-12 | 4 | 4.0% | 29 |
| EBV-21 | 98 | 5 | VH5-12-1 | 0 | 0.0% | 13 |
| CB-4 | 98 | 5 | VH5-12-1 | 0 | 0.0% | 13 |
| CLL-12 | 98 | 5 | VH5-12-1 | 0 | 0.0% | 13 |
| L3-4 | 98 | 5 | VH5-12-1 | 0 | 0.0% | 13 |
| CLL11 | 98 | 5 | VH5-12-1 | 0 | 0.0% | 17 |
| CORD3 | 98 | 5 | VH5-12-1 | 0 | 0.0% | 17 |
| CORD4 | 98 | 5 | VH5-12-1 | 0 | 0.0% | 17 |
| CORD8 | 98 | 5 | VH5-12-1 | 0 | 0.0% | 17 |
| CORD9 | 98 | 5 | VH5-12-1 | 0 | 0.0% | 17 |
| CD + 1 | 98 | 5 | VH5-12-1 | 0 | 0.0% | 17 |
| CD + 3 | 98 | 5 | VH5-12-1 | 0 | 0.0% | 17 |
| CD + 4 | 98 | 5 | VH5-12-1 | 0 | 0.0% | 17 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| CD − 1 | 98 | 5 | VH5-12-1 | 0 | 0.0% | 17 |
| CD − 5 | 98 | 5 | VH5-12-1 | 0 | 0.0% | 17 |
| VERG14 | 98 | 5 | VH5-12-1 | 0 | 0.0% | 17 |
| PBL1 | 98 | 5 | VH5-12-1 | 0 | 0.0% | 17 |
| PBL10 | 98 | 5 | VH5-12-1 | 0 | 0.0% | 17 |
| STRAb SA-1A | 127 | 5 | VH5-12-1 | 0 | 0.0% | 125 |
| DOB' | 122 | 5 | VH5-12-1 | 0 | 0.0% | 97 |
| VERG5 | 98 | 5 | VH5-12-1 | 0 | 0.0% | 17 |
| PBL2 | 98 | 5 | VH5-12-1 | 1 | 1.0% | 17 |
| Tu16 | 119 | 5 | VH5-12-1 | 1 | 1.0% | 49 |
| PBL12 | 98 | 5 | VH5-12-1 | 1 | 1.0% | 17 |
| CD + 2 | 98 | 5 | VH5-12-1 | 1 | 1.0% | 17 |
| CORD10 | 98 | 5 | VH5-12-1 | 1 | 1.0% | 17 |
| PBL9 | 98 | 5 | VH5-12-1 | 1 | 1.0% | 17 |
| CORD2 | 98 | 5 | VH5-12-1 | 2 | 2.0% | 17 |
| PBL6 | 98 | 5 | VH5-12-1 | 2 | 2.0% | 17 |
| CORD5 | 98 | 5 | VH5-12-1 | 2 | 2.0% | 17 |
| CD − 2 | 98 | 5 | VH5-12-1 | 2 | 2.0% | 17 |
| CORD1 | 98 | 5 | VH5-12-1 | 2 | 2.0% | 17 |
| CD − 3 | 98 | 5 | VH5-12-1 | 3 | 3.1% | 17 |
| VERG4 | 98 | 5 | VH5-12-1 | 3 | 3.1% | 17 |
| PBL13 | 98 | 5 | VH5-12-1 | 3 | 3.1% | 17 |
| PBL7 | 98 | 5 | VH5-12-1 | 3 | 3.1% | 17 |
| HAN | 19 | 5 | VH5-12-1 | 3 | 3.1% | 97 |
| VERG3 | 98 | 5 | VH5-12-1 | 3 | 3.1% | 17 |
| PBL3 | 98 | 5 | VH5-12-1 | 3 | 3.1% | 17 |
| VERG7 | 98 | 5 | VH5-12-1 | 3 | 3.1% | 17 |
| PBL5 | 94 | 5 | VH5-12-1 | 0 | 0.0% | 17 |
| CD − 4 | 98 | 5 | VH5-12-1 | 4 | 4.1% | 17 |
| CLL10 | 98 | 5 | VH5-12-1 | 4 | 4.1% | 17 |
| PBL11 | 98 | 5 | VH5-12-1 | 4 | 4.1% | 17 |
| CORD6 | 98 | 5 | VH5-12-1 | 4 | 4.1% | 17 |
| VERG2 | 98 | 5 | VH5-12-1 | 5 | 5.1% | 17 |
| 83P2 | 119 | 5 | VH5-12-1 | 0 | 0.0% | 103 |
| VERG9 | 98 | 5 | VH5-12-1 | 6 | 6.1% | 17 |
| CLL6 | 98 | 5 | VH5-12-1 | 6 | 6.1% | 17 |
| PBL8 | 98 | 5 | VH5-12-1 | 7 | 7.1% | 17 |
| Ab2022 | 120 | 5 | VH5-12-1 | 3 | 3.1% | 100 |
| CAV | 127 | 5 | VH5-12-4 | 0 | 0.0% | 97 |
| HOW' | 120 | 5 | VH5-12-4 | 0 | 0.0% | 97 |
| PET | 127 | 5 | VH5-12-4 | 0 | 0.0% | 97 |
| ANG | 121 | 5 | VH5-12-4 | 0 | 0.0% | 97 |
| KER | 121 | 5 | VH5-12-4 | 0 | 0.0% | 97 |
| 5.M13 | 118 | 5 | VH5-12-4 | 0 | 0.0% | 107 |
| Au2.1 | 118 | 5 | VH5-12-4 | 1 | 1.0% | 49 |
| WS1 | 126 | 5 | VH5-12-4 | 9 | 9.2% | 110 |
| TD Vn | 98 | 5 | VH5-12-4 | 1 | 1.0% | 16 |
| TEL13 | 116 | 5 | VH5-12-1 | 9 | 9.2% | 73 |
| E55 5.237 | 112 | 5 | VH5-12-4 | 2 | 2.0% | 26 |
| VERG1 | 98 | 5 | VH5-12-1 | 10 | 10.2% | 17 |
| CD4-74 | 117 | 5 | VH5-12-1 | 10 | 10.2% | 42 |
| 257-D | 125 | 5 | VH5-12-1 | 11 | 11.2% | 6 |
| CLL4 | 98 | 5 | VH5-12-1 | 11 | 11.2% | 17 |
| CLL8 | 98 | 5 | VH5-12-1 | 11 | 11.2% | 17 |
| Ab2 | 124 | 5 | VH5-12-1 | 12 | 12.2% | 120 |
| Vh383ex | 98 | 5 | VH5-12-1 | 12 | 12.2% | 120 |
| CLL3 | 98 | 5 | VH5-12-2 | 11 | 11.2% | 17 |
| Au59.1 | 122 | 5 | VH5-12-1 | 12 | 12.2% | 49 |
| TEL16 | 117 | 5 | VH5-12-1 | 12 | 12.2% | 73 |
| M61 | 104 | 5 | VH5-12-1 | 0 | 0.0% | 103 |
| Tu0 | 99 | 5 | VH5-12-1 | 5 | 5.1% | 49 |
| P2-51 | 122 | 5 | VH5-12-1 | 13 | 13.3% | 121 |
| P2-54 | 122 | 5 | VH5-12-1 | 11 | 11.2% | 121 |
| P1-56 | 119 | 5 | VH5-12-1 | 9 | 9.2% | 121 |
| P2-53 | 122 | 5 | VH5-12-1 | 10 | 10.2% | 121 |
| P1-51 | 123 | 5 | VH5-12-1 | 19 | 19.4% | 121 |
| P1-54 | 123 | 5 | VH5-12-1 | 3 | 3.1% | 121 |
| P3-69 | 127 | 5 | VH5-12-1 | 4 | 4.1% | 121 |
| P3-9 | 119 | 5 | VH5-12-1 | 4 | 4.1% | 121 |
| 1-185-37 | 125 | 5 | VH5-12-4 | 0 | 0.0% | 124 |
| 1-187-29 | 125 | 5 | VH5-12-4 | 0 | 0.0% | 124 |
| P1-58 | 128 | 5 | VH5-12-4 | 10 | 10.2% | 121 |
| P2-57 | 118 | 5 | VH5-12-4 | 3 | 3.1% | 121 |
| P2-55 | 123 | 5 | VH5-12-1 | 5 | 5.1% | 121 |
| P2-56 | 123 | 5 | VH5-12-1 | 20 | 20.4% | 121 |
| P2-52 | 122 | 5 | VH5-12-1 | 11 | 11.2% | 121 |
| P3-60 | 122 | 5 | VH5-12-1 | 8 | 8.2% | 121 |
| P1-57 | 123 | 5 | VH5-12-1 | 4 | 4.1% | 121 |
| P1-55 | 122 | 5 | VH5-12-1 | 14 | 14.3% | 121 |
| MD3-4 | 128 | 5 | VH5-12-4 | 12 | 12.2% | 5 |
| P1-52 | 121 | 5 | VH5-12-1 | 11 | 11.2% | 121 |
| CLL5 | 98 | 5 | VH5-12-1 | 13 | 13.3% | 17 |
| CLL7 | 98 | 5 | VH5-12-1 | 14 | 14.3% | 17 |
| L2F10 | 100 | 5 | VH5-12-1 | 1 | 1.0% | 46 |
| L3B6 | 98 | 5 | VH5-12-1 | 1 | 1.0% | 46 |
| VH6.A12 | 119 | 6 | VH6-35-1 | 13 | 12.9% | 122 |
| s5A9 | 102 | 6 | VH6-35-1 | 1 | 1.0% | 46 |
| s6G4 | 99 | 6 | VH6-35-1 | 1 | 1.0% | 46 |
| ss3 | 99 | 6 | VH6-35-1 | 1 | 1.0% | 46 |
| 6-1G1 | 101 | 6 | VH6-35-1 | 0 | 0.0% | 14 |
| F19L16 | 107 | 6 | VH6-35-1 | 0 | 0.0% | 68 |
| L16 | 120 | 6 | VH6-35-1 | 0 | 0.0% | 69 |
| M71 | 121 | 6 | VH6-35-1 | 0 | 0.0% | 103 |
| ML1 | 120 | 6 | VH6-35-1 | 0 | 0.0% | 69 |
| F19ML1 | 107 | 6 | VH6-35-1 | 0 | 0.0% | 68 |
| 15P1 | 127 | 6 | VH6-35-1 | 0 | 0.0% | 104 |
| VH6.N1 | 121 | 6 | VH6-35-1 | 0 | 0.0% | 122 |
| VH6.N11 | 123 | 6 | VH6-35-1 | 0 | 0.0% | 122 |
| VH6.N12 | 123 | 6 | VH6-35-1 | 0 | 0.0% | 122 |
| VH6.N2 | 125 | 6 | VH6-35-1 | 0 | 0.0% | 122 |
| VH6.N5 | 125 | 6 | VH6-35-1 | 0 | 0.0% | 122 |
| VH6.N6 | 127 | 6 | VH6-35-1 | 0 | 0.0% | 122 |
| VH6.N7 | 126 | 6 | VH6-35-1 | 0 | 0.0% | 122 |
| VH6.N8 | 123 | 6 | VH6-35-1 | 0 | 0.0% | 122 |
| VH6.N9 | 123 | 6 | VH6-35-1 | 0 | 0.0% | 122 |
| VH6.N10 | 123 | 6 | VH6-35-1 | 0 | 0.0% | 122 |
| VH6.A3 | 123 | 6 | VH6-35-1 | 0 | 0.0% | 122 |
| VH6.A1 | 124 | 6 | VH6-35-1 | 0 | 0.0% | 122 |
| VH6.A4 | 120 | 6 | VH6-35-1 | 0 | 0.0% | 122 |
| E55 6.16 | 116 | 6 | VH6-35-1 | 0 | 0.0% | 26 |
| E55 6.17 | 120 | 6 | VH6-35-1 | 0 | 0.0% | 26 |
| E55 6.6 | 120 | 6 | VH6-35-1 | 0 | 0.0% | 26 |
| VHGL 6.3 | 102 | 6 | VH6-35-1 | 0 | 0.0% | 26 |
| CB-201 | 118 | 6 | VH6-35-1 | 0 | 0.0% | 109 |
| VH6.N4 | 122 | 6 | VH6-35-1 | 0 | 0.0% | 122 |
| E54 6.4 | 109 | 6 | VH6-35-1 | 1 | 1.0% | 26 |
| VH6.A6 | 126 | 6 | VH6-35-1 | 1 | 1.0% | 122 |
| E55 6.14 | 120 | 6 | VH6-35-1 | 1 | 1.0% | 26 |
| E54 6.6 | 107 | 6 | VH6-35-1 | 1 | 1.0% | 26 |
| E55 6.10 | 112 | 6 | VH6-35-1 | 1 | 1.0% | 26 |
| E54 6.1 | 107 | 6 | VH6-35-1 | 2 | 2.0% | 26 |
| E55 6.13 | 120 | 6 | VH6-35-1 | 2 | 2.0% | 26 |
| E55 6.3 | 120 | 6 | VH6-35-1 | 2 | 2.0% | 26 |
| E55 6.7 | 116 | 6 | VH6-35-1 | 2 | 2.0% | 26 |
| E55 6.2 | 120 | 6 | VH6-35-1 | 2 | 2.0% | 26 |
| E55 6.X | 111 | 6 | VH6-35-1 | 2 | 2.0% | 26 |
| E55 6.11 | 111 | 6 | VH6-35-1 | 3 | 3.0% | 26 |
| VH6.A11 | 118 | 6 | VH6-35-1 | 3 | 3.0% | 122 |
| A10 | 107 | 6 | VH6-35-1 | 3 | 3.0% | 68 |
| E55 6.1 | 120 | 6 | VH6-35-1 | 4 | 4.0% | 26 |
| FK-001 | 124 | 6 | VH6-35-1 | 4 | 4.0% | 65 |
| VH6.A5 | 121 | 6 | VH6-35-1 | 4 | 4.0% | 122 |
| VH6.A7 | 123 | 6 | VH6-35-1 | 4 | 4.0% | 122 |
| HBp2 | 119 | 6 | VH6-35-1 | 4 | 4.0% | 4 |
| Au46.2 | 123 | 6 | VH6-35-1 | 5 | 5.0% | 49 |
| A431 | 106 | 6 | VH6-35-1 | 5 | 5.0% | 68 |
| VH6.A2 | 120 | 6 | VH6-35-1 | 5 | 5.0% | 122 |
| VH6.A9 | 125 | 6 | VH6-35-1 | 8 | 7.9% | 122 |
| VH6.A8 | 118 | 6 | VH6-35-1 | 10 | 9.9% | 122 |
| VH6-FF3 | 118 | 6 | VH6-35-1 | 2 | 2.0% | 123 |
| VH6.A10 | 126 | 6 | VH6-35-1 | 12 | 11.9% | 122 |
| VH6-EB10 | 117 | 6 | VH6-35-1 | 3 | 3.0% | 123 |
| VH6-E6 | 119 | 6 | VH6-35-1 | 6 | 5.9% | 123 |
| VH6-FE2 | 121 | 6 | VH6-35-1 | 6 | 5.9% | 123 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| VH6-EE6 | 116 | 6 | VH6-35-1 | 6 | 5.9% | 123 |
| VH6-FD10 | 118 | 6 | VH6-35-1 | 6 | 5.9% | 123 |
| VH6-EX8 | 113 | 6 | VH6-35-1 | 6 | 5.9% | 123 |
| VH6-FG9 | 121 | 6 | VH6-35-1 | 8 | 7.9% | 123 |
| VH6-E5 | 116 | 6 | VH6-35-1 | 9 | 8.9% | 123 |
| VH6-EC8 | 122 | 6 | VH6-35-1 | 9 | 8.9% | 123 |
| VH6-E10 | 120 | 6 | VH6-35-1 | 10 | 9.9% | 123 |
| VH6-FF11 | 122 | 6 | VH6-35-1 | 11 | 10.9% | 123 |
| VH6-FD2 | 115 | 6 | VH6-35-1 | 11 | 10.9% | 123 |
| CLL10 17-2 | 88 | 6 | VH6-35-1 | 4 | 4.0% | 29 |
| VH6-BB11 | 94 | 6 | VH6-35-1 | 4 | 4.0% | 123 |
| VH6-B4I | 93 | 6 | VH6-35-1 | 7 | 6.9% | 123 |
| JU17 | 102 | 6 | VH6-35-1 | 3 | 3.0% | 114 |
| VH6-BD9 | 96 | 6 | VH6-35-1 | 11 | 10.9% | 123 |
| VH6-BB9 | 94 | 6 | VH6-35-1 | 12 | 11.9% | 123 |

TABLE 3A assignment of rearranged V kappa sequences to their germline counterparts

| Family[1] | Name | Rearranged[2] | Sum |
|---|---|---|---|
| 1 | Vk1-1 | 28 | |
| 1 | Vk1-2 | 0 | |
| 1 | Vk1-3 | 1 | |
| 1 | Vk1-4 | 0 | |
| 1 | Vk1-5 | 7 | |
| 1 | Vk1-6 | 0 | |
| 1 | Vk1-7 | 0 | |
| 1 | Vk1-8 | 2 | |
| 1 | Vk1-9 | 9 | |
| 1 | Vk1-10 | 0 | |
| 1 | Vk1-11 | 1 | |
| 1 | Vk1-12 | 7 | |
| 1 | Vk1-13 | 1 | |
| 1 | Vk1-14 | 7 | |
| 1 | Vk1-15 | 2 | |
| 1 | Vk1-16 | 2 | |
| 1 | Vk1-17 | 16 | |
| 1 | Vk1-18 | 1 | |
| 1 | Vk1-19 | 33 | |
| 1 | Vk1-20 | 1 | |
| 1 | Vk1-21 | 1 | |
| 1 | Vk1-22 | 0 | |
| 1 | Vk1-23 | 0 | 119 entries |
| 2 | Vk2-1 | 0 | |
| 2 | Vk2-2 | 1 | |
| 2 | Vk2-3 | 0 | |
| 2 | Vk2-4 | 0 | |
| 2 | Vk2-5 | 0 | |
| 2 | Vk2-6 | 16 | |
| 2 | Vk2-7 | 0 | |
| 2 | Vk2-8 | 0 | |
| 2 | Vk2-9 | 1 | |
| 2 | Vk2-10 | 0 | |
| 2 | Vk2-11 | 7 | |
| 2 | Vk2-12 | 0 | 25 entries |
| 3 | Vk3-1 | 1 | |
| 3 | Vk3-2 | 0 | |
| 3 | Vk3-3 | 35 | |
| 3 | Vk3-4 | 115 | |
| 3 | Vk3-5 | 0 | |
| 3 | Vk3-6 | 0 | |
| 3 | Vk3-7 | 1 | |
| 3 | Vk3-8 | 40 | 192 entries |
| 4 | Vk4-1 | 33 | 33 entries |
| 5 | Vk5-1 | 1 | 1 entry |
| 6 | Vk6-1 | 0 | |

TABLE 3A-continued assignment of rearranged V kappa sequences to their germline counterparts

| Family[1] | Name | Rearranged[2] | Sum |
|---|---|---|---|
| 6 | Vk6-2 | 0 | 0 entries |
| 7 | Vk7-1 | 0 | 0 entries |

TABLE 3B assignment of rearranged V lambda sequences to their germline counterparts

| Family[1] | Name | Rearranged[2] | Sum |
|---|---|---|---|
| 1 | DPL1 | 1 | |
| 1 | DPL2 | 14 | |
| 1 | DPL3 | 6 | |
| 1 | DPL4 | 1 | |
| 1 | HUMLV117 | 4 | |
| 1 | DPL5 | 13 | |
| 1 | DPL6 | 0 | |
| 1 | DPL7 | 0 | |
| 1 | DPL8 | 3 | |
| 1 | DPL9 | 0 | 42 entries |
| 2 | DPL10 | 5 | |
| 2 | VLAMBDA 2.1 | 0 | |
| 2 | DPL11 | 23 | |
| 2 | DPL12 | 15 | |
| 2 | DPL13 | 0 | |
| 2 | DPL14 | 0 | 43 entries |
| 3 | DPL16 | 10 | |
| 3 | DPL23 | 19 | |
| 3 | Humlv318 | 9 | 38 entries |
| 7 | DPL18 | 1 | |
| 7 | DPL19 | 0 | 1 entries |
| 8 | DPL21 | 2 | |
| 8 | HUMLV801 | 6 | 8 entries |
| 9 | DPL22 | 0 | 0 entries |
| unassigned | DPL24 | 0 | 0 entries |
| 10 | gVLX-4.4 | 0 | 0 entries |

TABLE 3C assignment of rearranged V heavy chain sequences to their germline counterparts

| Family[1] | Name | Rearranged[2] | Sum |
|---|---|---|---|
| 1 | VH1-12-1 | 38 | |
| 1 | VH1-12-8 | 2 | |
| 1 | VH1-12-2 | 2 | |
| 1 | VH1-12-9 | 2 | |
| 1 | VH1-12-3 | 0 | |
| 1 | VH1-12-4 | 0 | |
| 1 | VH1-12-5 | 3 | |
| 1 | VH1-12-6 | 0 | |
| 1 | VH1-12-7 | 23 | |
| 1 | VH1-13-1 | 1 | |
| 1 | VH1-13-2 | 1 | |
| 1 | VH1-13-3 | 0 | |
| 1 | VH1-13-4 | 0 | |
| 1 | VH1-13-5 | 0 | |
| 1 | VH1-13-6 | 17 | |
| 1 | VH1-13-7 | 0 | |
| 1 | VH1-13-8 | 3 | |
| 1 | VH1-13-9 | 0 | |
| 1 | VH1-13-10 | 0 | |
| 1 | VH1-13-11 | 0 | |
| 1 | VH1-13-12 | 10 | |
| 1 | VH1-13-13 | 0 | |
| 1 | VH1-13-14 | 0 | |
| 1 | VH1-13-15 | 4 | |
| 1 | VH1-13-16 | 2 | |

TABLE 3C-continued assignment of rearranged V heavy chain sequences to their germline counterparts

| Family[1] | Name | Rearranged[2] | Sum |
|---|---|---|---|
| 1 | VH1-13-17 | 0 | |
| 1 | VH1-13-18 | 1 | |
| 1 | VH1-13-19 | 0 | |
| 1 | VH1-1X-1 | 1 | 110 entries |
| 2 | VH2-21-1 | 0 | |
| 2 | VH2-31-1 | 0 | |
| 2 | VH2-31-2 | 1 | |
| 2 | VH2-31-3 | 1 | |
| 2 | VH2-31-4 | 0 | |
| 2 | VH2-31-5 | 2 | |
| 2 | VH2-31-6 | 0 | |
| 2 | VH2-31-7 | 0 | |
| 2 | VH2-31-14 | 1 | |
| 2 | VH2-31-8 | 0 | |
| 2 | VH2-31-9 | 0 | |
| 2 | VH2-31-10 | 0 | |
| 2 | VH2-31-11 | 1 | |
| 2 | VH2-31-12 | 0 | |
| 2 | VH2-31-13 | 1 | 7 entries |
| 3 | VH3-11-1 | 0 | |
| 3 | VH3-11-2 | 0 | |
| 3 | VH3-11-3 | 5 | |
| 3 | VH3-11-4 | 0 | |
| 3 | VH3-11-5 | 1 | |
| 3 | VH3-11-6 | 1 | |
| 3 | VH3-11-7 | 0 | |
| 3 | VH3-11-8 | 5 | |
| 3 | VH3-13-1 | 9 | |
| 3 | VH3-13-2 | 3 | |
| 3 | VH3-13-3 | 0 | |
| 3 | VH3-13-4 | 0 | |
| 3 | VH3-13-5 | 0 | |
| 3 | VH3-13-6 | 0 | |
| 3 | VH3-13-7 | 32 | |
| 3 | VH3-13-8 | 4 | |
| 3 | VH3-13-9 | 0 | |
| 3 | VH3-13-10 | 46 | |
| 3 | VH3-13-11 | 0 | |
| 3 | VH3-13-12 | 11 | |
| 3 | VH3-13-13 | 17 | |
| 3 | VH3-13-14 | 8 | |
| 3 | VH3-13-15 | 4 | |
| 3 | VH3-13-16 | 3 | |
| 3 | VH3-13-17 | 2 | |
| 3 | VH3-13-18 | 1 | |
| 3 | VH3-13-19 | 13 | |
| 3 | VH3-13-20 | 1 | |
| 3 | VH3-13-21 | 1 | |
| 3 | VH3-13-22 | 0 | |
| 3 | VH3-13-23 | 0 | |
| 3 | VH3-13-24 | 4 | |
| 3 | VH3-13-25 | 1 | |
| 3 | VH3-13-26 | 6 | |
| 3 | VH3-14-1 | 1 | |
| 3 | VH3-14-4 | 15 | |
| 3 | VH3-14-2 | 0 | |
| 3 | VH3-14-3 | 0 | |
| 3 | VH3-1X-1 | 0 | |
| 3 | VH3-1X-2 | 0 | |
| 3 | VH3-1X-3 | 6 | |
| 3 | VH3-1X-4 | 0 | |
| 3 | VH3-1X-5 | 0 | |
| 3 | VH3-1X-6 | 11 | |
| 3 | VH3-1X-7 | 0 | |
| 3 | VH3-1X-8 | 1 | |
| 3 | VH3-1X-9 | 0 | 212 entries |
| 4 | VH4-11-1 | 0 | |
| 4 | VH4-11-2 | 20 | |
| 4 | VH4-11-3 | 0 | |
| 4 | VH4-11-4 | 0 | |

TABLE 3C-continued assignment of rearranged V heavy chain sequences to their germline counterparts

| Family[1] | Name | Rearranged[2] | Sum |
|---|---|---|---|
| 4 | VH4-11-5 | 0 | |
| 4 | VH4-11-6 | 0 | |
| 4 | VH4-11-7 | 5 | |
| 4 | VH4-11-8 | 7 | |
| 4 | VH4-11-9 | 3 | |
| 4 | VH4-11-10 | 0 | |
| 4 | VH4-11-11 | 0 | |
| 4 | VH4-11-12 | 4 | |
| 4 | VH4-11-13 | 0 | |
| 4 | VH4-11-14 | 0 | |
| 4 | VH4-11-15 | 0 | |
| 4 | VH4-11-16 | 1 | |
| 4 | VH4-21-1 | 0 | |
| 4 | VH4-21-2 | 0 | |
| 4 | VH4-21-3 | 1 | |
| 4 | VH4-21-4 | 1 | |
| 4 | VH4-21-5 | 1 | |
| 4 | VH4-21-6 | 1 | |
| 4 | VH4-21-7 | 0 | |
| 4 | VH4-21-8 | 0 | |
| 4 | VH4-21-9 | 0 | |
| 4 | VH4-31-1 | 0 | |
| 4 | VH4-31-2 | 0 | |
| 4 | VH4-31-3 | 0 | |
| 4 | VH4-31-4 | 2 | |
| 4 | VH4-31-5 | 0 | |
| 4 | VH4-31-6 | 0 | |
| 4 | VH4-31-7 | 0 | |
| 4 | VH4-31-8 | 0 | |
| 4 | VH4-31-9 | 0 | |
| 4 | VH4-31-10 | 0 | |
| 4 | VH4-31-11 | 0 | |
| 4 | VH4-31-12 | 4 | |
| 4 | VH4-31-13 | 7 | |
| 4 | VH4-31-14 | 0 | |
| 4 | VH4-31-15 | 0 | |
| 4 | VH4-31-16 | 0 | |
| 4 | VH4-31-17 | 0 | |
| 4 | VH4-31-18 | 0 | |
| 4 | VH4-31-19 | 0 | |
| 4 | VH4-31-20 | 0 | 57 entries |
| 5 | VH5-12-1 | 82 | |
| 5 | VH5-12-2 | 1 | |
| 5 | VH5-12-3 | 0 | |
| 5 | VH5-12-4 | 14 | 97 entries |
| 6 | VH6-35-1 | 74 | 74 entries |

TABLE 4A

Analysis of V kappa subgroup 1

| | Framework I | | | | | | | | | | | | | | | |
|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 |
| A | | 1 | | | | | | | 1 | | | | 102 | | 1 | |
| B | | | 1 | | | 1 | | | | | | | | | | |
| C | | | | | | | | | | | | | | 1 | | |
| D | 64 | | | | | | | | | | | | | | | |
| E | 8 | | 14 | | | | | | | | | | | | 1 | |
| F | | | | | | | | | 1 | 6 | | | | 1 | | |
| G | | | | | | | | | | | | | | | | 105 |
| H | | | | | | | | | | | | | | | | |
| I | | 65 | | | | | | | | | | | | | 4 | |
| K | | | 1 | | | | | | | | | | | | | |
| L | | 6 | | 21 | | | | | | | 96 | | 1 | | | |
| M | 1 | | | 66 | | | | | | | | | | | | |
| N | | | | | | | | | | | | | | | | |
| P | | | | | | | | 103 | | 1 | | 2 | | | 1 | |
| Q | | | 62 | | | 88 | | | | | 1 | | | | | |
| R | | | | | | | | | | | | | | | | |
| S | | | | | | | 89 | | 102 | 80 | | 103 | | 103 | | |
| T | | 1 | | | 88 | | | | | 18 | | | | | | |
| V | | 1 | 9 | | | | | | | | 8 | | 2 | | 98 | |
| W | | | | | | | | | | | | | | | | |
| X | 1 | | | | | | | | | | | | | | | |
| Y | | | | | | | | | | | | | | | | |
| — | | | | | | | | | | | | | | | | |
| unknown (?) | | | | | | | | | | | | | | | | |
| not sequenced | 31 | 31 | 18 | 18 | 17 | 16 | 16 | 2 | 1 | | | | | | | |
| sum of seq[2] | 74 | 74 | 87 | 87 | 88 | 89 | 89 | 103 | 104 | 105 | 105 | 105 | 105 | 105 | 105 | 105 |
| oomcaa[3] | 64 | 65 | 62 | 66 | 88 | 88 | 89 | 103 | 102 | 80 | 96 | 103 | 102 | 103 | 98 | 105 |
| mcaa[4] | D | I | Q | M | T | Q | S | P | S | S | L | S | A | S | V | G |
| rel. oomcaa[5] | 86% | 88% | 71% | 76% | 100% | 99% | 100% | 100% | 98% | 76% | 91% | 98% | 97% | 98% | 93% | 100% |
| pos occupied[6] | 4 | 5 | 5 | 2 | 1 | 2 | 1 | 1 | 3 | 4 | 3 | 2 | 3 | 3 | 5 | 1 |

| | Framework I | | | | | | | CDR I | | | | | | | |
|---|---|---|---|---|---|---|---|---|---|---|---|---|---|---|---|
| amino acid[1] | 17 | 18 | 19 | 20 | 21 | 22 | 23 | 24 | 25 | 26 | 27 | A | B | C | D |
| A | | | 1 | 1 | | 1 | | | 103 | | | | | | |
| B | | | | | | | | | | | 1 | | | | |
| C | | | | | | | 105 | | | | | | | | |
| D | 101 | | | | | | | | | | | | | | |
| E | 2 | | | | | | | 1 | 1 | | 2 | | | | |
| F | | | | | 2 | | | | | | | | | | |
| G | | | | | | | | | | 1 | | | | | |
| H | | | | | | | | | | | 1 | | | | |
| I | | | 6 | 4 | 101 | 1 | | | | | | | | | |
| K | | | | | | | | 2 | | | 1 | | | | |
| L | | | | | | | | 1 | | | | | | | |
| M | | | | | | | | | | | | | | | |
| N | | | | | | | | | | 1 | | | | | |
| P | | | | | | | | | | | | | | | |
| Q | | | | | | | | 20 | | | 100 | | | | |
| R | | 94 | | | | | | 81 | | | | | | | |
| S | | 5 | | 1 | | | | | | 102 | | | | | |
| T | | 6 | | 99 | | 103 | | | 1 | 1 | | | | | |
| V | | | 98 | | 2 | | | | | | | | | | |
| W | | | | | | | | | | | | | | | |
| X | 1 | | | | | | | | | | | | | | |
| Y | 1 | | | | | | | | | | | | | | |
| — | | | | | | | | | | | | 105 | 105 | 105 | 105 |
| unknown (?) | | | | | | | | | | | | | | | |
| not sequenced | | | | | | | | | | | | | | | |
| sum of seq[2] | 105 | 105 | 105 | 105 | 105 | 105 | 105 | 105 | 105 | 105 | 105 | 105 | 105 | 105 | 105 |
| oomcaa[3] | 101 | 94 | 98 | 99 | 101 | 103 | 105 | 81 | 103 | 102 | 100 | 105 | 105 | 105 | 105 |
| mcaa[4] | D | R | V | T | I | T | C | R | A | S | Q | — | — | — | — |
| rel. oomcaa[5] | 96% | 90% | 93% | 94% | 96% | 98% | 100% | 77% | 98% | 97% | 95% | 100% | 100% | 100% | 100% |
| pos occupied[6] | 4 | 3 | 3 | 4 | 3 | 3 | 1 | 5 | 3 | 4 | 5 | 1 | 1 | 1 | 1 |

| | CDR I | | | | | | | | | Framework II | | | | | |
|---|---|---|---|---|---|---|---|---|---|---|---|---|---|---|---|
| amino acid[1] | E | F | 28 | 29 | 30 | 31 | 32 | 33 | 34 | 35 | 36 | 37 | 38 | 39 | 40 |
| A | | | | | 1 | 1 | | 1 | 42 | | | | | | |
| B | | | | | | | | | | | | 1 | 1 | | |
| C | | | | | | | 1 | | | | | | | | |

TABLE 4A-continued

Analysis of V kappa subgroup 1

| | | | | | | | | | | | | | | | |
|---|---|---|---|---|---|---|---|---|---|---|---|---|---|---|---|
| D | | | 25 | | 1 | 5 | 7 | | | | | 1 | | | |
| E | | | | | | | 1 | | | | | 2 | | | |
| F | | | | 1 | 1 | | 7 | | | | 6 | | | | |
| G | | | 25 | | 7 | 3 | | | 4 | | | | | | |
| H | | | | | 1 | 2 | 2 | | 1 | | | 2 | | | |
| I | | | | 98 | 1 | 4 | | | 1 | | | | | | |
| K | | | | | | 7 | | | | | | | | 95 | |
| L | | | | | 2 | 1 | | 101 | | | | | | | |
| M | | | | | | | | | | | | | | | |
| N | | | 6 | | 16 | 42 | | | 50 | | | | | | |
| P | | | | | | | | | | | | | | | 102 |
| Q | | | | | | | | | | | | 98 | 103 | 2 | |
| R | | | | | 16 | 3 | 2 | | | | | | | 3 | 1 |
| S | | | 41 | 2 | 57 | 32 | 3 | 1 | 1 | | | | | | 1 |
| T | | | 7 | | | 4 | | | 4 | | | | | 1 | |
| V | | | 1 | 4 | 1 | | | 1 | | | | | | | |
| W | | | | | | | 21 | | | 104 | | | | | |
| X | | | | | | | | | 1 | | | | | | |
| Y | | | | | 1 | | 60 | | | | 98 | | | | |
| — | 105 | 105 | | | | | | | | | | | | | |
| unknown (?) | | | | | | | | | | | | | | 3 | |
| not sequenced | | | | | | 1 | 1 | 1 | 1 | 1 | 1 | 1 | 1 | 1 | 1 |
| sum of seq[2] | 105 | 105 | 105 | 105 | 105 | 104 | 104 | 104 | 104 | 104 | 104 | 104 | 104 | 104 | 104 |
| oomcaa[3] | 105 | 105 | 41 | 98 | 57 | 42 | 60 | 101 | 50 | 104 | 98 | 98 | 103 | 95 | 102 |
| mcaa[4] | — | — | S | I | S | N | Y | L | N | W | Y | Q | Q | K | P |
| rel. oomcaa[5] | 100% | 100% | 39% | 93% | 54% | 40% | 58% | 97% | 48% | 100% | 94% | 94% | 99% | 91% | 98% |
| pos occupied[6] | 1 | 1 | 6 | 4 | 12 | 11 | 9 | 4 | 8 | 1 | 2 | 5 | 2 | 4 | 3 |

| | Framework II | | | | | | | | | CDR II | | | | | |
|---|---|---|---|---|---|---|---|---|---|---|---|---|---|---|---|---|
| amino acid[1] | 41 | 42 | 43 | 44 | 45 | 46 | 47 | 48 | 49 | 50 | 51 | 52 | 53 | 54 | 55 | 56 |
| A | | | 94 | | | | | | | 50 | 95 | | | | | 3 |
| B | | | | | | | | | | | | | | | | 1 |
| C | | | | | | | | | | | | | | | | |
| D | | | | | | | | | | 21 | 1 | 1 | 1 | | | 1 |
| E | 1 | 3 | | | 1 | 1 | | | | 1 | | 1 | | | 33 | |
| F | | | | | | 1 | | | 3 | | | 1 | | | | |
| G | 100 | | 1 | | | | | | | 9 | 2 | | | | | 2 |
| H | | | | | | | | | 2 | | | | | | 1 | |
| I | | 1 | | | | 1 | | 100 | | | | | 1 | | | 3 |
| K | | 95 | | | 86 | | | | | 16 | | | 2 | | 5 | 1 |
| L | | 1 | | | | 89 | 103 | | | | | | | 101 | | |
| M | | | | | | | | 2 | | | | | | | | |
| N | | | | | 10 | | | | | 2 | | 1 | 25 | | | 6 |
| P | | | | 104 | | | | | | 1 | | | | | 1 | 1 |
| Q | | 1 | | | 1 | | | | | | | | | | 62 | |
| R | | | | | 3 | 3 | | | | | | | 1 | 1 | 2 | 1 |
| S | | | | | 1 | | | | 5 | 1 | 1 | 99 | 41 | 2 | | 68 |
| T | | 3 | | | 1 | | | | | 1 | 4 | 1 | 31 | | | 19 |
| V | | | 9 | | | 9 | | | | | 1 | | 1 | | | |
| W | | | | | | | | | | | | | | | | |
| X | | | | | 1 | | | | | | | | 1 | | | |
| Y | | | | | | | | | 92 | 1 | | | | | | |
| — | | | | | | | | | | | | | | | | |
| unknown (?) | 3 | | | | | | | | | | | | | | | |
| not sequenced | 1 | 1 | 1 | 1 | 1 | 1 | 2 | 3 | 3 | 2 | 1 | 1 | 1 | 1 | 1 | |
| sum of seq[2] | 104 | 104 | 104 | 104 | 104 | 104 | 103 | 102 | 102 | 103 | 104 | 104 | 104 | 104 | 104 | 105 |
| oomcaa[3] | 100 | 95 | 94 | 104 | 86 | 89 | 103 | 100 | 92 | 50 | 95 | 99 | 41 | 101 | 62 | 68 |
| mcaa[4] | G | K | A | P | K | L | L | I | Y | A | A | S | S | L | Q | S |
| rel. oomcaa[5] | 96% | 91% | 90% | 100% | 83% | 86% | 100% | 98% | 90% | 49% | 91% | 95% | 39% | 97% | 60% | 65% |
| pos occupied[6] | 2 | 6 | 3 | 1 | 8 | 6 | 1 | 2 | 4 | 10 | 6 | 6 | 9 | 3 | 6 | 10 |

| | Framework III | | | | | | | | | | | | | | |
|---|---|---|---|---|---|---|---|---|---|---|---|---|---|---|---|
| amino acid[1] | 57 | 58 | 59 | 60 | 61 | 62 | 63 | 64 | 65 | 66 | 67 | 68 | 69 | 70 | 71 |
| A | | | | | | | | | | 2 | 1 | 1 | 1 | | |
| B | | | 1 | | | | | | | | | | | | |
| C | | | | | | | | | | | | | | | |
| D | | | | | | | | | | | | | | 67 | |
| E | | | | | | | | | | | | 1 | | 30 | |
| F | | 1 | | | | 103 | | | | | 32 | | | | 102 |
| G | 105 | | | | | | | 105 | 4 | 101 | | 102 | | | |
| H | | | | | | | | | | | | | | 3 | |
| I | | 4 | | | | 1 | 3 | | | | | | | | |
| K | | | | | 1 | | | | | | | | | 1 | |

TABLE 4A-continued

Analysis of V kappa subgroup 1

| | | | | | | | | | | | | | | | |
|---|---|---|---|---|---|---|---|---|---|---|---|---|---|---|---|
| L | | | | | | | 1 | | | | | | | | |
| M | | | | | | | | | | | | | 1 | | |
| N | | | | | | | | | | | | | | | |
| P | | | 101 | 2 | | | | | | | | | | | |
| Q | | | | | | | | | 1 | | | | | | |
| R | | | | | 103 | | 1 | | 1 | 1 | | | 2 | | |
| S | | | 2 | 103 | | | 98 | | 96 | | 100 | | | | |
| T | | | 1 | | 1 | | 2 | | 3 | | | | 101 | | |
| V | | 99 | | | | 1 | | | | | | | | 1 | 1 |
| W | | | | | | | | | | | | | | | |
| X | | 1 | | | | | | | | 1 | | 1 | | 2 | |
| Y | | | | | | | | | | | 1 | | | 1 | 1 |
| — | | | | | | | | | | | | | | | |
| unknown (?) | | | | | | | | | | | | | | | |
| not sequenced | | | | | | | | | | | | | | | 1 |
| sum of seq[2] | 105 | 105 | 105 | 105 | 105 | 105 | 105 | 105 | 105 | 105 | 105 | 105 | 105 | 105 | 104 |
| oomcaa[3] | 105 | 99 | 101 | 103 | 103 | 103 | 98 | 105 | 96 | 101 | 100 | 102 | 101 | 67 | 102 |
| mcaa[4] | G | V | P | S | R | F | S | G | S | G | S | G | T | D | F |
| rel. oomcaa[5] | 100% | 94% | 96% | 98% | 98% | 98% | 93% | 100% | 91% | 96% | 95% | 97% | 96% | 64% | 98% |
| pos occupied[6] | 1 | 4 | 4 | 2 | 3 | 3 | 5 | 1 | 5 | 4 | 4 | 4 | 4 | 7 | 3 |

| | Framework III | | | | | | | | | | | | | | |
|---|---|---|---|---|---|---|---|---|---|---|---|---|---|---|---|
| amino acid[1] | 72 | 73 | 74 | 75 | 76 | 77 | 78 | 79 | 80 | 81 | 82 | 83 | 84 | 85 | 86 |
| A | 3 | | | | 1 | | | | 2 | | | | 101 | 1 | |
| B | | | | 1 | | | | 3 | | 2 | | | | | |
| C | | | | | | | | | | | | | | | |
| D | | | | | 1 | | | | | 16 | 101 | | | | |
| E | | | | | | | | | | 83 | | | | | |
| E | 1 | 21 | | | | | | | | | | 83 | | | |
| F | 1 | 21 | | | | | | | | | | 73 | | | |
| G | | | | | | 4 | | | | 1 | | | 2 | | |
| H | | | | | | | | | | | | | | | |
| I | | | | 99 | 5 | | | | | | | 17 | | | |
| K | | | | | | | | | | | | | | | 1 |
| L | | 81 | | | | | 103 | 1 | | | | 1 | | | |
| M | | | | | | | | | | | | | | | |
| N | | | | | 7 | 4 | | | | | | | | 1 | |
| P | | | | | | | | | 97 | | | | | 1 | |
| Q | | | | | | | | 97 | | | | | | | |
| R | | | | | 2 | 1 | | 2 | | | | | | | |
| S | 2 | | 1 | | 86 | 94 | | | 4 | | | 1 | | | 1 |
| T | 98 | | 102 | | 2 | 1 | | | | | | | | 97 | |
| V | | 2 | | 4 | | | 1 | | | | | 11 | | 1 | |
| W | | | | | | | | | | | | | | | |
| X | | | 1 | | | | | | | 1 | 2 | | | | |
| Y | | | | | | | | | | | | | | | 101 |
| — | | | | | | | | | | | | | | | |
| unknown (?) | | | | | | | | | | | | | | | |
| not sequenced | 1 | 1 | 1 | 1 | 1 | 1 | 1 | 2 | 2 | 2 | 2 | 2 | 2 | 3 | 2 |
| sum of seq[2] | 104 | 104 | 104 | 104 | 104 | 104 | 104 | 103 | 103 | 103 | 103 | 103 | 103 | 102 | 103 |
| oomcaa[3] | 98 | 81 | 102 | 99 | 86 | 94 | 103 | 97 | 97 | 83 | 101 | 73 | 101 | 97 | 101 |
| mcaa[4] | T | L | T | I | S | S | L | Q | P | E | D | F | A | T | Y |
| rel. oomcaa[5] | 94% | 78% | 98% | 95% | 83% | 90% | 99% | 94% | 94% | 81% | 98% | 71% | 98% | 95% | 98% |
| pos occupied[6] | 4 | 3 | 3 | 3 | 7 | 5 | 2 | 4 | 3 | 5 | 2 | 5 | 2 | 6 | 3 |

| | Framework III | | CDR III | | | | | | | | | | | | |
|---|---|---|---|---|---|---|---|---|---|---|---|---|---|---|---|
| amino acid[1] | 87 | 88 | 89 | 90 | 91 | 92 | 93 | 94 | 95 | A | B | C | D | E | F |
| A | | | | 1 | 7 | 1 | | 5 | 1 | | | | | | |
| B | | | 2 | 3 | | | | | | | | | | | |
| C | | 102 | | | | | | | | | | | | | |
| D | | | | | | 23 | 5 | 1 | | | | | | | |
| E | | | | | | 1 | 1 | | 1 | 1 | | | | | |
| F | 7 | | | | 3 | | | 13 | | | | | | | |
| G | | | | | 1 | | 1 | 2 | 1 | | 1 | | | | |
| H | 1 | | 4 | 6 | 7 | 3 | 1 | | | | | | | | |
| I | | | | | | 4 | 1 | 2 | 1 | | | | | | |
| K | | | | 7 | | 1 | | | | | | | | | |
| L | | | 7 | | 6 | 2 | | 18 | 2 | | | | | | |
| M | | | | | | | | | | | | | | | |
| N | | | | | 6 | 31 | 19 | 1 | | | | | | | |
| P | | | | | | | | 1 | 82 | 6 | | | | | |

TABLE 4A-continued

| Analysis of V kappa subgroup 1 | | | | | | | | | | | | | | | |
|---|---|---|---|---|---|---|---|---|---|---|---|---|---|---|---|
| Q | | | 90 | 86 | 1 | 2 | | | | | | | | | |
| R | | | | | 1 | | 2 | 2 | | | | | | | |
| S | | | | | 27 | 3 | 58 | 5 | 10 | | | | | | |
| T | | | | | 3 | 1 | 15 | 25 | | | | | | | |
| V | | | | | | | | 5 | | | | | | | |
| W | | | | | | | | 1 | | | | | | | |
| X | | | | | | | | | | | | | | | |
| Y | 93 | | | | 42 | 32 | 1 | 23 | | | | | | | |
| — | | | | | | | | | 3 | 82 | 88 | 89 | 89 | 89 | 89 |
| unknown (?) | 1 | | | | | | | | | | | | | | |
| not sequenced | 3 | 3 | 2 | 2 | 1 | 1 | 1 | 1 | 4 | 16 | 16 | 16 | 16 | 16 | 16 |
| oomcaa[3] | 93 | 102 | 90 | 86 | 42 | 32 | 58 | 25 | 82 | 82 | 88 | 89 | 89 | 89 | 89 |
| mcaa[4] | Y | C | Q | Q | Y | Y | S | T | P | — | — | — | — | — | — |
| rel. oomcaa[5] | 91% | 100% | 87% | 83% | 40% | 31% | 56% | 24% | 81% | 92% | 99% | 100% | 100% | 100% | 100% |
| pos occupied[6] | 3 | 1 | 4 | 5 | 11 | 12 | 10 | 14 | 8 | 3 | 2 | 1 | 1 | 1 | 1 |
| | CDR III | | Framework IV | | | | | | | | | | | | |
| amino acid[1] | 96 | 97 | 98 | 99 | 100 | 101 | 102 | 103 | 104 | 105 | 106 | A | 107 | 108 | sum |
| A | 1 | | | | | | | | | | | | | | 627 |
| B | | | | | 1 | | | | 1 | | | | | 19 | |
| C | | | | | | | | | | | | | | | 209 |
| D | 1 | | | | | | | | | 15 | | | | | 459 |
| E | | | | | 2 | | | | | 65 | | | | | 258 |
| F | 6 | | 86 | | | | | | | | 2 | | | | 451 |
| G | | | | 87 | 29 | 87 | | | | | | | | 2 | 894 |
| H | 2 | 1 | | | | | | | | | | | | | 40 |
| I | 5 | | | | | | | | 1 | | 72 | | | | 606 |
| K | 1 | 1 | | | | | | 77 | | | | | 79 | | 480 |
| L | 18 | 1 | 1 | | | | | | 22 | 4 | 2 | | | | 793 |
| M | | 1 | | | | | | | | | 5 | | | | 77 |
| N | 1 | | | | | | | | | | 1 | | 2 | | 232 |
| P | 6 | | | | 7 | | | | | | | | | 1 | 620 |
| Q | 1 | | | | 48 | | | | | 1 | | | | | 865 |
| R | 6 | | | | | | | 6 | | | | | 2 | 70 | 413 |
| S | 2 | 2 | | | | | | | | | | | | | 1636 |
| T | 2 | 82 | | | | | 87 | 3 | | | | | 2 | | 1021 |
| V | 2 | | | | | | | 1 | 63 | | 3 | | | | 440 |
| W | 15 | | | | | | | | | | | | | | 141 |
| X | | | | | | | | | | | | | | | 14 |
| Y | 16 | | | | | | | | | | | | | | 564 |
| — | 4 | 1 | | | | | | | | | | 85 | | 1 | 1250 |
| unknown (?) | | | | | | | | | | | | | | | 7 |
| not sequenced | 16 | 16 | 18 | 18 | 18 | 18 | 18 | 18 | 19 | 19 | 20 | 20 | 20 | 31 | 589 |
| sum of seq[2] | 89 | 89 | 87 | 87 | 87 | 87 | 87 | 87 | 86 | 86 | 85 | 85 | 85 | 74 | |
| oomcaa[3] | 18 | 82 | 86 | 87 | 48 | 87 | 87 | 77 | 63 | 65 | 72 | 85 | 79 | 70 | |
| mcaa[4] | L | t | F | G | G | G | T | K | V | E | I | — | K | R | |
| rel. oomcaa[5] | 20% | 92% | 99% | 100% | 55% | 100% | 100% | 89% | 73% | 76% | 85% | 100% | 93% | 95% | |
| pos occupied[6] | 17 | 7 | 2 | 1 | 5 | 1 | 1 | 4 | 3 | 5 | 6 | 1 | 4 | 4 | |

TABLE 4B

Analysis of V kappa subgroup 2

| | Framework I | | | | | | | | | | | | | | | | | | | | | | | CDRI | | |
|---|---|---|---|---|---|---|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| A | | | | | | | | | | | | | | | | | | | 22 | | | | | | | |
| B | | | | | | | | | | | | | | | | | | | | | | | | | | |
| C | | | | | | | | | | | | | | | | | | | | | | | 22 | | | |
| D | 14 | | | | | | | | | | | | | | | | | | | | | | | | | |
| E | 3 | | | | | | | | | | | | | | | | 15 | | | | | | | | | |
| F | | | | | | | | | 1 | 1 | | | | | | | | | | | | | | | | |
| G | | | | | | | | | | | | | | | | 22 | | | | | | | | | | |
| H | | | | | | | | | | | | | | | | | | | | | | | | | | |
| I | | 8 | | | | | | | | | | | | | | | | | | | 22 | | | | | |
| K | | | | | | | | | | | | | | | | | | | | | | | | 1 | | |
| L | | 3 | | 1 | | | | | 17 | | 18 | | | | 6 | | | | | | | | | | | |
| M | | | | 15 | | | | | | | | | | | | | | | | | | | | | | |
| N | | | | | | | | | | | | | | | | | | | | | | | | | | |
| P | | | | | | | | 18 | | | | 18 | | | 15 | | | 22 | | | | | | | | |
| Q | | | | | | 18 | | | | | | | | | | | 7 | | | | | 1 | | | | |
| R | | | | | | | | | | | | | | | | | | | | | | | | 21 | | |
| S | | | | | | | 18 | | | 17 | | | | | | | | | | 22 | | 21 | | | 22 | 22 |
| T | | | | | 17 | | | | | | | | | 21 | | | | | | | | | | | | |
| V | | 6 | 17 | 1 | | | | | | | | | 18 | | | | | | | | | | | | | |
| W | | | | | | | | | | | | | | | | | | | | | | | | | | |
| X | | | | | | | | | | | | | | | | | | | | | | | | | | |
| Y | | | | | | | | | | | | | | | | | | | | | | | | | | |
| — | | | | | | | | | | | | | | | | | | | | | | | | | | |
| unknown (?) | | | | | 1 | | | | | | | | | | | | | | | | | | | | | |
| not sequenced | 5 | 5 | 5 | 5 | 4 | 4 | 4 | 4 | 4 | 4 | 4 | 4 | 4 | 1 | 1 | | | | | | | | | | | |
| sum of seq[2] | 17 | 17 | 17 | 17 | 18 | 18 | 18 | 18 | 18 | 18 | 18 | 18 | 18 | 21 | 21 | 22 | 22 | 22 | 22 | 22 | 22 | 22 | 22 | 22 | 22 | 22 |
| oomcaa[3] | 14 | 8 | 17 | 15 | 17 | 18 | 18 | 18 | 17 | 17 | 18 | 18 | 18 | 21 | 15 | 22 | 15 | 22 | 21 | 22 | 21 | 22 | 22 | 22 | 22 | 22 |
| mcaa[4] | D | I | V | M | T | Q | S | P | L | S | L | P | V | T | P | G | E | P | S | C | R | S | S | A | S | I |
| rel. oomcaa[5] | 82% | 47% | 100% | 88% | 94% | 100% | 100% | 100% | 100% | 94% | 94% | 100% | 100% | 100% | 95% | 100% | 95% | 100% | 100% | 71% | 100% | 68% | 100% | 100% | 100% | 100% |
| pos occupied[6] | 2 | 3 | 1 | 3 | 1 | 1 | 1 | 1 | 2 | 2 | 1 | 1 | 1 | 1 | 2 | 1 | 2 | 2 | 1 | 2 | 1 | 1 | 1 | 1 | 1 | |

| | CDRI | | | | | | | | | | | | | | Framework II | | | | | | | | | | | |
|---|---|---|---|---|---|---|---|---|---|---|---|---|---|---|---|---|---|---|---|---|---|---|---|---|---|---|
| amino acid[1] | 27 | A | B | C | D | E | F | 28 | 29 | 30 | 31 | 32 | 33 | 34 | 35 | 36 | 37 | 38 | 39 | 40 | 41 | 42 | 43 | 44 | 45 | 46 |
| A | | | | | | | | | | | | | | | | | | | | | | | | | | |
| B | | | | | | | | | | | | | | | | | | | | | | | | | | |
| C | | | | | | | | | | | | | | | | | | | | | | | | | | |
| D | | | | | 1 | | | 9 | | 1 | 1 | | | 11 | | | | | | | | | | | | |
| E | | | | | | | | | | | | | | | | | | | | | | | | | 1 | |
| F | | | | | | | | | | 2 | | | | | | 7 | | | | | | | | | | |
| G | | | | | | 1 | | | 22 | | | | | | | | | | | | 22 | | | | | |
| H | | | | | 16 | | | | | | | 1 | | 1 | | | | | | | | | | | | |
| I | | | | | | | | | | | | | | | | | | | | | | | | | | 1 |
| K | | | | | | | | | | | 1 | | | | | | | | 15 | | | | | | | |

TABLE 4B-continued

Analysis of V kappa subgroup 2

| | | | | | | | | | | | | | | | | | | | | | | | | | | |
|---|---|---|---|---|---|---|---|---|---|---|---|---|---|---|---|---|---|---|---|---|---|---|---|---|---|---|
| L | 1 | | 22 | 13 | | | | | | | | | 22 | | | | 16 | | | | | | | | | 14 |
| M | | | | 1 | | | | | | | | | | | | | | | | | | | | | | |
| N | | | | | | | | 10 | | 7 | 12 | | | 9 | | | | | | | | | | | | |
| P | | | | | | | | | | | | | | | | | | | | 22 | | | | 21 | | |
| Q | 21 | | | | | | | | | | | | | | | | 6 | 22 | | | | 22 | | | 12 | |
| R | | | | | | 2 | | | | | | | | | | | | | 7 | | | | | | 8 | 7 |
| S | | 22 | | | | 19 | | 1 | | | | | | | | | | | | | | | 21 | | | |
| T | | | | | | | | | | | 8 | | | | | | | | | | | | | | | |
| V | | | | 8 | | | | | | | | | | | | | | | | | | | | | | |
| W | | | | | 1 | | | | | | | | | | 22 | | | | | | | | | | | |
| X | | | | | | | | 1 | | 1 | | | | 1 | | | | | | | | | | | | |
| Y | | | | | 4 | | | 1 | | 11 | | 21 | | | | 15 | | | | | | | | | | |
| — | | | | | | | 22 | | | | | | | | | | | | | | | | | | | |
| unknown (?) | | | | | | | | | | | | | | | | | | | | | | | | | | |
| not sequenced | | | | | | | | | | | | | | | | | | | | | | | 1 | 1 | 1 | |
| sum of seq[2] | 22 | 22 | 22 | 22 | 22 | 22 | 22 | 22 | 22 | 22 | 22 | 22 | 22 | 22 | 22 | 22 | 22 | 22 | 22 | 22 | 21 | 21 | 21 | 22 | 22 | 22 |
| oomcaa[3] | 21 | 22 | 22 | 13 | 16 | 19 | 22 | 10 | 22 | 11 | 12 | 21 | 22 | 11 | 22 | 15 | 16 | 22 | 15 | 22 | 22 | 22 | 21 | 21 | 12 | 14 |
| mcaa[4] | Q | S | L | L | H | S | — | N | G | Y | N | Y | L | D | W | Y | L | Q | K | P | G | Q | S | P | Q | L |
| rel. oomcaa[5] | 95% | 100% | 100% | 59% | 73% | 86% | 100% | 45% | 100% | 50% | 55% | 95% | 100% | 50% | 173% | 100% | 68% | 100% | 100% | 100% | 100% | 100% | 57% | 64% | | |
| pos occupied[6] | 2 | 1 | 1 | 3 | 4 | 3 | 1 | 5 | 1 | 5 | 4 | 2 | 1 | 4 | 1 | 2 | 1 | 2 | 1 | 1 | 1 | 1 | 1 | 3 | 3 | 2 |
| | Framework II | | | CDRI II | | | | | | | Framework III | | | | | | | | | | | | | | | |
| amino acid[1] | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 |
| A | | | | | | | | | 14 | | | | | | | | | | | | | | | | | |
| B | | | | | | | | | | | | | | | | | | | | | | | | | | |
| C | | | | | | | | | | | | | | | | | | | | | | | | | | |
| D | | | | | | | | | 7 | | | | | 22 | | | | 1 | | | | 1 | | 12 | | |
| E | | | | | | | | | | | | | | | | | | | | | | | | | | |
| F | | | | | | | | | | | | | | | | 21 | | | | | | | | | 22 | |
| G | | | | | 12 | | | | 1 | | 22 | | | | | | | 21 | | 22 | | 21 | | | | |
| H | | | | | | | | | | | | | | | | | | | | | | | | | | |
| I | | 22 | | | | | | | | | | | | | | | | | | | | | | | | |
| K | | | | 5 | | | | | | | | | | | | | | | | | | | | | | |
| L | 21 | | | 14 | 1 | | | | | | | | | | | | | | | | | | | | | |
| M | | | | | | | | | | | | | | | | | | | | | | | | | | |
| N | | | | | | | 18 | | | | | | | | | | | | | | | | | | | |
| P | | | | | | | | | | | | | | 22 | | | | | | | | | | | | |
| Q | | | | 1 | | | | | | | | | | | | | | | | | | | | | | |
| R | | | | 1 | | | | 22 | | | | | | | 20 | | | | 1 | | | | | | | |
| S | | | | | 2 | 22 | 2 | | | 22 | | | | | 1 | | 22 | | 21 | | 22 | | | | | |
| T | | | | | | | 1 | | | | | | | | 1 | | | | | | | | 22 | | | 21 |
| V | | | | | 6 | | | | | | | 22 | | | | 1 | | | | | | | | | | |
| W | | | | | | | | | | | | | | | | | | | | | | | | | | |
| X | | | | | | | | | | | | | | | | | | | | | | | | | | |
| Y | | | 21 | | | | 1 | | | | | | | | | | | | | | | | | | | |
| — | | | | | | | | | | | | | | | | | | | | | | | | | | |
| unknown (?) | | | | | | | | | | | | | | | | | | | | | | | | | | 1 |
| not sequenced | | | 1 | 1 | 1 | | | | | | | | | | | | | | | | | | | | | |

TABLE 4B-continued

Analysis of V kappa subgroup 2

| | | | | | | | | | | | | | | | | | | | | | | | | | | |
|---|---|---|---|---|---|---|---|---|---|---|---|---|---|---|---|---|---|---|---|---|---|---|---|---|---|---|
| sum of seq[2] | 22 | 22 | 21 | 21 | 21 | 22 | 22 | 22 | 22 | 22 | 22 | 22 | 22 | 22 | 22 | 22 | 22 | 22 | 22 | 22 | 22 | 22 | 22 | 22 | 22 | 22 |
| oomcaa[3] | 21 | 22 | 21 | 14 | 12 | 22 | 18 | 22 | 14 | 22 | 22 | 22 | 22 | 22 | 20 | 21 | 22 | 21 | 21 | 22 | 22 | 21 | 22 | 22 | 22 | 21 |
| mcaa[4] | L | I | Y | L | G | S | N | R | A | S | G | V | P | D | R | F | S | G | S | G | S | G | T | D | F | T |
| rel. oomcaa[5] | 95% | 100% | 100% | 67% | 57% | 100% | 82% | 100% | 64% | 100% | 100% | 100% | 100% | 100% | 91% | 95% | 100% | 95% | 95% | 100% | 100% | 95% | 100% | 100% | 100% | 95% |
| pos occupied[6] | 2 | 1 | 1 | 4 | 4 | 1 | 4 | 1 | 3 | 1 | 1 | 1 | 1 | 1 | 3 | 2 | 1 | 2 | 2 | 1 | 1 | 2 | 1 | 1 | 1 | 1 |
| | Framework III | | | | | | | | | | | | | | | | CDR III | | | | | | | | | |
| amino acid[1] | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C |
| A | | | | | | | | 20 | | | | | | | | | | | 14 | | | 1 | | | | |
| B | | | | | | | | | | | | | | | | | | 1 | | | 1 | | | | | |
| C | | | | | | | | | | | | | | | | 21 | | | | | | | | | | |
| D | | | | | | | | | 1 | 21 | | | | | | | | | | | | | | | | |
| E | | | | | | | 19 | | 20 | | | | | | | | | | | | | | | | | |
| F | | | | | | | | | | | | | | | | | | | | | | | | | | |
| G | | | | | | | 1 | | | | | 21 | | | | | | | 6 | | | 1 | | 2 | | |
| H | | | | | | | | | | | | | | | | | | | 1 | | 7 | | | | | |
| I | | 1 | 21 | | | | | | | | | | 1 | | | | | | | | | 1 | | | | |
| K | | 19 | | | | | | | | | | | | | | | | | | | | | | | | |
| L | 21 | 1 | | | | | | | | | | | 1 | | | | | | | 12 | | | 2 | | | |
| M | | | | | | | | | | | | | | | | | 21 | | | | | | | | | |
| N | | | | | | | | | | | | | | | | | | | | | | | | | | |
| P | | | | | | | | 1 | | | | | | | | | | | | | | 2 | 16 | 1 | | |
| Q | | | | | | | 1 | | | | | | | | | | | 20 | | | 13 | | | | | |
| R | | | | | 20 | | | | | | | | | | | | | | | 1 | | | | | | |
| S | | | | 20 | 1 | | | | | | | | | | | | | | | | | 3 | 2 | | | |
| T | | | | 1 | | | | | | | | | | | | | | | | 8 | | 7 | | | | |
| V | | | | | | 21 | | | | | 21 | | 19 | | | | | | | | | | | | | |
| W | | | | | | | | | | | | | | | | | | | | | | 6 | | | | |
| X | | | | | | | | | | | | | | | | | | | | | | | | | | |
| Y | | | | | | | | | | | | | | 21 | 21 | | | | | | | | | | | |
| — | | | | | | | | | | | | | | | | | | | | | | | | 14 | 17 | 17 |
| unknown (?) | | | | | | | | | | | | | | | | | | | | | | | | | | |
| not sequenced | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 2 | 5 | 5 | 5 |
| sum of seq[2] | 21 | 21 | 21 | 21 | 21 | 21 | 21 | 21 | 21 | 21 | 21 | 21 | 21 | 21 | 21 | 21 | 21 | 21 | 21 | 21 | 21 | 21 | 20 | 17 | 17 | 17 |
| oomcaa[3] | 21 | 19 | 21 | 20 | 20 | 21 | 19 | 20 | 20 | 21 | 21 | 21 | 19 | 21 | 21 | 21 | 21 | 20 | 14 | 12 | 13 | 7 | 16 | 14 | 17 | 17 |
| mcaa[4] | L | K | I | S | R | V | E | A | E | D | V | G | V | Y | Y | C | M | Q | A | L | Q | T | P | — | — | — |
| rel. oomcaa[5] | 100% | 90% | 100% | 95% | 95% | 100% | 90% | 95% | 95% | 100% | 100% | 100% | 90% | 100% | 100% | 100% | 100% | 95% | 67% | 57% | 62% | 33% | 80% | 82% | 100% | 100% |
| pos occupied[6] | 1 | 3 | 1 | 2 | 2 | 1 | 3 | 2 | 2 | 1 | 1 | 1 | 3 | 1 | 1 | 1 | 1 | 2 | 3 | 3 | 3 | 7 | 3 | 3 | 1 | 1 |

| | CDR III | | | | | Framework IV | | | | | | | | | | | | |
|---|---|---|---|---|---|---|---|---|---|---|---|---|---|---|---|---|---|---|
| amino acid[1] | D | E | F | 96 | 97 | 98 | 99 | 100 | 101 | 102 | 103 | 104 | 105 | 106 | A | 107 | 108 | sum |
| A | | | | | | | | | | | | | | | | | | 71 |
| B | | | | | | | | | | | | | 1 | | | | | 3 |
| C | | | | | | | | | | | | | | | | | | 43 |
| D | | | | | | | | | | | | | | | | | | 112 |
| E | | | | | | | | | | | | | 13 | | | | | 71 |

TABLE 4B-continued

Analysis of V kappa subgroup 2

| | | | | | | | | | | | | | | | | | | |
|---|---|---|---|---|---|---|---|---|---|---|---|---|---|---|---|---|---|---|
| F | | | | 1 | | 17 | | | | | | | | | | | | 72 |
| G | | | | | | | 17 | 2 | 16 | | | | 1 | | | | | 233 |
| H | | | | | | | | | | | | | | | | | | 26 |
| I | | | | 3 | | | | | | | | | | 14 | | | | 94 |
| K | | | | | | | | | | | 12 | | | | | 13 | 66 | |
| L | | | | 2 | | | | | | | | 11 | | | | | | 219 |
| M | | | | | | | | | | | | | | | | | | 37 |
| N | | | | | | | | | | | | | | | | | | 56 |
| P | | | | 1 | | | | | | | | | | | | | | 159 |
| Q | | | | 1 | | | | 14 | | | | | | | | | | 159 |
| R | | | | | | | | | | | 4 | | | | | | 12 | 126 |
| S | | | | | | | | | | | | | | | | | | 325 |
| T | | | | | 17 | | | | | 16 | | | | | | | | 140 |
| V | | | | | | | | | | | | 5 | | | | | | 146 |
| W | | | | 2 | | | | | | | | | | | | | | 31 |
| X | | | | | | | | | | | | | | | | | | 3 |
| Y | | | | 7 | | | | | | | | | | | | | | 123 |
| — | 17 | 17 | 17 | | | | | | | | | | | | 13 | | | 134 |
| unknown (? ) | | | | | | | | | | | | | | | | | | 2 |
| not sequenced | 5 | 5 | 5 | 5 | 5 | 5 | 5 | 6 | 6 | 6 | 6 | 6 | 7 | 8 | 9 | 9 | 10 | 211 |
| sum of seq[2] | 17 | 17 | 17 | 17 | 17 | 17 | 17 | 16 | 16 | 16 | 16 | 16 | 15 | 14 | 13 | 13 | 12 | |
| oomcaa[3] | 17 | 17 | 17 | 7 | 17 | 17 | 17 | 14 | 16 | 16 | 12 | 11 | 13 | 14 | 13 | 13 | 12 | |
| mcaa[4] | — | — | — | Y | T | F | G | Q | G | T | K | L | E | I | — | K | R | |
| rel. oomcaa[5] | 100% | 100% | 100% | 41% | 100% | 100% | 100% | 88% | 100% | 100% | 75% | 69% | 87% | 100% | 100% | 100% | 100% | |
| pos occupied[6] | 1 | 1 | 1 | 7 | 1 | 1 | 1 | 2 | 1 | 1 | 2 | 2 | 3 | 1 | 1 | 1 | 1 | |

TABLE 4C

Analysis of V kappa subgroup 3

| | Framework I | | | | | | | | | | | | | | | | | |
|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 |
| A | | 5 | | | | | 2 | | 27 | | | | | | 1 | | | |
| B | 1 | | | | | | | | | | | | | | | | | |
| C | | | | | | | | | | | | 2 | | | | | | |
| D | 2 | | | | | | | | 14 | | | | | | | | 6 | |
| E | 76 | | 27 | | | | | | | | | | | | | | 146 | 1 |
| F | | 1 | | | | | | | | | | | | 1 | | | | |
| G | 1 | | | | | | | | 82 | | | | | | 1 | 152 | 1 | 1 |
| H | | | | | | | | | | 1 | | | | | | | | |
| I | | 75 | | | | | | | | | | | | | | | | 1 |
| K | 3 | | | | | | | | | | | | | | | | | 1 |
| L | | 4 | 1 | 104 | | | 1 | | | | 150 | | 129 | | 1 | | | |
| M | 5 | | | 13 | | | | | | | | | | | | | | |
| N | | | | | | | | | | | | | | 5 | | | | |
| P | | | | | | | | 124 | | | | | | | 147 | | | |
| Q | | | | | | 123 | | | | | | | | | | | | |
| R | | | | | 1 | | | | | | | | | | | | | 175 |
| S | | | | | | | 119 | | 3 | 1 | | 150 | 1 | 141 | | | | |
| T | | 2 | | | 117 | | | | | 147 | | | | 5 | 1 | | | 1 |
| V | | 1 | 89 | 1 | | | 1 | | | | 1 | | 22 | | 1 | | | 1 |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 88 | 88 | 117 | 118 | 118 | 123 | 123 | 124 | 126 | 149 | 151 | 152 | 152 | 152 | 152 | 152 | 153 | 181 |
| oomcaa[3] | 76 | 75 | 89 | 104 | 117 | 123 | 119 | 124 | 82 | 147 | 150 | 150 | 129 | 141 | 147 | 152 | 146 | 175 |
| mcaa[4] | E | I | V | L | T | Q | S | P | G | T | L | S | L | S | P | G | E | R |
| rel. oomcaa[5] | 86% | 85% | 76% | 88% | 99% | 100% | 97% | 100% | 65% | 99% | 99% | 99% | 85% | 93% | 97% | 100% | 95% | 97% |
| pos occupied[6] | 6 | 6 | 3 | 3 | 2 | 1 | 4 | 1 | 4 | 3 | 2 | 2 | 3 | 4 | 6 | 1 | 3 | 7 |

| | Framework I | | | | | CDR I | | | | | | | | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | A | B | C | D | E | F | 28 | 29 | 30 |
| A | 178 | 2 | | | | | 166 | 1 | | | | | | | | | | 1 |
| B | | | | | | | | | | | | | | | | | | |
| C | | | | | 181 | | | 1 | | | | | | | | | | |
| D | | | | | | | | | | | | | | | | | 1 | 1 |
| E | | | | | | | | | 1 | | | | | | | | | |
| F | | | 7 | 1 | | | | | | | | | | | | 1 | | |
| G | | | | | | | 1 | 1 | | 1 | | | | | | | 2 | 7 |
| H | | | | | | | | | 17 | | | | | | | | 1 | |
| I | | 5 | 2 | | | | | | | | | | | | | 24 | 4 | 1 |
| K | | | | | | 5 | | | | | | | | | | | | 1 |
| L | | | 173 | | | | | | 1 | 1 | | | | | | 8 | 1 | |
| M | | | | | | | | | | | | | | | | | | |
| N | | | | | | | | | | 9 | | | | | | | 3 | 12 |
| P | | | | | | | | | | | | | | | | | | |
| Q | | | | | | | | | 159 | | | | | | | | | |
| R | | | | | | 176 | | 1 | 1 | 10 | | | | | | | 10 | 3 |
| S | | | | 180 | | | 7 | 175 | | 87 | | | | | | 72 | 86 | 151 |
| T | | 174 | | | | | 7 | 2 | | 1 | | | | | | 1 | 1 | 3 |
| V | 4 | 1 | | | | | 1 | | | 1 | | | | | | 76 | 68 | |
| W | | | | | | 1 | | | | | | | | | | | 5 | |
| X | | | | | | | | | | | | | | | | | | |
| Y | | | | 1 | | | | | 1 | | | | | | | | | 1 |
| — | | | | | | | | | | 72 | 182 | 182 | 182 | 182 | 182 | | | |
| unknown (?) | | | | | | | | | 1 | | | | | | | | | |
| not sequenced | | | | | | | | | | | | | | | | | | |
| sum of seq[2] | 182 | 182 | 182 | 182 | 181 | 182 | 182 | 181 | 181 | 182 | 182 | 182 | 182 | 182 | 182 | 182 | 182 | 181 |
| oomcaa[3] | 178 | 174 | 173 | 180 | 181 | 176 | 166 | 175 | 159 | 87 | 182 | 182 | 182 | 182 | 182 | 76 | 86 | 151 |
| mcaa[4] | A | T | L | S | C | R | A | S | Q | S | — | — | — | — | — | V | S | S |
| rel. oomcaa[5] | 98% | 96% | 95% | 99% | 100% | 97% | 91% | 97% | 88% | 48% | 100% | 100% | 100% | 100% | 100% | 42% | 47% | 83% |
| pos occupied[6] | 2 | 4 | 3 | 3 | 1 | 3 | 5 | 6 | 6 | 8 | 1 | 1 | 1 | 1 | 1 | 6 | 11 | 10 |

| | CDR I | | | | Framework II | | | | | | | | | | | | |
|---|---|---|---|---|---|---|---|---|---|---|---|---|---|---|---|---|---|
| amino acid[1] | 31 | 32 | 33 | 34 | 35 | 36 | 37 | 38 | 39 | 40 | 41 | 42 | 43 | 44 | 45 | 46 | 47 |
| A | 1 | | | 181 | | | | | | | | | 176 | | | | |
| B | | | | | | | | | | | | | | | | | |
| C | | | | | | | | | | | | | | | | | |

TABLE 4C-continued

Analysis of V kappa subgroup 3

| | | | | | | | | | | | | | | | | | |
|---|---|---|---|---|---|---|---|---|---|---|---|---|---|---|---|---|---|
| D | 2 | 1 | | | | | | | | | | | | | | | |
| E | | 1 | | | | | | | 1 | | | 1 | | | | | |
| F | | 7 | | | | 1 | | | | | | | | | | 1 | |
| G | 3 | 1 | | 2 | | | | | | 1 | 184 | | | | | | |
| H | | 2 | | | | 1 | | 12 | 1 | 1 | | | | | | | |
| I | 1 | | | | | | | | | | | | | | | | |
| K | 1 | 1 | | | | | | | | 153 | | | | | | 1 | |
| L | | 1 | 176 | | | | | 3 | | | | 2 | | 1 | | 179 | 174 |
| M | | | | | | | | | | | | | | | | | |
| N | 25 | 32 | | | | | | | | | | | | | 1 | | |
| P | 1 | | | | | | | | | 170 | | | 5 | 184 | | | |
| Q | 1 | 1 | | | | | 183 | 167 | 1 | | | 181 | | | | | |
| R | 18 | 16 | | 1 | | | 1 | | 27 | 5 | | | | | 182 | | |
| S | 118 | 4 | | | | | | | | 5 | | | | | | | |
| T | 8 | 1 | | | | | | | 1 | | | | 3 | | | | |
| V | 1 | | 7 | | | | | 3 | | 2 | | | | | | 3 | 9 |
| W | | | | | 185 | | | | | | | | | | | | |
| X | | | | | | | | | | | | | | | | | |
| Y | 1 | 115 | | | | 183 | | | | | | | | | | | |
| — | | | | | | | | | | | | | | | | | |
| unknown (?) | | | | | | | 1 | | | | | | | | 1 | | |
| not sequenced | | | | | | | | | | | | | | | | | |
| sum of seq[2] | 181 | 182 | 183 | 184 | 185 | 185 | 185 | 185 | 184 | 184 | 184 | 184 | 184 | 185 | 185 | 183 | 183 |
| oomcaa[3] | 118 | 115 | 176 | 181 | 185 | 183 | 183 | 167 | 153 | 170 | 184 | 181 | 176 | 184 | 182 | 179 | 174 |
| mcaa[4] | S | Y | L | A | W | Y | Q | Q | K | P | G | Q | A | P | R | L | L |
| rel. oomcaa[5] | 65% | 63% | 96% | 98% | 100% | 99% | 99% | 90% | 83% | 92% | 100% | 98% | 96% | 99% | 98% | 98% | 95% |
| pos occupied[6] | 13 | 12 | 2 | 3 | 1 | 3 | 2 | 4 | 6 | 6 | 1 | 3 | 3 | 2 | 3 | 3 | 2 |

| | Framework II | | CDR II | | | | | | | Framework III | | | | | | | | |
|---|---|---|---|---|---|---|---|---|---|---|---|---|---|---|---|---|---|---|
| amino acid[1] | 48 | 49 | 50 | 51 | 52 | 53 | 54 | 55 | 56 | 57 | 58 | 59 | 60 | 61 | 62 | 63 | 64 | 65 |
| A | | | 4 | 147 | | | | 176 | 1 | | | | 68 | | | | | |
| B | | | | | | | | | | | | | | | | | | |
| C | | | | 1 | | | | | | | | | | | | | | |
| D | | | 43 | | | | | 2 | | 4 | | | 112 | | | | 1 | |
| E | | | | | | | | | | | | | | | | | | |
| F | 1 | 4 | | | | | | | | | | | | | 183 | | | |
| G | | | 125 | | | | | 2 | 10 | 179 | | | | | | | 184 | 3 |
| H | | 9 | | 1 | | | | | | | | | 1 | | | | | |
| I | 178 | | | | | | | | 1 | | 168 | | | | 1 | | | |
| K | | | | | | 7 | 1 | | | | | | | 1 | | | | |
| L | 1 | | | | | | | | | | | | | | 1 | | | |
| M | 3 | | | | | 1 | | | | | | | | | | | | |
| N | | | 1 | | | 53 | | | 2 | | | | 1 | | | | | |
| P | | | | | 2 | | | 2 | 2 | | | 177 | | | | | | |
| Q | | 1 | | | | | | | | | | | | | | | | |
| R | | | 1 | | | 4 | 180 | | | | | | | 182 | | 2 | | 1 |
| S | | 3 | 6 | 4 | 179 | 74 | 1 | | 5 | | | 7 | | | | 180 | | 179 |
| T | | | | 11 | 2 | 44 | | | 164 | | 2 | 1 | | 2 | | 3 | | 2 |
| V | | | 3 | 19 | | | | 3 | | | 15 | | 3 | | | | | |
| W | | 1 | | | | | 1 | | | | | | | | | | | |
| X | | | | | | | | | | | | | | | | | | |
| Y | | 165 | | | | | | | | 2 | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 183 | 183 | 183 | 183 | 183 | 183 | 183 | 185 | 185 | 185 | 185 | 185 | 185 | 185 | 185 | 185 | 185 | 185 |
| oomcaa[3] | 178 | 165 | 125 | 147 | 179 | 74 | 180 | 176 | 164 | 179 | 168 | 177 | 112 | 182 | 183 | 180 | 184 | 179 |
| mcaa[4] | I | Y | G | A | S | S | R | A | T | G | I | P | D | R | F | S | G | S |
| rel. oomcaa[5] | 97% | 90% | 68% | 80% | 98% | 40% | 98% | 95% | 89% | 97% | 91% | 96% | 61% | 98% | 99% | 97% | 99% | 97% |
| pos occupied[6] | 4 | 6 | 7 | 6 | 3 | 6 | 4 | 5 | 7 | 3 | 3 | 3 | 5 | 3 | 3 | 3 | 2 | 4 |

| | Framework III | | | | | | | | | | | | | | | | |
|---|---|---|---|---|---|---|---|---|---|---|---|---|---|---|---|---|---|
| amino acid[1] | 66 | 67 | 68 | 69 | 70 | 71 | 72 | 73 | 74 | 75 | 76 | 77 | 78 | 79 | 80 | 81 | 82 |
| A | 3 | | 5 | 3 | 1 | | 3 | | | | | | | | | 3 | |
| B | | | | | | | | | | | | | | 1 | | | |
| C | | | | | | | | | | | | | | | | | |
| D | | | | | 152 | | | | | | | 1 | | | | 3 | 182 |
| E | 1 | | 1 | | 30 | | | | | | | | | 149 | | 175 | |
| F | | | | | | 183 | | 2 | | | 1 | | | | | | |
| G | 178 | | 177 | | | | | | | | | 3 | | | | | 1 |
| H | | | | | | | | | | | | | | | | | |
| I | | | | | | | 1 | | 3 | 178 | | | | | | | 1 |
| K | | | | | | | | | | | | | | | | 1 | |

TABLE 4C-continued

Analysis of V kappa subgroup 3

| | | | | | | | | | | | | | | | | | |
|---|---|---|---|---|---|---|---|---|---|---|---|---|---|---|---|---|---|
| L | | | | | | | | 182 | | | | | 178 | | 1 | | |
| M | 1 | | | | | | | | | | | | | | | | |
| N | | | | | | | 1 | | | 1 | 5 | | | | | | |
| P | | | | | | | | | | | | | | | 149 | | |
| Q | | | | | 1 | | | | | | | | | 34 | | | |
| R | | | | 2 | | | | | | | 1 | 111 | | | | | |
| S | | 185 | | 3 | | | 7 | | 2 | | 169 | 65 | | | 34 | | |
| T | | | | 177 | | | 172 | | 179 | | 8 | 4 | | | | | |
| V | 1 | | 1 | | | | | | | 4 | | | 6 | | | | |
| W | | | 1 | | | | | | | | | | | | | | |
| X | | | | | | | | | | | | | | | | | |
| Y | | | | | | 1 | | | | 1 | | | | | | | |
| — | | | | | | | | | | | | | | | | | |
| unknown (?) | 1 | | | | | | | | | | | | | | | | |
| not sequenced | | | | | | | | | | | | | | | | | |
| sum of seq[2] | 185 | 185 | 185 | 185 | 184 | 184 | 184 | 184 | 184 | 184 | 184 | 184 | 184 | 184 | 184 | 182 | 184 |
| oomcaa[3] | 178 | 185 | 177 | 177 | 152 | 183 | 172 | 182 | 179 | 178 | 169 | 111 | 178 | 149 | 149 | 175 | 182 |
| mcaa[4] | G | S | G | T | D | F | T | L | T | I | S | R | L | E | P | E | D |
| rel. oomcaa[5] | 96% | 100% | 96% | 96% | 83% | 99% | 93% | 99% | 97% | 97% | 92% | 60% | 97% | 81% | 81% | 96% | 99% |
| pos occupied[6] | 5 | 1 | 5 | 4 | 4 | 2 | 5 | 2 | 3 | 4 | 5 | 5 | 2 | 3 | 3 | 4 | 3 |

| | Framework III | | | | | | CDR III | | | | | | | | | | |
|---|---|---|---|---|---|---|---|---|---|---|---|---|---|---|---|---|---|
| amino acid[1] | 83 | 84 | 85 | 86 | 87 | 88 | 89 | 90 | 91 | 92 | 93 | 94 | 95 | A | B | C | D |
| A | | 174 | | | | | | | | 1 | 8 | 3 | 3 | | | | |
| B | | | | | | | | | | | | | | | | | |
| C | 2 | | | | 1 | 182 | | | 2 | | | 1 | | | | | |
| D | | | | | | | | | | 8 | 5 | | | | | | |
| E | | | | | | | | 2 | | 2 | | | | | | | |
| F | 178 | | 2 | 1 | 4 | | | | 5 | | 2 | | | | | | |
| G | | 2 | | | | | | | 1 | 104 | 15 | | 1 | 1 | 2 | | |
| H | | | 1 | | | | 1 | 7 | 4 | 1 | | | | | | | |
| I | 1 | | 9 | | | | | | | | 1 | | | 1 | | | |
| K | | | | | | | | | | | 2 | | | 1 | | | |
| L | 1 | | 7 | | 1 | | | 1 | | | | 2 | 7 | 5 | | | |
| M | | 1 | 5 | | | | | | | 1 | | | 1 | 2 | | | |
| N | | | | | | | | | | 28 | 71 | | | | | | |
| P | | | | | | | | | | | | 1 | 139 | 24 | | | |
| Q | | | | | | 1 | 181 | 155 | 1 | | 1 | | 3 | 1 | | | |
| R | | 3 | | | | | | 1 | 34 | 2 | 3 | | 2 | 2 | | | |
| S | 1 | | | | 2 | | | | 2 | 33 | 58 | 102 | 15 | 2 | | | |
| T | | 1 | | | | | | 8 | | 2 | 13 | 1 | 1 | 2 | | | |
| V | 1 | 3 | 159 | | | | | 7 | | | | | 3 | 1 | | | |
| W | | | | | | | | | | | | 69 | | | | | |
| X | | | | | | | | | | | | | | | | | |
| Y | | | 1 | 183 | 176 | | 1 | 2 | 134 | 1 | 1 | | | | | | |
| — | | | | | | | | | | | 3 | 3 | 7 | 127 | 167 | 169 | 169 |
| unknown (?) | | | | | | | | | | | | | | | | | |
| not sequenced | | | | | | | | | | | | | | 14 | 14 | 14 | 14 |
| sum of seq[2] | 184 | 184 | 184 | 184 | 184 | 183 | 183 | 183 | 183 | 183 | 183 | 182 | 182 | 169 | 169 | 169 | 169 |
| oomcaa[3] | 178 | 174 | 159 | 183 | 176 | 182 | 181 | 155 | 134 | 104 | 71 | 102 | 139 | 127 | 167 | 169 | 169 |
| mcaa[4] | F | A | V | Y | Y | C | Q | Q | Y | G | N | S | P | — | — | — | — |
| rel. oomcaa[5] | 97% | 95% | 86% | 99% | 96% | 99% | 99% | 85% | 73% | 57% | 39% | 56% | 76% | 75% | 99% | 100% | 100% |
| pos occupied[6] | 6 | 6 | 7 | 2 | 5 | 2 | 3 | 8 | 8 | 11 | 13 | 8 | 11 | 12 | 2 | 1 | 1 |

| | CDR III | | | | Framework IV | | | | | | | | | | | | |
|---|---|---|---|---|---|---|---|---|---|---|---|---|---|---|---|---|---|
| amino acid[1] | E | F | 96 | 97 | 98 | 99 | 100 | 101 | 102 | 103 | 104 | 105 | 106 | A | 107 | 108 | sum |
| A | | | | | | | 1 | | | | | | | | | | 1345 |
| B | | | | | | | | | | | | | | | | | 2 |
| C | | | 2 | | | | | | | | | | | | | | 375 |
| D | | | | 1 | | | | | | | | 23 | | | | | 564 |
| E | | | 1 | | | | | | | 3 | | 141 | | | | | 759 |
| F | | | 7 | | 166 | | | | | | | | 6 | | | | 765 |
| G | | | 1 | | | 166 | 41 | 166 | | | | | | | | 1 | 1804 |
| H | | | 2 | | | | | | | | | 1 | | | | | 64 |
| I | | | 4 | | | | | | | | | | 143 | | | | 803 |
| K | | | 1 | | | | 1 | | | 152 | | | | | 157 | | 489 |
| L | | | 42 | | | | | | | | 54 | | 1 | | | 2 | 1596 |
| M | | | | | | | | | | | | | 3 | | | | 36 |
| N | | | 1 | | | | | | 1 | | | | | | 3 | | 255 |
| P | | | 7 | 2 | | | 9 | | 1 | | 1 | | | | | | 1147 |
| Q | | | 3 | | | | 114 | | | 1 | | 1 | | | | | 1314 |
| R | | | 19 | | | | | | | 9 | | | 2 | | 4 | 134 | 1326 |
| S | | | 1 | 8 | | | | | 2 | | | | | | | | 2629 |

TABLE 4C-continued

Analysis of V kappa subgroup 3

| | | | | | | | | | | | | | | | | | |
|---|---|---|---|---|---|---|---|---|---|---|---|---|---|---|---|---|---|
| T | | | 1 | 154 | | | | | 162 | 1 | | | | | 1 | | 1593 |
| V | | | 2 | | | | | | | | 111 | | 11 | | | | 646 |
| W | | | 24 | | | | | | | | | | | | | | 287 |
| X | | | | | | | | | | | | | | | | | |
| Y | | | 43 | | | | | | | 1 | | | | | | | 1014 |
| — | 169 | 169 | 8 | 1 | 1 | 1 | 1 | 1 | 1 | 1 | 1 | 1 | 1 | 166 | 1 | 1 | 2151 |
| unknown (?) | | | | | | | | | | | | | | | | | 4 |
| not sequenced | 14 | 14 | 14 | 17 | 16 | 16 | 16 | 16 | 16 | 15 | 16 | 16 | 16 | 17 | 17 | 45 | 337 |
| sum of seq[2] | 169 | 169 | 169 | 166 | 167 | 167 | 167 | 167 | 167 | 168 | 167 | 167 | 167 | 166 | 166 | 138 | |
| oomcaa[3] | 169 | 169 | 43 | 154 | 166 | 166 | 114 | 166 | 162 | 152 | 111 | 141 | 143 | 166 | 157 | 134 | |
| mcaa[4] | — | — | Y | T | F | G | Q | G | T | K | V | E | I | — | K | R | |
| rel. oomcaa[5] | 100% | 100% | 25% | 93% | 99% | 99% | 68% | 99% | 97% | 90% | 66% | 84% | 86% | 100% | 95% | 97% | |
| pos occupied[6] | 1 | 1 | 18 | 5 | 2 | 2 | 6 | 2 | 5 | 7 | 4 | 5 | 7 | 1 | 5 | 4 | |

TABLE 4D

Analysis of V kappa subgroup 4

| | Framework I | | | | | | | | | | | | | | | | | |
|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 |
| A | | | | | | | | | | | | 24 | | | | | 1 | |
| B | | | | | | | | | | | | | | | | | | |
| C | | | | | | | | | | 1 | | | | | | 1 | | |
| D | 25 | | | | | | | | 26 | | | | | | | | | |
| E | | | | | | | | | | | | | | | | | 25 | |
| F | | | | | | | | | | | | | | | | | | |
| G | | | | | | | | | | | | 1 | | | | 24 | | |
| H | | | | | | | | | | | | | | | | | | |
| I | | 26 | | | | | | | | | | | | | | | | |
| K | | | | | | 1 | | | | | | | | | | | | |
| L | | | | 1 | | | | | | | 26 | | | | 26 | | | |
| M | | | | 24 | | | | | | | | | | | | | | |
| N | 1 | | | | | | | | | | | | | | | | | |
| P | | | | | | | | 26 | | | | 1 | | | | | | |
| Q | | | 1 | | | 25 | | | | | | | | | | | | |
| R | | | | | | | | | | | | | | | | | | 26 |
| S | | | | | | | 26 | | | 25 | | | | 26 | | 1 | | |
| T | | | | | 26 | | | | | | | | | | | | | |
| V | | | 25 | 1 | | | | | | | | | 26 | | | | | |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | | | | | | | | | | | | | | |
| not sequenced | 7 | 7 | 7 | 7 | 7 | 7 | 7 | 7 | 7 | 7 | 7 | 7 | 7 | 7 | 7 | 7 | 7 | 7 |
| sum of seq[2] | 26 | 26 | 26 | 26 | 26 | 26 | 26 | 26 | 26 | 26 | 26 | 26 | 26 | 26 | 26 | 26 | 26 | 26 |
| oomcaa[4] | 25 | 26 | 25 | 24 | 26 | 25 | 26 | 26 | 26 | 25 | 26 | 24 | 26 | 26 | 26 | 24 | 25 | 26 |
| mcaa[4] | D | I | V | M | T | Q | S | P | D | S | L | A | V | S | L | G | E | R |
| rel. oomcaa[5] | 96% | 100% | 96% | 92% | 100% | 96% | 100% | 100% | 100% | 96% | 100% | 92% | 100% | 100% | 100% | 92% | 96% | 100% |
| pos occupied[6] | 2 | 1 | 2 | 3 | 1 | 2 | 1 | 1 | 1 | 2 | 1 | 3 | 1 | 1 | 1 | 3 | 2 | 1 |

| | Framework I | | | | | CDR I | | | | | | | | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | A | B | C | D | E | F | 28 | 29 | 30 |
| A | 26 | | | | | | 1 | | | | 1 | | | | | | | |
| B | | | | | | | | | | | | | | | | | | |
| C | | | | | 33 | | | | | | | | | | | | | |
| D | | | | | | | | | | | 1 | | 1 | | | 1 | | |
| E | | | | | | | | | | | | | | | | | | |
| F | | | | | | | | | | | | | | | | | | |
| G | | | | | | | | | | | | | | | | | | |
| H | | | | | | | | | | | | | | | | | | |
| I | | | 26 | | | | | | | | 1 | | | | | | | |
| K | | | | | | 33 | | | | | | | | | | 2 | | 30 |
| L | | | | | | | | | | | 2 | 31 | | | | | | |
| M | | | | | | | | | | | | | | | | | | |
| N | | | | 26 | | | | | | | | | | | | 30 | 31 | 1 |
| P | | | | | | | 1 | | | | | | | | 1 | | | |
| Q | | | | | | | | | 32 | | | | | | | | | 1 |
| R | | | | | | | | | 1 | | | | | | | | 1 | 1 |
| S | | | | | | | 31 | 33 | | 33 | | | | 32 | 32 | | 1 | |

TABLE 4D-continued

Analysis of V kappa subgroup 4

| | | | | | | | | | | | | | | | | | | |
|---|---|---|---|---|---|---|---|---|---|---|---|---|---|---|---|---|---|---|
| T | | 26 | | | | | | | | | | | | 1 | | | | |
| V | | | | | | | | | | | 28 | 2 | | | | | | |
| W | | | | | | | | | | | | | | | | | | |
| X | | | | | | | | | | | | | | | | | | |
| Y | | | | | | | | | | | | | 32 | | | | | |
| — | | | | | | | | | | | | | | | | | | |
| unknown (?) | | | | | | | | | | | | | | | | | | |
| not sequenced | 7 | 7 | 7 | 7 | | | | | | | | | | | | | | |
| sum of seq[2] | 26 | 26 | 26 | 26 | 33 | 33 | 33 | 33 | 33 | 33 | 33 | 33 | 33 | 33 | 33 | 33 | 33 | 33 |
| oomcaa[3] | 26 | 26 | 26 | 26 | 33 | 33 | 31 | 33 | 32 | 33 | 28 | 31 | 32 | 32 | 32 | 30 | 31 | 30 |
| mcaa[4] | A | T | I | N | C | K | S | S | Q | S | V | L | Y | S | S | N | N | K |
| rel. oomcaa[5] | 100% | 100% | 100% | 100% | 100% | 100% | 94% | 100% | 97% | 100% | 85% | 94% | 97% | 97% | 97% | 91% | 94% | 91% |
| pos occupied[6] | 1 | 1 | 1 | 1 | 1 | 1 | 3 | 1 | 2 | 1 | 5 | 2 | 2 | 2 | 2 | 3 | 3 | 4 |

| | CDR I | | | | Framework II | | | | | | | | | | | | |
|---|---|---|---|---|---|---|---|---|---|---|---|---|---|---|---|---|---|
| amino acid[1] | 31 | 32 | 33 | 34 | 35 | 36 | 37 | 38 | 39 | 40 | 41 | 42 | 43 | 44 | 45 | 46 | 47 |
| A | | | | 32 | | | | | | 2 | | | | | | | |
| B | | | | | | | | | | | | | | | | | |
| C | | | | | | | | | | | | | | | | | |
| D | | | | | | | | | | | | | | | | | |
| E | | | | | | | | | | | 1 | | | | | | |
| F | | | | | | | | | | | | | | | | | |
| G | | | | | | | | | | | 32 | | | | | | |
| H | | | | | | 2 | | | | | | | | | | | |
| I | | | | | | | | | | | | | | | | | |
| K | | | | | | | | | 33 | | | | | | 32 | | |
| L | | | 33 | | | | | | | | | | | | | 29 | 33 |
| M | | | | | | | | | | | | | | | | | |
| N | 33 | | | | | | | | | | | | | | | | |
| P | | | | | | | | | | 31 | | | 31 | 33 | | | |
| Q | | | | | | | 32 | 33 | | | | 32 | | | | | |
| R | | | | | | | 1 | | | | | 1 | | | 1 | | |
| S | | | | | | | | | | | | | 2 | | | | |
| T | | | | 1 | | | | | | | | | | | | | |
| V | | | | | | | | | | | | | | | | 4 | |
| W | | | | | 33 | | | | | | | | | | | | |
| X | | | | | | | | | | | | | | | | | |
| Y | | 33 | | | | 31 | | | | | | | | | | | |
| — | | | | | | | | | | | | | | | | | |
| unknown (?) | | | | | | | | | | | | | | | | | |
| not sequenced | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 |
| oomcaa[3] | 33 | 33 | 33 | 32 | 33 | 31 | 32 | 33 | 33 | 31 | 32 | 32 | 31 | 33 | 32 | 29 | 33 |
| mcaa[4] | N | Y | L | A | W | Y | Q | Q | K | P | G | Q | P | P | K | L | L |
| rel. oomcaa[5] | 100% | 100% | 100% | 97% | 100% | 94% | 97% | 100% | 100% | 94% | 97% | 97% | 94% | 100% | 97% | 88% | 100% |
| pos occupied[6] | 1 | 1 | 1 | 2 | 1 | 2 | 2 | 1 | 1 | 2 | 2 | 2 | 2 | 1 | 2 | 2 | 1 |

| | Framework II | | CDR II | | | | | | | Framework III | | | | | | | | |
|---|---|---|---|---|---|---|---|---|---|---|---|---|---|---|---|---|---|---|
| amino acid[1] | 48 | 49 | 50 | 51 | 52 | 53 | 54 | 55 | 56 | 57 | 58 | 59 | 60 | 61 | 62 | 63 | 64 | 65 |
| A | | | | 30 | | | | | | | | | | | | | | |
| B | | | | | | | | | | | | | | | | | | |
| C | | | | | | | | | | | | | | | | | | |
| D | | | | | | | | | | | | | 33 | | | | | |
| E | | | | | | | | 32 | | | | | | | | | | |
| F | | | | | | | | | | | | | | | 33 | | | |
| G | | | | | | | | | | 33 | | | | | | 1 | 33 | |
| H | | | | | | | | | | | | | | | | | | |
| I | 32 | | | | | 1 | | | | | | | | | | | | |
| K | | | | | | | | | | | | | | | | | | |
| L | | | | | | | | | | | | | | | | | | |
| M | 1 | | | | | | | | | | | | | | | | | |
| N | | | | | | 2 | | | | | | | | | | | | |
| P | | | | | 1 | | | | | | | 33 | | 1 | | | | |
| Q | | | | | | | | | | | | | | | | | | |
| R | | | | | | | 33 | | | | | | | 32 | | | | |
| S | | | | 1 | 31 | 1 | | | 33 | | | | | | | 32 | | 33 |
| T | | | | 2 | 1 | 29 | | | | | | | | | | | | |
| V | | | | | | | | 1 | | | 33 | | | | | | | |
| W | | | 33 | | | | | | | | | | | | | | | |

TABLE 4D-continued

Analysis of V kappa subgroup 4

| | | | | | | | | | | | | | | | | | | |
|---|---|---|---|---|---|---|---|---|---|---|---|---|---|---|---|---|---|---|
| X | | | | | | | | | | | | | | | | | | |
| Y | | 33 | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 | 33 |
| oomcaa[3] | 32 | 33 | 30 | 31 | 29 | 33 | 32 | 33 | 33 | 33 | 33 | 33 | 32 | 33 | 32 | 33 | 33 | |
| mcaa[4] | I | Y | W | A | S | T | R | E | S | G | V | P | D | R | F | S | G | S |
| rel. oomcaa[5] | 97% | 100% | 100% | 91% | 94% | 88% | 100% | 97% | 100% | 100% | 100% | 100% | 100% | 97% | 100% | 97% | 100% | 100% |
| pos occupied[6] | 2 | 1 | 1 | 3 | 3 | 4 | 1 | 2 | 1 | 1 | 1 | 1 | 1 | 2 | 1 | 2 | 1 | 1 |

| | Framework III | | | | | | | | | | | | | | | | |
|---|---|---|---|---|---|---|---|---|---|---|---|---|---|---|---|---|---|
| amino acid[1] | 66 | 67 | 68 | 69 | 70 | 71 | 72 | 73 | 74 | 75 | 76 | 77 | 78 | 79 | 80 | 81 | 82 |
| A | | | | | | | | | | | | | | | 33 | | |
| B | | | | | | | | | | | | | | | | | |
| C | | | | | | | | | | | | | | | | | |
| D | | | | | 32 | | | | | | | | | | | | 33 |
| E | | | | | | | | | | | | | | | | 33 | |
| F | | | | | | 32 | | | | | | | | | | | |
| G | 33 | | 33 | | 1 | | | | | | | | | | | | |
| H | | | | | | | | | | | | | | | | | |
| I | | | | | | | | | | 33 | | | | | | | |
| K | | | | | | | | | | | | | | | | | |
| L | | | | | | | | 33 | | | | | 32 | | | | |
| M | | | | | | | | | | | | | 1 | | | | |
| N | | | | | | | | | | | 2 | 1 | | | | | |
| P | | | | | | | | | | | | | | | | | |
| Q | | | | | | | | | | | | | | 32 | | | |
| R | | | | | | | | | | | | | | 1 | | | |
| S | | 33 | | | | | | | | | 30 | 32 | | | | | |
| T | | | | 33 | | | 33 | | 33 | | 1 | | | | | | |
| V | | | | | | | 1 | | | | | | | | | | |
| W | | | | | | | | | | | | | | | | | |
| X | | | | | | | | | | | | | | | | | |
| Y | | | | | | | | | | | | | | | | | |
| — | | | | | | | | | | | | | | | | | |
| unknown (?) | | | | | | | | | | | | | | | | | |
| not sequenced | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 |
| oomcaa[3] | 33 | 33 | 33 | 33 | 32 | 32 | 33 | 33 | 33 | 33 | 30 | 32 | 32 | 32 | 33 | 33 | 33 |
| mcaa[4] | G | S | G | T | D | F | T | L | T | I | S | S | L | Q | A | E | D |
| rel. oomcaa[5] | 100% | 100% | 100% | 100% | 97% | 97% | 100% | 100% | 100% | 100% | 91% | 97% | 97% | 97% | 100% | 100% | 100% |
| pos occupied[6] | 1 | 1 | 1 | 1 | 2 | 2 | 1 | 1 | 1 | 1 | 3 | 2 | 2 | 2 | 1 | 1 | 1 |

| | Framework III | | | | | | CDR III | | | | | | | | | | |
|---|---|---|---|---|---|---|---|---|---|---|---|---|---|---|---|---|---|
| amino acid[1] | 83 | 84 | 85 | 86 | 87 | 88 | 89 | 90 | 91 | 92 | 93 | 94 | 95 | A | B | C | D |
| A | | 32 | | | | | | | | | | 1 | | | | | |
| B | | | | | | | | | | | | | | | | | |
| C | | | | | | 33 | | | | | | | | | | | |
| D | | | | | | | | | | 1 | 1 | | | | | | |
| E | | | | | | | | | | | | | | | | | |
| F | | | | | 1 | | | | | 1 | | | | | | | |
| G | | 1 | | | | | | | | | 2 | | | | | | |
| H | | | | | 1 | | 3 | | | | | | | | | | |
| I | | | | | | | | | | | | 2 | | | | | |
| K | | | | | | | | | | | | | | | | | |
| L | | | | | | | | 1 | | 2 | | 1 | 3 | | | | |
| M | | | | | | | | | | | | | | | | | |
| N | | | | | | | | | | | 4 | 4 | | | | | |
| P | | | | | | | | | | | | 1 | 29 | 1 | | | |
| Q | | | | | | | 30 | 32 | | | | | 1 | | | | |
| R | | | | | | | | | | | 1 | | | 1 | | | |
| S | | | | | | | | | 2 | | 23 | 2 | | | | | |
| T | | | | | | | | | | | 2 | 22 | | | | | |
| V | 33 | | 33 | | | | | | | | | | | | | | |
| W | | | | | | | | | | | | | | | | | |
| X | | | | | | | | | | | | | | | | | |
| Y | | | | 33 | 31 | | | | 31 | 29 | | | | | | | |
| — | | | | | | | | | | | | | | 13 | 15 | 15 | 15 |
| unknown (?) | | | | | | | | | | | | | | | | | |
| not sequenced | | | | | | | | | | | | | | 18 | 18 | 18 | 18 |
| sum of seq[2] | 33 | 33 | 33 | 33 | 33 | 33 | 33 | 33 | 33 | 33 | 33 | 33 | 33 | 15 | 15 | 15 | 15 |
| oomcaa[3] | 33 | 32 | 33 | 33 | 31 | 33 | 30 | 32 | 31 | 29 | 23 | 22 | 29 | 13 | 15 | 15 | 15 |

TABLE 4D-continued

Analysis of V kappa subgroup 4

| | | | | | | | | | | | | | | | | | |
|---|---|---|---|---|---|---|---|---|---|---|---|---|---|---|---|---|---|
| mcaa[4] | V | A | V | Y | Y | C | Q | Q | Y | Y | S | T | P | — | — | — | — |
| rel. oomcaa[5] | 100% | 97% | 100% | 100% | 94% | 100% | 91% | 97% | 94% | 88% | 70% | 67% | 88% | 87% | 100% | 100% | 100% |
| pos occupied[6] | 1 | 2 | 1 | 1 | 3 | 1 | 2 | 2 | 2 | 4 | 6 | 7 | 3 | 3 | 1 | 1 | 1 |

| | CDR III | | | | Framework IV | | | | | | | | | | | | |
|---|---|---|---|---|---|---|---|---|---|---|---|---|---|---|---|---|---|
| amino acid[1] | E | F | 96 | 97 | 98 | 99 | 100 | 101 | 102 | 103 | 104 | 105 | 106 | A | 107 | 108 | sum |
| A | | | | | | | | | | | | | | | | | 183 |
| B | | | | | | | | | | | | | | | | | |
| C | | | | | | | | | | | | | | | | | 68 |
| D | | | | | | | | | | | | | | | | | 154 |
| E | | | | | | | | | | | | 14 | | | | | 105 |
| F | | | | | 15 | | | | | | | | | | | | 82 |
| G | | | | | | 15 | 4 | 15 | | | | | | | | | 228 |
| H | | | | | | | | | | | | | | | | | 6 |
| I | | | | | | | | | | | | | 14 | | | | 135 |
| K | | | | | | | | | | 14 | | | | | 13 | | 158 |
| L | | | 1 | | | | | | | | 4 | | | | | | 258 |
| M | | | | 1 | | | | | | | | | | | | | 27 |
| N | | | | | | | | | | | | | | | 1 | | 136 |
| P | | | 4 | | | | | | 1 | | | | | | | | 195 |
| Q | | | 1 | | | | 11 | | | | 1 | | | | | | 264 |
| R | | | 2 | | | | | | | 1 | | 1 | | | 1 | 11 | 116 |
| S | | | 1 | 2 | | | | | | | | | 1 | | | | 499 |
| T | | | | 12 | | | | | 14 | | | | | | | | 236 |
| V | | | | | | | | | | | 9 | | | | | | 196 |
| W | | | 2 | | | | | | | | 1 | | | | | | 69 |
| X | | | | | | | | | | | | | | | | | |
| Y | | | 1 | | | | | | | | | | | | | | 518 |
| — | 15 | 15 | 3 | | | | | | | | | | | 15 | | | 106 |
| unknown (?) | | | | | | | | | | | | | | | | | |
| not sequenced | 18 | 18 | 18 | 18 | 18 | 18 | 18 | 18 | 18 | 18 | 18 | 18 | 18 | 18 | 18 | 22 | 518 |
| sum of seq[2] | 15 | 15 | 15 | 15 | 15 | 15 | 15 | 15 | 15 | 15 | 15 | 15 | 15 | 15 | 15 | 11 | |
| oomcaa[3] | 15 | 15 | 4 | 12 | 15 | 15 | 11 | 15 | 14 | 14 | 9 | 14 | 14 | 15 | 13 | 11 | |
| mcaa[4] | — | — | P | T | F | G | Q | G | T | K | V | E | I | — | K | R | |
| rel. oomcaa[5] | 100% | 100% | 27% | 80% | 100% | 100% | 73% | 100% | 93% | 93% | 60% | 93% | 93% | 100% | 87% | 100% | |
| pos occupied[6] | 1 | 1 | 8 | 3 | 1 | 1 | 2 | 1 | 2 | 2 | 4 | 2 | 2 | 1 | 3 | 1 | |

TABLE 5A

Analysis of V lambda subgroup 1

| | Framework I | | | | | | | | | | | | | | | | | |
|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 |
| A | | | | | | | | | | | 19 | | 18 | 20 | | | | |
| B | | | | | | | | | | | | | | | | | | |
| C | | | | | | | | | | | | | | | | | | |
| D | | | | | | | | | | | | | | | | | | |
| E | | | | | | | | | | | | | | | | | | 1 |
| F | | | | | | | | | | | | | | | | | | |
| G | | | | | | | | | | | | | 22 | | | 42 | | |
| H | 2 | | | | | | | | | | | | | | | | | |
| I | | | 1 | | | | | | | | 1 | | | | | | | |
| K | | | | | | | | | | | | | | | | | | 14 |
| L | | | 1 | 41 | | | | | | | 1 | | | | | | | |
| M | | | | | | | | | | | | | | | | | | |
| N | | | | | | | | | | | | | | | | | | |
| P | | | | | | | 41 | 41 | | | | | | 1 | 41 | | | |
| Q | 22 | | 1 | | | 41 | | | | | | | | | | | 42 | |
| R | | | | | | | | | | | | | | | | | | 25 |
| S | | 39 | | | | | | | 41 | | | 41 | | | 1 | | | 1 |
| T | | | | | 41 | | | | | | | | | 19 | | | | 1 |
| V | | 1 | 38 | | | | | | | | 20 | | 1 | 1 | | | | |
| W | | | | | | | | | | | | | | | | | | |
| X | | | | | | | | | | | | | | | | | | |
| Y | | | | | | | | | | | | | | | | | | |
| Z | 16 | | | | | | | | | | | | | | | | | |
| — | | | | | | | | | | 41 | | | | | | | | |
| unknown (?) | | | | | | | | | | | | | | | | | | |
| not sequenced | 2 | 2 | 1 | 1 | 1 | 1 | 1 | 1 | 1 | 1 | 1 | 1 | 1 | 1 | | | | |
| sum of seq[2] | 40 | 40 | 41 | 41 | 41 | 41 | 41 | 41 | 41 | 41 | 41 | 41 | 41 | 41 | 42 | 42 | 42 | 42 |

TABLE 5A-continued

Analysis of V lambda subgroup 1

| | | | | | | | | | | | | | | | | | | |
|---|---|---|---|---|---|---|---|---|---|---|---|---|---|---|---|---|---|---|
| oomcaa[3] | 22 | 39 | 38 | 41 | 41 | 41 | 41 | 41 | 41 | 20 | 41 | 22 | 20 | 41 | 42 | 42 | 25 | 42 |
| mcaa[4] | Q | S | V | L | T | Q | P | P | S | — | V | S | G | A | P | G | Q | R |
| rel. oomcaa[5] | 55% | 98% | 93% | 100% | 100% | 100% | 100% | 100% | 100% | 100% | 49% | 100% | 54% | 49% | 98% | 100% | 100% | 60% |
| pos occupied[6] | 3 | 2 | 4 | 1 | 1 | 1 | 1 | 1 | 1 | 1 | 4 | 1 | 3 | 4 | 2 | 1 | 1 | 5 |

| | Framework I | | | | | CDR I | | | | | | | | | | | |
|---|---|---|---|---|---|---|---|---|---|---|---|---|---|---|---|---|---|
| amino acid[1] | 19 | 20 | 21 | 22 | 23 | 24 | 25 | 26 | 27 | D | E | 28 | 29 | 30 | 31 | A | 32 |
| A | | 2 | | | | | | | 1 | | | | 2 | 2 | | | 1 |
| B | | | | | | | | | | | | | | | | | |
| C | | | | 42 | | | | | | | | | | | | | |
| D | | | | | | | | | | | 3 | | | 3 | 1 | | 3 |
| E | | | | | | | | | | | | | | | | | |
| F | | | | | | 1 | | | | 1 | | | | | | 1 | 1 |
| G | | | | | | | 42 | 3 | 1 | | | 2 | 39 | 4 | 2 | | |
| H | | | | | | | | | | | | | | | 2 | | |
| I | | 1 | 41 | | | | | | | | 1 | 37 | | | | | |
| K | | | | | | | | | | | 1 | | | 1 | | | |
| L | | | 1 | | | | | | | | | 1 | | | | | |
| M | | | | | | | | | | | | 1 | | | | | |
| N | | | | | | | | | 2 | 1 | 37 | | | 13 | 31 | 2 | |
| P | | | | | | | | | | | | | | | | | 1 |
| Q | | | | | | | | | | | | | | | | | 1 |
| R | | | | | | | | 1 | 1 | | | | | 5 | | | |
| S | | 1 | | 42 | | 38 | | 34 | 34 | 38 | | | | 13 | 1 | 1 | 3 |
| T | | 38 | | | | 3 | | 4 | 3 | 2 | | | 1 | | 1 | | 7 |
| V | | | | | | | | | | | | 1 | | | | | 2 |
| W | 42 | | | | | | | | | | | | | | | | |
| X | | | | | | | | | | | | | | | | | |
| Y | | | | | | | | | | | | | | | 4 | 1 | 20 |
| Z | | | | | | | | | | | | | | | | | |
| — | | | | | | | | | | | | | | | | 36 | |
| unknown (?) | | | | | | | | | | | | | | | | | |
| not sequenced | | | | | | | | | | | | | | | | 1 | 1 |
| sum of seq[2] | 42 | 42 | 42 | 42 | 42 | 42 | 42 | 42 | 42 | 42 | 42 | 42 | 42 | 42 | 42 | 41 | 41 |
| oomcaa[3] | 42 | 38 | 41 | 42 | 42 | 38 | 42 | 34 | 34 | 38 | 37 | 37 | 39 | 13 | 31 | 36 | 20 |
| mcaa[4] | V | T | I | S | C | S | G | S | S | S | N | I | G | N | N | — | Y |
| rel. oomcaa[5] | 100% | 90% | 98% | 100% | 100% | 90% | 100% | 81% | 81% | 90% | 88% | 88% | 93% | 31% | 74% | 88% | 49% |
| pos occupied[6] | 1 | 4 | 2 | 1 | 1 | 3 | 1 | 4 | 6 | 4 | 4 | 5 | 3 | 8 | 7 | 5 | 10 |

| | CDR I | | Framework II | | | | | | | | | | | | | | |
|---|---|---|---|---|---|---|---|---|---|---|---|---|---|---|---|---|---|
| amino acid[1] | 33 | 34 | 35 | 36 | 37 | 38 | 39 | 40 | 41 | 42 | 43 | 44 | 45 | 46 | 47 | 48 | 49 |
| A | | | | | | | | | | 4 | 40 | | | | | | |
| B | | | | | | | | | | | | | | | | | |
| C | | | | | | | | | | | | | | | | | |
| D | | 1 | | | | | | | 1 | | | | | | | | |
| E | | | | | | | | | | | | | 2 | | | | |
| F | | | | 1 | | | 4 | | | | | | | | | | 1 |
| G | 1 | | | | | | | | 39 | | | | | | | | |
| H | | 2 | | 1 | 1 | 6 | 1 | | | | | | | | | | 1 |
| I | | 1 | | | | | | | | | | | | | | 40 | |
| K | | | | | | | | | | 1 | | | 35 | | | | |
| L | | | | | | 1 | 31 | | | | | | | 41 | 40 | | |
| M | | | | | | | | | | 1 | | | | | | 1 | |
| N | 1 | 9 | | | | | | | | | | | 1 | | | | |
| P | | | | | | | | 42 | 1 | | | 42 | | | | | |
| Q | | | | | 39 | 34 | | | | | | | | | | | |
| R | | | | | 2 | | 1 | | 1 | | | | 4 | | | | |
| S | | 19 | | | | | | | | | 1 | | | | | | |
| T | | 2 | | | | | | | | 36 | 1 | | | | | | |
| V | 40 | | | | | 1 | 5 | | | | | | | 1 | 2 | 1 | |
| W | | | 42 | | | | | | | | | | | | | | |
| X | | | | | | | | | | | | | | | | | |
| Y | | | | 40 | | | | | | | | | | | | | 40 |
| — | | | | | | | | | | | | | | | | | |
| unknown (?) | | | | | | | | | | | | | | | | | |
| not sequenced | 1 | 1 | | | | | | | | | | | | | | | |
| sum of seq[2] | 41 | 41 | 42 | 42 | 42 | 42 | 42 | 42 | 42 | 42 | 42 | 42 | 42 | 42 | 42 | 42 | 42 |
| oomcaa[3] | 40 | 19 | 42 | 40 | 39 | 34 | 31 | 42 | 39 | 36 | 40 | 42 | 35 | 41 | 40 | 40 | 40 |
| mcaa[4] | V | S | W | Y | Q | Q | L | P | G | T | A | P | K | L | L | I | Y |
| rel. oomcaa[5] | 98% | 46% | 100% | 95% | 93% | 81% | 74% | 100% | 93% | 86% | 95% | 100% | 83% | 98% | 95% | 95% | 95% |
| pos occupied[6] | 2 | 7 | 1 | 3 | 3 | 4 | 5 | 1 | 4 | 4 | 3 | 1 | 4 | 2 | 2 | 3 | 3 |

TABLE 5A-continued

Analysis of V lambda subgroup 1

| | CDR II | | | | | | | | | | | | Framework III | | | | | |
|---|---|---|---|---|---|---|---|---|---|---|---|---|---|---|---|---|---|---|
| amino acid[1] | 50 | 51 | 52 | 53 | 54 | 55 | 56 | A | B | C | D | E | 57 | 58 | 59 | 60 | 61 | 62 |
| A | | | 1 | | | 1 | | | | | | | | | | | | |
| B | | | | | | | | | | | | | | | | | | |
| C | | | | | | | | | | | | | | | | | | |
| D | 13 | 10 | 8 | | | | | | | | | | | | | 38 | | |
| F | 5 | | | 1 | | | | | | | | | | | | | | 38 |
| G | 1 | | | | | | | | | | | | 41 | | | 2 | | |
| H | | | | 1 | | | | | | | | | | | | 1 | | |
| I | 1 | | | | | | | | | | | | | 17 | | | | 3 |
| K | 1 | 1 | | 18 | | | | | | | | | | | | | | |
| L | | | | 1 | 1 | | 1 | | | | | | | | 1 | | | |
| M | | | | 1 | | | | | | | | | | | | | | |
| N | 3 | 28 | 30 | 2 | | | | | | | | | | | | | | |
| P | | | | | | 38 | | | | | | | | | 38 | | | |
| Q | | | | 15 | | | | | | | | | | | | | | |
| R | 7 | | | 2 | 40 | | | | | | | | | | | | 42 | |
| S | 9 | 2 | 3 | 1 | | 2 | 40 | | | | | | | | 2 | | | |
| T | 1 | | | | | | | | | | | | | | | | | |
| V | | | | | | | | | | | | | | 24 | | | | 1 |
| W | | | | | 1 | | | | | | | | | | | | | |
| X | | | | | | | | | | | | | | | | | | |
| Y | 1 | 1 | | | | | | | | | | | | | | | | |
| Z | | | | | | | | | | | | | | | | | | |
| — | | | | | | | | 41 | 41 | 41 | 41 | 42 | | | | | | |
| unknown (?) | | | | | | | | | | | | | | | | | | |
| not sequenced | | | | | | 1 | 1 | | | | | | 1 | 1 | 1 | 1 | | |
| sum of seq[2] | 42 | 42 | 42 | 42 | 42 | 41 | 41 | 41 | 41 | 41 | 41 | 42 | 41 | 41 | 41 | 41 | 42 | 42 |
| oomcaa[3] | 13 | 28 | 30 | 18 | 40 | 38 | 40 | 41 | 41 | 41 | 41 | 42 | 41 | 24 | 38 | 38 | 42 | 38 |
| mcaa[4] | D | N | N | K | R | P | S | — | — | — | — | — | G | V | P | D | R | F |
| rel. oomcaa[5] | 31% | 67% | 71% | 43% | 95% | 93% | 98% | 100% | 100% | 100% | 100% | 100% | 100% | 59% | 93% | 93% | 100% | 90% |
| pos occupied[6] | 10 | 5 | 4 | 9 | 3 | 3 | 2 | 1 | 1 | 1 | 1 | 1 | 1 | 2 | 3 | 3 | 1 | 3 |

| | Framework III | | | | | | | | | | | | | | | | | |
|---|---|---|---|---|---|---|---|---|---|---|---|---|---|---|---|---|---|---|
| amino acid[1] | 63 | 64 | 65 | 66 | A | B | 67 | 68 | 69 | 70 | 71 | 72 | 73 | 74 | 75 | 76 | 77 | 78 |
| A | | 5 | | | | | | 1 | 3 | | 41 | | | 24 | | | | |
| B | | | | | | | | | | | | | | | | | | |
| C | | | | | | | | | | | | | | | | | | |
| D | | | | | | | | 1 | | | | | | | | | | |
| E | | | | | | | | | | | | | | | | | | |
| F | | | | | | | | | | | | | | | | | | |
| G | | 36 | | | | | | 40 | | | | | | 17 | | 1 | 42 | |
| H | | | | | | | | | | | | | | | | | | |
| I | | | | | | | | | | | | | | | 41 | | | |
| K | | | | 38 | | | | | | | | | | | | | | |
| L | | | | | | | | | | | | | 42 | | | | | 41 |
| M | | | | | | | | | | | | | | | | | | |
| N | | | | | | | | | | | | | | | | | | |
| P | | | | | | | | | | | | | | | | | | |
| Q | | | | | | | | | | | | | | | | | | |
| R | | | | 4 | | | | | | | | | | | | | | |
| S | 42 | | 42 | | | | 42 | | 1 | 42 | | 24 | | | | 20 | | |
| T | | 1 | | | | | | | 38 | | | 18 | | | | 21 | | |
| V | | | | | | | | | | | 1 | | | 1 | 1 | | | 1 |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | | | 42 | 42 | | | | | | | | | | | | |
| unknown (?) | | | | | | | | | | | | | | | | | | |
| not sequenced | | | | | | | | | | | | | | | | | | |
| sum of seq[2] | 42 | 42 | 42 | 42 | 42 | 42 | 42 | 42 | 42 | 42 | 42 | 42 | 42 | 42 | 42 | 42 | 42 | 42 |
| oomcaa[3] | 42 | 36 | 42 | 38 | 42 | 42 | 42 | 40 | 38 | 42 | 41 | 24 | 42 | 24 | 41 | 21 | 42 | 41 |
| mcaa[4] | S | G | S | K | — | — | S | G | T | S | A | S | L | A | I | T | G | L |
| rel. oomcaa[5] | 100% | 86% | 100% | 90% | 100% | 100% | 100% | 95% | 90% | 100% | 98% | 57% | 100% | 57% | 98% | 50% | 100% | 98% |
| pos occupied[6] | 1 | 3 | 1 | 2 | 1 | 1 | 1 | 3 | 3 | 1 | 2 | 2 | 1 | 3 | 2 | 3 | 1 | 2 |

| | Framework III | | | | | | | | | | CDR III | | | | | | | | |
|---|---|---|---|---|---|---|---|---|---|---|---|---|---|---|---|---|---|---|---|
| amino acid[1] | 79 | 80 | 81 | 82 | 83 | 84 | 85 | 86 | 87 | 88 | 89 | 90 | 91 | 92 | 93 | 94 | 95 | A | B |
| A | | 2 | | | | 38 | 1 | | | | 22 | 15 | | | 1 | | | | 16 |
| B | | | | | | | | | | | | | | | | | | | |

TABLE 5A-continued

Analysis of V lambda subgroup 1

| | | | | | | | | | | | | | | | | | | | |
|---|---|---|---|---|---|---|---|---|---|---|---|---|---|---|---|---|---|---|---|
| C | | | | | | | | | | 42 | | | | | | | | | |
| D | | | 1 | 41 | | | 37 | | | | | | | 39 | 17 | | | 7 | |
| E | 1 | | 24 | | 42 | | 1 | | | | | | | | | | | | 1 |
| F | | | | | | | | | 2 | | | | | | | | 1 | | |
| G | | | 15 | | | | | | | | 14 | | | | 1 | | | | 17 |
| H | 1 | | | | | | 2 | | 1 | | | | | | | | | | |
| I | | | | | | | 1 | | | | | | | | | | | 1 | |
| K | | | | | | | | | | | | | | | | | | 1 | |
| L | | | | | | | | | | | 1 | | | | | | 37 | | |
| M | | | | | | | | | | | | | | | | | | | |
| N | | | | 1 | | | | | | | | | | 2 | 2 | | | 9 | 1 |
| P | | 2 | | | | | | | | | | | | | | | 1 | | |
| Q | 31 | | | | | | | | | | 3 | | | | | | | | |
| R | 8 | | | | | | | | | | | | | | | 5 | 1 | 2 | |
| S | | 20 | | | | 1 | | | | | | 4 | | | 17 | 35 | | 18 | |
| T | | 17 | | | | 3 | | | | | | 22 | | | 1 | 1 | | 1 | |
| V | | 1 | | | | | | | | | 1 | | | | 1 | | 1 | | 2 |
| W | 1 | | 2 | | | | | | | | | | 38 | | | | | | |
| X | | | | | | | | | | | | | | | | | | | |
| Y | | | | | 3 | | | 42 | 39 | | | | 3 | | 1 | | | | |
| Z | | | | | | | | | | | | | | | | | | | |
| — | | | | | | | | | | | | | | | | | | 2 | 4 |
| unknown (?) | | | | | | | | | | | | | | | | | | | |
| not sequenced | | | | | | | | | | | 1 | 1 | 1 | 1 | 1 | 1 | 1 | 1 | 1 |
| sum of seq[2] | 42 | 42 | 42 | 42 | 42 | 42 | 42 | 42 | 42 | 42 | 41 | 41 | 41 | 41 | 41 | 41 | 41 | 41 | 41 |
| oomcaa[3] | 31 | 20 | 24 | 41 | 42 | 38 | 37 | 42 | 39 | 42 | 22 | 22 | 38 | 39 | 17 | 35 | 37 | 18 | 17 |
| mcaa[4] | Q | S | E | D | E | A | D | Y | Y | C | A | T | W | D | D | S | L | S | G |
| rel. oomcaa[5] | 74% | 48% | 57% | 98% | 100% | 90% | 88% | 100% | 93% | 100% | 54% | 54% | 93% | 95% | 41% | 85% | 90% | 44% | 41% |
| pos occupied[6] | 5 | 5 | 4 | 2 | 1 | 3 | 5 | 1 | 3 | 1 | 5 | 3 | 2 | 2 | 8 | 3 | 5 | 8 | 6 |

| | CDR III | | | | | Framework IV | | | | | | | | | | | | | |
|---|---|---|---|---|---|---|---|---|---|---|---|---|---|---|---|---|---|---|---|
| amino acid[1] | C | D | E | F | 96 | 97 | 98 | 99 | 100 | 101 | 102 | 103 | 104 | 105 | 106 | A | 107 | 108 | sum |
| A | | | | | 4 | 1 | | | | | | | | | | | | | 285 |
| B | | | | | | | | | | | | | | | | | | | |
| C | | | | | | | | | | | | | | | | | | | 84 |
| D | | | | | | | | | | | | | | | | | | | 224 |
| E | | | | | 1 | | | | 1 | | | | | | | | | | 81 |
| F | | | | | | | 36 | | | | | | | | | | | | 87 |
| G | 1 | | | | 5 | 1 | | 36 | 31 | 36 | | | | | | | 26 | | 559 |
| H | 1 | | | | | | | | | | | | | | | | | | 25 |
| I | | | | | | 1 | | | | | | | | | | | | | 188 |
| K | | | | | | | | | | | | 30 | | | | | | | 141 |
| L | 1 | | | | | 1 | | | | | | | 25 | | | 34 | | | 344 |
| M | | | | | | 1 | | | | | | | | | | | | | 5 |
| N | | | | | | | | | | | | 1 | | | | | | | 176 |
| P | | | | | 6 | | | | | | | | | | | | | 1 | 296 |
| Q | | | | | | | | | | | | 3 | | | | 1 | | 18 | 251 |
| R | | | | | 2 | | | | | | | 1 | | | | | 2 | | 156 |
| S | 1 | | | | 1 | | | | 1 | | | | | | | | 2 | | 720 |
| T | | | | | | | | | 3 | | 36 | 1 | | 36 | | | | | 359 |
| V | | | | | 9 | 34 | | | | | | | 11 | | 36 | 1 | | | 282 |
| W | | | | | 7 | | | | | | | | | | | | 1 | | 92 |
| X | | | | | | | | | | | | | | | | | | | |
| Y | | | | | 3 | | | | | | | | | | | | | | 202 |
| Z | | | | | | | | | | | | | | | | | | | 16 |
| — | 35 | 39 | 38 | 38 | 1 | | | | | | | | | | | | | | 524 |
| unknown (?) | | | | | | | | | | | | | | | | | | | |
| not sequenced | 3 | 3 | 3 | 3 | 3 | 3 | 4 | 4 | 6 | 6 | 6 | 6 | 6 | 6 | 6 | 6 | 10 | 22 | 141 |
| sum of seq[2] | 39 | 39 | 38 | 38 | 39 | 39 | 36 | 36 | 36 | 36 | 36 | 36 | 36 | 36 | 36 | 36 | 31 | 19 | |
| oomcaa[3] | 35 | 39 | 38 | 38 | 9 | 34 | 36 | 36 | 31 | 36 | 36 | 30 | 25 | 36 | 36 | 34 | 26 | 18 | |
| mcaa[4] | — | — | — | — | V | V | F | G | G | G | T | K | L | T | V | L | G | Q | |
| rel. oomcaa[5] | 90% | 100% | 100% | 100% | 23% | 87% | 100% | 100% | 86% | 100% | 100% | 83% | 69% | 100% | 100% | 94% | 84% | 95% | |
| pos occupied[6] | 5 | 1 | 1 | 1 | 10 | 6 | 1 | 1 | 4 | 1 | 1 | 5 | 2 | 1 | 1 | 3 | 4 | 2 | |

TABLE 5B

Analysis of V lambda subgroup 2

| | Framework I | | | | | | | | | | | | | | | | | | | | | | CDRI | | |
|---|---|---|---|---|---|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| A | | | | | 3 | | 1 | | | | | | 1 | | | 1 | | | | | | | | 3 | | 1 |
| B | | | | | | | | | | | | | | | | | | | | | | | | | | |
| C | | | | 42 | | | | | 1 | | | | | 1 | | | | | | | | | 42 | | | |
| D | | | | | | | | | | 39 | | 1 | 4 | | 5 | | | | | | | | | | | |
| E | | | | | | | | | | | | | | | 1 | | | | | | | | | | | |
| F | | 1 | | | | | | | | | | | 1 | | | 4 | | | | | 1 | | | | | |
| G | | | | | | 43 | | 1 | | | | 39 | 26 | | | | | | | | | | | | 43 | |
| H | | | | | | | | 1 | | | | | | | 1 | 1 | | | | | | | | | | |
| I | | 41 | | | 1 | | | | | | 6 | | | | | | | | | | 41 | | | 1 | | |
| K | | | | | | | | | | | | | | | 4 | | | | | | | | | | | |
| L | | 1 | | | | | | | | | | | | | | 4 | | | | | 1 | | | | | |
| M | | | | | | | | | | | | | | | | | | | | | | | | | | |
| N | | | | | | | | 1 | 3 | 4 | | 1 | 4 | 3 | 28 | | | | | | | | | | | |
| P | | | | | | | | 1 | | | | | | | | | | | | | | | | | | |
| Q | | | | | | | | | | | | | | | | | | | | | | | | | | |
| R | | | | | | | | | 1 | | | | 2 | | | | | | | | | | | | | |
| S | | | 42 | | 3 | | 3 | 35 | 38 | | | | 5 | 1 | 2 | 4 | 1 | 42 | | | | 42 | | 3 | 3 | |
| T | 43 | | | | 36 | | 39 | 3 | | | | 1 | | 1 | | | | | | 43 | | | | 36 | | 39 |
| V | | | | | | | | | | | 37 | | | | | | 41 | | | | | | | | | |
| W | | | | | | | | | | | | | | | | | | | 43 | | | | | | | |
| X | | | | | | | | | | | | | | | | | | | | | | | | | | |
| Y | | | | | | | | 1 | | | | 1 | | 37 | | 29 | | | | | | | | | | |
| Z | | | | | | | | | | | | | | | | | | | | | | | | | | |
| — | | | | | | | | | | | | | | | 1 | | | | | | | | | | | |
| unknown (?) | | | | | | | | | | | | | | | 1 | | | | | | | | | | | |
| not sequenced | | | 1 | 1 | | | | | | | | | | | | | 1 | 1 | | | | 1 | 1 | | | |
| sum of seq[2] | 40 | 42 | 42 | 40 | 42 | 42 | 42 | 42 | 42 | 42 | 42 | 42 | 43 | 43 | 43 | 43 | 43 | 43 | 43 | 43 | 43 | 42 | 42 | 43 | 43 | 43 |
| oomcaa[3] | 22 | 41 | 35 | 40 | 42 | 41 | 42 | 30 | 40 | 42 | 36 | 42 | 42 | 42 | 40 | 42 | 42 | 43 | 28 | 43 | 41 | 42 | 42 | 36 | 43 | 39 |
| mcaa[4] | Q | S | A | L | T | Q | P | A | S | — | V | S | G | S | P | G | Q | S | I | T | I | S | C | T | G | T |
| rel. oomcaa[5] | 55% | 98% | 83% | 100% | 100% | 98% | 100% | 71% | 95% | 100% | 86% | 100% | 98% | 98% | 93% | 98% | 98% | 100% | 65% | 100% | 95% | 100% | 100% | 84% | 100% | 91% |
| pos occupied[6] | 3 | 2 | 4 | 1 | 1 | 1 | 1 | 3 | 3 | 1 | 2 | 1 | 2 | 2 | 2 | 2 | 2 | 1 | 3 | 1 | 3 | 1 | 1 | 4 | 1 | 3 |

| | CDRI | | | | | | | | | | | | Framework II | | | | | | | | | | | | | |
|---|---|---|---|---|---|---|---|---|---|---|---|---|---|---|---|---|---|---|---|---|---|---|---|---|---|---|
| amino acid[1] | 27 | D | E | 28 | 29 | 30 | 31 | A | 32 | 33 | 34 | 35 | 36 | 37 | 38 | 39 | 40 | 41 | 42 | 43 | 44 | 45 | 46 | 47 | 48 | 49 |
| A | | | | | | 1 | | | 1 | | | | | | | | 1 | 4 | | 40 | | | | | | |
| B | | | | | | | | | | | | | | | | | | | | | | | | | | |
| C | | 1 | | | | | 1 | | | | | | | | | | | | | | | | | | | |
| D | | | 39 | | 1 | 4 | | 5 | | | | | | | | 1 | | 2 | | | | | | | | |
| E | | | | | | | | 1 | | | | | | | | | | | | | | | | | | |
| F | | | | | | 1 | | | 4 | | | | 2 | | | | | | | | | | | | | 7 |
| G | 1 | | | | 39 | 26 | | | | | | | | | | | | 36 | | | | | | | | |
| H | 1 | | | | | | | 1 | 1 | | | | | | 2 | 34 | | | | | | | | | | |
| I | | | | 6 | | | | | | | | | | | | | | | 1 | | | | 1 | 9 | 43 | |

TABLE 5B-continued

Analysis of V lambda subgroup 2

| | CDR II | | | | | | | | | | | | Framework III | | | | | | | | | | | | | |
|---|---|---|---|---|---|---|---|---|---|---|---|---|---|---|---|---|---|---|---|---|---|---|---|---|---|---|
| amino acid[1] | 50 | 51 | 52 | 53 | 54 | 55 | 56 | A | B | C | D | E | 57 | 58 | 59 | 60 | 61 | 62 | 63 | 64 | 65 | 66 | A | B | 67 | 68 |
| K | | | | | | | | 4 | | | | | | | | | | | 40 | | | 41 | | | | |
| L | | | | | | | | | 4 | | | | | | 1 | 1 | | | | | | | 38 | 6 | | |
| M | | | | | | | | | | | | | | | | | | | | | | | | 26 | | |
| N | 1 | 3 | 4 | | 1 | 4 | 3 | 28 | | | | | | | | 2 | | | | | | | | | | |
| P | 1 | | | | | | | | | | | | | | | | 41 | | | | 43 | | | | | |
| Q | | | | | | | | | | | | | | 41 | 39 | | | | | | | 2 | | | | |
| R | | 1 | | | | 2 | | | | | | | | 1 | | | | | 1 | | | | | | | |
| S | 35 | 38 | | | | 5 | 1 | 2 | 4 | 1 | 42 | | | | | 1 | | | | | | | | | 2 | |
| T | 3 | | | | 1 | | 1 | | | | | | | | | | | | 1 | | | | | | | |
| V | | | | 37 | | | | | | 41 | | | | | | | | 1 | | 3 | | | 4 | 2 | | |
| W | | | | | | | | | | | | 43 | | | | | | | | | | | | | | |
| X | | | | | | | | | | | | | | | | | | | | | | | | | | |
| Y | 1 | | | | 1 | | 37 | | 29 | | | | 41 | | | 5 | | | | | | | | | | 34 |
| Z | | | | | | | | | | | | | | | | | | | | | | | | | | |
| — | | | | | | | | 1 | | | | | | | | | | | | | | | | | | |
| unknown (?) | | | | | | | | 1 | | | | | | 1 | 1 | | | | | | | | | | | |
| not sequenced | | | | | | | | | | 1 | 1 | | | | | | | | | | | | | | | |
| sum of seq[2] | 43 | 43 | 43 | 43 | 43 | 43 | 43 | 43 | 43 | 42 | 42 | 43 | 43 | 43 | 43 | 43 | 43 | 43 | 43 | 43 | 43 | 43 | 43 | 43 | 43 | 43 |
| oomcaa[3] | 35 | 38 | 39 | 37 | 39 | 26 | 37 | 2829 | 41 | 42 | 43 | 41 | 41 | 39 | 34 | 41 | 36 | 40 | 40 | 43 | 41 | 38 | 26 | 43 | 34 | |
| mcaa[4] | S | S | D | V | G | G | Y | N | Y | V | S | W | Y | Q | Q | H | P | G | K | A | P | K | L | M | I | Y |
| rel. oomcaa[5] | 81% | 88% | 91% | 86% | 91% | 60% | 86% | 65% | 67% | 98% | 100% | 100% | 95% | 95% | 91% | 79% | 95% | 84% | 93% | 93% | 100% | 95% | 88% | 60% | 100% | 79% |
| pos occupied[6] | 7 | 4 | 2 | 2 | 5 | 7 | 5 | 7 | 6 | 2 | 1 | 1 | 2 | 2 | 3 | 5 | 3 | 4 | 4 | 2 | 1 | 2 | 3 | 4 | 1 | 3 |
| A | | | | | | | | | | | | | | | | | | | | 2 | | | | | | 3 |
| B | | | | | | | | | | | | | | | | | | | | | | | | | | |
| C | | | | | | | | | | | | | | | | | | | | | 1 | | | | | |
| D | 20 | 1 | 2 | 1 | | | | | | | | | | | | 17 | | | | | | | | | | 1 |
| E | 20 | | | 2 | | | | | | | | | | | | | | | | | | | | | | |
| F | | 1 | | | | | | | | | | | | | | | | 42 | | | | | | | | |
| G | 2 | 2 | | 1 | | | | | | | | | 43 | 1 | | | | | | 41 | | | | | | 39 |
| H | | | | 1 | | | | | | | | | | | | 2 | | | | | | | | | | |
| I | | | 1 | | | | | | | | | | | 3 | | | | | | | | | | | | |
| K | | | 1 | 21 | | | | | | | | | | | | | | | | | | 42 | | | | |
| L | | | | | | | | | | | | | | | | 1 | | 1 | | | | | | | | |
| M | | | 1 | | | | | | | | | | | | | | | | | | | | | | | |
| N | 1 | | 8 | 12 | | | | | | | | | | | | 19 | | | | | | | | | | |
| P | | | | | | 43 | | | | | | | | | 15 | | | | | | | | | | | |
| Q | | | | | | | | | | | | | | | | | | | | | | | | | | |
| R | | | 2 | | 43 | | | | | | | | | | | | 43 | | | | | 1 | | | | |
| S | | | 21 | 3 | | | 43 | | | | | | | | 28 | 2 | | | 43 | | 42 | | | | 42 | |
| T | | | 7 | | | | | | | | | | | | | | | | | | | | | | | |
| V | | 39 | | | | | | | | | | | | 39 | | | | | | | | | | | | |
| W | | | | | | | | | | | | | | | | | | | | | | | | | | |
| X | | | | | | | | | | | | | | | | | | | | | | | | | | |
| Y | | | | 2 | | | | | | | | | | | | 2 | | | | | | | | | | |
| Z | | | | | | | | | | | | | | | | | | | | | | | | | | |

TABLE 5B-continued

Analysis of V lambda subgroup 2

| | | | | | | | | | | | | | | | | | | | | | | | | | | |
|---|---|---|---|---|---|---|---|---|---|---|---|---|---|---|---|---|---|---|---|---|---|---|---|---|---|---|
| — | | | | | | | | 43 | 43 | 43 | 43 | 43 | | | | | | | | | | | 43 | 43 | | |
| unknown (?) | | | | | | | | | | | | | | | | | | | | | | | | | | |
| not sequenced | | | | | | | | | | | | | | | | | | | | | | | | | 1 | |
| sum of seq[2] | 43 | 43 | 43 | 43 | 43 | 43 | 43 | 43 | 43 | 43 | 43 | 43 | 43 | 43 | 43 | 43 | 43 | 43 | 43 | 43 | 43 | 43 | 43 | 43 | 42 | 43 |
| oomcaa[3] | 20 | 39 | 21 | 21 | 43 | 43 | 43 | 43 | 43 | 43 | 43 | 43 | 43 | 39 | 28 | 19 | 43 | 42 | 43 | 41 | 42 | 42 | 43 | 43 | 42 | 39 |
| mcaa[4] | D | V | S | K | R | P | S | — | — | — | — | — | G | V | S | N | R | F | S | G | S | K | — | — | S | G |
| rel. oomcaa[5] | 47% | 91% | 49% | 49% | 100% | 100% | 100% | 100% | 100% | 100% | 100% | 100% | 100% | 91% | 65% | 44% | 100% | 98% | 100% | 95% | 98% | 98% | 100% | 100% | 100% | 91% |
| pos occupied[6] | 4 | 4 | 8 | 8 | 1 | 1 | 1 | 1 | 1 | 1 | 1 | 1 | 1 | 3 | 2 | 6 | 1 | 2 | 1 | 2 | 2 | 2 | 1 | 1 | 1 | 3 |
| | Framework III | | | | | | | | | | | | | | | | | | | | CDR III | | | | | |
| amino acid[1] | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 |
| A | | 1 | 43 | | | | | | | | | 36 | | | | 43 | | | | | 2 | 1 | | 21 | | 1 |
| B | | | | | | | | | | | | | | | | | | | | | | | | | | |
| C | | | | | | | | | | | | | | | | | | | | 43 | 11 | | | | | |
| D | 2 | | | | | | | | | | | | 3 | 42 | | | 39 | | | | | | | | 3 | 1 |
| E | | | | | | | | | 1 | | | | 38 | | 43 | | | | | | | | | 1 | 1 | |
| F | | | | | | | | | | | | | | | | | | | 3 | | | | 3 | | | |
| G | | | | | | | | | 42 | | | | 1 | | | | | | | | | | | 1 | 21 | 3 |
| H | | | | | | | | | | | | | | | | | 2 | | | | | | 1 | | | |
| I | | | | | | | 35 | | | | | | | | | | | | | | | | | 1 | 1 | |
| K | 1 | | | | | | | | | | | | | | | | | | | | | | | | | |
| L | | | | | 43 | | | | | 43 | | | | | | | | | | | | | | | | |
| M | | | | | | | | | | | | | | | | | | | | | | | | | | |
| N | 38 | | | | | | | | | | | | 1 | 1 | | | 1 | | | | | | | | | 5 |
| P | | | | | | | | | | | | 2 | | | | | | | | | | | | | 1 | |
| Q | | | | | | | | | | | 41 | | | | | | | | | | | | | | | |
| R | | | | | | | | | | | 2 | | | | | | | | | | | | | 2 | | 3 |
| S | | 1 | | 43 | | | | 42 | | | | | | | | | | | 1 | | 30 | 41 | | | 12 | 23 |
| T | 1 | 41 | | | | 43 | | 1 | | | | 2 | | | | | | | | | | | | 16 | 4 | 4 |
| V | | | | | | | 8 | | | | | 3 | | | | | | | | | | | | 1 | | |
| W | | | | | | | | | | | | | | | | | | | | | | | | | | |
| X | | | | | | | | | | | | | | | | | | | | | | | | | | |
| Y | | | | | | | | | | | | | | | | | | 43 | 39 | | | | 39 | | | 1 |
| Z | | | | | | | | | | | | | | | | | | | | | | | | | | |
| — | | | | | | | | | | | | | | | | | | | | | | | | | | |
| unknown (?) | 1 | | | | | | | | | | | | | | | | 1 | | | | | | | | | 2 |
| not sequenced | | | | | | | | | | | | | | | | | | | | | | 1 | | | | |
| sum of seq[2] | 43 | 43 | 43 | 43 | 43 | 43 | 43 | 43 | 43 | 43 | 43 | 43 | 43 | 43 | 43 | 43 | 43 | 43 | 43 | 43 | 43 | 42 | 43 | 43 | 43 | 43 |
| oomcaa[3] | 38 | 41 | 43 | 43 | 43 | 43 | 35 | 42 | 42 | 43 | 41 | 36 | 38 | 42 | 43 | 43 | 39 | 43 | 39 | 43 | 30 | 41 | 39 | 21 | 21 | 23 |
| mcaa[4] | N | T | A | S | L | T | I | S | G | L | Q | A | E | D | E | A | D | Y | Y | C | S | S | Y | A | G | S |
| rel. oomcaa[5] | 88% | 95% | 100% | 100% | 100% | 100% | 81% | 98% | 98% | 100% | 95% | 84% | 88% | 98% | 100% | 100% | 91% | 100% | 91% | 100% | 70% | 98% | 91% | 49% | 49% | 53% |
| pos occupied[6] | 4 | 3 | 1 | 1 | 1 | 1 | 2 | 2 | 2 | 1 | 2 | 4 | 4 | 2 | 1 | 1 | 3 | 1 | 3 | 1 | 3 | 2 | 3 | 7 | 7 | 8 |

TABLE 5B-continued

Analysis of V lambda subgroup 2

| amino acid[1] | CDR III 95 | A | B | C | D | E | F | 96 | Framework IV 97 | 98 | 99 | 100 | 101 | 102 | 103 | 104 | 105 | 106 | A | 107 | 108 | sum |
|---|---|---|---|---|---|---|---|---|---|---|---|---|---|---|---|---|---|---|---|---|---|---|
| A | | | | | | | | 1 | 1 | | | 1 | | | | | | | | | | 280 |
| B | | | | | | | | | | | | | | | | | | | | | | |
| C | | | | | | | | | | | | | | | | | | | | | | 99 |
| D | 2 | | | | | | | 1 | | | | | | | | | | | | | | 188 |
| E | | | | | | | | | | | | | | | | | | | | | | 107 |
| F | 1 | | 1 | | | | | 5 | | 42 | | | | | | | | | | | | 113 |
| G | 4 | | | | | | | 1 | | | 42 | 33 | 42 | | | | | | | 19 | | 567 |
| H | | | | | | | | | | | | | | | | | | | | | | 48 |
| I | 1 | 2 | | | | | | 1 | 7 | | | | | | | | 1 | | | | | 184 |
| K | 3 | | | | | | | | | | | | | | 36 | | | | | | | 189 |
| L | | | 1 | 1 | | | | 6 | 5 | | | | | | | 28 | | | 40 | | | 264 |
| M | | | | | | | | 1 | 1 | | | | | | | | | | | | | 29 |
| N | 7 | 5 | | | | | | 1 | | | | | | | 1 | | | | | | | 146 |
| P | | | 4 | | | | | | | | | | | | | | | | | | | 238 |
| Q | 1 | 2 | | | | | | | | | | | | | 1 | | | | | | 14 | 250 |
| R | | | 1 | | | | | 5 | | | | 1 | | | 2 | | | | | 4 | | 121 |
| S | 14 | 9 | | | | | | 1 | | | | | | | | | 1 | | | 2 | | 831 |
| T | 3 | 21 | | | | | | | | | | 7 | | 41 | | | 40 | | | | | 398 |
| V | | | | | | | | 11 | 28 | | | | | | | 14 | | 42 | 1 | | | 327 |
| W | | | | | | | | 5 | | | | | | | | | | | | | | 48 |
| X | | | | | | | | | | | | | | | | | | | | | | |
| Y | 6 | | | | | | | 4 | | | | | | | 1 | | | | | | | 285 |
| Z | | | | | | | | | | | | | | | | | | | | | | 16 |
| — | 1 | 3 | 36 | 42 | 43 | 43 | 43 | | | | | | | | | | | | | | | 555 |
| unknown (?) | | | | | | | | | | | | | | | | | | | | | | 8 |
| not sequenced | | 1 | | | | | | | 1 | 1 | 1 | 1 | 1 | 2 | 2 | 1 | 1 | 1 | 2 | 1528 | 80 | |
| sum of seq[2] | 43 | 42 | 43 | 43 | 43 | 43 | 43 | 43 | 42 | 42 | 42 | 42 | 42 | 41 | 41 | 42 | 42 | 42 | 41 | 25 | 14 | |
| oomcaa[3] | 14 | 2136 | 42 | 43 | 43 | 43 | 11 | 28 | 42 | 42 | 33 | 42 | 41 | 36 | 28 | 40 | 42 | 40 | 19 | 14 | | |
| mcaa[4] | S | T | — | — | — | — | — | V | V | F | G | G | G | T | K | L | T | V | L | G | Q | |
| rel. oomcaa[5] | 33% | 50% | 84% | 98% | 100% | 100% | 100% | 26% | 67% | 100% | 100% | 79% | 100% | 100% | 88% | 67% | 95% | 100% | 98% | 76% | 100% | |
| pos occupied[6] | 11 | 6 | 5 | 2 | 1 | 1 | 1 | 13 | 5 | 1 | 1 | 4 | 1 | 1 | 5 | 2 | 3 | 1 | 2 | 3 | 1 | |

TABLE 5C

Analysis of V lambda subgroup 3

| | Framework I | | | | | | | | | | | | | | | | | |
|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 |
| A | | | | | 1 | | 1 | 2 | 7 | | | | | 20 | 1 | | | |
| B | | | | | | | | | | | | | | | | | | |
| C | | | | | | | | | | | | | | | | | | |
| D | | | 5 | | | | 10 | | | | | | | | | | | |
| E | | | 20 | | | | | | | | | | 1 | | | 1 | | |
| F | 1 | 1 | | | | | | | | | | 1 | | | 1 | | | |
| G | | | 1 | | | | | | | | | | | | | 37 | | |
| H | | | | | | | | | | | | | | | | | | |
| I | | | | | | | | | | | | | | | | | | |
| K | | | | | | | | | | | | | | | | | 2 | |
| L | | | | 37 | | | | | | | 4 | | 1 | | 9 | | | |
| M | | | | | | | | | | | | | | | | | | |
| N | | | | | | | | | | | | | | | | | | |
| P | | | | | | | 26 | 35 | 1 | | | | | | 27 | | | |
| Q | 4 | | 4 | | | 38 | | | | | | | | | | | 36 | |
| R | | | | | | | | | | | | | | | | | | |
| S | 13 | 14 | | | 1 | | 1 | | 28 | | | 37 | | 18 | | | | |
| T | | | | | 36 | | | 1 | | | | | | | | | | 38 |
| V | | | 8 | 1 | | | | | 2 | | 34 | | 36 | | | | | |
| W | | | | | | | | | | | | | | | | | | |
| X | | | | | | | | | | | | | | | | | | |
| Y | | 23 | | | | | | | | | | | | | | | | |
| Z | | | | | | | | | | | | | | | | | | |
| — | 20 | | | | | | | | | 38 | | | | | | | | |
| unknown (?) | | | | | | | | | | | | | | | | | | |
| not sequenced | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 |
| oomcaa[3] | 20 | 23 | 20 | 37 | 36 | 38 | 26 | 35 | 28 | 38 | 34 | 37 | 36 | 20 | 27 | 37 | 36 | 38 |
| mcaa[4] | — | Y | E | L | T | Q | P | P | S | — | V | S | V | A | P | G | Q | T |
| rel. oomcaa[5] | 53% | 61% | 53% | 97% | 95% | 100% | 68% | 92% | 74% | 100% | 89% | 97% | 95% | 53% | 71% | 97% | 95% | 100% |
| pos occupied[6] | 4 | 3 | 5 | 2 | 3 | 1 | 4 | 3 | 4 | 1 | 2 | 2 | 3 | 2 | 4 | 2 | 2 | 1 |

| | Framework I | | | | | CDR I | | | | | | | | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | D | E | 28 | 29 | 30 | 31 | A | 32 | 33 |
| A | 27 | | | 1 | | | | | 5 | | | | | 1 | 1 | | | 21 |
| B | | | | | | | | | | | | | | | | | | |
| C | | | | | 38 | | | | | | | | | | | | | |
| D | | | | | | | | 30 | 1 | | | | | 10 | | | 3 | |
| E | | | | | | | | 2 | 2 | | | | 1 | 3 | 6 | | | |
| F | | | | | | | | | | | | | | | 1 | | 2 | |
| G | | | | | | 9 | 38 | | 1 | | | | 23 | 4 | | | | |
| H | | | | | | | | 1 | | | | | | | | | 2 | |
| I | | | 38 | | | | | | | | | 9 | | | 1 | | | |
| K | | | | | | | | | 7 | | | | | 2 | 13 | | | |
| L | | | | | | | | | | | | 28 | | | | | | |
| M | | 1 | | | | | | | | | | | | | 1 | | | |
| N | | | | 2 | | | | 4 | 9 | | | 1 | | 2 | | | 1 | |
| P | 1 | | | 1 | | | | | | | | | 3 | | | | | |
| Q | | | | | | 10 | | | | | | | | | 4 | | | |
| R | | 25 | | | | | | | 2 | | | | 10 | 1 | | | | 1 |
| S | | 9 | | 1 | | 19 | | | 10 | | | | | 11 | 2 | | 8 | |
| T | | 3 | | 33 | | | | | 1 | | | | 1 | 4 | | | | |
| V | 10 | | | | | | | | | | | | | | | | 1 | 15 |
| W | | | | | | | | | | | | | | | | | | |
| X | | | | | | | | | | | | | | | | | | |
| Y | | | | | | | | 1 | | | | | | | 8 | | 20 | 1 |
| Z | | | | | | | | | | | | | | | | | | |
| — | | | | | | | | | | 38 | 38 | | | | | 37 | | |
| unknown (?) | | | | | | | | | | | | | | | | | | |
| not sequenced | | | | | | | | | | | | | | | | 1 | 1 | |
| sum of seq[2] | 38 | 38 | 38 | 38 | 38 | 38 | 38 | 38 | 38 | 38 | 38 | 38 | 38 | 38 | 37 | 37 | 37 | 38 |
| oomcaa[3] | 27 | 25 | 28 | 33 | 38 | 19 | 38 | 30 | 10 | 38 | 38 | 28 | 23 | 11 | 13 | 37 | 20 | 21 |
| mcaa[4] | A | R | I | T | C | S | G | D | S | — | — | L | G | S | K | — | Y | A |
| rel. oomcaa[5] | 71% | 66% | 100% | 87% | 100% | 50% | 100% | 79% | 26% | 100% | 100% | 74% | 61% | 29% | 35% | 100% | 54% | 55% |
| pos occupied[6] | 3 | 4 | 1 | 5 | 1 | 3 | 1 | 5 | 9 | 1 | 1 | 3 | 5 | 9 | 9 | 1 | 7 | 4 |

TABLE 5C-continued

Analysis of V lambda subgroup 3

| | Framework II | | | | | | | | | | | | | | | | CDR II | |
|---|---|---|---|---|---|---|---|---|---|---|---|---|---|---|---|---|---|---|
| amino acid[1] | 34 | 35 | 36 | 37 | 38 | 39 | 40 | 41 | 42 | 43 | 44 | 45 | 46 | 47 | 48 | 49 | 50 | 51 |
| A | 3 | | | | | | | | | 23 | | | | | | | | 1 |
| B | | | | | | | | | | | | | | | | | | |
| C | 5 | | | | | | | | | | | | | | | | | |
| D | 1 | | | | | | | | | | | | | | | | 9 | 22 |
| E | | | | | 1 | | | | | | | | | | | | 5 | 3 |
| F | | | 3 | | | | | | | | | | | | | 2 | | |
| G | | | | | | | | 36 | | | | | | | | | 9 | 2 |
| H | 9 | | | | | | | | 1 | | | | | | | 1 | 3 | |
| I | | | | | | | | | | | | 1 | | | 28 | | | |
| K | | | | | | 32 | | | | | | | | | | | 2 | 6 |
| L | | | | | 2 | | | | | | | 6 | 33 | 1 | | | | |
| M | | | | | | | | | | | | | 1 | | 1 | | | |
| N | 2 | | | | | | | | | | | | | | | | | 1 |
| P | | | | | | | 36 | | 1 | | 38 | | | | | | | |
| Q | | | | 37 | 35 | 1 | | | 36 | | | | | | | | 9 | |
| R | | | | 1 | | 4 | | 2 | | | | | | | | | 1 | 1 |
| S | 14 | | | | | 1 | 2 | | | 14 | | | | | | | | |
| T | | | | | | | | | | | | | | | | | | 2 |
| V | | | | | | | | | | 1 | | 31 | 4 | 37 | 9 | | | |
| W | | 38 | | | | | | | | | | | | | | | | |
| X | | | | | | | | | | | | | | | | | | |
| Y | 4 | | 35 | | | | | | | | | | | | | 35 | | |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 |
| oomcaa[3] | 14 | 38 | 35 | 37 | 35 | 32 | 36 | 36 | 36 | 23 | 38 | 31 | 33 | 37 | 28 | 35 | 9 | 22 |
| mcaa[4] | S | W | Y | Q | Q | K | P | G | Q | A | P | V | L | V | I | Y | D | D |
| rel. oomcaa[5] | 37% | 100% | 92% | 97% | 92% | 84% | 95% | 95% | 95% | 61% | 100% | 82% | 87% | 97% | 74% | 92% | 24% | 58% |
| pos occupied[6] | 7 | 1 | 2 | 2 | 3 | 4 | 2 | 2 | 3 | 3 | 1 | 3 | 3 | 2 | 3 | 3 | 7 | 8 |

| | CDR II | | | | | | | | | | Framework III | | | | | | | |
|---|---|---|---|---|---|---|---|---|---|---|---|---|---|---|---|---|---|---|
| amino acid[1] | 52 | 53 | 54 | 55 | 56 | A | B | C | D | E | 57 | 58 | 59 | 60 | 61 | 62 | 63 | 64 |
| A | | 1 | | | 1 | | | | | | | | | | | | | |
| B | | | | | | | | | | | | | | | | | | |
| C | | | | | | | | | | | | | | | | | | |
| D | 2 | 8 | | | | | | | | | | | | 9 | | | | |
| E | | 3 | | | | | | | | | | | | 27 | | | | |
| F | 1 | | | | | | | | | | | | | | | 38 | | |
| G | | | | | | | | | | | 38 | | | | | | | 38 |
| H | | 1 | | | | | | | | | | | | | | | | |
| I | 1 | | | | | | | | | | | 37 | | | | | | |
| K | 1 | 13 | | | | | | | | | | | | | | | | |
| L | | | | | | | | | | | | | | | | | | |
| M | | | | | | | | | | | | | | | | | | |
| N | 19 | 9 | | | | | | | | | | | | | | | | |
| P | | | | 37 | 1 | | | | | | | | 36 | | | | | |
| Q | | 1 | | | | | | | | | | | | | | | | |
| R | | 1 | 38 | | | | | | | | | | | | 38 | | | |
| S | 10 | 1 | | 1 | 36 | | | | | | | | 1 | | | | 38 | |
| T | 4 | | | | | | | | | | | | | | | | | |
| V | | | | | | | | | | | | | | | | | | |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | | | | 38 | 38 | 38 | 38 | 38 | | | | | | | | |
| unknown (?) | | | | | | | | | | | | | | 1 | | | | |
| not sequenced | | | | | | | | | | | | 1 | 1 | 1 | | | | |
| sum of seq[2] | 38 | 38 | 38 | 38 | 38 | 38 | 38 | 38 | 38 | 38 | 38 | 37 | 37 | 37 | 38 | 38 | 38 | 38 |
| oomcaa[4] | 19 | 13 | 38 | 37 | 36 | 38 | 38 | 38 | 38 | 38 | 38 | 37 | 36 | 27 | 38 | 38 | 38 | 38 |
| mcaa[4] | N | K | R | P | S | — | — | — | — | — | G | I | P | E | R | F | S | G |
| rel. oomcaa[5] | 50% | 34% | 100% | 97% | 95% | 100% | 100% | 100% | 100% | 100% | 100% | 100% | 97% | 73% | 100% | 100% | 100% | 100% |
| pos occupied[6] | 7 | 9 | 1 | 2 | 3 | 1 | 1 | 1 | 1 | 1 | 1 | 1 | 2 | 2 | 1 | 1 | 1 | 1 |

TABLE 5C-continued

Analysis of V lambda subgroup 3

| | Framework III | | | | | | | | | | | | | | | | | |
|---|---|---|---|---|---|---|---|---|---|---|---|---|---|---|---|---|---|---|
| amino acid[1] | 65 | 66 | A | B | 67 | 68 | 69 | 70 | 71 | 72 | 73 | 74 | 75 | 76 | 77 | 78 | 79 | 80 |
| A | | | | | | | | 1 | 36 | 1 | | 1 | | | | 11 | 1 | 34 |
| B | | | | | | | | | | | | | | | | | | |
| C | | | | | | | | | | | | | | | | | | |
| D | | | | | | | | | | | | | | | | | | |
| E | | | | | | | | | | | | | | | | | 10 | |
| F | | | | | | | | | | | | | | | | | | |
| G | | | | | | 37 | | | | | | | | | 28 | | | |
| H | | | | | | | 1 | | | | | | | | | | | |
| I | | | | | | | | | | 1 | | 1 | 37 | 1 | | | | |
| K | | | | | | | 1 | | | | | | | | | | | |
| L | | | | | | | | | | | 38 | | | | | | | |
| N | | 21 | | | | | 28 | | | | | | | 1 | | | | |
| P | | | | | | | | | | | | | | | | | | |
| Q | | | | | | 1 | | | | | | | | | | | 25 | |
| R | | | | | | | | | | | | | | 1 | 10 | | 1 | |
| S | 38 | 12 | | | 37 | | 2 | | | 11 | | | | 23 | | | | 1 |
| T | | 5 | | | 1 | | 6 | 37 | | 25 | | 36 | | 12 | | 13 | | 2 |
| V | | | | | | | | | 2 | | | | 1 | | | 14 | 1 | 1 |
| W | | | | | | | | | | | | | | | | | | |
| X | | | | | | | | | | | | | | | | | | |
| Y | | | | | | | | | | | | | | | | | | |
| Z | | | | | | | | | | | | | | | | | | |
| — | | | 38 | 38 | | | | | | | | | | | | | | |
| unknown (?) | | | | | | | | | | | | | | | | | | |
| not sequenced | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 |
| oomcaa[3] | 38 | 21 | 38 | 38 | 37 | 37 | 28 | 37 | 36 | 25 | 38 | 36 | 37 | 23 | 28 | 14 | 25 | 34 |
| mcaa[4] | S | N | — | — | S | G | N | T | A | T | L | T | I | S | G | V | Q | A |
| rel. oomcaa[6] | 100% | 55% | 100% | 100% | 97% | 97% | 74% | 97% | 95% | 66% | 100% | 95% | 97% | 61% | 74% | 37% | 66% | 89% |
| pos occupied[6] | 1 | 3 | 1 | 1 | 2 | 2 | 5 | 2 | 2 | 4 | 1 | 3 | 2 | 5 | 2 | 3 | 5 | 4 |

| | Framework III | | | | | | | CDR III | | | | | | | | | | |
|---|---|---|---|---|---|---|---|---|---|---|---|---|---|---|---|---|---|---|
| amino acid[1] | 81 | 82 | 83 | 84 | 85 | 86 | 87 | 88 | 89 | 90 | 91 | 92 | 93 | 94 | 95 | A | B | C |
| A | | | | 38 | | | | | 13 | 3 | | 2 | | | 1 | 2 | | |
| B | | | | | | | | | | | | | | | | | | |
| C | | | | | | | | 38 | | | | | | | | | | |
| D | | 38 | | | 37 | | | | | | | 32 | 1 | 1 | | 6 | | |
| E | 14 | | 38 | | 1 | | | | 1 | | | | | | | | 2 | |
| F | | | | | | | 2 | | | | | | 2 | | | | | |
| G | 10 | | | | | | | | | | | | | 3 | 14 | 3 | | |
| H | | | | | | | | | | | | | | | | | 12 | 1 |
| I | 1 | | | | | | | | | | | | | | | | | |
| K | | | | | | | | | | | | | | | | 1 | | |
| L | 2 | | | | | | | | 1 | | | | 1 | | 1 | | 1 | 1 |
| M | 10 | | | | | | | | | | | | | 1 | | | | |
| N | | | | | | | | | 10 | | | 2 | 1 | 2 | | 10 | 1 | |
| P | | | | | | | | | | | | | | 1 | | | | 3 |
| Q | | | | | | | | | 25 | | | | | | 1 | 1 | | |
| R | | | | | | | | | | | 10 | | 1 | 2 | | | 2 | |
| S | | | | | | | | | 1 | 14 | 1 | | 28 | 26 | 13 | | 1 | |
| T | | | | | | | | | | | 1 | | 3 | | 7 | 2 | | |
| V | 1 | | | | | | | | | 11 | | | | | | | | |
| W | | | | | | | | | | | 23 | | | | | | | |
| X | | | | | | | | | | | | | | | | | | |
| Y | | | | | | 38 | 36 | | | | | 1 | | 1 | | 1 | 3 | 1 |
| Z | | | | | | | | | | | | | | | | | | |
| — | | | | | | | | | | | | | | | | 10 | 15 | 31 |
| unknown (?) | | | | | | | | | | | | | | | | | | |
| not sequenced | | | | | | | | | | | | 1 | 1 | 1 | 1 | 2 | 1 | 1 |
| sum of seq[2] | 38 | 38 | 38 | 38 | 38 | 38 | 38 | 38 | 38 | 38 | 38 | 37 | 37 | 37 | 37 | 36 | 37 | 37 |
| oomcaa[3] | 14 | 38 | 38 | 38 | 37 | 38 | 36 | 38 | 25 | 14 | 23 | 32 | 28 | 26 | 14 | 10 | 15 | 31 |
| mcaa[4] | E | D | E | A | D | Y | Y | C | Q | S | W | D | S | S | G | N | — | — |
| rel. oomcaa[5] | 37% | 100% | 100% | 100% | 97% | 100% | 95% | 100% | 66% | 37% | 61% | 86% | 76% | 70% | 38% | 28% | 41% | 84% |
| pos occupied[6] | 6 | 1 | 1 | 1 | 2 | 1 | 2 | 1 | 5 | 3 | 5 | 4 | 7 | 8 | 6 | 9 | 8 | 5 |

| | CDR III | | | | Framework IV | | | | | | | | | | | | | |
|---|---|---|---|---|---|---|---|---|---|---|---|---|---|---|---|---|---|---|
| amino acid[1] | D | E | F | 96 | 97 | 98 | 99 | 100 | 101 | 102 | 103 | 104 | 105 | 106 | A | 107 | 108 | sum |
| A | | | | 4 | | | | | | | | | | | | | | 265 |
| B | | | | | | | | | | | | | | | | | | |

TABLE 5C-continued

| Analysis of V lambda subgroup 3 | | | | | | | | | | | | | | | | | | |
|---|---|---|---|---|---|---|---|---|---|---|---|---|---|---|---|---|---|---|
| C | | | | | | | | | | | | | | | 1 | | | 82 |
| D | | | | | | | | | | | | | | | | | | 225 |
| E | | | | 2 | | | | | | | 2 | | | | | | | 145 |
| F | | | | | | 35 | | | | | | | | | | | | 90 |
| G | 1 | | | 3 | 1 | | 35 | 31 | 35 | | | | | | | | 24 | 461 |
| H | | | | | | | | | | | | | | | | | | 32 |
| I | | | | | 4 | | | | | | | | | | | | | 160 |
| K | | | | | | | | | | | 30 | | | | | | | 110 |
| L | | | | 4 | 2 | | | | | | | 28 | | | 33 | | | 233 |
| M | | | | 1 | 1 | | | | | | | | | | | | | 17 |
| N | | | | | | | | | | | | | | | | | | 126 |
| P | | | | 1 | | | | | | | | | | | 1 | | | 249 |
| Q | | | | | | | | | | | | | | | | | 7 | 275 |
| R | | | | | | | | | | | 2 | | | | | | | 154 |
| S | | | 1 | | | | | | | | | | | | | | 2 | 501 |
| T | | | | | | | | 4 | | 35 | | | 35 | | | | | 347 |
| V | | | | 18 | 28 | | | | | | | 7 | | 35 | | | | 308 |
| W | | | | 1 | | | | | | | | | | | | | | 62 |
| X | | | | | | | | | | | | | | | | | | |
| Y | | | | 3 | | | | | | | | | | | | | | 211 |
| Z | | | | | | | | | | | | | | | | | | |
| — | 36 | 37 | 36 | | 1 | | | | | | | | | | | | | 603 |
| unknown (?) | | | | | | | | | | | | | | | | | | 1 |
| not sequenced | 1 | 1 | 1 | 1 | 1 | 3 | 3 | 3 | 3 | 3 | 4 | 3 | 3 | 3 | 4 | 11 | 28 | 89 |
| sum of seq[2] | 37 | 37 | 37 | 37 | 37 | 35 | 35 | 35 | 35 | 35 | 34 | 35 | 35 | 35 | 34 | 27 | 7 | |
| oomcaa[3] | 36 | 37 | 36 | 18 | 28 | 35 | 35 | 31 | 35 | 35 | 30 | 28 | 35 | 35 | 33 | 24 | 7 | |
| mcaa[4] | — | — | — | V | V | F | G | G | G | T | K | L | T | V | L | G | Q | |
| rel. oomcaa[5] | 97% | 100% | 97% | 49% | 76% | 100% | 100% | 89% | 100% | 100% | 88% | 80% | 100% | 100% | 97% | 89% | 100% | |
| pos occupied[6] | 2 | 1 | 2 | 9 | 6 | 1 | 1 | 2 | 1 | 1 | 3 | 2 | 1 | 1 | 2 | 3 | 1 | |

TABLE 6A

| Analysis of V heavy chain subgroup 1A | | | | | | | | | | | | | | | | | | | |
|---|---|---|---|---|---|---|---|---|---|---|---|---|---|---|---|---|---|---|---|
| | Framework I | | | | | | | | | | | | | | | | | | |
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | 1 | 14 | | | 60 | | | | | | | 24 | 1 | | |
| B | | | | | | | | | | | | | | | | | | | |
| C | | | | | | | | | | | | | | | | | | | |
| D | | | | | | | | | | | | | | | | | | | |
| E | 1 | | | | 2 | 1 | | 2 | | 64 | | | | | | | | | |
| F | | | | | | | | | | | | | | | | | | | |
| G | | | | | | | | 58 | 1 | | | | | | 64 | | | | |
| H | | | 2 | | | | | | | | | | | | | | | | |
| I | | 2 | | | | | | | | | | | | | | | | | |
| K | | 2 | | | | | | | | | | 57 | 64 | | | | | | 60 |
| L | | | 2 | 59 | | | | | | | 3 | | | | | | | | |
| M | | 1 | | | | | | | | | | | | | | | | | |
| N | | | | | | | | | | | | 6 | | | | | | | |
| P | | | | | | | | | | | | | | 63 | | | | | |
| Q | 53 | | 56 | | 2 | 45 | | | | | | | | | | | | | |
| R | | | | | | | | | | | 1 | | | | | | | | 3 |
| S | | | | | | | 60 | | 3 | | | | | 1 | | 40 | 63 | | |
| T | | | | | | | | | | | | | | | | | | | 1 |
| V | 2 | 55 | | 1 | 55 | | | | | | 61 | | | | | | | 64 | |
| W | | | | | | | | | | | | | | | | | | | |
| X | | | | | | | | | | | | | | | | | | | |
| Y | | | | | | | | | | | | | | | | | | | |
| Z | 3 | | | | | | | | | | | | | | | | | | |
| — | | | | | | | | | | | | | | | | | | | |
| unknown (?) | | | | | | | | | | | | | | | | | | | |
| not sequenced | 11 | 10 | 10 | 10 | 10 | 10 | 10 | 10 | 6 | 6 | 6 | 6 | 6 | 6 | 6 | 6 | 6 | 6 | 6 |
| sum of seq[2] | 59 | 60 | 60 | 60 | 60 | 60 | 60 | 60 | 64 | 64 | 64 | 64 | 64 | 64 | 64 | 64 | 64 | 64 | 64 |
| oomcaa[3] | 53 | 55 | 56 | 59 | 55 | 45 | 60 | 58 | 60 | 64 | 61 | 57 | 64 | 63 | 64 | 40 | 63 | 64 | 60 |
| mcaa[4] | Q | V | Q | L | V | Q | S | G | A | E | V | K | K | P | G | S | S | V | K |
| rel. oomcaa[5] | 90% | 92% | 93% | 98% | 92% | 75% | 100% | 97% | 94% | 100% | 95% | 89% | 100% | 98% | 100% | 63% | 98% | 100% | 94% |
| pos occupied[6] | 4 | 4 | 3 | 2 | 4 | 3 | 1 | 2 | 3 | 1 | 2 | 3 | 1 | 2 | 1 | 2 | 2 | 1 | 3 |

TABLE 6A-continued

Analysis of V heavy chain subgroup 1A

| | Framework I | | | | | | | | | | | CDR I | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |
| A | | | | | 62 | | | | 1 | | | | | | | 41 | | | |
| B | | | | | | | | | | | | | | | | | | | |
| C | | | 63 | | | | | | | | | | | | | | | | |
| D | | | | | | | | 1 | | | | | | | | | | | |
| E | | | | | | | | | | | | | | | | | | | |
| F | | | | | | | | | | 69 | | | | | 3 | | 3 | | |
| G | | | | | 1 | | 69 | 41 | | 1 | | | | | | 23 | | | |
| H | | | | | | | | | | | 1 | | | | 1 | | | 1 | |
| I | | | | | | | | | 1 | | | | | | | | 61 | 1 | |
| K | | | | 63 | | | | | | | 1 | 1 | | | | | | | |
| L | | | | | | | | | | | | | | | | 1 | 2 | | |
| M | | | | | | | | | | | | | | | | | 4 | | |
| N | | | | | | | | | | | 2 | 5 | | | | | | 4 | |
| P | | | | | | | | | | | | | | | | 1 | | | |
| R | | | 1 | 1 | | | | | | | 1 | 1 | | | | | | | |
| S | | 63 | | | | 68 | | 1 | | | 40 | 60 | | | 2 | | | 60 | |
| T | | 1 | | | 2 | | | | 68 | | 25 | 3 | | | | 3 | | 4 | |
| V | 64 | | | | | | | | | | | | | | | 1 | | | |
| W | | | | | | | | | | | | | | | | | | | 70 |
| X | | | | | | | | | | | | | | | | | | | |
| Y | | | | | | | | 27 | | | | | | | 64 | | | | |
| Z | | | | | | | | | | | | | | | | | | | |
| — | | | | | | | | | | | | | 70 | 70 | | | | | |
| unknown (?) | | | | | | | | | | | | | | | | | | | |
| not sequenced | 6 | 6 | 6 | 6 | 5 | 2 | 1 | | | | | | | | | | | | |
| sum of seq[2] | 64 | 64 | 64 | 64 | 65 | 68 | 69 | 70 | 70 | 70 | 70 | 70 | 70 | 70 | 70 | 70 | 70 | 70 | 70 |
| oomcaa[3] | 64 | 63 | 63 | 63 | 62 | 68 | 69 | 41 | 68 | 69 | 40 | 60 | 70 | 70 | 64 | 41 | 61 | 60 | 70 |
| mcaa[4] | V | S | C | K | A | S | G | G | T | F | S | S | — | — | Y | A | I | S | W |
| rel. oomcaa[5] | 100% | 98% | 98% | 98% | 95% | 100% | 100% | 59% | 97% | 99% | 57% | 86% | 100% | 100% | 91% | 59% | 87% | 86% | 100% |
| pos occupied[6] | 1 | 2 | 2 | 2 | 3 | 1 | 1 | 4 | 3 | 2 | 6 | 5 | 1 | 1 | 4 | 6 | 4 | 5 | 1 |

| | Framework II | | | | | | | | | | | | | | CDR II | | | | |
|---|---|---|---|---|---|---|---|---|---|---|---|---|---|---|---|---|---|---|---|
| amino acid[1] | 37 | 38 | 39 | 40 | 41 | 42 | 43 | 44 | 45 | 46 | 47 | 48 | 49 | 50 | 51 | 52 | A | B | C |
| A | | | | 70 | | | | | | | | | 1 | | | | 5 | | |
| B | | | | | | | | | | | | | | | | | | | |
| C | | | | | | | | | | | | | | | | | | | |
| D | | | | | | | | | | 1 | | | | | | | | | |
| E | | | | | | | | | | 69 | | | | | | | | | |
| F | | | | | | | | | | | | | | | 2 | | | | |
| G | | | | | 1 | 68 | | 69 | | | 1 | | 69 | 39 | | | 1 | | |
| H | | | | | 1 | | | | | | | | | | | | | | |
| I | 1 | | | | | | | | | | | | | | 65 | 38 | | | |
| K | | | | | | | | | | | | | | | | | | | |
| L | | | | | | 1 | | | 68 | | | 1 | | 1 | | | | | |
| M | | | | | | | | | | | | 67 | | | | 2 | | | |
| N | | | | | | | | | | | | | | | | 4 | | | |
| P | | | | | 68 | | | | 1 | | | | | | | | 44 | | |
| Q | | | 69 | | | | 69 | | | | | | | | | | | | |
| R | | 70 | 1 | | | 1 | | 1 | | | | | | 4 | | | | | |
| S | | | | | | | 1 | | | | 1 | 1 | | | | 22 | | | |
| T | | | | | | | | | | | | | | | 1 | 2 | 4 | | |
| V | 69 | | | | | | | | | | | 1 | | | 2 | 2 | 16 | | |
| W | | | | | | | | | 1 | | 67 | | | 26 | | | | | |
| X | | | | | | | | | | | | | | | | | | | |
| Y | | | | | | | | | | | 1 | | | | | | | | |
| Z | | | | | | | | | | | | | | | | | | | |
| — | | | | | | | | | | | | | | | | | | 70 | |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 69 | 70 | 69 | 70 | 68 | 68 | 69 | 69 | 68 | 69 | 67 | 67 | 69 | 39 | 65 | 38 | 44 | 70 | 70 |
| mcaa[4] | V | R | Q | A | P | G | Q | G | L | E | W | M | G | G | I | I | P | — | — |
| rel. oomcaa[5] | 99% | 100% | 99% | 100% | 97% | 97% | 99% | 99% | 97% | 99% | 96% | 96% | 99% | 56% | 93% | 54% | 63% | 100% | 100% |
| pos occupied[6] | 2 | 1 | 2 | 1 | 3 | 3 | 2 | 2 | 3 | 2 | 4 | 4 | 2 | 4 | 4 | 6 | 5 | 1 | 1 |

TABLE 6A-continued

Analysis of V heavy chain subgroup 1A

| | CDR II | | | | | | | | | | | | | | Framework III | | | | |
|---|---|---|---|---|---|---|---|---|---|---|---|---|---|---|---|---|---|---|---|
| amino acid[1] | 53 | 54 | 55 | 56 | 57 | 58 | 59 | 60 | 61 | 62 | 63 | 64 | 65 | 66 | 67 | 68 | 69 | 70 | 71 |
| A | | | | 1 | 34 | | | 69 | | | | | | | | | | | 43 |
| B | | | | | | | | | | | | | | | | | | | |
| C | | | | | | | | | | | | | | | | | | | |
| D | | | | 15 | | 1 | | | | | | | 2 | | | | | | |
| E | | | | | | | | | | | | 1 | | | | | | | |
| F | 3 | 39 | | | | | 1 | | | | 48 | | | | 3 | | 4 | | |
| G | | | 68 | 1 | | | | | | 3 | | | 67 | | | | | | |
| H | | | | | | 1 | | | | | | | | | | | | | |
| I | 34 | | | 4 | | | | | | | | | | | | 1 | 44 | | |
| K | | | | 1 | | 2 | 1 | | | 47 | | 1 | | 1 | | | | | |
| L | 2 | 4 | | 1 | 1 | | | | | | 22 | | | | 2 | | 1 | | 3 |
| M | 4 | | | | | | | | | | | | | | | | 21 | | |
| N | 3 | 22 | | 9 | | 59 | | | | 18 | | | | | | | | | |
| P | | | | 1 | 7 | | | | | | | | | | | | | | |
| Q | 1 | 1 | 1 | 1 | 1 | | | | 70 | | | 64 | | | | | | | |
| R | 1 | | | 2 | | | | | | 2 | | 1 | | 69 | | | | | |
| S | | 1 | 1 | | 1 | 2 | | 1 | | | | | | | | | | 5 | |
| T | 1 | 3 | | 34 | 26 | 4 | | | | | | 3 | | | | 66 | | 65 | 24 |
| V | 1 | | | | | | | | | | | | 1 | | 65 | 3 | | | |
| W | | | | | | | | | | | | | | | | | | | |
| X | | | | | | | | | | | | | | | | | | | |
| Y | 20 | | | | | 1 | 68 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 34 | 39 | 68 | 34 | 34 | 59 | 68 | 69 | 70 | 47 | 48 | 64 | 67 | 69 | 65 | 66 | 44 | 65 | 43 |
| mcaa[4] | I | F | G | T | A | N | Y | A | Q | K | F | Q | G | R | V | T | I | T | A |
| rel. oomcaa[5] | 49% | 56% | 97% | 49% | 49% | 84% | 97% | 99% | 100% | 67% | 69% | 91% | 96% | 99% | 93% | 94% | 63% | 93% | 61% |
| pos occupied[6] | 10 | 6 | 3 | 11 | 6 | 7 | 3 | 2 | 1 | 4 | 2 | 5 | 3 | 2 | 3 | 3 | 4 | 2 | 3 |

| | Framework III | | | | | | | | | | | | | | | | | | |
|---|---|---|---|---|---|---|---|---|---|---|---|---|---|---|---|---|---|---|---|
| amino acid[1] | 72 | 73 | 74 | 75 | 76 | 77 | 78 | 79 | 80 | 81 | 82 | A | B | C | 83 | 84 | 85 | 86 | 87 |
| A | | | | | | | 64 | | | 1 | | | | | | 3 | | | 1 |
| B | | | | | | | | | | | | | | | | | | | |
| C | | | | | | | | | | | | | | | | | | | |
| D | 70 | | | | | | | | | 2 | | | | | | | 26 | 70 | |
| E | | 33 | | | | | | | | 64 | | | | | | | 44 | | |
| F | | | | | | | | | | | | | | | | | | | |
| G | | | | | | | | | | | | | 1 | | | | | | |
| H | | | | | | | | 1 | | | | 1 | | | | | | | |
| I | | 1 | | | | 1 | | | | | 3 | 1 | 1 | | | | | | |
| K | | 8 | | | | | | | | | | | | | 3 | | | | |
| L | | | | | | | | | 3 | | 63 | | | 70 | | | | | |
| M | | | | | | | | | 67 | | | | | | | | | | 1 |
| N | | | | | 4 | | | | | | | 1 | 16 | | | | | | |
| P | | | | | | | | | | | | | | | | | | | |
| Q | | | | | | | | 1 | | 3 | | | | | | | | | |
| R | | 1 | | | 3 | | | | | | | 23 | 1 | | 62 | | | | |
| S | | | 70 | | 62 | | 1 | | | | | 41 | 49 | | | 67 | | | 1 |
| T | | 27 | | 67 | 1 | 69 | 2 | | | | | 3 | 2 | | 4 | | | | 67 |
| V | | | | 3 | | | 3 | | | | 4 | | | | 1 | | | | |
| W | | | | | | | | | | | | | | | | | | | |
| X | | | | | | | | | | | | | | | | | | | |
| Y | | | | | | | | 68 | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 70 | 33 | 70 | 67 | 62 | 69 | 64 | 68 | 67 | 64 | 63 | 41 | 49 | 70 | 62 | 67 | 44 | 70 | 67 |
| mcaa[4] | D | E | S | T | S | T | A | Y | M | E | L | S | S | L | R | S | E | D | T |
| rel. oomcaa[5] | 100% | 47% | 100% | 96% | 89% | 99% | 91% | 97% | 96% | 91% | 90% | 59% | 70% | 100% | 89% | 96% | 63% | 100% | 96% |
| pos occupied[6] | 1 | 5 | 1 | 2 | 4 | 2 | 4 | 3 | 2 | 4 | 3 | 6 | 6 | 1 | 4 | 2 | 2 | 1 | 4 |

TABLE 6A-continued

Analysis of V heavy chain subgroup 1A

| | Framework III | | | | | CDR III | | | | | | | | | | | | | |
|---|---|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 70 | | | | | 66 | 2 | 16 | | 1 | 1 | 1 | 4 | 1 | 2 | 2 | 1 | 1 | |
| B | | | | | | | | | | | | | | | | | | | |
| C | | | | | 70 | | | | | 1 | 1 | 16 | 2 | | 1 | 1 | 7 | 2 | 1 |
| D | | | | | | | | 16 | 5 | 3 | | 3 | 5 | 4 | 3 | 4 | | | 1 |
| E | | | | | | | | 9 | | | | 2 | | | 1 | | | 1 | |
| F | | 1 | 1 | 2 | | | | | | 1 | 3 | | 2 | | 3 | 1 | 2 | | 2 |
| G | | | | | | | 2 | 14 | 13 | 20 | 10 | 14 | 5 | 20 | 15 | 16 | 3 | 3 | 4 |
| H | | | | | | | | | | | | | | | 1 | 1 | 1 | | 1 |
| I | | 2 | | | | | | | 2 | 5 | 2 | 2 | | 2 | 2 | 1 | 1 | | |
| K | | | | | | | 5 | | | 2 | 1 | | | 1 | | | | | |
| L | | 2 | | | | | 1 | 4 | 4 | 2 | 5 | 2 | 1 | 1 | | 4 | 2 | | 1 |
| M | | 1 | | | | | | 1 | | 2 | | 1 | | 1 | | | 1 | 1 | |
| N | | | | | | | | | 2 | 2 | 1 | 2 | 1 | 2 | 2 | 2 | 2 | | |
| P | | | | | | | | | 20 | 3 | | 1 | 3 | 2 | 2 | 2 | 4 | 2 | 1 |
| Q | | | | | | | | | 1 | | | 1 | | 1 | 1 | 1 | | | |
| R | | | | | | | 55 | 1 | 5 | 7 | 8 | 1 | 4 | | 2 | | 1 | | 16 |
| S | | | | | | | 1 | 1 | 5 | 5 | 5 | 5 | 21 | 5 | 11 | 8 | 4 | 3 | |
| T | | | | | | 1 | 3 | 3 | 5 | 4 | 1 | 3 | 4 | 2 | 5 | 2 | | 1 | |
| V | | 64 | | | | 3 | | 3 | 2 | 4 | 3 | 3 | 3 | 4 | 2 | 2 | 2 | 1 | 2 |
| W | | | | | | | | | 1 | 1 | 3 | 1 | 1 | | | 2 | | 3 | |
| X | | | | | | | | | | | | | | | | | | | |
| Y | | | 69 | 68 | | | 1 | | 2 | 3 | 20 | 5 | 4 | 9 | 1 | 2 | 11 | 20 | 10 |
| Z | | | | | | | | | | | | | | | | | | | |
| — | | | | | | | | | 1 | 2 | 2 | 3 | 6 | 11 | 11 | 14 | 23 | 26 | 26 |
| unknown (?) | | | | | | | | | | | | | | | | | | 1 | |
| not sequenced | | | | | | | | 2 | 2 | 2 | 4 | 4 | 4 | 4 | 5 | 5 | 5 | 5 | 5 |
| sum of seq[2] | 70 | 70 | 70 | 70 | 70 | 70 | 70 | 68 | 68 | 68 | 66 | 66 | 66 | 66 | 65 | 65 | 65 | 65 | 65 |
| oomcaa[3] | 70 | 64 | 69 | 68 | 70 | 66 | 55 | 16 | 20 | 20 | 20 | 16 | 21 | 20 | 15 | 16 | 23 | 26 | 26 |
| mcaa[4] | A | V | Y | Y | C | A | R | A | P | G | Y | C | S | G | — | — | — | — | — |
| rel. oomcaa[5] | 100% | 91% | 99% | 97% | 100% | 94% | 79% | 24% | 29% | 29% | 30% | 24% | 32% | 30% | 23% | 25% | 35% | 40% | 40% |
| pos occupied[6] | 1 | 5 | 2 | 2 | 1 | 3 | 8 | 10 | 14 | 18 | 15 | 18 | 15 | 15 | 17 | 17 | 15 | 12 | 11 |

| | CDR III | | | | | | Framework IV | | | | | | | | | | | | |
|---|---|---|---|---|---|---|---|---|---|---|---|---|---|---|---|---|---|---|---|
| amino acid[1] | G | H | I | J | K | 101 | 102 | 103 | 104 | 105 | 106 | 107 | 108 | 109 | 110 | 111 | 112 | 113 | sum |
| A | 1 | 1 | 1 | 2 | | 1 | | | | | | | | | | | | | 670 |
| B | | | | | | | | | | | | | | | | | | | |
| C | | | | | | | | | | | | | | | | | | | 165 |
| D | 1 | 14 | | | | 59 | | 1 | 1 | | | | | | | | | | 308 |
| E | | 1 | | | | | 1 | 1 | | | | | | | | | | | 297 |
| F | 1 | | | | 28 | 2 | 2 | | | | | | | | | | | | 226 |
| G | 15 | 1 | 1 | 7 | | | | | 58 | | 59 | 1 | 1 | | | | | | 928 |
| H | | | | | | | | | | 1 | | | | | | | | | 14 |
| I | 1 | | | | | | 3 | | | | | | | | 4 | | | | 286 |
| K | | | | | | | | | | 3 | | 1 | | | | | | | 325 |
| L | | | 1 | | 1 | | 3 | | | 1 | | | 40 | 1 | | | | | 386 |
| M | | | | | 10 | | 1 | | | | | | 3 | | | | | | 189 |
| N | 1 | 1 | 4 | | | | | | | 1 | | | | | | | | | 176 |
| P | 4 | 1 | | 1 | | 1 | 5 | | | | | | | | | | | 1 | 238 |
| Q | | | | | | | | | | 52 | | | | | | | | | 494 |
| R | | | | | | | | | | 1 | | | | | | | | | 351 |
| S | 2 | 1 | | 2 | | 1 | | | | | | | | | | | 53 | 51 | 972 |
| T | | 1 | 1 | | | | | | | | | 54 | 11 | 1 | 51 | | 1 | | 736 |
| V | 1 | | | | | | 15 | | 1 | | | | 1 | 54 | | 54 | | 1 | 699 |
| W | | | 1 | 5 | 1 | | | 59 | | 1 | | | | | | | | | 243 |
| X | | | | | | | | | | | | | | | | | | | |
| Y | 6 | 9 | 10 | 7 | 1 | | 34 | | 1 | | | | | | | | | | 542 |
| Z | | | | | | | | | | | | | | | | | | | 3 |
| — | 31 | 34 | 46 | 39 | 21 | 1 | 1 | | | | | | | | | | | | 578 |
| unknown (?) | 1 | 1 | | 2 | 3 | | | | | | | | | | | | | | 8 |
| not sequenced | 5 | 5 | 5 | 5 | 5 | 5 | 5 | 9 | 9 | 10 | 11 | 14 | 14 | 14 | 15 | 16 | 16 | 17 | 406 |
| sum of seq[2] | 65 | 65 | 65 | 65 | 65 | 65 | 65 | 61 | 61 | 60 | 59 | 56 | 56 | 56 | 55 | 54 | 54 | 53 | |
| oomcaa[3] | 31 | 34 | 46 | 39 | 28 | 59 | 34 | 59 | 58 | 52 | 59 | 54 | 40 | 54 | 51 | 54 | 53 | 51 | |
| mcaa[4] | — | — | — | — | F | D | Y | W | G | Q | G | T | L | V | T | V | S | S | |
| rel. oomcaa[5] | 48% | 52% | 71% | 60% | 43% | 91% | 52% | 97% | 95% | 87% | 100% | 96% | 71% | 96% | 93% | 100% | 98% | 96% | |
| pos occupied[6] | 11 | 10 | 8 | 7 | 6 | 6 | 9 | 3 | 4 | 7 | 1 | 3 | 5 | 3 | 2 | 1 | 2 | 3 | |

TABLE 6B

Analysis of V heavy chain subgroup 1B

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | | | | | 32 | | | | | | | 34 | | | |
| B | | | | | | | | | | | | | | | | | | | |
| C | | | | | | | | | | | | | | | | | | | |
| D | | | | | | | | | | | | | | | | | | | |
| E | | 1 | | | 5 | 1 | | | | 35 | | | | | | | | | |
| F | | | | | | | | | | | | | | | | | | | |
| G | | | | | | | | 27 | | | | | | | 35 | | | | |
| H | | | 1 | | | | | | | | | | | 1 | | | | | |
| I | | | | | | | | | | | | | | | | | | | |
| K | | 3 | 1 | | | | | | | | | 34 | 33 | | | | | | 33 |
| L | | | 3 | 26 | 1 | | | | | | | | | | | | | | |
| M | | | | 1 | 1 | | | | | | | | | | | | | | |
| N | | | | | | | | | | | | | | | | | | | |
| P | | | | | | | | | 1 | | | | | 33 | | | 1 | | |
| Q | 21 | | 20 | | | 26 | | | | | | | | | | | | | |
| R | 1 | | | | | | | | | | | 1 | 2 | | | | | | |
| S | | | | | | | 27 | | | | | | | | | 1 | 34 | | |
| T | | | | | | | | | 1 | | | | | 1 | | | | | 2 |
| V | 3 | 21 | | | 20 | | | | | | 35 | | | | | | | 35 | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | 15 | 15 | 15 | 13 | 13 | 13 | 13 | 13 | 6 | 5 | 5 | 5 | 5 | 5 | 5 | 5 | 5 | 5 | 5 |
| sum of seq[2] | 25 | 25 | 25 | 27 | 27 | 27 | 27 | 27 | 34 | 35 | 35 | 35 | 35 | 35 | 35 | 35 | 35 | 35 | 35 |
| oomcaa[3] | 21 | 21 | 20 | 26 | 20 | 26 | 27 | 27 | 32 | 35 | 35 | 34 | 33 | 33 | 35 | 34 | 34 | 35 | 33 |
| mcaa[4] | Q | V | Q | L | V | Q | S | G | A | E | V | K | K | P | G | A | S | V | K |
| rel. oomcaa[5] | 84% | 84% | 80% | 96% | 74% | 96% | 100% | 100% | 94% | 100% | 100% | 97% | 94% | 94% | 100% | 97% | 97% | 100% | 94% |
| pos occupied[6] | 3 | 3 | 4 | 2 | 4 | 2 | 1 | 1 | 3 | 1 | 1 | 2 | 2 | 3 | 1 | 2 | 2 | 1 | 2 |

| | Framework I | | | | | | | | | | | CDR I | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |
| A | | | | | 30 | | | | | | | 2 | | | | 6 | | | |
| B | | | | | | | | | | | | | | | | | | | |
| C | | | 35 | | | | | | | | | | | | | | | | |
| D | | | | | | | | | | | | 1 | | | | 5 | | 1 | |
| E | | | | 3 | | | | | | | | 1 | | | | | | | |
| F | | | | | | | | 2 | | 39 | | | | | 2 | 2 | | | |
| G | | | | | 1 | | 40 | | | | 1 | 14 | | | | 1 | | | |
| H | | | | | | | | | | | | | | | 3 | 1 | | 34 | |
| I | 1 | | | | | | | | 1 | | 1 | | | | | | 9 | | |
| K | | | | 28 | | | | | | | | | | | | | | | |
| L | | | | | | | | | | 1 | | 1 | | | | | 5 | | |
| M | | | | | | | | | | | | | | | | | 23 | | |
| N | | | | | | | | 1 | | | 1 | 3 | | | | | 1 | 3 | |
| P | | | | | | | | | | | | | | | | 1 | | | |
| Q | | | | 2 | | | | | | | | 1 | | | | 1 | | 1 | |
| R | | | | 2 | | | | | 2 | | | | | | 1 | | | | |
| S | | 35 | | | | 40 | | | 5 | | 2 | 15 | | | 2 | 1 | | | |
| T | | | | | 3 | | | | 32 | | 34 | | | | | 1 | | | |
| V | 34 | | | | 1 | | | 1 | | | 1 | 1 | | | | 2 | 2 | | |
| W | | | | | | | | | | | | | | | | | | | 40 |
| X | | | | | | | | | | | | | | | | | | | |
| Y | | | | | | | | 36 | | | | 1 | | | 32 | 19 | | 1 | |
| Z | | | | | | | | | | | | | | | | | | | |
| — | | | | | | | | | | | | | 40 | 40 | | | | | |
| unknown (?) | | | | | | | | | | | | | | | | | | | |
| not sequenced | 5 | 5 | 5 | 5 | 5 | | | | | | | | | | | | | | |
| sum of seq[2] | 35 | 35 | 35 | 35 | 35 | 40 | 40 | 40 | 40 | 40 | 40 | 40 | 40 | 40 | 40 | 40 | 40 | 40 | 40 |
| oomcaa[3] | 34 | 35 | 35 | 28 | 30 | 40 | 40 | 36 | 32 | 39 | 34 | 15 | 40 | 40 | 32 | 19 | 23 | 34 | 40 |
| mcaa[4] | V | S | C | K | A | S | G | Y | T | F | T | S | — | — | Y | Y | M | H | W |
| rel. oomcaa[5] | 97% | 100% | 100% | 80% | 86% | 100% | 100% | 90% | 80% | 98% | 85% | 38% | 100% | 100% | 80% | 48% | 58% | 85% | 100% |
| pos occupied[6] | 2 | 1 | 1 | 4 | 4 | 1 | 1 | 4 | 4 | 2 | 6 | 10 | 1 | 1 | 5 | 11 | 5 | 5 | 1 |

TABLE 6B-continued

| Analysis of V heavy chain subgroup 1B | | | | | | | | | | | | | | | | | | | |
|---|---|---|---|---|---|---|---|---|---|---|---|---|---|---|---|---|---|---|---|
| | Framework II | | | | | | | | | | | | | | CDR II | | | | |
| amino acid[1] | 37 | 38 | 39 | 40 | 41 | 42 | 43 | 44 | 45 | 46 | 47 | 48 | 49 | 50 | 51 | 52 | A | B | C |
| A | | | | 39 | | | | 1 | | | | | 1 | | | | 7 | | |
| B | | | | | | | | | | | | | | | | | | | |
| C | | | | | | | | | | | | | | | | | | | |
| D | | 1 | | | | | | | | | | | | | | 1 | | | |
| E | | | | | | 1 | | | | 39 | | | | | | | | | |
| F | | | | | | | | | 2 | | | | | | 1 | | | | |
| G | | 1 | | | | 39 | | 28 | | | | | 39 | 1 | | | 1 | | |
| H | | | | | | | | | | | | | | | | | | | |
| I | | | | | | | | | | | | 3 | | | 34 | | | | |
| K | | | | | | | 1 | | | | | | | | | | | | |
| L | 2 | | | | 1 | | | | 37 | | | | | | 1 | | | | |
| M | | | | | | | | | | | | 37 | | 2 | 4 | | | | |
| N | | | | | | | | | | | | | | | | 35 | | | |
| P | | | | 1 | 34 | | | | 1 | | | | | | | 31 | | | |
| Q | | 1 | 39 | | | | 39 | | | 1 | | | | | | | | | |
| R | | 37 | 1 | | | | | 10 | | | | | | 4 | | | | | |
| S | | | | | 1 | | | 1 | | | | | | | | 2 | | | |
| T | | | | | 4 | | | | | | | | | | | 1 | | | |
| V | 38 | | | | | | | | | | | | | | | 1 | 1 | | |
| W | | | | | | | | | | | 40 | | | 33 | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | 40 | 40 | | |
| unknown (?) | | | | | | | | | | | | | | | | | | | |
| not sequenced | | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 | 40 |
| oomcaa[3] | 38 | 37 | 39 | 39 | 34 | 39 | 39 | 28 | 37 | 39 | 40 | 37 | 39 | 33 | 34 | 35 | 31 | 40 | 40 |
| mcaa[4] | V | R | Q | A | P | G | Q | G | L | E | W | M | G | W | I | N | P | — | — |
| rel. oomcaa[5] | 95% | 93% | 98% | 98% | 85% | 98% | 98% | 70% | 93% | 98% | 100% | 93% | 98% | 83% | 85% | 88% | 78% | 100% | 100% |
| pos occupied[6] | 2 | 4 | 2 | 2 | 4 | 2 | 2 | 4 | 3 | 2 | 1 | 2 | 2 | 4 | 4 | 5 | 4 | 1 | 1 |
| | CDR II | | | | | | | | | | | | | | Framework III | | | | |
| amino acid[1] | 53 | 54 | 55 | 56 | 57 | 58 | 59 | 60 | 61 | 62 | 63 | 64 | 65 | 66 | 67 | 68 | 69 | 70 | 71 |
| A | 1 | | | 1 | 2 | | | 27 | 2 | | | | 1 | | 1 | | | | 2 |
| B | | | | | | | | | | | | | | | | | | | |
| C | | | | | | | | | | | | | | | | | | | |
| D | | 1 | | 1 | | | | | | | | | 4 | | | | | | |
| E | 1 | 1 | | 2 | | 2 | | | 1 | | | | 1 | | | | | | 1 |
| F | 1 | | | | | | 4 | | | | 39 | | | | | | 3 | | |
| G | 9 | 1 | 39 | 15 | | 6 | | 1 | | | | | 34 | | | | | | |
| H | 2 | | | | | 1 | 1 | | | | | | | | | | | | |
| I | | | | | 1 | 1 | | | | | | | | | 1 | 1 | 13 | | |
| K | | 1 | | 2 | 2 | 8 | | | | 36 | | 1 | | | | | | | 1 |
| L | | | | | | | | | 1 | | 1 | | | | | | 1 | | |
| M | | | | | | | | | | | | | | | | | 23 | | |
| N | 20 | 12 | 1 | 17 | | 18 | | | | 1 | | | | | | | | | |
| P | | | | | | | | | | | | | | | | | | | |
| Q | | | | | | | | | 36 | | | 37 | | | | | | | |
| R | 3 | 1 | | | | 2 | | | | 1 | | 2 | | 37 | | | | | 34 |
| S | 1 | 20 | | 1 | | | 2 | 11 | | 1 | | | | | | | | | 1 |
| T | | 3 | | | 35 | 2 | | 1 | | 1 | | | | | | 39 | | 40 | 1 |
| V | | | | 1 | | | | | | | | | | | 38 | | | | |
| W | | | | | | | | | | | | | | 3 | | | | | |
| X | | | | | | | | | | | | | | | | | | | |
| Y | 2 | | | | | | 33 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 | 40 |
| oomcaa[3] | 20 | 20 | 39 | 17 | 35 | 18 | 33 | 27 | 36 | 36 | 39 | 37 | 34 | 37 | 38 | 39 | 23 | 40 | 34 |
| mcaa[4] | N | S | G | N | T | N | Y | A | Q | K | F | Q | G | R | V | T | M | T | R |
| rel. oomcaa[5] | 50% | 50% | 98% | 43% | 88% | 45% | 83% | 68% | 90% | 90% | 98% | 93% | 85% | 93% | 95% | 98% | 58% | 100% | 85% |
| pos occupied[6] | 9 | 8 | 2 | 8 | 4 | 8 | 4 | 4 | 4 | 5 | 2 | 3 | 4 | 2 | 3 | 2 | 4 | 1 | 6 |

TABLE 6B-continued

Analysis of V heavy chain subgroup 1B

| amino acid[1] | Framework III | | | | | | | | | | | | | | | | | | |
|---|---|---|---|---|---|---|---|---|---|---|---|---|---|---|---|---|---|---|---|
| | 72 | 73 | 74 | 75 | 76 | 77 | 78 | 79 | 80 | 81 | 82 | A | B | C | 83 | 84 | 85 | 86 | 87 |
| A | | | | 12 | | | 35 | | | | | | | | | 1 | 2 | | |
| B | | | | | | | | | | | | | | | | | | | |
| C | | | | | | | | | | | | | | | | | | | |
| D | 35 | | | | 1 | | | | | 4 | | | | | | | 19 | 40 | |
| E | | | | | | | | | | 35 | | | | | | | 19 | | |
| F | | | | | | | 1 | | | | | | | | | 2 | | | |
| G | | | | | | | | | | 1 | | 1 | 2 | | | | | | |
| H | 1 | | | | | | | | | | | | | | | | | | |
| I | | | | 22 | | 1 | | | | | | | | | | | | | |
| K | | | | | | | | | | | | | | | 1 | | | | |
| L | | | | | | | | | 2 | | 39 | | | 39 | | | | | |
| M | | 1 | | 1 | | | | | 37 | | 1 | | | | | | | | |
| N | 4 | | | | 7 | | | | | | | 1 | 2 | | | | | | |
| P | | | 3 | | | | | | | | | | | | | 1 | | | |
| Q | | | | | | | | | | | | | | | | | | | |
| R | | 1 | | | 4 | | | | | | | 2 | 16 | | 37 | | | | |
| S | | | 37 | | 27 | | | 1 | | | | 35 | 20 | | 1 | 36 | | | |
| T | | 38 | | 5 | 1 | 39 | | | | | | 1 | | | 1 | | | | 40 |
| V | | | | | | | 4 | | 1 | | | | | 1 | | | | | |
| W | | | | | | | | | | | | | | | | | | | |
| X | | | | | | | | | | | | | | | | | | | |
| Y | | | | | | | | 39 | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 | 40 |
| oomcaa[3] | 35 | 38 | 37 | 22 | 27 | 39 | 35 | 39 | 37 | 35 | 39 | 35 | 20 | 39 | 37 | 36 | 19 | 40 | 40 |
| mcaa[4] | D | T | S | I | S | T | A | Y | M | E | L | S | S | L | R | S | D | D | T |
| rel. oomcaa[5] | 88% | 95% | 93% | 55% | 68% | 98% | 88% | 98% | 93% | 88% | 98% | 88% | 50% | 98% | 93% | 90% | 48% | 100% | 100% |
| pos occupied[6] | 3 | 3 | 2 | 4 | 5 | 2 | 3 | 2 | 3 | 3 | 2 | 5 | 4 | 2 | 4 | 4 | 3 | 1 | 1 |

| amino acid[1] | Framework III | | | | | CDR III | | | | | | | | | | | | | |
|---|---|---|---|---|---|---|---|---|---|---|---|---|---|---|---|---|---|---|---|
| | 88 | 89 | 90 | 91 | 92 | 93 | 94 | 95 | 96 | 97 | 98 | 99 | 100 | A | B | C | D | E | F |
| A | 40 | | | | | 37 | 1 | 6 | | 1 | 1 | | 2 | 3 | 1 | 3 | | 1 | |
| B | | | | | | | | | | | | | | | | | | | |
| C | | | | | 37 | | 1 | | | | 3 | | | | 2 | 1 | | | |
| D | | 1 | | | | | | 7 | | 5 | 2 | 3 | 1 | 5 | 4 | | 1 | | 2 |
| E | | | | | | | | 2 | | 1 | | | 1 | 1 | | 2 | | 1 | |
| F | | | | 2 | 1 | | | | 1 | 1 | 3 | | | 2 | 1 | 1 | 1 | 1 | |
| G | | | | | | | 1 | 7 | 7 | 5 | 5 | 9 | 4 | 7 | 1 | 3 | | 2 | 2 |
| H | | | | | | | | 1 | | | | 2 | | | 1 | 1 | | | |
| I | | 1 | | | | | 1 | | 1 | 1 | 3 | 1 | 1 | 1 | 1 | 1 | 1 | | |
| K | | | | | | | 1 | | | 1 | | | | 1 | 1 | | 1 | | 1 |
| L | | 2 | | | 1 | | | 2 | 4 | 4 | 4 | 3 | | | 1 | 2 | 1 | 1 | 2 |
| M | | 2 | | | | | | | 2 | | 1 | 1 | | | | | | | |
| N | | | | | | | | | | 1 | | | 1 | | 1 | 1 | 1 | | |
| P | | | | 1 | | | | | 6 | 4 | | | | 1 | 1 | | 3 | 2 | |
| Q | | | | | | | | | | 1 | | | | | | | 1 | 2 | 1 |
| R | | | | | | 1 | 31 | | 5 | 1 | 1 | 3 | | | | | 1 | | 1 |
| S | | | 1 | 1 | | | 1 | 3 | 3 | 1 | 4 | 3 | 6 | 3 | 2 | 2 | 1 | | 1 |
| T | | | | | | | 2 | 1 | 1 | 2 | 2 | 1 | 5 | 1 | 1 | 1 | | 1 | |
| V | | 33 | | | | 1 | | 7 | 1 | 1 | | 1 | 3 | 1 | 2 | | 1 | | |
| W | | | | | | | | 1 | | 1 | | 2 | 2 | | 1 | 1 | | | |
| X | | | | | | | | | | | | | | | | | | | |
| Y | | | 38 | 35 | | | | | 5 | 5 | 4 | 2 | 3 | | 4 | 3 | 3 | 2 | 1 |
| Z | | | | | | | | | | | | | | | | | | | |
| — | | | | | | | | | 1 | 1 | 4 | 6 | 8 | 10 | 11 | 14 | 20 | 23 | 25 |
| unknown (?) | | | | | | | | | | | | | | | | | | | |
| not sequenced | | 1 | 1 | 1 | 1 | 1 | 1 | 3 | 3 | 3 | 3 | 3 | 4 | 4 | 4 | 4 | 4 | 4 | |
| sum of seq[2] | 40 | 39 | 39 | 39 | 39 | 39 | 39 | 37 | 37 | 37 | 37 | 37 | 37 | 36 | 36 | 36 | 36 | 36 | 36 |
| oomcaa[3] | 40 | 33 | 38 | 35 | 37 | 37 | 31 | 7 | 7 | 5 | 5 | 9 | 8 | 10 | 11 | 14 | 20 | 23 | 25 |
| mcaa[4] | A | V | Y | Y | C | A | R | D | G | D | G | G | — | — | — | — | — | — | — |
| rel. oomcaa[5] | 100% | 85% | 97% | 90% | 95% | 95% | 79% | 19% | 19% | 14% | 14% | 24% | 22% | 28% | 31% | 39% | 56% | 64% | 69% |
| pos occupied[6] | 1 | 5 | 2 | 4 | 3 | 3 | 8 | 10 | 12 | 18 | 13 | 13 | 12 | 12 | 17 | 14 | 13 | 10 | 9 |

TABLE 6B-continued

Analysis of V heavy chain subgroup 1B

| | CDR III | | | | | Framework IV | | | | | | | | | | | | | |
|---|---|---|---|---|---|---|---|---|---|---|---|---|---|---|---|---|---|---|---|
| amino acid[1] | G | H | I | J | K | 101 | 102 | 103 | 104 | 105 | 106 | 107 | 108 | 109 | 110 | 111 | 112 | 113 | sum |
| A | | | | 5 | | | | | | | | | | | | | | | 340 |
| B | | | | | | | | | | | | | | | | | | | |
| C | | | | | | | | | | | | | | | | | | | 79 |
| D | 2 | 1 | 2 | | | 27 | 2 | | | | | | | | | | | | 179 |
| E | 1 | | | | | | | | | 1 | | | | | | | | | 159 |
| F | | | | 2 | 15 | | 1 | | | | | | | | | | | | 130 |
| G | 1 | | 1 | 3 | | 1 | | | 27 | | 26 | | | | | 1 | | | 450 |
| H | | | | | | | 1 | | | | | | | | | | | | 51 |
| I | | | | | 1 | | 7 | | | | | | | | 3 | | | | 113 |
| K | | | 1 | | | | | | | 2 | | | | | | | | | 194 |
| L | | 1 | | | 2 | | | | | | | | 12 | | | 1 | | | 204 |
| M | 1 | | | | 4 | | | | | | | | 2 | | | | | | 144 |
| N | 3 | | 1 | | | 1 | 1 | | | | | | | | | | | | 138 |
| P | | | 1 | | | | 1 | | | 1 | | | | | | | | | 128 |
| Q | | | | | | | | | | 23 | | | | | | | | | 253 |
| R | | | | 1 | | | | | | | | | 1 | | | | | | 247 |
| S | | | | | | | 3 | | | | | | | | 1 | | 18 | 18 | 432 |
| T | | 1 | | 1 | | | | | | | | 21 | 6 | | 16 | | 1 | | 390 |
| V | 1 | 2 | 1 | | | 1 | 6 | | | | | | | 21 | | 18 | | | 342 |
| W | | 1 | | 4 | | | | 29 | | | | | | | | | | | 158 |
| X | | | | | | | | | | | | | | | | | | | |
| Y | 2 | 5 | 6 | 2 | | | 11 | | | | | | | | | | | | 294 |
| Z | | | | | | | | | | | | | | | | | | | |
| — | 25 | 25 | 23 | 18 | 11 | 6 | 3 | | | | | | | | | | | | 394 |
| unknown (?) | | | | | 3 | | | | | | | | | | | | | | 3 |
| not sequenced | 4 | 4 | 4 | 4 | 4 | 4 | 4 | 11 | 13 | 13 | 14 | 19 | 19 | 19 | 20 | 20 | 21 | 22 | 458 |
| sum of seq[2] | 36 | 36 | 36 | 36 | 36 | 36 | 36 | 29 | 27 | 27 | 26 | 21 | 21 | 21 | 20 | 20 | 19 | 18 | |
| oomcaa[3] | 25 | 25 | 23 | 18 | 15 | 27 | 11 | 29 | 27 | 23 | 26 | 21 | 12 | 21 | 16 | 18 | 18 | 18 | |
| mcaa[4] | — | — | — | — | F | D | Y | W | G | Q | G | T | L | V | T | V | S | S | |
| rel. oomcaa[5] | 69% | 69% | 64% | 50% | 42% | 75% | 31% | 100% | 100% | 85% | 100% | 100% | 57% | 100% | 80% | 90% | 95% | 100% | |
| pos occupied[6] | 8 | 7 | 8 | 8 | 5 | 5 | 10 | 1 | 1 | 4 | 1 | 1 | 4 | 1 | 3 | 3 | 2 | 1 | |

TABLE 6C

Analysis of V heavy chain subgroup 2

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | | | | | | 3 | | | | | | | | | |
| B | | | | | | | | | | | | | | | | | | | |
| C | | | | | | | | | | | | | | | | | | | |
| D | | | | | | | | | | | | | | | | | | | |
| E | 1 | | | | | 6 | | | | | | | | | | 2 | | | |
| F | | | | | | | | | | | | | | | | | | | |
| G | | | | | | | | 6 | | | | | | | | | | | |
| H | | | | | | | | | | | | | | | | | | | |
| I | | 1 | | | | | | | | | | | | | | | | | |
| K | | | | | 3 | | | | | | | | 6 | | 1 | | | | |
| L | | | | 6 | | | | | | | 6 | | | | | | | 6 | |
| M | | | | | | | | | | | | | | | | | | | |
| N | | | | | | | 1 | | | | | | | | | | | | |
| P | | | | | | | 1 | | 6 | | | | | 6 | | | 1 | | |
| Q | 2 | | | | | | | | | | | | | | | 4 | | | |
| R | | | | | 2 | | | | | | | | | | | | | | |
| S | | | | | | | 4 | | | | | | | | | | | | |
| T | | | 6 | | 1 | | | | | 2 | | | | | 5 | | 5 | | 6 |
| V | | 5 | | | | | | | | 1 | | 6 | | | | | | | |
| W | | | | | | | | | | | | | | | | | | | |
| X | | | | | | | | | | | | | | | | | | | |
| Y | | | | | | | | | | | | | | | | | | | |
| Z | 3 | | | | | | | | | | | | | | | | | | |
| — | | | | | | | | | | | | | | | | | | | |
| unknown (?) | | | | | | | | | | | | | | | | | | | |
| not sequenced | 1 | 1 | 1 | 1 | 1 | 1 | 1 | 1 | 1 | 1 | 1 | 1 | 1 | 1 | 1 | 1 | 1 | 1 | 1 |
| sum of seq[2] | 6 | 6 | 6 | 6 | 6 | 6 | 6 | 6 | 6 | 6 | 6 | 6 | 6 | 6 | 6 | 6 | 6 | 6 | 6 |

TABLE 6C-continued

Analysis of V heavy chain subgroup 2

| | | | | | | | | | | | | | | | | | | | |
|---|---|---|---|---|---|---|---|---|---|---|---|---|---|---|---|---|---|---|---|
| oomcaa[3] | 3 | 5 | 6 | 6 | 3 | 6 | 4 | 6 | 6 | 3 | 6 | 6 | 6 | 6 | 5 | 4 | 5 | 6 | 6 |
| mcaa[4] | Z | V | T | L | K | E | S | G | P | A | L | V | K | P | T | Q | T | L | T |
| rel. oomcaa[5] | 50% | 83% | 100% | 100% | 50% | 100% | 67% | 100% | 100% | 50% | 100% | 100% | 100% | 100% | 83% | 67% | 83% | 100% | 100% |
| pos occupied[6] | 3 | 2 | 1 | 1 | 3 | 1 | 3 | 1 | 1 | 3 | 1 | 1 | 1 | 1 | 2 | 2 | 2 | 1 | 1 |

| | Framework I | | | | | | | | | | | CDR I | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |
| A | | | | | | | | | 1 | | | | 1 | | | 1 | | | |
| B | | | | | | | | | | | | | | | | | | | |
| C | | | 7 | | | | | | | | | | | | | 2 | | | |
| D | | | | | | | | | | | | | 1 | | | | | | |
| E | | | | | | | | | | | | | | | | | | | |
| F | | | | | 3 | | | 6 | 1 | | | | | | | | | | |
| G | | | | | | | 7 | | | | | | | 4 | | 3 | | 3 | |
| H | | | | | | | | | | | | | | | | | | | |
| I | | | | | | | | | | | | | | 1 | | | | | |
| K | | | | | | | | | | | | | | | | | | | |
| L | 6 | | | | 2 | | | 1 | | 6 | | | | | | | | | |
| M | | | | | | | | | | | | | | | 5 | | | | |
| N | | | | | | | | | | | | 2 | | | | | | | |
| P | | | | | | | | | | | | | | | | | | | |
| Q | | | | | | | | | | | | | | | | | | | |
| R | | | | | | | | | | | | | | 2 | | 1 | | | |
| S | | | | 1 | | 6 | | | 6 | | 6 | 2 | 4 | | | | | 4 | |
| T | | 6 | | 6 | | | | | | | 1 | 3 | 1 | | | | | | |
| V | | | | | 2 | | | | | | | | | | 2 | | 7 | | |
| W | | | | | | | | | | | | | | | | | | | 7 |
| X | | | | | | | | | | | | | | | | | | | |
| Y | | | | | | 1 | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | 1 | 1 | | | | | | | | | | | | | | | | | |
| sum of seq[2] | 6 | 6 | 7 | 7 | 7 | 7 | 7 | 7 | 7 | 7 | 7 | 7 | 7 | 7 | 7 | 7 | 7 | 7 | 7 |
| oomcaa[3] | 6 | 6 | 7 | 6 | 3 | 6 | 7 | 6 | 6 | 6 | 6 | 3 | 4 | 4 | 5 | 3 | 7 | 4 | 7 |
| mcaa[4] | L | T | C | T | F | S | G | F | S | L | S | T | S | G | M | G | V | S | W |
| rel. oomcaa[5] | 100% | 100% | 100% | 86% | 43% | 86% | 100% | 86% | 86% | 86% | 86% | 43% | 57% | 57% | 71% | 43% | 100% | 57% | 100% |
| pos | 1 | 1 | 1 | 2 | 3 | 2 | 1 | 2 | 2 | 2 | 2 | 3 | 4 | 3 | 2 | 4 | 1 | 2 | 1 |
| occupied[6] | | | | | | | | | | | | | | | | | | | |

| | Framework II | | | | | | | | | | | | | | CDR II | | | | |
|---|---|---|---|---|---|---|---|---|---|---|---|---|---|---|---|---|---|---|---|
| amino acid[1] | 37 | 38 | 39 | 40 | 41 | 42 | 43 | 44 | 45 | 46 | 47 | 48 | 49 | 50 | 51 | 52 | A | B | C |
| A | | | | | | | | 6 | | | | | 7 | | | | | | |
| B | | | | | | | | | | | | | | | | | | | |
| C | | | | | | | | | | | | | | | | | | | |
| D | | | | | | | | | | | | | | | | 2 | | | |
| E | | | | | | | | | | 7 | | | | | | | | | |
| F | | | | | | | | | | | | | | | | 2 | | | |
| G | | | | 1 | | 7 | | 1 | | | | | | | | | | | |
| H | | | | | | | | | | | | | | 2 | | | | | |
| I | 7 | | | | | | | | | | | | | | 6 | | | | |
| K | | | | | | | 6 | | | | | | | | | | | | |
| L | | | | | | | | | 7 | | | 7 | | 2 | 1 | 1 | | | |
| M | | | | | | | | | | | | | | | | | | | |
| N | | | | | | | | | | | | | | | | | | | |
| P | | | | 5 | 7 | | | | | | | | | | | | | | |
| Q | | | 6 | | | | | | | | | | | | | | | | |
| R | | 7 | 1 | | | | 1 | | | | | | | 2 | | | | | |
| S | | | | 1 | | | | | | | | | | | | | | | |
| T | | | | | | | | | | | | | | | | | | | |
| V | | | | | | | | | | | | | | | | | | | |
| W | | | | | | | | | | | 7 | | | 1 | | | | | |
| X | | | | | | | | | | | | | | | | 1 | | | |
| Y | | | | | | | | | | | | | | | | 1 | 1 | | |
| Z | | | | | | | | | | | | | | | | | | | |
| — | | | | | | | | | | | | | | | | | 6 | 7 | 7 |
| unknown (?) | | | | | | | | | | | | | | | | | | | |
| not sequenced | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 |

TABLE 6C-continued

Analysis of V heavy chain subgroup 2

| | | | | | | | | | | | | | | | | | | | |
|---|---|---|---|---|---|---|---|---|---|---|---|---|---|---|---|---|---|---|---|
| oomcaa[3] | 7 | 7 | 6 | 5 | 7 | 7 | 6 | 6 | 7 | 7 | 7 | 7 | 7 | 2 | 6 | 2 | 6 | 7 | 7 |
| mcaa[4] | I | R | Q | P | P | G | K | A | L | E | W | L | A | H | I | D | — | — | — |
| rel. oomcaa[5] | 100% | 100% | 86% | 71% | 100% | 100% | 86% | 86% | 100% | 100% | 100% | 100% | 100% | 29% | 86% | 29% | 86% | 100% | 100% |
| pos occupied[6] | 1 | 1 | 2 | 3 | 1 | 1 | 2 | 2 | 1 | 1 | 1 | 1 | 1 | 4 | 2 | 5 | 2 | 1 | 1 |

| | CDR II | | | | | | | | | | | | | Framework III | | | | | |
|---|---|---|---|---|---|---|---|---|---|---|---|---|---|---|---|---|---|---|---|
| amino acid[1] | 53 | 54 | 55 | 56 | 57 | 58 | 59 | 60 | 61 | 62 | 63 | 64 | 65 | 66 | 67 | 68 | 69 | 70 | 71 |
| A | | | | | | | | | | | | | | | | | | | |
| B | | | | | | | | | | | | | | | | | | | |
| C | | | | | | | | | | | | | | | | | | | |
| D | | 3 | 6 | 5 | | | | | | | | | | | | | | | |
| E | | | | 1 | | | | | | | | 1 | | | | | | | |
| F | | | | | 1 | | 1 | | | | | | | | | | | | |
| G | | | | | | | | | | | | | | | | | | | |
| H | | | 1 | | | | 1 | | | | | | | | | | | | |
| I | | | | | | | | | | | | | | | | | 6 | | |
| K | | | | 1 | 6 | | | | | | | 4 | | | | | | | 6 |
| L | | | | | | | | | | | 7 | | | | 7 | | | | |
| M | | | | | | | | | | | | | | | | | | | |
| N | | 3 | | | | | | | | | | | | | | | | | |
| P | | | | | | | | | 2 | | | | | | | | | | |
| Q | | | | | | | | | | | | | | | | | | | |
| R | | | | | | 2 | | | 1 | | | 2 | | 7 | | | | | 1 |
| S | 2 | | | | | 2 | | 6 | | 7 | | | 4 | | | 1 | | 5 | |
| T | | | | | | | | | 4 | | | | 3 | | | 6 | | 2 | |
| V | | | | | | | | | | | | | | | | | 1 | | |
| W | 4 | | | | | | 1 | | | | | | | | | | | | |
| X | 1 | 1 | | | | | | 1 | | | | | | | | | | | |
| Y | | | | | | 3 | 4 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 |
| oomcaa[3] | 4 | 3 | 6 | 5 | 6 | 3 | 4 | 6 | 4 | 7 | 7 | 4 | 4 | 7 | 7 | 6 | 6 | 5 | 6 |
| mcaa[4] | W | D | D | D | K | Y | Y | S | T | S | L | K | S | R | L | T | I | S | K |
| rel. oomcaa[5] | 57% | 43% | 86% | 71% | 86% | 43% | 57% | 86% | 57% | 100% | 100% | 57% | 57% | 100% | 100% | 86% | 86% | 71% | 86% |
| pos occupied[6] | 3 | 3 | 2 | 3 | 2 | 3 | 4 | 2 | 3 | 1 | 1 | 3 | 2 | 1 | 1 | 2 | 2 | 2 | 2 |

| | Framework III | | | | | | | | | | | | | | | | | | |
|---|---|---|---|---|---|---|---|---|---|---|---|---|---|---|---|---|---|---|---|
| amino acid[1] | 72 | 73 | 74 | 75 | 76 | 77 | 78 | 79 | 80 | 81 | 82 | A | B | C | 83 | 84 | 85 | 86 | 87 |
| A | | | | | | | | | | | | | | | | | 1 | | |
| B | | | | | | | | | | | | | | | | | | | |
| C | | | | | | | | | | | | | | | | | | | |
| D | 6 | 1 | | | | | | | | | | | | | 6 | | | 7 | |
| E | | | | | | | | | | | | | | | | | | | |
| F | | | | | | | | | 1 | | | | | | | | | | |
| G | | | | | | | | | | | | | | | | | | | |
| H | | | | | | | | | | | | | | | | | | | |
| I | | | | | | | | | | 2 | | 1 | | | | | | | |
| K | | | | 6 | | | | | | | | | | | | | | | |
| L | | | | | | | | | 6 | | | | | | | | | | |
| M | | | | | | | | | | | 7 | | | 5 | | | | | |
| N | 1 | | | | 5 | | | | | | | | 6 | | 1 | | | | |
| P | | | | | | | | | | | | | | | | | 7 | | |
| Q | | | | | | 7 | | | | | | | | | | | | | |
| R | | | | 1 | | | | | | | | | | | | | | | |
| S | | | 7 | | 2 | | | | | | | | | | | | | | |
| T | | 6 | | | | | | | | 5 | | 5 | | | | | | | |
| V | | | | | | | 7 | 7 | | | | | | 1 | | | 6 | | 7 |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | 1 | 1 | 1 | | | | | |
| unknown (?) | | | | | | | | | | | | | | | | | | | |
| not sequenced | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 |
| oomcaa[3] | 6 | 6 | 7 | 6 | 5 | 7 | 7 | 7 | 6 | 5 | 7 | 5 | 6 | 5 | 6 | 7 | 6 | 7 | 7 |

TABLE 6C-continued

Analysis of V heavy chain subgroup 2

| | | | | | | | | | | | | | | | | | | | |
|---|---|---|---|---|---|---|---|---|---|---|---|---|---|---|---|---|---|---|---|
| mcaa[4] | D | T | S | K | N | Q | V | V | L | T | M | T | N | M | D | P | V | D | T |
| rel. oomcaa[5] | 86% | 86% | 100% | 86% | 71% | 100% | 100% | 100% | 86% | 71% | 100% | 71% | 86% | 71% | 86% | 100% | 86% | 100% | 100% |
| pos. occupied[6] | 2 | 2 | 1 | 2 | 2 | 1 | 1 | 1 | 2 | 2 | 1 | 3 | 2 | 3 | 2 | 1 | 2 | 1 | 1 |

| | Framework III | | | | | CDR III | | | | | | | | | | | | | |
|---|---|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 5 | | | | | 5 | | | | | | | 1 | 2 | 1 | | | | |
| B | | | | | | | | | | | | | | | | | | | |
| C | | | | | 7 | | | | | | | | | | | | | | |
| D | | | | | | | | | | | | | | | | | | | |
| E | | | | | | | | | | | | | 2 | | | 1 | | | |
| F | | | | | | | | | | | | | | | | | | | |
| G | 2 | | | | | | | | | | 1 | 1 | | 1 | 2 | 1 | 1 | 1 | 1 |
| H | | | | | | | 1 | | 1 | | | | | | | | | | |
| I | | | | | | | | 3 | | | 2 | | | | | | | | |
| K | | | | | | | | | | | | 1 | | | | | | | |
| L | | | | | | | | | | | | | 1 | | 1 | | | | |
| M | | | | | | | | | | | | | 1 | | | | | | |
| N | | | | | | | | | 1 | 2 | | | | | | | | | |
| P | | | | | | | | | 1 | 1 | | 1 | | 1 | | | | | |
| Q | | | | | | | | 1 | | | | | | | | | | | |
| R | | | | | | | 6 | 1 | | | 1 | | | 1 | | | | | |
| S | | | | | | | | | 1 | | 1 | 1 | | | | | | | |
| T | | 7 | | | | | | | 1 | | | 1 | | 1 | | | | | |
| V | | | | | | 2 | | 1 | 1 | 1 | | 1 | 1 | | | 1 | | | |
| W | | | | | | | | | | | 1 | | | | | | | | |
| X | | | | | | | | | | | | | | | | | | | |
| Y | | | 7 | 7 | | | | | | 2 | | | | | | 1 | 2 | 1 | 1 |
| Z | | | | | | | | | | | | | | | | | | | |
| — | | | | | | | | | | | | | | | 2 | 2 | 3 | 4 | 4 |
| unknown (?) | | | | | | | | | | | | | | | | | | | |
| not sequenced | | | | | | | | 1 | 1 | 1 | 1 | 1 | 1 | 1 | 1 | 1 | 1 | 1 | 1 |
| sum of seq[2] | 7 | 7 | 7 | 7 | 7 | 7 | 7 | 6 | 6 | 6 | 6 | 6 | 6 | 6 | 6 | 6 | 6 | 6 | 6 |
| oomcaa[3] | 5 | 7 | 7 | 7 | 7 | 5 | 6 | 3 | 1 | 2 | 2 | 1 | 2 | 2 | 2 | 2 | 3 | 4 | 4 |
| mcaa[4] | A | T | Y | Y | C | A | R | I | H | N | I | G | E | A | — | — | — | — | — |
| rel. oomcaa[5] | 71% | 100% | 100% | 100% | 100% | 71% | 86% | 50% | 17% | 33% | 33% | 17% | 33% | 33% | 33% | 33% | 50% | 67% | 67% |
| pos occupied[6] | 2 | 1 | 1 | 1 | 1 | 2 | 2 | 4 | 6 | 4 | 5 | 6 | 5 | 5 | 4 | 5 | 3 | 3 | 3 |

| | CDR III | | | | | Framework IV | | | | | | | | | | | | | |
|---|---|---|---|---|---|---|---|---|---|---|---|---|---|---|---|---|---|---|---|
| amino acid[1] | G | H | I | J | K | 101 | 102 | 103 | 104 | 105 | 106 | 107 | 108 | 109 | 110 | 111 | 112 | 113 | sum |
| A | | | | | | | | | | | | | | | 1 | | | | 35 |
| B | | | | | | | | | | | | | | | | | | | |
| C | | | | | | | | | | | | | | | | | | | 16 |
| D | | | | | | 6 | | | | | | | | | | | | | 43 |
| E | | | | | | | | | | | | | | | | | | | 21 |
| F | | | | | 3 | | | | | | | | | | | | | | 18 |
| G | | | | | | | | | 6 | | 6 | | | | | | | | 55 |
| H | | | | | | | | | | | | | | | | | | | 6 |
| I | | | | | | | | | | | | | | | | | | | 29 |
| K | | | | | | | | | | 1 | | | 1 | | | | | | 42 |
| L | | | | | 1 | | 1 | | | | | | 3 | | | | | | 78 |
| M | | | | | 2 | | | | | | | | | | | | | | 20 |
| N | | | 1 | | | | | | | | | | | | | | | | 23 |
| P | | | | | | | 1 | | | | | | 1 | | | | | | 41 |
| Q | | | | | | | | | | 3 | | | | | | | | | 23 |
| R | | | | | | | | | | 2 | | | | | | | | | 41 |
| S | | | | | | | | | | | | | | | | | 6 | 3 | 82 |
| T | | | | | | | | | | | | 6 | 1 | | 5 | | | | 102 |
| V | | | | | | | 3 | | | | | | | 6 | | 6 | | | 68 |
| W | 1 | | | 1 | | | | 6 | | | | | | | | | | | 29 |
| X | | | | | | | | | | | | | | | | | | | 4 |
| Y | 1 | | | 2 | | | 1 | | | | | | | | | | | | 35 |
| Z | | | | | | | | | | | | | | | | | | | 3 |
| — | 4 | 6 | 5 | 3 | | | | | | | | | | | | | | | 56 |
| unknown (?) | | | | | | | | | | | | | | | | | | | |
| not sequenced | 1 | 1 | 1 | 1 | 1 | 1 | 1 | 1 | 1 | 1 | 1 | 1 | 1 | 1 | 1 | 1 | 1 | 4 | 54 |
| sum of seq[2] | 6 | 6 | 6 | 6 | 6 | 6 | 6 | 6 | 6 | 6 | 6 | 6 | 6 | 6 | 6 | 6 | 6 | 3 | |
| oomcaa[3] | 4 | 6 | 5 | 3 | 3 | 6 | 3 | 6 | 6 | 3 | 6 | 6 | 3 | 6 | 5 | 6 | 6 | 3 | |
| mcaa[4] | — | — | — | — | F | D | V | W | G | Q | G | T | L | V | T | V | S | S | |

TABLE 6C-continued

| Analysis of V heavy chain subgroup 2 | | | | | | | | | | | | | | | | | | |
|---|---|---|---|---|---|---|---|---|---|---|---|---|---|---|---|---|---|---|
| rel. oomcaa[5] | 67% | 100% | 83% | 50% | 50% | 100% | 50% | 100% | 100% | 50% | 100% | 100% | 50% | 100% | 83% | 100% | 100% | 100% |
| pos occupied[6] | 3 | 1 | 2 | 3 | 3 | 1 | 4 | 1 | 1 | 3 | 1 | 1 | 4 | 1 | 2 | 1 | 1 | 1 |

TABLE 6D

| Analysis of V heavy chain subgroup 3 | | | | | | | | | | | | | | | |
|---|---|---|---|---|---|---|---|---|---|---|---|---|---|---|---|
| | Framework I | | | | | | | | | | | | | | |
| amino acid[1] | 1 | 2 | 3 | 4 | 5 | 6 | 7 | 8 | 9 | 10 | 11 | 12 | 13 | 14 | 15 |
| A | | | | | 1 | | 1 | | | 12 | | 1 | | 3 | 1 |
| B | | | 1 | | | 1 | | | | | | | 1 | | |
| C | | | | | | | | | | | | | | | |
| D | 1 | | | | | 1 | | | | 16 | | | | | |
| E | 110 | | 9 | | 15 | 166 | | | 9 | | | | 8 | | 2 |
| F | | | | | | | | | | | 4 | | | | |
| G | | | | | | | | 181 | 193 | 174 | | 1 | | | 202 |
| H | | | 5 | | | | | | | | | | 4 | | |
| I | | | | | | | | | | | | 9 | | | |
| K | | 5 | 3 | | | | | | | | | | 26 | | |
| L | | 1 | 5 | 176 | 43 | | | | | | 140 | | | 1 | |
| M | | 12 | | 1 | | | | | | | | | | | |
| N | | | | | | | | | | 1 | | | | | |
| P | | | | | | | | | | | | | 1 | 194 | |
| Q | 41 | | 138 | 1 | 3 | 12 | | | | | | | 162 | | |
| R | | | 6 | | | | | | | | | | 4 | | |
| S | | | | | | | 178 | | | 2 | | | | 8 | |
| T | | | | | | | 1 | | | | | | | | |
| V | 5 | 147 | | 1 | 118 | | | | | | 62 | 195 | | | |
| W | | | | | | | | | | | | | | | 1 |
| X | | | | | | | | | | | | | | | |
| Y | | | | | | | | | | | | | | | |
| Z | 8 | | | | | | | | | | | | | | |
| — | | | | | | | | | | | | | | | |
| unknown (?) | | | | | | | | | | | | | | | |
| not sequenced | 47 | 47 | 45 | 33 | 32 | 32 | 32 | 31 | 10 | 7 | 6 | 6 | 6 | 6 | 6 |
| sum of seq[2] | 165 | 165 | 167 | 179 | 180 | 180 | 180 | 181 | 202 | 205 | 206 | 206 | 206 | 206 | 206 |
| oomcaa[3] | 110 | 147 | 138 | 176 | 118 | 166 | 178 | 181 | 193 | 174 | 140 | 195 | 162 | 194 | 202 |
| mcaa[4] | E | V | Q | L | V | E | S | G | G | G | L | V | Q | P | G |
| rel. oomcaa[5] | 67% | 89% | 83% | 98% | 66% | 92% | 99% | 100% | 96% | 85% | 68% | 95% | 79% | 94% | 89% |
| pos occupied[6] | 5 | 4 | 7 | 4 | 5 | 4 | 3 | 1 | 2 | 5 | 3 | 4 | 7 | 4 | 4 |
| | Framework I | | | | | | | | | | | | | | |
| amino acid[1] | 16 | 17 | 18 | 19 | 20 | 21 | 22 | 23 | 24 | 25 | 26 | 27 | 28 | 29 | 30 |
| A | | | | | | | | | 183 | 192 | | 1 | | | |
| B | | | | | | | | | | | | | | | |
| C | | | | | | 1 | 209 | | | | | | | | |
| D | | | | | | | | | | | | | | | 7 |
| E | 8 | | | | | | | 8 | | | 3 | | 1 | | |
| F | | 1 | 1 | | | 1 | | | | | | 201 | | 201 | |
| G | 134 | | | | | | | | 2 | | 207 | | | | 3 |
| H | | | | | | | | | | | | | | | 1 |
| I | | | | | | | | 2 | | | | 3 | 17 | 1 | |
| K | | | | 15 | | | | | | | | | | | 4 |
| L | | | 205 | | 201 | | | | | | | 6 | | 3 | |
| M | | | 1 | | | | | | | | | | 1 | | |
| N | | | | | | | | | | | | | 10 | | 10 |
| P | | | | | | | | 1 | | | | | 2 | | |
| Q | | | 1 | | | | | | | | | | | | |
| R | 62 | | | 191 | | | | | | | | | | | 11 |
| S | | 206 | | | | 207 | | 4 | 2 | 209 | | | 15 | | 174 |
| T | 4 | 1 | | 2 | | | | 4 | 4 | | | 1 | 163 | | |
| V | | | | | 8 | | | 7 | 9 | | | | 1 | 6 | |
| W | | | | | | | | | | | | | | | |
| X | | | | | | | | | | | | | | | |
| Y | | | | | | | | | | | | | | | |
| Z | | | | | | | | | | | | | | | |
| — | | | | | | | | | | | | | | | |
| unknown (?) | | | | | | | | | | | | | | | |
| not sequenced | 4 | 4 | 4 | 4 | 3 | 3 | 3 | 3 | 3 | 3 | 1 | 1 | 2 | 1 | 2 |

TABLE 6D-continued

Analysis of V heavy chain subgroup 3

| | | | | | | | | | | | | | | | |
|---|---|---|---|---|---|---|---|---|---|---|---|---|---|---|---|
| sum of seq[2] | 208 | 208 | 208 | 208 | 209 | 209 | 209 | 209 | 209 | 209 | 211 | 211 | 210 | 211 | 210 |
| oomcaa[3] | 134 | 206 | 205 | 191 | 201 | 207 | 209 | 183 | 192 | 209 | 207 | 201 | 163 | 201 | 174 |
| mcaa[4] | G | S | L | R | L | S | C | A | A | S | G | F | T | F | S |
| rel. oomcaa[5] | 64% | 99% | 99% | 92% | 96% | 99% | 100% | 88% | 92% | 100% | 98% | 95% | 78% | 95% | 83% |
| pos occupied[6] | 4 | 3 | 4 | 3 | 2 | 3 | 1 | 7 | 5 | 1 | 3 | 4 | 8 | 4 | 7 |

| | CDR I | | | | | | | | Framework II | | | | | | |
|---|---|---|---|---|---|---|---|---|---|---|---|---|---|---|---|
| amino acid[1] | 31 | A | B | 32 | 33 | 34 | 35 | 36 | 37 | 38 | 39 | 40 | 41 | 42 | 43 |
| A | 1 | | | 17 | 80 | | 1 | | | 1 | | 187 | | 1 | |
| B | | | | | | | | | | | | | | | |
| C | | | | | | | | | | | | 1 | | 1 | |
| D | 26 | | | 3 | 7 | | 2 | | | | | | | | |
| E | 1 | | | | 10 | | | | | | | | | 1 | 1 |
| F | | | | 5 | | | | | | | | | | | |
| G | 13 | | | | 31 | | 1 | | | | | 2 | | 209 | |
| H | | | | 4 | | | 88 | | | | | | | | |
| I | 1 | | | 1 | | 15 | | | 12 | | | | | | |
| K | 7 | | | | | | | | | | 1 | | | | 202 |
| L | 3 | | | | | 3 | | | 2 | 3 | 1 | 2 | 1 | | |
| M | | | | | | 193 | | | | | | | | | |
| N | 35 | | | 8 | 3 | | 34 | | | | | | | | |
| P | | | | 1 | | | 1 | | | | | 4 | 191 | | |
| Q | | | | | | | | | | | 209 | | 1 | | 1 |
| R | 7 | | | | | | | | | 207 | | 7 | | | 8 |
| S | 103 | | | 17 | 8 | | 72 | | | | | 3 | 14 | | |
| T | 9 | | | | 15 | | 10 | | | | | 4 | 5 | | |
| V | 2 | | | | 7 | 1 | | | 197 | | | 2 | | | |
| W | | | | | 30 | | | 212 | | | | | | | |
| X | 1 | | | | | | | | | | | | | | |
| Y | 1 | | | 154 | 19 | | 3 | | | | | | | | |
| Z | | | | | | | | | | | | | | | |
| — | | 210 | 210 | | | | | | | | | | | | |
| unknown (?) | | | | | | | | | | | | | | | |
| not sequenced | 2 | | | 2 | 2 | | | | 1 | 1 | 1 | | | | |
| sum of seq[2] | 210 | 210 | 210 | 210 | 210 | 212 | 212 | 212 | 211 | 211 | 211 | 212 | 212 | 212 | 212 |
| oomcaa[3] | 103 | 210 | 210 | 154 | 80 | 193 | 88 | 212 | 197 | 207 | 209 | 187 | 191 | 209 | 202 |
| mcaa[4] | S | — | — | Y | A | M | H | W | V | R | Q | A | P | G | K |
| rel. oomcaa[5] | 49% | 100% | 100% | 73% | 38% | 91% | 42% | 100% | 93% | 98% | 99% | 88% | 90% | 99% | 95% |
| pos occupied[6] | 14 | 1 | 1 | 9 | 10 | 4 | 9 | 1 | 3 | 3 | 3 | 9 | 5 | 4 | 4 |

| | Framework II | | | | | | | CDR II | | | | | | | |
|---|---|---|---|---|---|---|---|---|---|---|---|---|---|---|---|
| amino acid[1] | 44 | 45 | 46 | 47 | 48 | 49 | 50 | 51 | 52 | A | B | C | 53 | 54 | 55 |
| A | 1 | | | | | 77 | 42 | | 1 | 2 | | 14 | | 7 | |
| B | | | 3 | | | | | | | 1 | | | | | |
| C | | | | | | | | | | | | | 1 | | |
| D | | | 1 | | | | | | | 7 | | | 94 | 8 | 3 |
| E | | | 198 | | | | | | 3 | 2 | 1 | | 2 | | 1 |
| F | | | | | | | 7 | 1 | 2 | 1 | | | | 1 | 8 |
| G | 207 | | | | | 33 | 11 | | 10 | 46 | | | 4 | 163 | 85 |
| H | | | | | | | 6 | | | 1 | | | | | |
| I | | | | | 3 | | 3 | 191 | | 1 | | | | | 1 |
| K | | | | | | | | 1 | 37 | 2 | 30 | | 3 | 1 | |
| L | | 211 | | | 5 | | 12 | 1 | | | | | | | |
| M | | | | | | | 1 | 1 | | | | | | | |
| N | | | | | | | 13 | | 7 | 9 | 2 | | 13 | 11 | 1 |
| P | | 1 | | | | | | | | 1 | | | 1 | | |
| Q | | | 7 | | | | 7 | | | 10 | | | | | |
| R | 1 | | | | | | 24 | 1 | 17 | 5 | 1 | | 2 | | 16 |
| S | 3 | | | 1 | | 102 | 11 | 9 | 118 | 43 | | 1 | 74 | 17 | 82 |
| T | | | | | | | 3 | 5 | 4 | 2 | | 13 | 12 | 3 | 3 |
| V | | | 3 | | 204 | | 49 | 2 | | 1 | | 6 | | | |
| W | | | | 210 | | | 1 | | 8 | 6 | | | | | |
| X | | | | | | | | | | | | | 4 | | 3 |
| Y | | | | 1 | | | 22 | | 5 | 58 | | | | | 8 |
| Z | | | | | | | | | | | | | | | |
| — | | | | | | | | | | 14 | 178 | 178 | 2 | 1 | 1 |
| unknown (?) | | | | | | | | | | | | | | | |
| not sequenced | | | | | | | | | | | | | | | |
| sum of seq[2] | 212 | 212 | 212 | 212 | 212 | 212 | 212 | 212 | 212 | 212 | 212 | 212 | 212 | 212 | 212 |
| oomcaa[3] | 207 | 211 | 198 | 210 | 204 | 102 | 49 | 191 | 118 | 58 | 178 | 178 | 94 | 163 | 85 |
| mcaa[4] | G | L | E | W | V | S | V | I | S | Y | — | — | D | G | G |

TABLE 6D-continued

Analysis of V heavy chain subgroup 3

| | | | | | | | | | | | | | | | |
|---|---|---|---|---|---|---|---|---|---|---|---|---|---|---|---|
| rel. oomcaa[5] | 98% | 100% | 93% | 99% | 96% | 48% | 23% | 90% | 56% | 27% | 84% | 84% | 44% | 77% | 40% |
| pos occupied[6] | 4 | 2 | 5 | 3 | 3 | 3 | 15 | 9 | 11 | 19 | 5 | 5 | 12 | 9 | 12 |

| | CDR II | | | | | | | | | | | Framework III | | | |
|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 |
| A | 9 | 1 | 2 | | 174 | 33 | | | | | | | 1 | | |
| B | 1 | 2 | | | | | | | | | | | | | |
| C | | | | | | | | | | | | | | | |
| D | 11 | | 17 | | | 160 | | | | | | | | | |
| E | 8 | 3 | 2 | | | 1 | | | 2 | | | | | | |
| F | 1 | | 3 | 2 | | | | | | | | 207 | | | |
| G | 5 | 1 | 5 | | 4 | 5 | | | | 212 | 1 | | | | |
| H | 1 | | 4 | | | | | | | | | | | | |
| I | 3 | 37 | 2 | | | | | 8 | | | | | 14 | 208 | |
| K | 1 | 61 | | | | | | | 199 | | 8 | | | | |
| L | 1 | 1 | 1 | | 1 | | | | | | | 1 | | 1 | |
| M | 8 | | 2 | | 1 | | | | | | | | | | |
| N | 51 | | 4 | | | 2 | | | 2 | | | | | | |
| P | 1 | 1 | | | 6 | 8 | 18 | | 1 | | | | | | |
| Q | 3 | 2 | | | | | | | 2 | | 2 | | | | |
| R | 5 | 4 | | | 5 | | | | 6 | | 201 | | | | |
| S | 48 | | 11 | | 4 | | 193 | | | | | 2 | 7 | | 211 |
| T | 42 | 97 | 5 | | 7 | | | | | | | | 189 | | 1 |
| V | | 2 | | | 10 | 2 | | 204 | | | | 1 | | 3 | |
| W | | | 2 | | | | | | | | | | | | |
| X | 4 | | 1 | | | 1 | | | | | | | | | |
| Y | 9 | | 151 | 210 | | | 1 | | | | | 1 | 1 | | |
| Z | | | | | | | | | | | | | | | |
| — | | | | | | | | | | | | | | | |
| unknown (?) | | | | | | | | | | | | | | | |
| not sequenced | | | | | | | | | | | | | | | |
| sum of seq[2] | 212 | 212 | 212 | 212 | 212 | 212 | 212 | 212 | 212 | 212 | 212 | 212 | 212 | 212 | 212 |
| oomcaa[3] | 51 | 97 | 151 | 210 | 174 | 160 | 193 | 204 | 199 | 212 | 201 | 207 | 189 | 208 | 211 |
| mcaa[4] | N | T | Y | Y | A | D | S | V | K | G | R | F | T | I | S |
| rel. oomcaa[5] | 24% | 46% | 71% | 99% | 82% | 75% | 91% | 96% | 94% | 100% | 95% | 98% | 89% | 89% | 100% |
| pos occupied[6] | 19 | 12 | 15 | 2 | 9 | 8 | 3 | 2 | 6 | 1 | 4 | 5 | 5 | 3 | 2 |

| | Framework III | | | | | | | | | | | | | | |
|---|---|---|---|---|---|---|---|---|---|---|---|---|---|---|---|
| amino acid[1] | 71 | 72 | 73 | 74 | 75 | 76 | 77 | 78 | 79 | 80 | 81 | 82 | A | B | C |
| A | | | | 57 | | | 1 | 8 | | | | | | 1 | |
| B | | | | | | | | | | | 2 | | | | |
| C | | | | | | | | | | | | | | | |
| D | | 199 | 38 | | 2 | 2 | | | 1 | | | | 10 | | |
| E | | 6 | | | 4 | | | | | | 5 | | | | |
| F | | | | | | | | | 13 | | | | | | |
| G | | | | | | | | | | | | | 1 | 4 | |
| H | | | | | | 1 | | | 1 | | 2 | | 2 | | |
| I | | | 1 | | | | 2 | 2 | | | | 3 | 1 | 1 | |
| K | | | | | 186 | 6 | | | | | | | 3 | | |
| L | | | | | | | | 188 | | 209 | | 3 | 1 | | 212 |
| M | 1 | | | | 2 | | 10 | 3 | | 2 | | 205 | | | |
| N | | 5 | 170 | | 2 | 188 | | | | | 3 | | 181 | 10 | |
| P | | | | | | | 1 | | | | | | | | |
| Q | | | | | 7 | | | | | | 199 | | | | |
| R | 211 | | | | 1 | 1 | | | | | | | 2 | 8 | |
| S | | | | 153 | 8 | 10 | 56 | | 3 | | | 6 | 186 | | |
| T | | | | | | | 142 | | | | 1 | | 4 | 2 | |
| V | | | | 1 | | | | 11 | | 1 | | 1 | | | |
| W | | | | | | | | | | | | | | | |
| X | | 2 | 2 | | | 4 | | | | | | | 1 | | |
| Y | | | | | | | | | 194 | | | | | | |
| Z | | | | | | | | | | | | | | | |
| — | | | | | | | | | | | | | | | |
| unknown (?) | | | | | | | | | | | | | | | |
| not sequenced | | | 1 | 1 | | | | | | | | | | | |
| sum of seq[2] | 212 | 212 | 211 | 211 | 212 | 212 | 212 | 212 | 212 | 212 | 212 | 212 | 212 | 212 | 212 |
| oomcaa[3] | 211 | 199 | 170 | 153 | 186 | 188 | 142 | 188 | 194 | 209 | 199 | 205 | 181 | 186 | 212 |
| mcaa[4] | R | D | N | S | K | N | T | L | Y | L | Q | M | N | S | L |
| rel. oomcaa[5] | 100% | 94% | 81% | 73% | 88% | 89% | 67% | 89% | 92% | 99% | 94% | 97% | 85% | 88% | 100% |
| pos occupied[6] | 2 | 4 | 4 | 3 | 8 | 7 | 6 | 5 | 5 | 3 | 6 | 4 | 11 | 7 | 1 |

TABLE 6D-continued

Analysis of V heavy chain subgroup 3

| | Framework III | | | | | | | | | | CDR III | | | |
|---|---|---|---|---|---|---|---|---|---|---|---|---|---|---|
| amino acid[1] | 83 | 84 | 85 | 86 | 87 | 88 | 89 | 90 | 91 | 92 | 93 | 94 | 95 | 96 |
| A | | 149 | 1 | | 1 | 207 | | | | | 173 | 2 | 15 | 9 |
| B | | | | | | | | | | | | | | |
| C | | | | | | | | | 1 | 210 | | 5 | 2 | |
| D | | 5 | 15 | 209 | | | | | | | | 2 | 54 | 7 |
| E | 1 | | 190 | | | | | | | | | | 11 | 2 |
| F | | | | | | | 1 | | 15 | | | 1 | | 9 |
| G | 1 | 1 | 6 | | | 4 | 1 | | | | 2 | 8 | 34 | 26 |
| H | | 1 | | | | | | | 1 | | | | | 3 |
| I | | 8 | | | | | 2 | | | | | | 4 | 15 |
| K | 30 | | | | | | | | | | | 60 | 4 | 3 |
| L | | | | | | | 18 | | | | | 1 | 6 | 11 |
| M | | | | | 2 | | 1 | | | | | | | 6 |
| N | | 1 | | 1 | | | | | | | | 2 | 20 | 4 |
| P | | 9 | | | | | | | | | 1 | 3 | 4 | 29 |
| Q | | | | 1 | | | | | | | | 5 | 3 | 9 |
| R | 177 | | | | | | | | | | | 103 | 9 | 30 |
| S | | 1 | | | 1 | | | | | | | 3 | 9 | 8 |
| T | 3 | 28 | | | 207 | | 1 | | | | 25 | 15 | 7 | 6 |
| V | | 9 | | | | | 187 | | | | 10 | 1 | 7 | 7 |
| W | | | | | | | | | | 1 | | | 3 | 4 |
| X | | | | 1 | | | | | | | | | | |
| Y | | | | | | | | 211 | 194 | | | | 12 | 9 |
| Z | | | | | | | | | | | | | | |
| — | | | | | | | | | | | | | 1 | 3 |
| unknown (?) | | | | | | | | | | | | | | |
| not sequenced | | | | | 1 | 1 | 1 | 1 | 1 | 1 | 1 | 1 | 7 | 12 |
| sum of seq[2] | 212 | 212 | 212 | 212 | 211 | 211 | 211 | 211 | 211 | 211 | 211 | 211 | 205 | 200 |
| oomcaa[3] | 177 | 149 | 190 | 209 | 207 | 207 | 187 | 211 | 194 | 210 | 173 | 103 | 54 | 30 |
| mcaa[4] | R | A | E | D | T | A | V | Y | Y | C | A | R | D | R |
| rel. oomcaa[5] | 83% | 70% | 90% | 99% | 98% | 98% | 89% | 100% | 92% | 100% | 82% | 49% | 26% | 15% |
| pos occupied[6] | 5 | 10 | 4 | 4 | 4 | 2 | 7 | 1 | 4 | 2 | 5 | 14 | 18 | 20 |

| | CDR III | | | | | | | | | | | | | |
|---|---|---|---|---|---|---|---|---|---|---|---|---|---|---|
| amino acid[1] | 97 | 98 | 99 | 100 | A | B | C | D | E | F | G | H | I | J |
| A | 11 | 7 | 13 | 7 | 9 | 6 | 2 | 3 | 5 | 5 | | 9 | | 13 |
| B | | | | | | | | | | | | | | |
| C | 1 | 13 | 5 | | 1 | 2 | 11 | 3 | | 2 | | | | |
| D | 6 | 11 | 7 | 10 | 4 | 2 | 3 | 10 | 3 | 3 | 1 | | 3 | 2 |
| E | 11 | 6 | 3 | 1 | 13 | | 1 | 1 | | | | | | |
| F | 6 | 3 | 5 | 4 | 5 | 5 | 6 | 3 | 5 | 7 | 2 | | 1 | 1 |
| G | 35 | 34 | 17 | 35 | 17 | 14 | 23 | 10 | 5 | 1 | 5 | 3 | 2 | 32 |
| H | 11 | 3 | 4 | 3 | 2 | 9 | 2 | | 1 | 3 | 1 | 2 | 8 | 1 |
| I | 10 | 2 | 11 | | | 3 | 1 | | | | | | | |
| K | 5 | 26 | 13 | 4 | 12 | 8 | 2 | 6 | 3 | 10 | 3 | | | |
| L | 7 | 26 | 13 | 4 | 12 | 8 | 2 | 6 | 3 | 10 | 3 | | | |
| M | 1 | | 1 | 2 | | | | | | | | 1 | | |
| N | 3 | 4 | 6 | 4 | 3 | 2 | 2 | 6 | | | | 2 | 5 | |
| P | 10 | 6 | 5 | 5 | 6 | 9 | 8 | 2 | 3 | 2 | 1 | | 3 | |
| Q | 2 | 4 | | 1 | 1 | 1 | 1 | 1 | | | | | 1 | |
| R | 19 | 4 | 10 | 9 | 7 | 5 | 5 | 2 | 3 | 1 | | 1 | | 2 |
| S | 11 | 16 | 28 | 27 | 25 | 24 | 8 | 11 | 9 | 3 | | 2 | 3 | 1 |
| T | 20 | 6 | 12 | 9 | 17 | 17 | 1 | 2 | 5 | 1 | 9 | 3 | 1 | |
| V | 15 | 13 | 7 | 15 | 4 | 3 | 6 | 2 | 12 | | 1 | 1 | 1 | 1 |
| W | 3 | 6 | 5 | 6 | 7 | 2 | 4 | | | | 1 | | 6 | 10 |
| X | | | | | 1 | | | | | | | | | |
| Y | 8 | 16 | 14 | 17 | 5 | 8 | 18 | 20 | 13 | 20 | 25 | 28 | 32 | 28 |
| Z | | | | | | | | | | | | | | |
| — | 4 | 12 | 21 | 35 | 54 | 73 | 87 | 102 | 110 | 126 | 135 | 134 | 120 | 91 |
| unknown (?) | | | | | | | | 3 | 2 | 1 | 1 | | | 3 |
| not sequenced | 13 | 14 | 14 | 14 | 14 | 15 | 19 | 21 | 22 | 23 | 23 | 23 | 25 | 25 |
| sum of seq[2] | 199 | 198 | 198 | 198 | 197 | 196 | 192 | 190 | 189 | 188 | 188 | 188 | 186 | 186 |
| oomcaa[3] | 35 | 34 | 28 | 35 | 54 | 73 | 87 | 102 | 110 | 126 | 135 | 134 | 120 | 91 |
| mcaa[4] | G | G | S | G | — | — | — | — | — | — | — | — | — | — |
| rel. oomcaa[5] | 18% | 17% | 14% | 18% | 27% | 37% | 45% | 54% | 58% | 67% | 72% | 71% | 65% | 49% |
| pos occupied[6] | 21 | 20 | 20 | 19 | 20 | 19 | 20 | 17 | 14 | 14 | 12 | 12 | 13 | 12 |

TABLE 6D-continued

Analysis of V heavy chain subgroup 3

| amino acid[1] | CDR III K | CDR III 101 | Framework IV 102 | 103 | 104 | 105 | 106 | 107 | 108 | 109 | 110 | 111 | 112 | 113 | sum |
|---|---|---|---|---|---|---|---|---|---|---|---|---|---|---|---|
| A | | 2 | 1 | | 1 | | | 2 | | | | | | | 1767 |
| B | | | | | | 1 | | | | | | | | | 13 |
| C | 1 | | | | | | | | | | | | | | 470 |
| D | | 146 | 2 | | | | | | | | | | | | 1121 |
| E | | 1 | | | | | 1 | | | | | | | | 832 |
| F | 65 | 1 | 2 | | | | | | | | | | | | 807 |
| G | | 6 | | | 140 | | 130 | | 1 | | | | | 2743 | |
| H | | | 4 | | | | | | | | | | | | 179 |
| I | 2 | | 15 | | | | | | | | 1 | 1 | | | 651 |
| K | | | | | | 13 | | | | | | | | | 933 |
| L | 2 | 1 | 10 | | | 1 | | | 91 | | | | | 2 | 1881 |
| M | 32 | | | | | | | | 6 | | | | | | 496 |
| N | | 2 | 1 | | | | | 1 | | | | | | | 844 |
| P | 9 | | 17 | | | | | 1 | 1 | | | | | | 568 |
| Q | | | | | | 111 | | | | | | | | | 949 |
| R | | 4 | | | | 8 | | | | | | | | | 1413 |
| S | 1 | 1 | 7 | 1 | | | | | | | | | 118 | 110 | 3009 |
| T | | | | | | | | 123 | 27 | | 122 | | | 1 | 1426 |
| V | | | 34 | | 1 | | | 1 | | 125 | | 119 | | | 1851 |
| W | | | | 158 | | | | | | | | | | | 686 |
| X | | 1 | | | | | | | | | | | 26 | | |
| Y | | | 82 | | | | | | | | | | | | 1598 |
| Z | | | | | | | | | | | | | | | 8 |
| — | 71 | 21 | 9 | 2 | 2 | 2 | 2 | 2 | 2 | 2 | 2 | 2 | 1 | 1 | 2023 |
| unknown (?) | 2 | | | | | | | | | | | | | | 12 |
| not sequenced | 26 | 25 | 27 | 50 | 67 | 75 | 78 | 81 | 83 | 84 | 86 | 89 | 92 | 97 | 1650 |
| sum of seq[2] | 185 | 186 | 184 | 161 | 144 | 136 | 133 | 130 | 128 | 127 | 125 | 122 | 119 | 114 | |
| oomcaa[3] | 71 | 146 | 82 | 158 | 140 | 111 | 130 | 123 | 91 | 125 | 122 | 119 | 118 | 110 | |
| mcaa[4] | — | D | Y | W | G | Q | G | T | L | V | T | V | S | S | |
| rel. oomcaa[5] | 38% | 78% | 45% | 98% | 97% | 82% | 98% | 95% | 71% | 98% | 98% | 98% | 99% | 96% | |
| pos occupied[6] | 8 | 11 | 12 | 3 | 4 | 6 | 3 | 6 | 6 | 2 | 3 | 3 | 2 | 4 | |

TABLE 6E

Analysis of V heavy chain subgroup 4

| amino acid[1] | Framework I 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| A | | | | | | | | | 19 | | | | | 1 | | | 1 | | 1 |
| B | | | | | | | | | | | | | | | | | | | |
| C | | | | | | | | | | | | | | | | | | | |
| D | | | | | | | | | | | | | | | | | | | |
| E | | | | | | 32 | | | | | | | | | | 44 | | | |
| F | | | | | | | | | | | | | | | | | | | |
| G | | | | | | | | 54 | 1 | 53 | | | | | | 2 | | | |
| H | | | 4 | | 2 | | | | | | | | | | | | | | |
| I | | | | | | | | | | | | | | | | | | | |
| K | | | | | | | | | | | | 1 | 54 | | | | | | 1 |
| L | | 7 | | 54 | | | | | | | 53 | 19 | | 1 | | | | 53 | |
| M | | | | | | | | | | | | | | | | | | | |
| N | | | | | | | | | | | | | | | | | | | |
| P | | | | | | | | | 33 | | | | | 51 | 1 | | | | |
| Q | 52 | | 50 | | 51 | 20 | | | | | | | | | | 7 | | | |
| R | 1 | | | | | | | | | | | | | | | | | | |
| S | | | | | | | 33 | | | | | | | | 52 | | | | 52 |
| T | | | | | | | | | 1 | | | | | | | | 52 | | |
| V | | 47 | | | | 1 | | | | | | 34 | | | | | | | |
| W | | | | | | | 20 | | | | | | | | | | | | |
| X | | | | | | | | | | | | | | | | | | | |
| Y | | | | | | | | | | | | | | | | | | | |
| Z | 1 | | | | | | | | | | | | | | | | | | |
| — | | | | | | | | | | | | | | | | | | | |
| unknown (?) | | | | | | | | | | | | | | | | | | | |
| not sequenced | 3 | 3 | 3 | 3 | 4 | 4 | 4 | 3 | 3 | 4 | 4 | 3 | 3 | 4 | 4 | 4 | 4 | 4 | 3 |
| sum of seq[2] | 54 | 54 | 54 | 54 | 53 | 53 | 53 | 54 | 54 | 53 | 53 | 54 | 54 | 53 | 53 | 53 | 53 | 53 | 54 |
| oomcaa[3] | 52 | 47 | 50 | 54 | 51 | 32 | 33 | 54 | 33 | 53 | 53 | 34 | 54 | 51 | 52 | 44 | 52 | 53 | 52 |
| mcaa[4] | Q | V | Q | L | Q | E | S | G | P | G | L | V | K | P | S | E | T | L | S |

TABLE 6E-continued

Analysis of V heavy chain subgroup 4

| | | | | | | | | | | | | | | | | | | | |
|---|---|---|---|---|---|---|---|---|---|---|---|---|---|---|---|---|---|---|---|
| rel. oomcaa[5] | 96% | 87% | 93% | 100% | 96% | 60% | 62% | 100% | 61% | 100% | 100% | 63% | 100% | 96% | 98% | 83% | 98% | 100% | 96% |
| pos occupied[6] | 3 | 2 | 2 | 1 | 2 | 3 | 2 | 1 | 4 | 1 | 1 | 3 | 1 | 3 | 2 | 3 | 2 | 1 | 3 |

| | Framework I | | | | | | | | | | | CDR I | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |
| A | | | | 22 | | | | | | | | | | | 1 | | | | |
| B | | | | | | | | | | | | | | | | | | | |
| C | | | 53 | | | | | | | | | | | | | 1 | | | |
| D | | | | 1 | | | | | | | | 4 | 1 | 1 | 1 | | | 1 | |
| E | | | | | | | | | | | | | | | | | | | |
| F | | | | | | 1 | | | | 22 | | | | | 1 | 1 | | | |
| G | | | | | | | 53 | 53 | | | | 21 | 3 | 4 | | | | 8 | |
| H | | | | | | | | 1 | | | | | | | 2 | | | | |
| I | | | | 1 | | | | | 1 | 32 | | | | | | | | | |
| K | | | | | | | | | | | | | | | | | | | |
| L | 50 | | | | | | | | | | | | | | | | | | |
| M | | | | | | | | | | | | | | | | | | | |
| N | | | | | | | | | | | 1 | 1 | | 2 | 2 | | | 1 | |
| P | 2 | | | | | | | | 3 | | | | | | | | | | |
| Q | | | | | | | | | | | | 1 | | | | | | | |
| R | | | | | | | 1 | | | | 3 | 2 | | 1 | | | | | |
| S | | | | 2 | | 35 | | | 51 | 1 | 52 | 25 | 5 | 9 | 1 | | | 44 | |
| T | | 53 | | 29 | | | | | | | | 2 | 1 | | | | | 3 | |
| V | 1 | | | | 55 | | 1 | | | 1 | | | | | | | | | |
| W | | | | | | | | | | | | | 1 | | | 2 | 56 | | 57 |
| X | | | | | | | | | | | | | | | | | | | |
| Y | | | | | | 19 | | 1 | | | | | | | 48 | 52 | | | |
| Z | | | | | | | | | | | | | | | | | | | |
| — | | | | | | | | | | | | | 45 | 39 | | | | | |
| unknown (?) | | | | | | | | | | | | | | | | | | | |
| not sequenced | 4 | 4 | 4 | 2 | 2 | 2 | 2 | 2 | 2 | 1 | 1 | 1 | | | 1 | 1 | 1 | | |
| sum of seq[2] | 53 | 53 | 53 | 55 | 55 | 55 | 55 | 55 | 55 | 56 | 56 | 56 | 56 | 56 | 56 | 56 | 56 | 57 | 57 |
| oomcaa[3] | 50 | 53 | 53 | 29 | 55 | 35 | 53 | 53 | 51 | 32 | 52 | 25 | 45 | 39 | 48 | 52 | 56 | 44 | 57 |
| mcaa[4] | L | T | C | T | V | S | G | G | S | I | S | S | — | — | Y | Y | W | S | W |
| rel. oomcaa[5] | 94% | 100% | 100% | 53% | 100% | 64% | 96% | 96% | 93% | 57% | 93% | 45% | 80% | 70% | 86% | 93% | 100% | 77% | 100% |
| pos occupied[6] | 3 | 1 | 1 | 5 | 1 | 3 | 3 | 3 | 3 | 4 | 3 | 7 | 6 | 6 | 7 | 4 | 1 | 5 | 1 |

| | Framework II | | | | | | | | | | | | | CDR II | | | | | |
|---|---|---|---|---|---|---|---|---|---|---|---|---|---|---|---|---|---|---|---|
| amino acid[1] | 37 | 38 | 39 | 40 | 41 | 42 | 43 | 44 | 45 | 46 | 47 | 48 | 49 | 50 | 51 | 52 | A | B | C |
| A | | | | | 8 | 1 | | | | | | | 1 | | | | | | |
| B | | | | | | | | | | | | | | | | | | | |
| C | | | | | | | | | | | | | | | | | | | |
| D | | | | | | | | | | | | | | | | 1 | | | |
| E | | | | | | 1 | | | | 56 | | | | 22 | | | | | |
| F | 1 | | | | | | | | | | | | | 1 | | 1 | | | |
| G | | | | | | 55 | | 55 | | | | | 56 | 1 | | | | | |
| H | | | | 2 | | | | | | | | | | | | | | | |
| I | 51 | | | | | | | | | | | 54 | | 1 | 54 | | | | |
| K | | | | | | | 54 | | | | | | | | | | | | |
| L | 1 | | | 1 | | | | | 55 | | | 2 | | | | | | | |
| M | | | | | | | | | | | | | | | | | | | |
| N | | | | | | | | | | | | | | | | 21 | | | |
| P | | | | 50 | 49 | | | | 2 | | | | | | | | | | |
| Q | | | 56 | | | | | | | 1 | | | | 1 | | | | | |
| R | | 57 | | | | | 3 | 2 | | | | | | 9 | | 1 | | | |
| S | 1 | | | 3 | | | | | | | | | | 7 | | 1 | | | |
| T | | | 1 | 1 | | | | | | | | | | | | | | | |
| V | 3 | | | | | | | | | | | 1 | | | 3 | | | | |
| W | | | | | | | | | | | 56 | | | | | | | | |
| X | | | | | | | | | | | | | | | | | | | |
| Y | | | | | | | | | | | 1 | | | 15 | | 32 | | | |
| Z | | | | | | | | | | | | | | | | | | | |
| — | | | | | | | | | | | | | | | | | 57 | 57 | 57 |
| unknown (?) | | | | | | | | | | | | | | | | | | | |
| not sequenced | | | | | | | | | | | | | | | | | | | |
| sum of seq[2] | 57 | 57 | 57 | 57 | 57 | 57 | 57 | 57 | 57 | 57 | 57 | 57 | 57 | 57 | 57 | 57 | 57 | 57 | 57 |
| oomcaa[2] | 51 | 57 | 56 | 50 | 49 | 55 | 54 | 55 | 55 | 56 | 56 | 54 | 56 | 22 | 54 | 32 | 57 | 57 | 57 |
| mcaa[4] | I | R | Q | P | P | G | K | G | L | E | W | I | G | E | I | Y | — | — | — |
| rel. oomcaa[5] | 89% | 100% | 98% | 88% | 86% | 96% | 95% | 96% | 96% | 98% | 98% | 95% | 98% | 39% | 95% | 56% | 100% | 100% | 100% |

TABLE 6E-continued

Analysis of V heavy chain subgroup 4

| | | | | | | | | | | | | | | | | | | | |
|---|---|---|---|---|---|---|---|---|---|---|---|---|---|---|---|---|---|---|---|
| pos occupied[6] | 5 | 1 | 2 | 5 | 2 | 3 | 2 | 2 | 2 | 2 | 2 | 3 | 2 | 8 | 2 | 6 | 1 | 1 | 1 |

| | CDR II | | | | | | | | | | | | | | Framework III | | | | |
|---|---|---|---|---|---|---|---|---|---|---|---|---|---|---|---|---|---|---|---|
| amino acid[1] | 53 | 54 | 55 | 56 | 57 | 58 | 59 | 60 | 61 | 62 | 63 | 64 | 65 | 66 | 67 | 68 | 69 | 70 | 71 |
| A | | | | | 1 | | | | | | | | | 1 | | 1 | | | 1 |
| B | | | | | | | | | | | | | | | | | | | |
| C | | | | | | | | | | | | | | | | | | | |
| D | 1 | | | | | 2 | | | | | | | | | 1 | | | | |
| E | | | | | | | | | | | | | | | | | | | |
| F | | | | | | | 3 | | | | | | | | | | | | |
| G | 1 | | 57 | 1 | | | | | | | | | 1 | | | | | | |
| H | 24 | | | | | 2 | | | | | | | | | | | | | |
| I | | | | 1 | 1 | | | | | | | | | | 1 | 1 | 48 | | 3 |
| K | | | | | | | | 1 | | | | 53 | | | | | | | |
| L | | | | | | | | | 1 | | 55 | | | | 1 | | | | 3 |
| M | | | | | | | | | | | | | | | | | 7 | | |
| N | | | | 2 | | 40 | | 53 | | | | | | | | 2 | | | |
| P | | | | | | | | | 54 | | 1 | | | | | | | | |
| Q | | | | | | | | | | | | | | | | | | | |
| R | | | | 2 | | | | | | | | 3 | | 56 | | | | | |
| S | | 52 | | 49 | | 1 | | 2 | | 56 | | | 56 | | | 1 | | 56 | |
| T | 8 | 5 | | 1 | 54 | 1 | | | 1 | | | 1 | | | | 51 | | 1 | |
| V | | | | 1 | 1 | | | | | | | | | | 53 | | 2 | | 50 |
| W | | | | | | | | | | | | | | | | | | | |
| X | | | | | | | | | | | | | | | | | | | |
| Y | 23 | | | | | 11 | 54 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | 1 | 1 | 1 | 1 | | | | 1 | 1 | | | |
| sum of seq[2] | 57 | 57 | 57 | 57 | 57 | 57 | 57 | 56 | 56 | 56 | 56 | 57 | 57 | 57 | 56 | 56 | 57 | 57 | 57 |
| oomcaa[3] | 24 | 52 | 57 | 49 | 54 | 40 | 54 | 53 | 54 | 56 | 55 | 53 | 56 | 56 | 53 | 51 | 48 | 56 | 50 |
| mcaa[4] | H | S | G | S | T | N | Y | N | P | S | L | K | S | R | V | T | I | S | V |
| rel. oomcaa[5] | 42% | 91% | 100% | 86% | 95% | 70 | 95% | 95% | 96% | 100% | 98% | 93% | 98% | 98% | 95% | 91% | 84% | 98% | 88% |
| pos occupied[6] | 5 | 2 | 1 | 7 | 4 | 6 | 2 | 3 | 3 | 1 | 2 | 3 | 2 | 2 | 4 | 5 | 3 | 2 | 4 |

| | Framework III | | | | | | | | | | | | | | | | | | |
|---|---|---|---|---|---|---|---|---|---|---|---|---|---|---|---|---|---|---|---|
| amino acid[1] | 72 | 73 | 74 | 75 | 76 | 77 | 78 | 79 | 80 | 81 | 82 | A | B | C | 83 | 84 | 85 | 86 | 87 |
| A | | | | 1 | | | | | | | | | | | | 55 | 57 | | |
| B | | | | | | | | | | | | | | | | | | | |
| C | | | | | | | | | | | | | | | | | | | |
| D | 55 | | | | | | | | 1 | | | | | | | | | 57 | |
| E | 1 | | | | | | | | | 1 | | | | | | | | | |
| F | | 1 | | | | | 54 | | | | | | 1 | | | | | | |
| G | | | | | | | | | | | | 1 | | | | | | | |
| H | | | | | | | | | | | | | | | | | | | |
| I | | | | | | | 1 | | | | | 1 | | | 3 | | | | |
| K | | 1 | | 51 | 3 | | | | | 46 | | 2 | | | | | | | |
| L | | | | 1 | | 3 | 1 | | 55 | | 53 | | | 2 | | | | | |
| M | | 2 | | | | | | | | 1 | 1 | | | 1 | | | | | |
| N | | | | 1 | 54 | | | | | 3 | | 3 | 1 | | | | | | |
| P | | | | | | | | | | | | | | | | | | | |
| Q | 1 | | | | | 54 | | | 1 | 1 | | | | | | | | | |
| R | | | | 2 | | | | | | 2 | | 2 | | | | 1 | | | |
| S | | 1 | 57 | | | | 1 | 57 | | 2 | 1 | 44 | 55 | | 1 | | | | 2 |
| T | | 52 | | | | | | | | 1 | | 4 | | | 53 | | | | 55 |
| V | | | | 1 | | | | | | | 2 | | | 54 | | 1 | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 57 | 57 | 57 | 57 | 57 | 57 | 57 | 57 | 57 | 57 | 57 | 57 | 57 | 57 | 57 | 57 | 57 | 57 | 57 |
| oomcaa[3] | 55 | 52 | 57 | 51 | 54 | 54 | 54 | 57 | 55 | 46 | 53 | 44 | 55 | 54 | 53 | 55 | 57 | 57 | 55 |
| mcaa[4] | D | T | S | K | N | Q | F | S | L | K | L | S | S | V | T | A | A | D | T |

TABLE 6E-continued

Analysis of V heavy chain subgroup 4

| | | | | | | | | | | | | | | | | | | | |
|---|---|---|---|---|---|---|---|---|---|---|---|---|---|---|---|---|---|---|---|
| rel. oomcaa[5] | 96% | 91% | 100% | 89% | 95% | 95% | 95% | 100% | 96% | 81% | 93% | 77% | 96% | 95% | 93% | 96% | 100% | 100% | 96% |
| pos occupied[6] | 3 | 5 | 1 | 6 | 2 | 2 | 4 | 1 | 3 | 8 | 4 | 7 | 3 | 3 | 3 | 3 | 1 | 1 | 2 |

| | Framework III | | | | | CDR III | | | | | | | | | | | | | |
|---|---|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 57 | | | | | 56 | | 3 | 3 | 3 | 2 | 5 | 4 | 2 | 2 | 4 | | 2 | 1 |
| B | | | | | | | | | | | | | | | | | | | |
| C | | | | | 57 | | | | | 1 | | | | 1 | | | | | |
| D | | | | | | | | 6 | | 5 | 5 | 5 | 4 | 3 | 2 | 4 | 3 | 1 | |
| E | | | | | | | | 6 | 1 | 1 | 2 | 1 | | | 1 | 3 | 1 | 2 | 1 |
| F | | | | | | | | | 4 | 1 | 1 | | 2 | 3 | 2 | 2 | | 1 | 1 |
| G | | | | | | | | 25 | 9 | 10 | 8 | 10 | 11 | 4 | 7 | 7 | 6 | 1 | 1 |
| H | | | | | | | | 1 | | | | 1 | | | | | | 1 | |
| I | | | | | | | | | 1 | | 2 | 4 | 1 | 3 | 2 | 3 | | 1 | |
| K | | | | | | | | 2 | 1 | | | | | | 2 | 2 | | | 1 |
| L | | 1 | | | | | | 2 | 6 | 7 | 3 | 5 | 3 | 2 | 4 | 1 | 5 | 3 | 3 |
| M | | 1 | | | | | | | 1 | 4 | | 3 | 1 | | 2 | 1 | | | |
| N | | | | | | | | | 3 | | | | | 2 | 1 | 1 | 5 | 1 | 1 |
| P | | | | | | | | | 4 | 5 | 3 | 1 | 1 | 2 | 1 | 1 | 1 | 2 | 3 |
| Q | | | | | | | | | | 1 | 1 | | 1 | | | 1 | 1 | | |
| R | | | | | | | 54 | 4 | 12 | 2 | 5 | 5 | 3 | 2 | 3 | 1 | 2 | | |
| S | | | | 1 | | | 1 | 1 | 4 | 8 | 8 | 1 | 2 | 5 | 7 | 4 | 2 | 1 | 1 |
| T | | | | | | | 1 | 1 | 2 | 1 | 3 | 4 | 4 | 3 | 3 | | | 1 | 1 |
| V | | 55 | | | | 1 | 1 | 4 | 2 | 2 | 5 | 4 | 4 | 7 | 3 | 1 | 2 | 1 | |
| W | | | | | | | | 1 | 2 | 1 | 2 | 2 | 4 | 5 | 1 | 1 | 2 | | 2 |
| X | | | | | | | | | | | | | | | | | | | |
| Y | | | 57 | 56 | | | | | 1 | 4 | 5 | 3 | 6 | 4 | 2 | 3 | 4 | 8 | 4 |
| — | | | | | | | | | | | 1 | 2 | 4 | 6 | 9 | 11 | 16 | 23 | 27 |
| unknown (?) | | | | | | | | | | | | | | | | | | | 1 |
| not sequenced | | | | | | | | 1 | 1 | 1 | 1 | 1 | 2 | 3 | 3 | 6 | 7 | 8 | 9 |
| sum of seq[2] | 57 | 57 | 57 | 57 | 57 | 57 | 57 | 56 | 56 | 56 | 56 | 56 | 55 | 54 | 54 | 51 | 50 | 49 | 48 |
| oomcaa[3] | 57 | 55 | 57 | 56 | 57 | 56 | 54 | 25 | 12 | 10 | 8 | 10 | 11 | 7 | 9 | 11 | 16 | 23 | 27 |
| mcaa[4] | A | V | Y | Y | C | A | R | G | R | G | G | G | G | V | — | — | — | — | — |
| rel. oomcaa[5] | 100% | 96% | 100% | 98% | 100% | 98% | 95% | 45% | 21% | 18% | 14% | 18% | 20% | 13% | 17% | 22% | 32% | 47% | 56% |
| pos occupied[6] | 1 | 3 | 1 | 2 | 1 | 2 | 4 | 12 | 16 | 16 | 16 | 16 | 16 | 18 | 16 | 18 | 13 | 15 | 13 |

| | CDR III | | | | | Framework IV | | | | | | | | | | | | | |
|---|---|---|---|---|---|---|---|---|---|---|---|---|---|---|---|---|---|---|---|
| amino acid[1] | G | H | I | J | K | 101 | 102 | 103 | 104 | 105 | 106 | 107 | 108 | 109 | 110 | 111 | 112 | 113 | sum |
| A | | 1 | 1 | 12 | | | | | | | | 1 | | | 1 | | | | 332 |
| B | | | | | | | | | | | | | | | | | | | |
| C | | | | | | | | | | | | | | | | | | | 113 |
| D | 1 | 2 | 1 | | | 41 | | | | | | | | | | | | | 210 |
| E | | | | | | | | | | | | | | | | | | | 176 |
| F | | | | | 31 | | | | | | | | | | | | | | 135 |
| G | 1 | 2 | 1 | 9 | | | | | 41 | | 40 | 1 | | | | | | | 674 |
| H | | 1 | | | | 2 | 1 | | | | | | | | 1 | | | | 45 |
| I | | | | | 1 | | 9 | | | | | 1 | | | | | | | 282 |
| K | | | | | | | | | | 3 | | | | | | | | | 278 |
| L | | 1 | | | | | 4 | | | | | | 19 | | | | | | 540 |
| M | | | | | 9 | | | | | | | | 9 | | | | | | 43 |
| N | | | 2 | | | | | | | | | 1 | | | | | | | 204 |
| P | 1 | 2 | 1 | | | | 3 | | | 2 | | | | | | | | 2 | 281 |
| Q | 3 | | | | | 1 | | | | 29 | | | | | | | | | 334 |
| R | 2 | 1 | | | | | 1 | | | 4 | | | 1 | | | | | | 250 |
| S | 1 | | | | | | 1 | | | 1 | | | | | | | 36 | 33 | 986 |
| T | 1 | | | | | | | | | 1 | | 33 | 8 | | 34 | | | | 532 |
| V | | | | | | | 12 | | | | | | | 36 | | 36 | | | 488 |
| W | 1 | | 3 | 2 | | | | 46 | | | | | | | | | | | 267 |
| X | | | | | | | | | | | | | | | | | | | |
| Y | 8 | 3 | 5 | 8 | | 2 | 16 | | | | | | | | | | | | 455 |
| Z | | | | | | | | | | | | | | | | | | | 1 |
| — | 29 | 34 | 31 | 14 | 4 | | | | | | | | | | | | | | 466 |
| unknown (?) | | | 1 | 1 | 1 | | | | | | | | | | | | | | 4 |
| not sequenced | 9 | 10 | 11 | 11 | 11 | 11 | 10 | 11 | 16 | 17 | 17 | 20 | 20 | 21 | 21 | 21 | 21 | 22 | 426 |
| sum of seq[2] | 48 | 47 | 46 | 46 | 46 | 46 | 47 | 46 | 41 | 40 | 40 | 37 | 37 | 36 | 36 | 36 | 36 | 35 | |
| oomcaa[3] | 29 | 34 | 31 | 14 | 31 | 41 | 16 | 46 | 41 | 29 | 40 | 33 | 19 | 36 | 34 | 36 | 36 | 33 | |
| mcaa[4] | — | — | — | — | F | D | Y | W | G | Q | G | T | L | V | T | V | S | S | |

TABLE 6E-continued

| Analysis of V heavy chain subgroup 4 | | | | | | | | | | | | | | | | | | | |
|---|---|---|---|---|---|---|---|---|---|---|---|---|---|---|---|---|---|---|---|
| rel. oomcaa[5] | 60% | 72% | 67% | 30% | 67% | 89% | 34% | 100% | 100% | 73% | 100% | 89% | 51% | 100% | 94% | 100% | 100% | 94% | |
| pos occupied[6] | 10 | 9 | 8 | 5 | 4 | 4 | 8 | 1 | 1 | 6 | 1 | 5 | 4 | 1 | 3 | 1 | 1 | 2 | |

TABLE 6F

Analysis of V heavy chain subgroup 5

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | 1 | | | 1 | 89 | | 1 | | | 1 | | | | | |
| B | | | | | | | | | | | | | | | | | | | |
| C | | | | | | | 1 | | | | | | | | | | | | |
| D | | | | | | | | | | 2 | | | | | | | | | |
| E | 88 | 1 | | | 2 | | | | 4 | 93 | | | | | | 92 | | | |
| F | | | | | | | | | | | | | | | | | 1 | | |
| G | 1 | | | | | | | 92 | | | | | | | 94 | | | | |
| H | | | | | | | | | | | | | | | | | | | |
| I | | | | | | | | | | | | | | | | | | | |
| K | | | | | | | | | | | | 94 | 94 | | | | | | 77 |
| L | | 1 | | 91 | | 2 | | | | | | | | | | | | 95 | |
| M | | | | | | | | | | | 3 | | | | | | | | 1 |
| N | | | | | | | | | | | | | | | | | | | |
| P | | | | 1 | | | | | 1 | | | | | 94 | | | | | |
| Q | 3 | | 92 | | 1 | 90 | | | | | | | | | | 3 | | | 1 |
| R | | | | | | 1 | | | | | | 1 | 1 | | 1 | | | | 17 |
| S | | | | | | | 92 | | | | | | | | | | 94 | | |
| T | | | | | | | | | | | | | | | | | | | |
| V | | 90 | | | 89 | | | | 1 | | 91 | | | | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | 5 | 5 | 5 | 5 | 4 | 4 | 4 | 4 | 2 | 2 | 2 | 2 | 2 | 2 | 2 | 2 | 2 | 2 | 1 |
| sum of seq[2] | 92 | 92 | 92 | 92 | 93 | 93 | 93 | 93 | 95 | 95 | 95 | 95 | 95 | 95 | 95 | 95 | 95 | 95 | 96 |
| oomcaa[3] | 88 | 90 | 92 | 91 | 89 | 90 | 92 | 92 | 89 | 93 | 91 | 94 | 94 | 94 | 94 | 92 | 94 | 95 | 77 |
| mcaa[4] | E | V | Q | L | V | Q | S | G | A | E | V | K | K | P | G | E | S | L | K |
| rel. oomcaa[5] | 96% | 98% | 100% | 99% | 96% | 97% | 99% | 99% | 94% | 98% | 96% | 99% | 99% | 99% | 99% | 97% | 99% | 100% | 80% |
| pos occupied[6] | 3 | 3 | 1 | 2 | 4 | 3 | 2 | 2 | 4 | 2 | 3 | 2 | 2 | 2 | 2 | 2 | 2 | 1 | 4 |

| | Framework I | | | | | | | | | | | CDR I | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |
| A | | | | | 3 | 2 | | | | | 4 | | | | | | | 8 | |
| B | | | | | | | | | | | | | | | | | | | |
| C | | | 96 | | | | | | 1 | | | 1 | | | | | | | |
| D | | | | | | | | | 2 | | | 2 | | | | | | 1 | |
| E | | | | | | | 2 | | | | | 1 | | | | | | | |
| F | | | | | | 3 | | 6 | | 97 | | | | | 2 | | | | |
| G | | | | | 92 | | 93 | | | | | 1 | | | | | | 72 | |
| H | | | | | | | | | | | | 1 | | | 4 | | | | |
| I | 96 | | | | | | | | | | 4 | | | | | | 93 | | |
| K | | | | 89 | | | | | 1 | | | | | | | | | | |
| L | | | | | | | | | | | | | | | | 1 | | | |
| M | | | | 1 | | | | | | | | | | | | | 1 | | |
| N | | | | 1 | | | | | 2 | | 4 | 14 | | | 2 | | | | |
| P | | | | | | 1 | | | | | | | | | | | | | |
| Q | | | | 4 | | | | | | | | | | | | | | | |
| R | | | | 1 | | | 1 | | 2 | | | | | | | 1 | | | |
| S | | 94 | | | 1 | 90 | | | 84 | | 10 | 61 | | | 2 | 2 | | 15 | |
| T | | 2 | | | | | | | 5 | | 75 | 16 | | | | | 2 | 1 | |
| V | | | | | | | | | | | | | | | | | 1 | | |
| W | | | | | | | | | | | | | | | | 93 | | | 97 |
| X | | | | | | | | | | | | | | | | | | | |
| Y | | | | | | | | 90 | | | | | | | 87 | | | | |
| Z | | | | | | | | | | | | | | | | | | | |
| — | | | | | | | | | | | | | 97 | 97 | | | | | |

TABLE 6F-continued

Analysis of V heavy chain subgroup 5

| | | | | | | | | | | | | | | | | | | | |
|---|---|---|---|---|---|---|---|---|---|---|---|---|---|---|---|---|---|---|---|
| unknown (?) | | | | | | | | | | | | | | | | | | | |
| not sequenced | 1 | 1 | 1 | 1 | 1 | 1 | 1 | 1 | | | | | | | | | | | |
| sum of seq[2] | 96 | 96 | 96 | 96 | 96 | 96 | 96 | 96 | 97 | 97 | 97 | 97 | 97 | 97 | 97 | 97 | 97 | 97 | 97 |
| oomcaa[3] | 96 | 94 | 96 | 89 | 92 | 90 | 93 | 90 | 84 | 97 | 75 | 61 | 97 | 97 | 87 | 93 | 93 | 72 | 97 |
| mcaa[4] | I | S | C | K | G | S | G | Y | S | F | T | S | — | — | Y | W | I | G | W |
| rel. oomcaa[5] | 100% | 98% | 100% | 93% | 96% | 94% | 97% | 94% | 87% | 100% | 77% | 63% | 100% | 100% | 90% | 96% | 96% | 74% | 100% |
| pos occupied[6] | 1 | 2 | 1 | 5 | 3 | 4 | 3 | 2 | 7 | 1 | 5 | 8 | 1 | 1 | 5 | 4 | 4 | 5 | 1 |

| | Framework II | | | | | | | | | | | | | | CDR II | | | | |
|---|---|---|---|---|---|---|---|---|---|---|---|---|---|---|---|---|---|---|---|
| amino acid[1] | 37 | 38 | 39 | 40 | 41 | 42 | 43 | 44 | 45 | 46 | 47 | 48 | 49 | 50 | 51 | 52 | A | B | C |
| A | 1 | | | | 1 | | | 1 | | | | | | | | | 1 | | |
| B | | | | | | | | | | | | | | | | | | | |
| C | | | | | | | | | | | | | | | | 1 | | | |
| D | | | | | | | | | | | | | | | | 14 | | | |
| E | | | | | | | 3 | | | 97 | | | | | | | | | |
| F | | | | | | | | | | | | | | 1 | | 2 | | | |
| G | | | | | | 97 | | 96 | | | | | 95 | | | | | | |
| H | | 1 | | | | | | | | | | | | | | 3 | 1 | | |
| I | | | | | | | | | | | | 1 | | 75 | 92 | | | | |
| K | | | | 1 | | | 94 | | | | | | | | | | | | |
| L | 2 | | | | | | | | 94 | | | 2 | | 2 | 1 | | | | |
| M | 1 | | | 92 | | | | | | | | 89 | | | 1 | | | | |
| N | | | | | | | | | | | | | | | | | | | |
| P | | 1 | | | 96 | | | | 2 | | | | | | | 1 | 93 | | |
| Q | | | 97 | | | | | | 1 | | | | | | | | | | |
| R | | 95 | | 1 | | | | | | | | | 1 | 14 | | | | | |
| S | | | | | | | | | | | | | | 1 | | | 1 | | |
| T | | | | 1 | | | | | | | | | | 3 | 1 | | 1 | | |
| V | 93 | | | 2 | | | | | | | | 5 | 1 | 1 | 2 | | | | |
| W | | | | | | | | | | | 94 | | | | | | | | |
| X | | | | | | | | | | | | | | | | | | | |
| Y | | | | | | | | | | | 3 | | | | | 76 | | | |
| Z | | | | | | | | | | | | | | | | | | | |
| — | | | | | | | | | | | | | | | | | | 97 | 97 |
| unknown (?) | | | | | | | | | | | | | | | | | | | |
| not sequenced | | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | 97 | 97 |
| oomcaa[3] | 93 | 95 | 97 | 92 | 96 | 97 | 94 | 96 | 94 | 97 | 94 | 89 | 95 | 75 | 92 | 76 | 93 | 97 | 97 |
| mcaa[4] | V | R | Q | M | P | G | K | G | L | E | W | M | G | I | I | Y | P | — | — |
| rel. oomcaa[5] | 96% | 98% | 100% | 95% | 99% | 100% | 97% | 99% | 97% | 100% | 97% | 92% | 98% | 77% | 95% | 78% | 96% | 100% | 100% |
| pos occupied[6] | 4 | 3 | 1 | 5 | 2 | 1 | 2 | 2 | 3 | 1 | 2 | 4 | 3 | 7 | 5 | 6 | 5 | 1 | 1 |

| | CDR II | | | | | | | | | | | | | | Framework III | | | | |
|---|---|---|---|---|---|---|---|---|---|---|---|---|---|---|---|---|---|---|---|
| amino acid[1] | 53 | 54 | 55 | 56 | 57 | 58 | 59 | 60 | 61 | 62 | 63 | 64 | 65 | 66 | 67 | 68 | 69 | 70 | 71 |
| A | 2 | 1 | | | 6 | | | | | 1 | | | | | | | | | 88 |
| B | | | | | | | | | | | | | | | | | | | |
| C | 1 | | | | | | | 1 | | | | | 1 | | | | | | |
| D | 8 | 93 | | 77 | | | | | | | | | 2 | | | | | | |
| E | | 2 | | 3 | | | | | | | | 2 | | | | | | | |
| F | | | | | | | 2 | | | | 91 | | | | 1 | | 3 | | |
| G | 69 | 1 | | 1 | | | | | | | | | 94 | | | | | | |
| H | | | | | | | | | | | | | | 15 | | | | | |
| I | | | | | 4 | 1 | | | | | 1 | | | | 3 | | 88 | | |
| K | | | | | | 2 | | | | | | | | | | | | | |
| L | | | | | | | | | 1 | | 4 | | | | | | | 2 | |
| M | | | | | | | | | | | | | | | | | 3 | | |
| N | | | | 2 | | 14 | 2 | | | | | | | | | | | | |
| P | | | 1 | | | | | | 95 | 1 | | 1 | | | | | | | |
| Q | | | | | | | | | | | | 91 | | 81 | | | | | |
| R | 1 | | | | | 78 | | | | | | 3 | | 1 | | | 1 | | |
| S | 16 | | 96 | 2 | 2 | | | 95 | 1 | 95 | 1 | | | | | 1 | | 95 | |
| T | | | | | 85 | 2 | | 1 | | | | | | | | 96 | | | |
| V | | | | | | | 1 | | | | | | | | 93 | | 2 | | 9 |
| W | | | | | | | | | | | | | | | | | | | |
| X | | | | | | | | | | | | | | | | | | | |

TABLE 6F-continued

| Analysis of V heavy chain subgroup 5 | | | | | | | | | | | | | | | | | | | |
|---|---|---|---|---|---|---|---|---|---|---|---|---|---|---|---|---|---|---|---|
| Y | | | | 12 | | | 92 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | 97 | 97 |
| oomcaa[3] | 69 | 93 | 96 | 77 | 85 | 78 | 92 | 95 | 95 | 95 | 91 | 91 | 94 | 81 | 93 | 96 | 88 | 95 | 88 |
| mcaa[4] | G | D | S | D | T | R | Y | S | P | S | F | Q | G | Q | V | T | I | S | A |
| rel. oomcaa[5] | 71% | 96% | 99% | 79% | 88% | 80% | 95% | 98% | 98% | 98% | 94% | 94% | 97% | 84% | 96% | 99% | 91% | 89% | 91% |
| pos occupied[6] | 6 | 4 | 2 | 6 | 4 | 5 | 4 | 3 | 3 | 3 | 4 | 4 | 3 | 3 | 3 | 2 | 5 | 2 | 2 |

| | Framework III | | | | | | | | | | | | | | | | | | |
|---|---|---|---|---|---|---|---|---|---|---|---|---|---|---|---|---|---|---|---|
| amino acid[1] | 72 | 73 | 74 | 75 | 76 | 77 | 78 | 79 | 80 | 81 | 82 | A | B | C | 83 | 84 | 85 | 86 | 87 |
| A | | | | | | 1 | 91 | | | | | | | | 1 | 96 | | | |
| B | | | | | | | | | | | | | | | | | | | |
| C | | | | | | | | | | | 1 | | | | | | | | |
| D | 97 | | | | | | | 1 | | | | | | | | | | 96 | |
| E | | 2 | | | | | | | | 1 | | | | | 1 | | | | |
| F | | | | | | | | 1 | | | | | | | | | | | |
| G | | | | | | | | | | | | 3 | 1 | | | | | | |
| H | | | | | | | | | | 3 | | | | | | | | | |
| I | | | | 91 | | | | | | | | | | | | | | | 2 |
| K | | 93 | | | | | | | | | | | | | 91 | | | | |
| L | | | | | | | | | 96 | | | | | 97 | | | | | |
| M | | | | 1 | | | | | | | | | | | | | | | |
| N | | | | | 7 | | | | | | | 2 | 2 | | | | | | 2 |
| P | | | 1 | | | | 1 | | | | | | | | | | | | |
| Q | | 1 | | | | | | | | 93 | | | | | | | | | |
| R | | 1 | | | 1 | | | | | | 1 | 1 | 3 | | 3 | | | | |
| S | | | 96 | 1 | 87 | 2 | 1 | 1 | | | | 90 | 91 | | | | 96 | | 5 |
| T | | | | 4 | 2 | 94 | 2 | | | | | 1 | | | 1 | 1 | 1 | | 88 |
| V | | | | | | | 2 | | 1 | | | | | | | | | 1 | |
| W | | | | | | | | | | | 95 | | | | | | | | |
| X | | | | | | | | | | | | | | | | | | | |
| Y | | | | | | | | 94 | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | 97 | 97 |
| oomcaa[3] | 97 | 93 | 96 | 91 | 87 | 94 | 91 | 94 | 96 | 93 | 95 | 90 | 91 | 97 | 91 | 96 | 96 | 96 | 88 |
| mcaa[4] | D | K | S | I | S | T | A | Y | L | Q | W | S | S | L | K | A | S | D | T |
| rel. oomcaa[5] | 100% | 96% | 99% | 94% | 90% | 97% | 94% | 97% | 99% | 96% | 98% | 93% | 94% | 100% | 94% | 99% | 99% | 99% | 91% |
| pos occupied[6] | 1 | 4 | 2 | 4 | 4 | 3 | 5 | 4 | 2 | 3 | 3 | 5 | 4 | 1 | 5 | 2 | 2 | 2 | 4 |

| | Framework III | | | | | CDR III | | | | | | | | | | | | | |
|---|---|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 93 | | | | | 92 | | 1 | 1 | 2 | | 3 | 4 | 3 | 2 | | 1 | | |
| B | | | | | | | | | | | | | | | | | | | |
| C | | | | | 95 | | | | | | 1 | 1 | 1 | | | 2 | | 1 | |
| D | | | | | | | | | 3 | 3 | 3 | 3 | 1 | 2 | 1 | 1 | 2 | | 2 |
| E | | | | | | | | 1 | 1 | 1 | 2 | | | 1 | 1 | | | | 1 |
| F | | | 2 | 6 | | | | | | 1 | | 3 | | | 3 | 2 | | 1 | |
| G | 4 | | | | | | | 1 | 9 | 11 | 12 | 12 | 5 | 2 | 4 | 3 | 10 | 2 | 1 |
| H | | | | | | | | 10 | 1 | | 2 | | | 1 | 1 | | 1 | | |
| I | | 1 | | | | | | | 3 | | 2 | 2 | 1 | 1 | 4 | 1 | 1 | | 1 |
| K | | 2 | | | | | 1 | 1 | 1 | | 1 | 3 | 1 | | | | | | |
| L | | 84 | | | | | | 11 | 2 | 3 | 1 | 1 | 2 | 5 | | 1 | | 1 | |
| M | | | | | | | | | | 2 | 1 | 1 | | 1 | 1 | 1 | 1 | | |
| N | | | | | | | | | 1 | | 2 | | 1 | 1 | 2 | | | 1 | |
| P | | | | | | | | 5 | 1 | 4 | 3 | 1 | 2 | | | | 1 | 1 | 1 |
| Q | | | | | | | 1 | 3 | 2 | | 1 | 1 | 4 | 2 | 1 | 2 | | | |
| R | | | | | | | 92 | 7 | 9 | 2 | 2 | | 2 | 1 | | 2 | | | |
| S | | 1 | | | | | 1 | 3 | 2 | 6 | 4 | 4 | 5 | 3 | 5 | 3 | 2 | 2 | |
| T | | 1 | | | | 1 | | 1 | 3 | 2 | 1 | 2 | 6 | 3 | 3 | 6 | 1 | | 1 |
| V | | | | | | 2 | | 2 | 4 | 4 | | 1 | | 1 | 2 | | | 1 | |
| W | | | | | | | | 1 | | 2 | 1 | | | | | 1 | | 2 | |
| X | | | | | | | | | | | | | | | | | | | |

TABLE 6F-continued

Analysis of V heavy chain subgroup 5

| | | | | | | | | | | | | | | | | | | | |
|---|---|---|---|---|---|---|---|---|---|---|---|---|---|---|---|---|---|---|---|
| Y | | | 94 | 89 | | | | | 1 | 6 | 3 | 6 | 9 | 8 | 7 | 2 | 1 | 2 | 6 |
| Z | | | | | | | | | | | | | | | | | | | |
| — | | | | | | | | | | | 1 | 1 | 2 | 8 | 10 | 16 | 23 | 30 | 30 |
| unknown (?) | | | | | | | | | | | | | | | | | | 1 | |
| not sequenced | | | 1 | 2 | 2 | 2 | 2 | 52 | 52 | 52 | 52 | 52 | 52 | 52 | 52 | 52 | 52 | 52 | 52 |
| sum of seq² | 97 | 97 | 96 | 95 | 95 | 95 | 95 | 45 | 45 | 45 | 45 | 45 | 45 | 45 | 45 | 45 | 45 | 45 | 45 |
| oomcaa³ | 93 | 84 | 94 | 89 | 95 | 92 | 92 | 11 | 9 | 11 | 12 | 12 | 9 | 8 | 10 | 16 | 23 | 30 | 30 |
| mcaa⁴ | A | M | Y | Y | C | A | R | L | G | G | G | G | Y | Y | — | — | — | — | — |
| rel. oomcaa⁵ | 96% | 87% | 98% | 94% | 100% | 97% | 97% | 24% | 20% | 24% | 27% | 27% | 20% | 18% | 22% | 36% | 51% | 67% | 67% |
| pos occupied⁶ | 2 | 5 | 2 | 2 | 1 | 3 | 4 | 13 | 16 | 14 | 18 | 16 | 15 | 16 | 15 | 14 | 11 | 11 | 9 |

| | CDR III | | | | | | Framework IV | | | | | | | | | | | | |
|---|---|---|---|---|---|---|---|---|---|---|---|---|---|---|---|---|---|---|---|
| amino acid¹ | G | H | I | J | K | 101 | 102 | 103 | 104 | 105 | 106 | 107 | 108 | 109 | 110 | 111 | 112 | 113 | sum |
| A | 1 | | | 4 | | 2 | | | | | | | | | | | | 1 | 611 |
| B | | | | | | | | | | | | | | | | | | | |
| C | | | | | | | | | | | | | | | | | | | 205 |
| D | 1 | 1 | 2 | | | 37 | 1 | | | | | | | | | | | | 458 |
| E | | | 1 | | | | | | | 1 | | | | | | | | | 404 |
| F | | | | | 26 | | 2 | | | | | | | | | | | | 256 |
| G | | | | 5 | | | | | 41 | | 41 | | | | | | | | 1065 |
| H | | | | | | | | | | | | | | | | | | | 44 |
| I | 1 | | | | | | 9 | | | | | | | | 2 | | | | 588 |
| K | | 2 | | | | | | | | 3 | | | | | | | | | 650 |
| L | 1 | | | | | | 2 | | | | | | 25 | 1 | | | | | 549 |
| M | | | | | 10 | | | | | | | | 8 | | | | | | 303 |
| N | | | | 2 | | | | | | | | | | | | | | | 64 |
| P | 1 | | | | | | 2 | | | | | 1 | | | | | 1 | | 414 |
| Q | | | | | | 3 | | | | 34 | | | | | | | | | 612 |
| R | | | | | | | | | | 3 | | | | | | | | | 351 |
| S | | | 1 | | 1 | | 2 | | | | | | | | | | 40 | 39 | 1545 |
| T | | | | | | | 1 | | | | | 40 | 8 | | 39 | | | | 604 |
| V | | | | | | | 11 | | | | | | | 40 | | 41 | | | 594 |
| W | 1 | | 1 | 1 | | | | 43 | | | | | | | | | | | 432 |
| X | | | | | | | | | | | | | | | | | | | |
| Y | 8 | 9 | 9 | 10 | | 1 | 13 | | | | | | | | | | | | 738 |
| Z | | | | | | | | | | | | | | | | | | | |
| — | 31 | 32 | 30 | 22 | 7 | 2 | 2 | | | | | | | | | | | | 635 |
| unknown (?) | | 1 | 1 | 1 | | | | | | | | | | | | | | | 4 |
| not sequenced | 52 | 52 | 52 | 52 | 53 | 52 | 52 | 54 | 56 | 56 | 56 | 56 | 56 | 56 | 56 | 56 | 56 | 57 | 1678 |
| sum of seq² | 45 | 45 | 45 | 45 | 44 | 45 | 45 | 43 | 41 | 41 | 41 | 41 | 41 | 41 | 41 | 41 | 41 | 40 | |
| oomcaa³ | 31 | 32 | 30 | 22 | 26 | 37 | 13 | 43 | 41 | 34 | 41 | 40 | 25 | 40 | 39 | 41 | 40 | 39 | |
| mcaa⁴ | — | — | — | — | F | D | Y | W | G | Q | G | T | L | V | T | V | S | S | |
| rel. oomcaa⁵ | 69% | 71% | 67% | 49% | 59% | 82% | 29% | 100% | 100% | 83% | 100% | 98% | 61% | 98% | 95% | 100% | 98% | 98% | |
| pos occupied⁶ | 8 | 4 | 6 | 6 | 4 | 5 | 10 | 1 | 1 | 4 | 1 | 2 | 3 | 2 | 2 | 1 | 2 | 2 | |

TABLE 6G

Analysis of V heavy chain subgroup 6

| | Framework I | | | | | | | | | | | | | | | | | | |
|---|---|---|---|---|---|---|---|---|---|---|---|---|---|---|---|---|---|---|---|
| amino acid¹ | 1 | 2 | 3 | 4 | 5 | 6 | 7 | 8 | 9 | 10 | 11 | 12 | 13 | 14 | 15 | 16 | 17 | 18 | 19 |
| A | | | | | | | | | | | | 1 | | | | | | | |
| B | | | | | | | | | | | | | | | | | | | |
| C | | | | | | | | | | | | | | | | | | | |
| D | | | | | | | | | | | | | | | | | | | |
| E | | | | | | | | | | | | | | | | | | | |
| F | | | | | | | | | | | | | | | | | | | |
| G | | | | | | | | 52 | | 67 | | | | | | | | | |
| H | | | | | | | | | | | | | | | | | | | |
| I | | | | | | | | | | | | | | | | | | | |
| K | | | | | | | | | | | | | 68 | | | | | | |
| L | | | | 52 | | | | | | | 68 | 1 | | | | | | 67 | 1 |
| M | | | | | | | | | | | | | | | | | | | |
| N | | | | | | | | | | | | | | | | | | | |
| P | | | | | | | | | 68 | | | | | 67 | | | | | 1 |
| Q | 52 | | 52 | | 51 | 52 | | | | | | | | | | 68 | | | |

TABLE 6G-continued

Analysis of V heavy chain subgroup 6

| | | | | | | | | | | | | | | | | | | | |
|---|---|---|---|---|---|---|---|---|---|---|---|---|---|---|---|---|---|---|---|
| R | | | | | 1 | | | | | 1 | | | | | | | | | |
| S | | | | | | | 52 | | | | | | | 1 | 68 | | | | 66 |
| T | | | | | | | | | | | | | | | | | | 1 | |
| V | | | | | | | | | | | | | | | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | 22 | 22 | 22 | 22 | 22 | 22 | 22 | 22 | 6 | 6 | 6 | 6 | 6 | 6 | 6 | 6 | 6 | 6 | 6 |
| sum of seq[2] | 52 | 52 | 52 | 52 | 52 | 52 | 52 | 52 | 68 | 68 | 68 | 68 | 68 | 68 | 68 | 68 | 68 | 68 | 68 |
| oomcaa[3] | 52 | 52 | 52 | 52 | 51 | 52 | 52 | 52 | 68 | 67 | 68 | 66 | 68 | 67 | 68 | 68 | 68 | 67 | 66 |
| mcaa[4] | Q | V | Q | L | Q | Q | S | G | P | G | L | V | K | P | S | Q | T | L | S |
| rel. oomcaa[5] | 100% | 100% | 100% | 100% | 98% | 100% | 100% | 100% | 100% | 99% | 100% | 97% | 100% | 99% | 100% | 100% | 100 | 99% | 97% |
| pos occupied[6] | 1 | 1 | 1 | 1 | 2 | 1 | 1 | 1 | 1 | 2 | 1 | 3 | 1 | 2 | 1 | 1 | 1 | 2 | 3 |

| | Framework I | | | | | | | | | | | CDR I | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |
| A | | 1 | | 67 | | | | | | | | | | | 66 | 67 | | | |
| B | | | | | | | | | | | | | | | | | | | |
| C | | | 68 | | | | | | | | | | | | | | | | |
| D | | | | | | | | 68 | | | | 1 | | | | | | 1 | |
| E | | | | | | | | | | | | | | | | | | | |
| F | | | | | | | | | | | 2 | | | | 1 | 1 | | | |
| G | | | | 1 | | | 69 | | | | | | | 3 | 1 | 2 | | | |
| H | | | | | | | | | | | | | | | | | | 1 | |
| I | | | | | 64 | | | | | | | | 2 | | | | | 1 | |
| K | | | | | | | | | | | | | 3 | | | | | | |
| L | 68 | | | | | | | | | | | | | | | | | | |
| M | | | | | | | | | | | | | | | | | | | |
| N | | | | | | | | 1 | | | | 2 | 66 | | | | | 70 | |
| P | | | | | | | | | | | | | | | | | | | |
| Q | | | | | | | | | | | | | | | | | | | |
| R | | | | | | | | | | | | 2 | 1 | | | | | | |
| S | | 1 | | | 1 | 69 | | | 69 | | 68 | 66 | | 67 | | 3 | | 1 | |
| T | | 67 | | | | | | | | | | 2 | 1 | 4 | | 1 | | | |
| V | | | | 1 | 4 | | | | | 70 | | | | | 6 | | | | |
| W | | | 1 | | | | | | | | | | | | | | 74 | | 74 |
| X | | | | | | | | | | | | | | | | | | | |
| Y | | | | | | | | | | | | | 1 | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | 6 | 5 | 5 | 5 | 5 | 5 | 5 | 5 | 5 | 4 | 4 | | | | | | | | |
| sum of seq[2] | 68 | 69 | 69 | 69 | 69 | 69 | 69 | 69 | 69 | 70 | 70 | 74 | 74 | 74 | 74 | 74 | 74 | 74 | 74 |
| oomcaa[1] | 68 | 67 | 68 | 67 | 64 | 69 | 69 | 68 | 69 | 70 | 68 | 66 | 66 | 67 | 66 | 67 | 74 | 70 | 74 |
| mcaa[4] | L | T | C | A | I | S | G | D | S | V | S | S | N | S | A | A | W | N | W |
| rel. oomcaa[5] | 100% | 97% | 99% | 97% | 93% | 100% | 100% | 99% | 100% | 100% | 97% | 89% | 89% | 91% | 89% | 91% | 100% | 95% | 100% |
| pos occupied[6] | 1 | 3 | 2 | 3 | 3 | 1 | 1 | 2 | 1 | 1 | 2 | 5 | 6 | 3 | 4 | 5 | 1 | 5 | 1 |

| | Framework II | | | | | | | | | | | | | | CDR II | | | | |
|---|---|---|---|---|---|---|---|---|---|---|---|---|---|---|---|---|---|---|---|
| amino acid[1] | 37 | 38 | 39 | 40 | 41 | 42 | 43 | 44 | 45 | 46 | 47 | 48 | 49 | 50 | 51 | 52 | A | B | C |
| A | | | | | | 1 | | | | | | | | | 1 | | | | |
| B | | | | | | | | | | | | | | | | | | | |
| C | | | | | | | | | | | | | | | | | | | |
| D | | | | | | | | | | | | | | | | | | | |
| E | | | | | | | | | | 74 | | | | | | | | | |
| F | 1 | | | | | | | | | | | | | | | 2 | 1 | | |
| G | | | | | | | | 74 | | | | | 74 | 1 | | | | | |
| H | | | | | | | | | | | | | | | | | 1 | | |
| I | 70 | | | | | | | | | | | | | | | | | | |
| K | | | 1 | | | | 1 | | | | | | | | | | | 1 | |
| L | | | 1 | | | | | | 74 | | | 74 | | | | | | | |
| M | | | | | | | | | | | | | | | | | | | |
| N | | | | | | | | | | | | | | | | | | | |
| P | | | | | 73 | | | | | | | | | | | | | | |
| Q | | | 72 | | | | | | | | | | | | | | | | |
| R | | 74 | | | | | 73 | | | | | | | 73 | | | | 72 | |

TABLE 6G-continued

Analysis of V heavy chain subgroup 6

| | | | | | | | | | | | | | | | | | | | |
|---|---|---|---|---|---|---|---|---|---|---|---|---|---|---|---|---|---|---|---|
| S | | | | 74 | 1 | 73 | | | | | | | | | | | | 1 | |
| T | | | | | | | | | | | | | | | 73 | | | | |
| V | 2 | | | | | | | | | | | | | | | | | | |
| W | | | | | | | | | | | 74 | | | | | | | | |
| X | | | | | | | | | | | | | | | | | | | |
| Y | 1 | | | | | | | | | | | | | | | 72 | 72 | | |
| Z | | | | | | | | | | | | | | | | | | | |
| — | | | | | | | | | | | | | | | | | | | 74 |
| unknown (?) | | | | | | | | | | | | | | | | | | | |
| not sequenced | | | | | | | | | | | | | | | | | | | |
| sum of seq[2] | 74 | 74 | 74 | 74 | 74 | 74 | 74 | 74 | 74 | 74 | 74 | 74 | 74 | 74 | 74 | 74 | 74 | 74 | 74 |
| oomcaa[3] | 70 | 74 | 72 | 74 | 73 | 73 | 73 | 74 | 74 | 74 | 74 | 74 | 74 | 73 | 73 | 72 | 72 | 72 | 74 |
| mcaa[4] | I | R | Q | S | P | S | R | G | L | E | W | L | G | R | T | Y | Y | R | — |
| rel. oomcaa[5] | 95% | 100% | 97% | 100% | 99% | 99% | 99% | 100% | 100% | 100% | 100% | 100% | 100% | 99% | 99% | 97% | 97% | 97% | 100% |
| pos occupied[6] | 4 | 1 | 3 | 1 | 2 | 2 | 2 | 1 | 1 | 1 | 1 | 1 | 1 | 2 | 2 | 2 | 3 | 3 | 1 |

| | CDR II | | | | | | | | | | | | | | Framework III | | | | |
|---|---|---|---|---|---|---|---|---|---|---|---|---|---|---|---|---|---|---|---|
| amino acid[1] | 53 | 54 | 55 | 56 | 57 | 58 | 59 | 60 | 61 | 62 | 63 | 64 | 65 | 66 | 67 | 68 | 69 | 70 | 71 |
| A | 1 | | | | | | | 73 | 1 | | | | | | | 2 | | | 6 |
| B | | | | | | | | | | | | | | | | | | | |
| C | | | | | | | 1 | | | | | | | | | | | | |
| D | | | | | | 68 | | | 1 | | | | | | | | | 2 | |
| E | | | | 1 | | 3 | | | 7 | | | 1 | | | | | | | |
| F | 1 | | | 7 | | | | | | | | | | | | | | | |
| G | | 1 | | | | 1 | | | | 1 | | | 8 | | | | | | |
| H | | | | 1 | | | | | | | | | | | | | | | |
| I | | | | | | | | | 1 | | | | | | 65 | 2 | 71 | | |
| K | | 66 | | | 1 | | | | | | | 67 | | | | | | 1 | |
| L | | | | 1 | | | | | 5 | | 2 | | | | 4 | | | | |
| M | | | | | | | | | | | | | | | 1 | | | | |
| N | | 1 | | 2 | 65 | 1 | | | | | | 1 | | | | | | 69 | |
| P | | | | | | | | 1 | 1 | | | | | | | | | | 66 |
| Q | | | | | | | | | | | | 2 | | 1 | | | | | |
| R | | 1 | 1 | | 1 | | | | | | | 3 | | 73 | | | | | |
| S | 72 | | | 2 | 2 | 1 | 1 | | | 73 | | | 66 | | | 1 | | 2 | 1 |
| T | | 5 | | | 4 | | | | | | | | | | | 69 | 1 | | |
| V | | | | | | | | | 58 | | 72 | | | | 4 | | 2 | | 1 |
| W | | | 73 | | | | | | | | | | | | | | | | |
| X | | | | | | | | | | | | | | | | | | | |
| Y | | | | 60 | 1 | | 72 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 74 | 74 | 74 | 74 | 74 | 74 | 74 | 74 | 74 | 74 | 74 | 74 | 74 | 74 | 74 | 74 | 74 | 74 | 74 |
| oomcaa[3] | 72 | 66 | 73 | 60 | 65 | 68 | 72 | 73 | 58 | 73 | 72 | 67 | 66 | 73 | 65 | 69 | 71 | 69 | 66 |
| mcaa[1] | S | K | W | Y | N | D | Y | A | V | S | V | K | S | R | I | T | I | N | P |
| rel. oomcaa[5] | 97% | 89% | 99% | 81% | 88% | 92% | 97% | 99% | 78% | 99% | 97% | 91% | 89% | 99% | 88% | 93% | 96% | 93% | 89% |
| pos occupied[6] | 3 | 5 | 2 | 7 | 6 | 5 | 3 | 2 | 7 | 2 | 2 | 5 | 2 | 2 | 4 | 4 | 3 | 4 | 4 |

| | Framework III | | | | | | | | | | | | | | | | | | |
|---|---|---|---|---|---|---|---|---|---|---|---|---|---|---|---|---|---|---|---|
| amino acid[1] | 72 | 73 | 74 | 75 | 76 | 77 | 78 | 79 | 80 | 81 | 82 | A | B | C | 83 | 84 | 85 | 86 | 87 |
| A | | 1 | | | | | | | | | | | | | | | 1 | | |
| B | | | | | | | | | | | | | | | | | | | |
| C | | | | | | | | | | | | | | | | | | | |
| D | 73 | | | | | | | | | | | 3 | | | | | | 73 | |
| F | | | | | | | 71 | | | | | | 1 | | | | | | |
| G | | | | | | | | | | | | | | | | | | 1 | |
| H | 1 | | | | | | | | | 2 | | 1 | | | | | | | |
| I | | 1 | | | | | 1 | | | | | | | | | | | | |
| K | | | | 70 | | | | | | | | 4 | | | | | | | |
| L | | 1 | | | | 1 | | | 74 | | 72 | | | | | | | | |
| M | | | | | | | | | | | 1 | | | 1 | | | | | |
| N | | | | | 74 | | | | | | | 63 | | | | | | | |
| P | | | | | | | | | | | | | | | | 70 | | | |
| Q | | | | | | 72 | | | | 71 | | | | | | | | | |
| R | | | | | | 1 | | | | 1 | | 1 | | | | | | | |
| S | | | 73 | | | | | 74 | | | | 1 | 73 | | 1 | 3 | | | |
| T | | 71 | 1 | 2 | | | | | | | | 1 | | | 73 | | | | |

TABLE 6G-continued

Analysis of V heavy chain subgroup 6

| | | | | | | | | | | | | | | | | | | | |
|---|---|---|---|---|---|---|---|---|---|---|---|---|---|---|---|---|---|---|---|
| V | | | | | | | 2 | | | | 1 | | | 73 | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | 1 | | | |
| sum of seq[2] | 74 | 74 | 74 | 74 | 74 | 74 | 74 | 74 | 74 | 74 | 74 | 74 | 74 | 74 | 74 | 73 | 74 | 74 | 74 |
| oomcaa[3] | 73 | 71 | 73 | 70 | 74 | 72 | 71 | 74 | 74 | 71 | 72 | 63 | 73 | 73 | 73 | 70 | 73 | 73 | 74 |
| mcaa[4] | D | T | S | K | N | Q | F | S | L | Q | L | N | S | V | T | P | E | D | T |
| rel. oomcaa[5] | 99% | 96% | 99% | 95% | 100% | 97% | 96% | 100% | 100% | 96% | 97% | 85% | 99% | 99% | 99% | 96% | 99% | 99% | 100% |
| pos occupied[6] | 2 | 4 | 2 | 3 | 1 | 3 | 3 | 1 | 1 | 3 | 3 | 7 | 2 | 2 | 2 | 2 | 2 | 2 | 1 |

| | Framework III | | | | | CDR III | | | | | | | | | | | | | |
|---|---|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 74 | | | | | 69 | | 11 | 1 | 3 | 12 | 4 | 3 | 2 | 5 | | 8 | | |
| B | | | | | | | | | | | | | | | | | | | |
| C | | | | | 73 | | | | | 1 | | 1 | | | 1 | | 1 | 1 | |
| D | | | | | | | | 19 | 4 | 3 | 7 | 4 | 3 | 1 | 6 | 1 | 1 | 1 | |
| E | | | | | | | | 10 | 4 | 2 | 1 | 2 | 2 | 1 | 2 | | | | |
| F | | | | 3 | | 1 | | 1 | 1 | 1 | | 1 | 2 | 3 | | 2 | | | 1 |
| G | | | | | | 1 | | 16 | 4 | 15 | 15 | 11 | 8 | 6 | 2 | 5 | 1 | 8 | 6 |
| H | | | | | | | | | 1 | | 1 | | | 1 | 1 | 1 | 1 | | |
| I | | 2 | | | | | | | 1 | 2 | | 2 | | 5 | 1 | | | | |
| K | | | | | | | 1 | 1 | 1 | 1 | 1 | 1 | 1 | | | | 1 | | |
| L | | | | | | | | 1 | 8 | 4 | 2 | 3 | 2 | 1 | | | | | 1 |
| M | | 2 | | | | | | | 1 | | | | 1 | | | 5 | | | |
| N | | | | 1 | | | | 1 | 3 | 1 | 2 | 1 | 1 | 1 | 3 | | 2 | | 1 |
| P | | | | | | | | | 10 | 4 | | 5 | 3 | | 5 | 1 | | 1 | |
| Q | | | | | | | | 1 | 1 | 1 | 1 | | | | | 1 | | | |
| R | | | | | 1 | | 69 | 1 | 7 | 8 | 1 | 8 | 8 | 3 | | 1 | 1 | 5 | |
| S | | | | | | | 3 | 5 | 5 | 5 | 7 | 6 | 7 | 3 | 4 | 2 | | | |
| T | | | 1 | | | | | 1 | 1 | 4 | 3 | 4 | 4 | 6 | 3 | 1 | | | 1 |
| V | | 70 | | | | 3 | 1 | 4 | 5 | 1 | 9 | | | 4 | | 9 | 5 | 1 | 1 |
| W | | | | | | | | 1 | 6 | 8 | | 3 | 2 | 4 | | | | | |
| X | | | | | | | | | | | | | | | | | | | |
| Y | | | 73 | 70 | | | | | 6 | 4 | 2 | 2 | 2 | 6 | 6 | 2 | 4 | 2 | 1 |
| Z | | | | | | | | | | | | | | | | | | | |
| — | | | | | | | | | 2 | 3 | 7 | 14 | 23 | 25 | 33 | 41 | 47 | 53 | 54 |
| unknown (?) | | | | | | | | | | | | | | | | | | | 6 |
| not sequenced | | | | | | | | | 1 | 2 | 2 | 1 | 1 | 1 | 1 | 1 | 1 | 1 | 1 |
| sum of seq[2] | 74 | 74 | 74 | 74 | 74 | 74 | 74 | 73 | 72 | 71 | 71 | 72 | 72 | 72 | 72 | 72 | 72 | 72 | 72 |
| oomcaa[3] | 74 | 70 | 73 | 70 | 73 | 69 | 69 | 19 | 10 | 15 | 15 | 14 | 23 | 25 | 33 | 41 | 47 | 53 | 54 |
| mcaa[4] | A | V | Y | Y | C | A | R | D | P | G | G | — | — | — | — | — | — | — | — |
| rel. oomcaa[5] | 100% | 95% | 99% | 95% | 99% | 93% | 93% | 26% | 14% | 21% | 21% | 19% | 32% | 35% | 46% | 57% | 65% | 74% | 75% |
| pos occupied[6] | 1 | 3 | 2 | 3 | 2 | 4 | 4 | 14 | 20 | 19 | 15 | 17 | 16 | 16 | 13 | 13 | 11 | 8 | 8 |

| | CDR III | | | | | Framework IV | | | | | | | | | | | | | |
|---|---|---|---|---|---|---|---|---|---|---|---|---|---|---|---|---|---|---|---|
| amino acid[1] | G | H | I | J | K | 101 | 102 | 103 | 104 | 105 | 106 | 107 | 108 | 109 | 110 | 111 | 112 | 113 | sum |
| A | | | | 10 | 1 | | | | | | | | 2 | | | | | | 494 |
| B | | | | | | | | | | | | | | | | | | | |
| C | | | | | | | | | | | | | | | | | | | 147 |
| D | | | | | | 62 | | | | | | | | 1 | | | | | 403 |
| E | | | 1 | | | | | | | | | | | | | | | | 186 |
| F | | | | | 38 | 4 | 2 | | | | | | | | | | 2 | | 150 |
| G | 1 | | | 17 | | | | | 49 | | 50 | | | | | | | | 571 |
| H | | 1 | 1 | 1 | | | 2 | | | | | | | | | | | | 18 |
| I | | | | | | | 9 | | | | | 3 | | 1 | | | | | 304 |
| K | | | | | | | | | | 1 | | | 1 | | | | | | 293 |
| L | 5 | | | | 8 | | 5 | | | | | | 26 | | | | | | 632 |
| M | | | | | 11 | | | | | | | | 8 | | | | | | 31 |
| N | | 1 | 3 | | | | | | | | | | | | | | | | 436 |
| P | | | | | | | 4 | | | 6 | | | | | | | | 1 | 387 |
| Q | | | | | | 1 | | | | 40 | | | | | | | | | 539 |
| R | | | | | | 1 | | | | 2 | | | | | | | | | 495 |
| S | | 1 | 1 | | | | 4 | | 1 | | | 1 | | | | | 43 | 46 | 1271 |
| T | | | | | | | | | | | | 45 | 4 | | 45 | | | | 640 |
| V | | | | | 2 | | 21 | | | | | | 2 | 46 | | 48 | | | 647 |

TABLE 6G-continued

Analysis of V heavy chain subgroup 6

| | | | | | | | | | | | | | | | | | | | |
|---|---|---|---|---|---|---|---|---|---|---|---|---|---|---|---|---|---|---|---|
| W | | | 4 | 4 | | | | 65 | | | | | 5 | | | | | | 398 |
| X | | | | | | | | | | | | | | | | | | | |
| Y | 8 | 8 | 12 | 12 | | | 19 | | | | | | | | | | | | 518 |
| Z | | | | | | | | | | | | | | | | | | | |
| — | 57 | 56 | 50 | 28 | 12 | 4 | 2 | | | | | | | | | | | | 585 |
| unknown (?) | 1 | 5 | | | | | | | | | | | | | | | | | 13 |
| not sequenced | 1 | 1 | 1 | 1 | 1 | 1 | 5 | 8 | 23 | 24 | 23 | 24 | 25 | 25 | 28 | 25 | 28 | 26 | 580 |
| sum of seq[2] | 72 | 72 | 72 | 72 | 72 | 72 | 68 | 65 | 50 | 49 | 50 | 49 | 48 | 48 | 45 | 48 | 45 | 47 | |
| oomcaa[3] | 57 | 56 | 50 | 28 | 38 | 62 | 21 | 65 | 49 | 40 | 50 | 45 | 26 | 46 | 45 | 48 | 43 | 46 | |
| mcaa[4] | — | — | — | — | F | D | V | W | G | Q | G | T | L | V | T | V | S | S | |
| rel. oomcaa[5] | 79% | 78% | 69% | 39% | 53% | 86% | 31% | 100% | 98% | 82% | 100% | 92% | 54% | 96% | 100% | 100% | 96% | 98% | |
| pos occupied[6] | 4 | 5 | 7 | 6 | 6 | 5 | 9 | 1 | 2 | 4 | 1 | 3 | 7 | 3 | 1 | 1 | 2 | 2 | |

APPENDIX TO TABLES 1A–C

A. References of Rearranged Sequences

References of Rearranged Human Kappa Sequences Used for Alignment

1 Alescio-Zonta, L. Et Baglioni, C. (1970) Eur.J.Biochem., 15, 450–463.

2 Andrews, D. W. Et Capra, J. D. (1981) Biochemistry, 20, 5816–5822.

3 Andris, J. S., Ehrlich, P. H., Ostberg, L. Et Capra, J. D. (1992) J.Immunol., 149, 4053–4059.

4 Atkinson, P. M., Lampman, G. W., Furie, B. C., Naparstek, Y., Schwartz, R. S., Stollar, B. D. Et Furie, B. (1985) J.Clin.Invest., 75, 1138–1143.

5 Aucouturier, P., Bauwens, M., Khamlichi, A. A., Denoroy, L., Spinelli, S., Touchard, G., Preud'homme, J.-L. Et Cogne, M. (1993) J.Immunol., 150, 3561–3568.

6 Avila, M. A., Vazques, J., Danielsson, L., Fernandez De Cossio, M. E. Et Borrebaeck, C. A. K. (1993) Gene, 127, 273–274.

7 Barbas Iii, C. F., Crowe, Jr., J. E., Cababa, D., Jones, T. M., Zebedee, S. L., Murphy, B. R., Chanock, R. M. Et Burton, D. R. (1992) Proc.Natl.Acad.Sci.Usa, 89, 10164–10168.

8 Barbas, C. F., Iii, et al. (1993) J-Mol-Biol., 230, 812–23.

9 Bentley, D. L. Et Rabbitts, T. H. (1980) Nature, 288, 730–733.

10 Bentley, D. L. Et Rabbitts, T. H. (1983) Cell, 32, 181–189.

11 Bentley, D. L. (1984) Nature, 307, 77–80.

12 Bhat, N. M., Bieber, M. M., Chapman, C. J., Stevenson, F. K. Et Teng, N. N. H. (1993) J.Immunol., 151, 5011–5021.

13 Blaison, G., Kuntz, J.-L. Et Pasquali, J.-L. (1991) Eur.J.Immunol., 21, 1221–1227.

14 Braun, H., Leibold, W., Barnikol, H. U. Et Hilschmann, N. (1971) Z.Physiol.Chem., 352, 647–651; (1972) Z.Physiol.Chem., 353, 1284–1306.

15 Capra, J. D. Et Kehoe, J. M. (1975) Adv.Immunology, 20, 1–40.; Andrews, D. W. Et Capra, J. D. (1981) Proc.Nat.Acad.Sci.Usa, 78, 3799–3803.

16 Capra, J. D. Et Kehoe, J. M. (1975) Adv.Immunology, 20, 1–40.; Ledford, D. K., Goni, F., Pizzolato, M., Franklin, E. C., Solomon, A. Et Frangione, B. (1983) J.Immunol., 131, 1322–1325.

17 Chastagner, P., Theze, J. Et Zouali, M. (1991) Gene, 101, 305–306.

18 Chen, P. P., Robbins, D. L., Jirik, F. R., Kipps, T. J. Et Carson, D. A. (1987) J.Exp.Med, 166, 1900–1905.

19 Chen, P. P., Robbins, D. L., Jirik, F. R., Kipps, T. J. Et Carson, D. A. (1987) J.Exp.Med, 166, 1900–1905; Liu, M.-F., Robbins, D. L., Crowley, J. J., Sinha, S., Kozin, F., Kipps, T. J., Carson, D. A. Et Chen, P. P. (1989) J.Immunol., 142, 688–694.

20 Chersi, A. Et Natali, P. G. (1978) Immunochemistry, 15, 585–589.

21 Co, M. S., Deschamps, M., Whitley, R. J. Et Queen, C. (1991) Proc.Natl.Acad.Sci.Usa, 88, 2869–2873.

22 Cuisinier, A.-M., Fumoux, F., Fougereau, M. Et Tonnelle, C. (1992) Mol.Immunol., 29, 1363–1373.

23 Davidson, A., Manheimer-Lory, A., Aranow, C., Peterson, R., Hannigan, N. Et Diamond, B. (1990) J.Clin.Invest., 85, 1401–1409.

24 Denomme, G. A., Mahmoudi, M., Edwards, J. Y., Massicotte, H., Cairns, E. Et Bell, D. A. (1993) Hum.Antibod.Hybridomas, 4, 98–103.

25 Dersimonian, H., Mcadam, K. P. W. J., Mackworth-Young, C. Et Stollar, B. D. (1989) J.Immunol., 142, 4027–4033.

26 Dreyer, W. J., Gray, W. R. Et Hood, L. (1967) Cold Spring Harbor Symp. Quantitative Biol., 32, 353–367.

27 Ebeling, S. B., Schutte, M. E. M. Et Logtenberg, T. (1993) Eur.J.Immunol., 23, 1405–1408.

28 Eulitz, M. Et Kley, H.-P. (1977) Immunochem., 14, 289–297.

29 Eulitz, M. Et Linke, R. P. (1982) Z.Physiol.Chem., 363, 1347–1358.

30 Eulitz, M., Breuer, M., Eblen, A., Weiss, D. T. Et Solomon, A. (1990) In Amyloid And Amyloidosis, Eds. J. B. Natvig, O. Forre, G. Husby, A. Husebekk, B. Skogen, K. Sletten Et P. Westermark, Kluwer Academic.

31 Eulitz, M., Gotze, D. Et Hilschmann, N. (1972) Z.Physiol.Chem., 353, 487–491; Eulitz, M. Et Hilschmann, N. (1974) Z.Physiol.Chem., 355, 842–866.

32 Eulitz, M., Kley, H. P. Et Zeitler, H. J. (1979) Z.Physiol.Chem., 360, 725–734.

33 Ezaki, I., Kanda, H., Sakai, K., Fukui, N., Shingu, M., Nobunaga, M. Et Watanabe, T. (1991) Arthritis And Rheumatism, 34, 343–350.

34 Felgenhauer, M., Kohl, J. Et Ruker, F. (1990) Nucl.Acids Res., 18, 4927.

35 Ferri, G., Stoppini, M., Iadarola, P., Bellotti, V. Et Merlini, G. (1989) Biochim.Biophys.Acta, 995, 103–108.

36 Gillies, S. D., Dorai, H., Wesolowski, J., Majeau, G., Young, D., Boyd, J., Gardner, J. Et James, K. (1989) Bio/Tech., 7, 799–804.

37 Goni, F. Et Frangione, B. (1983) Proc.Nat.Acad.Sci.Usa, 80, 4837–4841.

38 Goni, F. R., Chen, P. P., Mcginnis, D., Arjonilla, M. L., Fernandez, J., Carson, D., Solomon, A., Mendez, E. Et Frangione, B. (1989) J.Immunol., 142, 3158–3163.

39 Gorman, S. D., Clark, M. R., Routledge, E. G., Cobbold, S. P. Et Waldmann, H. (1991) Proc.Natl.Acad.Sci.Usa, 88, 4181–4185.

40 Gottlieb, P. D., Cunningham, B. A., Rutishauser, U. Et Edelman, G. M. (1970) Biochemistry, 9, 3155–3161.

41 Griffiths, A. D., Malmqvist, M., Marks, J. D., Bye, J. M., Embleton, M. J., Mccafferty, J., Baier, M., Holliger, K. P., Gorick, B. D., Hughes-Jones, N. C., Hoogenboom, H. R. Et Winter, G. (1993) Embo J., 12, 725–734.

42 Hieter, P. A., Max, E. E., Seidman, J. G., Maizel, J. V., Jr. Et Leder, P. (1980) Cell, 22, 197–207; Klobeck, H. G, Meindl, A., Combriato, G., Solomon, A. Et Zachau, H. G. (1985) Nucl.Acids Res., 13, 6499–6513; Weir, L. Et Leder, P. (1986)

43 Hilschmann, N. Et Craig, L. C. (1965) Proc.Nat.Acad.Sci.Usa, 53, 1403–1409; Hilschmann, N. (1967) Z.Physiol.Chem., 348, 1077–1080.

44 Hilschmann, N. Et Craig, L. C. (1965) Proc.Nat.Acad.Sci.Usa, 53, 1403–1409; Hilschmann, N. (1967) Z.Physiol.Chem., 348, 1718–1722; Hilschmann, N. (1969) Naturwissenschaften, 56, 195–205.

45 Hirabayashi, Y., Munakata, Y., Sasaki, T. Et Sano, H. (1992) Nucl.Acids Res., 20, 2601.

46 Jaenichen, H.-R., Pech, M., Lindenmaier, W., Wildgruber, N. Et Zachau, H. G. (1984) Nuc.Acids Res., 12, 5249–5263.

47 Jirik, F. R., Sorge, J., Fong, S., Heitzmann, J. G., Curd, J. G., Chen, P. P., Goldfien, R. Et Carson, D. A. (1986) Proc.Nat.Acad.Sci.Usa, 83, 2195–2199.

48 Kaplan, A. P. Et Metzger, H. (1969) Biochemistry, 8, 3944–3951; Klapper, D. G. Et Capra, J. D. (1976) Ann.Immunol.(Inst.Pasteur), 127c, 261–271.

49 Kennedy, M. A. (1991) J.Exp.Med., 173, 1033–1036.

50 Kim, H. S. Et Deutsch, H. F. (1988) Immunol., 64, 573–579.

51 Kipps, T. J., Tomhave, E., Chen, P. P. Et Carson, D. A. (1988) J.Exp.Med., 167, 840–852.

52 Kipps, T. J., Tomhave, E., Chen, P. P. Et Fox, R. I. (1989) J.Immunol., 142, 4261–4268.

53 Klapper, D. G. Et Capra, J. D. (1976) Ann.Immunol. (Inst.Pasteur), 127c, 261–271.

54 Klein, U., Kuppers, R. Et Rajewsky, K. (1993) Eur.J.Immunol., 23, 3272–3277.

55 Klobeck, H. G, Meindl, A., Combriato, G., Solomon, A. Et Zachau, H. G. (1985) Nucl.Acids Res., 13, 6499–6513.

56 Klobeck, H. G., Bornkammm, G. W., Combriato, G., Mocikat, R., Pohlenz, H. D. Et Zachau, H. G. (1985) Nucl.Acids Res., 13, 6515–6529.

57 Klobeck, H. G., Combriato, G. Et Zachau, H. G. (1984) Nuc.Acids Res., 12, 6995–7006.

58 Klobeck, H. G., Solomon, A. Et Zachau, H. G. (1984) Nature, 309, 73–76.

59 Knight, G. B., Agnello, V., Bonagura, V., Barnes, J. L., Panka, D. J. Et Zhang, Q.-X. (1993) J.Exp.Med., 178, 1903–1911.

60 Kohler, H., Shimizu, A., Paul, C. Et Putnam, F. W. (1970) Science, 169, 56–59. (Kaplan, A. P. Et Metzger, H. (1969) Biochemistry, 8, 3944–3951.)

61 Kratzin, H., Yang, C. Y., Krusche, J. U. Et Hilschmann, N. (1980) Z.Physiol.Chem., 361, 1591–1598.

62 Kunicki, T. J., Annis, D. S., Gorski, J. Et Nugent, D. J. (1991) J.Autoimmunity, 4, 433–446.

63 Larrick, J. W., Wallace, E. F., Coloma, M. J., Bruderer, U., Lang, A. B. Et Fry, K. E. (1992) Immunological Reviews, 130, 69–85.

64 Laure, C. J., Watanabe, S. Et Hilschmann, N. (1973) Z.Physiol.Chem., 354, 1503–1504.

65 Ledford, D. K., Goni, F., Pizzolato, M., Franklin, E. C., Solomon, A. Et Frangione, B. (1983) J.Immunol., 131, 1322–1325.

66 Ledford, D. K., Goni, F., Pizzolato, M., Franklin, E. C., Solomon, A. Et Frangione, B. (1983) J.Immunol., 131, 1322–1325.

67 Ledford, D. K., Goni, F., Pizzolato, M., Franklin, E. C., Solomon, A. Et Frangione, B. (1983) J.Immunol., 131, 1322–1325. Pons-Estel, B., Goni, F., Solomon, A. Et Frangione, B. (1984) J.Exp.Med., 160, 893.

68 Levy, S., Mendel, E., Kon, S., Avnur, Z. Et Levy, R. (1988) J.Exp.Med., 168, 475–489.

69 Liepnieks, J. J., Dwulet, F. E. Et Benson, M. D. (1990) Mol.Immunol., 27, 481–485.

70 Manheimer-Lory, A., Katz, J. B., Pillinger, M., Ghossein, C., Smith, A. Et Diamond, B. (1991) J.Exp.Med., 174, 1639–1652.

71 Mantovani, L., Wilder, R. L. Et Casali, P. (1993) J.Immunol., 151, 473–488.

72 Mariette, X., Tsapis, A. Et Brouet, J.-C. (1993) Eur.J.Immunol., 23, 846–851.

73 Marks, J. D., Hoogenboom, H. R., Bonnert, T. P., Mccafferty, J., Griffiths, A. D. Et Winter, G. (1991) J.Mol.Biol., 222, 581–597.

74 Marsh, P., Mills, F. Et Gould, H. (1985) Nuc.Acids Res., 13, 6531–6544.

75 Middaugh, C. R. Et Litman, G. W. (1987) J.Biol.Chem., 262, 3671–3673.

76 Milstein, C. Et Deverson, E. V. (1971) Biochem.J., 123, 945–958.

77 Milstein, C. (1969) Febs Letters, 2, 301–304.

78 Milstein, C. (1969) Febs Letters, 2, 301–304.

79 Milstein, C. P. Et Deverson, E. V. (1974) Eur.J.Biochem., 49, 377–391.

80 Moran, M. J., Andris, J. S., Matsumato, Y.-I., Capra, J. D. Et Hersh, E. M. (1993) Mol.Immunol., 30, 1543–1551.

81 Nakatani, T., Nomura, N., Horigome, K., Ohtsuka, H. Et Noguchi, H. (1989) Bio/Tech., 7, 805–810.

82 Nevskirk, M., Chen, P. P., Carson, D., Posnett, D. Et Capra, J. D. (1986) Mol.Immunol., 23, 239–244.

83 Newkirk, M. M., Gram, H., Heinrich, G. F., Ostberg, L., Capra, J. D. Et Wasserman, R. L. (1988) J.Clin.Invest., 81, 1511–1518.

84 Newkirk, M. M., Mageed, R. A., Jefferis, R., Chen, P. P. Et Capra, J. D. (1987) J.Exp.Med., 166, 550–564.

85 Olee, B. T., Lu, E. W., Huang, D.-F., Soto-Gil, R. W., Deftos, M., Kozin, F., Carson, D. A. Et Chen, P. P. (1992) J.Exp.Med., 175, 831–842.

86 Palm, W. Et Hilschmann, N. (1973) Z.Physiol.Chem., 354, 1651–1654; (1975) Z.Physiol.Chem., 356, 167–191.

87 Pascual, V., Victor, K., Lelsz, D., Spellerberg, M. B., Hamblin, T. J., Thompson, K. M., Randen, I., Natvig, J., Capra, J. D. Et Stevenson, F. K. (1991) J.Immunol., 146, 4385–4391.

88 Pascual, V., Victor, K., Randen, I., Thompson, K., Steinitz, M., Forre, O., Fu, S.-M., Natvig, J. B. Et Capra, J. D. (1992) Scand.J.Immunol., 36, 349–362.

89 Pech, M. Et Zachau, H. G. (1984) Nuc.Acids Res., 12, 9229–9236.

90 Pech, M., Jaenichen, H.-R., Pohlenz, H.-D., Neumaier, P. S., Klobeck, H.-G. Et Zachau, H. G. (1984) J.Mol.Biol., 176, 189–204.

91 Pons-Estel, B., Gion, F., Solomon, A. Et Frangione, B. (1984) J.Exp.Med., 160, 893–904.

92 Portolano, S., Mclachlan, S. M. Et Rapoport, B. (1993) J.Immunol., 151, 2839–2851.

93 Portolano, S., Seto, P., Chazenbalk, G. D., Nagayama, Y., Mclachlan, S. M. Et Rapoport, B. (1991) Biochem.Biophys.Res.Commun., 179, 372–377.

94 Pratt, L. F., Rassenti, L., Larrick, J., Robbins, B., Banks, P. M. Et Kipps, T. J. (1989) J.Immunol., 143, 699–705.
95 Prelli, F., Tummolo, D., Solomon, A. Et Frangione, B. (1986) J.Immunol., 136, 4169–4173.
96 Putnam, F. W., Whitley, E. J., Jr., Paul, C. Et Davidson, J. N. (1973) Biochemistry, 12, 3763–3780.
97 Randen, I., Pascual, V., Victor, K., Thompson, K. M., Forre, O., Capra, J. D. Et Natvig, J. B. (1993) Eur.J.Immunol., 23, 1220–1225.
98 Rassenti, L. Z., Pratt, L. F., Chen, P. P., Carson, D. A. Et Kipps, T. J. (1991) J.Immunol., 147, 1060–1066.
99 Reidl, L. S., Friedman, D. F., Goldman, J., Hardy, R. R., Jefferies, L. C. Et Silberstein, L. E. (1991) J.Immunol., 147, 3623–3631.
100 Riechmann, L., Clark, M., Waldmann, H. Et Winter, G. (1988) Nature, 332, 323–327.
101 Riesen, W., Rudikoff, S., Oriol, R. Et Potter, M. (1975) Biochemistry, 14, 1052–1057; Riesen, W. F., Braun, D. G. Et Jaton, J. C. (1976) Proc.Nat.Acad.Sci.Usa, 73, 2096–2100; Riesen, W. F. Et Jaton, J. C. (1976) Biochemistry, 15, 3829.
102 Rodilla Sala, E., Kratzin, D. H., Pick, A. I. Et Hilschmann, N. (1990) In Amyloid And Amyloidosis, Eds. J. B. Natvig, O. Forre, G. Husby, A. Husebekk, B. Skogen, K. Sletten Et P. Westermark, Kluwer Academic.
103 Schiechl, H. Et Hilschmann, N. (1971) Z.Physiol.Chem., 352, 111–115; (1972) Z.Physiol.Chem., 353, 345–370.
104. Schneider, M. Et Hilschmann, N. (1974) Z.Physiol.Chem., 355, 1164–1168.
105 Shearman, C. W., Pollock, D., White, G., Hehir, K., Moore, G. P., Kanzy, E. J. Et Kurrle, R. (1991) J.Immunol., 147, 4366–4373.
106 Shinoda, T. (1973) J.Biochem., 73, 433–446.
107 Shinoda, T. (1975) J.Biochem., 77, 1277–1296.
108 Shinoda, T., Takenawa, T., Hoshi, A. Et Isobe, T. (1990) In Amyloid And Amyloidosis, Eds. J. B. Natvig, O. Forre, G. Husby, A. Husebekk, B. Skogen, K. Sletten Et P. Westermark, Kluwer Academic Publishers, Dordrecht/ Boston/London, Pp.157-.
109 Silberstein, L. E., Litwin, S. Et Carmack, C. E. (1989) J.Exp.Med., 169, 1631–1643.
110 Sims, M. J., Hassal, D. G., Brett, S., Rowan, W., Lockyer, M. J., Angel, A., Lewis, A. P., Hale, G., Waldmann, H. Et Crowe, J. S. (1993) J.Immunol., 151, 2296–2308.
111 Spatz, L. A., Wong, K. K., Williams, M., Desai, R., Golier, J., Berman, J. E., Alt, F. W. Et Latov, N. (1990) J.Immunol., 144, 2821–2828.
112 Stavnezer, J., Kekish, O., Batter, D., Grenier, J., Balazs, I., Henderson, E. Et Zegers, B. J. M. (1985) Nuci.Acids Res., 13, 3495–3514.
113 Straubinger, B., Thiebe, R., Pech, M. Et Zachau, H. G. (1988) Gene, 69, 209–214.
114 Suter, L., Barnikol, H. U., Watanabe, S. Et Hilschmann, N. (1969) Z.Physiol.Chem., 350, 275–278; (1972) Z.Physiol.Chem., 353, 189–208.
115 Tempest, P. R., Bremner, P., Lambert, M., Taylor, G., Furze, J. M., Carr, F. J. Et Harris, W. J. (1991) Bio/Tech., 9, 266–271.
116 Titani, K., Shinoda, T. Et Putnam, F. W. (1969) J.Biol.Chem., 244, 3550–3560.
117 Toft, K. G., Olstad, O. K., Sletten, K. Et Westermark, P. (1990) In Amyloid And Amyloidosis, Eds. J. B. Natvig, O. Forre, G. Husby, A. Husebekk, B. Skogen, K. Sletten Et P. Westermark, Kluwer Academic.
118 Van Es, J. H., Aanstoot, H., Gmelig-Meyling, F. H. J., Derksen, R. H. W. M. Et Logtenberg, T. (1992) J.Immunol., 149, 2234–2240.
119 Victor, K. D., Pascual, V., Lefvert, A. K. Et Capra, J. D. (1992) Mol.Immunol., 29, 1501–1506.
120 Victor, K. D., Pascual, V., Williams, C. L., Lennon, V. A. Et Capra, J. D. (1992) Eur.J.Immunol., 22, 2231–2236.
121 Victor, K. D., Randen, I., Thompson, K., Forre, O., Natvig, J. B., Fu, S. M. Et Capra, J. D. (1991) J.Clin.Invest., 87, 1603–1613.
122 Wagner, S. D. Et Luzzatto, L. (1993) Eur.J.Immunol., 23, 391–397.
123 Watanabe, S. Et Hilschmann, N. (1970) Z.Physiol.Chem., 351, 1291–1295.
124 Weisbart, R. H., Wong, A. L., Noritake, D., Kacena, A., Chan, G., Ruland, C., Chin, E., Chen, I. S. Y. Et Rosenblatt, J. D. (1991) J.Immunol., 147, 2795–2801.
125 Weng, N.-P., Yu-Lee, L.-Y., Sanz, I., Patten, B. M. Et Marcus, D. M. (1992) J.Immunol., 149, 2518–2529.
126 Winkler, T. H., Fehr, H. Et Kalden, J. R. (1992) Eur.J.Immunol., 22, 1719–1728.

References of Rearranged Human Lambda Sequences Used for Alignment

1 Alexandre, D., Chuchana, P., Brockly, F., Blancher, A., Lefranc, G. Et Lefranc, M.-P. (1989) Nuc.Acids Res., 17, 3975.
2 Anderson, M. L. M., Brown, L., Mckenzie, E., Kellow, J. E. Et Young, B. D. (1985) Nuc.Acids Res., 13, 2931–2941.
3 Andris, J. S., Brodeur, B. R. Et Capra, J. D. (1993) Mol.Immunol., 30, 1601–1616.
4 Andris, J. S., Ehrlich, P. H., Ostberg, L. Et Capra, J. D. (1992) J.Immunol., 149, 4053–4059.
5 Baczko, K., Braun, D. G., Hess, M. Et Hilschmann, N. (1970) Z.Physiol.Chem., 351, 763–767; Baczko, K., Braun, D. G. Et Hilschmann, N. (1974) Z.Physiol.Chem., 355, 131–154.
6 Berinstein, N., Levy, S. Et Levy, R. (1989) Science, 244, 337–339.
7 Bhat, N. M., Bieber, M. M., Chapman, C. J., Stevenson, F. K. Et Teng, N. N. H. (1993) J.Immunol., 151, 5011–5021.
8 Cairns, E., Kwong, P. C., Misener, V., Ip, P., Bell, D. A. Et Siminovitch, K. A. (1989) J.Immunol., 143, 685–691.
9 Carroll, W. L., Yu, M., Link, M. P. Et Korsmeyer, S. J. (1989) J.Immunol., 143, 692–698.
10 Chen, B. L. Et Poljak, R. J. (1974) Biochemistry, 13, 1295–1302.
11 Chen, B. L., Chiu, Y. Y. H., Humphrey, R. L. Et Poijak, R. J. (1978) Biochim.Biophys.Acta, 537, 9–21.
12 Combriato, G. Et Klobeck, H. G. (1991) Eur.J.Immunol., 21, 1513–1522.
13 Cuisinier, A.-M., Fumoux, F., Fougereau, M. Et Tonnelle, C. (1992) Mol.Immunol., 29, 1363–1373.
14 Dwulet, F. E., Strako, K. Et Benson, M. D. (1985) Scand.J.Immunol., 22, 653–660.
15 Elahna, P., Livneh, A., Manheimer-Lory, A. J. Et Diamond, B. (1991) J.Immunol., 147, 2771–2776.
16 Engelhard, M., Hess, M. Et Hilschmann, N. (1974) Z.Physiol.Chem., 355, 85–88; Engelhard, M. Et Hilschmann, N. (1975) Z.Physiol.Chem., 356, 1413–1444.
17 Eulitz, M. (1974) Eur.J.Biochem., 50, 49–69.
18 Eulitz, M., Breuer, M. Et Linke, R. P. (1987) Biol.Che.Hoppe-Seyler, 368, 863–870.
19 Eulitz, M., Murphy, C., Weiss, D. T. Et Solomon, A. (1991) J.Immunol., 146, 3091–3096.
20 Fett, J. W. Et Deutsch, H. F. (1974) Biochemistry, 13, 4102–4114.
21 Fett, J. W. Et Deutsch, H. F. (1976) Immunochem., 13, 149–155.; Jabusch, J. R. Et Deutsch, H. F. (1982) Mol.Immunol., 19, 901–906.

22 Furey, W. Jr., Wang, B. C., Yoo, C. S. Et Sax, M. (1983) J.Mol.Biol., 167, 661–692.

23 Fykse, E.-M., Sletten, K., Husby, G. Et Cornwell, G. G., Iii (1988) Biochem.J., 256, 973–980.

24 Garver, F. A. Et Hilschmann, N. (1971) Febs Letters, 16, 128–132; (1972) Eur.J.Biochem., 26, 10–32.

25 Gawinowicz, M. A., Merlini, G., Birken, S., Osserman, E. F. Et Kabat, E. A. (1991) J.Immunol., 147, 915–920.

26 Ghiso, J., Solomon, A. Et Frangione, B. (1986) J.Immunol., 136, 716–719.

27 Griffiths, A. D., Maimqvist, M., Marks, J. D., Bye, J. M., Embleton, M. J., Mccafferty, J., Baier, M., Holliger, K. P., Gorick, B. D., Hughes-Jones, N. C., Hoogenboom, H. R. Et Winter, G. (1993) Embo J., 12, 725–734.

28 Gullasken, N., Idso, H., Nilsen, R., Sletten, K., Husby, G. Et Cornwell, G. G. (1990) In Amyloid And Amyloidosis, Eds. J. B. Natvig, O. Forre, G. Husby, A. Husebekk, B. Skogen, K. Sletten Et P. Westermark, Kluwer Academic.

29 Harindranath, N., Goldfarb, I. S., Ikematsu, H., Burastero, S. E., Wilder, R. L., Notkins, A. L. Et Casali, P. (1991) Int.Immunol., 3, 865–875.

30 Holm, E., Sletten, K. Et Husby, G. (1986) Biochem.J., 239, 545–551.

31 Hughes-Jones, N. C., Bye, J. M., Beale, D. Et Coadwell, J. (1990) Biochem.J., 268, 135–140.

32 Kametani, F., Yoshimura, K., Tonoike, H., Hoshi, A., Shinoda, T. Et Isobe, T. (1985) Biochem.Biophys.Res.Commun., 126, 848–852.

33 Kiefer, C. R., Mcguire, B. S., Jr., Osserman, E. F. Et Garver, F. A. (1983) J.Immunol., 131, 1871–1875.

34 Kiefer, C. R., Patton, H. M., Jr., Mcquire, B. S., Jr. Et Garver, F. A. (1980) J.Immunol., 124, 301–306.

35 Kishimoto, T., Okajima, H., Okumoto, T. Et Taniguchi, M. (1989) Nucl.Acids Res., 17, 4385.

36 Klafki, H.-W., Kratzin, H. D., Pick, A. I., Eckart, K. Et Hilschmann, N. (1990) In Amyloid And Amyloidosis, Eds. J. B. Natvig, O. Forre, G. Husby, A. Husebekk, B. Skogen, K. Sletten Et P. Westermark, Kluwer Academic.

37 Kohler, H., Rudofsky, S. Et Kluskens, L. (1975) J.Immunology, 114, 415–421.

38 Kojima, M., Odani, S. Et Ikenaka, T. (1980) Mol.Immunol., 17, 1407–1414.

39 Komori, S., Yamasaki, N., Shigeta, M., Isojima, S. Et Watanabe, T. (1988) Clin.Exp.Immunol., 71, 508–516.

40 Kratzin, H. D., Palm, W., Stangel, M., Schmidt, W. E., Friedrich, J. Et Hilschmann, N. (1989) Biol.Chem.Hoppe-Seyler, 370, 263–272.

41 Kratzin, H. D., Pick, A. I., Stangel, M. Et Hilschmann, N. (1990) In Amyloid And Amyloidosis, Eds. J. B. Natvig, O. Forre, G. Husby, A. Huscbekk, B. Skogen, K. Sletten Et P. Westermark, Kluwer Academic Publishers, Dordrecht/Boston/London, Pp 181-.

42 Langer, B., Steinmetz-Kayne, M. Et Hilschmnann, N. (1968) Z.Physiol.Chem., 349, 945–951.

43 Larrick, J. W., Danielsson, L., Brenner, C. A., Wallace, E. F., Abrahamson, M., Fry, K. E. Et Borrebaeck, C. A. K. (1989) Bio/Tech., 7, 934–938.

44 Levy, S., Mendel, E., Kon, S., Avnur, Z. Et Levy, R. (1988) J.Exp.Med., 168, 475–489.

45 Lewis, A. P., Lemon, S. M., Barber, K. A., Murphy, P., Parry, N. R., Peakman, T. C., Sims, M. J., Worden, J. Et Crowe, J. S. (1993) J.Immunol., 151, 2829–2838.

46 Liu, V. Y. S., Low, T. L. K., Infante, A. Et Putnam, F. W. (1976) Science, 193, 1017–1020; Infante, A. Et Putnam, F. W. (1979) J.Biol.Chem., 254, 9006–9016.

47 Lopez De Castro, J. A., Chiu, Y. Y. H. Et Poljak, R. J. (1978) Biochemistry, 17, 1718–1723.

48 Mantovani, L., Wilder, R. L. Et Casali, P. (1993) J.Immunol., 151, 473–488.

49 Marks, J. D., Hoogenboom, H. R., Bonnert, T. P., Mccafferty, J., Griffiths, A. D. Et Winter, G. (1991) J.Mol.Biol., 222, 581–597.

50 Mihaesco, E., Roy, J.-P., Congy, N., Peran-Rivat, L. Et Mihaesco, C. (1985) Eur.J.Biochem., 150, 349–357.

51 Milstein, C., Clegg, J. B. Et Jarvis, J. M. (1968) Biochem.J., 110, 631–652.

52 Moran, M. J., Andris, J. S., Matsumato, Y.-I., Capra, J. D. Et Hersh, E. M. (1993) Mol.Immunol., 30,1543–1551.

53 Nabeshima, Y. Et Ikenaka, T. (1979) Mol.Immunol., 16, 439–444.

54 Olee, B. T., Lu, E. W., Huang, D.-F., Soto-Gil, R. W., Deftos, M., Kozin, F., Carson, D. A. Et Chen, P. P. (1992) J.Exp.Med., 175, 831–842.

55 Pascual, V., Victor, K., Randen, I., Thompson, K., Steinitz, M., Forre, 0., Fu, S.-M., Natvig, J. B. Et Capra, J. D. (1992) Scand.J.Immunol., 36, 349–362.

56 Paul, E., Iliev, A. A., Livneh, A. Et Diamond, B. (1992) J.Immunol., 149, 3588–3595.

57 Pick, A. I., Kratzin, H. D., Barnikol-Watanabe, S. Et Hilschmann, N. (1990) In Amyloid And Amyloidosis, Eds. J. B. Natvig, O. Forre, G. Husby, A. Husebekk, B. Skogen, K. Sletten Et P. Westermark, Kluwer Academic.

58 Ponstingl, H. Et Hilschmann, N. (1969) Z.Physiol.Chem., 350, 1148–1152; (1971) Z.Physiol.Chem., 352, 859–877.

59 Ponstingl, H., Hess, M. Et Hilschmann, N. (1968) Z.Physiol.Chem., 349, 867–871; (1971) Z.Physiol.Chem., 352, 247–266.

60 Randen, I., Pascual, V., Victor, K., Thompson, K. M., Forre, O., Capra, J. D. Et Natvig, J. B. (1933) Eur.J.Immunol., 23, 1220–1225.

61 Scholz, R. Et Hilschmann, N. (1975) Z.Physiol.Chem., 356, 1333–1335.

62 Settmacher, U., Jahn, S., Siegel, P., Von Baehr, R. Et Hansen, A. (1993) Mol.Immunol., 30, 953–954.

63 Shinoda, T., Titani, K. Et Putnam, F. W. (1970) J.Biol.Chem., 245, 4475–4487.

64 Sletten, K., Husby, G. at Natvig, J. B. (1974) Scand.J.Immunol., 3, 833–836.; Sletten, K., Natvig, J. B., Husby, G. Et Juul, J. (1981) Biochem.J., 195, 561–572.

65 Solomon, A., Frangione, B. Et Franklin, E. C. (1982) J.Clin.Invest., 70, 453–460.; Frangione, B., Moloshok, T. Et Solomon, A. (1983) J.Immunol., 131, 2490–2493.

66 Takahashi, N., Takayasu, T., Isobe, T., Shinoda, T., Okuyama, T. Et Shimizu, A. (1979) J.Biochem., 86, 1523–1535.

67 Takahashi, N., Takayasu, T., Shinoda, T., Ito, S., Okuyama, T. Et Shimizu, A. (1980) Biomed.Res., 1, 321–333.

68 Takahashi, Y., Takahashi, N., Tetaert, D. Et Putnam, F. W. (1983) Proc.Nat.Acad.Sci.Usa, 80, 3686–3690.

69 Takayasu, T., Takahashi, N., Shinoda, T., Okuyama, . Et Tomioka, H. (1980) J.Biochem., 89, 421–436.

70 Titani, K., Wikler, M., Shinoda, T. Et Putnam, F. W. (1970) J.Biol.Chem., 245, 2171–2176.

71 Toft, K. G., Sletten, K. Et Husby, G. (1985) Biol.Chem.Hoppe-Seyler, 366, 617–625.

72 Tonoike, H., Kametani, F., Hoshi, A., Shinoda, T. Et Isobe, T. (1985) Biochem.Biophys.Res.Commun., 126, 1228–1234.

73 Tonoike, H., Kametani, F., Hoshi, A., Shinoda, T. Et Isobe, T. (1985) Febs Letters, 185, 139–141.

74 Tsujimoto, Y. Et Croce, C. M. (1984) Nucl.Acids Res., 12, 8407–8414.

75 Tsunetsugu-Yokota, Y., Minekawa, T., Shigemoto, K., Shirasawa, T. Et Takemori, T. (1992) Mol.Immunol., 29, 723–728.

76 Tveteraas, T., Sletten, K. Et Westermark, P. (1985) Biochem.J., 232, 183–190.

77 Vasicek, T. J. Et Leder, P. (1990) J.Exp.Med., 172, 609–620.

78 Victor, K. D., Randen, I., Thompson, K., Forre, O., Natvig, J. B., Fu, S. M. Et Capra J. D. (1991) J.Clin.Invest., 87, 1603–1613.

79 Weng, N.-P., Yu-Lee, L.-Y., Sanz, I., Patten, B. M. Et Marcus, D. M. (1992) J.Immunol., 149, 2518–2529.

80 Wikler, M. Et Putnam, F. W. (1970) J.Biol.Chem., 245, 4488–4507.

81 Winkler, T. H., Fehr, H. Et Kalden, J. R. (1992) Eur.J.Immunol., 22, 1719–1728.

82 Yago, K., Zenita, K., Ohwaki, I., Harada, Y., Nozawa, S., Tsukazaki, K., Iwamori, M., Endo, N., Yasuda, N., Okuma, M. Et Kannagi, R. (1993) Mol.Immunol., 30, 1481–1489.

83 Yamasaki, N., Komori, S. Et Watanabe, T. (1987) Mol.Immunol., 24, 981–985.

84 Zhu, D., Kim , H. S. Et Deutsch, H. F. (1983) Mol.Immunol., 20, 1107–11166.

85 Zhu, D., Zhang, H., Zhu, N. Et Luo, X. (1986) Scientia Sinica, 29, 746–755.

References of Rearranged Human Heavy Chain Sequences Used for Alignment

1 Adderson, E. E., Azmi, F. H., Wilson, P. M., Shackelford, P. G. Et Carroll, W. L. (1993) J.Immunol., 151, 800–809.

2 Adderson, E. E., Shackelford, P. G., Quinn, A. Et Carroll, W. L. (1991) J.Immunol., 147, 1667–1674.

3 Akahori, Y., Kurosawa, Y., Kamachi, Y., Torii, S. Et Matsuoka, H. (1990) J.Clin.Invest., 85, 1722–1727.

4 Andris, J. S., Brodeur, B. R. Et Capra, J. D. (1993) Mol.Immunol., 30, 1601–1616.

5 Andris, J. S., Ehrlich, P. H., Ostberg, L. Et Capra, J. D. (1992) J.Immunol., 149, 4053–4059.

6 Andris, J. S., Johnson, S., Zolla-Pazner, S. Et Capra, J. D. (1991) Proc.Natl.Acad.Sci.Usa, 88, 7783–7787.

7 Anker, R., Conley , M. E. Et Pollok, B. A. (1989) J.Exp.Med., 169, 2109–2119.

8 Atkinson, P. M., Lampman, G. W., Furie, B. C., Naparstek, Y., Schwartz, R. S., Stollar, B. D. Et Furie, B. (1985) J.Clin.Invest., 75, 1138–1143; Lampman, G. W., Furie, B., Schwartz, R. S., Stollar, B. D. Et Furie, B. C. (1989).

9 Avila, M. A., Vazques, J., Danielsson, L., Fernandez De Cossio, M. E. Et Borrebaeck, C. A. K. (1993) Gene, 127, 273–274.

10 Bakkus, M. H. C., Heirman, C., Van Riet, I., Van Camp, B. Et Thielemans, K. (1992) Blood, 80, 2326–2335.

11 Barbas Iii, C. F., Crowe, Jr., J. E., Cababa, D., Jones, T. M., Zebedee, S. L., Murphy, B. R., Chanock, R. M. Et Burton, D. R. (1992) Proc.Natl.Acad.Sci.Usa, 89, 10164–10168.

12 Barbas, C. F., Iii, Collet, T. A., Amberg, W., Roben, P., Binley, J. M., Hoekstra, D., Cababa, D., Jones, T. M., Williamson, R. A., Pilkington, G. R., Haigwood, N. L., Cabezas, E., Satterthwait, A. C., Sanz, I. Et Burton, D. R. (1993) J.Mol.Biol., 230, 812–823.

13 Berman, J. E., Humphries, C. G., Barth, J., Alt, F. W. Et Tucker, P. W. (1991) J.Exp.Med., 173, 1529–1535.

14 Berman, J. E., Mellis, S. J., Pollock, R., Smith, C. L., Suh, H., Heinke, B., Kowal, C., Surti, U., Chess, L., Cantor, C. R. Et Alt, F. W. (1988) Embo J., 7, 727–738.

15 Bhat, N. M., Bieber, M. M., Chapman, C. J., Stevenson, F. K. Et Teng, N. N. H. (1993) J.Immunol., 151, 5011–5021.

16 Bird, J., Galili, N., Link, M., Stites, D. Et Sklar, J. (1988) J.Exp.Med., 168, 229–245.

17 Cai, J., Humphries, C., Richardson, A. Et Tucker, P. W. (1992) J.Exp.Med., 176, 1073–1081.

18 Cairns, E., Kwong, P. C., Misener, V., Ip, P., Bell, D. A. Et Siminovitch, K. A. (1989) J.Immunol., 143, 685–691.

19 Capra, J. D. Et Hopper, J. E. (1976) Immunochemistry, 13, 995–999; Hopper, J. E., Noyes, C., Heinrikson, R. Et Kessel, J. W. (1976) J.Immunol., 116, 743–746.

20 Capra, J. D. Et Kehoe, J. M. (1974) Proc.Nat.Acad.Sci.Usa, 71, 845–848.

21 Carroll, W. L., Yu, M., Link, M. P. Et Korsmeyer, S. J. (1989) J.Immunol., 143, 692–698.

22 Chen, P. P., Liu, M.-F., Glass, C. A., Sinha, S., Kipps, T. J. Et Carson, D. A. (1989) Arthritis Et Rheumatism, 32, 72–76; Kipps, T. J., Tomhave, E., Pratt, L. F., Duffy, S., Chen, P. P. Et Carson, D. A. (1989) Proc.Natl.Acad.Sci.Usa, 86, 5913–5917.

23 Chiu, Y. Y. H., Lopez De Castro, J. A. Et Poljak, R. J. (1979) Biochemistry, 18, 553–560.

24 Cleary, M. L., Meeker, T. C., Levy, S., Lee, E., Trela, M., Sklar, J. Et Levy, R. (1986) Cell, 44, 97–106.

25 Cuisinier, A.-M., Fumoux, F., Fougereau, M. Et Tonnelle, C. (1992) Mol.Immunol., 29, 1363–1373.

26 Cuisinier, A.-M., Gauthier, L., Boubli, L., Fougereau, M. Et Tonnelle, C. (1993) Eur.J.Immunol., 23, 110–118.

27 Cunningham, B. A., Gottlieb, P. D., Pflumm, M. N. Et Edelman, G. M. (1971) Progress In Immunology (B. Amos, Ed.), Academic Press, New York., Pp.3–24.

28 Cunningham, B. A., Rutishauser, U., Gall, W. E., Gottlieb, P. D., Waxdal, M. J. Et Edelman, G. M. (1970) Biochemistry, 9, 3161–3170.

29 Deane, M. Et Norton, J. D. (1990) Eur.J.Immunol., 20, 2209–2217.

30 Deane, M. Et Norton, J. D. (1991) Leukemia, 5, 646–650.

31 Dersimonian, H., Schwartz, R. S., Barrett, K. J. Et Stollar, B. D. (1987) J.Immunol., 139, 2496–2501.

32 Dersimonian, H., Schwartz, R. S., Barrett, K. J. Et Stollar, B. D. (1987) J.Immunol., 139, 2496–2501; Chen, P. P., Liu, M.-F., Sinha, S. Et Carson, D. A. (1988) Arth.Rheum., 31, 1429–1431.

33 Desai, R., Spatz, L., Matsuda, T., Ilyas, A. A., Berman, J. E., Alt, F. W., Kabat, E. A. Et Latov, N. (1990) J.Neuroimmunol., 26, 35–41.

34 Ezaki, I., Kanda, H., Sakai, K., Fukui, N., Shingu, M., Nobunaga, M. Et Watanabe, T. (1991) Arthritis And Rheumatism, 34, 343–350.

35 Felgenhauer, M., Kohl, J. Et Ruker, F. (1990) Nucl.Acids Res., 18, 4927.

36 Florent, G., Lehman, D. Et Putnam, F. W. (1974) Biochemistry, 13, 2482–2498.

37 Friedlander, R. M., Nussenzweig, M. C. Et Leder, P. (1990) Nucl.Acids Res., 18, 4278.

38 Gawinowicz, M. A., Merlini, G., Birken, S., Osserman, E. F. Et Kabat, E. A. (1991) J.Immunol., 147, 915–920.

39 Gillies, S. D., Dorai, H., Wesolowski, J., Majeau, G., Young, D., Boyd, J., Gardner, J. Et James, K. (1989) Bio/Tech., 7, 799–804.

40 Goni, F. Et Frangione, B. (1983) Proc.Nat.Acad.Sci.Usa, 80, 4837–4841.

41 Gorman, S. D., Clark, M. R., Routledge, E. G., Cobbold, S. P. Et Waldmann, H. (1991) Proc.Natl.Acad.Sci.Usa, 88, 4181–4185.

42 Griffiths, A. D., Malmqvist, M., Marks, J. D., Bye, J. M., Embleton, M. J., Mccafferty, J., Baier, M., Holliger, K. P., Gorick, B. D., Hughes-Jones, N. C., Hoogenboom, H. R. Et Winter, G. (1993) Embo J., 12, 725–734.

43 Grillot-Courvalin, C., Brouet, J.-C., Piller, F., Rassenti, L. Z., Labaume, S., Silverman, G. J., Silberstein, L. Et Kipps, T. J. (1992) Eur.J.Immunol., 22, 1781–1788.

44 Guillaume, T., Rubinstein, D. B., Young, F., Tucker, L., Logtenberg, T., Schwartz, R. S. Et Barrett, K. L. (1990) J.Immunol., 145, 1934–1945;Young, F., Tucker, L., Rubinstein, D., Guillaume, T., Andre-Schwartz, J., Barrett, K. J., Schwartz, R. S. Et Logtenberg, T. (1990).

45 Harindranath, N., Goldfarb, I. S., Ikematsu, H., Burastero, S. E., Wilder, R. L., Notkins, A. L. Et Casali, P. (1991) Int.Immunol., 3, 865–875.

46 Hillson, J. L., Oppliger, I. R., Sasso, E. H., Milner, E. C. B. Et Wener, M. H. (1992) J.Immunol., 149, 3741–3752.

47 Hirabayashi, Y., Munakata, Y., Sasaki, T. Et Sano, H. (1992) Nucl.Acids Res., 20, 2601.

48 Hoch, S. Et Schwaber, J. (1987) J.Immunol., 139, 1689–1693.

49 Huang, C., Stewart, A. K., Schwartz, R. S. Et Stollar, B. D. (1992) J.Clin.Invest., 89, 1331–1343.

50 Hughes-Jones, N. C., Bye, J. M., Beale, D. Et Coadwell, J. (1990) Biochem.J., 268, 135–140.

51 Ikematsu, H., Harindranath, N., Ueki, Y., Notkins, A. L. Et Casali, P. (1993) J.Immunol., 150, 1325–1337.

52 Ikematsu, H., Kasaian, M. T., Schettino, E. W. Et Casali, P. (1993) J.Immunol., 151, 3604–3616.

53 Kelly, P. J., Pascual, V., Capra, J. D. Et Lipsky, P. E. (1992) J.Immunol., 148, 1294–1301.

54 Kipps, T. J. Et Duffy, S. F. (1991) J.Clin.Invest., 87, 2087–2096.

55 Kipps, T. J., Tomhave, E., Pratt, L. F., Duffy, S., Chen, P. P. Et Carson, D. A. (1989) Proc.Natl.Acad.Sci.Usa, 86, 5913–5917.

56 Kishimoto, T., Okajima, H., Okumoto, T. Et Taniguchi, M. (1989) Nucl.Acids Res., 17, 4385.

57 Knight, G. B., Agnello, V., Bonagura, V., Barnes, J. L., Panka, D. J. Et Zhang, Q.-X. (1993) J.Exp.Med., 178, 1903–1911.

58 Kohler, H., Shimizu, A., Paul, C., Moore, V. Et Putnam, F. W. (1970) Nature, 227, 1318–1320; Florent, G., Lehman, D. Et Putnam, F. W. (1974) Biochemistry, 13, 2482–2498.

59 Komori, S., Yamasaki, N., Shigeta, M., Isojima, S. Et Watanabe, T. (1988) Clin.Exp.Immunol., 71, 508–516.

60 Kon, S., Levy, S. Et Levy, R. (1987) Proc.Natl.Acad.Sci.Usa, 84, 5053–5057.

61 Kratzin, H., Altevogt, P., Ruban, E., Kortt, A., Staroscik, K. Et Hilschmann, N. (1975) Z.Physiol.Chem., 356, 1337–1342; Kratzin, H., Altevogt, P., Kortt, A., Ruban, E. Et Hilschmann, N. (1978) Z.Physiol.Chem., 359, 1717–1745.

62 Kudo, A., Ishihara, T., Nishimura, Y. Et Watanabe, T. (1985) Gene, 33, 181–189.

63 Kunicki, T. J., Annis, D. S., Gorski, J. Et Nugent, D. J. (1991) J.Autoimmunity, 4, 433–446.

64 Larrick, J. W., Wallace, E. F., Coloma, M. J., Bruderer, U., Lang, A. B. Et Fry, K. E. (1992) Immunological Reviews, 130, 69–85.

65 Lehman, D. W. Et Putnam, F. W. (1980) Proc.Nat.Acad.Sci.Usa, 77, 3239–3243.

66 Lewis, A. P., Lemon, S. M., Barber, K. A., Murphy, P., Parry, N. R., Peakman, T. C., Sims, M. J., Worden, J. Et Crowe, J. S. (1993) J.Immunol., 151, 2829–2838.

67 Liu, V. Y. S., Low, T. L. K., Infante, A. Et Putnam, F. W. (1976) Science, 193, 1017–1020.

68 Logtenberg, T., Young, F. M., Van Es, J., Gmelig-Meyling, F. H. J., Berman, J. E. Et Alt, F. W. (1989) J.Autoimmunity, 2, 203–213.

69 Logtenberg, T., Young, F. M., Van Es, J. H., Gmelig-Meyling, F. H. J. Et Alt, F. W. (1989) J.Exp.Med., 170, 1347–1355.

70 Manheimer-Lory, A., Katz, J. B., Pillinger, M., Ghossein, C., Smith, A. Et Diamond, B. (1991) J.Exp.Med., 174, 1639–1652.

71 Mantovani, L., Wilder, R. L. Et Casali, P. (1993) J.Immunol., 151, 473–488.

72 Mariette, X., Tsapis, A. Et Brouet, J.-C. (1993) Eur.J.Immunol., 23, 846–851.

73 Marks, J. D., Hoogenboom, H. R., Bonnert, T. P., Mccafferty, J., Griffiths, A. D. Et Winter, G. (1991) J.Mol.Biol., 222, 581–597.

74 Meeker, T. C., Grimaldi, J., O'rourke, R., Loeb, J. Juliusson, G. Et Einhorn, S. (1988) J.Immol., 141, 3994–3998.

75 Milili, M., Fougereau, M., Guglielmi, P. Et Schiff, C. (1991) Mol.Immunol., 28, 753–761.

76 Moran, M. J., Andris, J. S., Matsumato, Y.-I., Capra, J. D. Et Hersh, E. M. (1993) Mol.Immunol., 30,1543–1551.

77 Mortari, F., Wang, J.-Y. Et Schroeder, Jr., H. W. (1993) J.Immunol., 150, 1348–1357.

78 Newkirk, M. M., Gram, H., Heinrich, G. F., Ostberg, L., Capra, J. D. Et Wasserman, R. L. (1988) J.Clin.Invest., 81, 1511–1518.

79 Newkirk, M. M., Mageed, R. A., Jefferis, R., Chen, P. P. Et Capra, J. D. (1987) J.Exp.Med., 166, 550–564.

80 Nickerson, K. G., Berman, J., Glickman, E., Chess, L. Et Alt, F. W. (1989) J.Exp.Med., 169, 1391–1403.

81 Olee, B. T., Lu, E. W., Huang, D.-F., Soto-Gil, R. W., Deftos, M., Kozin, F., Carson, D. A. Et Chen, P. P. (1992) J.Exp.Med., 175, 831–842.

82 Pascual, V., Randen, I., Thompson, K., Sioud, M. Forre, O., Natvig, J. Et Capra, J. D. (1990) J.Clin.Invest., 86, 1320–1328.

83 Pascual, V., Randen, I., Thompson, K., Sioud, M. Forre, O., Natvig, J. Et Capra, J. D. (1990) J.Clin.Invest., 86, 1320–1328; Randen, I., Brown, D., Thompson, K. M., Hughes-Jones, N., Pascual, V., Victor, K., Capra, J. D., Forre, O. Et Natvig, J. B. (1992).

84 Pascual, V., Victor, K., Lelsz, D., Spellerberg, M. B., Hamblin, T. J., Thompson, K. M., Randen, I., Natvig, J., Capra, J. D. Et Stevenson, F. K. (1991) J.Immunol., 146, 4385–4391.

85 Pascual, V., Victor, K., Randen, I., Thompson, K., Steinitz, M., Forre, O., Fu, S.-M., Natvig, J. B. Et Capra, J. D. (1992) Scand.J.Immunol., 36, 349–362.

86 Pascual, V., Victor, K., Spellerberg, M., Hamblin, T. J., Stevenson, F. K. Et Capra, J. D. (1992) J.Immunol., 149, 2337–2344.

87 Ponstingl, H., Schwarz, J., Reichel, W. Et Hilschmann, N. (1970) Z.Physiol.Chem., 351, 1591–1594; Ponstingl, H. Et Hilschmann, N. (1976) Z.Physiol.Chem., 357, 1571–1604.

88 Portolano, S., Mclachlan, S. M. Et Rapoport, B. (1993) J.Immunol., 151, 2839–2851.

89 Portolano, S., Seto, P., Chazenbalk, G. D., Nagayama, Y., Mclachlan, S. M. Et Rapoport, B. (1991) Biochem.Biophys.Res.Commun., 170, 372–377.

90 Pratt, L. F., Szubin, R., Carson, D. A. Et Kipps, T. J. (1991) J.Immunol., 147, 2041–2046.

91 Press, E. M. Et Hogg, N. M. (1970) Biochem.J., 117, 641–660.

92 Putnam, F. W., Shimizu, A., Paul., C., Shinoda, T. Et Kohler, H. (1971) Ann.N.Y.Acad.Sci., 190, 83–103.

93 Putnam, F. W., Takahashi, N., Tetaert, D., Debuire, B. Et Lin, L. C. (1981) Proc.Nat.Acad.Sci.Usa, 78, 6168–6172;

Takahashi, N., Tetaert, D., Debuire, B., Lin, L. Et Putnam, F. W. (1982) Proc.Nat.Acad.Sci.Usa, 79, 2850–2854.
94 Raaphorst, F. M., Timmers, E., Kenter, M. J. H., Van Tol, M. J. D., Vossen, J. M. Et Schuurman, R. K. B. (1992) Eur.J.Immunol., 22, 247–251.
95 Rabbitts, T. H., Bentley, D. L., Dunnick, W., Forster, A., Matthyssens, G. Et Milstein, C. (1980) Cold Spring Harb.Symp.Quanti.Biol., 45, 867–878; Matthyssens, G. Et Rabbitts, T. H. (1980) Proc.Nat.Acad.Sci.Usa, 77, 6561–6565.
96 Randen, I., Pascual, V., Victor, K., Thompson, K. M., Forre, O., Capra, J. D. Et Natvig, J. B. (1993) Eur.J.Immunol., 23, 1220–1225.
97 Rassenti, L. Z. Et Kipps, T. J. (1993) J.Exp.Med., 177, 1039–1046.
98 Reidl, L. S., Friedman, D. F., Goldman, J., Hardy, R. R., Jefferies, L. C. Et Silberstein, L. E. (1991) J.Immunol., 147, 3623–3631.
99 Roudier, J., Silverman, G. J., Chen, P. P., Carson, D. A. Et Kipps, T. J. (1990) J.Immunol., 144, 1526–1530.
100 Sanz, I., Casali, P., Thomas, J. W., Notkins, A. L. Et Capra, J. D. (1989) J.Immunol., 142, 4054–4061.
101 Sanz, I., Dang, H., Takei, M., Talal, N. Et Capra J. D. (1989) J.Immunol., 142, 883–887.
102 Schmidt, W. E., Jung, H-.D., Palm, W. Et Hilschmann, N. (1983) Z.Physiol.Chem., 364, 713–747.
103 Schroeder, H. W., Jr. Et Wang, J. Y. (1990) Proc.Natl.Acad.Sci.Usa, 87, 6146–6150.
104 Schroeder, H. W., Jr., Hillson, J. L. Et Perlmutter, R. M. (1987) Science, 238, 791–793.
105 Schroeder, H. W., Jr., Hillson, J. L. Et Perlmutter, R. M. (1987) Science, 238, 791–793; Chen, P. P., Liu, M.-F., Glass, C. A., Sinha, S., Kipps, T. J. Et Carson, D. A. (1989) Arthritis Et Rheumatism, 32, 72–76.
106 Schroeder, H. W., Jr., Hillson, J. L. Et Perlmutter, R. M. (1987) Science, 238, 791–793; Chen, P. P., Liu, M.-F., Sinha, S. Et Carson, D. A. (1988) Arth.Rheum., 31, 1429–1431.
107 Schutte, M. E., Ebeling, S. B., Akkermans, K. E., Gmelig-Meyling, F. H. Et Logtenberg, T. (1991) Eur.J.Immunol., 21, 1115–1121.
108 Schutte, M. E., Ebeling, S. B., Akkermans, K. E., Gmelig-Meyling, F. H. J. Et Logtenberg, T. (1991) Eur.J.Immunol., 21, 1115–1121.
109 Settmacher, U., Jahn, S., Siegel, P., Von Baehr, R. Et Hansen, A. (1993) Mol.Immunol., 30, 953–954.
110 Shen, A., Humphries, C., Tucker, P. Et Blattner, F. (1987) Proc.Natl.Acad.Sci.Usa, 84, 8563–8567.
111 Shimizu, A., Nussenzweig, M. C., Mizuta, T.-R., Leder, P. Et Honjo, T. (1989) Proc.Natl.Acad.Sci.Usa, 86, 8020–8023.
112 Shin, E. K., Matsuda, F., Fujikura, J., Akamizu, T., Sugawa, H., Mori, T. Et Honjo, T. (1993) Eur.J.Immunol., 23, 2365–2367.
113 Silberstein, L. E., Litwin, S. Et Carmack, C. E. (1989) J.Exp.Med., 169, 1631–1643.
114 Singal, D. P., Frame, B., Joseph, S., Blajchman, M. A. Et Leber, B. F. (1993) Immunogenet., 38, 242.
115 Spatz, L. A., Wong, K. K., Williams, M., Desai, R., Golier, J., Berman, J. E., Alt, F. W. Et Latov, N. (1990) J.Immunol., 144, 2821–2828.
116 Steiner, L. A., Garcia-Pardo, A. Et Margolies, M. N. (1979) Biochemistry, 18, 4068–4080.
117 Stewart, A. K., Huang, C., Stollar, B. D. Et Schwartz, R. S. (1993) J.Exp.Med., 177, 409–418.
118 Thomas, J. W. (1993) J.Immunol., 150, 1375–1382.
119 Torano, A. Et Putnam, F. W. (1978) Proc.Nat.Acad.Sci.Usa, 75, 966–969.
120 Van Der Heijden, R. W. J., Bunschoten, H., Pascual, V., Uytdehaag, F. G. C. M., Osterhaus, A. D. M. E. Et Capra, J. D. (1990) J.Immunol., 144, 2835–2839.
121 Van Der Stoep, N., Van Der Linden, J. Et Logtenberg, T. (1993) J.Exp.Med., 177, 99–107.
122 Van Es, J. H., Gmelig-Meyling, F. H. J. Et Logtenberg, T. (1992) Eur.J.Immunol., 22, 2761–2764.
123 Varade, W. S., Marin, E., Kittelberger, A. M. Et Insel, R. A. (1993) J.Immunol., 150, 4985–4995.
124 Victor, K. D., Pascual, V., Lefvert, A. K. Et Capra, J. D. (1992) Mol.Immunol., 29, 1501–1506.
125 Victor, K. D., Pascual, V., Williams, C. L., Lennon, V. A. Et Capra, J. D. (1992) Eur.J.Immunol., 22, 2231–2236.
126 Watanabe, S., Barnikol, H. U., Horn, J., Bertram, J. Et Hilschmann, N. (1973) Z.Physiol.Chem., 354, 1505–1509.
127 Weng, N.-P., Yu-Lee, L.-Y., Sanz, I., Patten, B. M. Et Marcus, D. M. (1992) J.Immunol., 149, 2518–2529.
128 White, M. B., Word, C. J., Humphries, C. G., Blattner, F. R. Et Tucker, P. W. (1990) Mol.Cell.Biol., 10, 3690–3699.
129 Winkler, T. H., Fehr, H. Et Kalden, J. R. (1992) Eur.J.Immunol., 22, 1719–1728.
130 Yago, K., Zenita, K., Ohwaki, I., Harada, Y., Nozawa, S., Tsukazaki, K., Iwamori, M., Endo, N., Yasuda, N., Okuma, M. Et Kannagi, R. (1993) Mol.Immunol., 30, 1481–1489.
131 Zelenetz, A. D., Chen, T. T. Et Levy, R. (1992) J.Exp.Med., 176, 1137–1148.

B. References of Germline Sequences

References of Human Germline Kappa Sequences

1 Cox, J. P. L., Tomlinson, I. M. Et Winter, G. (1994) Eur.J.Immunol., 24, 827–836.
2 Huber, C., Et Al. (1993) Eur.J.Immunol., 23, 2868.
3 Klobeck, H. G., Bornkammm, G. W., Combriato, G., Mocikat, R., Pohlenz, H. D. Et Zachau, H. G. (1985) Nucl.Acids Res., 13, 6515–6529.
4 Lautner-Rieske, A., Huber, C., Meindl, A., Pargent, W., Schäble, K. F., Thiebe, R., Zocher, I. Et Zachau, H. G. (1992) Eur.J.Immunol. 22, 1023.
5 Lorenz, W., Schäble, K. F., Thiebe, R., Stavnezer, J. Et Zachau, H. G. (1988) Mol.Immunol., 25, 479.
6 Pargent, W., Meindl, A., Thiebe, R., Mitzel, S. Et Zachau, H. G. (1991) Eur.J.Immunol., 21, 1821–1827.
7 Pech, M. Et Zachau, H. G. (1984) Nuc.Acids Res., 12, 9229–9236.
8 Pech, M., Jaenichen, H.-R., Pohlenz, H.-D., Neumaier, P. S., Klobeck, H.-G. Et Zachau, H. G. (1984) J.Mol.Biol., 176, 189–204.
9 Scott, M. G., Crimmins, D. L., Mccourt, D. W., Chung, G., Schable, K. F., Thiebe, R., Quenzel, E.-M., Zachau, H. G. Et Nahm, M. H. (1991) J.Immunol., 147, 4007–4013.
10 Stavnezer, J., Kekish, O., Batter, D., Grenier, J., Balazs, I., Henderson, E. Et Zegers, B. J. M. (1985) Nucl.Acids Res., 13, 3495–3514.
11 Straubinger, B., Huber, E., Lorenz, W., Osterholzer, E., Pargent, W., Pech, M., Pohlenz, H.-D., Zimmer, F.-J. Et Zachau, H. G. (1988) J.Miol.Biol., 199, 23–34.
12 Straubinger, B., Thiebe, R., Huber, C., Osternolzer, E. Et Zachau, H. G. (1988) Biol.Chem.Hoppe-Seyer, 369, 601–607.

References of Human Germline Lambda Sequences

1 Williams, S. C. Et Winter, G. (1993) Eur.J.Immunol., 23, 1456–1461.

2 Siminovitch, K. A., Misener, V., Kwong, P. C., Song, Q.-L. Et Chen, P. P. (1989) J.Clin.Invest., 84,1675–1678.
3 Brockly, F., Alexandre, D., Chuchana, P., Huck, S., Lefranc, G. Et Lefranc, M.-P. (1989) Nuc.Acids.Res., 17, 3976.
4 Daley, M. D., Peng, H.-Q., Misener, V., Liu, X.-Y., Chen, P. P. Et Siminovitch, K. A. (1992) Mol.Immunol., 29, 1515–1518.
5 Deftos, M., Soto-Gil, R., Quan, M., Olee, T. Et Chen, P. P. (1994) Scand. J. Immunol., 39, 95.
6 Stiernholm, N. B. J., Kuzniar, B. Et Berinstein, N. L. (1994) J. Immunol., 152, 4969–4975.
7 Combriato, G. Et Klobeck, H. G. (1991) Eur.J.Immunol., 21, 1513–1522.
8 Anderson, M. L. M., Szajnert, M. F., Kaplan, J. C., Mccoll, L. Et Young, B. D. (1984) Nuc.Acids Res., 12, 6647–6661.

References of Human Germline Heavy Chain Sequences

1 Adderson, E. E., Azmi, F. H., Wilson, P. M., Shackelford, P. G. Et Carroll, W. L. (1993) J.Immunol., 151, 800–809.
2 Andris, J. S., Brodeur, B. R. Et Capra, J. D. (1993) Mol.Immunol., 30, 1601–1616.
3 Berman, J. E., Mellis, S. J., Pollock, R., Smith, C. L., Suh, H., Heinke, B., Kowal, C., Surti, U., Chess, L., Cantor, C. R. Et Alt, F. W. (1988) Embo J., 7, 727–738.
4 Buluwela, L. Et Rabbitts, T. H. (1988) Eur.J.Immunol., 18, 1843–1845.; Buluwela, L., Albertson, D. G., Sherrington, P., Rabbitts, P. H., Spurr, N. Et Rabbitts, T. H. (1988) Embo J., 7, 2003–2010.
5 Chen, P. P., Liu, M.-F., Sinha, S. Et Carson, D. A. (1988) Arth.Rheum., 31, 1429–1431.
6 Chen, P. P., Liu, M.-F., Glass, C. A., Sinha, S., Kipps, T. J. Et Carson, D. A. (1989) Arthritis Et Rheumatism, 32, 72–76.
7 Cook, G. P. et al. (1994) Nature Genetics 7, 162–168.
8 Haino, M. et al., (1994). J. Biol. Chem. 269, 2619–2626.
9 Humphries, C. G., Shen, A., Kuziel, W. A., Capra, J. D., Blattner, F. R. Et Tucker, P. W. (1988) Nature, 331, 446–449.
10 Kodaira, M., Kinashi, T., Umemura, I., Matsuda, F., Noma, T., Ono, Y. Et Honjo, T. (1986) J.Mol.Biol., 190, 529–541.
11 Lee, K. H., Matsuda, F., Kinashi, T., Kodaira, M. Et Honjo, T. (1987) J.Mol.Biol., 195, 761–768.
12 Matsuda, F., Lee, K. H., Nakai, S., Sato, T., Kodaira, M., Zong, S. Q., Ohno, H., Fukuhara, S. Et Honjo, T. (1988) Embo J., 7, 1047–1051.
13 Matsuda, F., Shin, E. K., Hirabayashi, Y., Nagaoka, H., Yoshida, M. C., Zong, S. O. Et Honjo, T. (1990) Embo J., 9, 2501–2506.
14 Matsuda, F., Shin, E. K., Nagaoka, H., Matsumura, R., Haino, M., Fukita, Y., Taka-Ishi, S., Imai, T., Riley, J. H., Anand, R. Et, Al. (1993) Nature Genet. 3, 88–94.
15 Nagaoka, H., Ozawa, K., Matsuda, F., Hayashida, H., Matsumura, R., Haino, M., Shin, E. K., Fukita, Y., Imai, T., Anand, R., Yokoyama, K., Eki, T., Soeda, E. Et Honjo, T. (1993). (Temporal)
16 Rechavi, G., Bienz, B., Ram, D., Ben-Neriah, Y., Cohen, J. B., Zakut, R. Et Givol, D. (1982) Proc.Nat.Acad.Sci.Usa, 79, 4405–4409.
17 Sanz, I., Kelly, P., Williams, C., Scholl, S., Tucker, P. Et Capra, J. D. (1989) Embo J., 8, 3741–3748.
18 Shin, E. K., Matsuda, F., Fujikura, J., Akamizu, T., Sugawa, H., Mori, T. Et Honjo, T. (1993) Eur.J.Immunol., 23, 2365–2367.
19 Tomlinson, Im., Walter, G., Marks, Jd., Llewelyn, Mb. Et Winter, G. (1992) J.Mol.Biol. 227, 776–798.
20 Van Der Maarel, S., Van Dijk, K. W., Alexander, C. M., Sasso, E. H., Bull, A. Et Milner, E. C. B. (1993) J.Immunol., 150, 2858–2868.
21 Van Dijk, K. W., Mortari, F., Kirkham, P. M., Schroeder, Jr., H. W. Et Milner, E. C. B. (1993) Eur.J.Immunol., 23, 832–839.
22 Van Es, J. H., Aanstoot, H., Gmelig-Meyling, F. H. J., Derksen, R. H. W. M. Et Logtenberg, T. (1992) J.Immunol., 149, 2234–2240.
23 Weng, N.-P., Snyder, J. G., Yu-Lee, L.-Y. Et Marcus, D. M. (1992) Eur.J.Immunol., 22, 1075–1082.
24 Winkler, T. H., Fehr, H. Et Kalden, J. R. (1992) Eur.J.Immunol., 22, 1719–1728.
25 Olee, T., Yang, P. M., Siminovitch, K. A., Olsen, N. J., Hillson, J. L., Wu, J., Kozin, F., Carson, D. A. Et Chen, P. P. (1991) J. Clin. Invest. 88, 193–203.
26 Chen, P. P. Et Yang, P. M. (1990) Scand. J. Immunol. 31, 593–599.
27 Tomlinson, M., Walter, G., Cook Et Winter, G. (Unpublished).

---

What is claimed is:

1. A method of preparing a library of nucleic acids, wherein each nucleic acid encodes an immunoglobulin variable domain comprising consensus framework sequences, comprising:

(a) identifying a plurality of immunoglobulin variable domain amino acid sequences, each comprising four consensus framework regions interspaced by three complementary determining regions CDR1, CDR2, and CDR3, wherein said consensus framework regions have been identified by the following steps:

(i) aligning a plurality of known human immunoglobulin sequences;

(ii) identifying the conserved framework regions of said known human immunoglobulin sequences;

(iii) comparing the amino acids at each corresponding position of said conserved framework regions; and (iv) deducing consensus framework regions from said comparing in step (a)(iii); and (b) synthesizing a plurality of nucleic acids encoding said plurality of immunoglobulin variable domain amino acid sequences provided in step (a), wherein each of said nucleic acids comprises DNA cleavage sites at the boundary between each consensus framework region and complementary determining region, and wherein each of said cleavage sites is unique within said nucleic acid but common to all nucleic acid sequences of said library at corresponding positions.

2. The method according to claim 1, wherein said known human immunoglobulin sequences in step (a)(i) are human Vκ immunoglobulin sequences.

3. The method according to claim 1, wherein said known human immunoglobulin sequences in step (a)(i) are human Vλ immunoglobulin sequences.

4. The method according to claim 1, wherein said known human immunoglobulin sequences in step (a)(i) are human VH immunoglobulin sequences.

5. The method according to claim 2, wherein each of said nucleic acids synthesized in step (b) are selected from the group consisting of Vκ1 (SEQ ID NO:42), Vκ2 (SEQ ID NO: 44), Vκ3 (SEQ ID NO: 46), and Vκ4 (SEQ ID NO: 48).

6. The method according to claim 3, wherein each of said nucleic acids synthesized in step (b) are selected from the group consisting of Vλ1 (SEQ ID NO:50), Vλ2 (SEQ ID NO: 52), and Vλ3 (SEQ ID NO: 54).

7. The method according to claim 4, wherein each of said nucleic acids synthesized in step (b) are selected from the group consisting of VH1A (SEQ ID NO:56), VH1B (SEQ ID NO: 58), VH2 (SEQ ID NO: 60), VH3 (SEQ ID NO: 62), VH4 (SEQ ID NO: 64), VH5 (SEQ ID NO: 66), and VH6 (SEQ ID NO: 68).

8. The method according to claim 1, further comprising inserting each of said nucleic acids into an expression vector.

9. The method according to claim 8, further comprising introducing each of said expression vectors into a host cell.

10. The method according to claim 9, wherein said nucleic acids encoding said immunoglobulin variable domain amino acid sequences comprise codons that are frequently used in said host cell.

11. The method according to claim 10, wherein each of said host cells is *E. coli.*

12. The method according to claim 11, wherein each of said expression vectors is a phagemid vector.

13. The method according to claim 1, wherein said CDR1 is selected from the group consisting of VH CDR1 germline sequences.

14. The method according to claim 13, wherein said CDR1 is selected from the group consisting of VH1-12-1, VH1-13-16, VH2-31-10, VH3-13-8, VH4-11-7, CH5-12-1, and VH6-35-1.

15. The method according to claim 1, wherein said CDR1 is selected from the group consisting of Vλ CDR1 germline sequences.

16. The method according to claim 15, wherein said CDR1 is selected from the group consisting of VHUMLV86, DPL11, and DPL23.

17. The method according to claim 1, wherein said CDR1 is selected from the group consisting of Vκ CDR1 germline sequences.

18. The method according to claim 17, wherein said CDR1 is selected from the group consisting of Vκ1-14, Vκ2-6, Vκ3-1, and Vκ4-1.

19. The method according to claim 1, wherein said CDR2 is selected from the group consisting of VH CDR2 germline sequences.

20. The method according to claim 19, wherein said CDR2 is selected from the group consisting of VH1-12-1, VH1-13-6, VH2-31-3, VH3-13-8, VH4-11-8, VH4-31-17, VH5-12-1, and VH6-35-1.

21. The method according to claim 1, wherein said CDR2 is selected from the group consisting of Vλ CDP2 germline sequences.

22. The method according to claim 21, wherein said CDR2 is selected from the group consisting of DPL5, DPL12, and HUMLV318.

23. The method according to claim 1, wherein said CDR2 is selected from the group consisting of Vκ CDR2 germline sequences.

24. The method according to claim 23, wherein said CDR2 is selected from the group consisting of Vκ1-2, Vκ2-6, Vκ3-4, and Vκ4-1.

25. The method according to claim 1, wherein said CDR3 is selected from random amino acid sequences.

* * * * *